(12) United States Patent
Nardi et al.

(10) Patent No.: US 9,540,349 B2
(45) Date of Patent: Jan. 10, 2017

(54) SUBSTITUTED PYRIMIDINE COMPOUNDS

(71) Applicant: Grünenthal GmbH, Aachen (DE)

(72) Inventors: Antonio Nardi, Herzogenrath (DE); Florian Jakob, Aachen (DE); Ingo Konetzki, Aachen (DE); Tobias Craan, Aachen (DE); Christian Hesslinger, Zoznegg (DE)

(73) Assignee: GRUENENTHAL GMBH, Aachen (DE)

(*) Notice: Subject to any disclaimer, the term of this patent is extended or adjusted under 35 U.S.C. 154(b) by 0 days.

(21) Appl. No.: 14/800,053

(22) Filed: Jul. 15, 2015

(65) Prior Publication Data
US 2016/0016937 A1 Jan. 21, 2016

(30) Foreign Application Priority Data
Jul. 16, 2014 (EP) .................................... 14002452

(51) Int. Cl.
| | |
|---|---|
| C07D 403/04 | (2006.01) |
| C07D 401/14 | (2006.01) |
| C07D 487/08 | (2006.01) |
| C07D 403/14 | (2006.01) |
| C07D 491/107 | (2006.01) |
| C07D 409/14 | (2006.01) |
| C07D 413/14 | (2006.01) |
| C07D 405/14 | (2006.01) |
| C07D 417/14 | (2006.01) |
| C07D 471/04 | (2006.01) |

(52) U.S. Cl.
CPC ........... *C07D 403/04* (2013.01); *C07D 401/14* (2013.01); *C07D 403/14* (2013.01); *C07D 405/14* (2013.01); *C07D 409/14* (2013.01); *C07D 413/14* (2013.01); *C07D 417/14* (2013.01); *C07D 471/04* (2013.01); *C07D 487/08* (2013.01); *C07D 491/107* (2013.01)

(58) Field of Classification Search
None
See application file for complete search history.

(56) References Cited

U.S. PATENT DOCUMENTS

| | | | |
|---|---|---|---|
| 5,019,587 A | 5/1991 | Von Der Saal et al. | |
| 2006/0293343 A1 | 12/2006 | Naganuma et al. | |
| 2016/0016938 A1* | 1/2016 | Nardi .................. | C07D 403/04 514/210.18 |
| 2016/0024053 A1* | 1/2016 | Konetzki ........... | C07D 491/107 514/210.18 |

FOREIGN PATENT DOCUMENTS

| | | |
|---|---|---|
| EP | 1958947 A1 | 8/2008 |
| WO | 2003051366 A2 | 6/2003 |
| WO | 2006002421 A2 | 1/2006 |
| WO | 2011072241 A1 | 6/2011 |
| WO | 2014170020 A1 | 10/2014 |

OTHER PUBLICATIONS

C. Schudt, et al., "PDE isoenzymes as targets for anti-asthma drugs", Eur Respir J., 1955, 8, 1179-1183.
F. Mori, et al., "The human area postrema and other nuclei related to the emetic reflex express cAMP phosphodiesterases 4B and 4D", 2010, Journal of Chemical Neuroanatomy, 40, 36-42.
K. H. Banner, et al., "2 PDE4 Inhibitors—A Review of the Current Field", 2009, Progress in Medicinal Chemistry, 47, 37-74.
A. Robichaud, et al., "α2-adrenoceptor-mediated anesthesia, a behavioral correlate of emesis", The Journal of Clinical Investigation, Oct. 2002, vol. 110, No. 7, 1045-52.
Ji Hyun Lee, et al., "Dynamic Regulation of Cystic Fibrosis Transmembrane Conductance Regulator by Competitive Interactions of Molecular Adaptors", Journal of Biological Chemistry, Apr. 2007, vol. 282, 10414-22.
Mark A. Giembycz, "4D of not 4D—the emetogenic basis of PDE4 inhibitors uncovered?", Dec. 2002, Trends in Pharmacological Sciences, vol. 23, No. 12.
Kenji Naganuma, et al., "Discovery of selective PDE4B inhibitors", 2009, Bioorganic & Medicinal Chemistry Letters, 19, 3174-3176.
L.J. Ravin, "Prefomulation", Chapter 76, Gennaro (Ed), Remington's Pharmaceutical Sciences, 17th Ed., 1985.
A.R. Disanto, "Bioavailability and Bioequivalency Testing", Chapter 77, Gennaro (Ed), Remington's Pharmaceutical Sciences, 17th Ed., 1985.
A.M. Knevel, "Separation", Chapter 78, Gennaro (Ed), Remington's Pharmaceutical Sciences, 17th Ed., 1985.
G.B. Phillips, "Sterilization", Chapter 79, Gennaro (Ed), Remington's Pharmaceutical Sciences, 17th Ed., 1985.
F.P. Siegel, "Tonicity, Osmoticity, Osmolality, and Osmolarity", Chapter 80, Gennaro (Ed), Remington's Pharmaceutical Sciences, 17th Ed., 1985.

(Continued)

*Primary Examiner* — Anna Pagonakis
(74) *Attorney, Agent, or Firm* — Norris McLaughlin & Marcus PA

(57) ABSTRACT

The invention relates to novel substituted pyrimidine compounds of general formula (I)

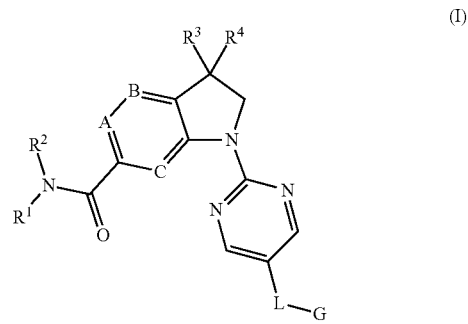

in which the chemical groupings, substituents, variables and indices are as defined in the description, and to their use as medicaments, in particular as medicaments for the treatment of conditions and diseases that can be treated by inhibition of the PDE4 enzyme.

26 Claims, No Drawings

(56) References Cited

OTHER PUBLICATIONS

R.L. Giles, et al., "Plastic Packaging Materials", Chapter 81, Gennaro (Ed), Remington's Pharmaceutical Sciences, 17th Ed., 1985.
C.J. Lintner, "Stability of Pharmaceutical Products", Chapter 82, Gennaro (Ed), Remington's Pharmaceutical Sciences, 17th Ed., 1985.
C.R. Erskine, "Quality Assurance and Control", Chapter 83, Gennaro (Ed), Remington's Pharmaceutical Sciences, 17th Ed., 1985.
J.G. Nairn, "Solutions, Emulsions, Suspensions and Extractives", Chapter 84, Gennaro (Ed), Remington's Pharmaceutical Sciences, 17th Ed., 1985.
K.E. Avis, "Parenteral Preparations", Chapter 85, Gennaro (Ed), Remington's Pharmaceutical Sciences, 17th Ed., 1985.
S.J. Turco, et al., "Intravenous Admixtures", Chapter 86, Gennaro (Ed), Remington's Pharmaceutical Sciences, 17th Ed., 1985.
J.D. Mullins, "Ophthalmic Preparations", Chapter 87, Gennaro (Ed), Remington's Pharmaceutical Sciences, 17th Ed., 1985.
L.H. Block, "Medicated Applications", Chapter 88, Gennaro (Ed), Remington's Pharmaceutical Sciences, 17th Ed., 1985.
E.G. Ripple, "Powders", Chapter 89, Gennaro (Ed), Remington's Pharmaceutical Sciences, 17th Ed., 1985.
R.E. King, et al., "Oral Solid Dosage Forms", Chapter 90, Gennaro (Ed), Remington's Pharmaceutical Sciences, 17th Ed., 1985.
S.C. Porter, "Coating of Pharmaceutical Dosage Forms", Chapter 91, Gennaro (Ed), Remington's Pharmaceutical Sciences, 17th Ed., 1985.
M.A. Longer, et al., "Sustained-Release Drug Delivery Systems", Chapter 92, Gennaro (Ed), Remington's Pharmaceutical Sciences, 17th Ed., 1985.
J.J.Sclarro, et al., "Aerosols", Chapter 93, Gennaro (Ed), Remington's Pharmaceutical Sciences, 17th Ed., 1985.
A. R. Muci, et al., "Practical Palladium Catalysts for C-N and C-O Bond Formation", Topics in Current Chemistry, 2002, vol. 219.
A. Suzuki, "Carbon-carbon bonding made easy", ChemComm, 4759-4763, 2005.
D. Robertson, et al., "Dihydropyridazinone Cardiotonics: Synthesis and Inotropic Activity of 5'41,4,5,6-Tetrahydro-6-oxo-3-pyridazinyl)spiro[cycloalkane-1,3'3H]indol]-2'(1'H)-ones", J. Med. Chem., 1987, vol. 30, 824-829.
A. Brennfuhrer, et al., " Palladium-Catalyzed Carbonylation Reactions of Aryl Halides and Related Compounds", Angew Chem, Int. Ed., 2009, 48, 4114-4133.
N. Saldou, et al. "Comparison of Recombinant Human PD4E Isoforms: Interaction with Substrate and Inhibitors", Cell. Signal., vol. 10, No. 6, 427-440, 1998.
T. Goto, et al., "Identification of the 5,5-dioxo-7,8-dihydro-6H-thiopyrano[3,2-d] pyrimidine derivatives as highly selective PDE4B inhibitors", Bioorganic & Medicinal Chemistry Letters, 2014, p. 893-899.
C. J. Mitchell, et al., "Pyrazolopyridines as potent PDE4B inhibitors: 5-Heterocycle SAR", Bioorganic & Medicinal Chemistry Letters, 20, 2010, p. 5803-5806.

* cited by examiner

SUBSTITUTED PYRIMIDINE COMPOUNDS

This application claims foreign priority benefit under 35 U.S.C. §119 of European Patent Application No. 14 002 452.2, filed Jul. 16, 2014, the disclosures of which patent application is incorporated herein by reference.

The present invention relates to novel substituted pyrimidine compounds that are useful as medicaments. This invention also relates to uses of the compounds to make medicaments and treatments comprising the administration of the compounds to humans in need of the treatments. This invention also relates to the preparation of said novel compounds. Moreover this invention relates to pharmaceutical compositions and kits comprising the compounds.

It is known that Phosphodiesterases (abbreviated as PDEs), or more accurately 3',5'-cyclonucleotide phosphodiesterases, are enzymes that catalyse the hydrolysis of the second messengers cAMP (cyclic adenosine monophosphate)- and cGMP (cyclic guanosine monophosphate) to 5'-AMP (5'-adenosine monophosphate)- and 5'-GMP (5'-guanosine monophosphate). Phosphodiesterases are a group of enzymes encompassing 11 gene families (PDE1-11), which differ inter alia through their affinity to cAMP and cGMP. Inhibition of phosphodiesterases thus represents a mechanism for modulating cellular processes and can be used to alleviate or cure disease conditions. Inhibitors of specific PDEs are known.

The discovery that the second messenger cAMP plays an important role in many inflammatory processes and that PDE4 is strongly expressed in cells that control inflammation processes (see inter alia Schudt, C. et al. (1995). PDE isoenzymes as targets for anti-asthma drugs. *European Respiratory Journal* 8, 1179-1183), has led to the development of PDE4 inhibitors having an anti-inflammatory effect. One such PDE4 inhibitor having an anti-inflammatory effect is roflumilast for example (known under the trade name Daxas®), which was approved as a medicament for the treatment of COPD (chronic obstructive pulmonary disease). In addition to the desired anti-inflammatory effect of roflumilast, however, side-effects such as nausea, diarrhoea and headaches are observed, which limit the dose in humans.

Undesired side-effects in humans were observed with other PDE4 inhibitors too, so the therapeutic range (therapeutic window) of such medicaments is relatively narrow. The provision of PDE4 inhibitors having less severe or fewer side-effects and a better therapeutic window would therefore be desirable.

Phosphodiesterase 4 (PDE4) is cAMP-specific and encompasses 4 different subtypes (PDE4A, PDE4B, PDE4C and PDE4D). As is described below, efforts are being made to find subtype-selective PDE4 inhibitors, above all PDE4B-selective inhibitors, that have less severe or no side-effects, such that the therapeutic range of these compounds is increased significantly.

The inhibition of PDE4D is associated with the occurrence of undesired side-effects, such as for example diarrhoea, vomiting and nausea (see in this regard Mori, F. et al. (2010). The human area postrema and other nuclei related to the emetic reflex express cAMP phosphodiesterases 4B and 4D. *Journal of Chemical Neuroanatomy* 40, 36-42; Press, N. J.; Banner K. H (2009). PDE4 inhibitors—A review of the current field. *Progress in Medicinal Chemistry* 47, 37-74; Robichaud, A. et al. (2002). Deletion of phosphodiesterase 4D in mice shortens α2-adrenoceptor-mediated anesthesia, a behavioral correlate of emesis. *The Journal of Clinical Investigation* 110, 1045-52; or Lee et al., (2007). Dynamic regulation of CFTR by competitive interactions of molecular adaptors. *Journal of Biological Chemistry* 282, 10414-10422); or Giembycz, M. A. (2002). 4D or not 4D—the emetogenic basis of PDE4 inhibitors uncovered? *Trends in Pharmacological Sciences* 23, 548).

Several pyrimidine compounds exhibiting PDE4B selectivity have been disclosed (Bioorg. Med. Chem. Lett. 19 (2009) p. 3174-3176). Some of the compounds listed are said to show a 10-times higher inhibitory 25 activity against PDE4B than against PDE4D. These compounds are substantially encompassed by the general formula described in US 2006/0293343A1, disclosing specific pharmaceutically effective PDE4-inhibiting pyrimidine compounds having an anti-inflammatory effect.

Based on the above, there is a need for compounds (active ingredients) that are preferably PDE4B-selective (which means that with a given amount of active ingredient inhibit PDE4B but without inhibiting or only weakly inhibiting the PDE4D subtype). The advantage of such a PDE4B selectivity, as mentioned above, is that various side-effects do not (should not) occur or occur only to a small extent and that therefore a greater therapeutic range (=therapeutic window) of the pharmaceutical active ingredient is (should be) obtained. The therapeutic range of a pharmaceutical active ingredient or medicament describes the gap between its therapeutic dose and a dose that would lead to a toxic or undesired effect. The greater the therapeutic range, the rarer or more unlikely the occurrence of certain toxic or undesired side-effects and hence the safer and more acceptable the pharmaceutical active ingredient or medicament. The therapeutic range is often also referred to as the therapeutic window or therapeutic index. These names are used synonymously in the present application.

The inventors have now found novel substituted pyrimidine compounds that display the desired inhibiting and PDE4B-selective property. They are therefore particularly suitable for the treatment of diseases and conditions in which inhibition of the PDE4 enzyme, in particular the PDE4B enzyme, is advantageous.

In a first aspect of the invention, the invention thus relates to substituted pyrimidine compounds of the following formula (I)

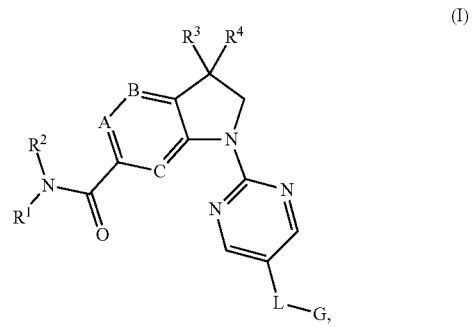

wherein

A, B and C independently represent CH or N;

$R^1$ and $R^2$ independently represent hydrogen or $(C_1-C_6)$-alkyl, whereby said $(C_1-C_6)$-alkyl is unsubstituted or substituted with at least one substituent $X^1$, or a group U, which is a 3- to 12-membered mono- or bi-cycloaliphatic ring, which is unsubstituted or substituted with at least one substituent $X^2$, whereby said group U may be connected to the nitrogen atom via a $C_{1-6}$-alkylene group, which in turn is unsubstituted or substituted with at least one substituent independently selected from the group consisting of F, Cl, $CF_3$, =O, $OCF_3$ and OH, or a group V, which is a 3- to 12-membered mono- or bi-cyclic heterocycloaliphatic ring containing at least one heteroatom selected from the group consisting of O, S and N as a ring member, and which mono- or bicyclic heterocycloaliphatic ring is unsubstituted or substituted with at least one substituent $X^3$, whereby said group V may be connected to the nitrogen atom via a $C_{1-6}$-alkylene group, which in turn may be unsubstituted or substituted with at least one substituent independently selected from the group consisting of F, Cl, $CF_3$, =O, $OCF_3$ and OH, or a group W which is phenyl or 5- or 6-membered heteroaryl, wherein said phenyl or said heteroaryl is unsubstituted or substituted with at least one substituent $X^4$ and may be condensed with a 4-, 5-, 6- or 7-membered ring, being carbocyclic or heterocyclic, wherein said condensed ring may be saturated, partially unsaturated or aromatic and may be substituted with at least on substituent $X^5$, and whereby group W may be connected to the nitrogen atom via a $C_{1-6}$-alkylene group, which in turn may be unsubstituted or substituted with at least one substituent independently selected from the group consisting of F, Cl, $CF_3$, =O, $OCF_3$ and OH, or $R^1$ and $R^2$ together with the nitrogen atom to which they are attached form a 3- to 12-membered monocyclic or bicyclic non-aromatic ring wherein said ring may contain at least one additional heteroatom selected from the group consisting of O, S and N and wherein said ring is unsubstituted or substituted with at least one substituent $X^6$;

$R^3$ and $R^4$ independently represent hydrogen, $(C_1-C_6)$-alkyl or $(C_3-C_6)$-cycloalkyl, wherein said $(C_1-C_6)$-alkyl and $(C_3-C_6)$-cycloalkyl are each unsubstituted or substituted with at least one substituent $Y^1$, or $R^3$ and $R^4$ together with the carbon atom to which they are attached form a 3- to 6-membered cycloalkyl ring, which is unsubstituted or substituted with at least one substituent $Y^2$;

L represents a bond, O, S, $(C_1-C_6)$-alkylene or $(C_2-C_6)$-alkenylene, whereby the aforementioned alkylenes or alkenylenes are in each case unsubstituted or substituted with at least one substituent selected from the group consisting of F, Cl, $CF_3$, =O, $OCF_3$ and OH;

G represents a phenyl or 5- or 6-membered heteroaryl, wherein said phenyl or said heteroaryl may be substituted with at least one substituent Z;

$X^1$, $X^2$, $X^3$, $X^5$ and $X^6$, at each occurrence are independently selected from the group consisting of OH, =O, CN, nitro, halogen, $(C_1-C_6)$-alkyl, $(C_1-C_6)$-hydroxyalkyl, $(C_1-C_6)$-alkoxy, $S(C_1-C_6)$-alkyl, $S(O)—(C_1-C_6)$-alkyl, $S(O)_2—(C_1-C_6)$-alkyl, $(C_1-C_6)$-haloalkyl, $S(C_1-C_6)$-haloalkyl, $(C_1-C_6)$-haloalkoxy, $(C_1-C_6)$-cyanoalkyl, $(C_3-C_8)$-cycloalkyl, $NH_2$, $NH(C_1-C_6)$-alkyl, $N((C_1-C_6)$-alkyl$)_2$, NH—CO—$(C_1-C_6)$-alkyl, NH—SO—$(C_1-C_6)$-alkyl, NH—$S(O)_2$—$(C_1-C_6)$-alkyl, $NH((C_1-C_6)$-alkylen)-SO—$(C_1-C_6)$-alkyl, $NH((C_1-C_6)$-alkylen)-$SO_2$—$(C_1-C_6)$-alkyl, $NHCONH_2$, NH—CO—NH—$(C_1-C_6)$-alkyl, $NH((C_1-C_6)$-alkylen)-CO—$N((C_1-C_6)$-alkyl$)_2$, CO—$(C_1-C_6)$-alkyl, $CO_2H$, CO—O—$(C_1-C_6)$-alkyl, $CONH_2$, CO—$NH(C_1-C_6)$alkyl and CO—$N((C_1-C_6)$-alkyl$)_2$;

$X^4$ at each occurrence are independently selected from the group consisting of OH, CN, nitro, halogen, $(C_1-C_6)$-alkyl, $(C_1-C_6)$-hydroxyalkyl, $(C_1-C_6)$-alkoxy, $S(C_1-C_6)$-alkyl, $S(O)—(C_1-C_6)$-alkyl, $S(O)_2—(C_1-C_6)$-alkyl, $(C_1-C_6)$-haloalkyl, $S(C_1-C_6)$-haloalkyl, $(C_1-C_6)$-haloalkoxy, $(C_1-C_6)$-cyanoalkyl, $(C_3-C_8)$-cycloalkyl, $NH_2$, $NH(C_1-C_6)$-alkyl, $N((C_1-C_6)$-alkyl$)_2$, NH—CO—$(C_1-C_6)$-alkyl, NH—SO—$(C_1-C_6)$-alkyl, NH—$S(O)_2$—$(C_1-C_6)$-alkyl, $NH((C_1-C_6)$-alkylen)-SO—$(C_1-C_6)$-alkyl, $NH((C_1-C_6)$-alkylen)-$SO_2$—$(C_1-C_6)$-alkyl, $NHCONH_2$, NH—CO—NH—$(C_1-C_6)$-alkyl, $NH((C_1-C_6)$-alkylen)-CO—$N((C_1-C_6)$-alkyl$)_2$, $CO_2H$, CO—O—$(C_1-C_6)$-alkyl, $CONH_2$, CO—$NH(C_1-C_6)$alkyl and CO—$N((C_1-C_6)$-alkyl$)_2$;

$Y^1$ and $Y^2$, at each occurrence are independently from one another selected from the group consisting of OH, =O, CN, nitro, halogen, $(C_1-C_6)$-alkyl, $(C_1-C_6)$-hydroxyalkyl, $(C_1-C_6)$-alkoxy, $S(C_1-C_6)$-alkyl, $S(O)—(C_1-C_6)$-alkyl, $S(O)_2$—$(C_1-C_6)$-alkyl, $(C_1-C_6)$-haloalkyl, $S(C_1-C_6)$-haloalkyl, $(C_1-C_6)$-haloalkoxy, $(C_1-C_6)$-cyanoalkyl, $(C_3-C_8)$-cycloalkyl, $NH_2$, $NH(C_1-C_6)$-alkyl, $N((C_1-C_6)$-alkyl$)_2$, NH—CO—$(C_1-C_6)$-alkyl, NH—SO—$(C_1-C_6)$-alkyl, NH—$S(O)_2$—$(C_1-C_6)$-alkyl, $NH((C_1-C_6)$-alkylen)-SO—$(C_1-C_6)$-alkyl, $NH((C_1-C_6)$-alkylen)-$SO_2$—$(C_1-C_6)$-alkyl, $NHCONH_2$, NH—CO—NH—$(C_1-C_6)$-alkyl, $NH((C_1-C_6)$-alkylen)-CO—$N((C_1-C_6)$-alkyl$)_2$, $CO_2H$, CO—O—$(C_1-C_6)$-alkyl, $CONH_2$, CO—$NH(C_1-C_6)$alkyl and CO—$N((C_1-C_6)$-alkyl$)_2$;

Z at each occurrence is independently selected from the group consisting of halogen, OH, CN, SH, $(C_1-C_6)$-alkyl, $(C_2-C_6)$-alkenyl, $(C_2-C_6)$-alkinyl, $(C_1-C_6)$-hydroxyalkyl, $(C_1-C_6)$-cyanoalkyl, $(C_1-C_6)$-alkoxy, $(C_1-C_6)$-thioalkyl, $(C_1-C_6)$-haloalkyl, $(C_1-C_6)$-thiohaloalkyl, $(C_1-C_6)$-haloalkoxy, $(C_1-C_6)$-alkylen-S—$(C_1-C_6)$-alkyl, $(C_3-C_8)$-cycloalkyl, $(C_3-C_6)$-cycloalkyl-$(C_1-C_3)$-alkylenyl, hydroxyl-$(C_3-C_6)$-cycloalkyl, $(C_3-C_8)$-heterocycloalkyl, $NH_2$, $NH(C_1-C_6)$-alkyl, $N((C_1-C_6)$-alkyl$)_2$, NH—CO—$(C_1-C_6)$-alkyl, NH—CO—O—$(C_1-C_6)$-alkyl, NH—$C(O)NH_2$, NH—CO—NH—$(C_1-C_6)$-alkyl, NH—CO—$N((C_1-C_6)$-alkyl$)_2$, $NH((C_1-C_6)$-alkylen)-CO—O—$(C_1-C_6)$-alkyl, $NH((C_1-C_6)$-alkylen)-$CONH_2$, $NH((C_1-C_6)$-alkylen)-CO—NH—$(C_1-C_6)$-alkyl, $NH((C_1-C_6)$-alkylen)-CO—$N((C_1-C_6)$-alkyl$)_2$, NH—$S(O)_2$OH, NH—$S(O)_2(C_1-C_6)$-alkyl, NH—$S(O)_2O(C_1-C_6)$-alkyl, NH—$S(O)_2NH_2$, NH—$S(O)_2NH(C_1-C_6)$-alkyl, NH—$S(O)_2N((C_1-C_6)$-alkyl$)_2$, $NH((C_1-C_6)$-alkylen)-$S(O)_2OH$, $NH((C_1-C_6)$-alkylen)-$S(O)_2(C_1-C_6)$-alkyl, $NH((C_1-C_6)$-alkylen)-$S(O)_2O(C_1-C_6)$-alkyl, $NH((C_1-C_6)$-alkylen)-$S(O)_2NH_2$, $NH((C_1-C_6)$-alkylen)-$S(O)_2NH(C_1-C_6)$-alkyl, $CO_2H$, $CO(C_1-C_6)$-alkyl, CO—O$(C_1-C_6)$-alkyl, O—$CO(C_1-C_6)$-alkyl, O—CO—O$(C_1-C_6)$-alkyl, $CONH_2$, CO—$NH(C_1-C_6)$-alkyl, CO—$N((C_1-C_6)$-alkyl$)_2$, O—CO—$NH(C_1-C_6)$-alkyl, O—CO—$N((C_1-C_6)$-alkyl$)_2$, O—$S(O)_2$—$(C_1-C_6)$-alkyl, O—$S(O)_2OH$, O—$S(O)_2$—$(C_1-C_6)$-alkoxy, O—S$(O)_2$ $NH_2$, O—$S(O)_2$—$NH(C_1-C_6)$-alkyl, O—$S(O)_2$—$N((C_1-C_6)$-alkyl$)_2$, $S(O)(C_1-C_6)$-alkyl, $S(O)_2(C_1-C_6)$-alkyl, $CH_2S(O)(C_1-C_6)$-alkyl, $CH_2S(O)_2(C_1-C_6)$- alkyl, $S(O)_2OH$, $S(O)_2O(C_1-C_6)$-alkyl, $S(O)_2NH_2$, $S(O)_2NH(C_1-C_6)$-alkyl, and $S(O)_2N((C_1-C_6)$-alkyl$)_2$; optionally in the form of a single stereoisomer or a mixture of stereoisomers, in the form of the free compound and/or a physiologically acceptable salt and/or a physiologically acceptable solvate thereof.

Preferred are compounds of formula (I), wherein

A, B and C independently represent CH or N;

$R^1$ and $R^2$ independently represent hydrogen or $(C_1-C_6)$-alkyl, whereby said $(C_1-C_6)$-alkyl is unsubstituted or substituted with 1, 2, 3, 4 or 5 substituents $X^1$, or a group U, which is a 3- to 12-membered mono- or bi-cycloaliphatic ring, which is unsubstituted or substituted with 1, 2, 3, 4 or 5 substituents $X^2$, whereby said group U may be connected to the nitrogen atom via a $C_{1-3}$-alkylene group, which in turn is unsubstituted or substituted with 1, 2 or 3 substituents independently selected from the group consisting of F, Cl, $CF_3$, =O, $OCF_3$ and OH, or a group V, which is a 3- to 12-membered mono- or bi-cyclic heterocycloaliphatic ring containing at 1, 2 or 3 heteroatoms selected from the group consisting of O, S and N as ring members, and which mono- or bicyclic heterocycloaliphatic ring is unsubstituted or substituted with 1, 2, 3, 4 or 5 substituents $X^3$; whereby said group V may be connected to the nitrogen atom via a $C_{1-3}$-alkylene group, which in turn is unsubstituted or substituted with 1, 2 or 3 substituents independently selected from the group consisting of F, Cl, $CF_3$, =O, $OCF_3$ and OH, or a group W which is phenyl or 5- or 6-membered heteroaryl, wherein said phenyl or said heteroaryl is unsubstituted or substituted with 1, 2, 3, 4, or 5 substituents $X^4$, and wherein said phenyl or said heteroaryl may be condensed with a 4-, 5-, 6- or 7-membered ring, being carbocyclic or heterocyclic, wherein said condensed ring may be saturated, partially unsaturated or aromatic and is unsubstituted or substituted with 1, 2, 3, 4 or 5 substitutents $X^5$; and wherein said group W may be connected to the nitrogen atom via a $C_{1-3}$-alkylene group, which in turn may be unsubstituted or substituted with at least one substituent independently selected from the group consisting of F, Cl, $CF_3$, =O, $OCF_3$ and OH, or $R^1$ and $R^2$ together with the nitrogen atom to which they are attached form a 3- to 12-membered monocyclic or bicyclic non-aromatic ring wherein said ring may contain 1, 2 or 3 additional heteroatoms selected from the group consisting of O, S and N and wherein said ring is unsubstituted or substituted with 1, 2, 3, 4 or 5 substituents $X^6$;

$R^3$ and $R^4$, independently of one another, each represent hydrogen, $(C_1-C_6)$-alkyl or $(C_3-C_6)$-cycloalkyl, wherein said $(C_1-C_6)$-alkyl and $(C_3-C_6)$-cycloalkyl are each unsubstituted or substituted with 1, 2, 3, 4 or 5 substituents $Y^1$; or $R^3$ and $R^4$ together with the carbon atom to which they are attached form a 3- to 6-membered cycloalkyl ring, which is unsubstituted or substituted with 1, 2, 3, 4 or 5 substituents $Y^2$;

L represents a bond, O, S, $(C_1-C_6)$-alkylene or $(C_2-C_6)$-alkenylene, whereby the aforementioned alkylenes or alkenylenes are in each case unsubstituted or substituted with 1, 2 or 3 substituents independently selected from the group consisting of F, Cl, $CF_3$, =O, $OCF_3$ and OH;

G represents a phenyl or 5- or 6-membered heteroaryl, wherein said phenyl or said heteroaryl is unsubstituted or substituted with 1, 2, 3, 4 or 5 substituents Z;

$X^1$, $X^2$, $X^3$, $X^5$ and $X^6$, at each occurrence are independently from one another selected from the group consisting of OH, =O, CN, F, Cl, Br, $CHF_2$, $CH_2F$, $CF_3$, $OCF_3$, $SCF_3$, $(C_1-C_6)$-alkyl, $(C_1-C_6)$-hydroxyalkyl, $(C_1-C_6)$-alkoxy, $S(C_1-C_6)$-alkyl, $S(O)—(C_1-C_6)$-alkyl, $S(O)_2—(C_1-C_6)$-alkyl, $(C_1-C_6)$-cyanoalkyl, $(C_3-C_6)$-cycloalkyl, $NH_2$, $NH(C_1-C_6)$-alkyl, $N((C_1-C_6)$-alkyl$)_2$, NH—CO—$(C_1-C_6)$-alkyl, NH—SO—$(C_1-C_6)$-alkyl, NH—$S(O)_2$—$(C_1-C_6)$-alkyl, $CO_2H$, CO—$(C_1-C_6)$-alkyl, CO—O—$(C_1-C_6)$-alkyl, $CONH_2$, CO—NH$(C_1-C_6)$alkyl and CO—N$((C_1-C_6)$-alkyl$)_2$;

$X^4$ at each occurrence is independently selected from the group consisting of OH, CN, F, Cl, Br, $CHF_2$, $CH_2F$, $CF_3$, $OCF_3$, $SCF_3$, $(C_1-C_6)$-alkyl, $(C_1-C_6)$-hydroxyalkyl, $(C_1-C_6)$-alkoxy, $S(C_1-C_6)$-alkyl, $S(O)—(C_1-C_6)$-alkyl, $S(O)_2—(C_1-C_6)$-alkyl, $(C_1-C_6)$-cyanoalkyl, $(C_3-C_6)$-cycloalkyl, $NH_2$, $NH(C_1-C_6)$-alkyl, $N((C_1-C_6)$-alkyl$)_2$, NH—CO—$(C_1-C_6)$-alkyl, NH—SO—$(C_1-C_6)$-alkyl, NH—$S(O)_2$—$(C_1-C_6)$-alkyl, $CO_2H$, CO—O—$(C_1-C_6)$-alkyl, $NHCONH_2$, NH—CO—NH—$(C_1-C_6)$-alkyl, $N((C_1-C_6)$-alkyl)-CO—N$((C_1-C_6)$-alkyl$)_2$, $CO_2H$, CO—O—$(C_1-C_6)$-alkyl, $CONH_2$, $CONH_2$, CO—NH$(C_1-C_6)$alkyl and CO—N$((C_1-C_6)$-alkyl$)_2$;

$Y^1$ and $Y^2$, at each occurrence are independently from one another selected from the group consisting of OH, =O, CN, F, Cl, Br, $CHF_2$, $CH_2F$, $CF_3$, $OCF_3$, $SCF_3$, $(C_1-C_6)$-alkyl, $(C_1-C_6)$-hydroxyalkyl, $(C_1-C_6)$-alkoxy, $S(C_1-C_6)$-alkyl, $S(O)—(C_1-C_6)$-alkyl, $S(O)_2—(C_1-C_6)$-alkyl, $(C_1-C_6)$-cyanoalkyl, $(C_3-C_6)$-cycloalkyl, $NH_2$, $NH(C_1-C_6)$-alkyl, $N((C_1-C_6)$-alkyl$)_2$, NH—CO—$(C_1-C_6)$-alkyl, NH—SO—$(C_1-C_6)$-alkyl, NH—$S(O)_2$—$(C_1-C_6)$-alkyl, $CO_2H$, CO—O—$(C_1-C_6)$-alkyl, $CONH_2$, CO—NH$(C_1-C_6)$alkyl and CO—N$((C_1-C_6)$-alkyl$)_2$;

Z at each occurrence is independently selected from the group consisting of F, Cl, Br, $CHF_2$, $CH_2F$, $CF_3$, $OCF_3$, $SCF_3$, OH, CN, SH, nitro, $(C_1-C_6)$-alkyl, $(C_2-C_6)$-alkenyl, $(C_2-C_6)$-alkinyl, $(C_1-C_6)$-hydroxyalkyl, $(C_1-C_6)$-cyanoalkyl, $(C_1-C_6)$-alkoxy, $(C_1-C_6)$-thioalkyl, $(C_1-C_6)$-alkylen-S—$(C_1-C_6)$-alkyl, $(C_3-C_6)$-cycloalkyl, hydroxyl-$(C_3-C_6)$-cycloalkyl, $(C_3-C_8)$-heterocycloalkyl, $NH_2$, $NH(C_1-C_6)$-alkyl, $N((C_1-C_6)$-alkyl$)_2$, NH—CO—$(C_1-C_6)$-alkyl, NH—CO—O—$(C_1-C_6)$-alkyl, NH—$S(O)_2OH$, NH—$S(O)_2(C_1-C_6)$-alkyl, NH—$S(O)_2O(C_1-C_6)$-alkyl, NH—$S(O)_2NH_2$, NH—$S(O)_2NH(C_1-C_6)$-alkyl, NH—$S(O)_2N((C_1-C_6)$-alkyl$)_2$, $NH((C_1-C_6)$-alkylen)-$S(O)_2OH$, $NH((C_1-C_6)$-alkylen)-$S(O)_2$ $(C_1-C_6)$-alkyl, $NH((C_1-C_6)$-alkylen)-$S(O)_2O(C_1-C_6)$-alkyl, $NH((C_1-C_6)$-alkylen)-$S(O)_2NH_2$, $NH((C_1-C_6)$-alkylen)-$S(O)_2NH(C_1-C_6)$-alkyl, $CO_2H$, $CO(C_1-C_6)$-alkyl, CO—O$(C_1-C_6)$-alkyl, O—CO$(C_1-C_6)$-alkyl, $CONH_2$, CO—NH$(C_1-C_6)$-alkyl, CO—N$((C_1-C_6)$-alkyl$)_2$, O—CO—NH$(C_1-C_6)$-alkyl, O—CO—N$((C_1-C_6)$-alkyl$)_2$, O—S$(O)_2$—$(C_1-C_6)$-alkyl, O—$S(O)_2OH$, O—$S(O)_2$—$(C_1-C_6)$-alkoxy, O—$S(O)_2NH_2$, O—$S(O)_2$—NH$(C_1-C_6)$-alkyl, O—$S(O)_2$—N$((C_1-C_6)$-alkyl$)_2$, $S(O)(C_1-C_6)$-alkyl, $S(O)_2$ $(C_1-C_6)$-alkyl, $CH_2S(O)(C_1-C_6)$-alkyl, $CH_2S(O)_2(C_1-C_6)$-alkyl, $S(O)_2OH$, $S(O)_2O(C_1-C_6)$-alkyl, $S(O)_2NH_2$, $S(O)_2NH(C_1-C_6)$-alkyl, and $S(O)_2N((C_1-C_6)$-alkyl$)_2$;

optionally in the form of a single stereoisomer or a mixture of stereoisomers, in the form of the free compound and/or a physiologically acceptable salt and/or a physiologically acceptable solvate thereof.

More preferred are compounds of formula (I), wherein A, B and C independently represent CH or N;

$R^1$ and $R^2$ independently represent hydrogen or $(C_1-C_6)$-alkyl, whereby said $(C_1-C_6)$-alkyl is unsubstituted or substituted with 1, 2, 3 or 5 substituents $X^1$; whereby at each occurrence $X^1$ is independently selected from the group consisting of F, Cl, Br, CN, $(C_1-C_6)$-alkoxy, OH, $CONH_2$, $CONH(C_1-C_6)$-alkyl, $CON((C_1-C_6)$-alkyl$)_2$, $NH_2$, $NH(C_1-C_6)$-alkyl and $N((C_1-C_6)$-alkyl$)_2$, or a group U, which is a 3- to 12-membered mono- or bi-cycloaliphatic ring, which is unsubstituted or substituted with 1, 2, 3, 4 or 5 substituents $X^2$, whereby at each occurrence $X^2$ is independently selected from the group consisting of OH, =O, CN, F, Cl, Br, $CF_3$, $CHF_2$, $CH_2F$, $OCF_3$, $(C_1-C_6)$-alkyl, $(C_1-C_6)$-alkoxy, $NH_2$, $NH(C_1-C_6)$-alkyl, $N((C_1-C_6)$-alkyl$)_2$, NH—CO—$(C_1-C_6)$-alkyl, $CO_2H$, CO—O—$(C_1-C_6)$-alkyl, $CONH_2$, CO—NH$(C_1-C_6)$alkyl and CO—N$((C_1-C_6)$-alkyl$)_2$; and whereby said group U may be connected to the nitrogen atom via a $C_{1-3}$-alkylene group, which in turn is unsubstituted or substituted with 1, 2 or 3 substituents independently selected from the group consisting of F, Cl, $CF_3$, =O, $OCF_3$ and OH, or a group V, which is a 3- to 12-membered mono- or bi-cyclic heterocycloaliphatic ring containing at 1, 2 or 3 heteroatoms selected from the group consisting of O, S and N as ring members, and which mono- or bicyclic heterocycloaliphatic ring is unsubstituted or substituted with 1, 2, 3, 4 or 5 substituents $X^3$, whereby at each occurrence $X^3$ is independently selected from the group consisting of OH, =O, CN, F, Cl, Br, $CF_3$, $CHF_2$, $CH_2F$, $OCF_3$, $(C_1\text{-}C_6)$-alkyl, $(C_1\text{-}C_6)$-alkoxy, $NH_2$, $NH(C_1\text{-}C_6)$-alkyl, $N((C_1\text{-}C_6)\text{-alkyl})_2$, NH—CO—$(C_1\text{-}C_6)$-alkyl, $CO_2H$, CO—O—$(C_1\text{-}C_6)$-alkyl, $CONH_2$, CO—NH$(C_1\text{-}C_6)$alkyl and CO—N$((C_1\text{-}C_6)$-alkyl$)_2$; and whereby said group V may be connected to the nitrogen atom via a $C_{1-3}$-alkylene group, which in turn is unsubstituted or substituted with 1, 2 or 3 substituents independently selected from the group consisting of F, Cl, $CF_3$, =O, $OCF_3$ and OH, or a group W which is phenyl or 5- or 6-membered heteroaryl, wherein said phenyl or said heteroaryl is unsubstituted or substituted with 1, 2, 3, 4, or 5 substituents $X^4$, whereby at each occurrence $X^4$ is independently selected from the group consisting of OH, CN, F, Cl, Br, $CF_3$, $CHF_2$, $CH_2F$, $OCF_3$, $(C_1\text{-}C_6)$-alkyl, $(C_1\text{-}C_6)$-hydroxyalkyl, $(C_1\text{-}C_6)$-alkoxy, S(O)—$(C_1\text{-}C_6)$-alkyl, $S(O)_2$—$(C_1\text{-}C_6)$-alkyl, $(C_3\text{-}C_6)$-cycloalkyl, $NH_2$, $NH(C_1\text{-}C_6)$-alkyl, $N((C_1\text{-}C_6)\text{-alkyl})_2$, NH—CO—$(C_1\text{-}C_6)$-alkyl, NH—SO—$(C_1\text{-}C_6)$-alkyl, NH—S$(O)_2$—$(C_1\text{-}C_6)$-alkyl, $N((C_1\text{-}C_6)$-alkyl)-CO—$(C_1\text{-}C_6)$-alkyl, $N((C_1\text{-}C_6)$-alkyl)-SO—$(C_1\text{-}C_6)$-alkyl, $N((C_1\text{-}C_6)$-alkyl)-$SO_2$—$(C_1\text{-}C_6)$-alkyl, $NHCONH_2$, NH—CO—NH—$(C_1\text{-}C_6)$-alkyl, $N((C_1\text{-}C_6)$-alkyl)-CO—N$((C_1\text{-}C_6)$-alkyl$)_2$, $CO_2H$, CO—O—$(C_1\text{-}C_6)$-alkyl, $CONH_2$, CO—NH$(C_1\text{-}C_6)$alkyl and CO—N$((C_1\text{-}C_6)$-alkyl$)_2$; and wherein said phenyl or said heteroaryl may be condensed with a 4-, 5-, 6- or 7-membered ring, being carbocyclic or heterocyclic, wherein said condensed ring may be saturated, partially unsaturated or aromatic and is unsubstituted or substituted with 1, 2, 3, 4 or 5 substitutents $X^5$, whereby at each occurrence $X^5$ is independently selected from the group consisting of OH, =O, CN, F, Cl, Br, $CF_3$, $CHF_2$, $CH_2F$, $OCF_3$, $(C_1\text{-}C_6)$-alkyl, $(C_1\text{-}C_6)$-alkoxy, $NH_2$, $NH(C_1\text{-}C_6)$-alkyl, $N((C_1\text{-}C_6)\text{-alkyl})_2$, NH—CO—$(C_1\text{-}C_6)$-alkyl, $CO_2H$, CO—O—$(C_1\text{-}C_6)$-alkyl, $CONH_2$, CO—NH$(C_1\text{-}C_6)$alkyl and CO—N$((C_1\text{-}C_6)$-alkyl$)_2$; and wherein said group W may be connected to the nitrogen atom via a $C_{1-3}$-alkylene group, which in turn may be unsubstituted or substituted with at least one substituent independently selected from the group consisting of F, Cl, $CF_3$, =O, $OCF_3$ and OH, or $R^1$ and $R^2$ together with the nitrogen atom to which they are attached form a 3- to 12-membered monocyclic or bicyclic non-aromatic ring wherein said ring may contain at least one additional heteroatom selected from the group consisting of O, S and N and wherein said ring is unsubstituted or substituted with at least one substituent $X^6$; whereby at each occurrence $X^6$ is independently selected from the group consisting of OH, =O, CN, F, Cl, Br, $CF_3$, $CHF_2$, $CH_2F$, $OCF_3$, $(C_1\text{-}C_6)$-alkyl, $(C_1\text{-}C_6)$-hydroxyalkyl, $(C_1\text{-}C_6)$-cyanoalkyl, $(C_1\text{-}C_6)$-alkoxy, $(C_3\text{-}C_6)$-cycloalkyl, $NH_2$, $NH(C_1\text{-}C_6)$-alkyl, $N((C_1\text{-}C_6)\text{-alkyl})_2$, NH—CO—$(C_1\text{-}C_6)$-alkyl, $CO_2H$, CO—$(C_1\text{-}C_6)$-alkyl, CO—O—$(C_1\text{-}C_6)$-alkyl, $CONH_2$, CO—NH$(C_1\text{-}C_6)$alkyl and CO—N$((C_1\text{-}C_6)$-alkyl$)_2$; $R^3$ and $R^4$, independently of one another, each represent hydrogen, $(C_1\text{-}C_6)$-alkyl or $(C_3\text{-}C_6)$-cycloalkyl, wherein said $(C_1\text{-}C_6)$-alkyl and $(C_3\text{-}C_6)$-cycloalkyl are each unsubstituted or substituted with 1, 2, 3, 4 or 5 substituents $Y^1$, wherein at each occurrence $Y^1$ is independently selected from the group consisting of OH, =O, CN, F, Cl, Br, $CF_3$, $CHF_2$, $CH_2F$, $OCF_3$, $(C_1\text{-}C_6)$-alkyl, $(C_1\text{-}C_6)$-alkoxy, $NH_2$, $NH(C_1\text{-}C_6)$-alkyl, $N((C_1\text{-}C_6)\text{-alkyl})_2$, NH—CO—$(C_1\text{-}C_6)$-alkyl, $CO_2H$, CO—O—$(C_1\text{-}C_6)$-alkyl, $CONH_2$, CO—NH$(C_1\text{-}C_6)$alkyl and CO—N$((C_1\text{-}C_6)$-alkyl$)_2$, or $R^3$ and $R^4$ together with the carbon atom to which they are attached form a 3- to 6-membered cycloalkyl ring, which is unsubstituted or substituted with 1, 2, 3, 4 or 5 substituents $Y^2$, wherein at each occurrence $Y^2$ is independently selected from the group consisting of OH, =O, CN, F, Cl, Br, $CF_3$, $CHF_2$, $CH_2F$, $OCF_3$, $(C_1\text{-}C_6)$-alkyl, $(C_1\text{-}C_6)$-alkoxy, $NH_2$, $NH(C_1\text{-}C_6)$-alkyl, $N((C_1\text{-}C_6)\text{-alkyl})_2$, NH—CO—$(C_1\text{-}C_6)$-alkyl, $CO_2H$, CO—O—$(C_1\text{-}C_6)$-alkyl, $CONH_2$, CO—NH$(C_1\text{-}C_6)$alkyl and CO—N$((C_1\text{-}C_6)$-alkyl$)_2$;

L represents a bond, O, S, or $(C_1\text{-}C_6)$-alkylene, whereby the aforementioned alkylenes are in each case unsubstituted or substituted with 1, 2 or 3 substituents independently selected from the group consisting of F, Cl, $CF_3$, =O, $OCF_3$ and OH;

G represents a phenyl or 5- or 6-membered heteroaryl, wherein said phenyl or said heteroaryl is unsubstituted or substituted with 1, 2, 3, 4 or 5 substituents Z; whereby at each occurrence Z is independently selected from the group consisting of F, Cl, Br, $CHF_2$, $CH_2F$, $CF_3$, $OCF_3$, $SCF_3$, OH, CN, SH, nitro, $(C_1\text{-}C_6)$-alkyl, $(C_2\text{-}C_6)$-alkenyl, $(C_2\text{-}C_6)$-alkinyl, $(C_1\text{-}C_6)$-hydroxyalkyl, $(C_1\text{-}C_6)$-cyanoalkyl, $(C_1\text{-}C_6)$-alkoxy, $(C_1\text{-}C_6)$-thioalkyl, $(C_1\text{-}C_6)$-alkylen-S—$(C_1\text{-}C_6)$-alkyl, $(C_3\text{-}C_6)$-cycloalkyl, hydroxyl-$(C_3\text{-}C_6)$-cycloalkyl, $(C_3\text{-}C_8)$-heterocycloalkyl, $NH_2$, $NH(C_1\text{-}C_6)$-alkyl, $N((C_1\text{-}C_6)\text{-alkyl})_2$, NH—CO—$(C_1\text{-}C_6)$-alkyl, NH—CO—O—$(C_1\text{-}C_6)$-alkyl, NH—$S(O)_2OH$, NH—$S(O)_2(C_1\text{-}C_6)$-alkyl, NH—$S(O)_2O(C_1\text{-}C_6)$-alkyl, NH—$S(O)_2NH_2$, NH—$S(O)_2NH(C_1\text{-}C_6)$-alkyl, NH—$S(O)_2N((C_1\text{-}C_6)$-alkyl$)_2$, $NH((C_1\text{-}C_6)$-alkylen)-$S(O)_2OH$, $NH((C_1\text{-}C_6)$-alkylen)-$S(O)_2(C_1\text{-}C_6)$-alkyl, $NH((C_1\text{-}C_6)$-alkylen)-$S(O)_2O(C_1\text{-}C_6)$-alkyl, $NH((C_1\text{-}C_6)$-alkylen)-$S(O)_2NH_2$, $NH((C_1\text{-}C_6)$-alkylen)-$S(O)_2NH(C_1\text{-}C_6)$-alkyl, $CO_2H$, $CO(C_1\text{-}C_6)$-alkyl, CO—O—$(C_1\text{-}C_6)$-alkyl, O—$CO(C_1\text{-}C_6)$-alkyl, $CONH_2$, CO—NH$(C_1\text{-}C_6)$-alkyl, CO—N$((C_1\text{-}C_6)$-alkyl$)_2$, O—CO—NH$(C_1\text{-}C_6)$-alkyl, O—CO—N$((C_1\text{-}C_6)$-alkyl$)_2$, O—$S(O)_2$—$(C_1\text{-}C_6)$-alkyl, O—$S(O)_2OH$, O—$S(O)_2$—$(C_1\text{-}C_6)$-alkoxy, O—$S(O)_2NH_2$, O—$S(O)_2$—NH$(C_1\text{-}C_6)$-alkyl, O—$S(O)_2$—N$((C_1\text{-}C_6)$-alkyl$)_2$, $S(O)(C_1\text{-}C_6)$-alkyl, $S(O)_2(C_1\text{-}C_6)$-alkyl, $CH_2S(O)(C_1\text{-}C_6)$-alkyl, $CH_2S(O)_2(C_1\text{-}C_6)$-alkyl, $S(O)_2OH$, $S(O)_2O(C_1\text{-}C_6)$-alkyl, $S(O)_2NH_2$, $S(O)_2NH(C_1\text{-}C_6)$-alkyl, and $S(O)_2N((C_1\text{-}C_6)$-alkyl$)_2$; optionally in the form of a single stereoisomer or a mixture of stereoisomers, in the form of the free compound and/or a physiologically acceptable salt and/or a physiologically acceptable solvate thereof.

In one embodiment of compounds of formula (I) each of A, B and C represents CH.

In a further embodiment of compounds of formula (I) $R^1$ and $R^2$ independently represent hydrogen or an alkyl selected from the group consisting of methyl, ethyl, n-propyl, i-propyl, n-butyl, i-butyl, s-butyl and t-butyl, whereby said alkyl is unsubstituted or substituted with 1, 2 or 3 substituents independently from one another selected from the group consisting of methoxy, ethoxy, OH, F, Cl, CN, C(O)OH, $CONH_2$, $CONH(CH_3)$, $CON(CH_3)_2$, $NH_2$, $NH(CH_3)$ and $N(CH_3)_2$, or

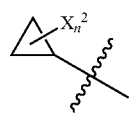

U1

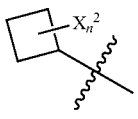

U2

-continued

U3 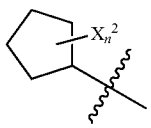

U4 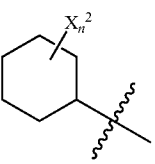

U5 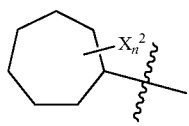

U6 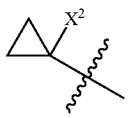

U7 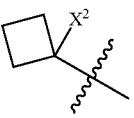

U8 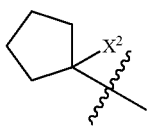

U9 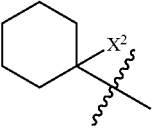

U10 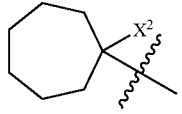

U11 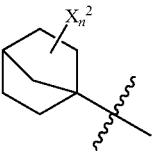

represent one of the following groups U1 to U11 whereby at each occurrence n is 0, 1, 2, 3, 4 or 5, and whereby at each occurrence $X^2$ is independently selected from the group consisting of OH, =O, CN, F, Cl, Br, $CF_3$, $CHF_2$, $CH_2F$, $OCF_3$, ($C_1$-$C_6$)-alkyl, ($C_1$-$C_6$)-alkoxy, $NH_2$, NH($C_1$-$C_6$)-alkyl, N(($C_1$-$C_6$)-alkyl)$_2$, NH—CO—($C_1$-$C_6$)-alkyl, $CO_2H$, CO—O—($C_1$-$C_6$)-alkyl, $CONH_2$, CO—NH ($C_1$-$C_6$)alkyl and CO—N(($C_1$-$C_6$)-alkyl)$_2$, and whereby said group U may be connected to the nitrogen atom via a $C_{1-3}$-alkylene group, which in turn is unsubstituted or substituted with 1, 2 or 3 substituents independently selected from the group consisting of F, Cl, $CF_3$, =O, $OCF_3$ and OH, and wherein said group U1 to U11 may be connected to the nitrogen atom via a $C_{1-3}$-alkylene group, which in turn may be unsubstituted or substituted with at least one substituent independently selected from the group consisting of F, Cl, $CF_3$, =O, $OCF_3$ and OH, or represent one of the following groups V1 to V35:

V1 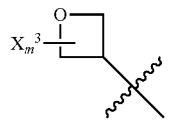

V2 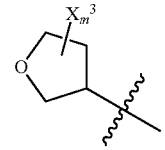

V3 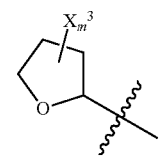

V4 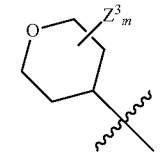

V5 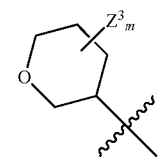

V6 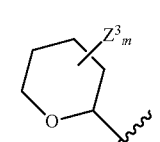

V7 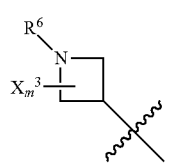

V8 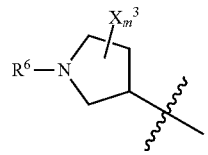

V9 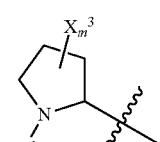

| | |
|---|---|
| 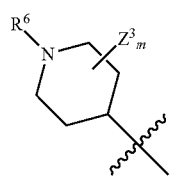 V10 | 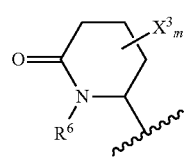 V19 |
| 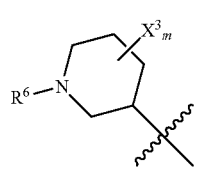 V11 | 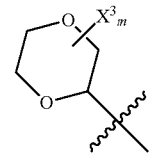 V20 |
| 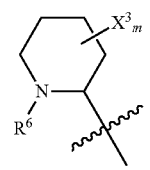 V12 | 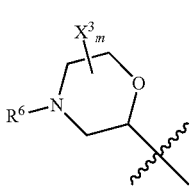 V21 |
| 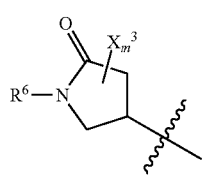 V13 | 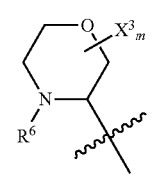 V22 |
| 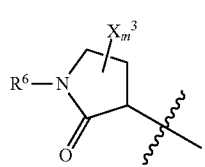 V14 | 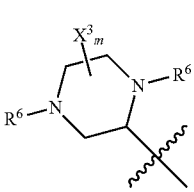 V23 |
| 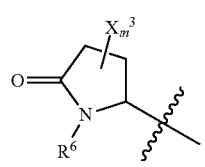 V15 | 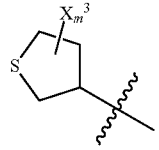 V24 |
| 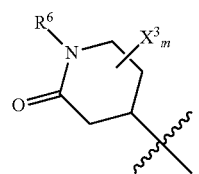 V16 | 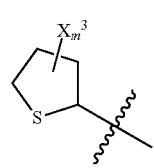 V25 |
| 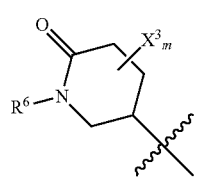 V17 | 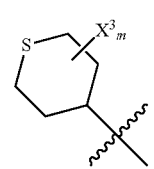 V26 |
| 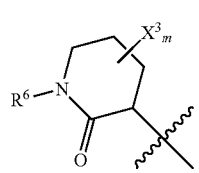 V18 | 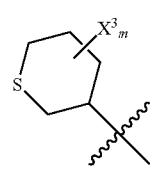 V27 |

-continued

V28 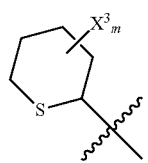

V29 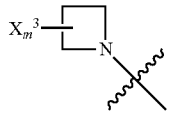

V30 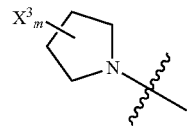

V31 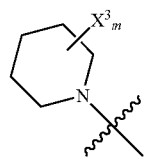

V32 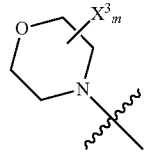

V33 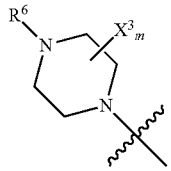

V34 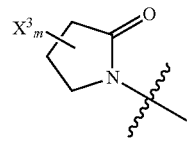

V35 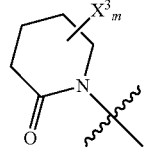

wherein $R^6$ is H, $(C_1\text{-}C_6)$-alkyl, $(C_1\text{-}C_6)$-hydroxyalkyl, $(C_1\text{-}C_6)$-cyanoalkyl, $(C_3\text{-}C_6)$-cycloalkyl, CO—$(C_1\text{-}C_6)$-alkyl or $SO_2$—$(C_1\text{-}C_6)$-alkyl;

at each occurrence m is 0, 1, 2, 3, 4 or 5, and $X^3$ at each occurrence is independently selected from the group consisting of OH, =O, CN, F, Cl, Br, $CF_3$, $CHF_2$, $CH_2F$, $OCF_3$, $(C_1\text{-}C_6)$-alkyl, $(C_1\text{-}C_6)$-alkoxy, $NH_2$, $NH(C_1\text{-}C_6)$-alkyl, $N((C_1\text{-}C_6)\text{-alkyl})_2$, NH—CO—$(C_1\text{-}C_6)$-alkyl, $CO_2H$, CO—O—$(C_1\text{-}C_6)$-alkyl, $CONH_2$, CO—$NH(C_1\text{-}C_6)$alkyl and CO—$N((C_1\text{-}C_6)\text{-alkyl})_2$; and whereby said group V may be connected to the nitrogen atom via a $C_{1-3}$-alkylene group, which in turn is unsubstituted or substituted with 1, 2 or 3 substituents independently selected from the group consisting of F, Cl, $CF_3$, =O, $OCF_3$ and OH, and wherein said group V1 to V35 may be connected to the nitrogen atom via a $C_{1-3}$-alkylene group, which in turn may be unsubstituted or substituted with at least one substituent independently selected from the group consisting of F, Cl, $CF_3$, =O, $OCF_3$ and OH, or represent one of the following groups W1 to W47

W1 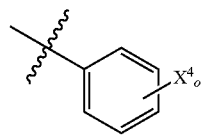

W2 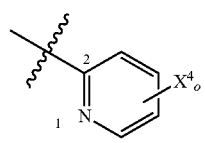

W3 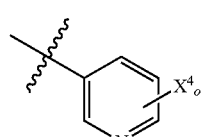

W4 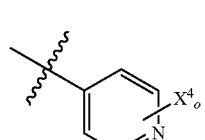

W5 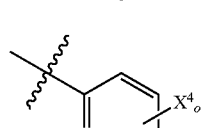

W6 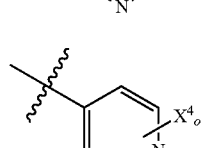

W7 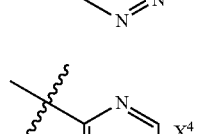

W8 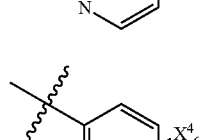

W9 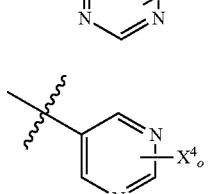

-continued
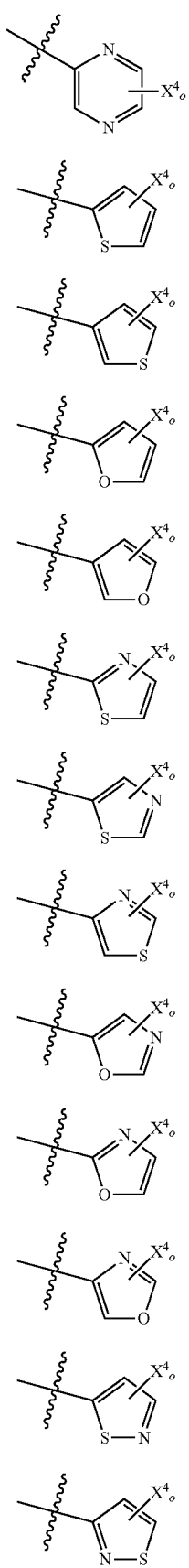
W10
W11
W12
W13
W14
W15
W16
W17
W18
W19
W20
W21
W22
-continued
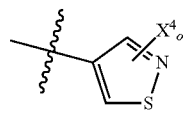 W23
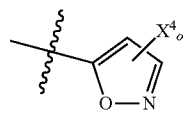 W24
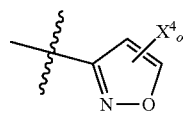 W25
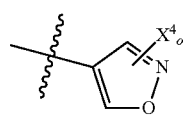 W26
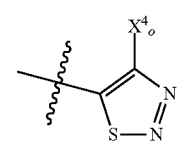 W27
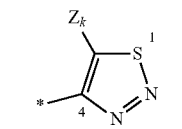 W28
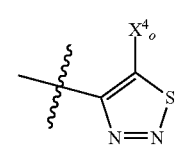 W29
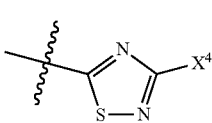 W30
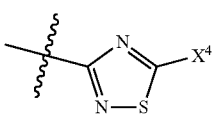 W31
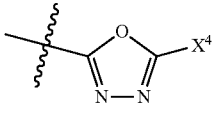 W32
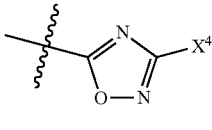 W33
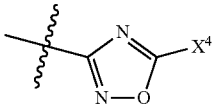 W34 wherein
R⁷ is selected H, CH₃ or CH₂CH₃;
at each occurrence o represents 0, 1, 2, 3, 4 or 5;
X⁴ at each occurrence is independently selected from the group consisting of OH, CN, F, Cl, Br, $(C_1-C_6)$-alkyl, $(C_1-C_6)$-hydroxyalkyl, $(C_1-C_6)$-alkoxy, $S(O)-(C_1-C_6)$-alkyl, $S(O)_2-(C_1-C_6)$-alkyl, $CF_3$, $CHF_2$, $CH_2F$, $OCF_3$, $(C_3-C_6)$-cycloalkyl, $NH_2$, $NH(C_1-C_6)$-alkyl, $N((C_1-C_6)$-alkyl$)_2$, $NH-CO-(C_1-C_6)$-alkyl, $NH-SO-(C_1-C_6)$-alkyl, $NH-S(O)_2-(C_1-C_6)$-alkyl, $N((C_1-C_6)$-alkyl$)$-$CO-(C_1-C_6)$-alkyl, $N((C_1-C_6)$-alkyl$)$-$SO-(C_1-C_6)$-alkyl, $N((C_1-C_6)$-alkyl$)$-$SO_2-(C_1-C_6)$-alkyl, $NHCONH_2$, $NH-CO-NH-(C_1-C_6)$-alkyl, $N((C_1-C_6)$-alkyl$)$-$CO-N((C_1-C_6)$-alkyl$)_2$, $CO_2H$, $CO-O-(C_1-C_6)$-alkyl, $CONH_2$, $CO-NH(C_1-C_6)$ alkyl and $CO-N((C_1-C_6)$-alkyl$)_2$; and wherein said group W may be connected to the nitrogen atom via a $C_{1-3}$-alkylene group, which in turn may be unsubstituted or substituted with at least one substituent independently selected from the group consisting of F, Cl, $CF_3$, $=O$, $OCF_3$ and OH, and wherein said group W1 to W47 may be connected to the nitrogen atom via a $C_{1-3}$-alkylene group, which in turn may be unsubstituted or substituted with at least one substituent independently selected from the group consisting of F, Cl, $CF_3$, $=O$, $OCF_3$ and OH.

In another embodiment of compounds of formula (I)
R¹ and R² together with the nitrogen atom to which they are attached form a ring selected from the following groups Q1 to Q34:

-continued
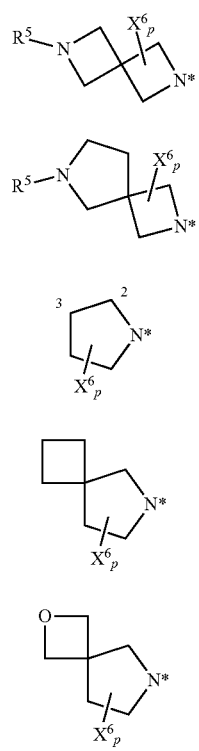
Q4
Q5
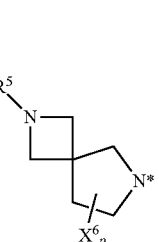
Q6
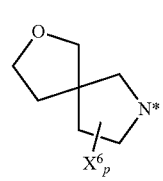
Q7
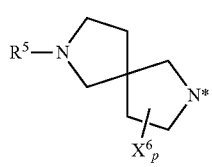
Q8
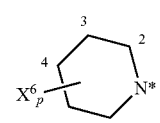
Q9
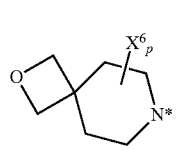
Q10
Q11
-continued
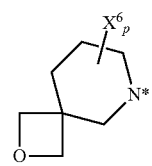
Q14
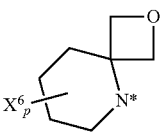
Q15
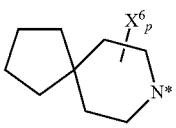
Q16
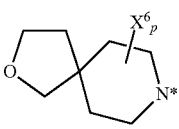
Q17
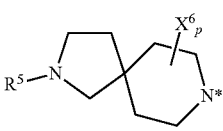
Q18
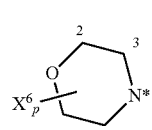
Q19
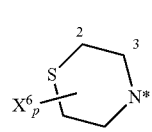
Q20
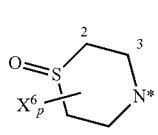
Q21
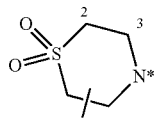
Q22
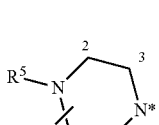
Q23
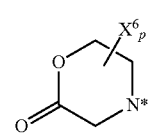
Q24
Q12
Q13

-continued

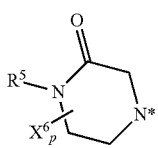
Q25

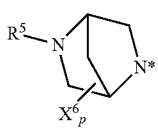
Q26

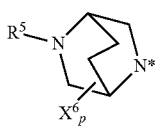
Q27

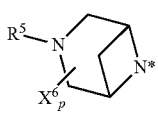
Q28

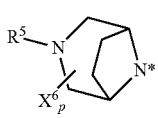
Q29

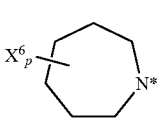
Q30

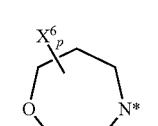
Q31

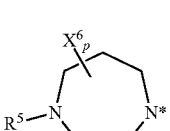
Q32

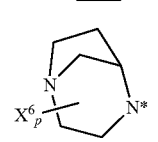
Q33

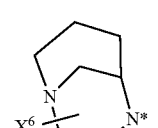
Q34

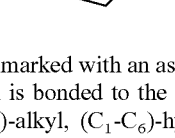

in which the site marked with an asterisk (*) indicates the binding site, which is bonded to the carbonyl group;

$R^5$ is H, $(C_1-C_6)$-alkyl, $(C_1-C_6)$-hydroxyalkyl, $(C_1-C_6)$-cyanoalkyl, $(C_3-C_6)$-cycloalkyl, CO—$(C_1-C_6)$-alkyl or SO$_2$—$(C_1-C_6)$-alkyl;

at each occurrence p is 0, 1, 2, 3, 4 or 5; and $X^6$ at each occurrence is independently selected from the group consisting of OH, =O, CN, F, Cl, Br, CF$_3$, CHF$_2$, CH$_2$F, OCF$_3$, $(C_1-C_6)$-alkyl, $(C_1-C_6)$-hydroxyalkyl, $(C_1-C_6)$-cyanoalkyl, $(C_1-C_6)$-alkoxy, $(C_3-C_6)$-cycloalkyl, NH$_2$, NH$(C_1-C_6)$-alkyl, N$((C_1-C_6)$-alkyl)$_2$, NH—CO—$(C_1-C_6)$-alkyl, CO$_2$H, CO—$(C_1-C_6)$-alkyl, CO—O—$(C_1-C_6)$-alkyl, CONH$_2$, CO—NH$(C_1-C_6)$alkyl and CO—N$((C_1-C_6)$-alkyl)$_2$.

In a further embodiment of compounds of formula (I) the substructure M

M represents one of the following substructures M1 to M61:

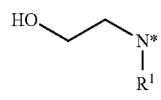
M1

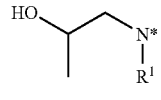
M2

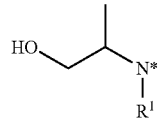
M3

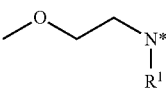
M4

M5

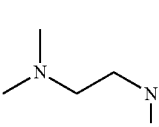
M6

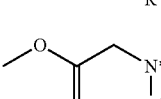
M7

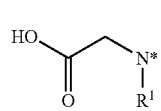
M8

M9

M10

M11

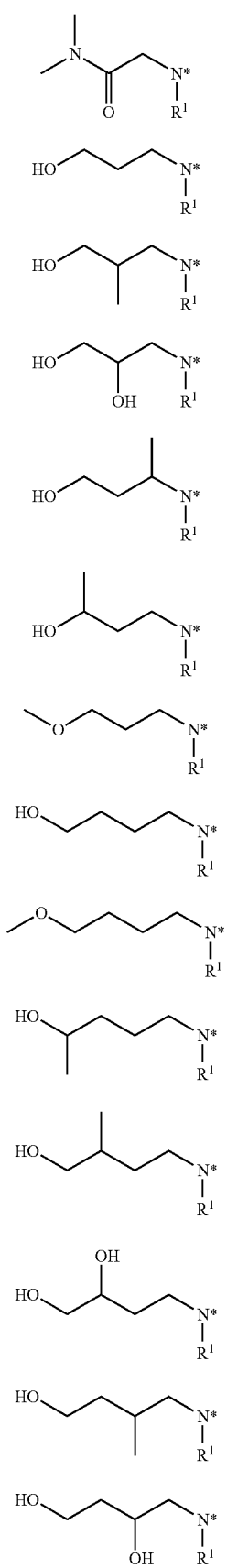
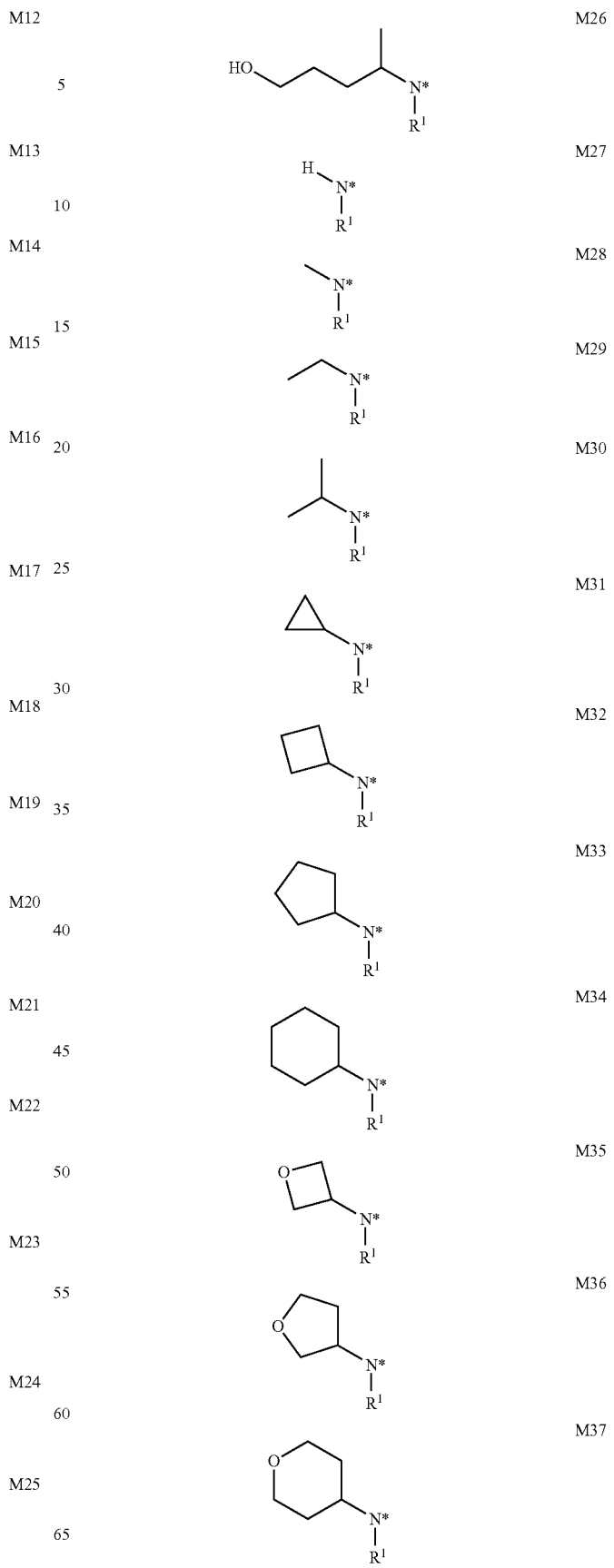

25
-continued
M38 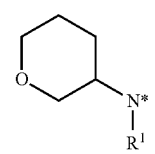
M39 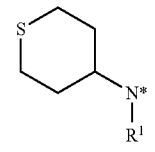
M40 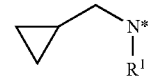
M41 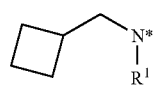
M42 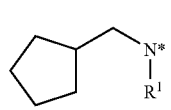
M43 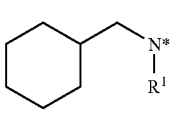
M44 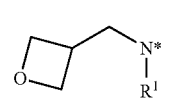
M45 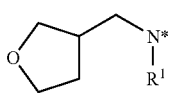
M46 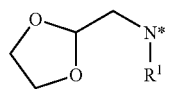
M47 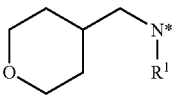
M48 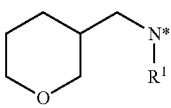
M49 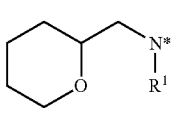
M50 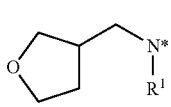
M51 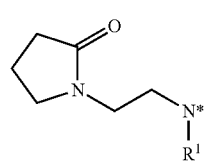
26
-continued
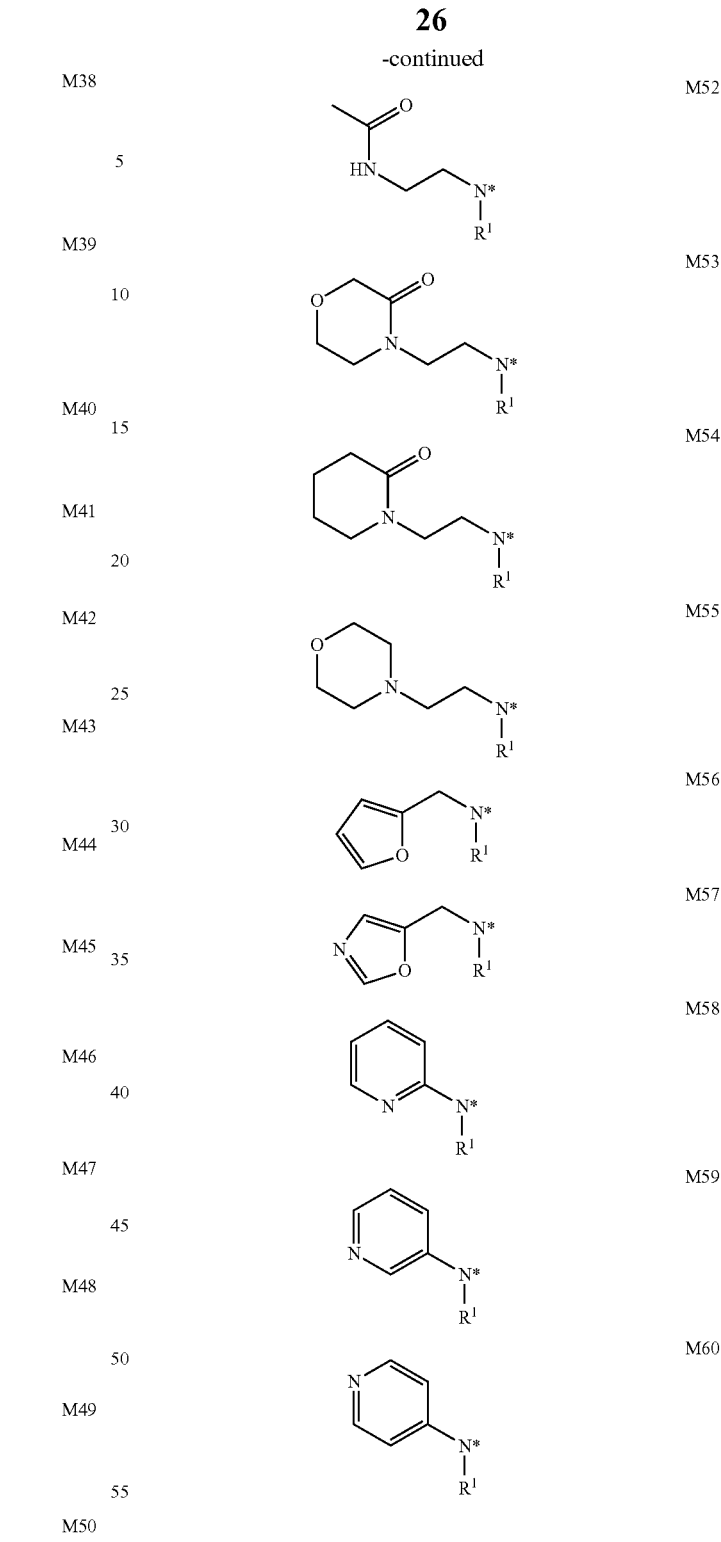
wherein $R^1$ is H, $CH_3$, $CH_2CH_3$, $CH(CH_3)_2$, $CH_2CH_2OH$, $CH_2CH_2OCH_3$ or cyclopropyl.
In preferred embodiment of the first aspect of the invention, the compounds of formula (I) are characterized in that $R^1$ and $R^2$ together with the nitrogen atom to which they are attached form a ring selected from the following groups Q'1 to Q'63:

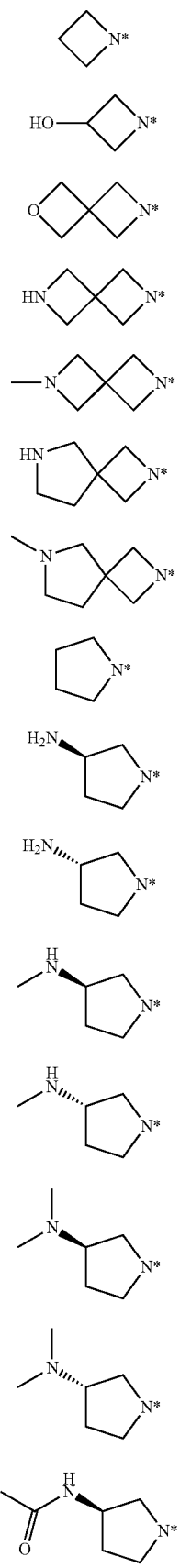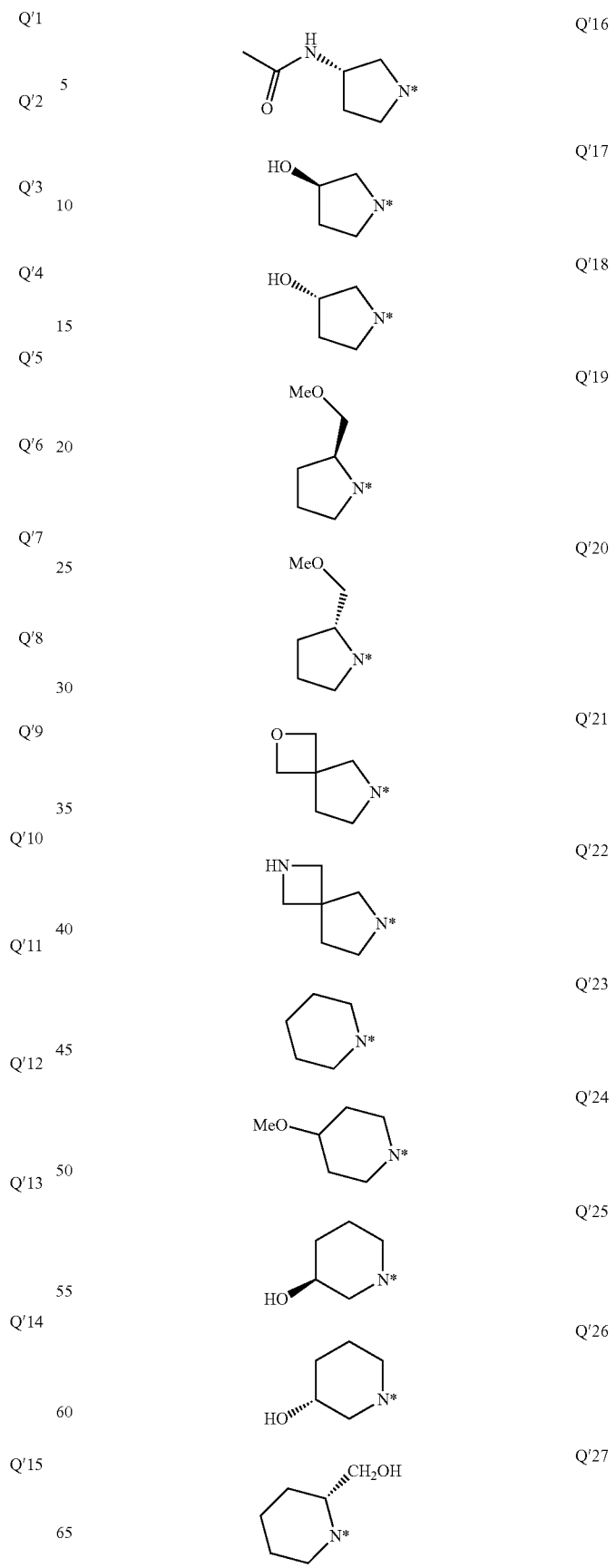

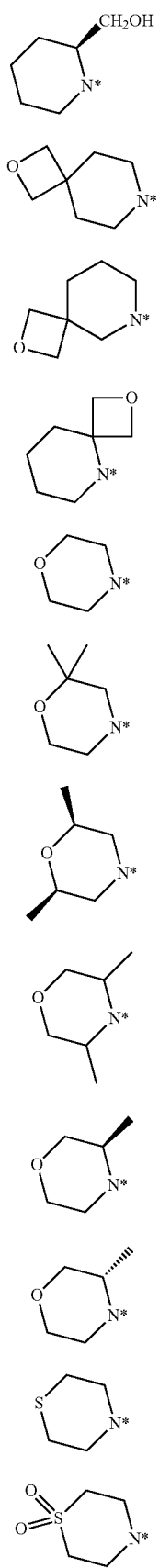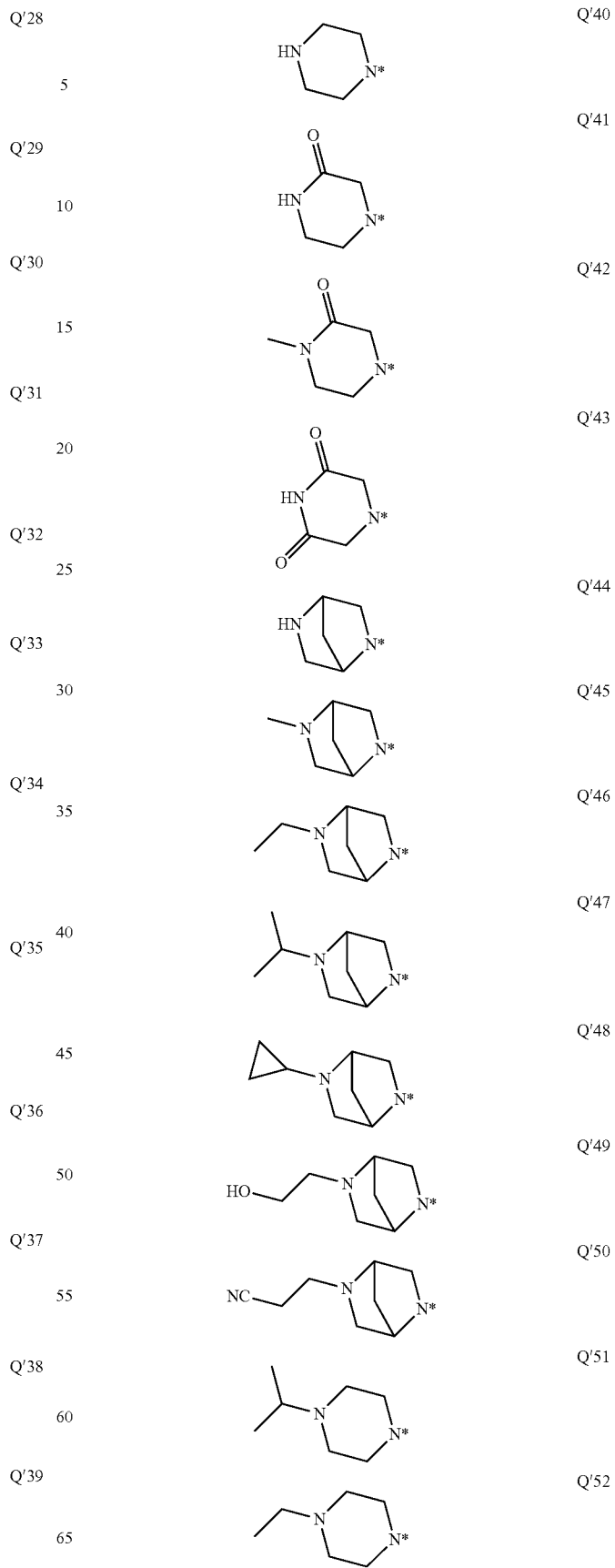

-continued

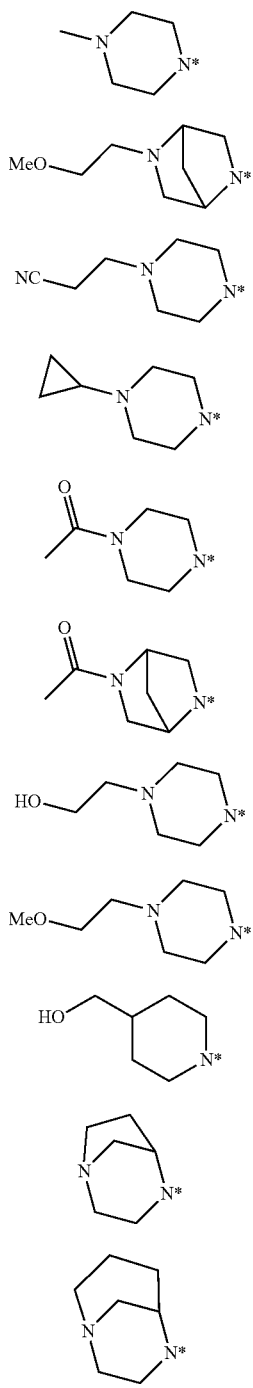

| | |
|---|---|
| Q'53 | |
| Q'54 | |
| Q'55 | |
| Q'56 | |
| Q'57 | |
| Q'58 | |
| Q'59 | |
| Q'60 | |
| Q'61 | |
| Q'62 | |
| Q'63 | |

In still another embodiment of compounds of formula (I) $R^3$ and $R^4$ each represent $CH_3$, or
$R^3$ and $R^4$ together with the carbon atom to which they are attached form a cyclopropyl or cyclobutyl ring.

In preferred embodiment of the first aspect of the invention, the compounds of formula (I) are characterized in that $R^3$ and $R^4$ together with the carbon atom to which they are attached form a cyclopropyl.

In a further embodiment of the compounds of formula (I), L represents bond, $CH_2$, or an oxygen atom. In preferred embodiment of the first aspect of the invention, the compounds of formula (I) are characterized in that L is bond.

In still a further embodiment of compounds of formula (I), G is one of the following groups G1 to G44

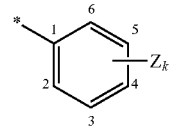

G1

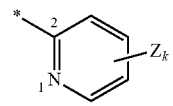

G2

G3

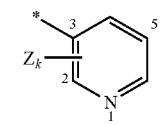

G4

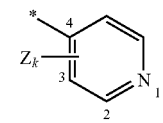

G5

G6

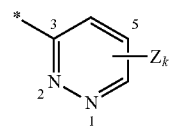

G7

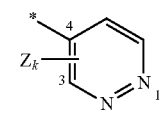

G8

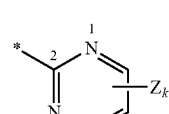

G9

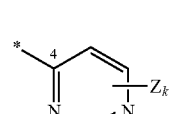

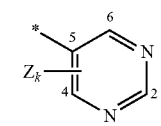

G10

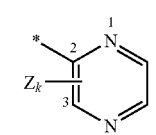

G11 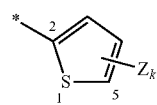
G12 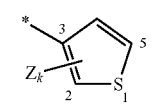
G13 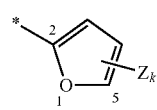
G14 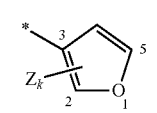
G15 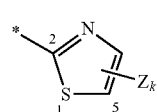
G16 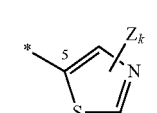
G17 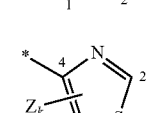
G18 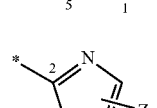
G19 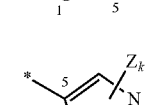
G20 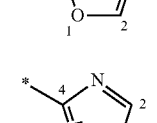
G21 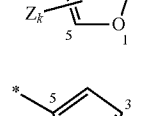
G22 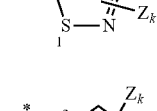
G23 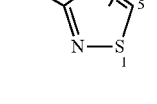
G24 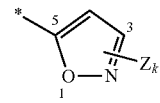
G25 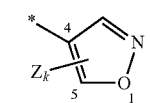
G26 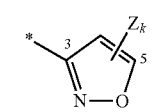
G27 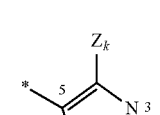
G28 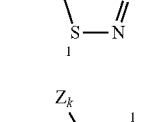
G29 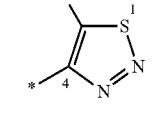
G30 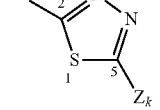
G31 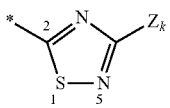
G32 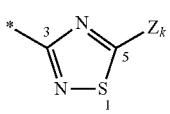
G33 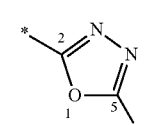
G34 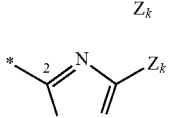
G35 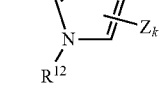

-continued

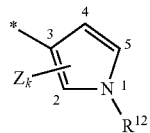
G36

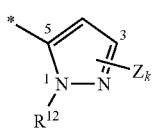
G37

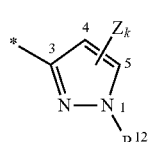
G38

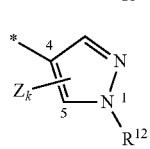
G39

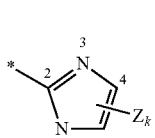
G40

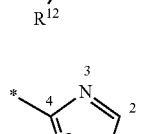
G41

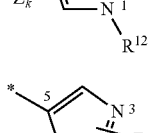
G42

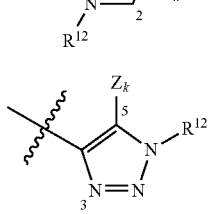
G43

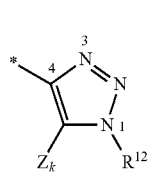
G44 in which the site marked with an asterisk (*) indicates the binding site, which is bonded to the pyrimidine ring;

$R^{12}$ is selected H, $CH_3$ or $CH_2CH_3$;

k at each occurrence 0, 1, 2, 3, 4 or 5; and

Z at each occurrence is independently selected from the group consisting of F, Cl, Br, $CF_3$, $CHF_2$, $CH_2F$, $OCF_3$, OH, CN, $(C_1-C_4)$-alkyl, $(C_1-C_4)$-hydroxyalkyl, $(C_1-C_4)$-alkoxy, $(C_3-C_6)$-cycloalkyl, hydroxyl-$(C_3-C_6)$-cycloalkyl, $(C_3-C_8)$-heterocycloalkyl, $NH_2$, $NH(C_1-C_4)$-alkyl, $N((C_1-C_4)$-alkyl$)_2$, $NH-CO-(C_1-C_4)$-alkyl, $NH-CO-NH-(C_1-C_6)$-alkyl, $NH-CO-N((C_1-C_6)$-alkyl$)_2$, $NH-S(O)_2(C_1-C_4)$-alkyl, $CONH_2$, $CO-NH(C_1-C_6)$-alkyl, $CO-N((C_1-C_6)$-alkyl$)_2$, $S(O)_2NH_2$, $S(O)_2NH(C_1-C_6)$-alkyl, $S(O)_2N((C_1-C_6)$-alkyl$)_2$, $CH_2S(O)(C_1-C_6)$-alkyl, $CH_2S(O)_2(C_1-C_6)$-alkyl, $S(O)(C_1-C_4)$-alkyl and $S(O)_2(C_1-C_4)$-alkyl.

In a preferred embodiment of the first aspect of the invention, G is select from G1 or G2, wherein k at each occurrence 0, 1, 2 or 3; and Z at each occurrence is independently selected from the group consisting of F, Cl, $CF_3$, $CHF_2$, $CH_2F$, $OCF_3$, OH, CN, $(C_1-C_4)$-alkyl, $(C_1-C_4)$-hydroxyalkyl, $(C_1-C_4)$-alkoxy, $(C_3-C_6)$-cycloalkyl, hydroxyl-$(C_3-C_6)$-cycloalkyl, $(C_3-C_8)$-heterocycloalkyl, $NH_2$, $NH(C_1-C_4)$-alkyl, $N((C_1-C_4)$-alkyl$)_2$, $NH-CO-(C_1-C_4)$-alkyl, $NH-S(O)_2(C_1-C_4)$-alkyl, $CONH_2$, $CO-NH(C_1-C_6)$-alkyl, $CO-N((C_1-C_6)$-alkyl$)_2$, $S(O)_2NH_2$, $S(O)_2NH(C_1-C_6)$-alkyl, $S(O)_2N((C_1-C_6)$-alkyl$)_2$, $CH_2S(O)(C_1-C_6)$-alkyl, $CH_2S(O)_2(C_1-C_6)$-alkyl, $S(O)(C_1-C_4)$-alkyl and $S(O)_2(C_1-C_4)$-alkyl.

A preferred embodiment of the compounds of formula (I) are compounds of formula (I'),

(I')

wherein $R^1$ and $R^2$ together with the nitrogen atom to which they are attached form one of the following heterocycles Q19, Q23, Q25 or Q26,

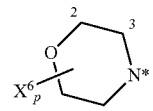
Q19

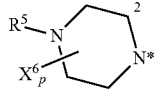
Q23

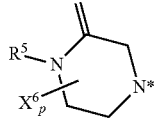
Q25

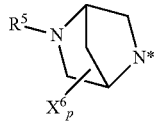
Q26 in which the site marked with an asterisk (*) indicates the binding site, which is bonded to the carbonyl group;

$R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, $C(O)$-cyclopropyl, $CH_2CH_2CN$, $CH_2CH_2OH$ or $CH_2CH_2OCH_3$;

at each occurrence p is 0, 1, 2 or 3; and $X^6$ represents H, $C(O)CH_3$, $C(O)CH_2CH_3$, $CH_3$, $CH_2CH_3$, $CH_2CH_2CH_3$, $CH(CH_3)_2$, $CH_2CH_2CH_3$, $CH_2CH(CH_3)_2$, $CH(CH_3)(CH_2CH_3)$, $CH(CH_3)_3$, cyclopropyl, cyclobutyl, cyclopentyl and cyclohexyl, OH, $OCH_3$, $OCH_2CH_3$, $OCH(CH_3)_2$, $NH_2$, $N(H)CH_3$, $N(CH_3)_2$, $N(H)C(O)CH_3$, $CH_2OH$, $CH_2CH_2OH$, $CH_2OCH_3$ or $CH_2CH_2OCH_3$.

or in which $R^1$ stands for $CH_3$ or cyclopropyl and $R^2$ stands for $CH_2CH_2OH$, $CH_2CH_2CH_2OH$, (R)—$CH_2CH(OH)CH_2OH$, (S)—$CH_2CH(OH)CH_2CH_2OH$, (R)-2-$CH_2CH(CH_3)OH$, (S)—$CH_2CH(CH_3)OH$, (R)—$CH(CH_3)CH_2OH$, (S)—$CH(CH_3)CH_2OH$;

and G is selected from the group consisting of G1 to G44 as defined above, $R^{12}$ at each occurrence is independently selected from the group consisting of hydrogen, methyl and ethyl;

k at each occurrence 0, 1, 2, 3, 4 or 5; and

Z at each occurrence is independently selected from the group consisting of F, Cl, Br, $CF_3$, $CHF_2$, $CH_2F$, $OCF_3$, OH, CN, $(C_1-C_4)$-alkyl, $(C_1-C_4)$-hydroxyalkyl, $(C_1-C_4)$-alkoxy, $(C_3-C_6)$-cycloalkyl, hydroxyl-$(C_3-C_6)$-cycloalkyl, $(C_3-C_8)$-heterocycloalkyl, $NH_2$, $NH(C_1-C_4)$-alkyl, $N((C_1-C_4)$-alkyl$)_2$, NH—CO—$(C_1-C_4)$-alkyl, NH—$S(O)_2(C_1-C_4)$-alkyl, $CONH_2$, CO—$NH(C_1-C_6)$-alkyl, CO—$N((C_1-C_6)$-alkyl$)_2$, $S(O)_2NH_2$, $S(O)_2NH(C_1-C_6)$-alkyl, $S(O)_2N((C_1-C_6)$-alkyl$)_2$, $CH_2S(O)(C_1-C_6)$-alkyl, $CH_2S(O)_2(C_1-C_6)$-alkyl, $S(O)(C_1-C_4)$-alkyl and $S(O)_2(C_1-C_4)$- alkyl.

In another preferred embodiment of the first aspect of the invention, the compounds of formula (I) are compounds of formula (I'),

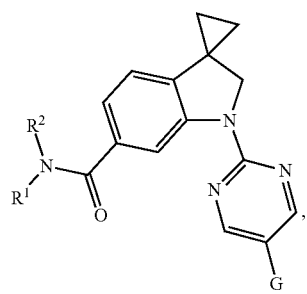

(I')

wherein $R^1$ and $R^2$ together with the nitrogen atom to which they are attached form one of the following heterocycles Q'32, Q'33, Q'34, Q'35, Q'36, Q'37; Q'40, Q'41, Q'42, Q'44, Q'46, Q'49, Q'50, Q'52, Q'53, Q'54, Q'55, Q'57, Q'58, Q'59 or Q'60 as defined above or in which $R^1$ stands for $CH_3$ or cyclopropyl and $R^2$ stands for $CH_2CH_2OH$, $CH_2CH_2CH_2OH$, (R)—$CH_2CH(OH)CH_2OH$, (S)—$CH_2CH(OH)CH_2CH_2OH$, (R)-2-$CH_2CH(CH_3)OH$, (S)—$CH_2CH(CH_3)OH$, (R)—$CH(CH_3)CH_2OH$, (S)—$CH(CH_3)CH_2OH$;

and G is selected from the group consisting of G1, G2, G3, G4, G9, G11, G12, G13, G16, G21, G25, G35, G36, G38 and G39 as defined above, $R^{12}$ at each occurrence is independently selected from the group consisting of H, $CH_3$ and $CH_2CH_3$;

k at each occurrence 0, 1, 2, 3, 4 or 5; and

Z at each occurrence is independently selected from the group consisting of F, Cl, Br, $CF_3$, $CHF_2$, $CH_2F$, $OCF_3$, OH, CN, $(C_1-C_4)$-alkyl, $(C_1-C_4)$-hydroxyalkyl, $(C_1-C_4)$-alkoxy, $(C_3-C_6)$-cycloalkyl, hydroxyl-$(C_3-C_6)$-cycloalkyl, $(C_3-C_8)$-heterocycloalkyl, $NH_2$, $NH(C_1-C_4)$-alkyl, $N((C_1-C_4)$-alkyl$)_2$, NH—CO—$(C_1-C_4)$-alkyl, NH—$S(O)_2(C_1-C_4)$-alkyl, $CONH_2$, CO—$NH(C_1-C_6)$-alkyl, CO—$N((C_1-C_6)$-alkyl$)_2$, $S(O)_2NH_2$, $S(O)_2NH(C_1-C_6)$-alkyl, $S(O)_2N((C_1-C_6)$-alkyl$)_2$, $CH_2S(O)(C_1-C_6)$-alkyl, $CH_2S(O)_2(C_1-C_6)$-alkyl, $S(O)(C_1-C_4)$-alkyl and $S(O)_2(C_1-C_4)$- alkyl.

In further embodiments the invention relates to compounds of formulae I-a to 1-u:

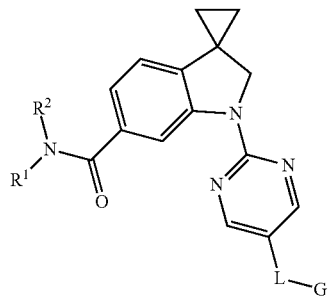

I-a

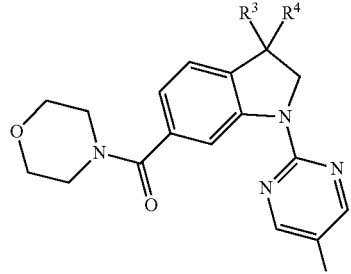

I-b

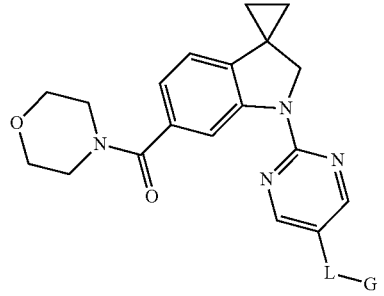

I-c

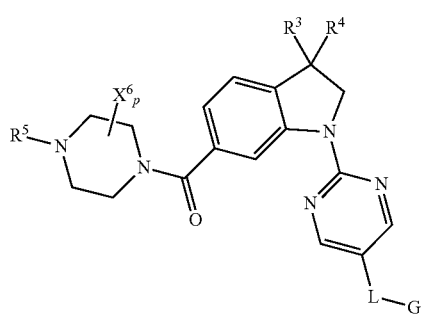

I-d

I-e
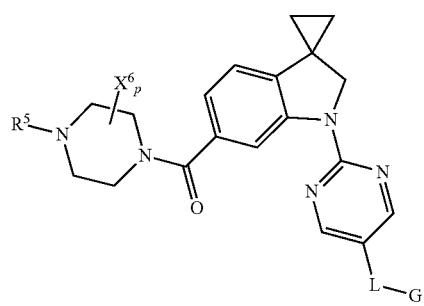
I-f
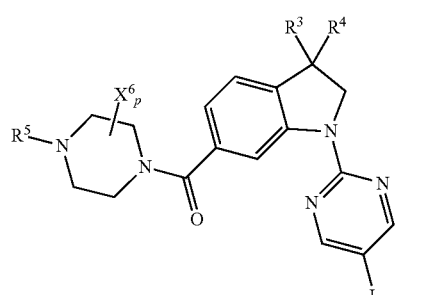
I-g
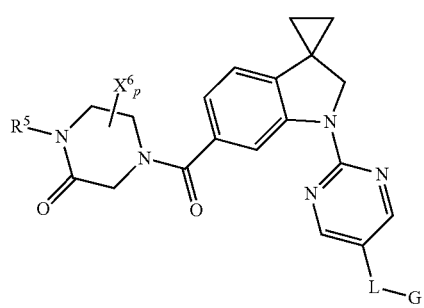
I-h
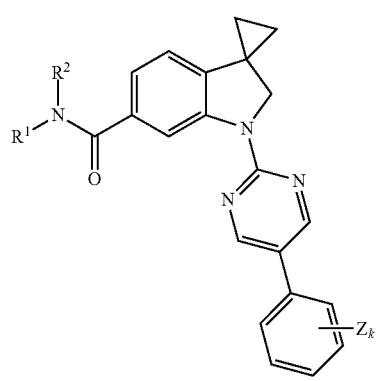
I-i
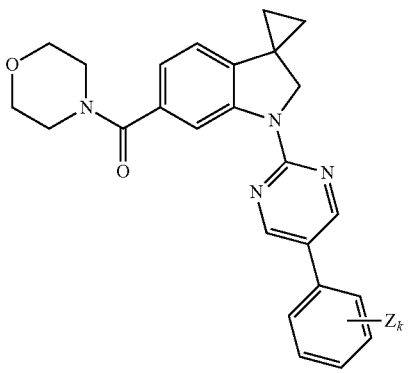
I-j
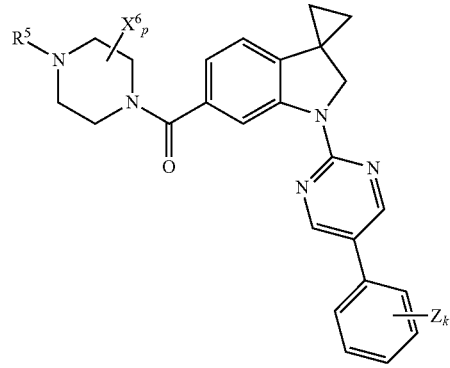
I-k
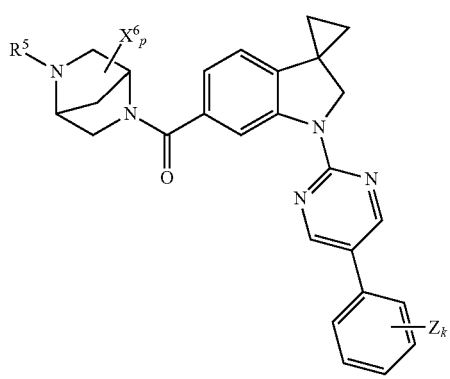
I-l
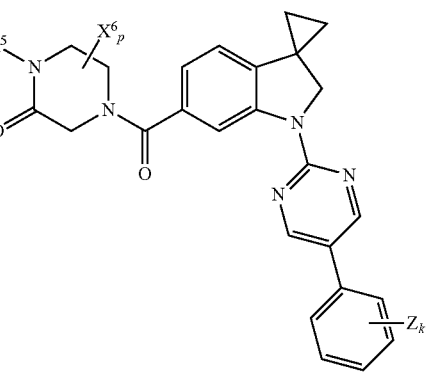

-continued
I-m
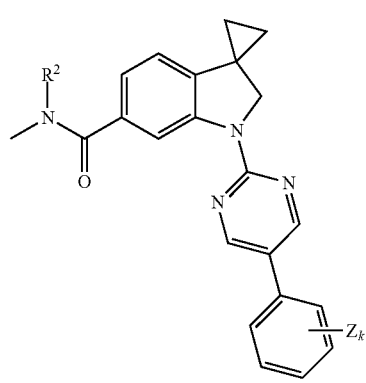
I-n
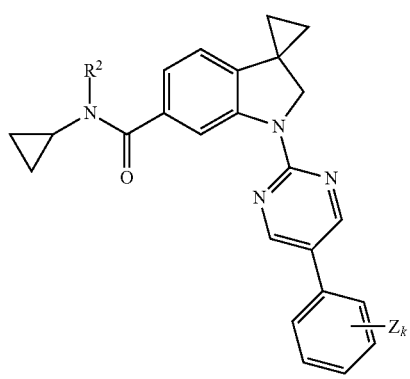
I-o
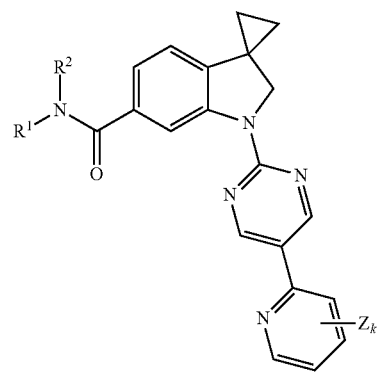
I-p
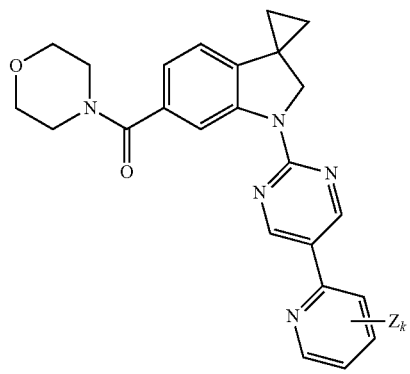
-continued
I-q
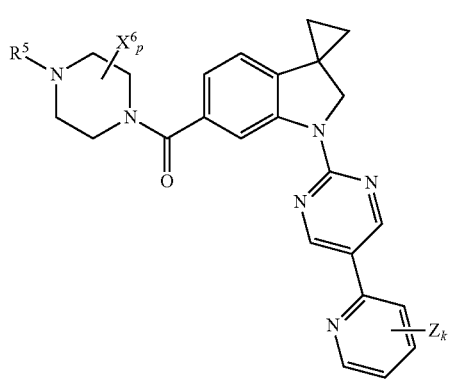
I-r
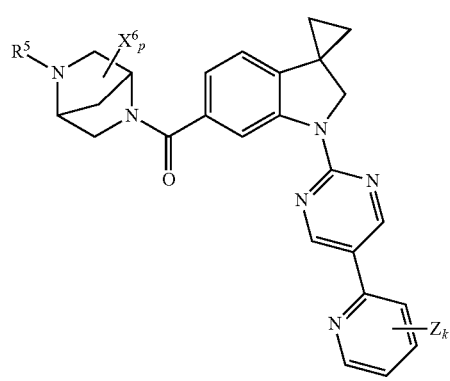
I-s
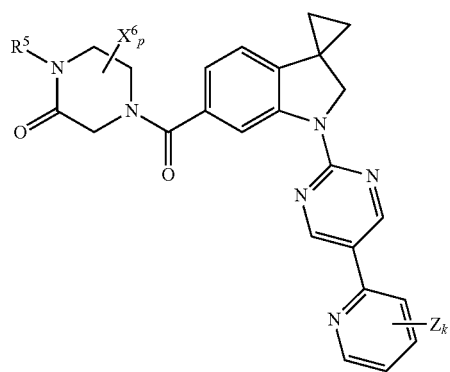
I-t
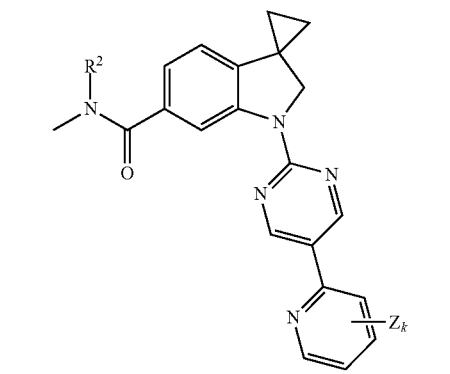

-continued

I-u

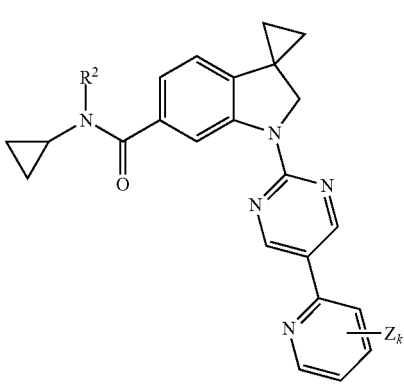

wherein the particular radicals, variables and indices have the meanings described herein in connection with the compounds according to the invention and preferred embodiments thereof.

In an embodiment a) the invention relates to a compound of formula I-a, wherein the substructure M is selected from the group consisting of M1 to M12, M25 and M27 to M30, $R^1$ is H or $CH_3$ or cyclopropyl, L represents bond or $CH_2$ or O, G is selected from the group consisting of G1, G2, G3, G4, G9, G11, G12, G13, G16, G21, G25, G35, G36, G38 and G39, Z is selected from the group consisting of F, Cl, CN, $CF_3$, $CHF_2$, $CH_2F$, $OCF_3$, OH, $OCH_3$, $OC_2H_5$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $N(CH_3)_2$, $NHCOCH_3$, $CH_2OH$, cyclopropyl, cyclobutyl, cyclopentyl and cyclohexyl, $R^{12}$ represents H or $CH_3$ and k is 0, 1, or 2.

In an embodiment b) the invention relates to a compound of formula I-b, wherein each of $R^3$ and $R^4$ represent $CH_3$, or $R^3$ and $R^4$ together with the carbon atom connecting them represent cyclopropyl or cyclobutyl, L represents a bond or $CH_2$ or O, G is selected from the group consisting of G1, G2, G3, G4, G9, G11, G12, G13, G16, G21, G25, G35, G36, G38 and G39, Z is selected from the group consisting of F, Cl, CN, $CF_3$, $CHF_2$, $CH_2F$, $OCF_3$, OH, $OCH_3$, $OC_2H_5$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $N(CH_3)_2$, $NHCOCH_3$, $CH_2OH$, cyclopropyl, cyclobutyl, cyclopentyl and cyclohexyl, $R^{12}$ represents H or $CH_3$ and k is 0, 1, or 2.

In an embodiment c) the invention relates to a compound of formula I-c, wherein L represents bond or $CH_2$ or O, G is selected from the group consisting of G1, G2, G3, G4, G9, G11, G12, G13, G16, G21, G25, G35, G36, G38 and G39, Z is selected from the group consisting of F, Cl, CN, $CF_3$, $CHF_2$, $CH_2F$, $OCF_3$, OH, $OCH_3$, $OC_2H_5$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $N(CH_3)_2$, $NHCOCH_3$, $CH_2OH$, cyclopropyl, cyclobutyl, cyclopentyl and cyclohexyl, $R^{12}$ represents H or $CH_3$ and k is 0, 1, or 2.

In an embodiment d) the invention relates to a compound of formula I-d, wherein each of $R^3$ and $R^4$ represent methyl, or $R^3$ and $R^4$ together with the carbon atom connecting them represent cyclopropyl or cyclobutyl, L represents bond or $CH_2$ or O, G is selected from the group consisting of G1, G2, G3, G4, G9, G11, G12, G13, G16, G21, G25, G35, G36, G38 and G39, Z is selected from the group consisting of F, Cl, CN, $CF_3$, $CHF_2$, $CH_2F$, $OCF_3$, $OCH_3$, $OC_2H_5$, $CH_3$, $CH_2CH_3$, $CH_2CH_2CH_3$, $CH(CH_3)_2$, $CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $N(CH_3)_2$, $NHCOCH_3$, $CH_2OH$, cyclopropyl, cyclobutyl, cyclopentyl and cyclohexyl, $R^{12}$ represents H or $CH_3$, k is 0, 1, or 2, $R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, $C(O)$-cyclopropyl, $CH_2CH_2CN$, $CH_2CH_2OH$ or $CH_2CH_2OCH_3$; at each occurrence p is 0, 1, 2 or 3; and each $X^6$ represents $CH_3$, $CH_2CH_3$, $CH_2CH_2CH_3$, $CH(CH_3)_2$, $CH(CH_3)_3$, cyclopropyl, cyclobutyl, cyclopentyl cyclohexyl, OH, $OCH_3$, $OCH_2CH_3$, $OCH(CH_3)_2$, $NH_2$, N(H)$CH_3$, $N(CH_3)_2$, N(H)C(O)$CH_3$, $CH_2OH$, $CH_2CH_2OH$, $CH_2OCH_3$ or $CH_2CH_2OCH_3$.

In an embodiment e) the invention relates to a compound of formula I-e, wherein L represents bond or $CH_2$ or O, G is selected from the group consisting of G1, G2, G3, G4, G9, G11, G12, G13, G16, G21, G25, G35, G36, G38 and G39, Z is selected from the group consisting of F, Cl, CN, $CF_3$, $CHF_2$, $CH_2F$, $OCF_3$, $OCH_3$, $OC_2H_5$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $N(CH_3)_2$, $NHCOCH_3$, $CH_2OH$, cyclopropyl, cyclobutyl, cyclopentyl and cyclohexyl, $R^{12}$ represents H or $CH_3$, k is 0, 1, or 2, $R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, $C(O)$-cyclopropyl, $CH_2CH_2CN$, $CH_2CH_2OH$ or $CH_2CH_2OCH_3$; at each occurrence p is 0, 1, 2 or 3; and each $X^6$ represents $CH_3$, $CH_2CH_3$, $CH_2CH_2CH_3$, $CH(CH_3)_2$, $CH(CH_3)_3$, cyclopropyl, cyclobutyl, cyclopentyl cyclohexyl, OH, $OCH_3$, $OCH_2CH_3$, $OCH(CH_3)_2$, $NH_2$, N(H)$CH_3$, $N(CH_3)_2$, N(H)C(O)$CH_3$, $CH_2OH$, $CH_2CH_2OH$, $CH_2OCH_3$ or $CH_2CH_2OCH_3$.

In an embodiment f) the invention relates to a compound of formula I-f, wherein each of $R^3$ and $R^4$ represent $CH_3$, or $R^3$ and $R^4$ together with the carbon atom connecting them represent cyclopropyl or cyclobutyl, L represents bond or $CH_2$ or O, G is selected from the group consisting of G1, G2, G3, G4, G9, G11, G12, G13, G16, G21, G25, G35, G36, G38 and G39, Z is selected from the group consisting of F, Cl, CN, $CF_3$, $CHF_2$, $CH_2F$, $OCF_3$, $OCH_3$, $OC_2H_5$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $N(CH_3)_2$, $NHCOCH_3$, $CH_2OH$, cyclopropyl, cyclobutyl, cyclopentyl and cyclohexyl, $R^{12}$ represents H or $CH_3$, k is 0, 1, or 2, $R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, $C(O)$-cyclopropyl, $CH_2CH_2CN$, $CH_2CH_2OH$ or $CH_2CH_2OCH_3$; at each occurrence p is 0, 1, 2 or 3; and each $X^6$ represents $CH_3$, $CH_2CH_3$, $CH_2CH_2CH_3$, $CH(CH_3)_2$, $CH(CH_3)_3$, cyclopropyl, cyclobutyl, cyclopentyl cyclohexyl, OH, $OCH_3$, $OCH_2CH_3$, $OCH(CH_3)_2$, $NH_2$, N(H)$CH_3$, $N(CH_3)_2$, N(H)C(O)$CH_3$, $CH_2OH$, $CH_2CH_2OH$, $CH_2OCH_3$ or $CH_2CH_2OCH_3$.

In an embodiment g) the invention relates to a compound of formula I-g, wherein L represents bond or $CH_2$ or O, G is selected from the group consisting of G1, G2, G3, G4, G9, G11, G12, G13, G16, G21, G25, G35, G36, G38 and G39, Z is selected from the group consisting of F, Cl, CN, $CF_3$, $CHF_2$, $CH_2F$, $OCF_3$, $OCH_3$, $OC_2H_5$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $N(CH_3)_2$, $NHCOCH_3$, $CH_2OH$, cyclopropyl, cyclobutyl, cyclopentyl and cyclohexyl, $R^{12}$ represents H or $CH_3$, k is 0, 1, or 2, $R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, $C(O)$-cyclopropyl, $CH_2CH_2CN$, $CH_2CH_2OH$ or $CH_2CH_2OCH_3$; at each occurrence p is 0, 1, 2 or 3; and each $X^6$ represents $CH_3$, $CH_2CH_3$, $CH_2CH_2CH_3$, $CH(CH_3)_2$, $CH(CH_3)_3$, cyclopropyl, cyclobutyl, cyclopentyl cyclohexyl, OH, $OCH_3$, $OCH_2CH_3$, $OCH(CH_3)_2$, $NH_2$, $N(H)CH_3$, $N(CH_3)_2$, $N(H)C(O)CH_3$, $CH_2OH$, $CH_2CH_2OH$, $CH_2OCH_3$ or $CH_2CH_2OCH_3$.

In an embodiment h) the invention relates to a compound of formula I-h, wherein the substructure M is selected from the group consisting of M1 to M12, M25 and M27 to M30, $R^1$ is H or $CH_3$ or cyclopropyl, Z is selected from the group consisting of F, Cl, CN, $CF_3$, $CHF_2$, $CH_2F$, $OCF_3$, OH, $OCH_3$, $OC_2H_5$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $N(CH_3)_2$, $NHCOCH_3$, $CH_2OH$, cyclopropyl, cyclobutyl, cyclopentyl and cyclohexyl, and k is 0, 1, or 2.

In an embodiment i) the invention relates to a compound of formula I-i, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2$-c-propyl), $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, and k is 0, 1, or 2.

In an embodiment j) the invention relates to a compound of formula I-j, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2$-c-propyl), $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, $R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, $C(O)$-cyclopropyl, $CH_2CH_2CN$, $CH_2CH_2OH$ or $CH_2CH_2OCH_3$; p is 0, 1, 2 or 3; and each $X^6$ represents $CH_3$, $CH_2CH_3$, $CH_2CH_2CH_3$, $CH(CH_3)_2$, $CH(CH_3)_3$, cyclopropyl, cyclobutyl, cyclopentyl cyclohexyl, OH, $OCH_3$, $OCH_2CH_3$, $OCH(CH_3)_2$, $NH_2$, $N(H)CH_3$, $N(CH_3)_2$, $N(H)C(O)CH_3$, $CH_2OH$, $CH_2CH_2OH$, $CH_2OCH_3$ or $CH_2CH_2OCH_3$.

In an embodiment k) the invention relates to a compound of formula I-k, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2$-c-propyl), $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, $R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, $C(O)$-cyclopropyl, $CH_2CH_2CN$, $CH_2CH_2OH$ or $CH_2CH_2OCH_3$; p is 0, 1, 2 or 3; and each $X^6$ represents $CH_3$, $CH_2CH_3$, $CH_2CH_2CH_3$, $CH(CH_3)_2$, $CH(CH_3)_3$, cyclopropyl, cyclobutyl, cyclopentyl cyclohexyl, OH, $OCH_3$, $OCH_2CH_3$, $OCH(CH_3)_2$, $NH_2$, $N(H)CH_3$, $N(CH_3)_2$, $N(H)C(O)CH_3$, $CH_2OH$, $CH_2CH_2OH$, $CH_2OCH_3$ or $CH_2CH_2OCH_3$.

In an embodiment l) the invention relates to a compound of formula I-l, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2$-c-propyl), $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, $R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, $C(O)$-cyclopropyl, $CH_2CH_2CN$, $CH_2CH_2OH$ or $CH_2CH_2OCH_3$; p is 0, 1, 2 or 3; and each $X^6$ represents $CH_3$, $CH_2CH_3$, $CH_2CH_2CH_3$, $CH(CH_3)_2$, $CH(CH_3)_3$, cyclopropyl, cyclobutyl, cyclopentyl cyclohexyl, OH, $OCH_3$, $OCH_2CH_3$, $OCH(CH_3)_2$, $NH_2$, $N(H)CH_3$, $N(CH_3)_2$, $N(H)C(O)CH_3$, $CH_2OH$, $CH_2CH_2OH$, $CH_2OCH_3$ or $CH_2CH_2OCH_3$.

In an embodiment m) the invention relates to a compound of formula I-m, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2$-c-propyl), $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, and $R^2$ represents $CH_2CH_2OH$, $CH_2CH_2CH_2OH$, (R)-2-$CH_2CH(CH_3)OH$, (S)—$CH_2CH(CH_3)OH$, (R)—$CH(CH_3)CH_2OH$(S)—$CH(CH_3)CH_2OH$, (R)—$CH_2CH(OH)CH_2CH_2OH$ or (S)—$CH_2CH(OH)CH_2CH_2OH$.

In an embodiment n) the invention relates to a compound of formula I-n, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2$-c-propyl), $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, and $R^2$ represents $CH_2CH_2OH$, $CH_2CH_2CH_2OH$, (R)-2-$CH_2CH(CH_3)OH$, (S)—$CH_2CH(CH_3)OH$, (R)—$CH(CH_3)CH_2OH$(S)—$CH(CH_3)CH_2OH$, (R)—$CH_2CH(OH)CH_2CH_2OH$ or (S)—$CH_2CH(OH)CH_2CH_2OH$.

In an embodiment o) the invention relates to a compound of formula I-o, wherein the substructure M is selected from the group consisting of M1 to M12, M25 and M27 to M30, $R^1$ is H or $CH_3$ or cyclopropyl, Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2$-c-propyl), $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, and k is 0, 1, or 2.

In an embodiment p) the invention relates to a compound of formula I-p, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2\text{-c-propyl})$, $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, and k is 0, 1, or 2.

In an embodiment q) the invention relates to a compound of formula I-q, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2\text{-c-propyl})$, $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, $R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, C(O)-cyclopropyl, $CH_2CH_2CN$, $CH_2CH_2OH$ or $CH_2CH_2OCH_3$; p is 0, 1, 2 or 3; and each $X^6$ represents $CH_3$, $CH_2CH_3$, $CH_2CH_2CH_3$, $CH(CH_3)_2$, $CH(CH_3)_3$, cyclopropyl, cyclobutyl, cyclopentyl cyclohexyl, OH, $OCH_3$, $OCH_2CH_3$, $OCH(CH_3)_2$, $NH_2$, $N(H)CH_3$, $N(CH_3)_2$, $N(H)C(O)CH_3$, $CH_2OH$, $CH_2CH_2OH$, $CH_2OCH_3$ or $CH_2CH_2OCH_3$.

In an embodiment r) the invention relates to a compound of formula I-r, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2\text{-c-propyl})$, $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, $R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, C(O)-cyclopropyl, $CH_2CH_2CN$, $CH_2CH_2OH$ or $CH_2CH_2OCH_3$; p is 0, 1, 2 or 3; and each $X^6$ represents $CH_3$, $CH_2CH_3$, $CH_2CH_2CH_3$, $CH(CH_3)_2$, $CH(CH_3)_3$, cyclopropyl, cyclobutyl, cyclopentyl cyclohexyl, OH, $OCH_3$, $OCH_2CH_3$, $OCH(CH_3)_2$, $NH_2$, $N(H)CH_3$, $N(CH_3)_2$, $N(H)C(O)CH_3$, $CH_2OH$, $CH_2CH_2OH$, $CH_2OCH_3$ or $CH_2CH_2OCH_3$.

In an embodiment s) the invention relates to a compound of formula I-s, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2\text{-c-propyl})$, $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, $R^5$ is H, $CH_3$, $CH_2CH_3$, $CH_2CH_2CH_3$, $CH(CH_3)_2$, cyclopropyl, $C(O)CH_3$, $C(O)CH_2CH_3$, $C(O)CH_2CH_2CH_3$, $C(O)CH(CH_3)_2$, C(O)-cyclopropyl, $CH_2CH_2CN$, $CH_2CH_2OH$ or $CH_2CH_2OCH_3$; p is 0, 1, 2 or 3; and each $X^6$ represents $CH_3$, $CH_2CH_3$, $CH_2CH_2CH_3$, $CH(CH_3)_2$, $CH(CH_3)_3$, cyclopropyl, cyclobutyl, cyclopentyl cyclohexyl, OH, $OCH_3$, $OCH_2CH_3$, $OCH(CH_3)_2$, $NH_2$, $N(H)CH_3$, $N(CH_3)_2$, $N(H)C(O)CH_3$, $CH_2OH$, $CH_2CH_2OH$, $CH_2OCH_3$ or $CH_2CH_2OCH_3$.

In an embodiment t) the invention relates to a compound of formula I-t, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2\text{-c-propyl})$, $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, and $R^2$ represents $CH_2CH_2OH$, $CH_2CH_2CH_2OH$, (R)-2-$CH_2CH(CH_3)OH$, (S)—$CH_2CH(CH_3)OH$, (R)—$CH(CH_3)CH_2OH$(S)—$CH(CH_3)CH_2OH$, (R)—$CH_2CH(OH)CH_2CH_2OH$ or (S)—$CH_2CH(OH)CH_2CH_2OH$.

In an embodiment u) the invention relates to a compound of formula I-u, wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2\text{-c-propyl})$, $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, and $R^2$ represents $CH_2CH_2OH$, $CH_2CH_2CH_2OH$, (R)-2-$CH_2CH(CH_3)OH$, (S)—$CH_2CH(CH_3)OH$, (R)—$CH(CH_3)CH_2OH$(S)—$CH(CH_3)CH_2OH$, (R)—$CH_2CH(OH)CH_2CH_2OH$ or (S)—$CH_2CH(OH)CH_2CH_2OH$.

In yet another preferred embodiment the invention relates to a compound selected from the group consisting of the compounds given in tables 1 to 5 below.

The term "single stereoisomer" in the sense of the present invention preferably means an individual enantiomer or diastereomer. The term "mixture of stereoisomers" means in the sense of this invention the racemate and mixtures of enantiomers and/or diastereomers in any mixing ratio.

The term "physiologically acceptable salt" in the sense of this invention preferably comprises a salt of at least one compound according to the present invention and at least one physiologically acceptable acid or base.

A physiologically acceptable salt of at least one compound according to the present invention and at least one physiologically acceptable acid or one physiologically acceptable base preferably refers in the sense of this invention to a salt of at least one compound according to the present invention with at least one inorganic or organic acid or with at least one inorganic or organic base respectively which is physiologically acceptable—in particular when used in human beings and/or other mammals.

The term "physiologically acceptable solvate" in the sense of this invention preferably comprises an adduct of one compound according to the present invention and/or a physiologically acceptable salt of at least one compound according to the present invention with distinct molecular equivalents of one solvent or more solvents.

In the context of the present invention, the term "halogen" preferably represents the radicals F, Cl, Br and I, in particular the radicals F and Cl, yet more particularly preferred F.

Unless otherwise specified, the term "($C_1$-$C_6$)-alkyl" is understood to mean branched and unbranched alkyl groups consisting of 1 to 6 hydrocarbon atoms. Examples of ($C_1$-$C_6$)-alkyl radicals are methyl, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, n- pentyl, 1-methylbutyl, 2-methylbutyl, 3-methylbutyl, 1,1-dimethylpropyl, 1,2-dimethylpropyl, 2,2-dimethylpropyl, n-hexyl, 1-methylpentyl, 2-methylpentyl, 3-methylpentyl, 4-methylpentyl. ($C_1$-$C_4$)-alkyl radicals are preferred, ($C_1$-$C_3$)-alkyl radicals being particularly preferred, in particular $CH_3$, $CH_2CH_3$, $CH_2CH_2CH_3$ or $CH(CH_3)_2$. Unless otherwise stated, the definitions of propyl, butyl, pentyl and hexyl encompass all possible isomeric forms of the individual radicals.

Unless otherwise specified, a haloalkyl radical is understood to be an alkyl radical in which at least one hydrogen is exchanged for a halogen atom, preferably fluorine, chlorine, bromine, particularly preferably fluorine. The haloalkyl radicals can be branched or unbranched and optionally mono- or polysubstituted.

Preferred haloalkyl radicals are $CHF_2$, $CH_2F$, $CF_3$, $CH_2CH_2F$, $CH_2CHF_2$, $CH_2CF_3$. ($C_1$-$C_6$)-haloalkyl radicals are preferred, with ($C_1$-$C_4$)-haloalkyl radicals being particularly preferred and ($C_1$-$C_3$)-haloalkyl radicals most particularly preferred, in particular $CHF_2$, $CH_2F$, $CF_3$, $CH_2CH_2F$, $CH_2CHF_2$ and $CH_2CF_3$. Unless otherwise specified, a haloalkoxy radical is understood to be an alkoxy radical in which at least one hydrogen is exchanged for a halogen atom, preferably fluorine, chlorine, bromine, particularly preferably fluorine. The haloalkoxy radicals can be branched or unbranched and optionally mono- or polysubstituted. Preferred haloalkoxy radicals are $OCHF_2$, $OCH_2F$, $OCF_3$, $OCH_2$—$CFH_2$, $OCH_2CF_2H$, $OCH_2CF_3$. ($C_1$-$C_6$)-haloalkoxy radicals are preferred, with ($C_1$-$C_4$)-haloalkoxy radicals being particularly preferred and ($C_1$-$C_3$)-haloalkoxy radicals most particularly preferred, in particular $OCHF_2$, $OCH_2F$, $OCF_3$, $OCH_2$—$CFH_2$, $OCH_2CF_2H$, $OCH_2CF_3$.

Unless otherwise specified, a hydroxyalkyl radical is understood to be an alkyl radical in which at least one hydrogen is exchanged for a hydroxyl group. The hydroxyalkyl radicals can be branched or unbranched and optionally mono- or polysubstituted. ($C_1$-$C_6$)-hydroxyalkyl radicals are preferred, with ($C_1$-$C_4$)-hydroxyalkyl radicals being particularly preferred and ($C_1$-$C_3$)-hydroxyalkyl radicals most particularly preferred, in particular $CH_2OH$, $CH_2CH_2OH$ and $CH_2CH_2CH_2OH$.

Unless otherwise specified, a cyanoalkyl radical is understood to be an alkyl radical in which at least one hydrogen is exchanged for a cyano group. The hydroxyalkyl radicals can be branched or unbranched and optionally mono- or polysubstituted. ($C_1$-$C_6$)-cyanoalkyl radicals are preferred, with ($C_1$-$C_4$)-cyanoalkyl radicals being particularly preferred and ($C_1$-$C_3$)-cyanoalkyl radicals most particularly preferred, in particular $CH_2CN$, $CH_2CH_2CN$ and $CH_2CH_2CH_2CN$.

In the context of the present invention, the expression "$C_1$-$C_3$-alkylene group" or "$C_1$-$C_6$-alkylene group" includes acyclic saturated hydrocarbon radicals having 1, 2 or 3 carbon atoms or 1, 2, 3, 4, 5 or 6 carbon atoms, respectively, which can be branched or unbranched and unsubstituted or substituted once or several times, for example 2, 3, 4 or 5 times, by identical or different substituents and which link a corresponding moiety to the main structure. Alkylene groups can preferably be chosen from the group consisting of $CH_2$, $CH_2CH$—, $CH(CH_3)$, $CH_2CH_2CH_2$, $CH(CH_3)CH_2$, $CH(CH_2CH_3)$, $CH_2(CH_2)_2CH_2$, $CH(CH_3)CH_2CH_2$, $CH_2CH$ ($CH_3$)$CH_2$, $C(CH_3)_2$ $CH_2$, $CH(CH_2CH_2CH_3)$, $C(CH_3)(CH_2CH_3)$, $CH_2$ $(CH_2)_3$ $CH_2$, $CH(CH_3)CH_2CH_2CH_2$, $CH_2CH(CH_3)$ $CH_2CH_2$, $CH(CH_3)CH_2CH(CH_3)$, $CH(CH_3)CH(CH_3)CH_2$, $C(CH_3)_2$ $CH_2CH_2$, $CH_2C(CH_3)_2CH_2$, $CH(CH_2CH_3)$ $CH_2CH_2$, $CH_2CH(CH_2CH_3)CH_2$, $C(CH_3)_2CH(CH_3)$, $CH(CH_2CH_3)CH(CH_3)$, $C(CH_3)(CH_2CH_3)CH_2$, $CH(CH_2CH_2CH_3)CH_2$, $C(CH_2CH_2CH_3)CH_2$, $CH(CH_2CH_2CH_2CH_3)$, $C(CH_3)(CH_2CH_2CH_3)$, $C(CH_2CH_3)_2$ and $CH_2(CH_2)_4CH_2$. The alkylene groups can particularly preferably be chosen from the group consisting of $CH_2$, $CH_2CH_2$ and $CH_2CH_2CH_2$.

In the context of the present invention, the expression "$C_{2-6}$-alkenylene group" includes acyclic hydrocarbon radicals having 2, 3, 4, 5 or 6 C atoms, which are unsaturated once or several times, for example 2, 3 or 4 times, and can be branched- or straight-chain (unbranched) and unsubstituted or substituted once or several times, for example 2, 3, 4 or 5 times, by identical or different radicals and which link a corresponding radical to the main structure. In this context, the alkenylene groups contain at least one C═C double bond. The alkenylene groups can preferably be chosen from the group consisting of CH═CH, CH═CHCH$_2$, C(CH$_3$)═CH$_2$, CH═CHCH$_2$CH$_2$, CH$_2$CH═CHCH$_2$, CH═CHCH═CH, C(CH$_3$)═CHCH$_2$, CH═C(CH$_3$)CH$_2$, C(CH$_3$)═C(CH$_3$), C(CH$_2$CH$_3$)═CH, CH═CHCH$_2$CH$_2$CH$_2$, CH$_2$CH═CH$_2$CH$_2$CH$_2$, CH═C═CHCH$_2$CH$_2$ and CH═CHCH$_2$CH═CH$_2$.

Unless otherwise specified, the term "($C_2$-$C_6$)-alkenyl" is understood to mean branched and unbranched unsaturated alkyl groups consisting of 2 to 6 hydrocarbon atoms and having at least one double bond. Examples of ($C_2$-$C_6$)-alkenyls are ethenyl (also referred to as vinyl), prop-1-enyl, prop-2-enyl (also referred to as allyl), but-1-enyl, but-2-enyl, but-3-enyl, pent-1-enyl and hex-1-enyl. The designation ($C_2$-$C_6$) alkenyl includes all possible isomers, i.e. structural isomers (constitutional isomers) and stereoisomers ((Z) and (E) isomers). Unless otherwise specified, the term "($C_2$-$C_6$)-alkinyl" is understood to mean branched and unbranched unsaturated alkyl groups consisting of 2 to 6 hydrocarbon atoms and having at least one triple bond. Examples of ($C_2$-$C_6$)-alkinyls are ethinyl.

Unless otherwise specified, the term "3- to 12-membered mono- or bicycloaliphatic ring" is understood to mean cyclic aliphatic (cycloaliphatic) hydrocarbons containing 3, 4, 5, 6, 7, 8, 9, 10, 11 or 12 carbon atoms, wherein the hydrocarbons in each case can be saturated or unsaturated (but not aromatic), unsubstituted or mono- or polysubstituted. The cycloaliphatic residues can be bound to the respective superordinate general structure via any desired and possible ring member of the cycloaliphatic residue. The $C_{3-12}$ cycloaliphatic residue can furthermore be singly or multiply bridged such as, for example, in the case of adamantyl, bicyclo[2.2.1]heptyl or bicyclo[2.2.2]octyl. Preferred $C_{3-12}$ cycloaliphatic residues are selected from the group consisting of cyclopropyl, cyclobutyl, cyclopentyl, cyclohexyl, cycloheptyl, cyclooctyl, cyclononyl, cyclodecyl, adamantyl, cyclopentenyl, cyclohexenyl, cycloheptenyl, cyclooctenyl,

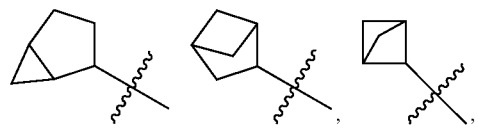

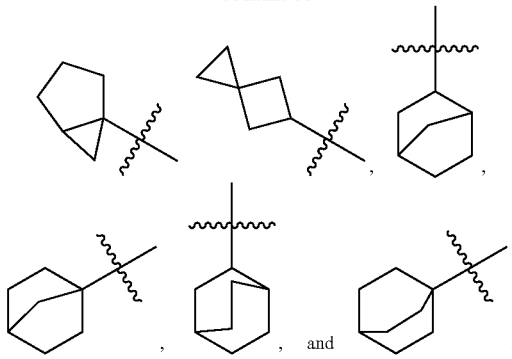

Preferred C$_{3-8}$ cycloaliphatic residues are selected from the group consisting of cyclopropyl, cyclobutyl, cyclopentyl, cyclohexyl, cycloheptyl, cyclooctyl, cyclopentenyl and cyclohexenyl. Particularly preferred C$_{3-12}$ cycloaliphatic and C$_{3-8}$ cycloaliphatic residues are C$_{3-6}$ cycloaliphatic residues such as cyclopropyl, cyclobutyl, cyclopentyl, cyclohexyl, cyclopentenyl and cyclohexenyl, in particular cyclopropyl.

In the context of this invention, the expression "C$_{3-8}$-cycloalkyl" or "C$_{3-6}$-cycloalkyl" denotes cyclic saturated hydrocarbons having 3, 4, 5, 6, 7 or 8 or having 3, 4, 5 or 6 carbon atoms respectively, which can be unsubstituted or substituted once or several times, for example by 2, 3, 4 or 5 identical or different radicals, on one or more ring members. C$_{3-8}$-cycloalkyl can preferably be chosen from the group consisting of cyclopropyl, cyclobutyl, cyclopentyl, cyclohexyl, cycloheptyl and cyclooctyl. C$_{3-6}$-cycloalkyl can preferably be chosen from the group consisting of cyclopropyl, cyclobutyl, cyclopentyl, and cyclohexyl.

Unless otherwise specified, the term "3- to 12-membered heterocycloaliphatic residue" is understood to mean heterocycloaliphatic saturated or unsaturated (but not aromatic) residues having 3 to 12, i.e. 3, 4, 5, 6, 7, 8, 9, 10, 11 or 12 ring members, in which in each case at least one, if appropriate also two or three carbon atoms are replaced by a heteroatom or a heteroatom group each selected independently of one another from the group consisting of O, S, S(=O), S(=O)$_2$, N, NH and N(C$_{1-6}$-alkyl) such as N(CH$_3$), wherein the ring members can be unsubstituted or mono- or polysubstituted. The residues may be mono- or bicyclic.

Unless otherwise specified, the term "5- or 6-membered heteroaryl" is understood to represent a 5- or 6-membered cyclic aromatic residue containing at least 1, if appropriate also 2, 3, 4 or 5 heteroatoms, wherein the heteroatoms are each preferably selected independently of one another from the group S, N and O and the heteroaryl residue can be unsubstituted or mono- or polysubstituted; e.g. substituted by 2, 3, 4 or 5 substituents, whereby the substituents can be the same or different and be in any desired and possible position of the heteroaryl. The binding to the superordinate general structure can be carried out via any desired and possible ring member of the heteroaryl residue if not indicated otherwise. The heteroaryl may be condensed with a 4-, 5-, 6- or 7-membered ring, being carbocyclic or heterocyclic, wherein the heteroatoms of the heterocyclic ring are each preferably selected independently of one another from the group S, N and O, and wherein said condensed ring may be saturated, partially unsaturated or aromatic and may be unsubstituted or mono- or polysubstituted; e.g. substituted by 2, 3, 4 or 5 substituents, whereby the substituents can be the same or different and be in any desired and possible position. Examples of such heteroaryl moieties are benzofuranyl, benzoimidazolyl, benzo-thienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazo-thiazolyl, indazolyl, indolizinyl, indolyl, isoquinolinyl, isoxazoyl, isothiazolyl, indolyl, naphthyridinyl, oxazolyl, oxa-diazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

Within the scope of the present invention, the symbol

used in the formulae denotes a link of a corresponding residue to the respective superordinate general structure.

In connection with non-aromatic moieties such as "alkyl", "alkenyl", "alkinyl", "alkylene", alkenylene", "cycloaliphatic", "heterocycloaliphatic", "carbocyclic ring", "heterocyclic", "cycloalkyl" and "heterocyclyl", in the context of this invention the term "substituted" is understood as meaning replacement of a hydrogen radical by a substituent selected from the group consisting of =O, OH, CN, halogen, SH, nitro, (C$_1$-C$_6$)-alkyl, (C$_2$-C$_6$)-alkenyl, (C$_2$-C$_6$)-alkinyl, (C$_1$-C$_6$)-hydroxyalkyl, (C$_1$-C$_6$)-cyanoalkyl, (C$_1$-C$_6$)-alkoxy, (C$_1$-C$_6$)-thioalkyl, (C$_1$-C$_6$)-haloalkyl, (C$_1$-C$_6$)-thiohaloalkyl, (C$_1$-C$_6$)-haloalkoxy, (C$_1$-C$_6$)-alkylen-S—(C$_1$-C$_6$)-alkyl, (C$_3$-C$_8$)-cycloalkyl, (C$_3$-C$_6$)-cycloalkyl-(C$_1$-C$_3$)-alkylenyl, (C$_3$-C$_8$)-heterocycloalkyl, NH$_2$, NH(C$_1$-C$_6$)-alkyl, N((C$_1$-C$_6$)-alkyl)$_2$, NH—CO—(C$_1$-C$_6$)-alkyl, NH—CO—O—(C$_1$-C$_6$)-alkyl, NH—C(O)NH$_2$, NH—CO—NH—(C$_1$-C$_6$)-alkyl, NH—CO—N((C$_1$-C$_6$)-alkyl)$_2$, NH((C$_1$-C$_6$)-alkylen)-CO—O—(C$_1$-C$_6$)-alkyl, NH((C$_1$-C$_6$)-alkylen)-CONH$_2$, NH((C$_1$-C$_6$)-alkylen)-CO—NH—(C$_1$-C$_6$)-alkyl, NH((C$_1$-C$_6$)-alkylen)-CO—N((C$_1$-C$_6$)-alkyl)$_2$, NH—S(O)$_2$OH, NH—S(O)$_2$(C$_1$-C$_6$)-alkyl, NH—S(O)$_2$O(C$_1$-C$_6$)-alkyl, NH—S(O)$_2$NH$_2$, NH—S(O)$_2$NH(C$_1$-C$_6$)-alkyl, NH—S(O)$_2$N((C$_1$-C$_6$)-alkyl)$_2$, NH((C$_1$-C$_6$)-alkylen)-S(O)$_2$OH, NH((C$_1$-C$_6$)-alkylen)-S(O)$_2$(C$_1$-C$_6$)-alkyl, NH((C$_1$-C$_6$)-alkylen)-S(O)$_2$O(C$_1$-C$_6$)-alkyl, NH((C$_1$-C$_6$)-alkylen)-S(O)$_2$NH$_2$, NH((C$_1$-C$_6$)-alkylen)-S(O)$_2$NH(C$_1$-C$_6$)-alkyl, CO$_2$H, CO(C$_1$-C$_6$)-alkyl, CO—O(C$_1$-C$_6$)-alkyl, O—CO(C$_1$-C$_6$)-alkyl, O—CO—O(C$_1$-C$_6$)-alkyl, CONH$_2$, CO—NH(C$_1$-C$_6$)-alkyl, CO—N((C$_1$-C$_6$)-alkyl)$_2$, O—CO—NH(C$_1$-C$_6$)-alkyl, O—CO—N((C$_1$-C$_6$)-alkyl)$_2$, O—S(O)$_2$—(C$_1$-C$_6$)-alkyl, O—S(O)$_2$OH, O—S(O)$_2$—(C$_1$-C$_6$)-alkoxy, O—S(O)$_2$NH$_2$, O—S(O)$_2$—NH(C$_1$-C$_6$)-alkyl, O—S(O)$_2$—N((C$_1$-C$_6$)-alkyl)$_2$, S(O)(C$_1$-C$_6$)-alkyl, S(O)$_2$(C$_1$-C$_6$)-alkyl, S(O)$_2$OH, S(O)$_2$O(C$_1$-C$_6$)-alkyl, S(O)$_2$NH$_2$, S(O)$_2$NH(C$_1$-C$_6$)-alkyl, and S(O)$_2$N((C$_1$-C$_6$)-alkyl)$_2$. If a moiety is substituted with more than 1 substituent, e.g. by 2, 3, 4, or 5 substituents, these substituents may be present either on different or on the same atoms, e.g. as in the case of CF$_3$ or CH$_2$CF$_3$, or at different places, as in the case of CH(Cl)—CH=CH—CHCl$_2$. Substitution with more than 1 substituent may include identical or different substituents, such as, for example, in the case of CH(OH)—CH=CH—CHCl$_2$.

Preferably, the substituents may be selected from the group consisting of F, Cl, Br, CF$_3$, CHF$_2$, CH$_2$F, OCF$_3$, OH, CN, (C$_1$-C$_4$)-alkyl, (C$_1$-C$_4$)-hydroxyalkyl, (C$_1$-C$_4$)-alkoxy, ($C_3$-$C_6$)-cycloalkyl, $NH_2$, $NH(C_1$-$C_4)$-alkyl, $N((C_1$-$C_4)$-alkyl)$_2$, NH—CO—($C_1$-$C_4$)-alkyl, NH—CO—NH—($C_1$-$C_6$)-alkyl, NH—CO—N(($C_1$-$C_6$)-alkyl)$_2$, NH—S(O)$_2$($C_1$-$C_4$)-alkyl, $CONH_2$, CO—NH($C_1$-$C_6$)-alkyl, CO—N(($C_1$-$C_6$)-alkyl)$_2$, S(O)($C_1$-$C_4$)-alkyl and S(O)$_2$($C_1$-$C_4$)-alkyl.

In connection with aromatic moieties such as "phenyl" and "heteroaryl", in the context of this invention the term "substituted" is understood as meaning replacement of a hydrogen radical by a substituent selected from the group consisting of OH, halogen, CN, SH, nitro, ($C_1$-$C_6$)-alkyl, ($C_2$-$C_6$)-alkenyl, ($C_2$-$C_6$)-alkinyl, ($C_1$-$C_6$)-hydroxyalkyl, ($C_1$-$C_6$)-cyanoalkyl, ($C_1$-$C_6$)-alkoxy, ($C_1$-$C_6$)-thioalkyl, ($C_1$-$C_6$)-haloalkyl, ($C_1$-$C_6$)-thiohaloalkyl, ($C_1$-$C_6$)-haloalkoxy, ($C_1$-$C_6$)-alkylen-S—($C_1$-$C_6$)-alkyl, ($C_3$-$C_8$)-cycloalkyl, ($C_3$-$C_6$)-cycloalkyl-($C_1$-$C_3$)-alkylenyl, ($C_3$-$C_8$)-heterocycloalkyl, $NH_2$, $NH(C_1$-$C_6)$-alkyl, $N((C_1$-$C_6)$-alkyl)$_2$, NH—CO—($C_1$-$C_6$)-alkyl, NH—CO—O—($C_1$-$C_6$)-alkyl, NH—C(O)$NH_2$, NH—CO—NH—($C_1$-$C_6$)-alkyl, NH—CO—N(($C_1$-$C_6$)-alkyl)$_2$, NH(($C_1$-$C_6$)-alkylen)-CO—O—($C_1$-$C_6$)-alkyl, NH(($C_1$-$C_6$)-alkylen)-$CONH_2$, NH(($C_1$-$C_6$)-alkylen)-CO—NH—($C_1$-$C_6$)-alkyl, NH(($C_1$-$C_6$)-alkylen)-CO—N(($C_1$-$C_6$)-alkyl)$_2$, NH—S(O)$_2$OH, NH—S(O)$_2$($C_1$-$C_6$)-alkyl, NH—S(O)$_2$O($C_1$-$C_6$)-alkyl, NH—S(O)$_2$$NH_2$, NH—S(O)$_2$NH($C_1$-$C_6$)-alkyl, NH—S(O)$_2$N(($C_1$-$C_6$)-alkyl)$_2$, NH(($C_1$-$C_6$)-alkylen)-S(O)$_2$OH, NH(($C_1$-$C_6$)-alkylen)-S(O)$_2$($C_1$-$C_6$)-alkyl, NH(($C_1$-$C_6$)-alkylen)-S(O)$_2$O($C_1$-$C_6$)-alkyl, NH(($C_1$-$C_6$)-alkylen)-S(O)$_2$$NH_2$, NH(($C_1$-$C_6$)-alkylen)-S(O)$_2$NH($C_1$-$C_6$)-alkyl, $CO_2$H, CO($C_1$-$C_6$)-alkyl, CO—O($C_1$-$C_6$)-alkyl, O—CO($C_1$-$C_6$)-alkyl, O—CO—O—($C_1$-$C_6$)-alkyl, $CONH_2$, CO—NH($C_1$-$C_6$)-alkyl, CO—N(($C_1$-$C_6$)-alkyl)$_2$, O—CO—NH($C_1$-$C_6$)-alkyl, O—CO—N(($C_1$-$C_6$)-alkyl)$_2$, O—S(O)$_2$—($C_1$-$C_6$)-alkyl, O—S(O)$_2$OH, O—S(O)$_2$—($C_1$-$C_6$)-alkoxy, O—S(O)$_2$$NH_2$, O—S(O)$_2$—NH($C_1$-$C_6$)-alkyl, O—S(O)$_2$—N(($C_1$-$C_6$)-alkyl)$_2$, S(O)($C_1$-$C_6$)-alkyl, S(O)$_2$($C_1$-$C_6$)-alkyl, S(O)$_2$OH, S(O)$_2$O($C_1$-$C_6$)-alkyl, S(O)$_2$$NH_2$, S(O)$_2$NH($C_1$-$C_6$)-alkyl, and S(O)$_2$N(($C_1$-$C_6$)-alkyl)$_2$. If a moiety is substituted with more than 1 substituent, e.g. by 2, 3, 4, or 5 substituents, these substituents may be identical or different. Preferably, the substituents may be selected from the group consisting of F, Cl, Br, $CF_3$, $CHF_2$, $CH_2F$, $OCF_3$, OH, CN, ($C_1$-$C_4$)-alkyl, ($C_1$-$C_4$)-hydroxyalkyl, ($C_1$-$C_4$)-alkoxy, ($C_3$-$C_6$)-cycloalkyl, $NH_2$, NH($C_1$-$C_4$)-alkyl, N(($C_1$-$C_4$)-alkyl)$_2$, NH—CO—($C_1$-$C_4$)-alkyl, NH—CO—NH—($C_1$-$C_6$)-alkyl, NH—CO—N(($C_1$-$C_6$)-alkyl)$_2$, NH—S(O)$_2$($C_1$-$C_4$)-alkyl, $CONH_2$, CO—NH($C_1$-$C_6$)-alkyl, CO—N(($C_1$-$C_6$)-alkyl)$_2$, S(O)($C_1$-$C_4$)-alkyl and S(O)$_2$($C_1$-$C_4$)-alkyl.

Owing to their excellent pharmacological activity, the compounds according to the first aspect of the invention, in particular according to the general structure of formulae (I), (I'), I-a to I-u, are suitable for the treatment of various diseases or conditions in which inhibition of the PDE4 enzyme is advantageous. Such conditions and diseases are inter alia inflammatory diseases of the joints, in particular rheumatoid arthritis, psoriatic arthritis, ankylosing spondylitis (Bechterew's disease), gout, osteoarthritis;

inflammatory diseases of the skin, in particular psoriasis, atopic dermatitis, lichen planus;

inflammatory diseases of the eyes, in particular uveitis;

gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps;

inflammatory diseases of the internal organs, in particular SLE (systemic lupus erythematosus) including lupus nephritis, chronic prostatitis, interstitial cystitis;

hyperplastic diseases, in particular benign prostatic hyperplasia;

respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia;

diseases of the fibrotic spectrum, in particular hepatic fibrosis, systemic sclerosis, scleroderma;

cancers, in particular haematopoietic cancers, inter alia B-cell lymphoma, T-cell lymphoma, in particular CLL and CML (chronic lymphatic and chronic myeloid leukaemia), ALL and AML (acute lymphatic and acute myeloid leukaemia), and gliomas;

metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension);

psychological disorders, in particular schizophrenia, depression, in particular bipolar or manic depression, dementia, memory loss, generalised anxiety disorder (GAD); and diseases of the peripheral or central nervous system, in particular Parkinson's disease, multiple sclerosis, Alzheimer's disease, stroke, ALS (amyotrophic lateral sclerosis).

One of the advantages of the compounds according to the first aspect of the invention, in particular according to the general structure of formulae (I), (I'), I-a to I-u, is that they are selective PDE4B inhibitors. The advantage of this selectivity lies in the fact that the PDE4D enzyme for example is not inhibited or is only partly inhibited, and hence the use of such selective PDE4B inhibitors gives rise to no side-effects or to markedly reduced side-effects. Undesired side-effects are for example emesis and nausea, in particular indisposition, vomiting and sickness. The therapeutic range of the compounds according to the invention is therefore advantageous.

In a second aspect of the invention, the invention therefore also provides a pharmaceutical composition (medicament) containing at least one compound according to the first aspect of the invention, in particular according to the general structure of formulae (I), (I'), I-a to I-u, in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio.

In a third aspect of the invention, the invention therefore also provides a compound according to the first aspect of the invention, in particular according to the general structure of formulae (I), (I'), I-a to I-u, in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio for use as a medicament, in particular for the treatment of conditions or diseases that can be treated by inhibition of the PDE4 enzyme, in particular the PDE4B enzyme.

In a fourth aspect of the invention, the invention therefore also provides a compound according to the first aspect of the invention, in particular of the general structure of formulae (I), (I'), I-a to I-u, in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of inflammatory diseases of the joints, in particular rheumatoid arthritis, psoriatic arthritis, ankylosing spondylitis (Bechterew's disease), gout, osteoarthritis; and/or inflammatory diseases of the skin, in particular psoriasis, atopic dermatitis, lichen planus; and/or inflammatory diseases of the eyes, in particular uveitis; gastrointestinal diseases and complaints, in particular inflammatory diseases of the digestive organs, above all Crohn's disease, ulcerative colitis, and acute and chronic inflammations of the gall bladder and bile ducts, of pseudopolyps and juvenile polyps; inflammatory diseases of the internal organs, in particular SLE (systemic lupus erythematosus) including lupus nephritis, chronic prostatitis, interstitial cystitis; and/or hyperplastic diseases, in particular benign prostatic hyperplasia; respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; diseases of the fibrotic spectrum, in particular hepatic fibrosis, systemic sclerosis, scleroderma; cancers, in particular haematopoietic cancers, inter alia B-cell lymphomas, T-cell lymphomas, in particular CLL and CML (chronic lymphatic and chronic myeloid leukaemia), ALL and AML (acute lymphatic and acute myeloid leukaemia), and gliomas; metabolic diseases, in particular type 2 diabetes, metabolic syndrome, obesity/adiposity, fatty liver disease (not alcohol-induced), and cardiovascular diseases, in particular arteriosclerosis, PAH (pulmonary arterial hypertension); psychological disorders, in particular schizophrenia, depression, in particular bipolar or manic depression, dementia, memory loss, generalised anxiety disorder (GAD); and/or diseases of the peripheral or central nervous system, in particular Parkinson's disease, multiple sclerosis, Alzheimer's disease, stroke, ALS (amyotrophic lateral sclerosis).

In a preferred embodiment of the fourth aspect of the invention, the invention therefore also provides a compound according to the first aspect of the invention, in particular according to the general structure of formulae (I), (I'), I-a to I-u, the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio for use as a medicament for the treatment of inflammatory diseases of the joints (in particular rheumatoid arthritis, psoriatic arthritis, ankylosing spondylitis (Bechterew's disease), gout, osteoarthritis), the skin (in particular psoriasis, atopic dermatitis, lichen planus) or the eyes (in particular uveitis), of respiratory or lung diseases associated with elevated mucus production, inflammation and/or obstruction of the respiratory tract, in particular COPD (chronic obstructive pulmonary disease), chronic bronchitis, asthma, pulmonary fibrosis, allergic and non-allergic rhinitis, obstructive sleep apnoea, cystic fibrosis, chronic sinusitis, emphysema, cough, alveolitis, ARDS (acute respiratory distress syndrome), pulmonary oedema, bronchiectasis, pneumonia; of metabolic diseases, in particular type 2 diabetes, metabolic syndrome, obesity/adiposity, fatty liver disease (not alcohol-induced), and/or cardiovascular diseases, in particular arteriosclerosis and PAH (pulmonary arterial hypertension).

In another aspect of the invention, the invention also provides the use of a compound according to the first aspect of the invention, in particular according to the general structure of formulae (I), (I'), I-a to I-u, in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio to produce a medicament for the treatment of the diseases and conditions according to the fourth aspect of the invention.

In yet another aspect of the invention, the invention also provides a method for the treatment of the diseases and conditions according to the fourth aspect of the invention in a human, which is characterised in that a therapeutically effective amount of at least one compound according to the first aspect of the invention, in particular according to the general structure of formulae (I), (I'), I-a to I-u, in the presented form or in the form of its acids or bases or in the form of the pharmaceutically safe, in particular physiologically acceptable salts, or in the form of its solvates, optionally in the form of its racemates, its pure stereoisomers, in particular enantiomers or diastereomers, or in the form of mixtures of stereoisomers, in particular enantiomers or diastereomers, in any mixing ratio, is administered.

The amount of active ingredient to be administered to the person or patient varies and is dependent on the patient's weight, age and medical history and on the type of administration, the indication and the severity of the illness. Conventionally 0.1 to 5000 mg/kg, in particular 1 to 500 mg/kg, preferably 2 to 250 mg/kg of body weight of at least one compound according to the first aspect of the invention, in particular according to the general structure of formulae (I), (I'), I-a to I-u, are administered.

All embodiments, in particular the preferred embodiments, of the first aspect of the invention apply mutatis mutandis to all other aspects of the invention.

The medicaments, drugs and pharmaceutical compositions according to the invention can take the form of and be administered as liquid, semi-solid or solid dosage forms and as for example injection solutions, drops, juices, syrups, sprays, suspensions, granules, tablets, pellets, transdermal therapeutic systems, capsules, plasters, suppositories, ointments, creams, lotions, gels, emulsions or aerosols and contain, in addition to at least one compound according to the first aspect of the invention, in particular according to the general structure of formulae (I), (I'), I-a to I-u, according to the pharmaceutical form and depending on the administration route, pharmaceutical auxiliary substances such as for example carrier materials, fillers, solvents, diluting agents, surface-active substances, dyes, preservatives, disintegrants, slip additives, lubricants, flavourings and/or binders.

The choice of auxiliary substances and the amounts thereof to use depends on whether the medicament/drug is to be administered by oral, subcutaneous, parenteral, intravenous, vaginal, pulmonary, intraperitoneal, transdermal, intramuscular, nasal, buccal or rectal means or locally, for example for infections of the skin, mucous membranes and eyes. Preparations in the form of inter alia tablets, pastilles, capsules, granules, drops, juices and syrups are suitable for oral administration; solutions, suspensions, easily reconstitutable powders for inhalation and sprays are suitable for parenteral, topical and inhalative administration. Compounds according to the first aspect of the invention in a depot formulation, in dissolved form or in a plaster, optionally with addition of agents promoting skin penetration, are suitable preparations for percutaneous administration. Preparation forms that are suitable for rectal, transmucosal, parenteral, oral or percutaneous administration can deliver the compounds according to the first aspect of the invention, on a delayed release basis.

Preparation of the medicaments and pharmaceutical compositions according to the invention takes place using agents, equipment, methods and procedures that are well-known from the prior art of pharmaceutical formulation, such as are described for example in "Remington's Pharmaceutical Sciences", Ed. A. R. Gennaro, 17$^{th}$ edition, Mack Publishing Company, Easton PD (1985), in particular in part 8, chapters 76 to 93.

Unless indicated otherwise the compounds according to the invention can be synthesized according to general knowledge in the field of organic chemistry and in a manner as described here (cf. reaction schemes below) or analogously. The reaction conditions in the synthesis routes described herein are known to the skilled person and are for some cases exemplified in the synthesis examples herein. The necessary starting materials are either commercially available or can also be obtained according to general knowledge in the field of organic chemistry.

If not stated otherwise, all chemical moieties; variables and indices in the compounds shown in the following reaction schemes are as defined in the context of the compound of formula (I) and the various embodiments thereof.

In another aspect of the invention, the invention also provides the process for the preparation of a compound of formula (II)

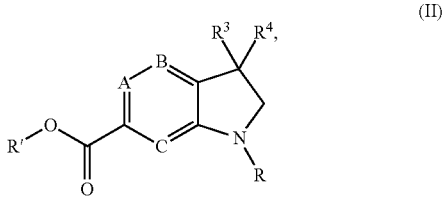

(II)

wherein A, B, C, R$^3$ and R$^4$ are as defined herein before, and R represents H, (C$_1$-C$_6$)-alkyl or CO(C$_1$-C$_6$)-alkyl, encompassing reacting a compound of general formula (III)

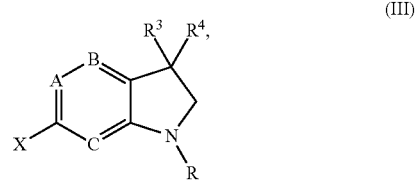

(III)

wherein X is Cl, Br or I, and A, B, C, R$^3$, R$^4$ and R are as defined in formula (II), with R'—OH, wherein R' represents (C$_1$-C$_6$)-alkyl, in the presence of a catalyst, selected from Pd(II) or Pd(0) catalysts, preferably [1,1'-bis(diphenyl-phosphino)ferrocene]dichloropalladium (II) (Pd(dppf)Cl$_2$); Palladium(II)acetate (Pd(OAc)$_2$); tetrakis-(triphenylphosphine)palladium(0) (Pd(PPh$_3$)$_4$); tris (dibenzylideneacetone)dipalladium(0) (Pd$_2$dba$_3$); under CO pressure of 30 to 50 bar, preferably 35 to 45 bar, at a temperature between 50° C. and 200° C., preferably 80° C. to 150° C., more preferably 90° C. to 120° C., in the presence of an organic base, selected from triethylamine, N,N-diisopropyl-N-ethyl-amine, N-methyl-piperidine or N-methyl-morpholine, in an aprotic organic solvent, preferably selected from N,N-dimethylformamide (DMF), N,N-dimethylacetamide (DMA), 1,8-diazabicyclo[5.4.0]undec-7-ene (DBU), dimethylsulfoxide (DMSO), N-methyl-pyrrolidinone (NMP), N-butyl-pyrrolidinone (NBP) or hexamethylphosphoramide (HMPA).

The invention further relates to a method (a) for producing a compound of formula (I) encompassing the step 1.8:

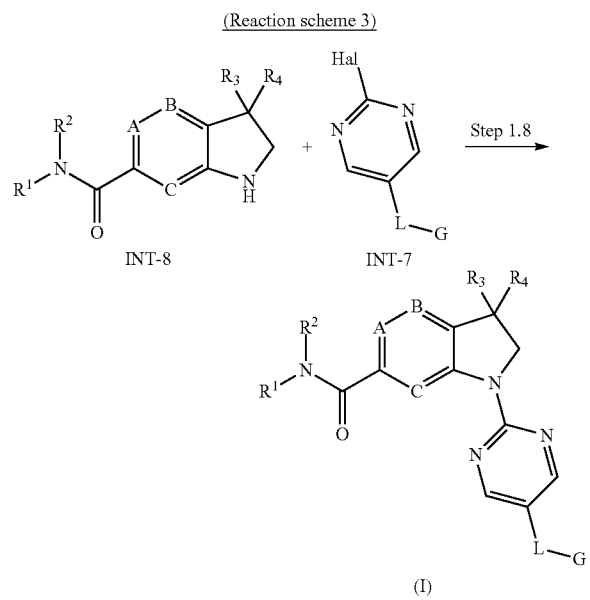

(Reaction scheme 3)

In step 1.8, INT-8 together with INT-7, wherein Hal represents a halogen atom, preferably Cl or Br, are (i) either subjected to a palladium-catalysed Buchwald-Hartwig cross coupling reaction which leads to the compound according to the invention (cf. Muci, A. R. Et al. Topic Current Chemistry 131, 219, 2002), or (ii) heated up in a high boiling point solvent like, e.g. n-butanol or DMSO.

INT-7 can be prepared by known methods by using commercially available starting materials. For example by using halogenated pyrimidines which are reacted with commercially available organoboranes in a suzuki cross-coupling reaction (cf. Akira Suzuki, Chem. Comm., 4759-4763, 2005) or by following the protocol as given in the experimental section.

The intermediate INT-8 may be obtained via the following sequences of reaction steps:

(a) Preparation of the Intermediate Compound INT-4

Reaction scheme 1:

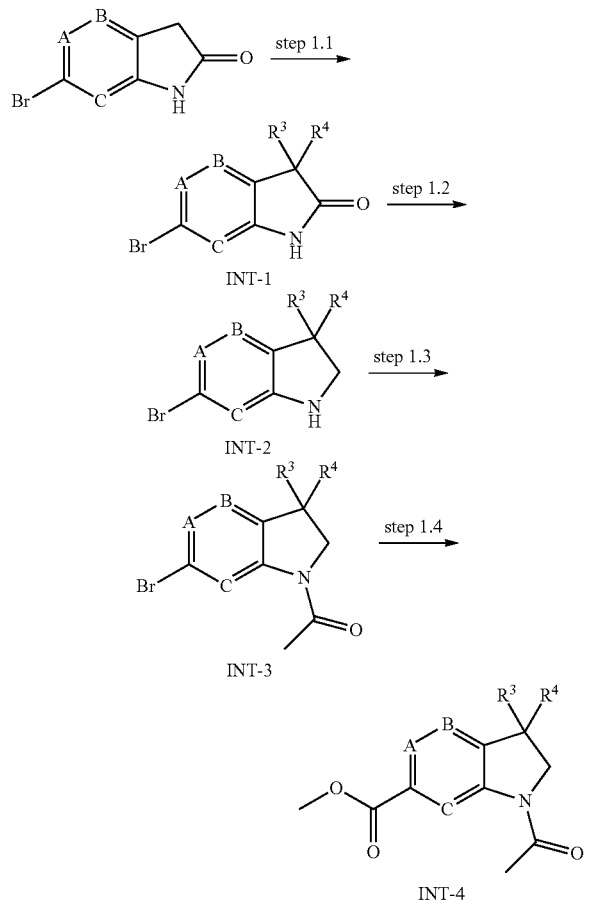

In step 1.1, the commercially available 6-bromoindolin-2-one is reacted with the desired haloalkyl compound in the presence of a base to afford the corresponding indolones INT-1. In the presence of a base 6-bromoindolin-2-one can undergo double alkylation at the □-carbon atom using haloalkyls as electro-philes. This step 1.1 can either be a double intermolecular alkylation using monohaloalkyl derivatives like e.g. iodomethane or a intermolecular alkylation followed by intramolecular cyclization using corresponding dihaloalkyl derivatives like e.g. 1,2-dibromoethane.

In the next step 1.2 the carbonyl group of INT-1 is removed via hydrogenation with LiAlH$_4$ which leads to the compound INT-2. In step 1.3 the nitrogen atom is acetylated with acetylchloride, which leads to the corresponding N-acetyl-arylbromide INT-3 in the presence of a base and dimethylaminopyridine (DAMP) as catalyst. In step 1.4 the compound INT-3 is carbonylated with carbon monoxide in the presence of a palladium catalyst which leads to the compound INT-4.

Steps 1.1 to 1.4 are performed analogous to known methods (cf., for example, J. Med. Chem., 30(5), 824-9, 1987; WO 2006/002421; WO2011/072241; WO2003/051366; Angew. Chem., Int. Ed., 48(23), 4114-4133, 2009).

(b) Preparation of the Intermediate Compound INT-8

Reaction scheme 2:

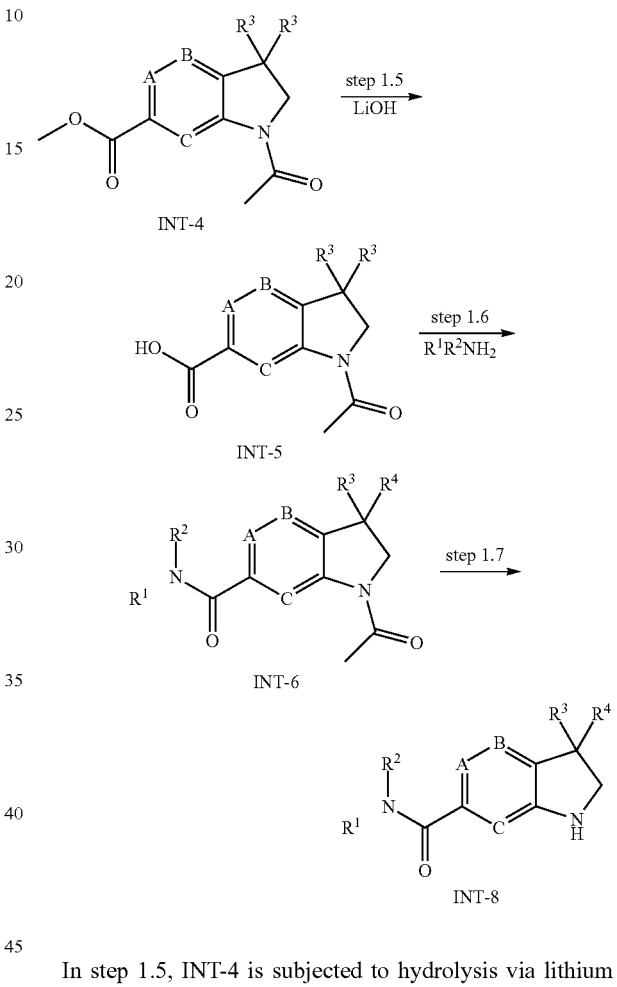

In step 1.5, INT-4 is subjected to hydrolysis via lithium hydroxide which yields the corresponding carboxylic acid INT-5. In step 1.6, INT-5 is reacted with a suitable amine to give the amide derivative INT-6 (cf. Anne Brennführer et al. Angew. Chem., Int. Ed., 48 (23), 4114-4133, 2009). In step 1.7 the N-acetyl-group of INT-6 is removed under acidic conditions to yield INT-8.

The invention further relates to a method (b) for producing a compound of formula (I) encompassing the sequence of reactions steps according to reaction scheme 4:

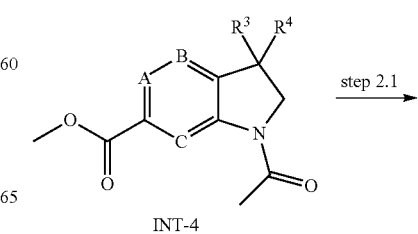

Reaction scheme 5:

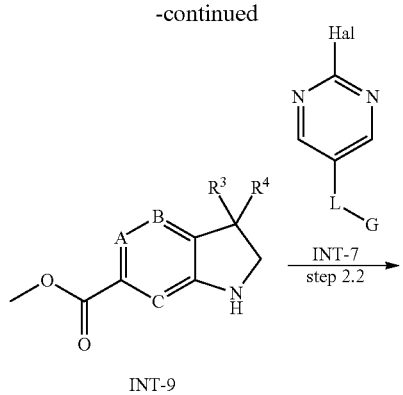

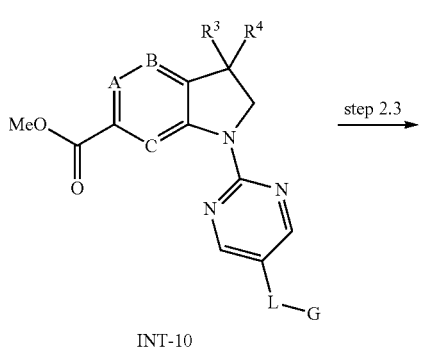

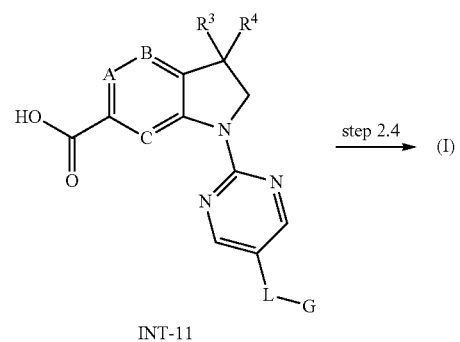

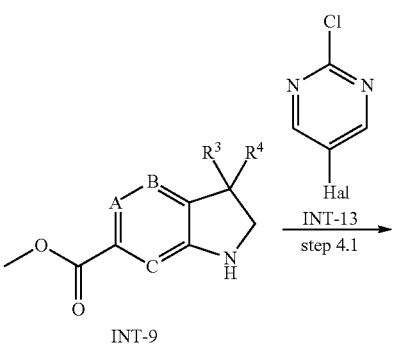

INT-4, which is prepared according to the procedure described in route 1 (a), is in step 2.1 de-acetylated under acidic conditions which leads to INT-9 (cf. Robertson, David W. et al. J. Med. Chem., 30 (5), 824-9, 1987; WO 2006/002421). In step 2.2. INT-9 together with INT-7, wherein Hal stands for a halogen atom, preferably Cl and Br, are (i) subjected to a palladium-catalysed Buchwald-Hartwig cross coupling reaction similar to step 1.8 of route 1, which leads to INT-10. In step 2.3, the methyl ester of INT-10 is cleaved under basic conditions (preferably by addition of LiOH) which leads to INT-11. The carboxylic group of the INT-11 is turned into an amide in the presence of an appropriate amine (e.g. an amine having the formula $R^1R^2NH$) which leads to the compound of formula (I).

The invention further relates to a method (c) for producing a compound of formula (I) encompassing the sequence of reactions steps according to reaction scheme 5:

INT-8, which is prepared according to the procedure described in route 1 (a) and (b), can be subjected in a step 3.1 to a cross-coupling reaction with a compound INT-13, wherein Hal represents a halogen atom, preferably Br, in a Pd-catalysed Buchwald-Hartwig cross coupling reaction similar to step 1.8 of route 1, which leads to INT-12. In a step 3.2 INT-12 is reacted with INT 14 in a Suzuki reaction leading to the compound of formula (I) wherein L is a bond.

The invention further relates to a method (d) for producing a compound of formula (I) encompassing the sequence of reactions steps according to reaction scheme 6:

Reaction scheme 6:

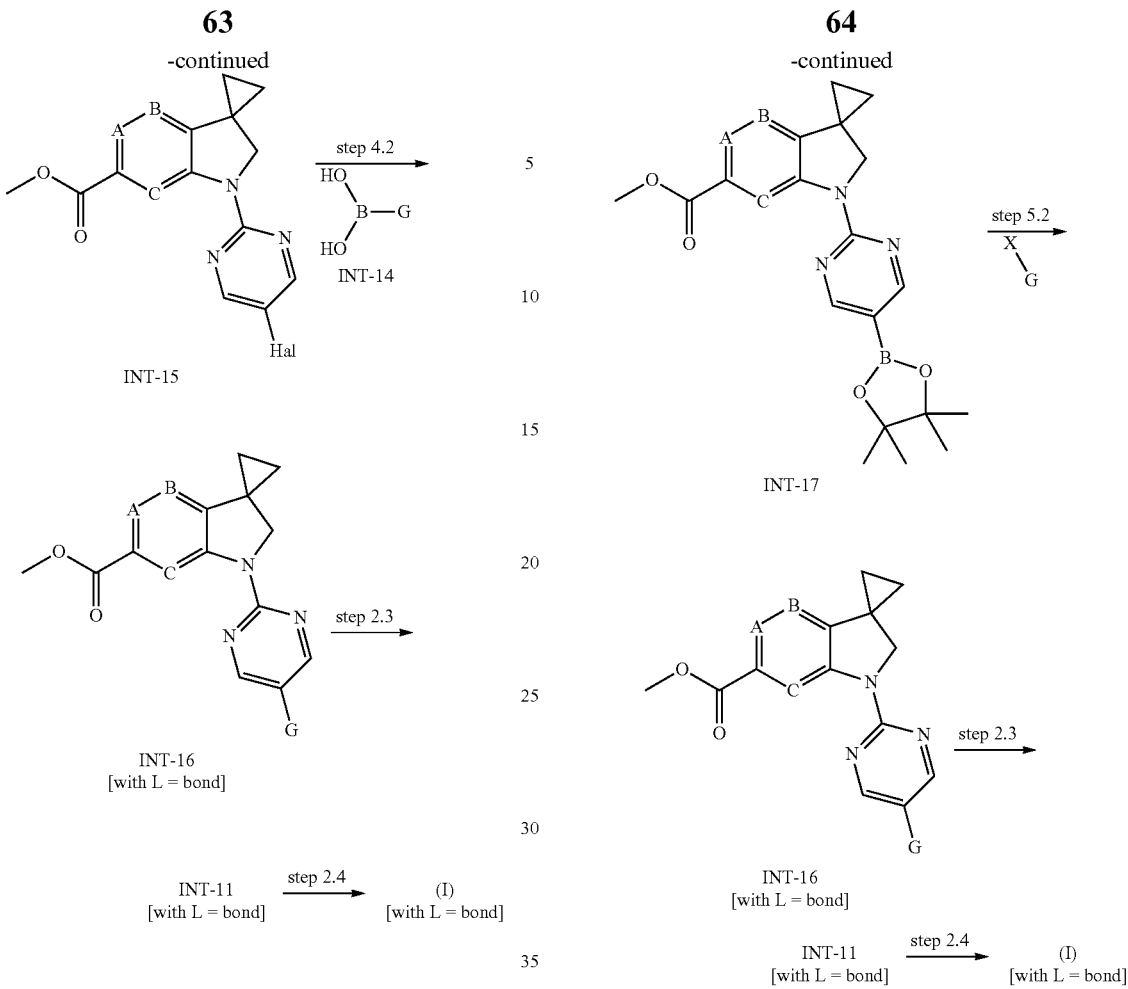

Int-9 can be subjected in step 4.1 in a nucleophilic aromatic substitution with Int-13, wherein Hal represents a halogen atom, preferably Br (cf. March's Advanced Organic Chemistry: Reactions, Mechanisms, and Structure; Sixth Edition, 2007, 875). Suzuki cross coupling (A. Suzuki et al., *Chem. Rev.*, 1995, 2457-2483; A. S. Guram et al., *Org. Lett.*, 2006, 1787-1789; A. J. J. Lennox, *Chem. Soc. Rev.*, 2014, 412-443) of Int-15 with Int-14 leads to compound Int-16 wherein L is a bond.

The invention further relates to a method (e) for producing a compound of formula (I) encompassing the sequence of reactions steps according to reaction scheme 7:

Reaction scheme 7:

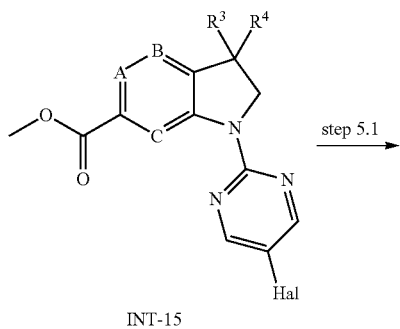

One alternate route for the synthesis of Int-16 wherein L is a bond is described in scheme 7. Int-15 can be converted to the corresponding boronic acid ester derivative Int-17 (step 5.1) following standard Miyaura borylation reaction conditions (Miyaura et al., J. Org. Chem., 1995, 60, 7508). Int-16 can then be prepared starting from Int-17 following Suzuki cross coupling reaction conditions by using different aryl- and heteroarylhalide derivatives G-X (X=Br, OTf, Cl) (step 5.2).

The invention further relates to a method (f) for producing a compound of formula (I) encompassing the sequence of reactions steps according to reaction scheme 8:

Reaction scheme 8:

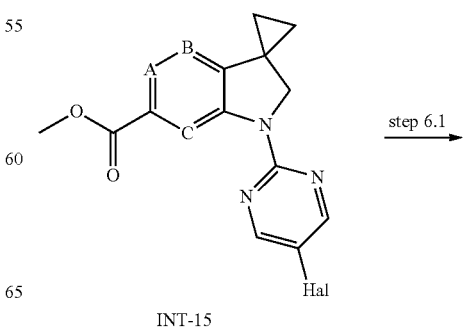

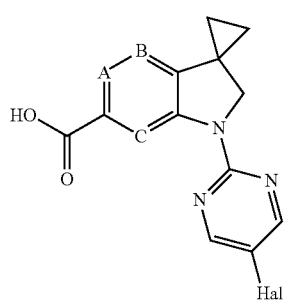

INT-18

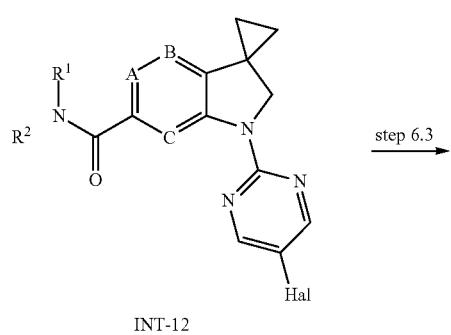

INT-12

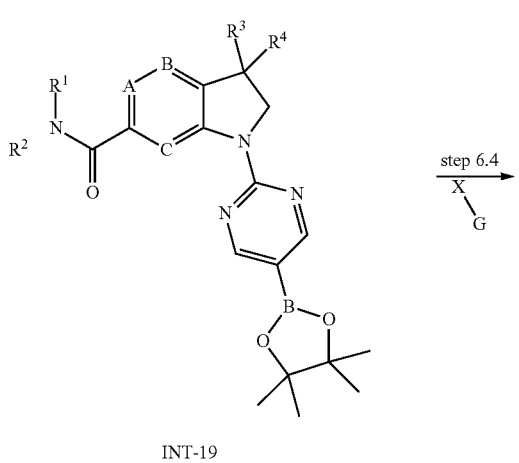

INT-19

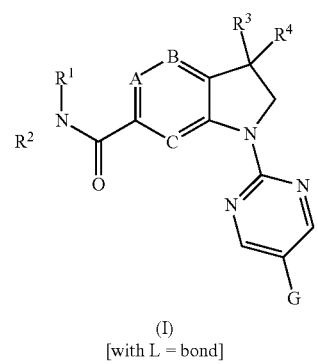

(I)
[with L = bond]

Soponification of Int-15 followed by amidation of Int-18 gives access to int-12. Int-19 can be prepared in analogy to the methodology described in scheme 7 using Miyaura borylation reaction conditions. Suzuki cross of Int-19 with G-X (X=Br, OTf, Cl) gives access to (I).

In the following the present invention is illustrated by way of examples without limiting the invention thereto.

EXAMPLES

The compounds according to the invention can be produced in the manner described below. The following abbreviations are used in the descriptions of the experiments:

AcCl: acetyl chloride, Ar: argon, Ataphos: Bis[di-tert-butyl(4-dimethylaminophenyl)phosphine]dichloro-palladium(II), CC: column chromatography, $CF_3$-Tol: trifluorotoluene, m-CPBA: 3-chlorobenzoperoxoic acid, DIPEA: diisopropylethylamine, DMAP: N,N-dimethyl-4-aminopyridine, DME: dimethoxyethane, DMF: dimethylformamide, EDCl: N-Ethyl-N'-(3-dimethylaminopropyl)carbodiimide hydrochloride, $Et_2O$: diethyl ether, TEA: triethylamine, EtOAc: ethyl acetate, EtOH: ethanol, HOAt: 1-Hydroxy-7-azabenzotriazole, $iPr_2NH$: diisopropylamine, $LiAlH_4$: lithium aluminium hydride, MeOH: methanol, MeOH: methanol, n-BuLi: n-butyllithium, NMM: N-methylmorpholine, $Pd(dppf)Cl_2$: [1,1'-bis(diphenylphosphino)ferrocene]-dichloropalladium(II), $Pd(PPh_3)_4$: tetrakis(triphenylphosphine)palladium(0), $Pd_2dba_3$:tris(dibenzylideneacetone)dipalladium(0), pet ether: petroleum ether, RM: reaction mixture, rt or RT: room temperature (23° C.+/−3° C.), [(t-Bu)$_3$PH]BF$_4$: tri-t-butylphosphonium tetrafluoroborate, TBTU: O-(benzotriazol-1-yl)-N,N,N',N'-tetramethyluronium tetrafluoroborate; TEA: triethylamine, TFA: 2,2,2-trifluoroacetic acid, THF: tetrahydrofuran, Tol: toluene.

In the tables, the following abbreviations were used: Me=methyl, Et=ethyl; cy-prop=cyclo propyl; cy-but=cyclobutyl.

TABLE 1

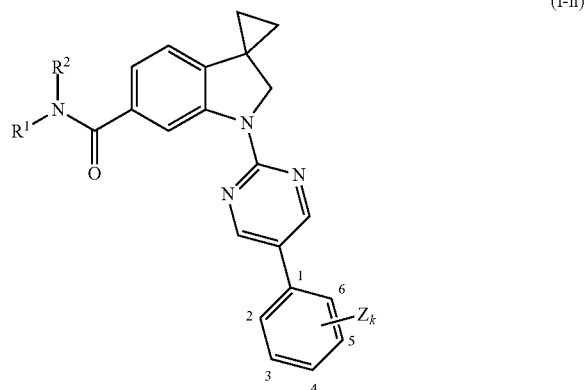

(I-h)

| Cpd No. | R¹, R² | Z | k | Name |
|---|---|---|---|---|
| 1 | Q'32 | 2-F | 1 | [1-[5-(2-Fluorophenyl)-pyrimidin-2-yl]-spiro[1,2-dihydro-indole-3,1'-cyclopropane]-6-yl]-morpholin-4-yl-methanone |
| 2 | M28; with R¹ = CH₃ | 2-F | 1 | 1-[5-(2-Fluorophenyl)-pyrimidin-2-yl]-N,N-dimethyl-spiro[1,2-dihydro-indole-3,1'-cyclopropane]-6-carboxylic acid amide |
| 3 | Q'8 | 2-F | 1 | [1-[5-(2-Fluorophenyl)-pyrimidin-2-yl]-spiro[1,2-dihydro-indole-3,1'-cyclopropane]-6-yl]-pyrrolidin-1-yl-methanone |
| 4 | Q'41 | 2-F | 1 | 4-[1-[5-(2-Fluorophenyl)-pyrimidin-2-yl]-spiro[1,2-dihydro-indole-3,1'-cyclopropane]-6-carbonyl]-piperazin-2-one |
| 5 | Q'40 | 2-F | 1 | [1-[5-(2-Fluorophenyl)-pyrimidin-2-yl]-spiro[1,2-dihydro-indole-3,1'-cyclopropane]-6-yl]-piperazin-1-yl-methanone |
| 6 | Q'32 | 2-Cl | 1 | [1-[5-(2-Chlorophenyl)-pyrimidin-2-yl]-spiro[1,2-dihydro-indole-3,1'-cyclopropane]-6-yl]-morpholin-4-yl-methanone |
| 7 | Q'32 | — | 0 | Morpholin-4-yl-[1-(5-phenyl-pyrimidin-2-yl)-spiro[1,2-dihydro-indole-3,1'-cyclopropane]-6-yl]-methanone |
| 8 | Q'32 | 2-F, 4-F | 2 | [1-[5-(2,4-Difluoro-phenyl)-pyrimidin-2-yl]-spiro[1,2-dihydro-indole-3,1'-cyclopropane]-6-yl]-morpholin-4-yl-methanone |
| 12 | Q'32 | 2-Me | 1 | Morpholin-4-yl-[1-(5-o-tolyl-pyrimidin-2-yl)-spiro[1,2-dihydro-indole-3,1'-cyclopropane]-6-yl]-methanone |
| 13 | Q'32 | 2-OCF₃ | 1 | Morpholin-4-yl-[1-[5-[2-(trifluoromethyloxy)-phenyl]-pyrimidin-2-yl]-spiro[1,2-dihydro-indole-3,1'-cyclopropane]-6-yl]-methanone |
| 14 | Q'32 | 2-CF₃ | 1 | Morpholin-4-yl-[1-[5-[2-(trifluoromethyl)-phenyl]-pyrimidin-2-yl]-spiro[1,2-dihydro-indole-3,1'-cyclopropane]-6-yl]-methanone |
| 15 | Q'32 | 2-F, 3-F | 2 | [1-[5-(2,3-Difluoro-phenyl)-pyrimidin-2-yl]-spiro[1,2-dihydro-indole-3,1'-cyclopropane]-6-yl]-morpholin-4-yl-methanone |
| 16 | Q'32 | 2-F, 5-OMe | 2 | [1-[5-(2-Fluoro-5-methoxy-phenyl)-pyrimidin-2-yl]-spiro[1,2-dihydro-indole-3,1'-cyclopropane]-6-yl]-morpholin-4-yl-methanone |
| 17 | Q'32 | 2-F, 4-OMe | 2 | [1-[5-(2-Fluoro-5-methoxy-phenyl)-pyrimidin-2-yl]-spiro[1,2-dihydro-indole-3,1'-cyclopropane]-6-yl]-morpholin-4-yl-methanone |
| 18 | Q'32 | 2-CN | 1 | 2-[2-[6-(Morpholine-4-carbonyl)-spiro[1,2-dihydro-indole-3,1'-cyclopropane]-1-yl]-pyrimidin-5-yl]-benzonitrile |
| 19 | Q'32 | 2-F, 6-OMe | 2 | [1-[5-(2-Fluoro-6-methoxy-phenyl)-pyrimidin-2-yl]-spiro[1,2-dihydro-indole-3,1'-cyclopropane]-6-yl]-morpholin-4-yl-methanone |
| 20 | Q'32 | 2-F, 6-CN | 2 | 3-Fluoro-2-[2-[6-(morpholine-4-carbonyl)-spiro[1,2-dihydro-indole-3,1'-cyclopropane]-1-yl]-pyrimidin-5-yl]-benzonitrile |
| 21 | Q'32 | 2-CONMe₂ | 2 | N,N-Dimethyl-2-[2-[6-(morpholine-4-carbonyl)-spiro[1,2-dihydro-indole-3,1'-cyclopropane]-1-yl]-pyrimidin-5-yl]-benzamide |
| 22 | Q'32 | 2-F, 5-CN | 2 | 4-Fluoro-3-[2-[6-(morpholine-4-carbonyl)-spiro[1,2-dihydro-indole-3,1'-cyclopropane]-1-yl]-pyrimidin-5-yl]-benzonitrile |
| 23 | Q'32 | 2-F, 5-CF₃ | 2 | [1-[5-[2-Fluoro-5-(trifluoromethyl)-phenyl]-pyrimidin-2-yl]-spiro[1,2-dihydro-indole-3,1'-cyclopropane]-6-yl]-morpholin-4-yl-methanone |
| 24 | Q'32 | 2-F, 6-CF₃ | 2 | [1-[5-[2-Fluoro-6-(trifluoromethyl)-phenyl]-pyrimidin-2-yl]-spiro[1,2-dihydro-indole-3,1'-cyclopropane]-6-yl]-morpholin-4-yl-methanone |
| 25 | Q'32 | 2-CONH₂ | 1 | 2-[2-[6-(Morpholine-4-carbonyl)-spiro[1,2-dihydro-indole-3,1'-cyclopropane]-1-yl]-pyrimidin-5-yl]-benzamide |
| 26 | Q'32 | 2-F, 4-CONH₂ | 2 | 3-Fluoro-4-[2-[6-(morpholine-4-carbonyl)-spiro[1,2-dihydro-indole-3,1'-cyclopropane]-1-yl]-pyrimidin-5-yl]-benzamide |
| 27 | Q'32 | 2-F, 6-F | 2 | [1-[5-(2,6-Difluoro-phenyl)-pyrimidin-2-yl]-spiro[1,2-dihydro-indole-3,1'-cyclopropane]-6-yl]-morpholin-4-yl-methanone |

TABLE 1-continued (I-h)

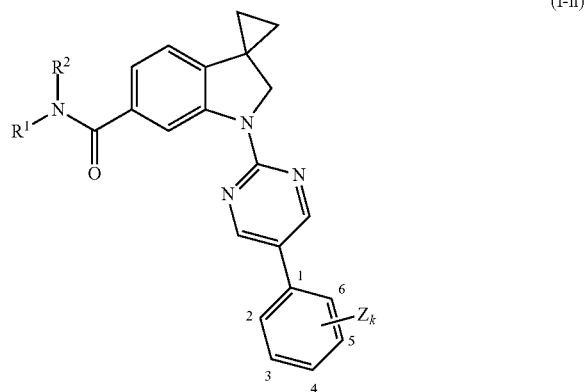

| Cpd No. | R¹, R² | Z | k | Name |
|---|---|---|---|---|
| 28 | Q'32 | 2-SO₂Me | 1 | [1-[5-(2-Methylsulfonyl-phenyl)-pyrimidin-2-yl]-spiro[1,2-dihydro-indole-3,1'-cyclopropane]-6-yl]-morpholin-4-yl-methanone |
| 29 | Q'32 | 2-F, 4-SO₂Me | 2 | [1-[5-(2-Fluoro-4-methylsulfonyl-phenyl)-pyrimidin-2-yl]-spiro[1,2-dihydro-indole-3,1'-cyclopropane]-6-yl]-morpholin-4-yl-methanone |
| 30 | Q'32 | 2-F, 4-CN | 2 | 3-Fluoro-4-[2-[6-(morpholine-4-carbonyl)-spiro[1,2-dihydro-indole-3,1'-cyclopropane]-1-yl]-pyrimidin-5-yl]-benzonitrile |
| 31 | Q'32 | 2-OMe | 1 | [1-[5-(2-Methoxyphenyl)-pyrimidin-2-yl]-spiro[1,2-dihydro-indole-3,1'-cyclopropane]-6-yl]-morpholin-4-yl-methanone |
| 32 | Q'32 | 2-F, 6-CONH₂ | 1 | 3-Fluoro-2-[2-[6-(morpholine-4-carbonyl)-spiro[1,2-dihydro-indole-3,1'-cyclopropane]-1-yl]-pyrimidin-5-yl]-benzamide |
| 33 | Q'29 | 2-F | 1 | [1-[5-(2-Fluorophenyl)-pyrimidin-2-yl]-spiro[1,2-dihydro-indole-3,1'-cyclopropane]-6-yl]-(2-oxa-7-azaspiro[3.5]nonan-7-yl)-methanone |
| 34 | Q'59 | 2-F | 1 | [1-[5-(2-Fluorophenyl)-pyrimidin-2-yl]-spiro[1,2-dihydro-indole-3,1'-cyclopropane]-6-yl]-[4-(2-hydroxy-ethyl)-piperazin-1-yl]-methanone |
| 35 | Q'32 | 2-F, 5-CONH₂ | 2 | 4-Fluoro-3-[2-[6-(morpholine-4-carbonyl)-spiro[1,2-dihydro-indole-3,1'-cyclopropane]-1-yl]-pyrimidin-5-yl]-benzamide |
| 36 | Q'2 | 2-F | 1 | [1-[5-(2-Fluorophenyl)-pyrimidin-2-yl]-spiro[1,2-dihydro-indole-3,1'-cyclopropane]-6-yl]-(3-hydroxy-azetidin-1-yl)-methanone |
| 37 | Q'51 | 2-F | 1 | [1-[5-(2-Fluorophenyl)-pyrimidin-2-yl]-spiro[1,2-dihydro-indole-3,1'-cyclopropane]-6-yl]-(4-isopropyl-piperazin-1-yl)-methanone |
| 38 | Q'42 | 2-F | 1 | 4-[1-[5-(2-Fluorophenyl)-pyrimidin-2-yl]-spiro[1,2-dihydro-indole-3,1'-cyclopropane]-6-carbonyl]-1-methyl-piperazin-2-one |
| 39 | Q'32 | 2-CHF₂ | 1 | [1-[5-[2-(Difluoro-methyl)-phenyl]-pyrimidin-2-yl]-spiro[1,2-dihydro-indole-3,1'-cyclopropane]-6-yl]-morpholin-4-yl-methanone |
| 40 | Q'11 | 2-F | 1 | [(3R)-3-Amino-pyrrolidin-1-yl]-[1-[5-(2-fluorophenyl)-pyrimidin-2-yl]-spiro[1,2-dihydro-indole-3,1'-cyclopropane]-6-yl]-methanone |
| 41 | M5; with R¹ = H | 2-F | 1 | N-(2-Amino-ethyl)-1-[5-(2-fluorophenyl)-pyrimidin-2-yl]-N-methyl-spiro[1,2-dihydro-indole-3,1'-cyclopropane]-6-carboxylic acid amide |
| 42 | Q'32 | 2-F, 5-SO₂Me | 2 | [1-[5-(2-Fluoro-5-methylsulfonyl-phenyl)-pyrimidin-2-yl]-spiro[1,2-dihydro-indole-3,1'-cyclopropane]-6-yl]-morpholin-4-yl-methanone |
| 43 | Q'32 | 4-F | 1 | [1-[5-(4-Fluorophenyl)-pyrimidin-2-yl]-spiro[1,2-dihydro-indole-3,1'-cyclopropane]-6-yl]-morpholin-4-yl-methanone |
| 44 | Q'17 | 2-F | 1 | [1-[5-(2-Fluorophenyl)-pyrimidin-2-yl]-spiro[1,2-dihydro-indole-3,1'-cyclopropane]-6-yl]-[(3R)-3-hydroxy-pyrrolidin-1-yl]-methanone |
| 45 | Q'18 | 2-F | 1 | [1-[5-(2-Fluorophenyl)-pyrimidin-2-yl]-spiro[1,2-dihydro-indole-3,1'-cyclopropane]-6-yl]-(3S)-3-hydroxy-pyrrolidin-1-yl]-methanone |
| 46 | M31; with R¹ = CH₃ | 2-F | 1 | N-Cyclopropyl-1-[5-(2-fluorophenyl)-pyrimidin-2-yl]-N-methyl-spiro[1,2-dihydro-indole-3,1'-cyclopropane]-6-carboxylic acid amide |
| 47 | Et; Et | 2-F | 1 | N,N-Diethyl-1-[5-(2-fluorophenyl)-pyrimidin-2-yl]-spiro[1,2-dihydro-indole-3,1'-cyclopropane]-6-carboxylic acid amide |
| 48 | Q'32 | 3-OMe | 1 | [1-[5-(3-Methoxyphenyl)-pyrimidin-2-yl]-spiro[1,2-dihydro-indole-3,1'-cyclopropane]-6-yl]-morpholin-4-yl-methanone |
| 49 | Q'40 | — | 0 | [1-(5-Phenyl-pyrimidin-2-yl)-spiro[1,2-dihydro-indole-3,1'-cyclopropane]-6-yl]-piperazin-1-yl-methanone |

TABLE 1-continued (I-h)

| Cpd No. | R¹, R² | Z | k | Name |
|---|---|---|---|---|
| 50 | Q'32 | 3-F, 5-F | 2 | [1-[5-(3,5-Difluoro-phenyl)-pyrimidin-2-yl]-spiro[1,2-dihydro-indole-3,1'-cyclopropane]-6-yl]-morpholin-4-yl-methanone |
| 51 | Q'32 | 3-Cl | 1 | [1-[5-(3-Chlorophenyl)-pyrimidin-2-yl]-spiro[1,2-dihydro-indole-3,1'-cyclopropane]-6-yl]-morpholin-4-yl-methanone |
| 52 | Q'32 | 2-F, 5-Me | 2 | [1-[5-(2-Fluoro-5-methyl-phenyl)-pyrimidin-2-yl]-spiro[1,2-dihydro-indole-3,1'-cyclopropane]-6-yl]-morpholin-4-yl-methanone |
| 53 | Q'32 | 3-F, 4-F | 2 | [1-[5-(3,4-Difluoro-phenyl)-pyrimidin-2-yl]-spiro[1,2-dihydro-indole-3,1'-cyclopropane]-6-yl]-morpholin-4-yl-methanone |
| 54 | Q'32 | 3-CONH₂ | 1 | 3-[2-[6-(Morpholine-4-carbonyl)-spiro[1,2-dihydro-indole-3,1'-cyclopropane]-1-yl]-pyrimidin-5-yl]-benzamide |
| 55 | Q'41 | — | 0 | 4-[1-(5-Phenyl-pyrimidin-2-yl)-spiro[1,2-dihydro-indole-3,1'-cyclopropane]-6-carbonyl]-piperazin-2-one |
| 56 | Q'32 | 3-CN | 1 | 3-[2-[6-(Morpholine-4-carbonyl)-spiro[1,2-dihydro-indole-3,1'-cyclopropane]-1-yl]-pyrimidin-5-yl]-benzonitrile |
| 57 | Q'32 | 3-F | 1 | [1-[5-(3-Fluorophenyl)-pyrimidin-2-yl]-spiro[1,2-dihydro-indole-3,1'-cyclopropane]-6-yl]-morpholin-4-yl-methanone |
| 58 | Q'32 | 2-F, 5-Cl | 2 | [1-[5-(5-Chloro-2-fluoro-phenyl)-pyrimidin-2-yl]-spiro[1,2-dihydro-indole-3,1'-cyclopropane]-6-yl]-morpholin-4-yl-methanone |
| 59 | Q'8 | — | 0 | [1-(5-Phenyl-pyrimidin-2-yl)-spiro[1,2-dihydro-indole-3,1'-cyclopropane]-6-yl]-pyrrolidin-1-yl-methanone |
| 60 | Q'53 | 2-F | 1 | [1-[5-(2-Fluorophenyl)-pyrimidin-2-yl]-spiro[1,2-dihydro-indole-3,1'-cyclopropane]-6-yl]-(4-methyl-piperazin-1-yl)-methanone |
| 61 | M28; with R¹ = H | 2-F | 1 | 1-[5-(2-Fluorophenyl)-pyrimidin-2-yl]-N-methyl-spiro[1,2-dihydro-indole-3,1'-cyclopropane]-6-carboxylic acid amide |
| 62 | Q'32 | 2-c-propyl | 1 | [1-[5-(2-Cyclopropyl-phenyl)-pyrimidin-2-yl]-spiro[1,2-dihydro-indole-3,1'-cyclopropane]-6-yl]-morpholin-4-yl-methanone |
| 63 | Q'32 | 4-CONH₂ | 1 | 4-[2-[6-(Morpholine-4-carbonyl)-spiro[1,2-dihydro-indole-3,1'-cyclopropane]-1-yl]-pyrimidin-5-yl]-benzamide |
| 64 | Q'3 | 2-F | 1 | [1-[5-(2-Fluorophenyl)-pyrimidin-2-yl]-spiro[1,2-dihydro-indole-3,1'-cyclopropane]-6-yl]-(2-oxa-6-azaspiro[3.3]heptan-6-yl)-methanone |
| 65 | Q'32 | 2-F, 4-CONMe₂ | 2 | 3-Fluoro-N,N-dimethyl-4-[2-[6-(morpholine-4-carbonyl)-spiro[1,2-dihydro-indole-3,1'-cyclopropane]-1-yl]-pyrimidin-5-yl]-benzamide |
| 66 | Q'56 | 2-F | 1 | (4-Cyclopropyl-piperazin-1-yl)-[1-[5-(2-fluorophenyl)-pyrimidin-2-yl]-spiro[1,2-dihydro-indole-3,1'-cyclopropane]-6-yl]-methanone |
| 67 | Q'32 | 2-F, 5-OCF₃ | 2 | [1-[5-[2-Fluoro-5-(trifluoromethyloxy)-phenyl]-pyrimidin-2-yl]-spiro[1,2-dihydro-indole-3,1'-cyclopropane]-6-yl]-morpholin-4-yl-methanone |
| 68 | Q'21 | 2-F | 1 | [1-[5-(2-Fluorophenyl)-pyrimidin-2-yl]-spiro[1,2-dihydro-indole-3,1'-cyclopropane]-6-yl]-(2-oxa-7-azaspiro[3.4]octan-7-yl)-methanone |
| 69 | Q'32 | 2-F, 6-Me | 2 | [1-[5-(2-Fluoro-6-methyl-phenyl)-pyrimidin-2-yl]-spiro[1,2-dihydro-indole-3,1'-cyclopropane]-6-yl]-morpholin-4-yl-methanone |
| 70 | Q'40 | 2-c-propyl | 1 | [1-[5-(2-Cyclopropyl-phenyl)-pyrimidin-2-yl]-spiro[1,2-dihydro-indole-3,1'-cyclopropane]-6-yl]-piperazin-1-yl-methanone |
| 71 | Q'40 | 2-F, 4-F | 2 | [1-[5-(2,4-Difluoro-phenyl)-pyrimidin-2-yl]-spiro[1,2-dihydro-indole-3,1'-cyclopropane]-6-yl]-piperazin-1-yl-methanone |
| 72 | Q'40 | 2-F, 5-OCF₃ | 2 | [1-[5-[2-Fluoro-5-(trifluoromethyloxy)-phenyl]-pyrimidin-2-yl]-spiro[1,2-dihydro-indole-3,1'-cyclopropane]-6-yl]-piperazin-1-yl-methanone |

TABLE 1-continued (I-h)

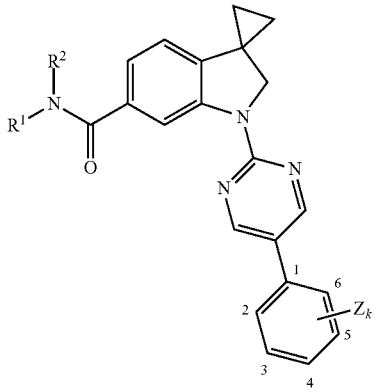

| Cpd No. | R¹, R² | Z | k | Name |
|---|---|---|---|---|
| 73 | Q'40 | 2-F, 5-OMe | 2 | [1-[5-(2-Fluoro-5-methoxy-phenyl)-pyrimidin-2-yl]-spiro[1,2-dihydro-indole-3,1'-cyclopropane]-6-yl]-piperazin-1-yl-methanone |
| 74 | Q'22 | 2-F | 1 | (2,6-Diazaspiro[3.4]octan-6-yl)-[1-[5-(2-fluorophenyl)-pyrimidin-2-yl]-spiro[1,2-dihydro-indole-3,1'-cyclopropane]-6-yl]-methanone |
| 75 | M20; with R¹ = H | 2-F | 1 | 1-[5-(2-Fluorophenyl)-pyrimidin-2-yl]-N-(3-methoxy-propyl)-spiro[1,2-dihydro-indole-3,1'-cyclopropane]-6-carboxylic acid amide |
| 76 | Q'55 | 2-F | 1 | 3-[4-[1-[5-(2-Fluorophenyl)-pyrimidin-2-yl]-spiro[1,2-dihydro-indole-3,1'-cyclopropane]-6-carbonyl]-piperazin-1-yl]-propionitrile |
| 77 | Q'14 | 2-F | 1 | [(3R)-3-Dimethylamino-pyrrolidin-1-yl]-[1-[5-(2-fluorophenyl)-pyrimidin-2-yl]-spiro[1,2-dihydro-indole-3,1'-cyclopropane]-6-yl]-methanone |
| 78 | M51; with R¹ = H | 2-F | 1 | 1-[5-(2-Fluorophenyl)-pyrimidin-2-yl]-N-[2-(2-oxo-pyrrolidin-1-yl)-ethyl]-spiro[1,2-dihydro-indole-3,1'-cyclopropane]-6-carboxylic acid amide |
| 79 | Q'30 | 2-F | 1 | [1-[5-(2-Fluorophenyl)-pyrimidin-2-yl]-spiro[1,2-dihydro-indole-3,1'-cyclopropane]-6-yl]-(2-oxa-8-azaspiro[3.5]nonan-8-yl)-methanone |
| 80 | Q'31 | 2-F | 1 | [1-[5-(2-Fluorophenyl)-pyrimidin-2-yl]-spiro[1,2-dihydro-indole-3,1'-cyclopropane]-6-yl]-(2-oxa-5-azaspiro[3.5]nonan-5-yl)-methanone |
| 81 | M37; with R¹ = H | 2-F | 1 | 1-[5-(2-Fluorophenyl)-pyrimidin-2-yl]-N-tetrahydro-pyran-4-yl-spiro[1,2-dihydro-indole-3,1'-cyclopropane]-6-carboxylic acid amide |
| 82 | M47; with R¹ = H | 2-F | 1 | 1-[5-(2-Fluorophenyl)-pyrimidin-2-yl]-N-(tetrahydro-pyran-4-yl-methyl)-spiro[1,2-dihydro-indole-3,1'-cyclopropane]-6-carboxylic acid amide |
| 83 | M12; with R¹ = H | 2-F | 1 | N-[(Dimethyl-carbamoyl)-methyl]-1-[5-(2-fluorophenyl)-pyrimidin-2-yl]-spiro[1,2-dihydro-indole-3,1'-cyclopropane]-6-carboxylic acid amide |
| 84 | Q'23 | 2-F | 1 | [1-[5-(2-Fluorophenyl)-pyrimidin-2-yl]-spiro[1,2-dihydro-indole-3,1'-cyclopropane]-6-yl]-piperidin-1-yl-methanone |
| 85 | Q'57 | 2-F | 1 | 1-[4-[1-[5-(2-Fluorophenyl)-pyrimidin-2-yl]-spiro[1,2-dihydro-indole-3,1'-cyclopropane]-6-carbonyl]-piperazin-1-yl]-ethanone |
| 86 | Q'52 | 2-F | 1 | (4-Ethyl-piperazin-1-yl)-[1-[5-(2-fluorophenyl)-pyrimidin-2-yl]-spiro[1,2-dihydro-indole-3,1'-cyclopropane]-6-yl]-methanone |
| 87 | M47; with R¹ = CH₃ | 2-F | 1 | N-([1,3]Dioxolan-2-yl-methyl)-1-[5-(2-fluorophenyl)-pyrimidin-2-yl]-N-methyl-spiro[1,2-dihydro-indole-3,1'-cyclopropane]-6-carboxylic acid amide |
| 88 | M60; with R¹ = CH₃ | 2-F | 1 | 1-[5-(2-Fluorophenyl)-pyrimidin-2-yl]-N-methyl-N-pyridin-4-yl-spiro[1,2-dihydro-indole-3,1'-cyclopropane]-6-carboxylic acid amide |
| 89 | Q'1 | 2-F | 1 | (Azetidin-1-yl)-[1-[5-(2-fluorophenyl)-pyrimidin-2-yl]-spiro[1,2-dihydro-indole-3,1'-cyclopropane]-6-yl]-methanone |
| 90 | M29; with R¹ = CH₃ | 2-F | 1 | N-Ethyl-1-[5-(2-fluorophenyl)-pyrimidin-2-yl]-N-methyl-spiro[1,2-dihydro-indole-3,1'-cyclopropane]-6-carboxylic acid amide |
| 91 | M56; with R¹ = CH₃ | 2-F | 1 | 1-[5-(2-Fluorophenyl)-pyrimidin-2-yl]-N-(furan-2-yl-methyl)-N-methyl-spiro[1,2-dihydro-indole-3,1'-cyclopropane]-6-carboxylic acid amide |
| 92 | Q'19 | 2-F | 1 | [1-[5-(2-Fluorophenyl)-pyrimidin-2-yl]-spiro[1,2-dihydro-indole-3,1'-cyclopropane]-6-yl]-[(2S)-2-(methoxymethyl)-pyrrolidin-1-yl]-methanone |

TABLE 1-continued (I-h)

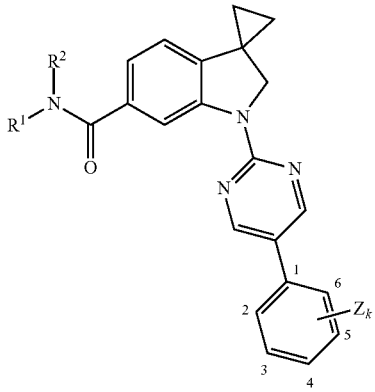

| Cpd No. | R¹, R² | Z | k | Name |
|---|---|---|---|---|
| 93 | Q'38 | 2-F | 1 | [1-[5-(2-Fluorophenyl)-pyrimidin-2-yl]-spiro[1,2-dihydro-indole-3,1'-cyclopropane]-6-yl]-thiomorpholin-4-yl-methanone |
| 94 | Q'59 | 2-F | 1 | [1-[5-(2-Fluorophenyl)-pyrimidin-2-yl]-spiro[1,2-dihydro-indole-3,1'-cyclopropane]-6-yl]-[4-(2-hydroxy-ethyl)-piperazin-1-yl]-methanone |
| 95 | M1; with R¹ = CH₃ | 2-F | 1 | 1-[5-(2-Fluorophenyl)-pyrimidin-2-yl]-N-(2-hydroxy-ethyl)-N-methyl-spiro[1,2-dihydro-indole-3,1'-cyclopropane]-6-carboxylic acid amide |
| 96 | Q'25/Q'26 | 2-F | 1 | [1-[5-(2-Fluorophenyl)-pyrimidin-2-yl]-spiro[1,2-dihydro-indole-3,1'-cyclopropane]-6-yl]-(3-hydroxy-piperidin-1-yl)-methanone |
| 97 | Q'27/Q'28 | 2-F | 1 | [1-[5-(2-Fluorophenyl)-pyrimidin-2-yl]-spiro[1,2-dihydro-indole-3,1'-cyclopropane]-6-yl]-[2-(hydroxymethyl)-piperidin-1-yl]-methanone |
| 98 | Q'61 | 2-F | 1 | [1-[5-(2-Fluorophenyl)-pyrimidin-2-yl]-spiro[1,2-dihydro-indole-3,1'-cyclopropane]-6-yl]-[4-(hydroxymethyl)-piperidin-1-yl]-methanone |
| 99 | M7; with R¹ = CH₃ | 2-F | 1 | N-[2-(Dimethylamino)ethyl]-1-[5-(2-fluorophenyl)-pyrimidin-2-yl]-N-methyl-spiro[1,2-dihydro-indole-3,1'-cyclopropane]-6-carboxylic acid amide |
| 100 | Q'24 | 2-F | 1 | [1-[5-(2-Fluorophenyl)-pyrimidin-2-yl]-spiro[1,2-dihydro-indole-3,1'-cyclopropane]-6-yl]-(4-methoxy-piperidin-1-yl)-methanone |
| 101 | Q'35 | 2-F | 1 | (3,5-Dimethyl-morpholin-4-yl)-[1-[5-(2-fluorophenyl)-pyrimidin-2-yl]-spiro[1,2-dihydro-indole-3,1'-cyclopropane]-6-yl]-methanone |
| 102 | M37; with R¹ = CH₃ | 2-F | 1 | 1-[5-(2-Fluorophenyl)-pyrimidin-2-yl]-N-methyl-N-tetrahydro-pyran-4-yl-spiro[1,2-dihydro-indole-3,1'-cyclopropane]-6-carboxylic acid amide |
| 103 | Q'36/Q'37 | 2-F | 1 | [1-[5-(2-Fluorophenyl)-pyrimidin-2-yl]-spiro[1,2-dihydro-indole-3,1'-cyclopropane]-6-yl]-(3-methyl-morpholin-4-yl)-methanone |
| 104 | Q'34 | 2-F | 1 | [(2R,6S)-2,6-Dimethyl-morpholin-4-yl]-[1-[5-(2-fluorophenyl)-pyrimidin-2-yl]-spiro[1,2-dihydro-indole-3,1'-cyclopropane]-6-yl]-methanone |
| 105 | Q'33 | 2-F | 1 | (2,2-Dimethyl-morpholin-4-yl)-[1-[5-(2-fluorophenyl)-pyrimidin-2-yl]-spiro[1,2-dihydro-indole-3,1'-cyclopropane]-6-yl]-methanone |
| 106 | Q'39 | 2-F | 1 | (1,1-Dioxo-[1,4]thiazinan-4-yl)-[1-[5-(2-fluorophenyl)-pyrimidin-2-yl]-spiro[1,2-dihydro-indole-3,1'-cyclopropane]-6-yl]-methanone |
| 107 | Q'44 | 2-F | 1 | (2,5-Diazabicyclo[2.2.1]heptan-2-yl)-[1-[5-(2-fluorophenyl)-pyrimidin-2-yl]-spiro[1,2-dihydro-indole-3,1'-cyclopropane]-6-yl]-methanone |
| 108 | Q'9 | — | 0 | [(3R)-3-Amino-pyrrolidin-1-yl]-[1-(5-phenyl-pyrimidin-2-yl)-spiro[1,2-dihydro-indole-3,1'-cyclopropane]-6-yl]-methanone |
| 109 | Q'40 | 3-F, 5-CN | 2 | 4-Fluoro-3-[2-[6-(piperazine-1-carbonyl)-spiro[1,2-dihydro-indole-3,1'-cyclopropane]-1-yl]-pyrimidin-5-yl]-benzonitrile |
| 110 | Q'13 | 2-F | 1 | [(3R)-3-Dimethylamino-pyrrolidin-1-yl]-[1-[5-(2-fluorophenyl)-pyrimidin-2-yl]-spiro[1,2-dihydro-indole-3,1'-cyclopropane]-6-yl]-methanone |
| 111 | Q'6 | 2-F | 1 | (2,7-Diazaspiro[3.4]octan-2-yl)-[1-[5-(2-fluorophenyl)-pyrimidin-2-yl]-spiro[1,2-dihydro-indole-3,1'-cyclopropane]-6-yl]-methanone |
| 112 | Q'4 | 2-F | 1 | (2,6-Diazaspiro[3.3]heptan-2-yl)-[1-[5-(2-fluorophenyl)-pyrimidin-2-yl]-spiro[1,2-dihydro-indole-3,1'-cyclopropane]-6-yl]-methanone |
| 113 | Q'32 | 2-CONH₂, 5-OMe | 2 | 4-Methoxy-2-[2-[6-(morpholine-4-carbonyl)-spiro[1,2-dihydro-indole-3,1'-cyclopropane]-1-yl]-pyrimidin-5-yl]-benzamide |

TABLE 1-continued (I-h)

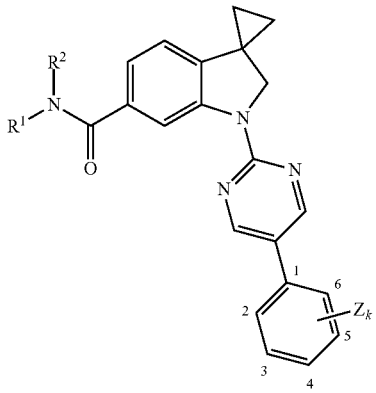

| Cpd No. | $R^1, R^2$ | Z | k | Name |
|---|---|---|---|---|
| 114 | Q'9 | 2-F, 3-F | 2 | [(3R)-3-Amino-pyrrolidin-1-yl]-[1-[5-(2,3-difluoro-phenyl)-pyrimidin-2-yl]-spiro[1,2-dihydro-indole-3,1'-cyclopropane]-6-yl]-methanone |
| 115 | Q'10 | 2-F | 1 | [(3S)-3-Amino-pyrrolidin-1-yl]-[1-[5-(2-fluorophenyl)-pyrimidin-2-yl]-spiro[1,2-dihydro-indole-3,1'-cyclopropane]-6-yl]-methanone |
| 116 | Q'40 | 2-F, 5-CONH$_2$ | 2 | 4-Fluoro-3-[2-[6-(piperazine-1-carbonyl)-spiro[1,2-dihydro-indole-3,1'-cyclopropane]-1-yl]-pyrimidin-5-yl]-benzamide |
| 117 | Q'7 | 2-F | 1 | [1-[5-(2-Fluorophenyl)-pyrimidin-2-yl]-spiro[1,2-dihydro-indole-3,1'-cyclopropane]-6-yl]-(7-methyl-2,7-diazaspiro[3.4]octan-2-yl)-methanone |
| 118 | Q'9 | 3-CONH$_2$ | 1 | 3-[2-[6-[(3R)-3-Amino-pyrrolidine-1-carbonyl]-spiro[1,2-dihydro-indole-3,1'-cyclopropane]-1-yl]-pyrimidin-5-yl]-benzamide |
| 119 | Q'40 | 2-F, 4-CONH$_2$ | 2 | 3-Fluoro-4-[2-[6-(piperazine-1-carbonyl)-spiro[1,2-dihydro-indole-3,1'-cyclopropane]-1-yl]-pyrimidin-5-yl]-benzamide |
| 120 | Q'5 | 2-F | 1 | [1-[5-(2-Fluorophenyl)-pyrimidin-2-yl]-spiro[1,2-dihydro-indole-3,1'-cyclopropane]-6-yl]-(6-methyl-2,6-diazaspiro[3.3]heptan-2-yl)-methanone |
| 121 | Q'11 | 2-F | 1 | [1-[5-(2-Fluorophenyl)-pyrimidin-2-yl]-spiro[1,2-dihydro-indole-3,1'-cyclopropane]-6-yl]-[(3R)-3-methylamino-pyrrolidin-1-yl]-methanone |
| 122 | Q'40 | 2-CONH$_2$, 5-OMe | 2 | 4-Methoxy-2-[2-[6-(piperazine-1-carbonyl)-spiro[1,2-dihydro-indole-3,1'-cyclopropane]-1-yl]-pyrimidin-5-yl]-benzamide |
| 123 | Q'9 | 2-F, 5-CN | 2 | 3-[2-[6-[(3R)-3-Amino-pyrrolidine-1-carbonyl]-spiro[1,2-dihydro-indole-3,1'-cyclopropane]-1-yl]-pyrimidin-5-yl]-4-fluoro-benzonitrile |
| 124 | M28; with $R^1$ = CH$_3$ | — | 0 | N,N-Dimethyl-1-(5-phenyl-pyrimidin-2-yl)-spiro[1,2-dihydro-indole-3,1'-cyclopropane]-6-carboxylic acid amide |
| 125 | M28; with $R^1$ = CH$_3$ | 3-F | 1 | 1-[5-(3-Fluorophenyl)-pyrimidin-2-yl]-N,N-dimethyl-spiro[1,2-dihydro-indole-3,1'-cyclopropane]-6-carboxylic acid amide |
| 126 | M1; with $R^1$ = CH$_3$ | 3-F, 5-F | 2 | 1-[5-(3,5-Difluoro-phenyl)-pyrimidin-2-yl]-N-(2-hydroxy-ethyl)-N-methyl-spiro[1,2-dihydro-indole-3,1'-cyclopropane]-6-carboxylic acid amide |
| 127 | M27; with $R^1$ = H | 2-F | 1 | 1-[5-(2-Fluorophenyl)-pyrimidin-2-yl]-spiro[1,2-dihydro-indole-3,1'-cyclopropane]-6-carboxylic acid amide |
| 128 | Q'41 | 3-F, 5-F | 2 | 4-[1-[5-(3,5-Difluoro-phenyl)-pyrimidin-2-yl]-spiro[1,2-dihydro-indole-3,1'-cyclopropane]-6-carbonyl]-piperazin-2-one |
| 129 | M1; with $R^1$ = CH$_3$ | 3-F | 1 | 1-[5-(3-Fluorophenyl)-pyrimidin-2-yl]-N-(2-hydroxy-ethyl)-N-methyl-spiro[1,2-dihydro-indole-3,1'-cyclopropane]-6-carboxylic acid amide |
| 130 | Q'8 | 3-F | 1 | [1-[5-(3-Fluorophenyl)-pyrimidin-2-yl]-spiro[1,2-dihydro-indole-3,1'-cyclopropane]-6-yl]-pyrrolidin-1-yl-methanone |

TABLE 2

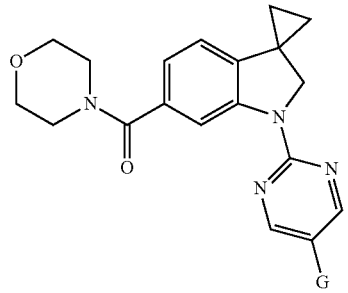

(I-c)

with L = bond

| Cpd. No. | G | Z | R¹² | k | Name |
|---|---|---|---|---|---|
| 131 | G11 | 5-Cl | — | 1 | [1-[5-(5-Chloro-thiophen-2-yl)-pyrimidin-2-yl]-spiro[1,2-dihydro-indole-3,1'-cyclopropane]-6-yl]-morpholin-4-yl-methanone |
| 132 | G12 | 2-Cl | — | 1 | [1-[5-(2-Chloro-thiophen-3-yl)-pyrimidin-2-yl]-spiro[1,2-dihydo-indole-3,1'-cyclopropane]-6-yl]-morpholin-4-yl-methanone |
| 133 | G11 | 3-Cl | — | 1 | [1-[5-(3-Chloro-thiophen-2-yl)-pyrimidin-2-yl]-spiro[1,2-dihydro-indole-3,1'-cyclopropane]-6-yl]-morpholin-4-yl-methanone |
| 134 | G37 | 3-CF₃ | Me | 1 | [1-[5-[2-Methyl-5-(trifluoromethyl)-2H-pyrazol-3-yl]-pyrimidin-2-yl]-spiro[1,2-dihydro-indole-3,1'-cyclopropane]-6-yl]-morpholin-4-yl-methanone |
| 135 | G25 | 3-Me, 5-Me | — | 2 | [1-[5-(3,5-Dimethyl-isoxazol-4-yl)-pyrimidin-2-yl]-spiro[1,2-di-hydro-indole-3,1'-cyclopropane]-6-yl]-morpholin-4-yl-methanone |
| 136 | G36 | — | Me | 0 | [1-[5-(1-Methyl-1H-pyrrol-3-yl)-pyrimidin-2-yl]-spiro[1,2-dihydro-indole-3,1'-cyclopropane]-6-yl]-morpholin-4-yl-methanone |
| 137 | G38 | — | Me | 0 | [1-[5-(1-Methyl-1H-pyrazol-3-yl)-pyrimidin-2-yl]-spiro[1,2-dihydro-indole-3,1'-cyclopropane]-6-yl]-morpholin-4-yl-methanone |
| 138 | G39 | — | Me | 0 | [1-[5-(1-Methyl-1H-pyrazol-4-yl)-pyrimidin-2-yl]-spiro[1,2-dihydro-indole-3,1'-cyclopropane]-6-yl]-morpholin-4-yl-methanone |
| 139 | G11 | 3-OMe | — | 1 | [1-[5-(3-Methoxy-thiophen-2-yl)-pyrimidin-2-yl]-spiro[1,2-dihydro-indole-3,1'-cyclopropane]-6-yl]-morpholin-4-yl-methanone |
| 140 | G39 | 5-CF₃ | H | 1 | Morpholin-4-yl-[1-[5-[5-(trifluoromethyl)-1H-pyrazol-4-yl]-pyrimidin-2-yl]-spiro[1,2-dihydro-indole-3,1'-cyclopropane]-6-yl]-methanone |
| 141 | G35 | — | Me | 0 | [1-[5-(1-Methyl-1H-pyrrol-2-yl)-pyrimidin-2-yl]-spiro[1,2-dihydro-indole-3,1'-cyclopropane]-6-yl]-morpholin-4-yl-methanone |
| 142 | G13 | 5-CH₂OH | — | 1 | [1-[5-[5-(Hydroxymethyl)-furan-2-yl]-pyrimidin-2-yl]-spiro[1,2-di-hydro-indole-3,1'-cyclopropane]-6-yl]-morpholin-4-yl-methanone |
| 143 | G11 | 5-CN | — | 2 | 5-[2-[6-(Morpholine-4-carbonyl)-spiro[1,2-dihydro-indole-3,1'-cyclopropane]-1-yl]-pyrimidin-5-yl]-thiophene-2-carbonitrile |
| 144 | G39 | 3-Me, 5-Me | H | 2 | [1-[5-(3,5-Dimethyl-1H-pyrazol-4-yl)-pyrimidin-2-yl]-spiro[1,2-di-hydro-indole-3,1'-cyclopropane]-6-yl]-morpholin-4-yl-methanone |
| 145 | G3 | 2-F | — | 1 | [1-[5-(2-Fluoro-pyridin-3-yl)-pyrimidin-2-yl]-spiro[1,2-dihydro-indole-3,1'-cyclopropane]-6-yl]-morpholin-4-yl-methanone |
| 146 | G4 | — | — | 0 | Morpholin-4-yl-[1-(5-pyridin-4-yl-pyrimidin-2-yl)-spiro[1,2-dihydro-indole-3,1'-cyclopropane]-6-yl]-methanone |
| 147 | G4 | 3-F | — | 1 | [1-[5-(3-Fluoro-pyridin-4-yl)-pyrimidin-2-yl]-spiro[1,2-dihydro-indole-3,1'-cyclopropane]-6-yl]-morpholin-4-yl-methanone |
| 148 | G11 | 5-F | — | 1 | [1-[5-(5-Fluoro-thiophen-2-yl)-pyrimidin-2-yl]-spiro[1,2-dihydro-indole-3,1'-cyclopropane]-6-yl]-morpholin-4-yl-methanone |
| 149 | G11 | 5-CH₂OH | — | 1 | [1-[5-[5-(Hydroxymethyl)-thiophen-2-yl]-pyrimidin-2-yl]-spiro[1,2-dihydro-indole-3,1'-cyclopropane]-6-yl]-morpholin-4-yl-methanone |
| 150 | G2 | — | — | 0 | Morpholin-4-yl-[1-(5-pyridin-2-yl-pyrimidin-2-yl)-spiro[1,2-dihydro-indole-3,1'-cyclopropane]-6-yl]-methanone |
| 151 | G2 | 6-F | — | 1 | [1-[5-(6-Fluoro-pyridin-2-yl)-pyrimidin-2-yl]-spiro[1,2-dihydro-indole-3,1'-cyclopropane]-6-yl]-morpholin-4-yl-methanone |
| 152 | G11 | 5-CONH₂ | — | 1 | 5-[2-[6-(Morpholine-4-carbonyl)-spiro[1,2-dihydro-indole-3,1'-cyclopropane]-1-yl]-pyrimidin-5-yl]-thiophene-2-carboxylic acid amide |
| 153 | G11 | 3-CN | — | 1 | 2-[2-[6-(Morpholine-4-carbonyl)-spiro[1,2-dihydro-indole-3,1'-cyclopropane]-1-yl]-pyrimidin-5-yl]-thiophene-3-carbonitrile |
| 154 | G16 | 2-Me, 4-Me | — | 2 | [1-[5-(2,4-Dimethyl-thiazol-5-yl)-pyrimidin-2-yl]-spiro[1,2-dihydro-indole-3,1'-cyclopropane]-6-yl]-morpholin-4-yl-methanone |
| 155 | G21 | 3-Me | — | 1 | [1-[5-(3-Methyl-isothiazol-5-yl)-pyrimidin-2-yl]-spiro[1,2-dihydro-indole-3,1'-cyclopropane]-6-yl]-morpholin-4-yl-methanone |
| 156 | G13 | 5-CONH₂ | — | 1 | 5-[2-[6-(Morpholine-4-carbonyl)-spiro[1,2-dihydro-indole-3,1'-cyclopropane]-1-yl]-pyrimidin-5-yl]-furan-2-carboxylic acid amide |
| 157 | G3 | 5-F | — | 1 | [1-[5-(5-Fluoro-pyridin-3-yl)-pyrimidin-2-yl]-spiro[1,2-dihydro-indole-3,1'-cyclopropane]-6-yl]-morpholin-4-yl-methanone |
| 158 | G11 | 5-NHCOMe | — | 1 | N-[5-[2-[6-Morpholine-4-carbonyl)-spiro[1,2-dihydro-indole-3,1'-cyclopropane]-1-yl]-pyrimidin-5-yl]-thiophen-2-yl]-acetamide |

TABLE 2-continued (I-c)

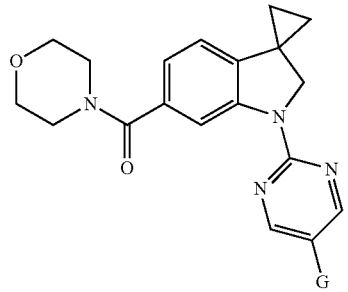

with L = bond

| Cpd. No. | G | Z | R¹² | k | Name |
|---|---|---|---|---|---|
| 159 | G4 | 2-Me | — | 1 | [1-[5-(2-Methyl-pyridin-4-yl)-pyrimidin-2-yl]-spiro[1,2-dihydro-indole-3,1'-cyclopropane]-6-yl]-morpholin-4-yl-methanone |
| 160 | G4 | 2-F | — | 1 | [1-[5-(2-Fluoro-pyridin-4-yl)-pyrimidin-2-yl]-spiro[1,2-dihydro-indole-3,1'-cyclopropane]-6-yl]-morpholin-4-yl-methanone |
| 161 | G11 | 4-CN | — | 1 | 5-[2-[6-(Morpholine-4-carbonyl)-spiro[1,2-dihydro-indole-3,1'-cyclopropane]-1-yl]-pyrimidin-5-yl]-thiophene-3-carbonitrile |
| 162 | G9 | — | — | 0 | Morpholin-4-yl-[1-(5-pyrimidin-5-yl-pyrimidin-2-yl)-spiro[1,2-dihydro-indole-3,1'-cyclopropane]-6-yl]-methanone |
| 163 | G3 | 2-F, 5-F | — | 2 | [1-[5-(2,5-Difluoro-pyridin-3-yl)-pyrimidin-2-yl]-spiro[1,2-dihydro-indole-3,1'-cyclopropane]-6-yl]-morpholin-4-yl-methanone |
| 164 | G2 | 4-CONH₂ | — | 1 | 2-[2-[6-(Morpholine-4-carbonyl)-spiro[1,2-dihydro-indole-3,1'-cyclopropane]-1-yl]-pyrimidin-5-yl]-pyridine-4-carboxylic acid amide |
| 165 | G2 | 5-F | — | 1 | [1-[5-(5-Fluoro-pyridin-2-yl)-pyrimidin-2-yl]-spiro[1,2-dihydro-indole-3,1'-cyclopropane]-6-yl]-morpholin-4-yl-methanone |
| 166 | G4 | 3-F, 5-F | — | 2 | [1-[5-(3,5-Difluoro-pyridin-4-yl)-pyrimidin-2-yl]-spiro[1,2-dihydro-indole-3,1'-cyclopropane]-6-yl]-morpholin-4-yl-methanone |
| 167 | G3 | 2-Me | — | 1 | [1-[5-(2-Methyl-pyridin-3-yl)-pyrimidin-2-yl]-spiro[1,2-dihydro-indole-3,1'-cyclopropane]-6-yl]-morpholin-4-yl-methanone |
| 181 | G2 | 4-NH₂ | — | 1 | [1-[5-(4-Amino-pyridin-2-yl)-pyrimidin-2-yl]-spiro[1,2-dihydro-indole-3,1'-cyclopropane]-6-yl]-morpholin-4-yl-methanone |
| 182 | G2 | 4-OMe | — | 1 | [1-[5-(4-Methoxy-pyridin-2-yl)-pyrimidin-2-yl]-spiro[1,2-dihydro-indole-3,1'-cyclopropane]-6-yl]-morpholin-4-yl-methanone |
| 185 | G8 | 2-Me | — | 1 | [1-[5-(2-Methyl-pyrimidin-4-yl)-pyrimidin-2-yl]-spiro[1,2-dihydro-indole-3,1'-cyclopropane]-6-yl]-morpholin-4-yl-methanone |
| 186 | G2 | 6-Me | — | 1 | [1-[5-(6-Methyl-pyridin-2-yl)-pyrimidin-2-yl]-spiro[1,2-dihydro-indole-3,1'-cyclopropane]-6-yl]-morpholin-4-yl-methanone |
| 187 | G2 | 4-F | — | 1 | [1-[5-(4-Fluoro-pyridin-2-yl)-pyrimidin-2-yl]-spiro[1,2-dihydro-indole-3,1'-cyclopropane]-6-yl]-morpholin-4-yl-methanone |
| 190 | G8 | — | — | 1 | Morpholin-4-yl-[1-[5-pyrimidin-4-yl-pyrimidin-2-yl)-spiro[1,2-dihydro-indole-3,1'-cyclopropane]-6-yl]-methanone |
| 191 | G5 | — | — | 1 | Morpholin-4-yl-[1-[5-pyridazin-3-yl-pyrimidin-2-yl)-spiro[1,2-dihydro-indole-3,1'-cyclopropane]-6-yl]-methanone |
| 192 | G2 | 4-Me | — | 1 | [1-[5-(4-Methyl-pyridin-2-yl)-pyrimidin-2-yl]-spiro[1,2-dihydro-indole-3,1'-cyclopropane]-6-yl]-morpholin-4-yl-methanone |
| 194 | G2 | 4-CF₃ | — | 1 | 1-[5-(3-Cyano-phenyl)-pyrimidin-2-yl]-N-(2-hydroxy-ethyl)-N-methyl-spiro[1,2-dihydro-indole-3,1'-cyclopropane]-6-carboxylic acid amide |
| 195 | G5 | 6-Me | — | 1 | Morpholin-4-yl-[1-[5-[4-(trifluoromethyl)-pyridin-2-yl]-pyrimidin-2-yl]-spiro[1,2-dihydro-indole-3,1'-cyclopropane]-6-yl]-methanone |
| 196 | G2 | 4-OH | — | 1 | [1-[5-(6-Methyl-pyridazin-3-yl)-pyrimidin-2-yl]-spiro[1,2-dihydro-indole-3,1'-cyclopropane]-6-yl]-morpholin-4-yl-methanone |
| 200 | G6 | — | — | — | Morpholin-4-yl-[1-[5-pyridazin-4-yl-pyrimidin-2-yl)-spiro[1,2-dihydro-indole-3,1'-cyclopropane]-6-yl]-methanone |
| 201 | G5 | 6-OMe | — | 1 | [1-[5-(6-Methoxy-pyridazin-3-yl)-pyrimidin-2-yl]-spiro[1,2-dihydro-indole-3,1'-cyclopropane]-6-yl]-morpholin-4-yl-methanone |
| 205 | G8 | 6-F | — | 1 | [1-[5-(6-Fluoro-pyrimidin-4-yl)-pyrimidin-2-yl]-spiro[1,2-dihydro-indole-3,1'-cyclopropane]-6-yl]-morpholin-4-yl-methanone |
| 206 | G8 | 6-Cl | — | 1 | [1-[5-(6-Chloro-pyrimidin-4-yl)-pyrimidin-2-yl]-spiro[1,2-dihydro-indole-3,1'-cyclopropane]-6-yl]-morpholin-4-yl-methanone |
| 207 | G11 | 5-C(CH₃)₂OH | — | 1 | [1-[5-[5-(1-Hydroxy-1-methyl-ethyl)-thiophen-2-yl]-pyrimidin-2-yl]-spiro[1,2-dihydro-indole-3,1'-cyclopropane]-6-yl]-morpholin-4-yl-methanone |
| 208 | G2 | 4-NMe₂ | — | 1 | [1-[5-(4-Dimethylamino-pyridin-2-yl)-pyrimidin-2-yl]-spiro[1,2-dihydro-indole-3,1'-cyclopropane]-6-yl]-morpholin-4-yl-methanone |

TABLE 3

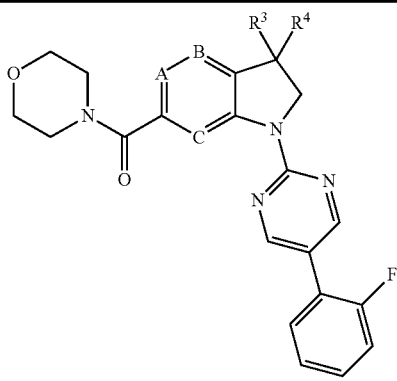

| Cpd No. | A | B | C | R³/R⁴ | Name |
|---|---|---|---|---|---|
| 9 | CH | CH | CH | Me/Me | [1-[5-(2-Fluorophenyl)-pyrimidin-2-yl]-3,3-dimethyl-1,2-dihydro-indol-6-yl]-morpholin-4-yl-methanone |
| 168 | N | CH | CH | together with connecting C-atom: cyclo-propyl | [1-[5-(2-Fluorophenyl)-pyrimidin-2-yl]-spiro[1,2-dihydro-pyrrolo[3,2-c]pyridine-3,1'-cyclopropane]-6-yl]-morpholin-4-yl-methanone |
| 169 | CH | N | CH | together with connecting C-atom: cyclo-propyl | [1-[5-(2-Fluorophenyl)-pyrimidin-2-yl]-spiro[1,2-dihydro-pyrrolo[3,2-b]pyridine-3,1'-cyclopropane]-6-yl]-morpholin-4-yl-methanone |
| 170 | CH | CH | N | together with connecting C-atom: cyclo-propyl | [1-[5-(2-Fluorophenyl)-pyrimidin-2-yl]-spiro[1,2-dihydro-pyrrolo[2,3-b]pyridine-3,1'-cyclopropane]-6-yl]-morpholin-4-yl-methanone |
| 171 | CH | CH | CH | together with connecting C-atom: cyclo-butyl | [1-[5-(2-Fluorophenyl)-pyrimidin-2-yl]-spiro[1,2-dihydro-pyrrolo[2,3-b]pyridine-3,1'-cyclobutane]-6-yl]-morpholin-4-yl-methanone |

TABLE 4

(I-a)

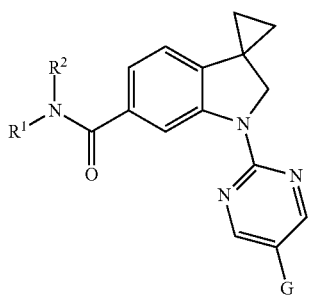

with L = bond

| Cpd No. | R¹, R² | G | R¹² | Z | k | Name |
|---|---|---|---|---|---|---|
| 172 | Q'11 | G36 | Me | — | 0 | [(3R)-3-Amino-pyrrolidin-1-yl]-[1-[5-(1-methyl-1H-pyrrol-3-yl)-pyrimidin-2-yl]-spiro[1,2-dihydro-indole-3,1'-cyclopropane]-6-yl]-methanone |
| 173 | Q'11 | G39 | Me | — | 0 | [(3R)-3-Amino-pyrrolidin-1-yl]-[1-[5-(1-methyl-1H-pyrazol-4-yl)-pyrimidin-2-yl]-spiro[1,2-dihydro-indole-3,1'-cyclopropane]-6-yl]-methanone |
| 174 | M28; R¹ = CH₃ | G3 | — | 2-F | 1 | 1-[5-(2-Fluoro-pyridin-3-yl)-pyrimidin-2-yl]-N,N-dimethyl-spiro[1,2-dihydro-indole-3,1'-cyclopropane]-6-carboxylic acid amide |
| 175 | Q'8 | G2 | — | — | 0 | [1-(5-Pyridin-2-yl-pyrimidin-2-yl)-spiro[1,2-dihydro-indole-3,1'-cyclopropane]-6-yl]-pyrrolidin-1-yl-methanone |
| 176 | Q'41 | G3 | — | 2-F | 1 | 4-[1-[5-(2-Fluoro-pyridin-3-yl)-pyrimidin-2-yl]-spiro[1,2-dihydro-indole-3,1'-cyclopropane]-6-carbonyl]-piperazin-2-one |
| 177 | Q'41 | G11 | — | 5-OMe | 1 | 4-[1-[5-(3-Methoxy-thiophen-2-yl)-pyrimidin-2-yl]-spiro[1,2-dihydro-indole-3,1'-cyclopropane]-6-carbonyl]-piperazin-2-one |
| 180 | Q'41 | G2 | — | — | 0 | 4-[1-(5-Pyridin-2-yl-pyrimidin-2-yl)-spiro[1,2-dihydro-indole-3,1'-cyclopropane]-6-carbonyl]-piperazin-2-one |

TABLE 4-continued

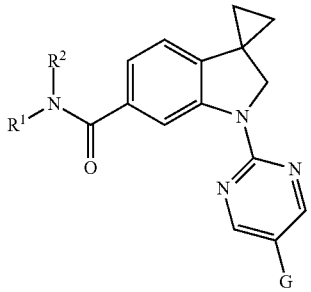

(I-a)

with L = bond

| Cpd No. | R¹, R² | G | R¹² | Z | k | Name |
|---|---|---|---|---|---|---|
| 188 | Q'41 | G1 | — | 2-F | 1 | 4-[1-[5-(3-Fluorophenyl)-pyrimidin-2-yl]-spiro[1,2-dihydro-indole-3,1'-cyclopropane]-6-carbonyl]-piperazin-2-one |
| 189 | Q'41 | G1 | — | 3-OMe | 1 | 4-[1-[5-(3-Methoxyphenyl)-pyrimidin-2-yl]-spiro[1,2-dihydro-indole-3,1'-cyclopropane]-6-carbonyl]-piperazin-2-one |
| 193 | M1; R¹ = CH₃ | G1 | — | 3-CN | 1 | 1-[5-(3-Cyano-phenyl)-pyrimidin-2-yl]-N-(2-hydroxy-ethyl)-N-methyl-spiro[1,2-dihydro-indole-3,1'-cyclopropane]-6-carboxylic acid amide |
| 197 | M1; R¹ = CH₃ | G1 | — | 3-OMe | 1 | N-(2-Hydroxy-ethyl)-1-[5-(3-methoxyphenyl)-pyrimidin-2-yl]-N-methyl-spiro[1,2-dihydro-indole-3,1'-cyclopropane]-6-carboxylic acid amide |
| 198 | M1; R¹ = CH₃ | G1 | — | 3-CONH₂ | 1 | 1-[5-(3-Carbamoyl-phenyl)-pyrimidin-2-yl]-N-(2-hydroxy-ethyl)-N-methyl-spiro[1,2-dihydro-indole-3,1'-cyclopropane]-6-carboxylic acid amide |
| 199 | M1; R¹ = CH₃ | G39 | Me | — | — | N-(2-Hydroxy-ethyl)-N-methyl-1-[5-(1-methyl-1H-pyrazol-4-yl)-pyrimidin-2-yl]-spiro[1,2-dihydro-indole-3,1'-cyclopropane]-6-carboxylic acid amide |
| 202 | Q'43 | G1 | — | — | 0 | 4-[1-(5-Phenyl-pyrimidin-2-yl)-spiro[1,2-dihydro-indole-3,1'-cyclopropane]-6-carbonyl]-piperazine-2,6-dione |
| 203 | Q'15 | G1 | — | — | 0 | N-[(3R)-1-[1-(5-Phenyl-pyrimidin-2-yl)-spiro[1,2-di-hydro-indole-3,1'-cyclopropane]-6-carbonyl]-pyrrolidin-3-yl]-acetamide |
| 204 | Q'15 | G1 | — | 2-F | 1 | N-[(3R)-1-[1-[5-(2-Fluorophenyl)-pyrimidin-2-yl]-spiro[1,2-dihydro-indole-3,1'-cyclopropane]-6-carbonyl]-pyrrolidin-3-yl]-acetamide |

TABLE 5

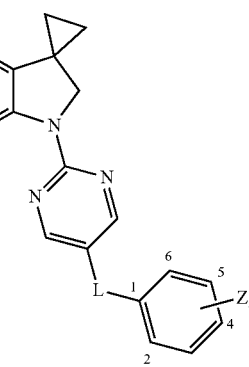

| Compound No. | L | Z | k | Name |
|---|---|---|---|---|
| 178 | CH₂ | 2-F | 1 | [1-[5-[(2-Fluorophenyl)-methyl]-pyrimidin-2-yl]-spiro[1,2-dihydro-indole-3,1'-cyclopropane]-6-yl]-morpholin-4-yl-methanone |

TABLE 5-continued

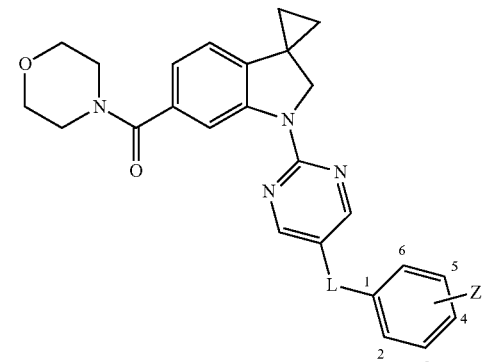

| Compound No. | L | Z | k | Name |
|---|---|---|---|---|
| 179 | O | 2-F | 1 | [1-[5-(2-Fluoro-phenoxy)-pyrimidin-2-yl]-spiro[1,2-dihydro-indole-3,1'-cyclopropane]-6-yl]-morpholin-4-yl-methanone |

TABLE 6

| Cpd No. | Structure | Name |
|---|---|---|
| 209 | 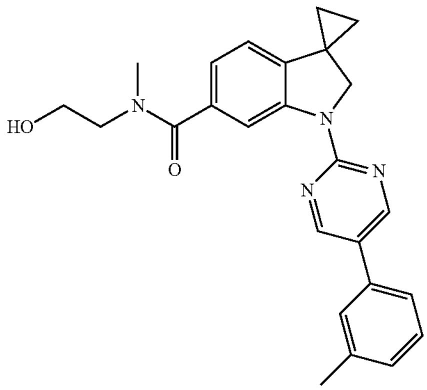 [SMILES: Cc1cccc(-c2cnc(N3CC4(CC4)c4ccc(C(=O)N(C)CCO)cc43)nc2)c1] | N-(2-Hydroxy-ethyl)-N-methyl-1-(5-m-tolyl-pyrimidin-2-yl)-spiro[1,2-dihydro-indole-3,1'-cyclopropane]-6-carboxylic acid amide |
| 210 | 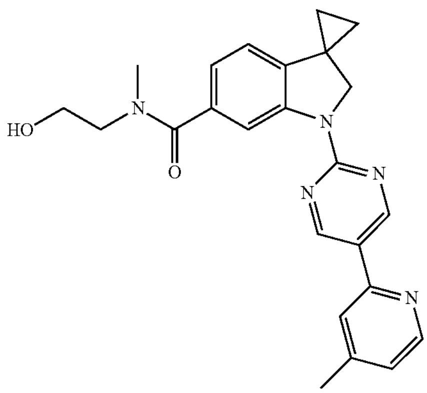 [SMILES: Cc1ccnc(-c2cnc(N3CC4(CC4)c4ccc(C(=O)N(C)CCO)cc43)nc2)c1] | N-(2-Hydroxy-ethyl)-N-methyl-1-[5-(4-methyl-pyridin-2-yl)-pyrimidin-2-yl]-spiro[1,2-dihydro-indole-3,1'-cyclopropane]-6-carboxylic acid amide |
| 211 | 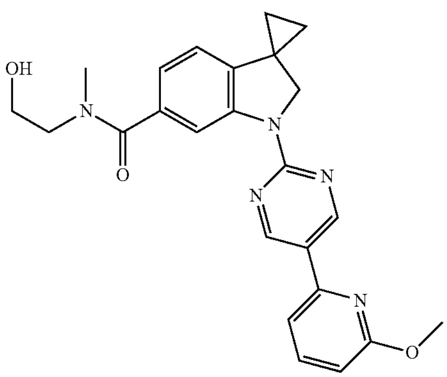 [SMILES: COc1cccc(-c2cnc(N3CC4(CC4)c4ccc(C(=O)N(C)CCO)cc43)nc2)n1] | N-(2-Hydroxy-ethyl)-1-[5-(6-methoxy-pyridin-2-yl)-pyrimidin-2-yl]-N-methyl-spiro[1,2-dihydro-indole-3,1'-cyclopropane]-6-carboxylic acid amide |
| 212 | 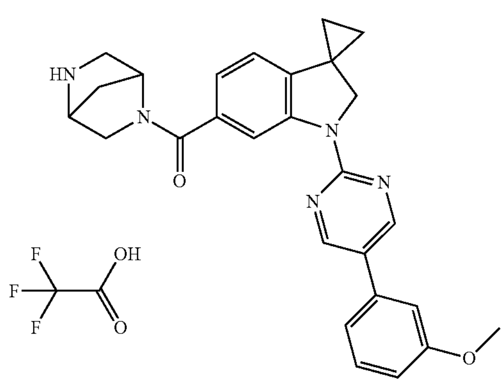 [SMILES: O=C(O)C(F)(F)F ; COc1cccc(-c2cnc(N3CC4(CC4)c4ccc(C(=O)N5CC6CC5CN6)cc43)nc2)c1] | (2,5-Diazabicyclo[2.2.1]heptan-2-yl)-[1-[5-(3-methoxyphenyl)-pyrimidin-2-yl]-spiro[1,2-dihydro-indole-3,1'-cyclopropane]-6-yl]-methanone; 2,2,2-trifluoro-acetic acid |

TABLE 6-continued

| Cpd No. | Structure | Name |
|---|---|---|
| 213 | 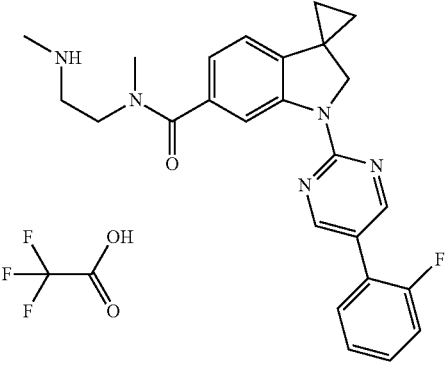 [SMILES: O=C(O)C(F)(F)F ; CNCCN(C)C(=O)c1ccc2c(c1)N(c1ncc(-c3ccccc3F)cn1)CC21CC1] | 1-[5-(2-Fluorophenyl)-pyrimidin-2-yl]-N-methyl-N-(2-methylamino-ethyl)-spiro[1,2-dihydro-indole-3,1'-cyclopropane]-6-carboxylic acid amide; 2,2,2-trifluoro-acetic acid |
| 214 | 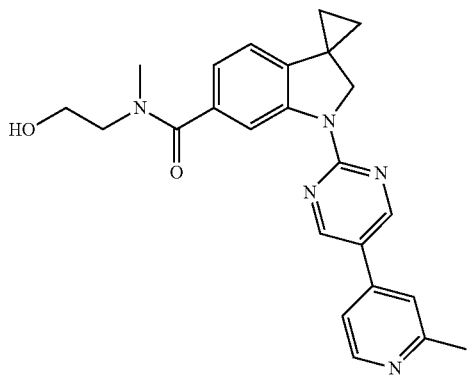 [SMILES: Cc1cc(-c2cnc(N3CC4(CC4)c4ccc(C(=O)N(C)CCO)cc43)nc2)ccn1] | N-(2-Hydroxy-ethyl)-N-methyl-1-[5-(2-methyl-pyridin-4-yl)-pyrimidin-2-yl]-spiro[1,2-dihydro-indole-3,1'-cyclopropane]-6-carboxylic acid amide |
| 215 | 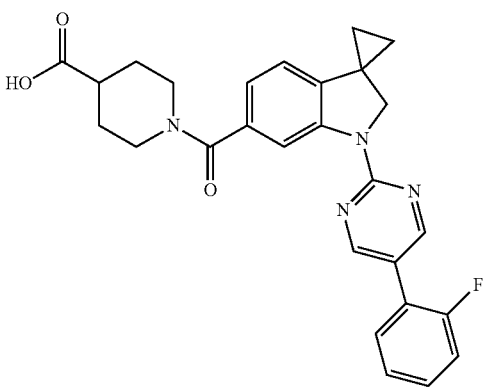 [SMILES: O=C(O)C1CCN(C(=O)c2ccc3c(c2)N(c2ncc(-c4ccccc4F)cn2)CC32CC2)CC1] | 1-[1-[5-(2-Fluorophenyl)-pyrimidin-2-yl]-spiro[1,2-dihydro-indole-3,1'-cyclopropane]-6-carbonyl]-piperidine-4-carboxylic acid |
| 216 | 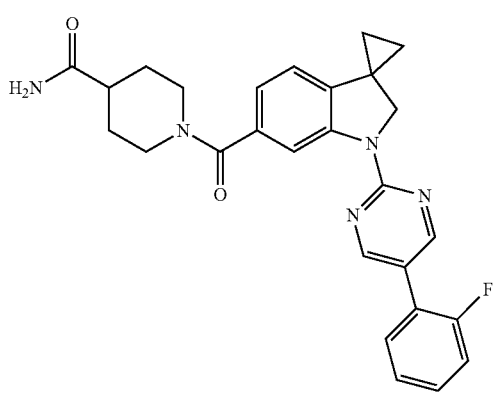 [SMILES: NC(=O)C1CCN(C(=O)c2ccc3c(c2)N(c2ncc(-c4ccccc4F)cn2)CC32CC2)CC1] | 1-[1-[5-(2-Fluorophenyl)-pyrimidin-2-yl]-spiro[1,2-dihydro-indole-3,1'-cyclopropane]-6-carbonyl]-piperidine-4-carboxylic acid amide |

TABLE 6-continued

| Cpd No. | Structure | Name |
|---|---|---|
| 217 | 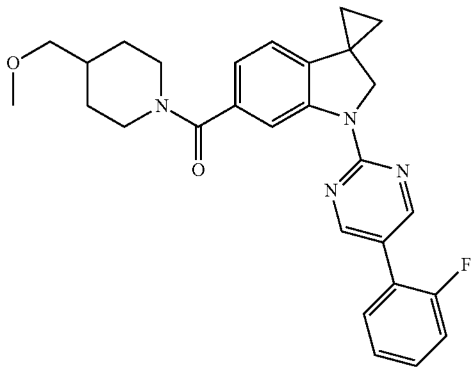 [SMILES: COCC1CCN(C(=O)c2ccc3c(c2)N(c2ncc(-c4ccccc4F)cn2)CC32CC2)CC1] | [1-[5-(2-Fluorophenyl)-pyrimidin-2-yl]-spiro[1,2-dihydro-indole-3,1'-cyclopropane]-6-yl]-[4-(methoxymethyl)-piperidin-1-yl]-methanone |
| 218 | 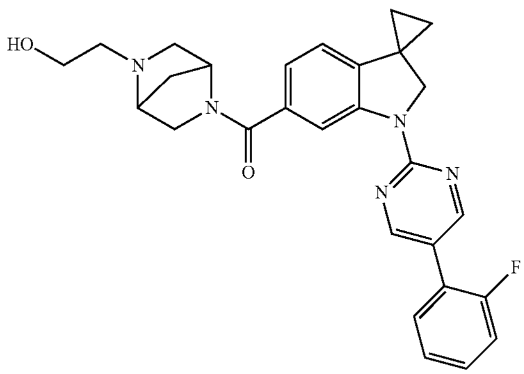 [SMILES: O=C(c1ccc2c(c1)N(c1ncc(-c3ccccc3F)cn1)CC21CC1)N1CC2CC1CN2CCO] | [1-[5-(2-Fluorophenyl)-pyrimidin-2-yl]-spiro[1,2-dihydro-indole-3,1'-cyclopropane]-6-yl]-[5-(2-hydroxy-ethyl)-2,5-diazabicyclo[2.2.1]heptan-2-yl]-methanone |
| 219 | 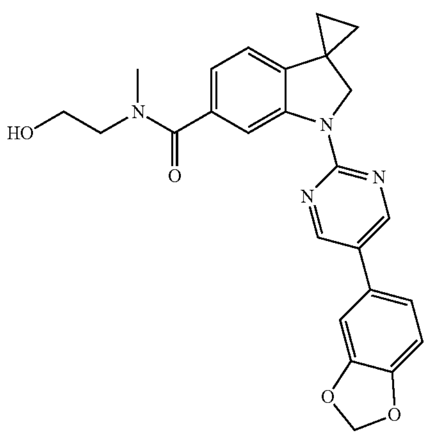 [SMILES: CN(CCO)C(=O)c1ccc2c(c1)N(c1ncc(-c3ccc4c(c3)OCO4)cn1)CC21CC1] | 1-[5-(1,3-Benzodioxol-5-yl)-pyrimidin-2-yl]-N-(2-hydroxy-ethyl)-N-methyl-spiro[1,2-dihydro-indole-3,1'-cyclopropane]-6-carboxylic acid amide |
| 220 | 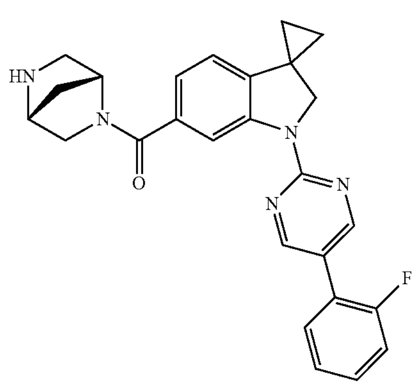 [SMILES: O=C(c1ccc2c(c1)N(c1ncc(-c3ccccc3F)cn1)CC21CC1)N1C[C@H]2C[C@@H]1CN2] | [(1R,4R)-2,5-Diazabicyclo[2.2.1]heptan-2-yl]-[1-[5-(2-fluorophenyl)-pyrimidin-2-yl]-spiro[1,2-dihydro-indole-3,1'-cyclopropane]-6-yl]-methanone |

TABLE 6-continued

| Cpd No. | Structure | Name |
|---|---|---|
| 221 | 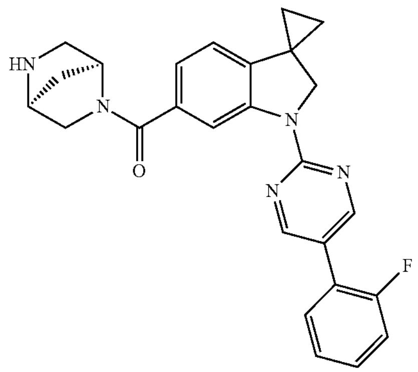 [SMILES: O=C(c1ccc2c(c1)N(c1ncc(-c3ccccc3F)cn1)CC21CC1)N1C[C@@H]2C[C@H]1CN2] | [(1S,4S)-2,5-Diazabicyclo[2.2.1]heptan-2-yl]-[1-[5-(2-fluorophenyl)-pyrimidin-2-yl]-spiro[1,2-dihydro-indole-3,1'-cyclopropane]-6-yl]-methanone |
| 222 | 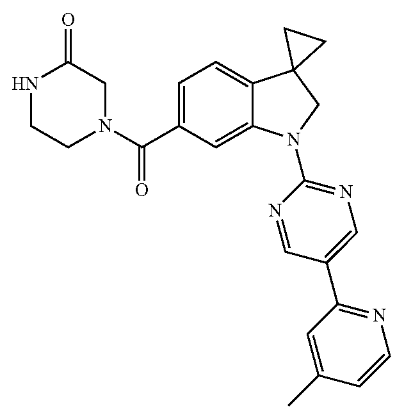 [SMILES: Cc1ccnc(-c2cnc(N3CC4(CC4)c4ccc(C(=O)N5CCNC(=O)C5)cc43)nc2)c1] | 4-[1-[5-(4-Methyl-pyridin-2-yl)-pyrimidin-2-yl]-spiro[1,2-dihydro-indole-3,1'-cyclopropane]-6-carbonyl]-piperazin-2-one |
| 223 | 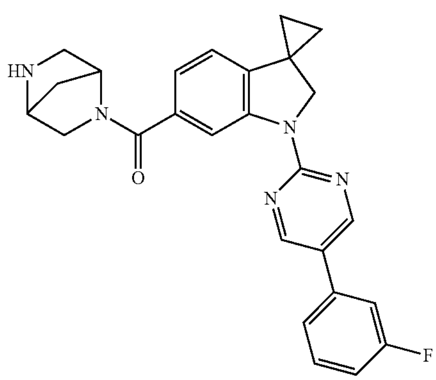 [SMILES: O=C(c1ccc2c(c1)N(c1ncc(-c3cccc(F)c3)cn1)CC21CC1)N1CC2CC1CN2] | (2,5-Diazabicyclo[2.2.1]heptan-2-yl)-[1-[5-(3-fluorophenyl)-pyrimidin-2-yl]-spiro[1,2-dihydro-indole-3,1'-cyclopropane]-6-yl]-methanone |
| 224 | 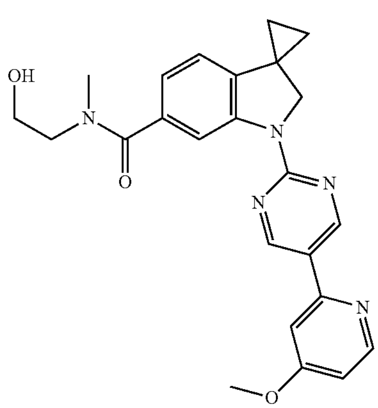 [SMILES: COc1ccnc(-c2cnc(N3CC4(CC4)c4ccc(C(=O)N(C)CCO)cc43)nc2)c1] | N-(2-Hydroxy-ethyl)-1-[5-(4-methoxy-pyridin-2-yl)-pyrimidin-2-yl]-N-methyl-spiro[1,2-dihydro-indole-3,1'-cyclopropane]-6-carboxylic acid amide |

TABLE 6-continued

| Cpd No. | Structure | Name |
|---|---|---|
| 225 | 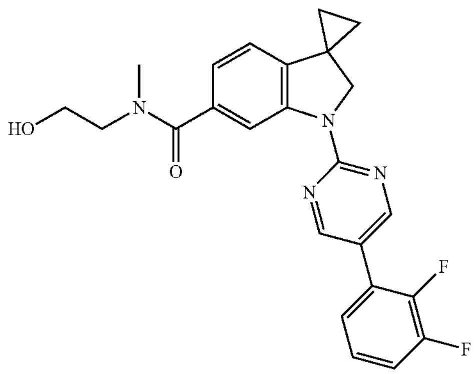 [SMILES: CN(CCO)C(=O)c1ccc2c(c1)N(c1ncc(-c3cccc(F)c3F)cn1)CC21CC1] | 1-[5-(2,3-Difluoro-phenyl)-pyrimidin-2-yl]-N-(2-hydroxy-ethyl)-N-methyl-spiro[1,2-dihydro-indole-3,1'-cyclopropane]-6-carboxylic acid amide |
| 226 | 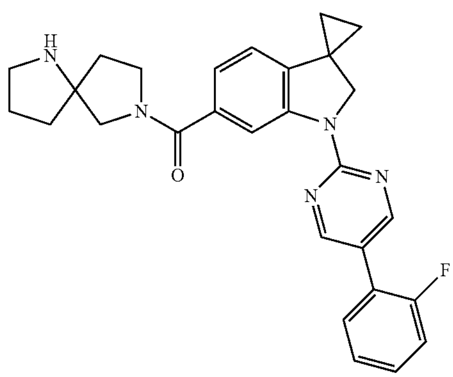 [SMILES: O=C(c1ccc2c(c1)N(c1ncc(-c3ccccc3F)cn1)CC21CC1)N1CCC2(CCCN2)C1] | (1,7-Diazaspiro[4.4]nonan-7-yl)-[1-[5-(2-fluorophenyl)-pyrimidin-2-yl]-spiro[1,2-dihydro-indole-3,1'-cyclopropane]-6-yl]-methanone |
| 227 | 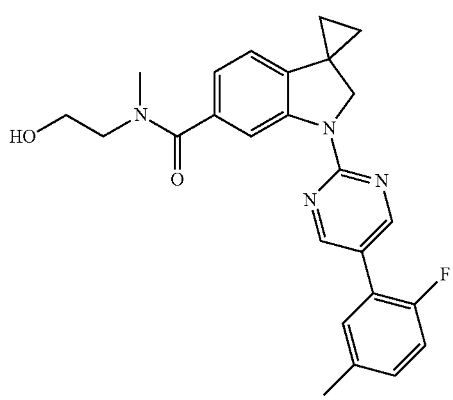 [SMILES: Cc1ccc(F)c(-c2cnc(N3CC4(CC4)c4ccc(C(=O)N(C)CCO)cc43)nc2)c1] | 1-[5-(2-Fluoro-5-methyl-phenyl)-pyrimidin-2-yl]-N-(2-hydroxy-ethyl)-N-methyl-spiro[1,2-dihydro-indole-3,1'-cyclopropane]-6-carboxylic acid amide |
| 228 | 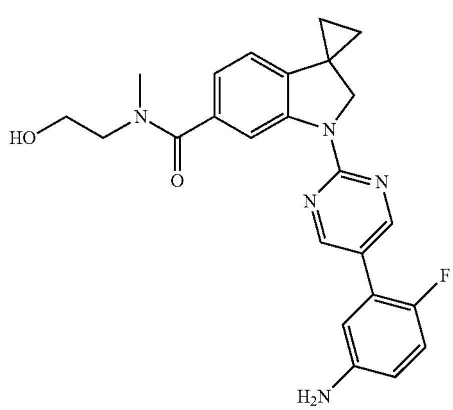 [SMILES: CN(CCO)C(=O)c1ccc2c(c1)N(c1ncc(-c3cc(N)ccc3F)cn1)CC21CC1] | 1-[5-(5-Amino-2-fluoro-phenyl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 229 | 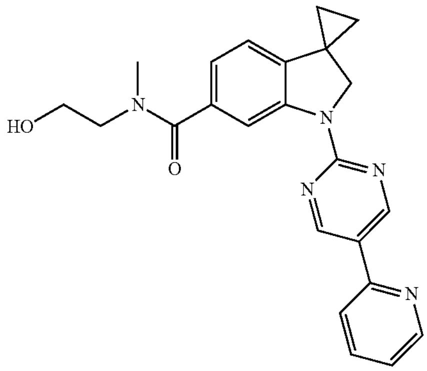 [SMILES: CN(CCO)C(=O)c1ccc2c(c1)N(c1ncc(-c3ccccn3)cn1)CC21CC1] | N-(2-Hydroxy-ethyl)-N-methyl-1-(5-pyridin-2-yl-pyrimidin-2-yl)-spiro[1,2-dihydro-indole-3,1'-cyclopropane]-6-carboxylic acid amide |
| 230 | 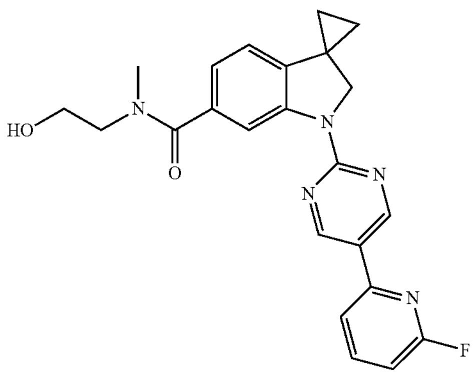 [SMILES: CN(CCO)C(=O)c1ccc2c(c1)N(c1ncc(-c3cccc(F)n3)cn1)CC21CC1] | 1-[5-(6-Fluoro-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 231 | 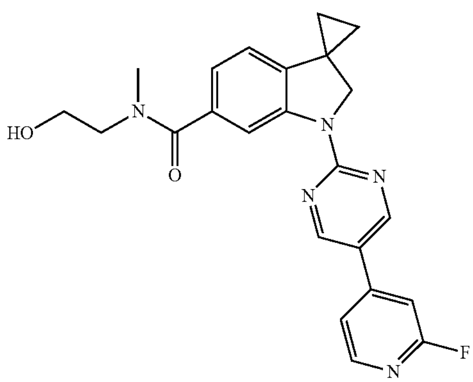 [SMILES: CN(CCO)C(=O)c1ccc2c(c1)N(c1ncc(-c3ccnc(F)c3)cn1)CC21CC1] | 1-[5-(2-Fluoro-pyridin-4-yl)-pyrimidin-2-yl]-N-(2-hydroxy-ethyl)-N-methyl-spiro[1,2-dihydro-indole-3,1'-cyclopropane]-6-carboxylic acid amide |
| 232 | 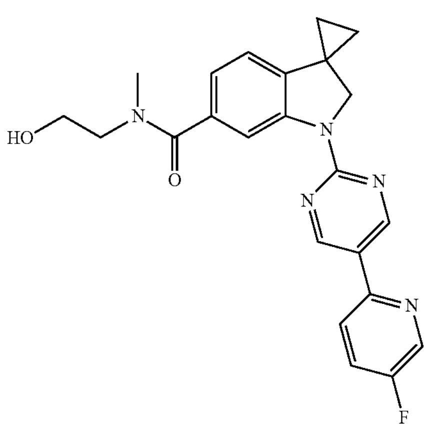 [SMILES: CN(CCO)C(=O)c1ccc2c(c1)N(c1ncc(-c3ccc(F)cn3)cn1)CC21CC1] | 1-[5-(5-Fluoro-pyridin-2-yl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 233 | 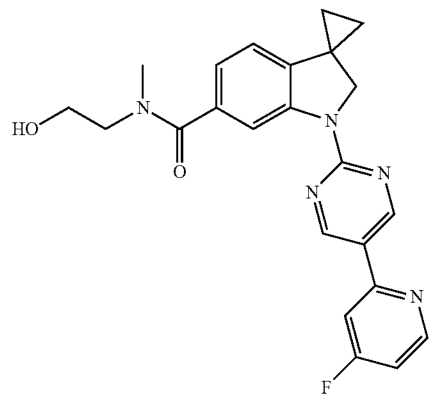 [SMILES: CN(CCO)C(=O)c1ccc2c(c1)N(c1ncc(-c3cc(F)ccn3)cn1)CC21CC1] | 1-[5-(4-Fluoro-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 234 | 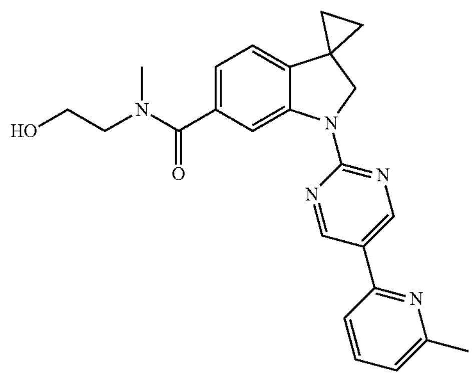 [SMILES: Cc1cccc(-c2cnc(N3CC4(CC4)c4ccc(C(=O)N(C)CCO)cc43)nc2)n1] | N-(2-Hydroxy-ethyl)-N-methyl-1-[5-(6-methyl-pyridin-2-yl)-pyrimidin-2-yl]-spiro[1,2-dihydro-indole-3,1'-cyclopropane]-6-carboxylic acid amide |
| 235 | 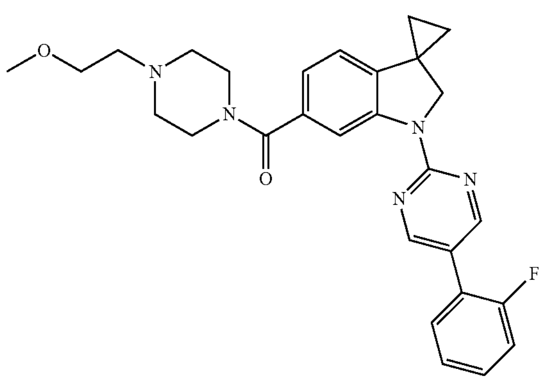 [SMILES: COCCN1CCN(C(=O)c2ccc3c(c2)N(c2ncc(-c4ccccc4F)cn2)CC32CC2)CC1] | [1-[5-(2-Fluorophenyl)-pyrimidin-2-yl]-spiro[1,2-dihydro-indole-3,1'-cyclopropane]-6-yl]-[4-(2-methoxy-ethyl)-piperazin-1-yl]-methanone |
| 236 | 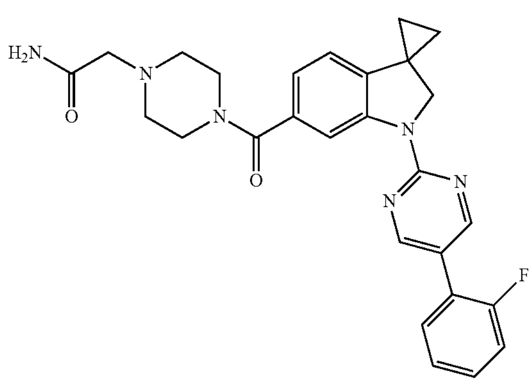 [SMILES: NC(=O)CN1CCN(C(=O)c2ccc3c(c2)N(c2ncc(-c4ccccc4F)cn2)CC32CC2)CC1] | 2-[4-[1-[5-(2-Fluorophenyl)-pyrimidin-2-yl]-spiro[1,2-dihydro-indole-3,1'-cyclopropane]-6-carbonyl]-piperazin-1-yl]-acetamide |

TABLE 6-continued

| Cpd No. | Structure | Name |
|---|---|---|
| 237 | 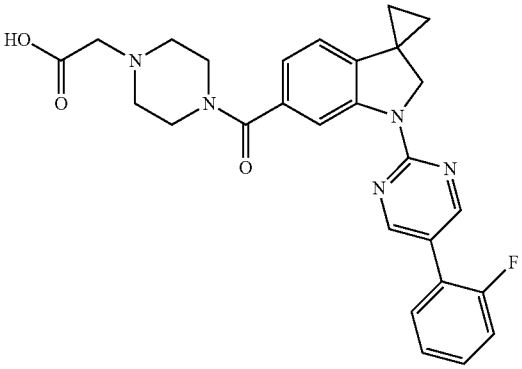 | 2-[4-[1-[5-(2-Fluorophenyl)-pyrimidin-2-yl]-spiro[1,2-dihydro-indole-3,1'-cyclopropane]-6-carbonyl]-piperazin-1-yl]-acetic acid |
| 238 | 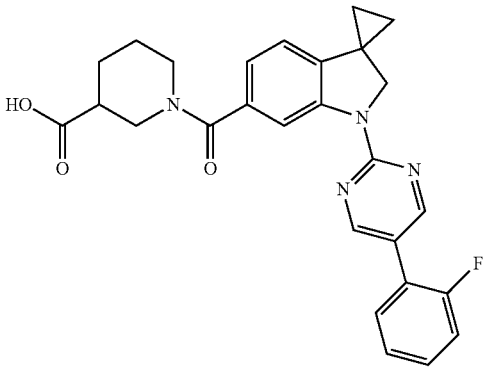 [SMILES: O=C(O)C1CCCN(C(=O)c2ccc3c(c2)N(c2ncc(-c4ccccc4F)cn2)CC32CC2)C1] | 1-[1-[5-(2-Fluorophenyl)-pyrimidin-2-yl]-spiro[1,2-dihydro-indole-3,1'-cyclopropane]-6-carbonyl]-piperidine-3-carboxylic acid |
| 239 | 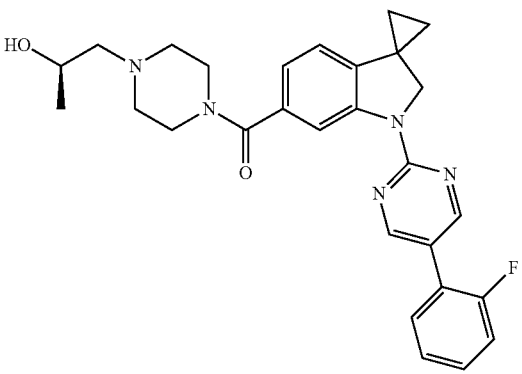 | [1-[5-(2-Fluorophenyl)-pyrimidin-2-yl]-spiro[1,2-dihydro-indole-3,1'-cyclopropane]-6-yl]-[4-[(2R)-2-hydroxy-propyl]-piperazin-1-yl]-methanone |
| 240 | 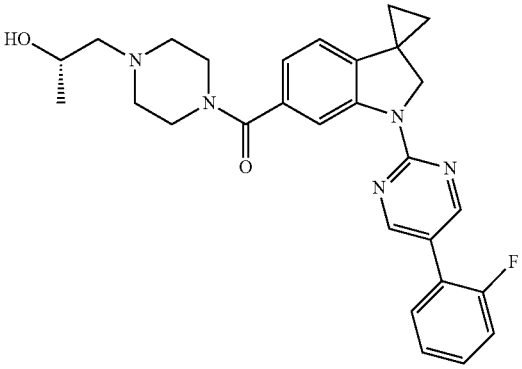 [SMILES: C[C@H](O)CN1CCN(C(=O)c2ccc3c(c2)N(c2ncc(-c4ccccc4F)cn2)CC32CC2)CC1] | [1-[5-(2-Fluorophenyl)-pyrimidin-2-yl]-spiro[1,2-dihydro-indole-3,1'-cyclopropane]-6-yl]-[4-[(2S)-2-hydroxy-propyl]-piperazin-1-yl]-methanone |

TABLE 6-continued

| Cpd No. | Structure | Name |
|---|---|---|
| 241 | 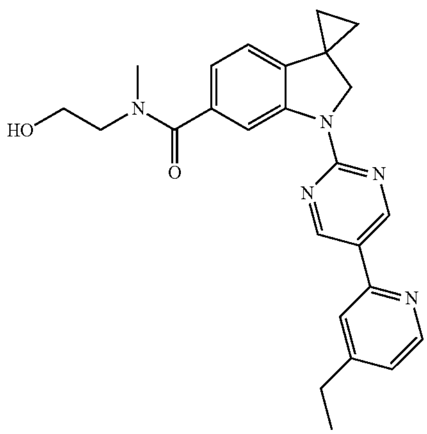 [SMILES: CCc1ccnc(-c2cnc(N3CC4(CC4)c4ccc(C(=O)N(C)CCO)cc43)nc2)c1] | 1-[5-(4-Ethyl-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 242 | 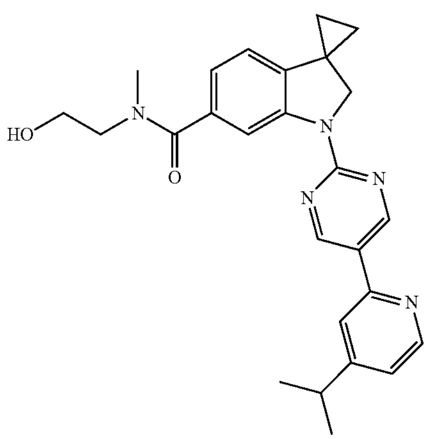 [SMILES: CC(C)c1ccnc(-c2cnc(N3CC4(CC4)c4ccc(C(=O)N(C)CCO)cc43)nc2)c1] | N-(2-Hydroxy-ethyl)-1-[5-(4-isopropyl-pyridin-2-yl)-pyrimidin-2-yl]-N-methyl-spiro[1,2-dihydro-indole-3,1'-cyclopropane]-6-carboxylic acid amide |
| 243 | 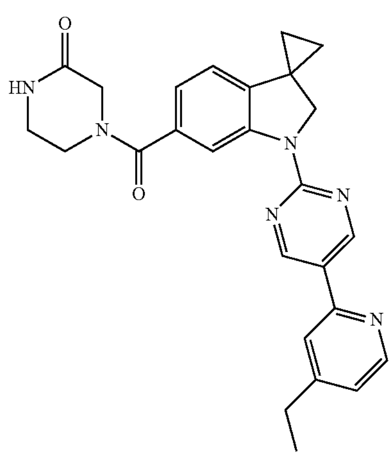 [SMILES: CCc1ccnc(-c2cnc(N3CC4(CC4)c4ccc(C(=O)N5CCNC(=O)C5)cc43)nc2)c1] | 4-[1-[5-(4-Ethyl-pyridin-2-yl)-pyrimidin-2-yl]-spiro[1,2-dihydro-indole-3,1'-cyclopropane]-6-carbonyl]-piperazin-2-one |

TABLE 6-continued

| Cpd No. | Structure | Name |
|---|---|---|
| 244 | 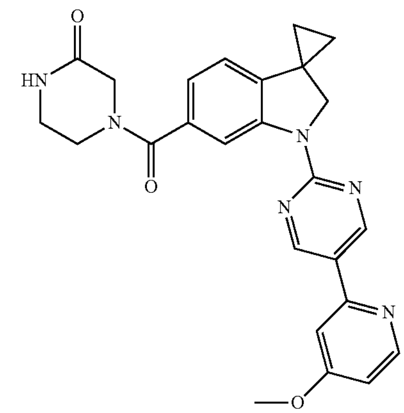 [SMILES: COc1ccnc(-c2cnc(N3CC4(CC4)c4ccc(C(=O)N5CCNC(=O)C5)cc43)nc2)c1] | 4-[1-[5-(4-Methoxy-pyridin-2-yl)-pyrimidin-2-yl]-spiro[1,2-dihydro-indole-3,1'-cyclopropane]-6-carbonyl]-piperazin-2-one |
| 245 | 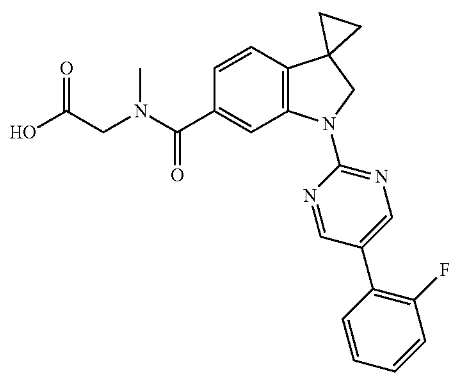 [SMILES: CN(CC(=O)O)C(=O)c1ccc2c(c1)N(c1ncc(-c3ccccc3F)cn1)CC21CC1] | 2-[[1-[5-(2-Fluorophenyl)-pyrimidin-2-yl]-spiro[1,2-dihydro-indole-3,1'-cyclopropane]-6-carbonyl]-methyl-amino]-acetic acid |
| 246 | 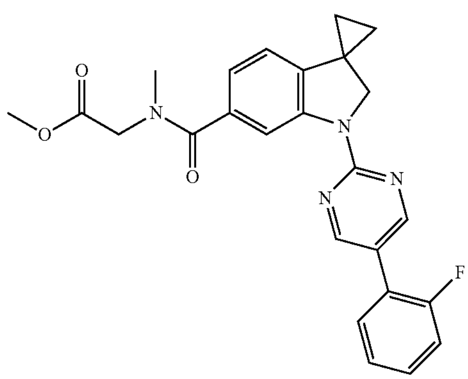 [SMILES: COC(=O)CN(C)C(=O)c1ccc2c(c1)N(c1ncc(-c3ccccc3F)cn1)CC21CC1] | 2-[[1-[5-(2-Fluorophenyl)-pyrimidin-2-yl]-spiro[1,2-dihydro-indole-3,1'-cyclopropane]-6-carbonyl]-methyl-amino]-acetic acid methyl ester |
| 248 | 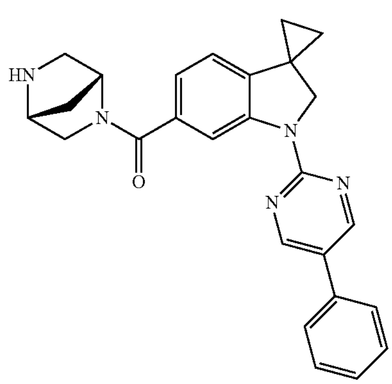 [SMILES: O=C(c1ccc2c(c1)N(c1ncc(-c3ccccc3)cn1)CC21CC1)N1C[C@H]2C[C@@H]1CN2] | [(1R,4R)-2,5-Diazabicyclo[2.2.1]heptan-2-yl]-[1-(5-phenyl-pyrimidin-2-yl)-spiro[1,2-dihydro-indole-3,1'-cyclopropane]-6-yl]-methanone |

TABLE 6-continued

| Cpd No. | Structure | Name |
|---|---|---|
| 249 | 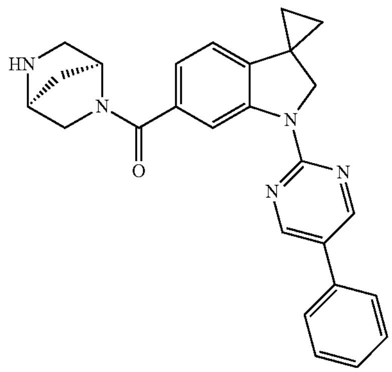 [SMILES: O=C(c1ccc2c(c1)N(c1ncc(-c3ccccc3)cn1)CC21CC1)N1C[C@@H]2C[C@H]1CN2] | [(1S,4S)-2,5-Diazabicyclo[2.2.1]heptan-2-yl]-[1-(5-phenyl-pyrimidin-2-yl)-spiro[1,2-dihydro-indole-3,1'-cyclopropane]-6-yl]-methanone |
| 250 | 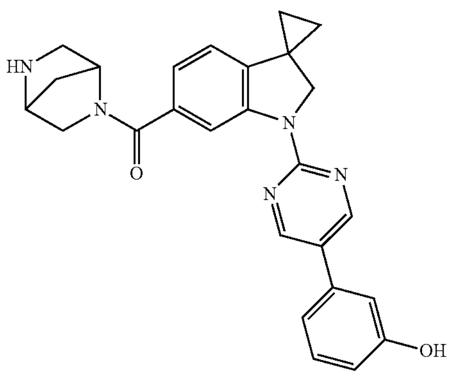 [SMILES: O=C(c1ccc2c(c1)N(c1ncc(-c3cccc(O)c3)cn1)CC21CC1)N1CC2CC1CN2] | (2,5-Diazabicyclo[2.2.1]heptan-2-yl)-[1-[5-(3-hydroxyphenyl)-pyrimidin-2-yl]-spiro[1,2-dihydro-indole-3,1'-cyclopropane]-6-yl]-methanone |
| 251 | 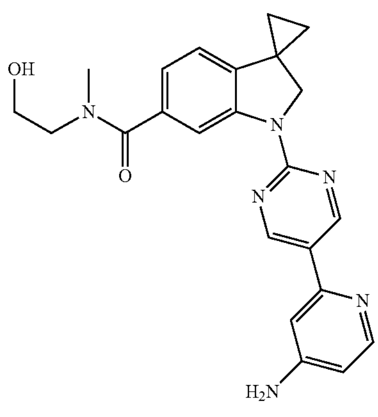 [SMILES: CN(CCO)C(=O)c1ccc2c(c1)N(c1ncc(-c3cc(N)ccn3)cn1)CC21CC1] | 1-[5-(4-Amino-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 252 | 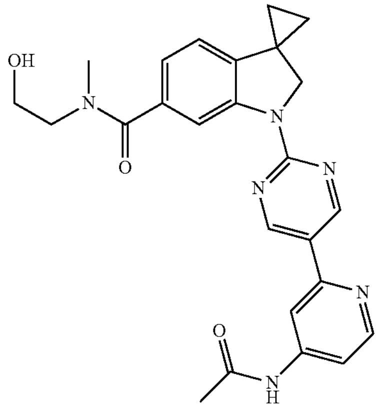 [SMILES: CC(=O)Nc1ccnc(-c2cnc(N3CC4(CC4)c4ccc(C(=O)N(C)CCO)cc43)nc2)c1] | 1-[5-(4-Acetylamino-pyridin-2-yl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 253 | 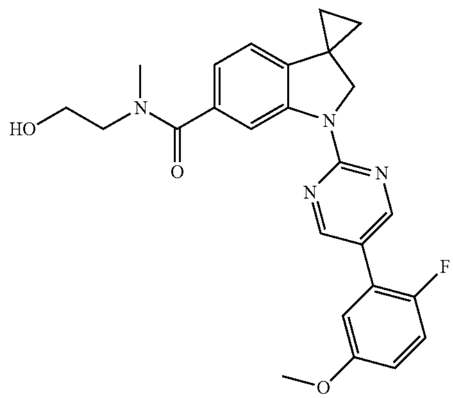 [SMILES: COc1ccc(F)c(-c2cnc(N3CC4(CC4)c4ccc(C(=O)N(C)CCO)cc43)nc2)c1] | 1-[5-(2-Fluoro-5-methoxy-phenyl)-pyrimidin-2-yl]-N-(2-hydroxy-ethyl)-N-methyl-spiro[1,2-dihydro-indole-3,1'-cyclopropane]-6-carboxylic acid amide |
| 254 | 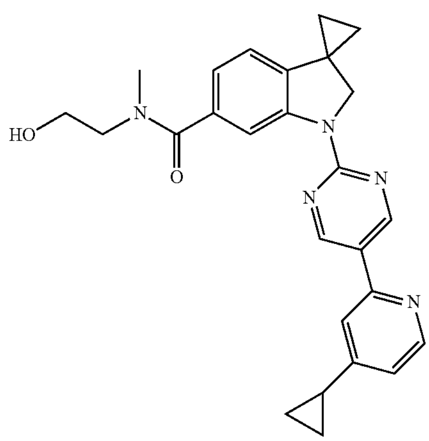 [SMILES: CN(CCO)C(=O)c1ccc2c(c1)N(c1ncc(-c3cc(C4CC4)ccn3)cn1)CC21CC1] | 1-[5-(4-Cyclopropyl-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 255 | 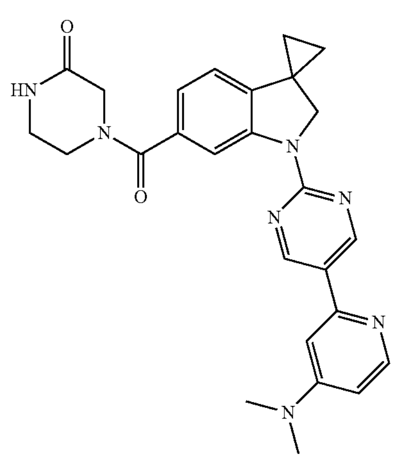 [SMILES: CN(C)c1ccnc(-c2cnc(N3CC4(CC4)c4ccc(C(=O)N5CCNC(=O)C5)cc43)nc2)c1] | 4-[1-[5-(4-Dimethylamino-pyridin-2-yl)-pyrimidin-2-yl]-spiro[1,2-dihydro-indole-3,1'-cyclopropane]-6-carbonyl]-piperazin-2-one |

TABLE 6-continued

| Cpd No. | Structure | Name |
|---|---|---|
| 256 | 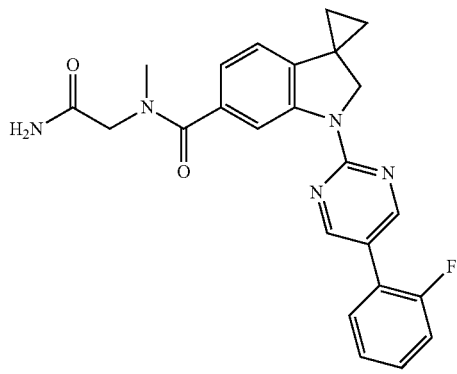 [SMILES: CN(CC(N)=O)C(=O)c1ccc2c(c1)N(c1ncc(-c3ccccc3F)cn1)CC21CC1] | N-(Carbamoyl-methyl)-1-[5-(2-fluorophenyl)-pyrimidin-2-yl]-N-methyl-spiro[1,2-dihydro-indole-3,1'-cyclopropane]-6-carboxylic acid amide |
| 257 | 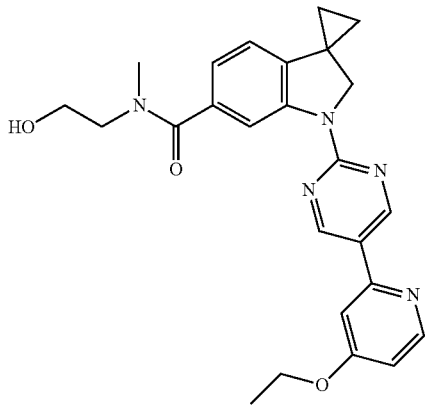 [SMILES: CCOc1ccnc(-c2cnc(N3CC4(CC4)c4ccc(C(=O)N(C)CCO)cc43)nc2)c1] | 1-[5-(4-Ethoxy-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 258 | 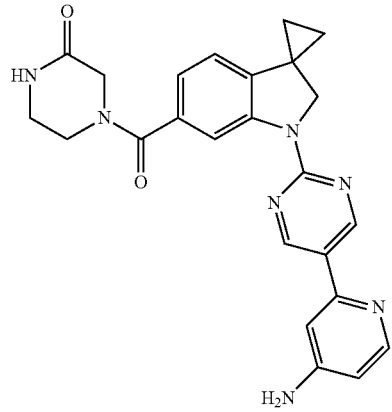 [SMILES: Nc1ccnc(-c2cnc(N3CC4(CC4)c4ccc(C(=O)N5CCNC(=O)C5)cc43)nc2)c1] | 4-[1-[5-(4-Amino-pyridin-2-yl)-pyrimidin-2-yl]-spiro[1,2-dihydro-indole-3,1'-cyclopropane]-6-carbonyl]-piperazin-2-one |
| 259 | 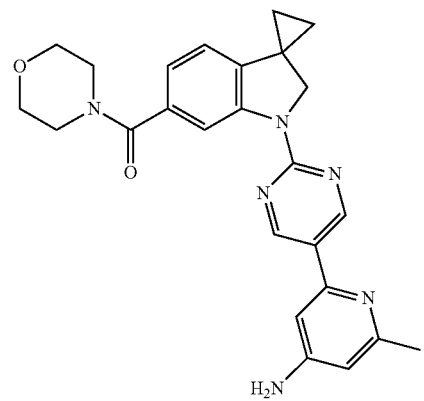 [SMILES: Cc1cc(N)cc(-c2cnc(N3CC4(CC4)c4ccc(C(=O)N5CCOCC5)cc43)nc2)n1] | [1-[5-(4-Amino-6-methyl-pyridin-2-yl)-pyrimidin-2-yl]-spiro[1,2-dihydro-indole-3,1'-cyclopropane]-6-yl]-morpholin-4-yl-methanone |

TABLE 6-continued

| Cpd No. | Structure | Name |
|---|---|---|
| 260 | 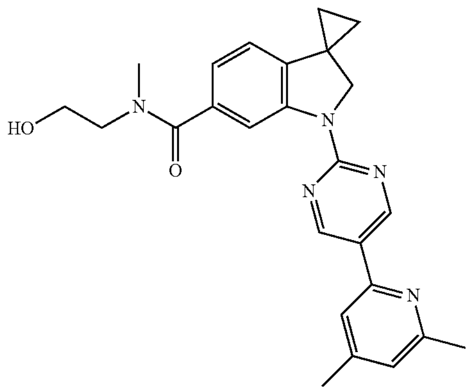 [SMILES: Cc1cc(C)nc(-c2cnc(N3CC4(CC4)c4ccc(C(=O)N(C)CCO)cc43)nc2)c1] | 1-[5-(4,6-Dimethyl-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 261 | 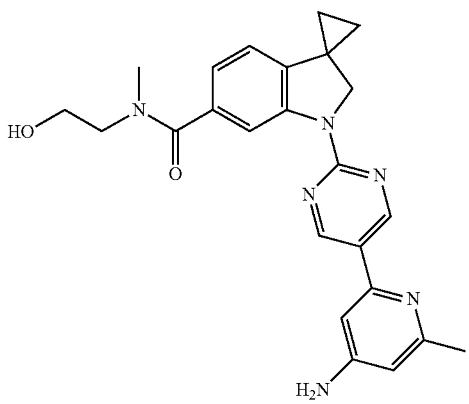 [SMILES: Cc1cc(N)cc(-c2cnc(N3CC4(CC4)c4ccc(C(=O)N(C)CCO)cc43)nc2)n1] | 1-[5-(4-Amino-6-methyl-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 262 | 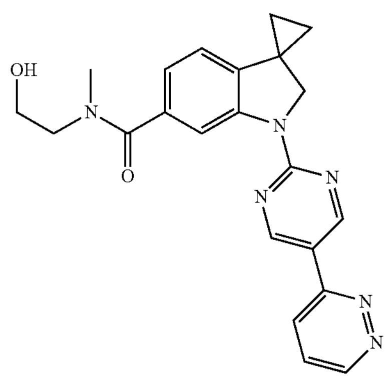 [SMILES: CN(CCO)C(=O)c1ccc2c(c1)N(c1ncc(-c3cccnn3)cn1)CC21CC1] | N-(2-Hydroxy-ethyl)-N-methyl-1-(5-pyridazin-3-yl-pyrimidin-2-yl)-spiro[1,2-dihydro-indole-3,1'-cyclopropane]-6-carboxylic acid amide |
| 263 | 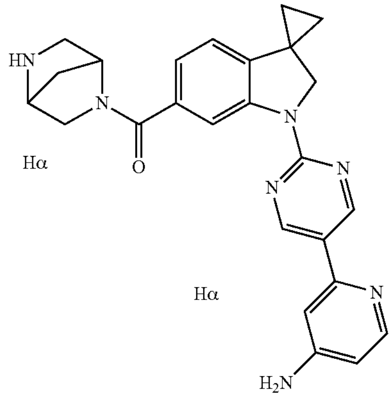 [SMILES: Nc1ccnc(-c2cnc(N3CC4(CC4)c4ccc(C(=O)N5CC6CC5CN6)cc43)nc2)c1] | [1-[5-(4-Amino-pyridin-2-yl)-pyrimidin-2-yl]-spiro[1,2-dihydro-indole-3,1'-cyclopropane]-6-yl]-(2,5-diazabicyclo[2.2.1]heptan-2-yl)-methanone dihydrochloride |

TABLE 6-continued

| Cpd No. | Structure | Name |
|---|---|---|
| 264 | 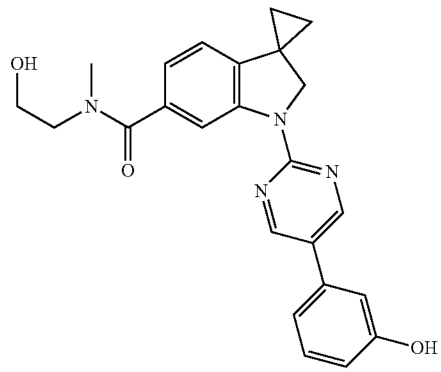 [SMILES: CN(CCO)C(=O)c1ccc2c(c1)N(c1ncc(-c3cccc(O)c3)cn1)CC21CC1] | N-(2-Hydroxy-ethyl)-1-[5-(3-hydroxyphenyl)-pyrimidin-2-yl]-N-methyl-spiro[1,2-dihydro-indole-3,1'-cyclopropane]-6-carboxylic acid amide |
| 265 | 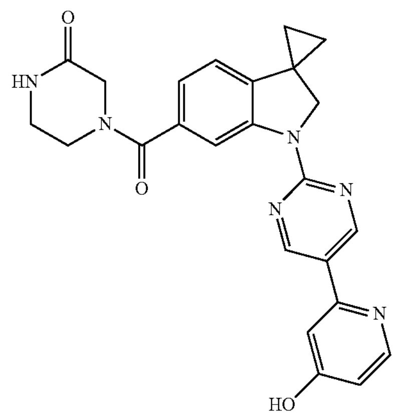 [SMILES: O=C1CN(C(=O)c2ccc3c(c2)N(c2ncc(-c4cc(O)ccn4)cn2)CC32CC2)CCN1] | 4-[1-[5-(4-Hydroxy-pyridin-2-yl)-pyrimidin-2-yl]-spiro[1,2-dihydro-indole-3,1'-cyclopropane]-6-carbonyl]-piperazin-2-one |
| 266 | 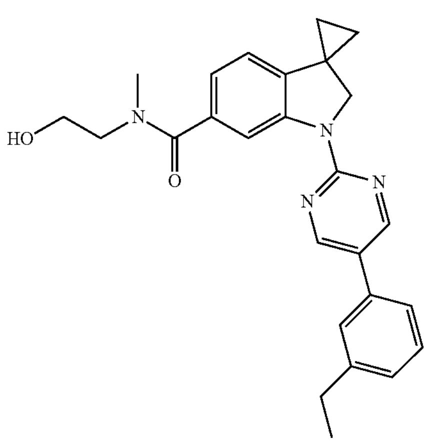 [SMILES: CCc1cccc(-c2cnc(N3CC4(CC4)c4ccc(C(=O)N(C)CCO)cc43)nc2)c1] | 1-[5-(3-Ethyl-phenyl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 267 | 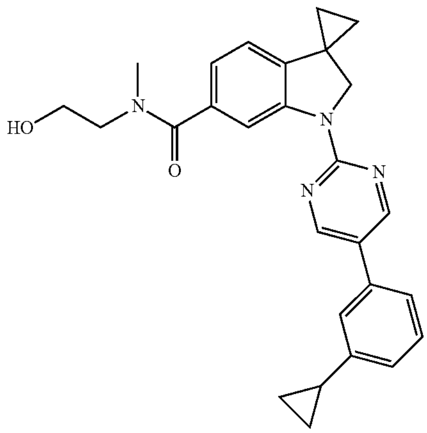 [SMILES: CN(CCO)C(=O)c1ccc2c(c1)N(c1ncc(-c3cccc(C4CC4)c3)cn1)CC21CC1] | 1-[5-(3-Cyclopropyl-phenyl)-pyrimidin-2-yl]-N-(2-hydroxy-ethyl)-N-methyl-spiro[1,2-dihydro-indole-3,1'-cyclopropane]-6-carboxylic acid amide |
| 268 | 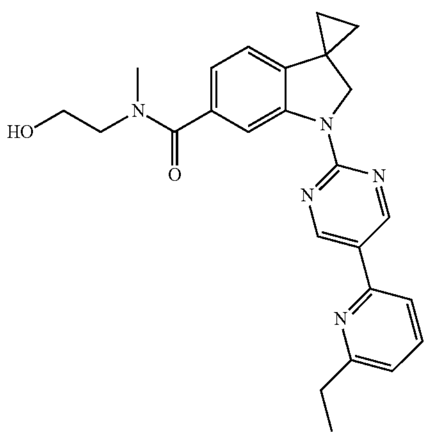 [SMILES: CCc1cccc(-c2cnc(N3CC4(CC4)c4ccc(C(=O)N(C)CCO)cc43)nc2)n1] | 1-[5-(6-Ethyl-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 269 | 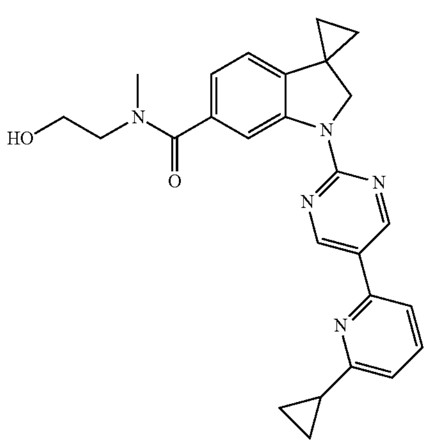 [SMILES: CN(CCO)C(=O)c1ccc2c(c1)N(c1ncc(-c3cccc(C4CC4)n3)cn1)CC21CC1] | 1-[5-(6-Cyclopropyl-pyridin-2-yl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 270 | 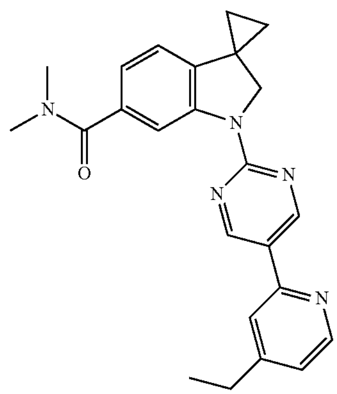 [SMILES: CCc1ccnc(-c2cnc(N3CC4(CC4)c4ccc(C(=O)N(C)C)cc43)nc2)c1] | 1-[5-(4-Ethyl-pyridin-2-yl)-pyrimidin-2-yl]-N,N-dimethyl-spiro[1,2-dihydro-indole-3,1'-cyclopropane]-6-carboxylic acid amide |
| 271 | 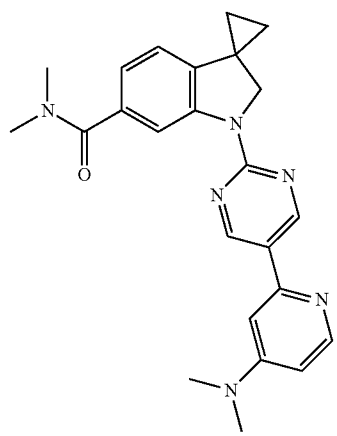 [SMILES: CN(C)C(=O)c1ccc2c(c1)N(c1ncc(-c3cc(N(C)C)ccn3)cn1)CC21CC1] | 1-[5-(4-Dimethylamino-pyridin-2-yl)-pyrimidin-2-yl]-N,N-dimethyl-spiro[1,2-dihydro-indole-3,1'-cyclopropane]-6-carboxylic acid amide |
| 272 | 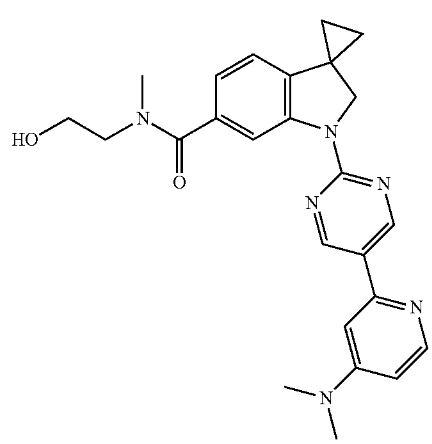 [SMILES: CN(CCO)C(=O)c1ccc2c(c1)N(c1ncc(-c3cc(N(C)C)ccn3)cn1)CC21CC1] | 1-[5-(4-Dimethylamino-pyridin-2-yl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 273 | 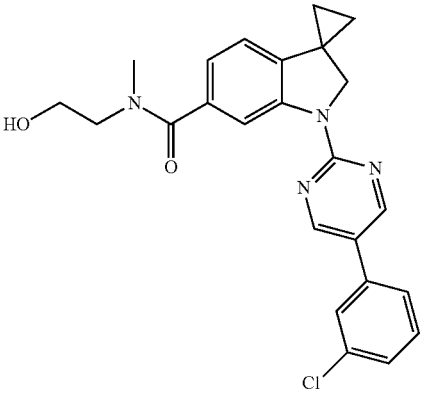 [SMILES: CN(CCO)C(=O)c1ccc2c(c1)N(c1ncc(-c3cccc(Cl)c3)cn1)CC21CC1] | 1-[5-(3-Chlorophenyl)-pyrimidin-2-yl]-N-(2-hydroxy-ethyl)-N-methyl-spiro[1,2-dihydro-indole-3,1'-cyclopropane]-6-carboxylic acid amide |
| 274 | 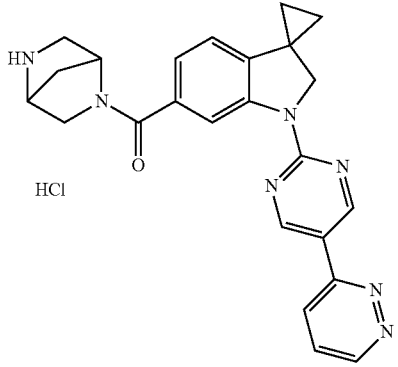 [SMILES: O=C(c1ccc2c(c1)N(c1ncc(-c3cccnn3)cn1)CC21CC1)N1CC2CC1CN2 ; Cl] | (2,5-Diazabicyclo[2.2.1]heptan-2-yl)-[1-(5-pyridazin-3-yl-pyrimidin-2-yl)-spiro[1,2-dihydro-indole-3,1'-cyclopropane]-6-yl]-methanone hydrochloride |
| 275 | 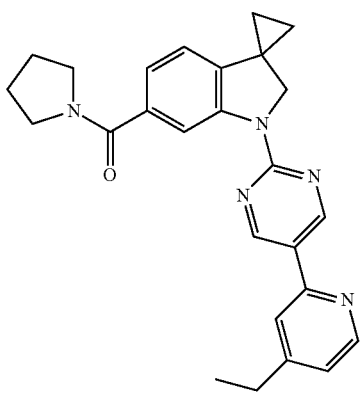 [SMILES: CCc1ccnc(-c2cnc(N3CC4(CC4)c4ccc(C(=O)N5CCCC5)cc43)nc2)c1] | [1-[5-(4-Ethyl-pyridin-2-yl)-pyrimidin-2-yl]-spiro[1,2-dihydro-indole-3,1'-cyclopropane]-6-yl]-pyrrolidin-1-yl-methanone |
| 276 | 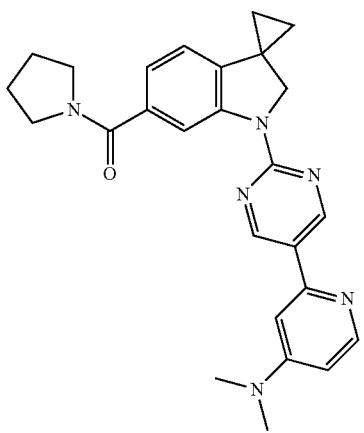 [SMILES: CN(C)c1ccnc(-c2cnc(N3CC4(CC4)c4ccc(C(=O)N5CCCC5)cc43)nc2)c1] | [1-[5-(4-Dimethylamino-pyridin-2-yl)-pyrimidin-2-yl]-spiro[1,2-dihydro-indole-3,1'-cyclopropane]-6-yl]-pyrrolidin-1-yl-methanone |

TABLE 6-continued

| Cpd No. | Structure | Name |
|---|---|---|
| 277 | 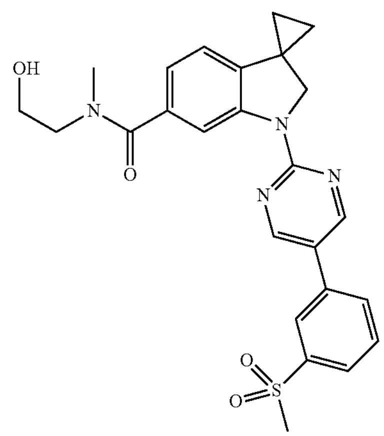 | N-(2-Hydroxy-ethyl)-N-methyl-1-[5-(3-methylsulfonyl-phenyl)-pyrimidin-2-yl]-spiro[1,2-dihydro-indole-3,1'-cyclopropane]-6-carboxylic acid amide |
| 278 | 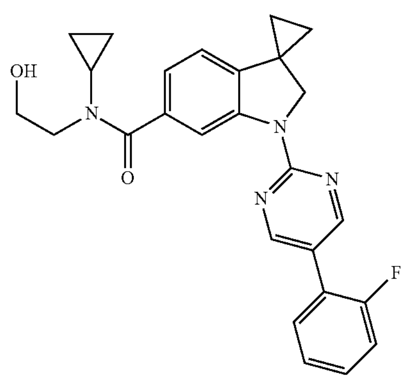 [SMILES: O=C(c1ccc2c(c1)N(c1ncc(-c3ccccc3F)cn1)CC21CC1)N(CCO)C1CC1] | N-Cyclopropyl-1-[5-(2-fluorophenyl)-pyrimidin-2-yl]-N-(2-hydroxy-ethyl)-spiro[1,2-dihydro-indole-3,1'-cyclopropane]-6-carboxylic acid amide |
| 279 | 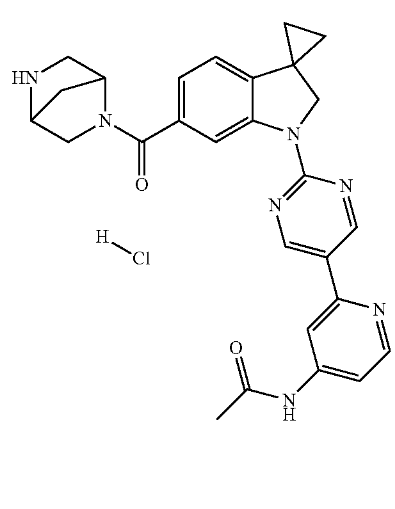 [SMILES: CC(=O)Nc1ccnc(-c2cnc(N3CC4(CC4)c4ccc(C(=O)N5CC6CC5CN6)cc43)nc2)c1 ; Cl] | N-[2-[2-[6-(2,5-Diazabicyclo[2.2.1]heptane-2-carbonyl)-spiro[1,2-dihydro-indole-3,1'-cyclopropane]-1-yl]-pyrimidin-5-yl]-pyridin-4-yl]-acetamide hydrochloride |

TABLE 6-continued

| Cpd No. | Structure | Name |
|---|---|---|
| 280 | 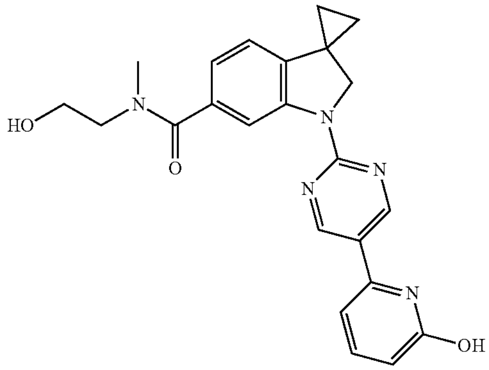 [SMILES: CN(CCO)C(=O)c1ccc2c(c1)N(c1ncc(-c3cccc(O)n3)cn1)CC21CC1] | N-(2-Hydroxy-ethyl)-1-[5-(6-hydroxy-pyridin-2-yl)-pyrimidin-2-yl]-N-methyl-spiro[1,2-dihydro-indole-3,1'-cyclopropane]-6-carboxylic acid amide |
| 281 | 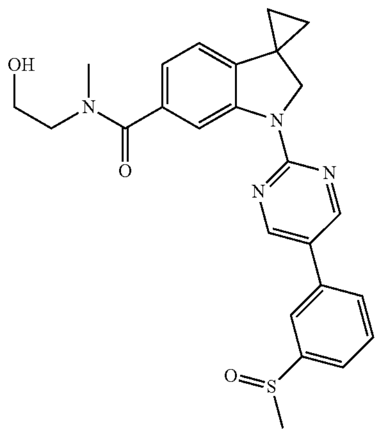 [SMILES: CN(CCO)C(=O)c1ccc2c(c1)N(c1ncc(-c3cccc(S(C)=O)c3)cn1)CC21CC1] | N-(2-Hydroxy-ethyl)-N-methyl-1-[5-[3-(methylsulfinyl)-phenyl]-pyrimidin-2-yl]-spiro[1,2-dihydro-indole-3,1'-cyclopropane]-6-carboxylic acid amide |
| 282 | 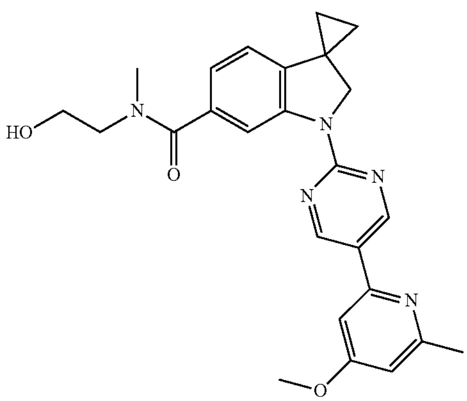 [SMILES: COc1cc(C)nc(-c2cnc(N3CC4(CC4)c4ccc(C(=O)N(C)CCO)cc43)nc2)c1] | N-(2-Hydroxy-ethyl)-1-[5-(4-methoxy-6-methyl-pyridin-2-yl)-pyrimidin-2-yl]-N-methyl-spiro[1,2-dihydro-indole-3,1'-cyclopropane]-6-carboxylic acid amide |
| 283 | 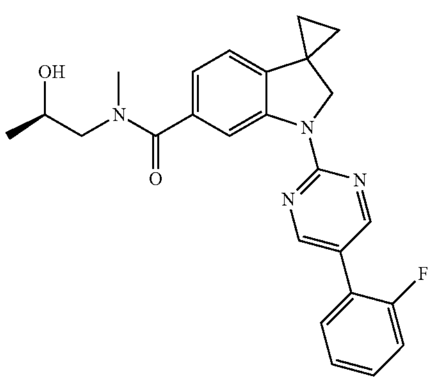 [SMILES: C[C@@H](O)CN(C)C(=O)c1ccc2c(c1)N(c1ncc(-c3ccccc3F)cn1)CC21CC1] | 1-[5-(2-Fluorophenyl)-pyrimidin-2-yl]-N-[(2R)-2-hydroxy-propyl]-N-methyl-spiro[1,2-dihydro-indole-3,1'-cyclopropane]-6-carboxylic acid amide |

TABLE 6-continued

| Cpd No. | Structure | Name |
|---|---|---|
| 284 | 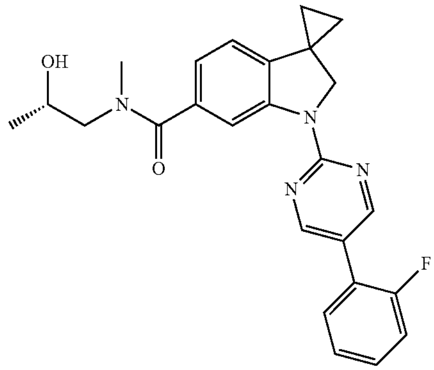 [SMILES: C[C@H](O)CN(C)C(=O)c1ccc2c(c1)N(c1ncc(-c3ccccc3F)cn1)CC21CC1] | 1-[5-(2-Fluorophenyl)-pyrimidin-2-yl]-N-[(2S)-2-hydroxy-propyl]-N-methyl-spiro[1,2-dihydro-indole-3,1'-cyclopropane]-6-carboxylic acid amide |
| 285 | 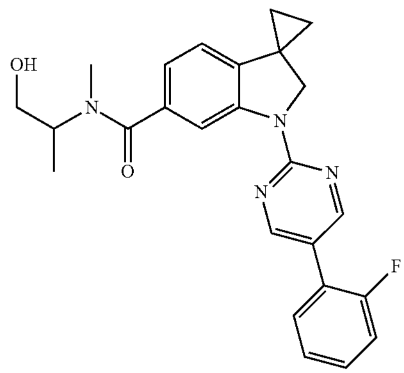 [SMILES: CC(CO)N(C)C(=O)c1ccc2c(c1)N(c1ncc(-c3ccccc3F)cn1)CC21CC1] | 1-[5-(2-Fluorophenyl)-pyrimidin-2-yl]-N-(2-hydroxy-1-methyl-ethyl)-N-methyl-spiro[1,2-dihydro-indole-3,1'-cyclopropane]-6-carboxylic acid amide |
| 286 | 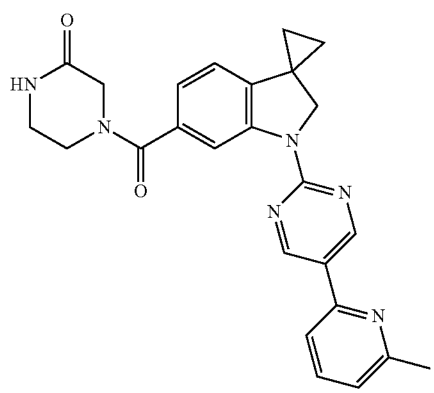 [SMILES: Cc1cccc(-c2cnc(N3CC4(CC4)c4ccc(C(=O)N5CCNC(=O)C5)cc43)nc2)n1] | 4-[1-[5-(6-Methyl-pyridin-2-yl)-pyrimidin-2-yl]-spiro[1,2-dihydro-indole-3,1'-cyclopropane]-6-carbonyl]-piperazin-2-one |
| 287 | 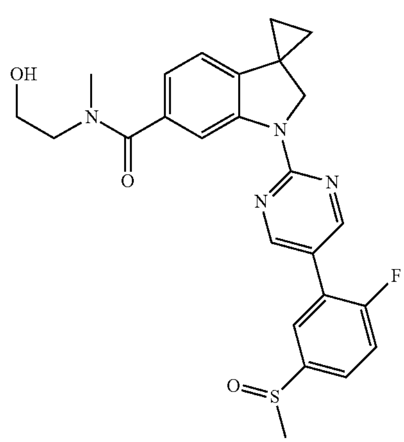 [SMILES: CN(CCO)C(=O)c1ccc2c(c1)N(c1ncc(-c3cc(S(C)=O)ccc3F)cn1)CC21CC1] | 1-[5-[2-Fluoro-5-(methylsulfinyl)-phenyl]-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 288 | 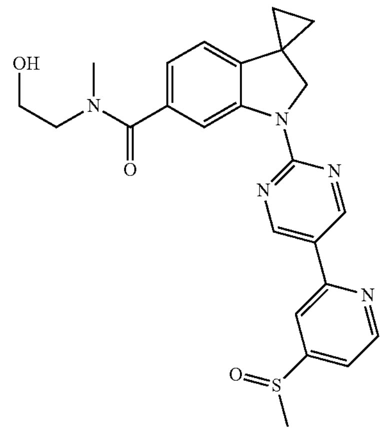 [SMILES: CN(CCO)C(=O)c1ccc2c(c1)N(c1ncc(-c3cc(S(C)=O)ccn3)cn1)CC21CC1] | N-(2-Hydroxy-ethyl)-N-methyl-1-[5-[4-(methylsulfinyl)-pyridin-2-yl]-pyrimidin-2-yl]-spiro[1,2-dihydro-indole-3,1'-cyclopropane]-6-carboxylic acid amide |
| 289 | 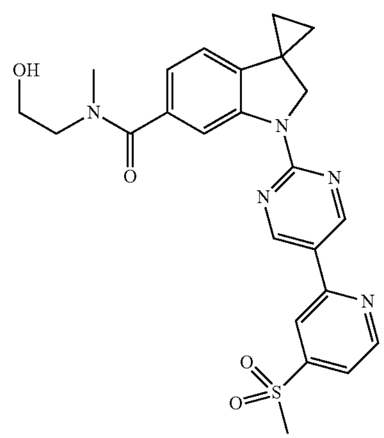 [SMILES: CN(CCO)C(=O)c1ccc2c(c1)N(c1ncc(-c3cc(S(C)(=O)=O)ccn3)cn1)CC21CC1] | N-(2-Hydroxy-ethyl)-N-methyl-1-[5-(4-methylsulfonyl-pyridin-2-yl)-pyrimidin-2-yl]-spiro[1,2-dihydro-indole-3,1'-cyclopropane]-6-carboxylic acid amide |
| 290 | 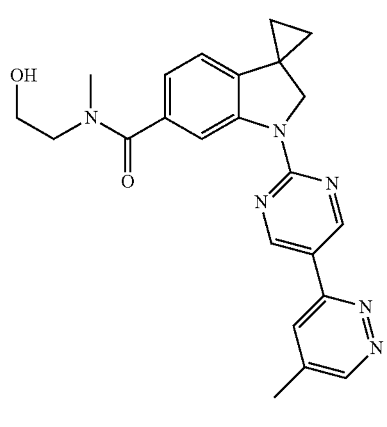 [SMILES: Cc1cnnc(-c2cnc(N3CC4(CC4)c4ccc(C(=O)N(C)CCO)cc43)nc2)c1] | N-(2-Hydroxy-ethyl)-N-methyl-1-[5-(5-methyl-pyridazin-3-yl)-pyrimidin-2-yl]-spiro[1,2-dihydro-indole-3,1'-cyclopropane]-6-carboxylic acid amide |

TABLE 6-continued

| Cpd No. | Structure | Name |
|---|---|---|
| 291 | 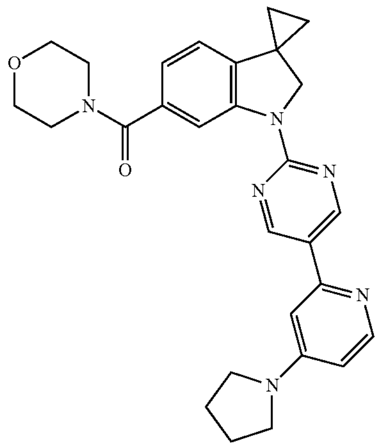 [SMILES: O=C(c1ccc2c(c1)N(c1ncc(-c3cc(N4CCCC4)ccn3)cn1)CC21CC1)N1CCOCC1] | Morpholin-4-yl-[1-[5-(4-pyrrolidin-1-yl-pyridin-2-yl)-pyrimidin-2-yl]-spiro[1,2-dihydro-indole-3,1'-cyclopropane]-6-yl]-methanone |
| 292 | 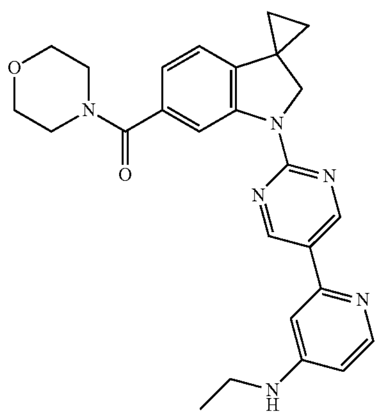 [SMILES: CCNc1ccnc(-c2cnc(N3CC4(CC4)c4ccc(C(=O)N5CCOCC5)cc43)nc2)c1] | [1-[5-(4-Ethylamino-pyridin-2-yl)-pyrimidin-2-yl]-spiro[1,2-dihydro-indole-3,1'-cyclopropane]-6-yl]-morpholin-4-yl-methanone |
| 293 | 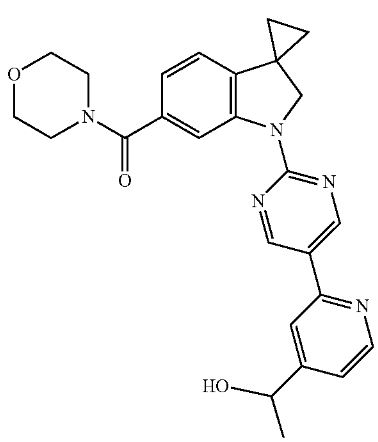 [SMILES: CC(O)c1ccnc(-c2cnc(N3CC4(CC4)c4ccc(C(=O)N5CCOCC5)cc43)nc2)c1] | [1-[5-[4-(1-Hydroxy-ethyl)-pyridin-2-yl]-pyrimidin-2-yl]-spiro[1,2-dihydro-indole-3,1'-cyclopropane]-6-yl]-morpholin-4-yl-methanone |

TABLE 6-continued

| Cpd No. | Structure | Name |
|---|---|---|
| 294 | 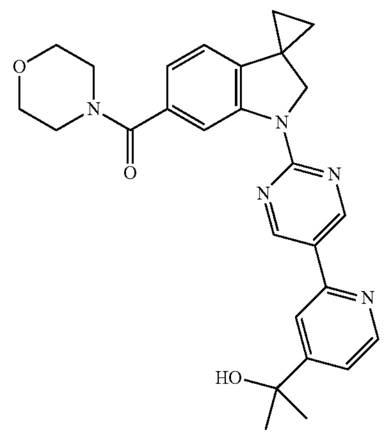 [SMILES: CC(C)(O)c1ccnc(-c2cnc(N3CC4(CC4)c4ccc(C(=O)N5CCOCC5)cc43)nc2)c1] | [1-[5-[4-(1-Hydroxy-1-methyl-ethyl)-pyridin-2-yl]-pyrimidin-2-yl]-spiro[1,2-dihydro-indole-3,1'-cyclopropane]-6-yl]-morpholin-4-yl-methanone |
| 295 | 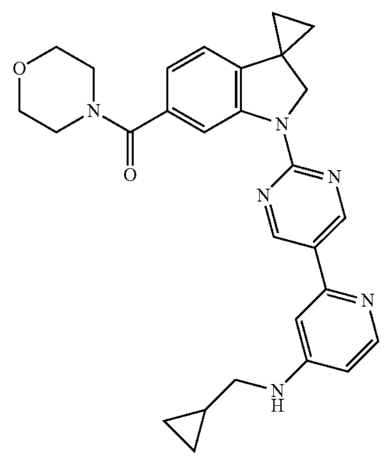 [SMILES: O=C(c1ccc2c(c1)N(c1ncc(-c3cc(NCC4CC4)ccn3)cn1)CC21CC1)N1CCOCC1] | [1-[5-[4-(Cyclopropyl-methylamino)-pyridin-2-yl]-pyrimidin-2-yl]-spiro[1,2-dihydro-indole-3,1'-cyclopropane]-6-yl]-morpholin-4-yl-methanone |
| 296 | 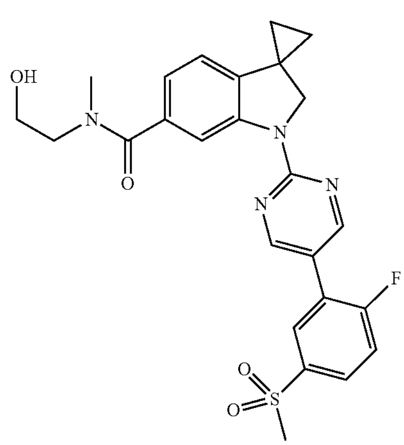 [SMILES: CN(CCO)C(=O)c1ccc2c(c1)N(c1ncc(-c3cc(S(C)(=O)=O)ccc3F)cn1)CC21CC1] | 1-[5-(2-Fluoro-5-methylsulfonyl-phenyl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 297 | 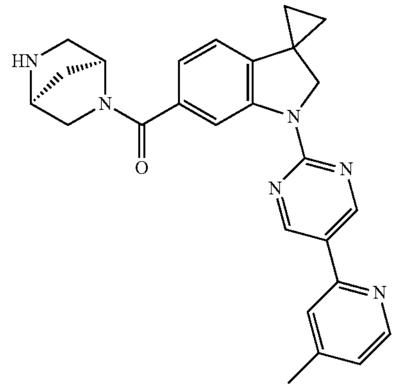 [SMILES: Cc1ccnc(-c2cnc(N3CC4(CC4)c4ccc(C(=O)N5C[C@@H]6C[C@H]5CN6)cc43)nc2)c1] | [(1S,4S)-2,5-Diazabicyclo[2.2.1]heptan-2-yl]-[1-[5-(4-methyl-pyridin-2-yl)-pyrimidin-2-yl]-spiro[1,2-dihydro-indole-3,1'-cyclopropane]-6-yl]-methanone |
| 298 | 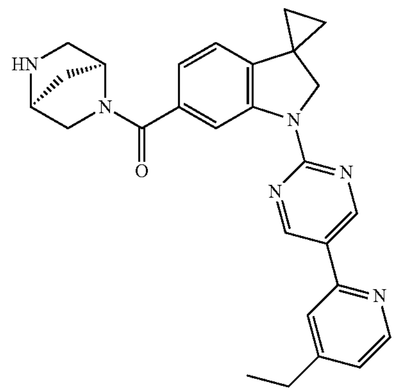 [SMILES: CCc1ccnc(-c2cnc(N3CC4(CC4)c4ccc(C(=O)N5C[C@@H]6C[C@H]5CN6)cc43)nc2)c1] | [(1S,4S)-2,5-Diazabicyclo[2.2.1]heptan-2-yl]-[1-[5-(4-ethyl-pyridin-2-yl)-pyrimidin-2-yl]-spiro[1,2-dihydro-indole-3,1'-cyclopropane]-6-yl]-methanone |
| 299 | 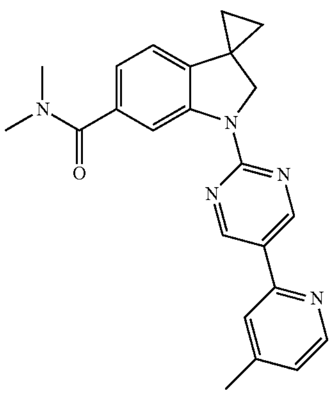 [SMILES: Cc1ccnc(-c2cnc(N3CC4(CC4)c4ccc(C(=O)N(C)C)cc43)nc2)c1] | N,N-Dimethyl-1-[5-(4-methyl-pyridin-2-yl)-pyrimidin-2-yl]-spiro[1,2-dihydro-indole-3,1'-cyclopropane]-6-carboxylic acid amide |
| 300 | 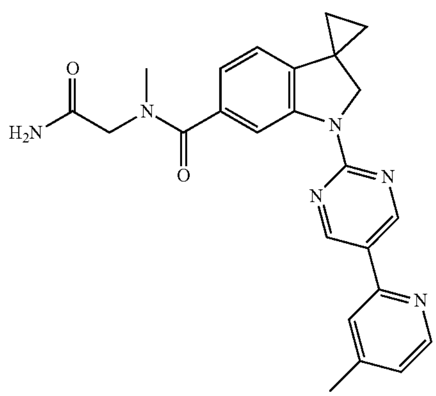 [SMILES: Cc1ccnc(-c2cnc(N3CC4(CC4)c4ccc(C(=O)N(C)CC(N)=O)cc43)nc2)c1] | N-(Carbamoyl-methyl)-N-methyl-1-[5-(4-methyl-pyridin-2-yl)-pyrimidin-2-yl]-spiro[1,2-dihydro-indole-3,1'-cyclopropane]-6-carboxylic acid amide |

TABLE 6-continued

| Cpd No. | Structure | Name |
|---|---|---|
| 301 | 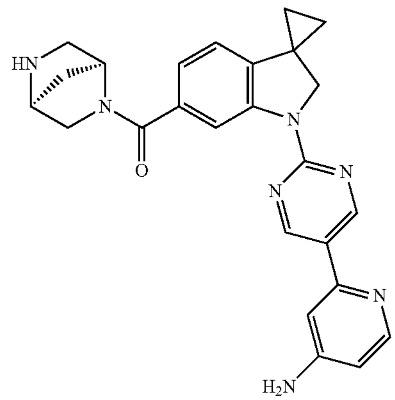 [SMILES: Nc1ccnc(-c2cnc(N3CC4(CC4)c4ccc(C(=O)N5C[C@@H]6C[C@H]5CN6)cc43)nc2)c1] | [1-[5-(4-Amino-pyridin-2-yl)-pyrimidin-2-yl]-spiro[1,2-dihydro-indole-3,1'-cyclopropane]-6-yl]-[(1S,4S)-2,5-diazabicyclo[2.2.1]heptan-2-yl]-methanone |
| 302 | 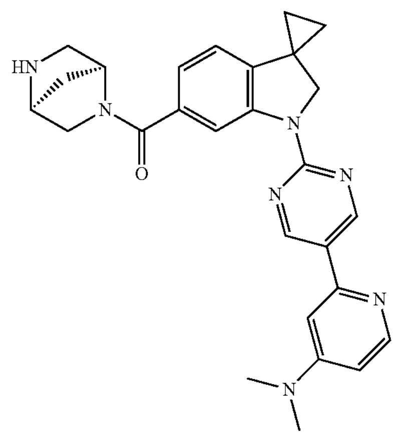 [SMILES: CN(C)c1ccnc(-c2cnc(N3CC4(CC4)c4ccc(C(=O)N5C[C@@H]6C[C@H]5CN6)cc43)nc2)c1] | [(1S,4S)-2,5-Diazabicyclo[2.2.1]heptan-2-yl]-[1-[5-(4-dimethylamino-pyridin-2-yl)-pyrimidin-2-yl]-spiro[1,2-dihydro-indole-3,1'-cyclopropane]-6-yl]-methanone |
| 303 | 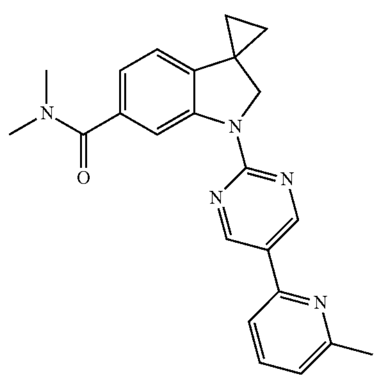 | N,N-Dimethyl-1-[5-(6-methyl-pyridin-2-yl)-pyrimidin-2-yl]-spiro[1,2-dihydro-indole-3,1'-cyclopropane]-6-carboxylic acid amide |
| 304 | 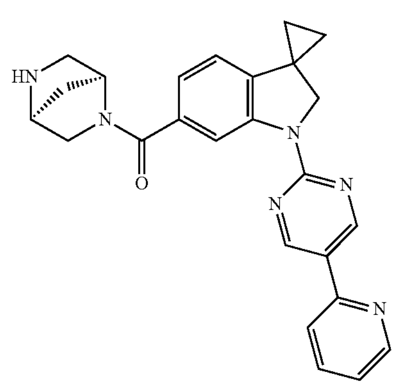 [SMILES: O=C(c1ccc2c(c1)N(c1ncc(-c3ccccn3)cn1)CC21CC1)N1C[C@@H]2C[C@H]1CN2] | [(1S,4S)-2,5-Diazabicyclo[2.2.1]heptan-2-yl]-[1-(5-pyridin-2-yl-pyrimidin-2-yl)-spiro[1,2-dihydro-indole-3,1'-cyclopropane]-6-yl]-methanone |

TABLE 6-continued

| Cpd No. | Structure | Name |
|---|---|---|
| 305 | 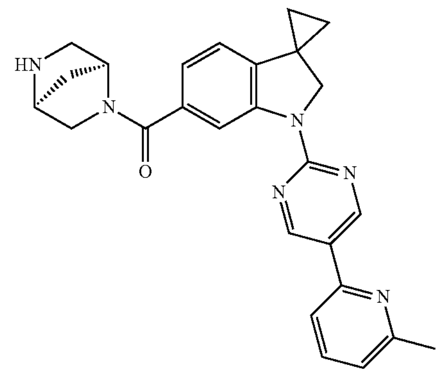 [SMILES: Cc1cccc(-c2cnc(N3CC4(CC4)c4ccc(C(=O)N5C[C@@H]6C[C@H]5CN6)cc43)nc2)n1] | [(1S,4S)-2,5-Diazabicyclo[2.2.1]heptan-2-yl]-[1-[5-(6-methyl-pyridin-2-yl)-pyrimidin-2-yl]-spiro[1,2-dihydro-indole-3,1'-cyclopropane]-6-yl]-methanone |
| 306 | 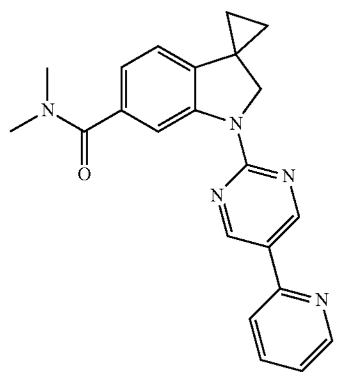 [SMILES: CN(C)C(=O)c1ccc2c(c1)N(c1ncc(-c3ccccn3)cn1)CC21CC1] | N,N-Dimethyl-1-(5-pyridin-2-yl-pyrimidin-2-yl)-spiro[1,2-dihydro-indole-3,1'-cyclopropane]-6-carboxylic acid amide |
| 307 | 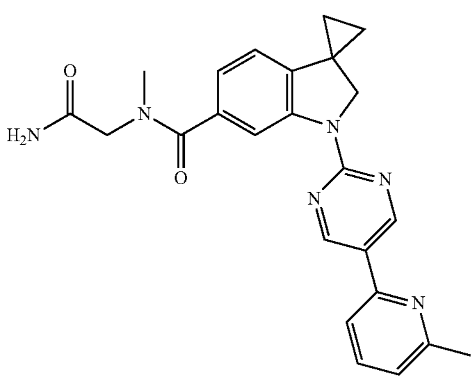 [SMILES: Cc1cccc(-c2cnc(N3CC4(CC4)c4ccc(C(=O)N(C)CC(N)=O)cc43)nc2)n1] | N-(Carbamoyl-methyl)-N-methyl-1-[5-(6-methyl-pyridin-2-yl)-pyrimidin-2-yl]-spiro[1,2-dihydro-indole-3,1'-cyclopropane]-6-carboxylic acid amide |
| 308 | 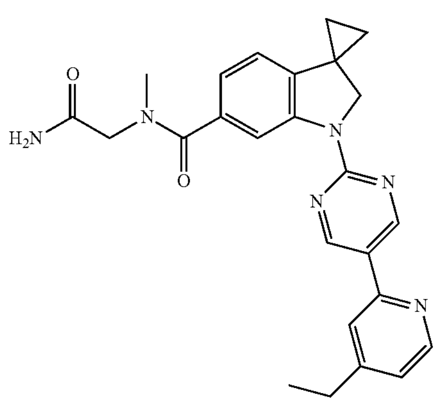 [SMILES: CCc1ccnc(-c2cnc(N3CC4(CC4)c4ccc(C(=O)N(C)CC(N)=O)cc43)nc2)c1] | N-(Carbamoyl-methyl)-1-[5-(4-ethyl-pyridin-2-yl)-pyrimidin-2-yl]-N-methyl-spiro[1,2-dihydro-indole-3,1'-cyclopropane]-6-carboxylic acid amide |

TABLE 6-continued

| Cpd No. | Structure | Name |
|---|---|---|
| 309 | 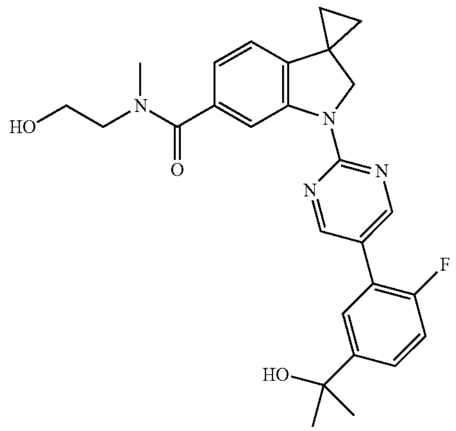 [SMILES: CN(CCO)C(=O)c1ccc2c(c1)N(c1ncc(-c3cc(C(C)(C)O)ccc3F)cn1)CC21CC1] | 1-[5-[2-Fluoro-5-(1-hydroxy-1-methyl-ethyl)-phenyl]-pyrimidin-2-yl]-N-(2-hydroxy-ethyl)-N-methyl-spiro[1,2-dihydro-indole-3,1'-cyclopropane]-6-carboxylic acid amide |
| 310 | 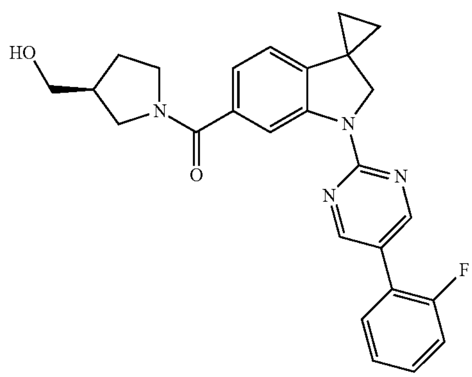 [SMILES: O=C(c1ccc2c(c1)N(c1ncc(-c3ccccc3F)cn1)CC21CC1)N1CC[C@H](CO)C1] | [1-[5-(2-Fluorophenyl)-pyrimidin-2-yl]-spiro[1,2-dihydro-indole-3,1'-cyclopropane]-6-yl]-[(3S)-3-(hydroxymethyl)-pyrrolidin-1-yl]-methanone |
| 311 | 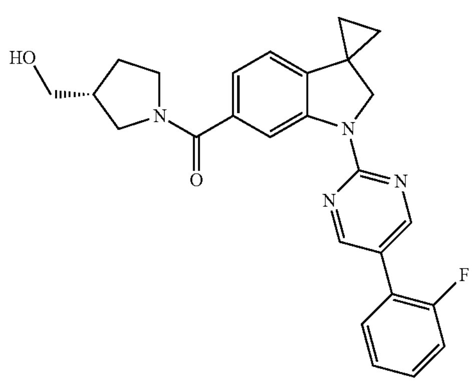 [SMILES: O=C(c1ccc2c(c1)N(c1ncc(-c3ccccc3F)cn1)CC21CC1)N1CC[C@@H](CO)C1] | [1-[5-(2-Fluorophenyl)-pyrimidin-2-yl]-spiro[1,2-dihydro-indole-3,1'-cyclopropane]-6-yl]-[(3R)-3-(hydroxymethyl)-pyrrolidin-1-yl]-methanone |

TABLE 6-continued

| Cpd No. | Structure | Name |
|---|---|---|
| 312 | 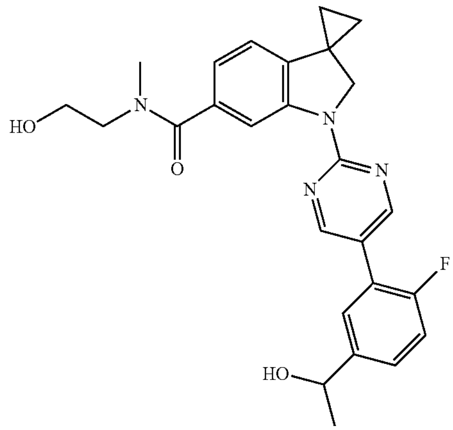 [SMILES: CC(O)c1ccc(F)c(-c2cnc(N3CC4(CC4)c4ccc(C(=O)N(C)CCO)cc43)nc2)c1] | 1-[5-[2-Fluoro-5-(1-hydroxy-ethyl)-phenyl]-pyrimidin-2-yl]-N-(2-hydroxy-ethyl)-N-methyl-spiro[1,2-dihydro-indole-3,1'-cyclopropane]-6-carboxylic acid amide |
| 313 | 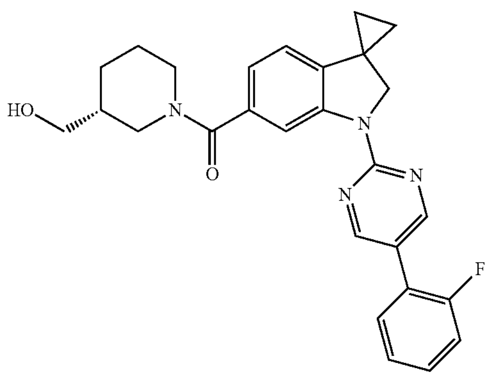 | [1-[5-(2-Fluorophenyl)-pyrimidin-2-yl]-spiro[1,2-dihydro-indole-3,1'-cyclopropane]-6-yl]-[(3R)-3-(hydroxymethyl)-piperidin-1-yl]-methanone |
| 314 | 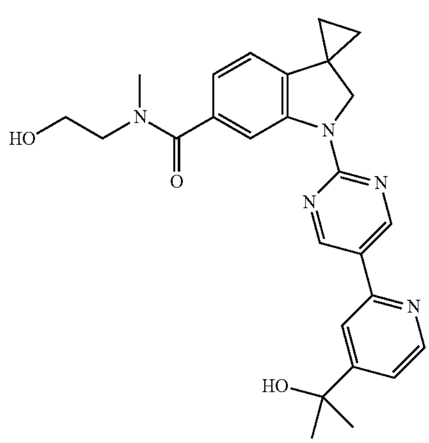 [SMILES: CN(CCO)C(=O)c1ccc2c(c1)N(c1ncc(-c3cc(C(C)(C)O)ccn3)cn1)CC21CC1] | N-(2-Hydroxy-ethyl)-1-[5-[4-(1-hydroxy-1-methyl-ethyl)-pyridin-2-yl]-pyrimidin-2-yl]-N-methyl-spiro[1,2-dihydro-indole-3,1'-cyclopropane]-6-carboxylic acid amide |

TABLE 6-continued

| Cpd No. | Structure | Name |
|---|---|---|
| 315 | 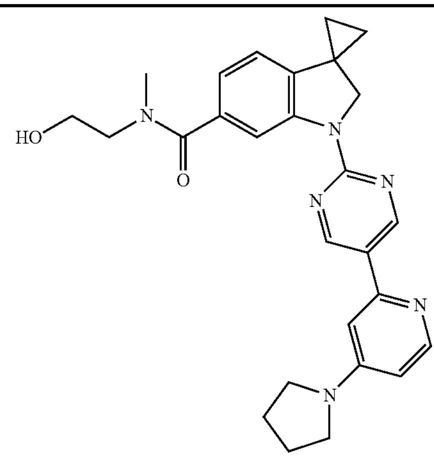 | N-(2-Hydroxy-ethyl)-N-methyl-1-[5-(4-pyrrolidin-1-yl-pyridin-2-yl)-pyrimidin-2-yl]-spiro[1,2-dihydro-indole-3,1'-cyclopropane]-6-carboxylic acid amide |
| 316 | 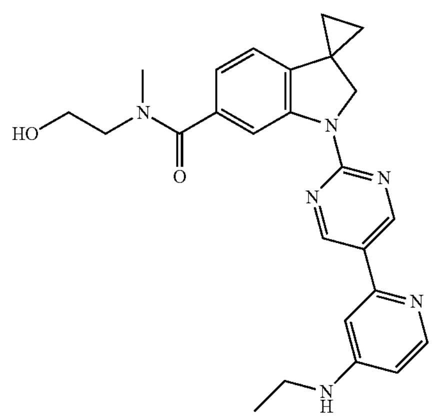 [SMILES: CCNc1ccnc(-c2cnc(N3CC4(CC4)c4ccc(C(=O)N(C)CCO)cc43)nc2)c1] | 1-[5-(4-Ethylamino-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 317 | 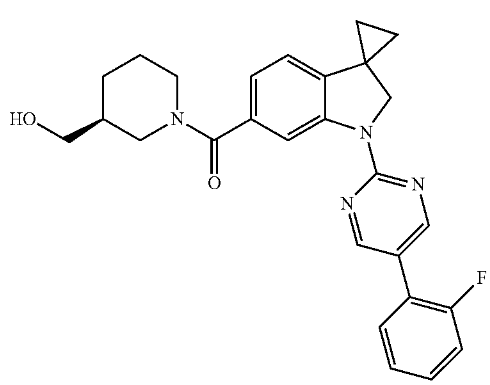 | [1-[5-(2-Fluorophenyl)-pyrimidin-2-yl]-spiro[1,2-dihydro-indole-3,1'-cyclopropane]-6-yl]-[(3S)-3-(hydroxymethyl)-piperidin-1-yl]-methanone |

TABLE 6-continued

| Cpd No. | Structure | Name |
|---|---|---|
| 318 | 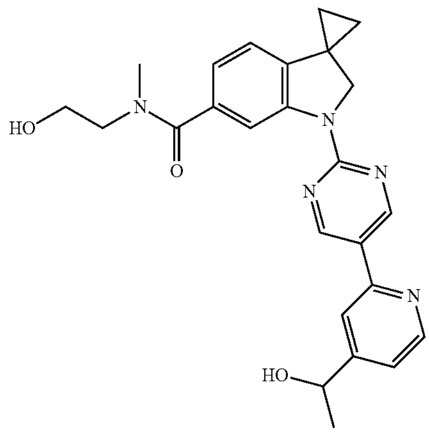 [SMILES: CC(O)c1ccnc(-c2cnc(N3CC4(CC4)c4ccc(C(=O)N(C)CCO)cc43)nc2)c1] | N-(2-Hydroxy-ethyl)-1-[5-[4-(1-hydroxy-ethyl)-pyridin-2-yl]-pyrimidin-2-yl]-N-methyl-spiro[1,2-dihydro-indole-3,1'-cyclopropane]-6-carboxylic acid amide |
| 319 | 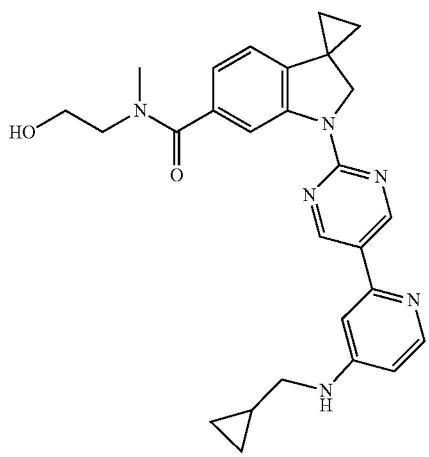 [SMILES: CN(CCO)C(=O)c1ccc2c(c1)N(c1ncc(-c3cc(NCC4CC4)ccn3)cn1)CC21CC1] | 1-[5-[4-(Cyclopropyl-methylamino)-pyridin-2-yl]-pyrimidin-2-yl]-N-(2-hydroxy-ethyl)-N-methyl-spiro[1,2-dihydro-indole-3,1'-cyclopropane]-6-carboxylic acid amide |
| 320 | 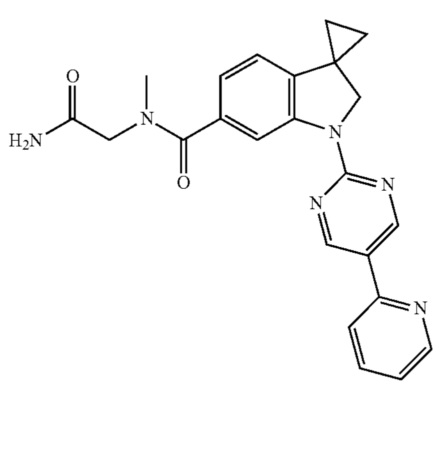 [SMILES: CN(CC(N)=O)C(=O)c1ccc2c(c1)N(c1ncc(-c3ccccn3)cn1)CC21CC1] | N-(Carbamoyl-methyl)-N-methyl-1-(5-pyridin-2-yl-pyrimidin-2-yl)-spiro[1,2-dihydro-indole-3,1'-cyclopropane]-6-carboxylic acid amide |

TABLE 6-continued

| Cpd No. | Structure | Name |
|---|---|---|
| 321 | 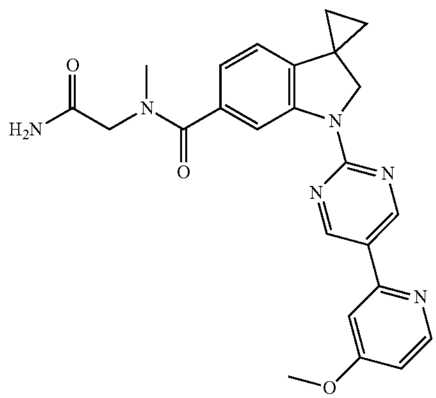 [SMILES: COc1ccnc(-c2cnc(N3CC4(CC4)c4ccc(C(=O)N(C)CC(N)=O)cc43)nc2)c1] | N-(Carbamoyl-methyl)-1-[5-(4-methoxy-pyridin-2-yl)-pyrimidin-2-yl]-N-methyl-spiro[1,2-dihydro-indole-3,1'-cyclopropane]-6-carboxylic acid amide |
| 322 | 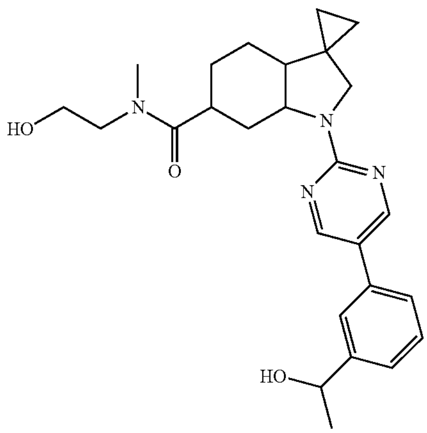 [SMILES: CC(O)c1cccc(-c2cnc(N3CC4(CC4)C4CCC(C(=O)N(C)CCO)CC43)nc2)c1] | N-(2-Hydroxy-ethyl)-1-[5-[3-(1-hydroxy-ethyl)-phenyl]-pyrimidin-2-yl]-N-methyl-spiro[1,2-dihydro-indole-3,1'-cyclopropane]-6-carboxylic acid amide |
| 323 | 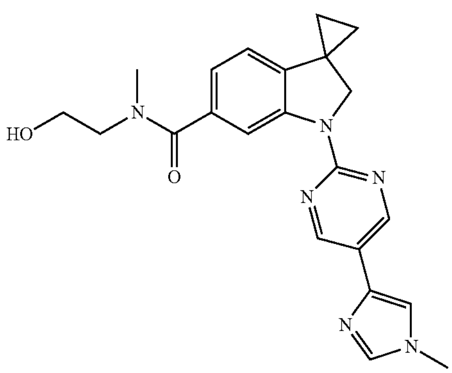 [SMILES: CN(CCO)C(=O)c1ccc2c(c1)N(c1ncc(-c3cn(C)cn3)cn1)CC21CC1] | N-(2-Hydroxy-ethyl)-N-methyl-1-[5-(1-methyl-1H-imidazol-4-yl)-pyrimidin-2-yl]-spiro[1,2-dihydro-indole-3,1'-cyclopropane]-6-carboxylic acid amide |
| 324 | 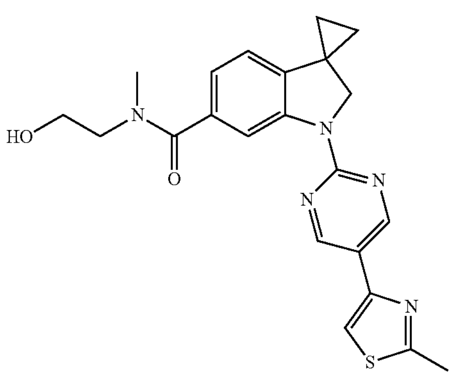 [SMILES: Cc1nc(-c2cnc(N3CC4(CC4)c4ccc(C(=O)N(C)CCO)cc43)nc2)cs1] | N-(2-Hydroxy-ethyl)-N-methyl-1-[5-(2-methyl-thiazol-4-yl)-pyrimidin-2-yl]-spiro[1,2-dihydro-indole-3,1'-cyclopropane]-6-carboxylic acid amide |

TABLE 6-continued

| Cpd No. | Structure | Name |
|---|---|---|
| 325 | 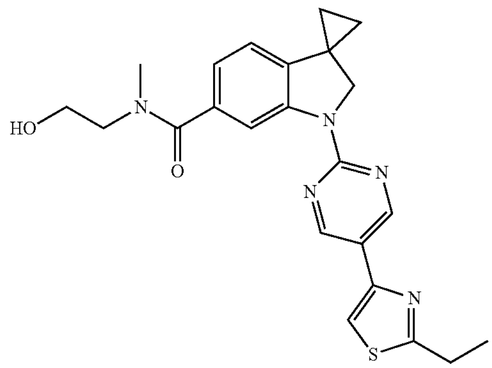 [SMILES: CCc1nc(-c2cnc(N3CC4(CC4)c4ccc(C(=O)N(C)CCO)cc43)nc2)cs1] | 1-[5-(2-Ethyl-thiazol-4-yl)-pyrimidin-2-yl]-N-(2-hydroxy-ethyl)-N-methyl-spiro[1,2-dihydro-indole-3,1'-cyclopropane]-6-carboxylic acid amide |
| 326 | 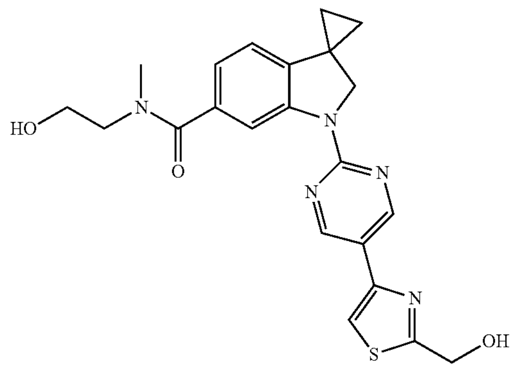 [SMILES: CN(CCO)C(=O)c1ccc2c(c1)N(c1ncc(-c3csc(CO)n3)cn1)CC21CC1] | N-(2-Hydroxy-ethyl)-1-[5-[2-(hydroxymethyl)-thiazol-4-yl]-pyrimidin-2-yl]-N-methyl-spiro[1,2-dihydro-indole-3,1'-cyclopropane]-6-carboxylic acid amide |
| 327 | 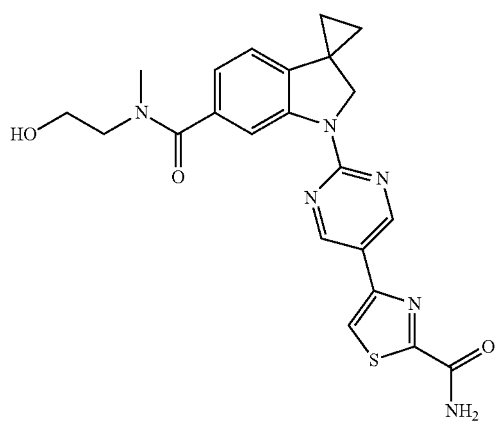 [SMILES: CN(CCO)C(=O)c1ccc2c(c1)N(c1ncc(-c3csc(C(N)=O)n3)cn1)CC21CC1] | 4-[2-[6-[(2-Hydroxy-ethyl)-methyl-carbamoyl]-spiro[1,2-dihydro-indole-3,1'-cyclopropane]-1-yl]-pyrimidin-5-yl]-thiazole-2-carboxylic acid amide |
| 328 | 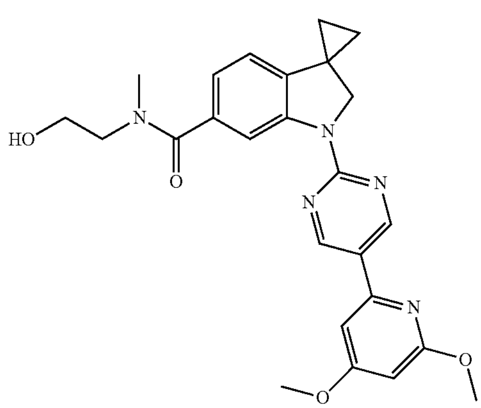 [SMILES: COc1cc(OC)nc(-c2cnc(N3CC4(CC4)c4ccc(C(=O)N(C)CCO)cc43)nc2)c1] | 1-[5-(4,6-Dimethoxy-pyridin-2-yl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 329 | 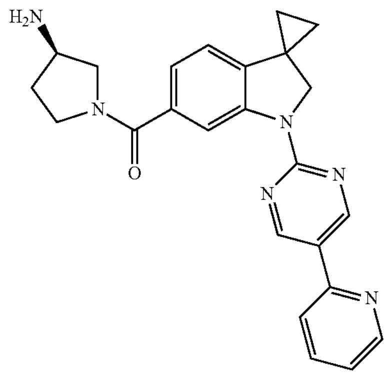 [SMILES: N[C@@H]1CCN(C(=O)c2ccc3c(c2)N(c2ncc(-c4ccccn4)cn2)CC32CC2)C1] | [(3R)-3-Amino-pyrrolidin-1-yl]-[1-(5-pyridin-2-yl-pyrimidin-2-yl)-spiro[1,2-dihydro-indole-3,1'-cyclopropane]-6-yl]-methanone |
| 330 | 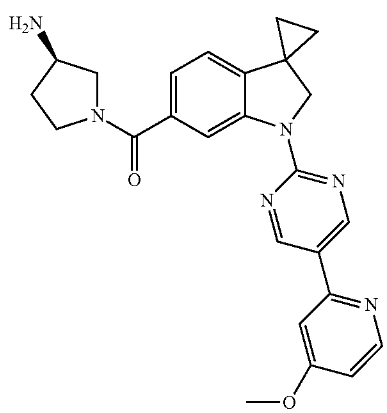 [SMILES: COc1ccnc(-c2cnc(N3CC4(CC4)c4ccc(C(=O)N5CC[C@@H](N)C5)cc43)nc2)c1] | [(3R)-3-Amino-pyrrolidin-1-yl]-[1-[5-(4-methoxy-pyridin-2-yl)-pyrimidin-2-yl]-spiro[1,2-dihydro-indole-3,1'-cyclopropane]-6-yl]-methanone |
| 331 | 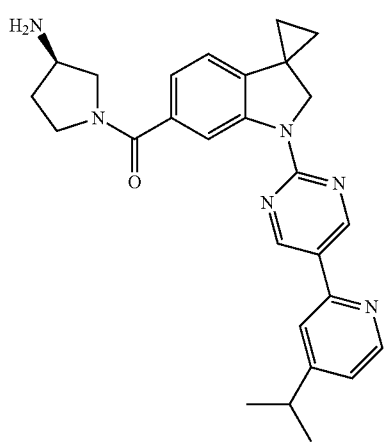 [SMILES: CC(C)c1ccnc(-c2cnc(N3CC4(CC4)c4ccc(C(=O)N5CC[C@@H](N)C5)cc43)nc2)c1] | [(3R)-3-Amino-pyrrolidin-1-yl]-[1-[5-(4-isopropyl-pyridin-2-yl)-pyrimidin-2-yl]-spiro[1,2-dihydro-indole-3,1'-cyclopropane]-6-yl]-methanone |

TABLE 6-continued

| Cpd No. | Structure | Name |
|---|---|---|
| 332 | 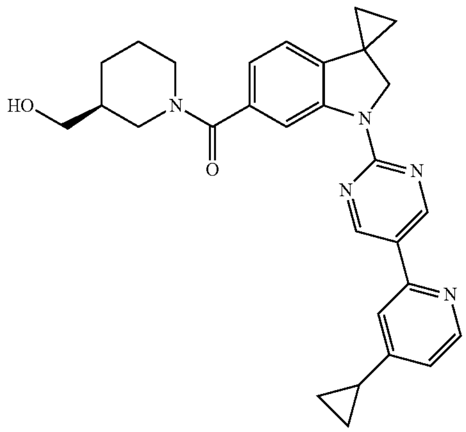 [SMILES: O=C(c1ccc2c(c1)N(c1ncc(-c3cc(C4CC4)ccn3)cn1)CC21CC1)N1CCC[C@H](CO)C1] | [1-[5-(4-Cyclopropyl-pyridin-2-yl)-pyrimidin-2-yl]-spiro[1,2-dihydro-indole-3,1'-cyclopropane]-6-yl]-[(3S)-3-(hydroxymethyl)-piperidin-1-yl]-methanone |
| 333 | 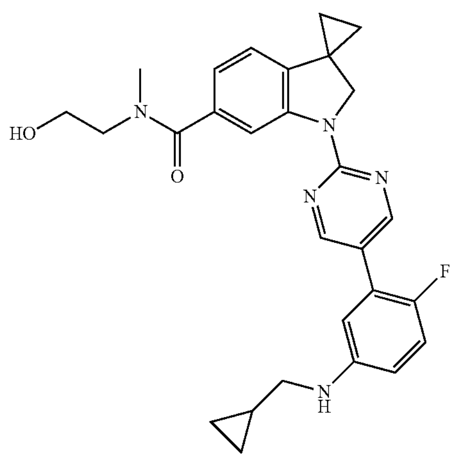 [SMILES: CN(CCO)C(=O)c1ccc2c(c1)N(c1ncc(-c3cc(NCC4CC4)ccc3F)cn1)CC21CC1] | 1-[5-[5-(Cyclopropyl-methylamino)-2-fluoro-phenyl]-pyrimidin-2-yl]-N-(2-hydroxy-ethyl)-N-methyl-spiro[1,2-dihydro-indole-3,1'-cyclopropane]-6-carboxylic acid amide |
| 334 | 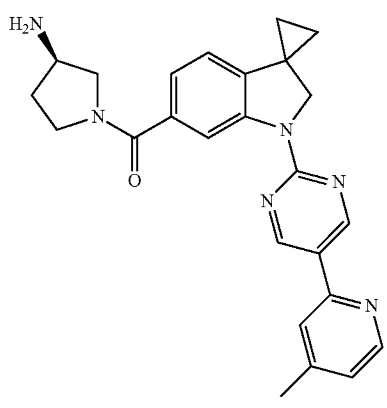 [SMILES: Cc1ccnc(-c2cnc(N3CC4(CC4)c4ccc(C(=O)N5CC[C@@H](N)C5)cc43)nc2)c1] | [(3R)-3-Amino-pyrrolidin-1-yl]-[1-[5-(4-methyl-pyridin-2-yl)-pyrimidin-2-yl]-spiro[1,2-dihydro-indole-3,1'-cyclopropane]-6-yl]-methanone |

TABLE 6-continued

| Cpd No. | Structure | Name |
|---|---|---|
| 335 | 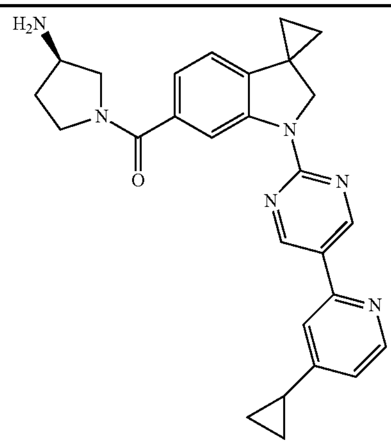 | [(3R)-3-Amino-pyrrolidin-1-yl]-[1-[5-(4-cyclopropyl-pyridin-2-yl)-pyrimidin-2-yl]-spiro[1,2-dihydro-indole-3,1'-cyclopropane]-6-yl]-methanone |
| 336 | 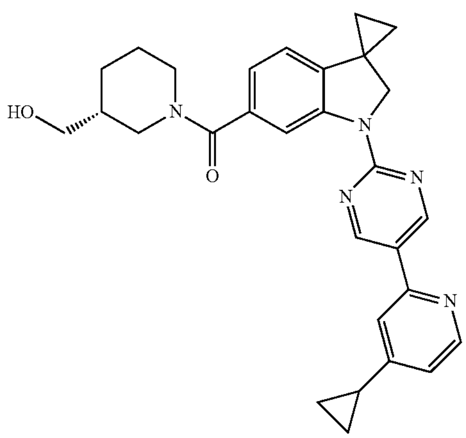 [SMILES: O=C(c1ccc2c(c1)N(c1ncc(-c3cc(C4CC4)ccn3)cn1)CC21CC1)N1CCC[C@@H](CO)C1] | [1-[5-(4-Cyclopropyl-pyridin-2-yl)-pyrimidin-2-yl]-spiro[1,2-dihydro-indole-3,1'-cyclopropane]-6-yl]-[(3R)-3-(hydroxymethyl)-piperidin-1-yl]-methanone |
| 337 | 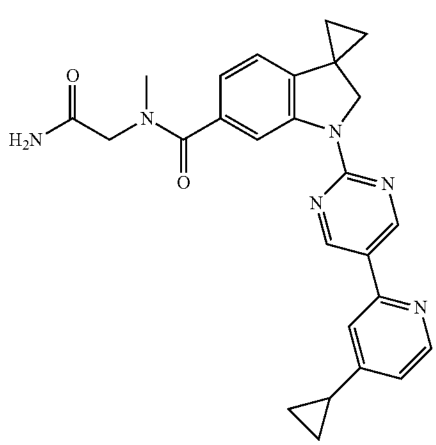 [SMILES: CN(CC(N)=O)C(=O)c1ccc2c(c1)N(c1ncc(-c3cc(C4CC4)ccn3)cn1)CC21CC1] | N-(Carbamoyl-methyl)-1-[5-(4-cyclopropyl-pyridin-2-yl)-pyrimidin-2-yl]-N-methyl-spiro[1,2-dihydro-indole-3,1'-cyclopropane]-6-carboxylic acid amide |

TABLE 6-continued

| Cpd No. | Structure | Name |
|---|---|---|
| 338 | 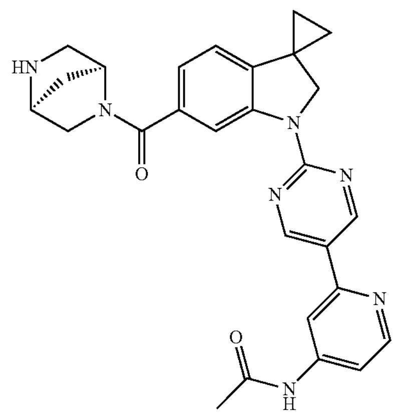 [SMILES: CC(=O)Nc1ccnc(-c2cnc(N3CC4(CC4)c4ccc(C(=O)N5C[C@@H]6C[C@H]5CN6)cc43)nc2)c1] | N-[2-[2-[6-[(1S,4S)-2,5-Diazabicyclo[2.2.1]heptane-2-carbonyl]-spiro[1,2-dihydro-indole-3,1'-cyclopropane]-1-yl]-pyrimidin-5-yl]-pyridin-4-yl]-acetamide |
| 339 | 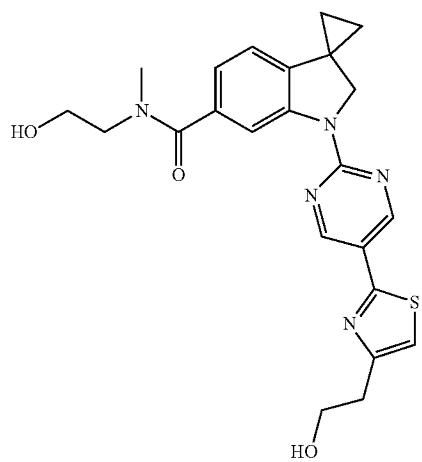 [SMILES: CN(CCO)C(=O)c1ccc2c(c1)N(c1ncc(-c3nc(CCO)cs3)cn1)CC21CC1] | N-(2-Hydroxy-ethyl)-1-[5-[4-(2-hydroxy-ethyl)-thiazol-2-yl]-pyrimidin-2-yl]-N-methyl-spiro[1,2-dihydro-indole-3,1'-cyclopropane]-6-carboxylic acid amide |
| 340 | 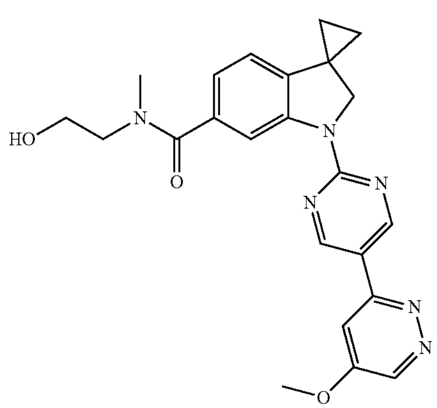 [SMILES: COc1cnnc(-c2cnc(N3CC4(CC4)c4ccc(C(=O)N(C)CCO)cc43)nc2)c1] | N-(2-Hydroxy-ethyl)-1-[5-(5-methoxy-pyridazin-3-yl)-pyrimidin-2-yl]-N-methyl-spiro[1,2-dihydro-indole-3,1'-cyclopropane]-6-carboxylic acid amide |

| Cpd No. | Structure | Name |
|---|---|---|
| 341 | 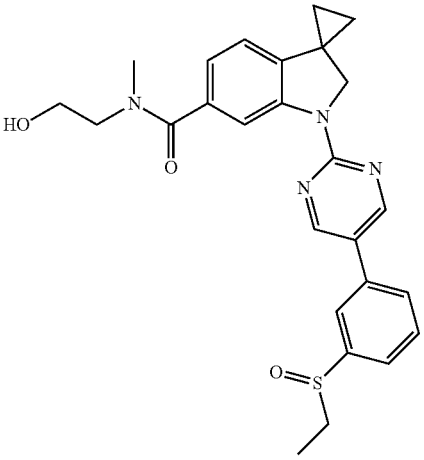 [SMILES: CCS(=O)c1cccc(-c2cnc(N3CC4(CC4)c4ccc(C(=O)N(C)CCO)cc43)nc2)c1] | 1-[5-[3-(Ethylsulfinyl)-phenyl]-pyrimidin-2-yl]-N-(2-hydroxy-ethyl)-N-methyl-spiro[1,2-dihydro-indole-3,1'-cyclopropane]-6-carboxylic acid amide |
| 342 | 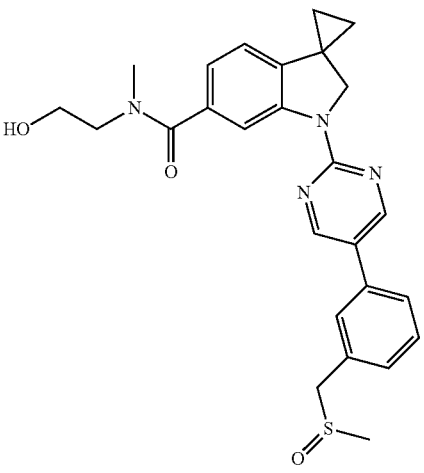 [SMILES: CN(CCO)C(=O)c1ccc2c(c1)N(c1ncc(-c3cccc(CS(C)=O)c3)cn1)CC21CC1] | N-(2-Hydroxy-ethyl)-N-methyl-1-[5-[3-[(methylsulfinyl)-methyl]-phenyl]-pyrimidin-2-yl]-spiro[1,2-dihydro-indole-3,1'-cyclopropane]-6-carboxylic acid amide |
| 343 | 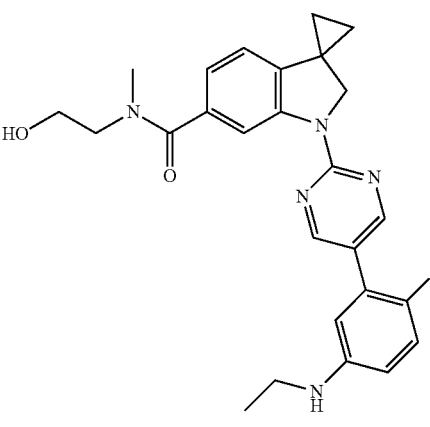 | 1-[5-(5-Ethylamino-2-fluoro-phenyl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 344 | 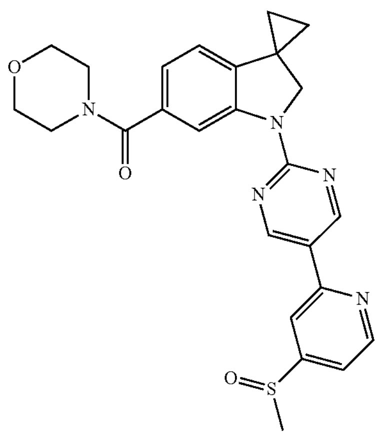 [SMILES: CS(=O)c1ccnc(-c2cnc(N3CC4(CC4)c4ccc(C(=O)N5CCOCC5)cc43)nc2)c1] | [1-[5-[4-(Methylsulfinyl)-pyridin-2-yl]-pyrimidin-2-yl]-spiro[1,2-dihydro-indole-3,1'-cyclopropane]-6-yl]-morpholin-4-yl-methanone |
| 345 | 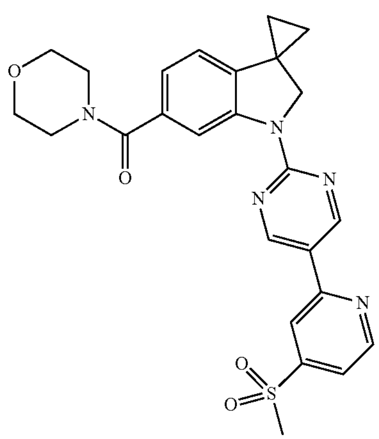 [SMILES: CS(=O)(=O)c1ccnc(-c2cnc(N3CC4(CC4)c4ccc(C(=O)N5CCOCC5)cc43)nc2)c1] | [1-[5-(4-Methylsulfonyl-pyridin-2-yl)-pyrimidin-2-yl]-spiro[1,2-dihydro-indole-3,1'-cyclopropane]-6-yl]-morpholin-4-yl-methanone |
| 346 | 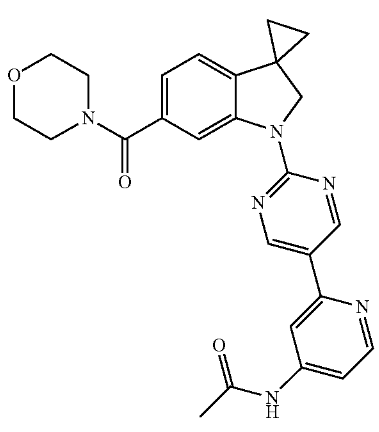 [SMILES: CC(=O)Nc1ccnc(-c2cnc(N3CC4(CC4)c4ccc(C(=O)N5CCOCC5)cc43)nc2)c1] | N-[2-[2-[6-(Morpholine-4-carbonyl)-spiro[1,2-dihydro-indole-3,1'-cyclopropane]-1-yl]-pyrimidin-5-yl]-pyridin-4-yl]-acetamide |

TABLE 6-continued

| Cpd No. | Structure | Name |
|---|---|---|
| 347 | 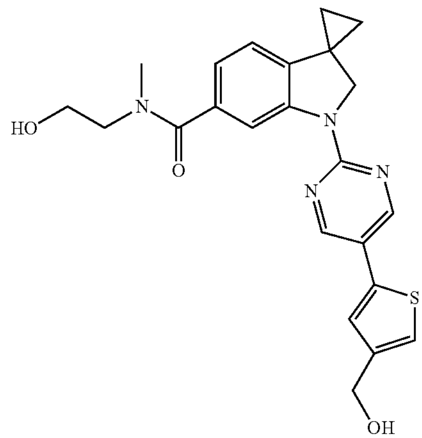 [SMILES: CN(CCO)C(=O)c1ccc2c(c1)N(c1ncc(-c3cc(CO)cs3)cn1)CC21CC1] | N-(2-Hydroxy-ethyl)-1-[5-[4-(hydroxymethyl)-thiophen-2-yl]-pyrimidin-2-yl]-N-methyl-spiro[1,2-dihydro-indole-3,1'-cyclopropane]-6-carboxylic acid amide |
| 348 | 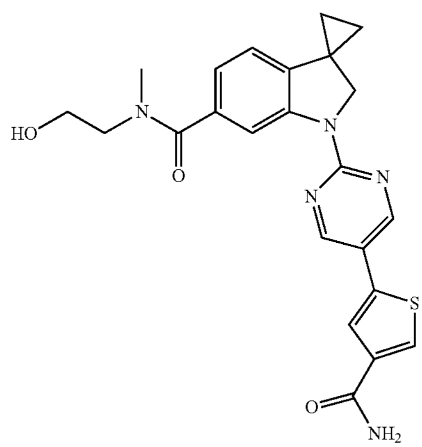 [SMILES: CN(CCO)C(=O)c1ccc2c(c1)N(c1ncc(-c3cc(C(N)=O)cs3)cn1)CC21CC1] | 1-[5-(4-Carbamoyl-thiophen-2-yl)-pyrimidin-2-yl]-N-(2-hydroxy-ethyl)-N-methyl-spiro[1,2-dihydro-indole-3,1'-cyclopropane]-6-carboxylic acid amide |
| 349 | 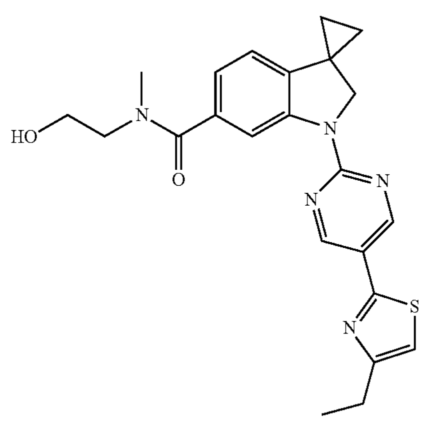 [SMILES: CCc1csc(-c2cnc(N3CC4(CC4)c4ccc(C(=O)N(C)CCO)cc43)nc2)n1] | 1-[5-(4-Ethyl-thiazol-2-yl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 350 | 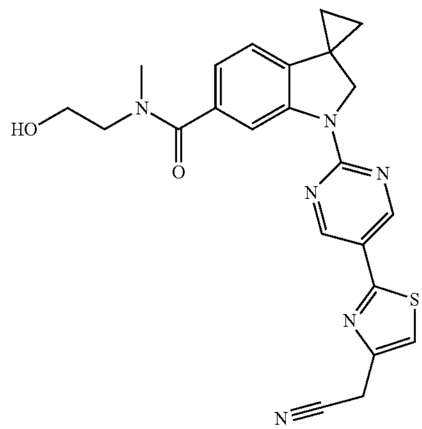 [SMILES: CN(CCO)C(=O)c1ccc2c(c1)N(c1ncc(-c3nc(CC#N)cs3)cn1)CC21CC1] | 1-[5-[4-(Cyano-methyl)-thiazol-2-yl]-pyrimidin-2-yl]-N-(2-hydroxy-ethyl)-N-methyl-spiro[1,2-dihydro-indole-3,1'-cyclopropane]-6-carboxylic acid amide |
| 351 | 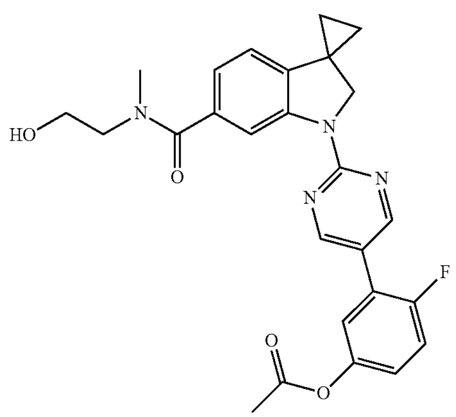 [SMILES: CC(=O)Oc1ccc(F)c(-c2cnc(N3CC4(CC4)c4ccc(C(=O)N(C)CCO)cc43)nc2)c1] | [1-[5-[4-(1-Hydroxy-cyclopropyl)-pyridin-2-yl]-pyrimidin-2-yl]-spiro[1,2-dihydro-indole-3,1'-cyclopropane]-6-yl]-morpholin-4-yl-methanone |
| 352 | 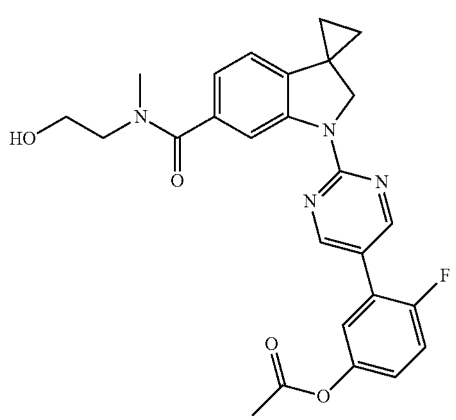 [SMILES: CC(=O)Oc1ccc(F)c(-c2cnc(N3CC4(CC4)c4ccc(C(=O)N(C)CCO)cc43)nc2)c1] | Acetic acid [4-fluoro-3-[2-[6-[(2-hydroxy-ethyl)-methyl-carbamoyl]-spiro[1,2-dihydro-indole-3,1'-cyclopropane]-1-yl]-pyrimidin-5-yl]-phenyl] ester |

TABLE 6-continued

| Cpd No. | Structure | Name |
|---|---|---|
| 354 | 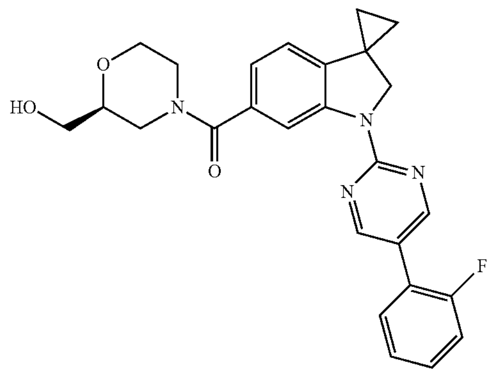 [SMILES: O=C(c1ccc2c(c1)N(c1ncc(-c3ccccc3F)cn1)CC21CC1)N1CCO[C@H](CO)C1] | [1-[5-(2-Fluorophenyl)-pyrimidin-2-yl]-spiro[1,2-dihydro-indole-3,1'-cyclopropane]-6-yl]-[(2S)-2-(hydroxymethyl)-morpholin-4-yl]-methanone |
| 355 | 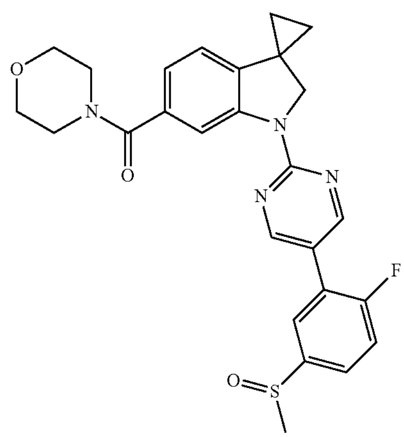 [SMILES: CS(=O)c1ccc(F)c(-c2cnc(N3CC4(CC4)c4ccc(C(=O)N5CCOCC5)cc43)nc2)c1] | [1-[5-[2-Fluoro-5-(methylsulfinyl)-phenyl]-pyrimidin-2-yl]-spiro[1,2-dihydro-indole-3,1'-cyclopropane]-6-yl]-morpholin-4-yl-methanone |
| 356 | 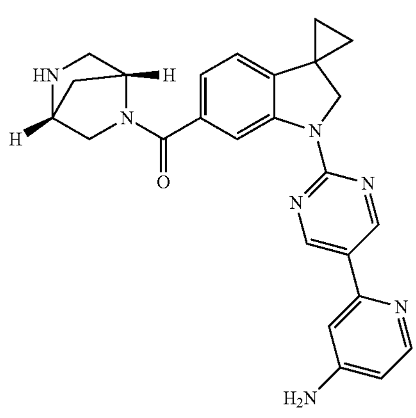 [SMILES: Nc1ccnc(-c2cnc(N3CC4(CC4)c4ccc(C(=O)N5C[C@H]6C[C@@H]5CN6)cc43)nc2)c1] | [1-[5-(4-Amino-pyridin-2-yl)-pyrimidin-2-yl]-spiro[1,2-dihydro-indole-3,1'-cyclopropane]-6-yl]-[(1R,4R)-2,5-diazabicyclo[2.2.1]heptan-2-yl]-methanone |

TABLE 6-continued

| Cpd No. | Structure | Name |
|---|---|---|
| 357 | 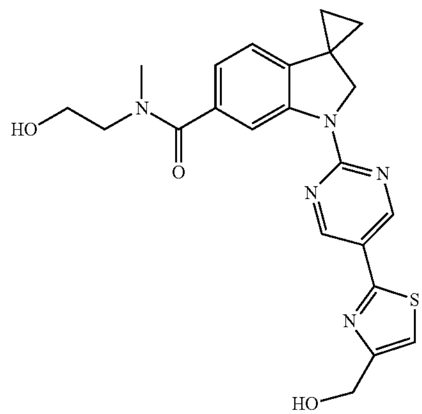 [SMILES: CN(CCO)C(=O)c1ccc2c(c1)N(c1ncc(-c3nc(CO)cs3)cn1)CC21CC1] | N-(2-Hydroxy-ethyl)-1-[5-[4-(hydroxymethyl)-thiazol-2-yl]-pyrimidin-2-yl]-N-methyl-spiro[1,2-dihydro-indole-3,1'-cyclopropane]-6-carboxylic acid amide |
| 358 | 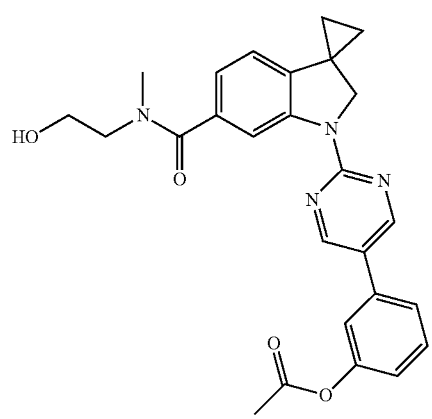 [SMILES: CC(=O)Oc1cccc(-c2cnc(N3CC4(CC4)c4ccc(C(=O)N(C)CCO)cc43)nc2)c1] | Acetic acid [3-[2-[6-[(2-hydroxy-ethyl)-methyl-carbamoyl]-spiro[1,2-dihydro-indole-3,1'-cyclopropane]-1-yl]-pyrimidin-5-yl]-phenyl] ester |
| 359 | 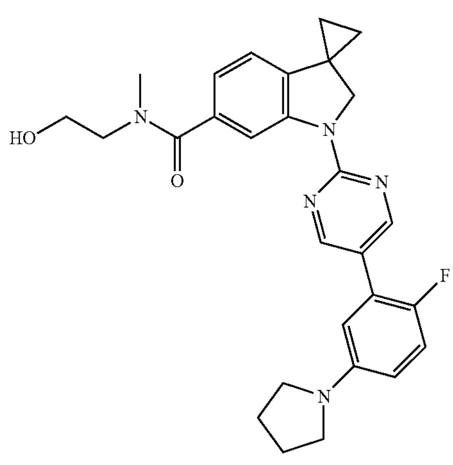 [SMILES: CN(CCO)C(=O)c1ccc2c(c1)N(c1ncc(-c3cc(N4CCCC4)ccc3F)cn1)CC21CC1] | 1-[5-(2-Fluoro-5-pyrrolidin-1-yl-phenyl)-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 360 | 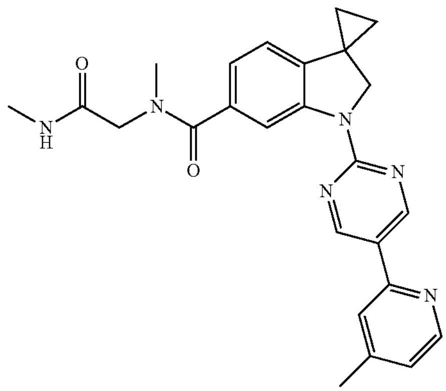 [SMILES: CNC(=O)CN(C)C(=O)c1ccc2c(c1)N(c1ncc(-c3cc(C)ccn3)cn1)CC21CC1] | N-Methyl-N-(methylcarbamoyl-methyl)-1-[5-(4-methyl-pyridin-2-yl)-pyrimidin-2-yl]-spiro[1,2-dihydro-indole-3,1'-cyclopropane]-6-carboxylic acid amide |
| 361 | 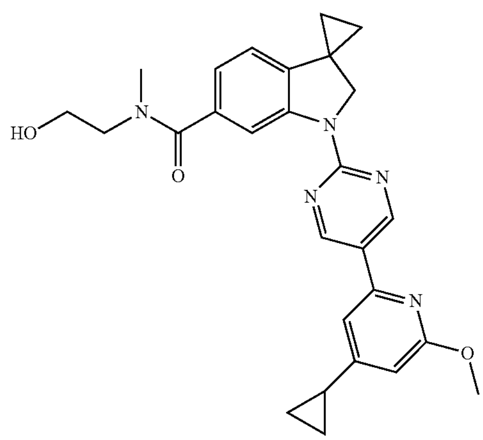 [SMILES: COc1cc(C2CC2)cc(-c2cnc(N3CC4(CC4)c4ccc(C(=O)N(C)CCO)cc43)nc2)n1] | 1-[5-(4-Cyclopropyl-6-methoxy-pyridin-2-yl)-pyrimidin-2-yl]-N-(2-hydroxy-ethyl)-N-methyl-spiro[1,2-dihydro-indole-3,1'-cyclopropane]-6-carboxylic acid amide |
| 362 | 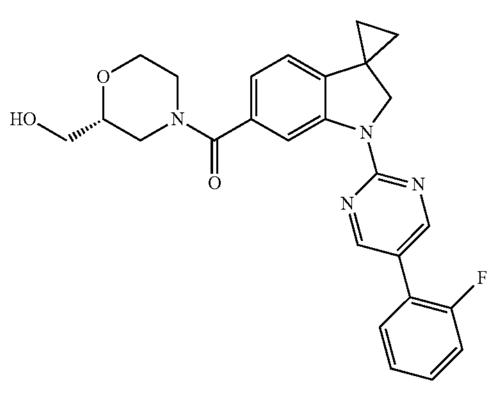 [SMILES: O=C(c1ccc2c(c1)N(c1ncc(-c3ccccc3F)cn1)CC21CC1)N1CCO[C@@H](CO)C1] | [1-[5-(2-Fluorophenyl)-pyrimidin-2-yl]-spiro[1,2-dihydro-indole-3,1'-cyclopropane]-6-yl]-[(2R)-2-(hydroxymethyl)-morpholin-4-yl]-methanone |

TABLE 6-continued

| Cpd No. | Structure | Name |
|---|---|---|
| 363 | 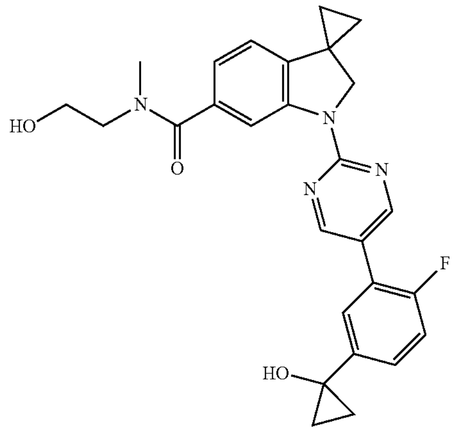 [SMILES: CN(CCO)C(=O)c1ccc2c(c1)N(c1ncc(-c3cc(C4(O)CC4)ccc3F)cn1)CC21CC1] | 1-[5-[2-Fluoro-5-(1-hydroxy-cyclopropyl)-phenyl]-pyrimidin-2-yl]-N-(2-hydroxy-ethyl)-N-methyl-spiro[1,2-dihydro-indole-3,1'-cyclopropane]-6-carboxylic acid amide |
| 364 | 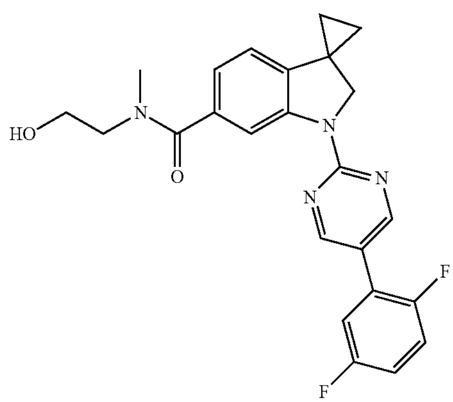 [SMILES: CN(CCO)C(=O)c1ccc2c(c1)N(c1ncc(-c3cc(F)ccc3F)cn1)CC21CC1] | 1-[5-(2,5-Difluoro-phenyl)-pyrimidin-2-yl]-N-(2-hydroxy-ethyl)-N-methyl-spiro[1,2-dihydro-indole-3,1'-cyclopropane]-6-carboxylic acid amide |
| 365 | 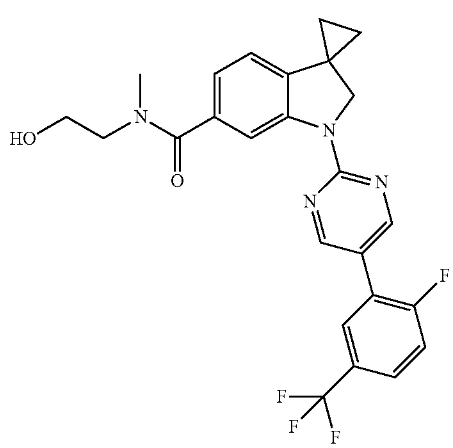 [SMILES: CN(CCO)C(=O)c1ccc2c(c1)N(c1ncc(-c3cc(C(F)(F)F)ccc3F)cn1)CC21CC1] | 1-[5-[2-Fluoro-5-(trifluoromethyl)-phenyl]-pyrimidin-2-yl]-N-(2-hydroxy-ethyl)-N-methyl-spiro[1,2-dihydro-indole-3,1'-cyclopropane]-6-carboxylic acid amide |

TABLE 6-continued

| Cpd No. | Structure | Name |
|---|---|---|
| 366 | 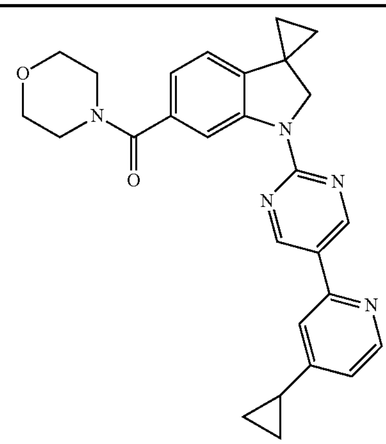 | [1-[5-(4-Cyclopropyl-pyridin-2-yl)-pyrimidin-2-yl]-spiro[1,2-dihydro-indole-3,1'-cyclopropane]-6-yl]-morpholin-4-yl-methanone |
| 367 | 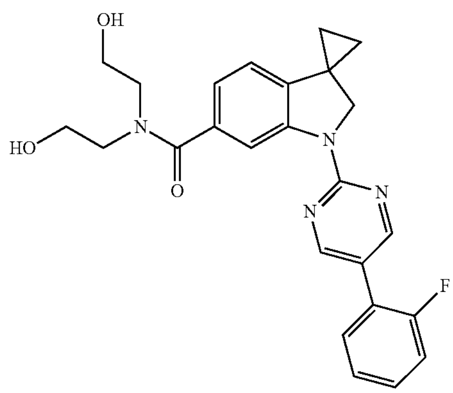 [SMILES: O=C(c1ccc2c(c1)N(c1ncc(-c3ccccc3F)cn1)CC21CC1)N(CCO)CCO] | 1-[5-(2-Fluorophenyl)-pyrimidin-2-yl]-N,N-bis(2-hydroxy-ethyl)-spiro[1,2-dihydro-indole-3,1'-cyclopropane]-6-carboxylic acid amide |
| 368 | 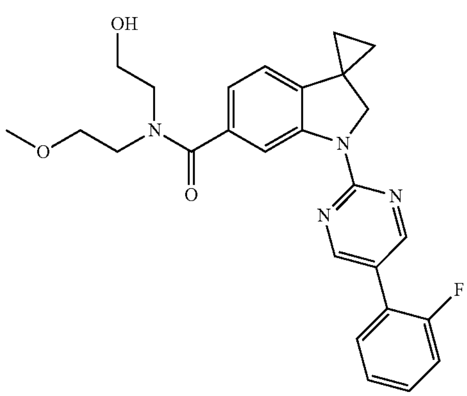 [SMILES: COCCN(CCO)C(=O)c1ccc2c(c1)N(c1ncc(-c3ccccc3F)cn1)CC21CC1] | 1-[5-(2-Fluorophenyl)-pyrimidin-2-yl]-N-(2-hydroxy-ethyl)-N-(2-methoxy-ethyl)-spiro[1,2-dihydro-indole-3,1'-cyclopropane]-6-carboxylic acid amide |
| 369 | 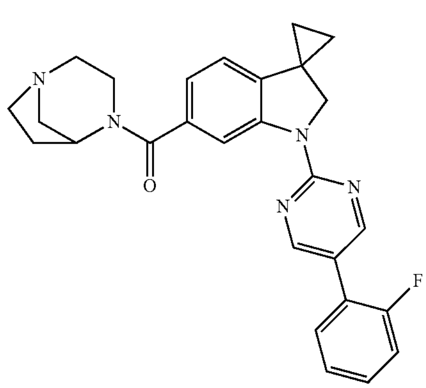 [SMILES: O=C(c1ccc2c(c1)N(c1ncc(-c3ccccc3F)cn1)CC21CC1)N1CCN2CCC1C2] | 1,4-Diazabicyclo[3.2.1]octan-4-yl(1'-(5-(2-fluorophenyl)pyrimidin-2-yl)spiro[cyclopropane-1,3'-indolin]-6'-yl)methanone |

179

A: Preparation of the Compounds According to the Invention

A-1: Preparation of: (1'-(5-(2-fluorophenyl)pyrimidin-2-yl)spiro[cyclopropane-1,3'-indoline]-6'-yl)(morpholino)methanone (Compound 1)

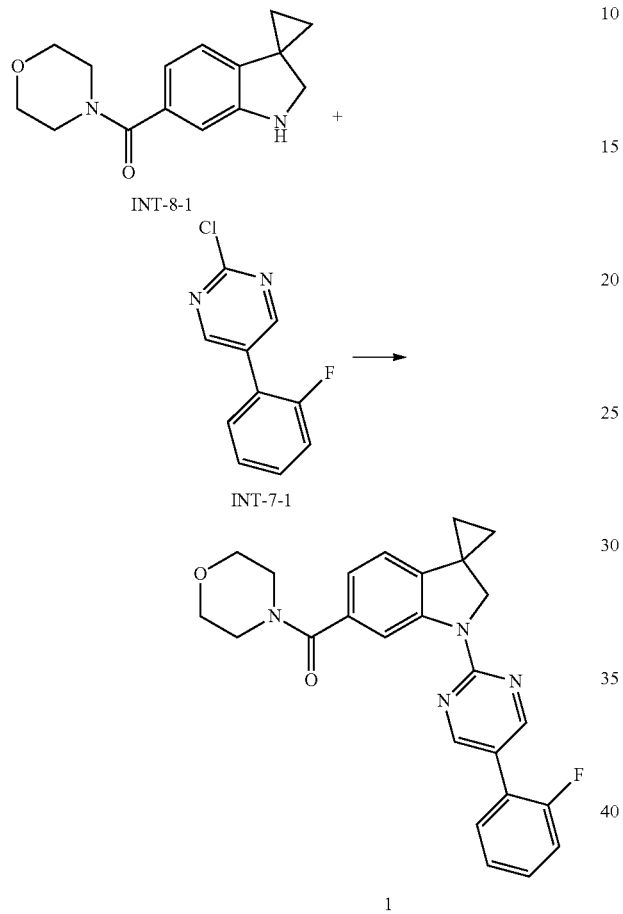

Step 1.8

A suspension of INT-8-1 (250 mg, 0.97 mmol), INT-7-1 (222 mg, 1.07 mmol) and $Cs_2CO_3$ (568 mg, 1.74 mmol) in a mixture of 1,4-dioxane: $CF_3$-Tol (3:1) (5 mL) was flushed thoroughly with Ar for 10 min. $Pd(OAc)_2$ (21.7 mg, 0.097 mmol) and Xantphos (112 mg, 0.19 mmol) were added and the reaction mixture was heated in a microwave at 110° C. for 1 h. The reaction mixture was partitioned between water (20 mL) and EtOAc (20 mL). The aqueous phase was extracted with EtOAc (2×10 mL). Aqueous work up, removal of the solvent followed by a purification step led to (1'-(5-(2-fluorophenyl)pyrimidin-2-yl)-spiro[cyclopropane-1,3'-indoline]-6'-yl)(morpholino)methanone as a white solid (234 mg, 0.54 mmol, 56%). LCMS: calculated for [M+H]$^+$: 431. found: 431.

$^1$H NMR (400 MHz, DMSO-d$_6$) δ 8.86 (s, 2H), 8.41 (s, 1H), 7.67 (t, J=7.9 Hz, 1H), 7.51-7.42 (m, 1H), 7.42-7.31 (m, 2H), 6.97 (d, J=7.6 Hz, 1H), 6.88 (d, J=7.6 Hz, 1H), 4.28 (s, 2H), 3.86-3.37 (m, 8H), 1.26-1.19 (m, 2H), 1.19-1.11 (m, 2H).

180

A-2: Preparation of: (1'-(5-(2-fluorophenyl)pyrimidin-2-yl)spiro[cyclopropane-1,3'-indoline]-6'-yl)(morpholino)methanone (Compound 1)

Step 2.1: synthesis of INT-9-1: methyl spiro[cyclopropane-1,3'-indoline]-6'-carboxylate

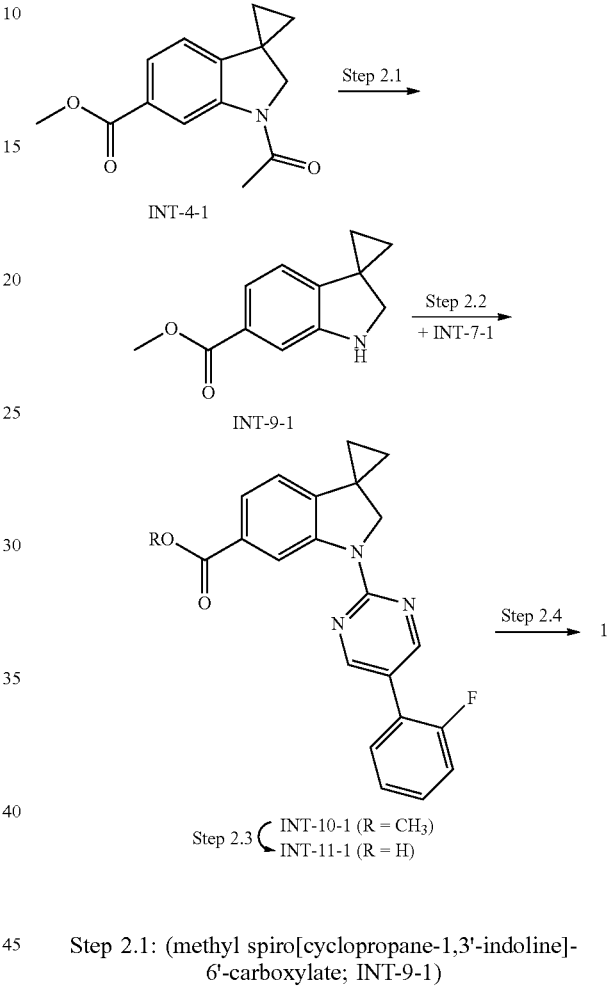

Step 2.1: (methyl spiro[cyclopropane-1,3'-indoline]-6'-carboxylate; INT-9-1)

Conc. HCl (37.5 mL, 450 mmol) was added slowly to a stirred solution of indoline INT-4-1 (3.0 g, 12.2 mmol) in MeOH (75.0 mL) at rt. The reaction mixture was heated at 50° C. for 2 h and then heated to reflux for 1.5 h. The reaction mixture was cooled to rt and partitioned between saturated aqueous $NaHCO_3$ and EtOAc. The aqueous phase was extracted with EtOAc. Aqueous work up and removal of the solvent led to methyl spiro[cyclopropane-1,3'-indoline]-6'-carboxylate as an off white solid (2.40 g, 11.8 mmol, 97%). LCMS: calculated for [M+H]$^+$: 204. found: 204.

Step 2.2: (methyl 1'-(5-(2-fluorophenyl)pyrimidin-2-yl)spiro[cyclopropane-1,3'-indoline]-6'-carboxylate; INT-10-1)

INT-9-1 (250 mg, 1.23 mmol), and pyrimidine INT-7-1 (282 mg, 1.35 mmol) and $Cs_2CO_3$ (721 mg, 2.21 mmol) are reacted in dry THF (10 mL) in the presence of $Pd(OAc)_2$ (13.8 mg, 0.062 mmol) and Xantphos (71.2 mg, 0.12 mmol) according to the procedure described under A-1 above.

Methyl 1'-(5-(2-fluorophenyl)pyrimidin-2-yl)spiro[cyclopropane-1,3'-indoline]-6'-carboxylate (INT-10-1) has been isolated as a pale solid. (0.36 g, 0.96 mmol, 78%). LCMS: calculated for [M+H]$^+$: 376. found: 376.

Step 2.3: (1'-(5-(2-fluorophenyl)pyrimidin-2-yl)spiro[cyclopropane-1,3'-indoline]-6'-carboxylic acid; INT-11-1)

A solution of LiOH.H$_2$O (201 mg, 4.79 mmol) in water (1.0 mL) was added to a stirred solution of INT-10-1 (360 mg, 0.96 mmol) in THF (3.0 mL) at rt. The biphasic reaction mixture was heated at 50° C. for 18 h. The reaction mixture was cooled to rt, diluted with water (5 mL) and acidified to pH~5 by addition of 2M aqueous HCl. The solids were filtered off, rinsed with water (5 mL) and air-dried to give 1'-(5-(2-fluoro-phenyl)pyrimidin-2-yl)spiro[cyclopropane-1,3'-indoline]-6'-carboxylic acid as a white solid. (0.29 g, 0.80 mmol, 83%). LCMS: calculated for [M+H]$^+$: 362. found: 362.

Step 2.4

EDCl (184 mg, 0.96 mmol) and HOAt (11.0 mg, 0.080 mmol) were added to a suspension of INT-11-1 (289 mg, 0.80 mmol) and morpholine (0.077 mL, 0.88 mmol) in dry DMF (3.5 mL) at rt and the reaction mixture was stirred at rt for 2 h. The mixture was partitioned between 0.5M aqueous HCl (20 mL) and EtOAc (20 mL). Aqueous work up, removal of the solvent followed by a purification step led to (1'-(5-(2-fluorophenyl)pyrimidin-2-yl)spiro[cyclopropane-1,3'-indoline]-6'-yl)(morpholino)methanone as a white solid. (0.19 g, 0.45 mmol, 55%) LCMS: calculated for [M+H]$^+$: 431. found: 431.

$^1$H NMR (400 MHz, DMSO-d$_6$) δ 8.86 (s, 2H), 8.41 (s, 1H), 7.67 (t, J=7.9 Hz, 1H), 7.51-7.42 (m, 1H), 7.42-7.31 (m, 2H), 6.97 (d, J=7.6 Hz, 1H), 6.88 (d, J=7.6 Hz, 1H), 4.28 (s, 2H), 3.86-3.37 (m, 8H), 1.26-1.19 (m, 2H), 1.19-1.11 (m, 2H).

A-3: Preparation of: 1'-(5-(2-fluorophenyl)pyrimidin-2-yl)-N,N-dimethylspiro[cyclopropane-1,3'-indoline]-6'-carboxamide (compound 2)

Step 2.4

EDCl (117 mg, 0.61 mmol) and HOAt (3.77 mg, 0.028 mmol), INT-11-1 (200 mg, 0.55 mmol) and dimethylamine (2M solution in THF, 0.33 mL, 0.66 mmol) in dry DMF (1.0 mL) were reacted according to the method described in A-2 for step 2.4 above. 1'-(5-(2-fluorophenyl)pyrimidin-2-yl)-N,N-dimethylspiro[cyclopropane-1,3'-indoline]-6'-carboxamide has been isolated as a white solid (0.13 g, 0.34 mmol, 61%) LCMS: calculated for [M+H]$^+$: 389. found: 389.

$^1$H NMR (400 MHz, DMSO-d$_6$) δ 8.85 (d, J=1.3 Hz, 2H), 8.38 (d, J=1.2 Hz, 1H), 7.67 (td, J=7.9, 1.7 Hz, 1H), 7.50-7.42 (m, 1H), 7.41-7.31 (m, 2H), 6.95 (dd, J=7.6, 1.4 Hz, 1H), 6.87 (d, J=7.6 Hz, 1H), 4.28 (s, 2H), 3.03-2.89 (m, 6H), 1.26-1.11 (m, 4H).

A-4: Preparation of: (1'-(5-(2-fluorophenyl)pyrimidin-2-yl)spiro[cyclopropane-1,3'-indoline]-6'-yl)(pyrrolidin-1-yl)methanone (compound 3)

Step 2.4

EDCl (117 mg, 0.61 mmol) and HOAt (3.77 mg, 0.028 mmol), INT-11-1 (200 mg, 0.55 mmol) and pyrrolidine (0.055 mL, 0.66 mmol) in dry DMF (1.0 mL) were reacted according to the method described in A-2 for step 2.4 above. (1'-(5-(2-fluorophenyl)pyrimidin-2-yl)spiro[cyclopropane-1,3'-indoline]-6'-yl)(pyrrolidin-1-yl)methanone has been isolated as a white solid (0.13 g, 0.31 mmol, 57%) LCMS: calculated for [M+H]$^+$: 415. found: 415.

$^1$H NMR (400 MHz, DMSO-d$_6$) δ 8.85 (d, J=1.2 Hz, 2H), 8.50 (d, J=1.2 Hz, 1H), 7.67 (td, J=7.9, 1.7 Hz, 1H), 7.50-7.42 (m, 1H), 7.41-7.31 (m, 2H), 7.08 (dd, J=7.7, 1.4 Hz, 1H), 6.86 (d, J=7.7 Hz, 1H), 4.28 (s, 2H), 3.47 (t, J=6.8 Hz, 2H), 3.42 (t, J=6.4 Hz, 2H), 1.93-1.75 (m, 4H), 1.27-1.11 (m, 4H).

A-5: Preparation of: 4-(1'-(5-(2-fluorophenyl)pyrimidin-2-yl)spiro[cyclopropane-1,3'-indoline]-6'-ylcarbonyl)piperazin-2-one (compound 4)

Step 2.4

EDCl (175 mg, 0.92 mmol) and HOAt (5.65 mg, 0.042 mmol), INT-11-1 (300 mg, 0.83 mmol) and piperazine-2-one (99.7 mg, 1.00 mmol) in dry DMF (2.0 mL) were reacted according to the method described in A-2 for step 2.4 above. 4-(1'-(5-(2-Fluorophenyl)pyrimidin-2-yl)spiro[cyclopropane-1,3'-indoline]-6'-ylcarbonyl)piperazin-2-one has been isolated as a white solid. (0.13 g, 0.29 mmol, 35%) LCMS: calculated for [M+H]$^+$: 444. found: 444.

$^1$H NMR (400 MHz, DMSO-d$_6$) δ 8.85 (d, J=1.3 Hz, 2H), 8.43 (d, J=1.0 Hz, 1H), 8.14 (s, 1H), 7.67 (td, J=7.9, 1.7 Hz, 1H), 7.50-7.42 (m, 1H), 7.42-7.31 (m, 2H), 7.01 (dd, J=7.6, 1.2 Hz, 1H), 6.90 (d, J=7.6 Hz, 1H), 4.29 (s, 2H), 4.17-3.89 (m, 2H), 3.83-3.46 (m, 2H), 3.30-3.20 (m, 2H), 1.26-1.14 (m, 4H).

A-6: Preparation of: (1'-(5-(2-fluorophenyl)pyrimidin-2-yl)spiro[cyclopropane-1,3'-indoline]-6'-yl)(piperazin-1-yl)methanone (compound 5)

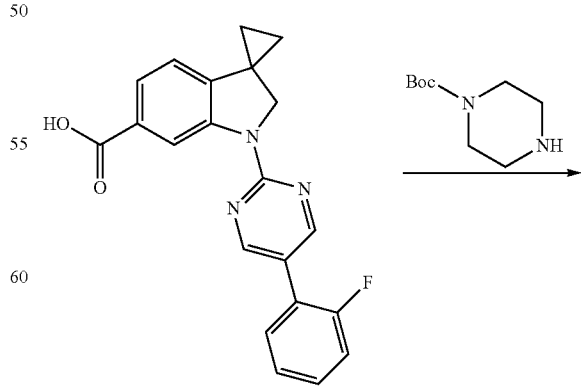

INT-11-1

-continued

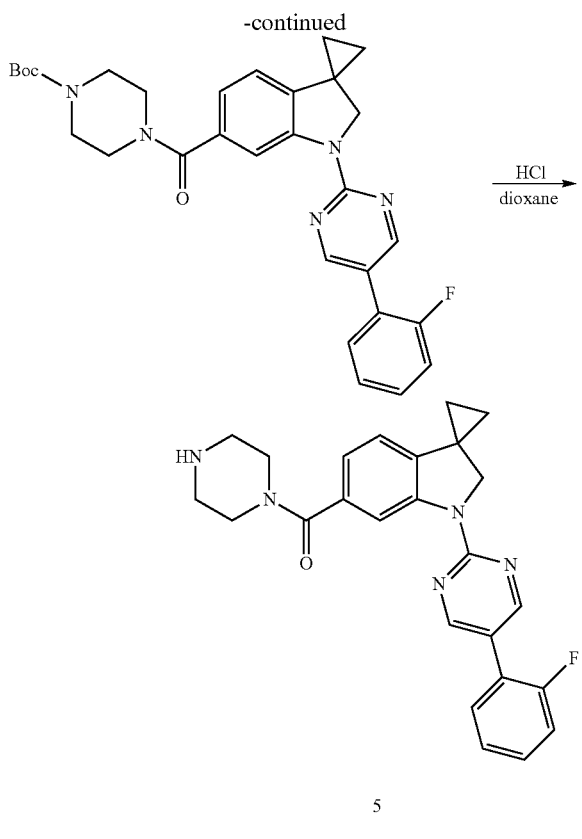

5

Step 2.4

EDCl (117 mg, 0.61 mmol) and HOAt (3.77 mg, 0.028 mmol), INT-11-1 (200 mg, 0.55 mmol) and t-butyl piperazine-1-carboxylate (124 mg, 0.66 mmol) in dry DMF (1.0 mL) were reacted according to the method described in A-2 for step 2.4 above. The intermediate amide containing the BOC group has been isolated as a white solid. (0.23 g, 0.43 mmol, 78%) LCMS: calculated for [M+H]$^+$: 530. found: 530. For removal of the BOC group from the intermediate amide, a 4M solution of HCl in dioxane (2.0 mL, 8.00 mmol) was added to this latter intermediate amide (230 mg, 0.43 mmol). After hydrogenous work up (1'-(5-(2-fluoro-phenyl)pyrimidin-2-yl)spiro[cyclopropane-1,3'-indoline]-6'-yl)(piperazin-1-yl)methanone was isolated as a white solid. (130 mg, 0.30 mmol, 70%) LCMS: calculated for [M+H]$^+$: 430. found: 430.
$^1$H NMR (400 MHz, DMSO-d$_6$) δ 8.85 (d, J=1.3 Hz, 2H), 8.38 (d, J=1.2 Hz, 1H), 7.67 (td, J=7.9, 1.7 Hz, 1H), 7.50-7.42 (m, 1H), 7.41-7.31 (m, 2H), 6.93 (dd, J=7.6, 1.3 Hz, 1H), 6.87 (d, J=7.6 Hz, 1H), 4.28 (s, 2H), 3.67-3.35 (m, 5H), 2.82-2.60 (m, 4H), 1.26-1.10 (m, 4H).

A-7: Preparation of: (1'-(5-(2-chlorophenyl)pyrimidin-2-yl)spiro[cyclopropane-1,3'-indoline]-6'-yl)(morpholino)methanone (compound 6)

Step 1.8

Reaction of INT-8-1 (200 mg, 0.77 mmol), INT-7-2 (192 mg, 0.85 mmol), Cs$_2$CO$_3$ (454 mg, 1.40 mmol) in 1,4-dioxane (3 mL)/CF$_3$-Tol (1 mL) in the presence of Pd(OAc)$_2$ (17.4 mg, 0.077 mmol) and Xantphos (90 mg, 0.16 mmol) according to the method described under A-1 above, let to (1'-(5-(2-chloro-phenyl)pyrimidin-2-yl)spiro[cyclopropane-1,3'-indoline]-6'-yl)(morpholino)methanone as a white solid (130 mg, 0.29 mmol, 38%). LCMS calculated for [M+H]$^+$: 447. found: 447.
$^1$H NMR (400 MHz, DMSO-d$_6$) δ 8.76 (s, 2H), 8.41 (d, J=1.2 Hz, 1H), 7.66-7.61 (m, 1H), 7.58-7.54 (m, 1H), 7.51-7.41 (m, 2H), 6.97 (dd, J=7.6, 1.3 Hz, 1H), 6.89 (d, J=7.6 Hz, 1H), 4.28 (s, 2H), 3.83-3.37 (m, 8H), 1.27-1.10 (m, 4H).

A-8: Preparation of: morpholino(1'-(5-phenylpyrimidin-2-yl)spiro[cyclopropane-1,3'-indoline]-6'-yl)methanone (compound 7)

Step 1.8

Reaction of INT-8-1 (200 mg, 0.77 mmol), INT-7-3 (162 mg, 0.85 mmol), Cs$_2$CO$_3$ (454 mg, 1.40 mmol) in 1,4-dioxane (3 mL)/CF$_3$-Tol (1 mL) in the presence of Pd(OAc)$_2$ (17.4 mg, 0.077 mmol) and Xantphos (90 mg, 0.16 mmol) according to the method described under A-1 above, let to morpholino(1'-(5-phenylpyrimidin-2-yl)spiro[cyclopropane-1,3'-indoline]-6'-yl)methanone. (150 mg, 0.36 mmol, 47%). LCMS calculated for [M+H]$^+$: 413. found: 413.
$^1$H NMR (400 MHz, DMSO-d$_6$) δ 8.99 (s, 2H), 8.42 (d, J=1.2 Hz, 1H), 7.80-7.72 (m, 2H), 7.50 (m, 2H), 7.39 (m, 1H), 6.95 (dd, J=7.6, 1.4 Hz, 1H), 6.87 (d, J=7.6 Hz, 1H), 4.28 (s, 2H), 3.80-3.37 (m, 8H), 1.27-1.10 (m, 4H).

A-9: Preparation of: (1'-(5-(2,4-difluorophenyl)pyrimidin-2-yl)spiro[cyclopropane-1,3'-indoline]-6'-yl)(morpholino)methanone (compound 8)

Step 1.8

Reaction of INT-8-1 (200 mg, 0.77 mmol), INT-7-4 (173 mg, 0.85 mmol), Cs$_2$CO$_3$ (454 mg, 1.40 mmol) in 1,4-dioxane (3 mL)/CF$_3$-Tol (1 mL) in the presence of Pd(OAc)$_2$ (17.4 mg, 0.077 mmol) and Xantphos (90 mg, 0.16 mmol) according to the method described under A-1 above, let to (1'-(5-(2,4-di-fluorophenyl)pyrimidin-2-yl)spiro[cyclopropane-1,3'-indoline]-6'-yl)(morpholino)methanone 150 mg, 0.33 mmol, 43%). LCMS calculated for [M+H]$^+$: 449. found: 449.
$^1$H NMR (400 MHz, DMSO-d$_6$) δ 8.82 (s, 2H), 8.40 (s, 1H), 7.77-7.67 (m, 1H), 7.45 (td, J=8.5, 2.4 Hz, 1H), 7.26 (td, J=8.5, 2.4 Hz, 1H), 6.97 (d, J=7.6 Hz, 1H), 6.88 (d, J=7.6 Hz, 1H), 4.27 (s, 2H), 3.81-3.38 (m, 8H), 1.26-1.08 (m, 4H).

A-10: Preparation of: (1'-(5-(2-fluorobenzyl)pyrimidin-2-yl)spiro[cyclopropane-1,3'-indoline]-6'-yl)(morpholino)methanone (compound 178)

Step 1.8

Reaction of INT-8-1 (316 mg, 1.23 mmol), INT-7-5 (300 mg, 1.35 mmol), Cs$_2$CO$_3$ (599 mg, 1.84 mmol) in 1,4-dioxane (4 mL)/CF$_3$-Tol (1.25 mL) in the presence of, Pd(OAc)$_2$ (27.5 mg, 0.12 mmol) and Xantphos (142 mg, 0.25 mmol) according to the method described under A-1 above, let to (1'-(5-(2-fluoro-benzyl)pyrimidin-2-yl)spiro[cyclopropane-1,3'-indoline]-6'-yl)(morpholino)methanone as white crystals (151 mg, 0.34 mmol, 28%). LCMS: calculated for [M+H]$^+$: 445. found: 445.
$^1$H NMR (400 MHz, DMSO-d$_6$) δ 8.52 (s, 2H), 8.30 (d, J=1.2 Hz, 1H), 7.43-7.24 (m, 2H), 7.17 (m, 2H), 6.91 (dd, J=7.6, 1.1 Hz, 1H), 6.83 (d, J=7.6 Hz, 1H), 4.18 (s, 2H), 3.93 (s, 2H), 3.74-3.37 (m, 8H), 1.22-1.04 (m, 4H).

A-11: Preparation of: (1'-(5-(2-fluorophenyl)pyrimidin-2-yl)spiro[cyclobutane-1,3'-indoline]-6'-yl)(morpholino)methanone (compound 171)

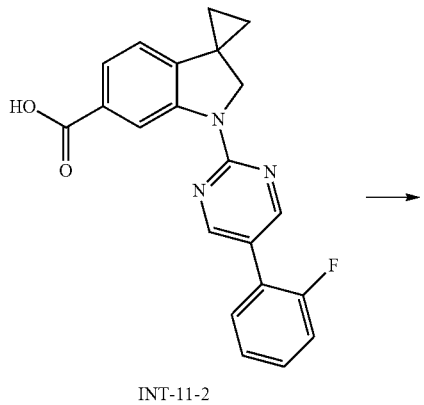

INT-11-2

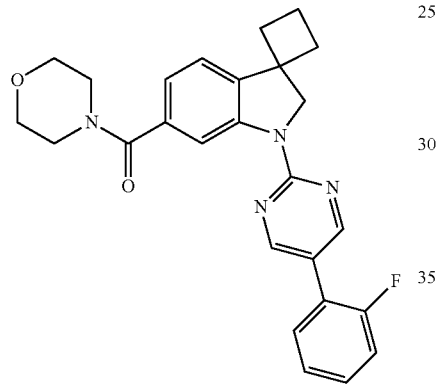

171

Step 2.4

EDCl (153 mg, 0.80 mmol) and HOAt (9.1 mg, 0.067 mmol), INT-11-2 (250 mg, 0.67 mmol) and morpholine (0.064 mL, 0.73 mmol) in dry DMF (3.5 mL) were reacted according to the method described in A-2 for step 2.4 above. (1'-(5-(2-Fluorophenyl)pyrimidin-2-yl)spiro[cyclobutane-1,3'-indoline]-6'-yl)(morpholino)methanone has been isolated as a white solid. (203 mg, 0.46 mmol, 69%). LCMS: calculated for [M+H]$^+$: 445. found: 445.

$^1$H NMR (400 MHz, DMSO-d$_6$) δ 8.85 (d, J=1.5 Hz, 2H), 8.36 (d, J=1.4 Hz, 1H), 7.66 (td, J=7.9, 1.9 Hz, 1H), 7.62 (d, J=7.6 Hz, 1H), 7.52-7.42 (m, 1H), 7.41-7.30 (m, 2H), 7.07 (dd, J=7.6, 1.5 Hz, 1H), 4.40 (s, 2H), 2.47-2.27 (m, 4H), 2.15-2.01 (m, 2H).

A-12: Preparation of: morpholino(1'-(5-o-tolylpyrimidin-2-yl)spiro[cyclopropane-1,3'-indoline]-6'-yl)methanone (compound 12)

Step 1.8

To a stirred solution of compound INT-8-1 (0.200 g, 0.772 mmol, 1 eq) and compound INT-7-6 (0.165 g, 0.771 mmol, 1.1 eq) in 1-butanol (10 mL), was added conc.H$_2$SO$_4$ (75 mg, 0.765 mmol, 1.0 eq) and heated to 120° C. for 3 h. The RM was evaporated and basified (pH~8) with aq.NaHCO$_3$ and extracted with DCM (10 mL), dried (Na$_2$SO$_4$) and evaporated. The crude product was purified by column chromatography (100-200 mesh) using 40% EtOAc in pet ether as eluent to get morpholino(1'-(5-o-tolylpyrimidin-2-yl)spiro[cyclopropane-1,3'-indoline]-6'-yl)methanone (0.82 g, ~25%). TLC system: 2:3 EtOAc/pet ether, R$_f$: 0.4.

$^1$H NMR (300 MHz, DMSO-d$_6$): δ 8.67 (s, 2H), 8.40 (d, J=1.4 Hz, 1H), 7.40-7.26 (m, 4H), 6.95 (dd, J=7.6, 1.5 Hz, 1H), 6.87 (d, J=7.6 Hz, 1H), 4.28 (s, 2H), 3.60 (brs, 8H), 2.32 (s, 3H), 1.32-1.20 (m, 2H), 1.15-1.12 (m, 2H). UPLC: found [M+H]$^+$: 427.0

A-13: Preparation of: morpholino(1'-(5-(2-(trifluoromethoxy)phenyl)pyrimidin-2-yl)spiro[cyclopropane-1,3'-indoline]-6'-yl)methanone (compound 13)

Step 1.8

Reaction according to A-12 using INT-7-7 (106.2 mg, 0.387 mmol, 1.0 eq) and INT-8-1 (100 mg, 0.387 mmol, 1.0 eq) in 1-butanol (5 mL), conc.H$_2$SO$_4$ (38 mg, 0.387 mmol, 1.0 eq) yields morpholino(1'-(5-(2-(trifluoromethoxy)phenyl)pyrimidin-2-yl)spiro[cyclopropane-1,3'-indoline]-6'-yl)methanone as a white solid. (60 mg, ~31%). TLC system: EtOAc/pet ether (5:5), R$_f$: 0.45.

$^1$H NMR (300 MHz, DMSO-d$_6$): δ 8.78 (s, 2H), 8.40 (s, 1H), 7.69-7.65 (m, 1H), 7.61-7.51 (m, 3H), 6.98-6.95 (m, 1H), 6.88 (d, J=7.6 Hz, 1H), 4.29 (s, 2H), 3.61 (brs, 8H), 1.22-1.15 (m, 4H). UPLC: found [M+H]$^+$: 496.9

A-14: Preparation of: morpholino(1'-(5-(2-(trifluoromethyl)phenyl)pyrimidin-2-yl)spiro[cyclopropane-1,3'-indoline]-6'-yl)methanone (compound 14)

Step 2.8

Reaction according to A-12 using INT-7-8 (0.220 g, 0.850 mmol, 1.1 eq) and INT-8-1 (0.200 g, 0.774 mmol, 1 eq) in 1-butanol (10 mL), conc.H$_2$SO$_4$ (75 mg, 0.765 mmol, 1.0 eq) yields morpholino(1'-(5-(2-(trifluoromethyl)phenyl)pyrimidin-2-yl)spiro[cyclopropane-1,3'-indoline]-6'-yl)methanone (0.89 g, ~25%). TLC system: 2:3 EtOAc/pet ether, R$_f$: 0.4.

$^1$H NMR (400 MHz, DMSO-d$_6$) δ 8.61 (s, 2H), 8.39 (d, J=1.2 Hz, 1H), 7.91 (d, J=8.0 Hz, 1H), 7.81-7.78 (m, 1H), 7.70-7.66 m, 1H), 7.56 (d, J=7.6 Hz, 1H), 6.97-6.97 (m, 1H), 6.88 (d, J=7.6 Hz, 1H), 4.28 (s, 2H), 3.60 (br s, 8H), 1.22-1.15 (m, 4H). UPLC: found [M+H]$^+$: 480.9

A-15: Preparation of: (1'-(5-(2,3-difluorophenyl) pyrimidin-2-yl)spiro[cyclopropane-1,3'-indoline]-6'-yl)(morpholino)methanone (compound 15)

Step 2.8

Reaction according to A-12 using INT-7-9 (209 mg, 0.926 mmol, 1.2 eq) and INT-8-1 (200 mg, 0.772 mmol, 1.0 eq) in n-butanol (5 mL), conc.H$_2$SO$_4$ (90 mg, 0.92 mmol, 1.2 eq) yields (1'-(5-(2,3-di-fluorophenyl)pyrimidin-2-yl)spiro[cyclopropane-1,3'-indoline]-6'-yl)(morpholino)methanone as a white solid (90 mg, ~26%). TLC system: EtOAc/pet ether (1:1), R$_f$: 0.6.

$^1$H NMR (400 MHz, DMSO-d$_6$): δ 8.88 (d, J=1.5 Hz, 2H), 8.41 (d, J=1.5 Hz, 1H), 7.53-7.44 (m, 2H), 7.37-7.33 (m,

1H), 6.98 (dd, J=7.6, 1.5 Hz, 1H), 6.89 (d, J=7.6 Hz, 1H), 4.28 (s, 2H), 3.61 (brs, 8H), 1.30-1.04 (m, 4H). UPLC: found [M+H]$^+$: 448.9

A-16: Preparation of: (1'-(5-(2-fluoro-5-methoxyphenyl)pyrimidin-2-yl)spiro[cyclopropane-1,3'-indoline]-6'-yl)(morpholino)methanone (compound 16)

Step 2.8

Reaction according to A-12 using INT-7-10 (0.276 g, 1.16 mmol, 1.2 eq) and INT-8-1 (0.250 g, 0.968 mmol, 1.0 eq) in 1-butanol (5 mL), conc.H$_2$SO$_4$ (51 mg, 0.968 mmol, 1.0 eq) yields (1'-(5-(2-fluoro-5-methoxyphenyl)pyrimidin-2-yl)spiro[cyclopropane-1,3'-indoline]-6'-yl)(morpholino)methanone (0.180 g, ~40%) TLC system: EtOAc/pet ether (4:6), R$_f$: 0.5. $^1$H NMR (400 MHz, DMSO-d$_6$): δ 8.86 (d, J=1.6 Hz, 2H), 8.40 (s, 1H), 7.29 (dd, J=10.4, 9.0 Hz, 1H), 7.20 (dd, J=6.4, 3.1 Hz, 1H), 7.02-6.93 (m, 2H), 6.88 (d, J=7.6 Hz, 1H), 4.28 (s, 2H), 3.81 (s, 3H), 3.61 (brs, 8H), 1.28-1.10 (m, 4H). UPLC: found [M+H]$^+$: 461.0

A-17: Preparation of: (1'-(5-(2-fluoro-4-methoxyphenyl)pyrimidin-2-yl)spiro[cyclopropane-1,3'-indoline]-6'-yl)(morpholino)methanone (compound 17)

Step 2.8

Reaction according to A-12 using INT-8-1 (0.200 g, 0.774 mmol, 1 eq) and INT-7-11 (0.221 g, 0.926 mmol, 1.2 eq) in 1-butanol (5 mL), conc.H$_2$SO$_4$ (75 mg, 0.765 mmol, 1.0 eq) yields 1'-(5-(2-fluoro-4-methoxyphenyl)pyrimidin-2-yl)spiro[cyclopropane-1,3'-indoline]-6'-yl)(morpholino)methanone (0.62 g, ~20%) TLC system; 2:3 EtOAc/pet ether, R$_f$: 0.5.
$^1$H NMR (300 MHz, DMSO-d$_6$): δ 8.77 (s, 2H), 8.37 (s, 1H), 7.54 (t, J=9.0 Hz, 1H), 7.07-6.88 (m, 3H), 6.85 (d, J=7.6 Hz, 1H), 4.25 (s, 2H), 3.81 (s, 3H), 3.58 (brs, 8H), 1.20 (s, 2H), 1.12 (s, 2H). UPLC: found [M+H]$^+$: 461.0

A-18: Preparation of: 2-(2-(6'-(morpholine-4-carbonyl)spiro[cyclopropane-1,3'-indoline]-1'-yl)pyrimidin-5-yl)benzonitrile (compound 18)

Step 2.8

Reaction according to A-12 using INT-7-12 (90 mg, 0.42 mmol, 1.0 eq) and INT-8-1 (110 mg, 0.42 mmol, 1.0 eq) in n-butanol (5 mL), conc.H$_2$SO$_4$ (40 mg, 0.42 mmol, 1.0 eq) yields 2-(2-(6'-(morpholine-4-carbonyl)spiro[cyclopropane-1,3'-indoline]-1'-yl)pyrimidin-5-yl)benzonitrile (60 mg, ~32%) as a white solid. TLC system: EtOAc/pet ether (7:3), R$_f$: 0.6.
$^1$H NMR (300 MHz, DMSO-d$_6$): δ 8.88 (s, 2H), 8.41 (s, 1H), 7.99 (d, J=7.7 Hz, 1H), 7.86-7.77 (m, 1H), 7.74 (d, J=7.8 Hz, 1H), 7.63-7.58 (m, 1H), 6.97 (dd, J=7.6, 1.5 Hz, 1H), 6.88 (d, J=7.6 Hz, 1H), 4.29 (s, 2H), 3.59 (brs, 8H), 1.26-1.10 (m, 4H). UPLC: found [M+H]$^+$: 437.9

A-19: Preparation of: (1'-(5-(2-fluoro-6-methoxyphenyl)pyrimidin-2-yl)spiro[cyclopropane-1,3'-indoline]-6'-yl)(morpholino)methanone (compound 19)

Step 2.8

Reaction according to A-12 using INT-7-13 (234 mg, 0.98 mmol, 1.0 eq) and INT-8-1 (230 mg, 0.98 mmol, 1.0 eq) in 1-butanol (5 mL), conc.H$_2$SO$_4$ (87 mg, 0.98 mmol, 1.0 eq) yields (1'-(5-(2-fluoro-6-methoxyphenyl)pyrimidin-2-yl)spiro[cyclopropane-1,3'-indoline]-6'-yl)(morpholino)methanone (48 mg, ~11%) as a off-white solid. TLC system: EtOAc/pet ether (5:5), R$_f$: 0.45.
$^1$H NMR (300 MHz, DMSO-d$_6$): δ 8.65 (d, J=1.2 Hz, 2H), 8.39 (s, 1H), 7.44 (d, J=6.9 Hz, 1H), 7.0-6.93 (m, 3H), 6.88 (d, J=7.6 Hz, 1H), 4.28 (s, 2H), 3.82 (s, 3H), 3.61 (brs, 8H), 1.27-1.15 (m, 4H). UPLC: found [M+H]$^+$: 460.9

A-20: Preparation of: 3-fluoro-2-(2-(6'-(morpholine-4-carbonyl)spiro[cyclopropane-1,3'-indoline]-1'-yl)pyrimidin-5-yl)benzonitrile (compound 20)

Step 2.8

Reaction according to A-12 using INT-7-14 (135 mg, 0.58 mmol, 1.0 eq) and INT-8-1 (150 mg, 0.58 mmol, 1.0 eq) in n-butanol (5 mL), conc.H$_2$SO$_4$ (40 mg, 0.42 mmol) yields 3-fluoro-2-(2-(6'-(morpholine-4-carbonyl)spiro[cyclopropane-1,3'-indoline]-1'-yl)pyrimidin-5-yl)benzonitrile (50 mg, ~19%) as a off white solid. TLC system: EtOAc/pet ether (7:3), R$_f$: 0.4
$^1$H NMR (300 MHz, DMSO-d$_6$): δ 8.86 (s, 2H), 8.39 (s, 1H), 7.90 (d, J=7.7 Hz, 1H), 7.80-7.74 (m, 1H), 7.71-7.65 (m, 1H), 7.00 (dd, J=7.8, 1.5 Hz, 1H), 6.90 (d, J=7.6 Hz, 1H), 4.31 (s, 2H), 3.60 (brs, 8H), 1.28-1.10 (m, 4H). UPLC: found [M+H]$^+$: 456.0

A-21: Preparation of: N,N-dimethyl-2-(2-(6'-(morpholine-4-carbonyl)spiro[cyclopropane-1,3'-indoline]-1'-yl)pyrimidin-5-yl)benzamide (compound 21)

Step 2.8

Reaction according to A-12 using INT-7-15 (200 mg, 0.76 mmol, 1.0 eq) and INT-8-1 (296 mg, 1.14 mmol, 1.5 eq) in 1-butanol (5 mL), conc.H$_2$SO$_4$ (75 mg, 0.98 mmol, 1.2 eq) yields N,N-dimethyl-2-(2-(6'-(morpholine-4-carbonyl)spiro[cyclopropane-1,3'-indoline]-1'-yl)pyrimidin-5-yl)benzamide (60 mg, ~16%) as a pale brown solid. TLC system: EtOAc/pet ether (5:5), R$_f$: 0.15.
$^1$H NMR (300 MHz, DMSO-d$_6$): δ 8.62 (s, 2H), 8.38 (s, 1H), 7.60-7.42 (m, 3H), 7.38 (d, J=7.4 Hz, 1H), 7.00-6.83 (m, 2H), 4.26 (s, 2H), 3.61 (brs, 8H), 2.87 (s, 3H), 2.58 (s, 3H), 1.27-1.06 (m, 4H). UPLC: found [M+H]$^+$: 484.4

A-22: Preparation of: 4-fluoro-3-(2-(6'-(morpholine-4-carbonyl)spiro[cyclopropane-1,3'-indoline]-1'-yl)pyrimidin-5-yl)benzonitrile (compound 22)

Step 2.8

Reaction according to A-12 using INT-8-1 (200 mg, 0.774 mmol, 1.0 eq) and INT-7-16 (217 mg, 0.928 mmol, 1.2 eq) in n-butanol (10 mL), conc.H$_2$SO$_4$ (75 mg, 0.76 mmol, 1.0 eq) yields 4-fluoro-3-(2-(6'-(morpholine-4-carbonyl)spiro[cyclopropane-1,3'-indoline]-1'-yl)pyrimidin-5-yl)benzonitrile (65 mg, ~20%) as a off white solid. TLC system: EtOAc/pet ether (7:3), R$_f$: 0.4
$^1$H NMR (400 MHz, DMSO-d$_6$): δ 8.90 (s, 2H), 8.41 (s, 1H), 8.27 (dd, J=7.3, 2.2 Hz, 1H), 7.99-7.95 (m, 1H), 7.64-7.59 (m, 1H), 6.99 (dd, J=7.7, 1.4 Hz, 1H), 6.89 (d, J=7.6 Hz, 1H), 4.29 (s, 2H), 3.61 (brs, 8H), 1.23-1.15 (m, 2H). UPLC: found [M+H]$^+$: 455.9.

A-23: Preparation of: (1'-(5-(2-fluoro-5-(trifluoromethyl)phenyl)pyrimidin-2-yl)spiro[cyclopropane-1,3'-indoline]-6'-yl)(morpholino)methanone (compound 23)

Step 2.8

Reaction according to A-12 using INT-7-17 (160 mg, 0.581 mmol, 1.0 eq) and INT-8-1 (150 mg, 0.81 mmol, 1.0 eq) in 1-butanol (5 mL), conc.H$_2$SO$_4$ (68 mg, 0.697 mmol, 1.2 eq) yields (1'-(5-(2-fluoro-5-(trifluoromethyl)phenyl)pyrimidin-2-yl)spiro[cyclopropane-1,3'-indoline]-6'-yl)(morpholino)methanone (60 mg; ~31%). TLC system: EtOAc/pet ether (1:1); R$_f$: 0.4.

$^1$H NMR (300 MHz, DMSO-d$_6$): δ 8.92 (d, J=1.5 Hz, 2H), 8.42 (d, J=1.4 Hz, 1H), 8.13-8.05 (m, 1H), 7.84-7.82 (m, 1H), 7.62 (t, J=9.5 Hz, 1H), 6.98 (dd, J=7.7, 1.5 Hz, 1H), 6.89 (d, J=7.6 Hz, 1H), 4.29 (s, 2H), 3.61 (brs, 8H), 1.28-1.11 (m, 4H). UPLC: found [M+H]$^+$: 498.9

The compound 24 to 179 have been prepared in an analogous way as described in A-23 using the appropriate intermediates.

A-25: Preparation of: N-(2-hydroxyethyl)-1'-(5-(4-methoxypyridin-2-yl)pyrimidin-2-yl)-N-methylspiro[cyclopropane-1,3'-indoline]-6'-carboxamide (compound 224)

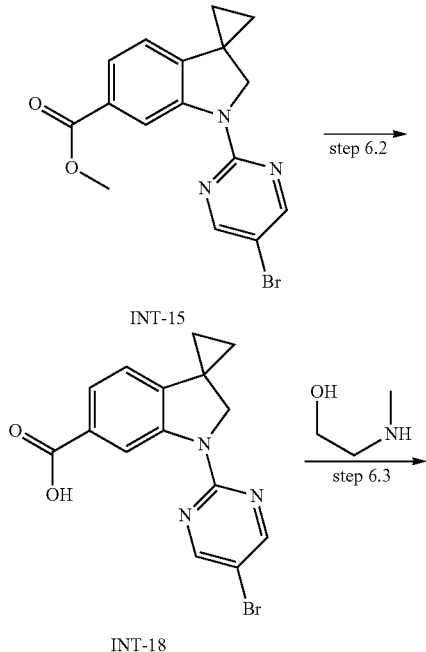

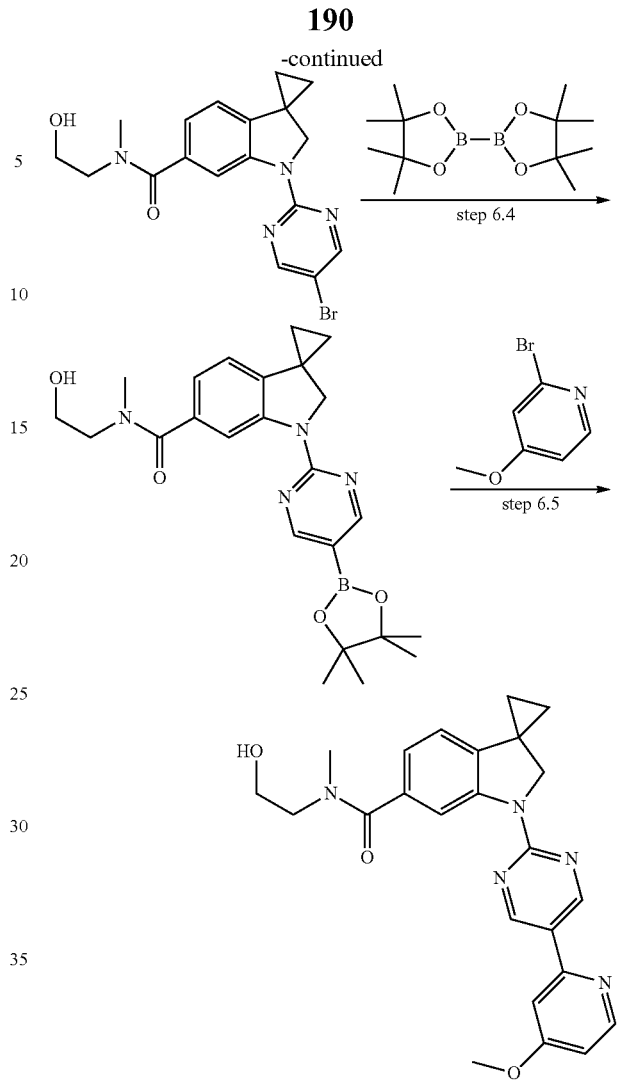

Step 6.1 (Synthesis of INT-15)

To a solution of INT-9 (5 g, 24.6 mmol, 1 eq) in n-BuOH (70 mL), DIPEA (22 mL, 123 mmol, 5 eq), and 5-bromo-2-chloro pyrimidine (5.7 g, 29.5 mmol, 1.2 eq) were added at RT. The reaction mixture was then heated at 140° C. for 48 h in the sealed tube. After completion of reaction, reaction mixture was evaporated under reduced pressure and crude was purified by CC. The eluted compound was further purified by re-crystallization from EtOAc-Hexane to afford methyl 1'-(5-bromo-pyrimidin-2-yl)spiro[cyclopropane-1,3'-indoline]-6'-carboxylate (2.3 g, 26%) as white solid.

Step 6.2 (Synthesis of INT-18)

To a solution of methyl 1'-(5-bromopyrimidin-2-yl)spiro[cyclopropane-1,3'-indoline]-6'-carboxylate (3 g, 8.3 mmol, 1 eq) in THF (30 mL), MeOH (15 mL) and H$_2$O (15 mL), LiOH (1.6 g, 41.6 mmol, 5 eq) was added at RT. Reaction mixture was stirred at RT for 16 h. After completion of reaction by, RM was evaporated under reduced pressure to get the crude product. Crude product was dissolved in H$_2$O (100 mL) and washed with Et$_2$O (2×100 mL). After acidification of aqueous layer with 2N HCl (aq.), a solid was precipitated out of the solvent. The solid was filtered through sintered funnel and dried under reduced pressure. The solid was triturated with Et₂O-pentane to afford 1'-(5-bromopyrimidin-2-yl)spiro[cyclopropane-1,3'-indoline]-6'-carboxylic acid (3.5 g, 72%) as white solid.

Step 6.3

To a solution of 1'-(5-bromopyrimidin-2-yl)spiro[cyclopropane-1,3'-indoline]-6'-carboxylic acid (2.7 g, 7.82 mmol, 1 eq) in DMF (30 mL), the TBTU (3.01 g, 9.38 mmol, 1.2 eq), NMM (1.57 g, 15.64 mmol, 2 eq) and 2-methylaminoethanol (1.76 g, 23.4 mmol, 3 eq) were added at RT. Reaction mixture was then stirred at RT for 16 h. After completion of reaction, RM was quenched with ice water (400 ml) and a solid was precipitated out. Filter off the solid and re-dissolved in EtOAc (500 mL). The EtOAc solution of the compound was washed with water (2×400 ml), brine (400 mL), dried over Na₂SO₄, filtered and evaporated under reduced pressure to get the crude product. The crude was triturated with Et₂O-hexane (3 times) to afford 1'-(5-bromopyrimidin-2-yl)-N-(2-hydroxyethyl)-N-methylspiro[cyclopropane-1,3'-indoline]-6'-carboxamide (2.7 g, 87%) as white solid.

Step 6.4

To a solution of 1'-(5-bromopyrimidin-2-yl)-N-(2-hydroxyethyl)-N-methylspiro[cyclopropane-1,3'-indoline]-6'-carboxamide (2.5 g, 6.2 mmol, 1 eq) in 1,4-dioxane were added KOAC (0.912 g, 9.31 mmol, 1.5 eq) and bispincolatediborane (3.14 g, 12.43 mmol, 2 eq). The solution was degassed with Ar for 20 min followed by addition of Pd(dppf)Cl₂ (0.25 g, 0.31 mmol, 0.05 eq). The reaction mixture was refluxed for 16 h. After completion of reaction, RM was diluted with water (50 mL), extracted with EtOAc (3×50 mL). Combined organic layer was washed with water (50 mL), brine (50 mL), dried over anhydrous Na₂SO₄ and evaporated to get 5 g of crude N-(2-hydroxyethyl)-N-methyl-1'-(5-(4,4,5,5-tetramethyl-1,3,2-dioxaborolan-2-yl)pyrimidin-2-yl)spiro[cyclopropane-1,3'-indoline]-6'-carboxamide, which was used for next step without further purification.

Step 6.5

To a stirred solution of N-(2-hydroxyethyl)-N-methyl-1'-(5-(4,4,5,5-tetramethyl-1,3,2-dioxaborolan-2-yl)pyrimidin-2-yl)spiro[cyclopropane-1,3'-indoline]-6'-carboxamide (0.4 g, 0.88 mmol, 1 eq.) in 1,4-dioxane (20 mL) was added K₂CO₃ (0.242 g, 1.76 mmol, 3 eq), 2-bromo-4-methoxypyridine (0.267 g, 1.76 mmol, 2 eq) and degassed with Ar for 5 min. Then was added Pd(PPh₃)₄ (0.051 g, 0.04 mmol, 0.05 eq.) and the mixture was heated to reflux for 16 h. After completion of the reaction, the RM was filtered on celite bed and washed with EtOAc. The crude product was purified by CC to afford N-(2-hydroxyethyl)-1'-(5-(4-methoxypyridin-2-yl)pyrimidin-2-yl)-N-methylspiro[cyclopropane-1,3'-indoline]-6'-carboxamide (0.092 g, 24%) as white solid.

¹H NMR (400 MHz, DMSO-d₆): δ 1.14-1.22 (4H), 2.99 (s, 3H), 3.48-3.51 (2H), 3.52-5.55 (1H), 3.91 (s, 3H), 4.29 (s, 2H), 4.70-4.80 (1H), 6.85-6.87 (1H), 6.93-6.97 (2H), 8.40 (s, 1H), 8.46-8.48 (1H), 9.29 (s, 2H).

A-26: Preparation of: N-(2-(2-(6'-(2,5-diazabicyclo[2.2.1]heptane-2-carbonyl)spiro[cyclopropane-1,3'-indolin]-1'-yl)pyrimidin-5-yl)pyridin-4-yl)acetamide.HCl (compound 279)

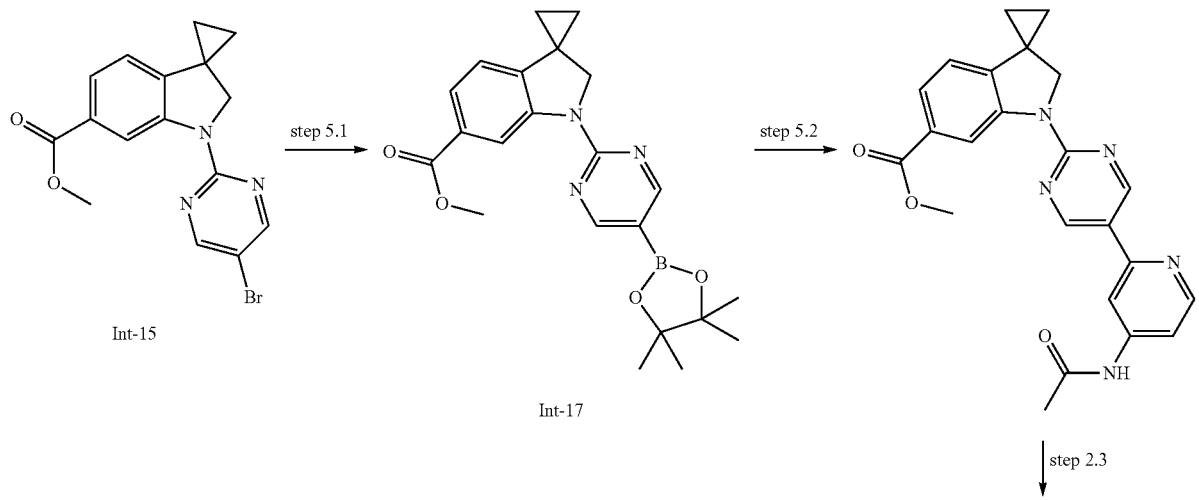

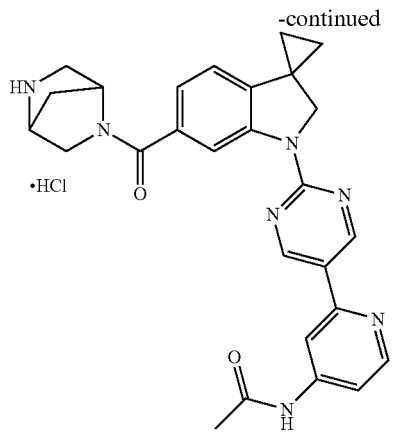
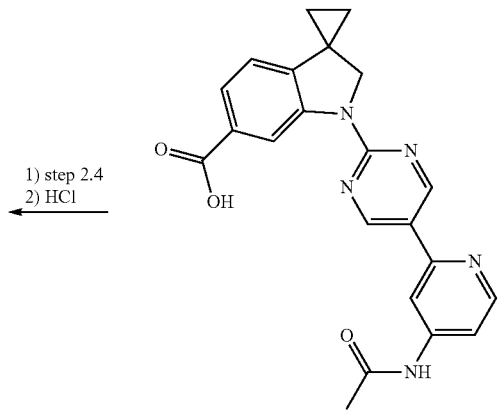

Step 5.1 (Synthesis of INT-17)

To a solution of INT-15 (0.6 g, 1.67 mmol, 1 eq) in 1,4-dioxane (15 mL) were added KOAc (0.491 g, 5.01 mmol, 3.0 eq) and bispincolatediborane (0.509 g, 2.0 mmol, 1.12 eq). The solution was degassed with Ar for 20 min followed by addition of PdCl$_2$(dppf).DCM (68 mg, 0.05 mmol, 0.05 eq). The reaction mixture was refluxed for 16 h. After completion of reaction, RM was filtered through cintered and evaporated under reduced pressure to get the crude product which was used for the next step without further purification.

Step 5.2

To methyl 1'-(5-(4,4,5,5-tetramethyl-1,3,2-dioxaborolan-2-yl)pyrimidin-2-yl)spiro[cyclopropane-1,3'-indoline]-6'-carboxylate in 1,4-dioxane (10 mL), N-(2-bromo-pyridin-4-yl)-acetamide (0.54 g, 2.51 mmol, 1.5 eq) and K$_2$CO$_3$ (2M) (0.46 g, 3.34 mmol, 2.0 eq) was added at RT. After degassing the reaction mixture with Ar, Pd(PPh$_3$)$_4$ (96 mg, 0.083 mmol, 0.05 eq) was added at RT and the reaction mixture was heated at 110° C. for another 16 h. After completion of reaction, RM was filtered through cintered and diluted with water (50 mL). The crude product was extracted with EtOAc (3×75 mL). Combined organic layer was washed with water (50 mL), brine (50 mL), dried over anhydrous Na$_2$SO$_4$ and evaporated to get the crude product which was purified by CC to afford methyl 1'-(5-(4-acetamidopyridin-2-yl)pyrimidin-2-yl)spiro[cyclopropane-1,3'-indoline]-6'-carboxylate (300 mg, 43%) as brown solid.

Step 2.3

To a solution of methyl 1'-(5-(4-acetamidopyridin-2-yl)pyrimidin-2-yl)spiro[cyclopropane-1,3'-indoline]-6'-carboxylate (0.25 g, 0.60 mmol, 1 eq) in THF (8 mL), MeOH (4 mL) and H$_2$O (2 mL), NaOH (96 mg, 2.41 mmol, 4 eq) was added at RT. RM was stirred at RT for 16 h. After completion of reaction, reaction mixture was evaporated under reduced pressure to get the crude product. Crude product was dissolved in H$_2$O (50 mL) and washed with Et$_2$O (2×50 mL). After acidification of aqueous layer with 2N HCl (aq.), the crude product was extracted with EtOAc (3×75 mL). Combined organic layer was washed with water (50 mL), brine (50 mL), dried over anhydrous Na$_2$SO$_4$ and evaporated to get the crude product. The solid was triturated with Et$_2$O-pentane to afford 1'-(5-(4-acetamidopyridin-2-yl)pyrimidin-2-yl)spiro-[cyclopropane-1,3'-indoline]-6'-carboxylic acid (0.235 g, 98%) as white solid.

Step 2.4

To a solution of 1'-(5-(4-acetamidopyridin-2-yl)pyrimidin-2-yl)spiro[cyclopropane-1,3'-indoline]-6'-carboxylic acid (0.25 g, 0.62 mmol, 1 eq) in DMF (5 mL), the TBTU (0.24 g, 0.747 mmol, 1.2 eq), NMM (0.126 g, 1.25 mmoL, 2 eq) and 2,5-diaza-bicyclo[2.2.1]heptane-2-carboxylic acid tert-butyl ester (0.123 g, 0.623 mmol, 1 eq) were added at RT. RM was then stirred at RT for 16 h. After completion of reaction, reaction mixture was quenched with ice water (40 mL) and a solid was precipitated out. The solid was filtered off and re-dissolved in EtOAc (50 mL). The EtOAc solution of the desired compound was washed with water (2×40 mL), brine (40 mL), dried over Na$_2$SO$_4$, filtered and evaporated under reduced pressure to get the crude product. The crude product was triturated with Et$_2$O-hexane (3×) to afford tert-butyl 5-(1'-(5-(4-acetamidopyridin-2-yl)pyrimidin-2-yl)spiro[cyclopropane-1,3'-indolin]-6'-ylcarbonyl)-2,5-diazabicycle-[2.2.1]heptane-2-carboxylate (0.35 g, 96.9%) as white solid. For removal of the Boc-group tert-butyl 5-(1'-(5-(4-acetamidopyridin-2-yl)pyrimidin-2-yl)spiro[cyclopropane-1,3'-indolin]-6'-ylcarbonyl)-2,5-diazabicycle-[2.2.1]heptane-2-carboxylate (100 mg, 0.17 mmol, 1 eq) was added 1,4-dioxane-HCl (10.0 mL) at RT.

The reaction was continued stirring for 6 h. After completion of reaction, the solvent was evaporated under reduced pressure to get the crude product which was triturated with Et$_2$O to afford compound N-(2-(2-(6'-(2,5-diazabicyclo[2.2.1]heptane-2-carbonyl)spiro[cyclopropane-1,3'-indolin]-1'-yl)pyrimidin-5-yl)-pyridin-4-yl)acetamide as HCl salt (60 mg, 73%) as white solid.

$^1$H NMR (400 MHz, DMSO-d$_6$, T=373K): δ 1.16-1.26 (4H), 1.91-1.94 (1H), 2.13 (s, 3H), 3.33-3.36 (1H), 3.47-4.51 (1H), 3.70 (s, 2H), 4.34 (s, 2H), 4.43-4.45 (1H), 4.72-4.74 (1H), 6.89-6.91 (1H), 7.14-7.17 (1H), 7.55-7.57 (1H), 8.11-8.12 (1H), 8.51-8.53 (1H), 8.56 (s, 1H), 8.90-8.98 (1H), 9.13 (s, 2H), 9.32-9.37 (1H), 10.30-10.33 (1H).

A-27: Preparation of: N-(2-hydroxyethyl)-N-methyl-1'-(5-(5-methylpyridazin-3-yl)pyrimidin-2-yl)spiro[cyclopropane-1,3'-indoline]-6'-carboxamide (compound 290)

Step 6.4

To a solution of N-(2-hydroxyethyl)-N-methyl-1'-(5-(4,4,5,5-tetramethyl-1,3,2-dioxaborolan-2-yl)pyrimidin-2-yl)spiro[cyclopropane-1,3'-indoline]-6'-carboxamide (0.3 g, 0.666 mmol, 1 eq) iso-amyl alcohol (6 mL) and H₂O, trifluoro-methanesulfonic acid 5-methyl-pyridazin-3-yl ester (0.193 g, 0.799 mmol, 1.2 eq) and K₂CO₃ (0.275 g, 1.998 mmol, 3.0 eq) was added at RT. After degassing the reaction mixture with Ar, Ataphos (47.1 mg, 0.066 mmol, 0.1 eq) was added at RT and the reaction mixture was heated at 80° C. for another 16 h. After completion of reaction (monitored by TLC), reaction mixture was filtered through cintered and diluted with water (20 mL). The aqueous layer was extracted with EtOAc (3×50 mL). Combined organic layer was washed with water (50 mL), brine (50 mL), dried over anhydrous Na₂SO₄ and evaporated to get the crude product which was purified by column chromatography to afford N-(2-hydroxyethyl)-N-methyl-1'-(5-(5-methyl-pyridazin-3-yl)pyrimidin-2-yl)spiro[cyclopropane-1,3'-indoline]-6'-carboxamide (70 mg, 25%) as white solid.

$^1$H NMR (400 MHz, DMSO-d₆,): δ 1.15-1.23 (4H), 2.33 (s, 3H), 3.00 (s, 3H), 3.52-3.65 (3H), 4.31 (s, 2H), 4.76-4.79 (1H), 6.86-6.89 (1H), 6.98-7.00 (1H), 8.15 (s, 1H), 8.42 (s, 1H), 9.09 (s, 1H), 9.34 (s, 2H).

A 28: Preparation of: (1'-(5-(5-(2-hydroxypropan-2-yl)thiophen-2-yl)pyrimidin-2-yl)spiro[cyclopropane-1,3'-indolin]-6'-yl)(morpholino)methanone (compound 205)

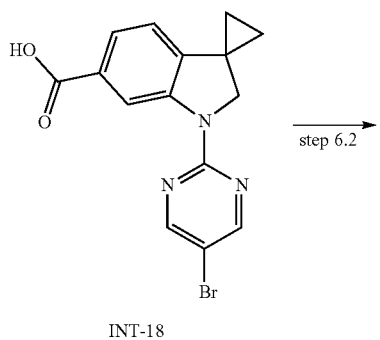

INT-18

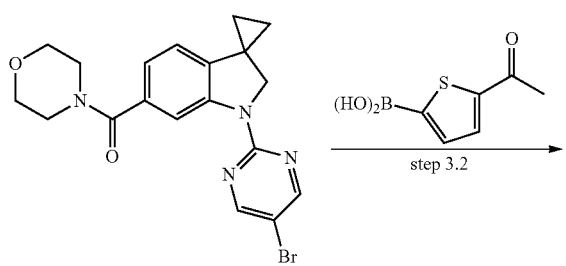

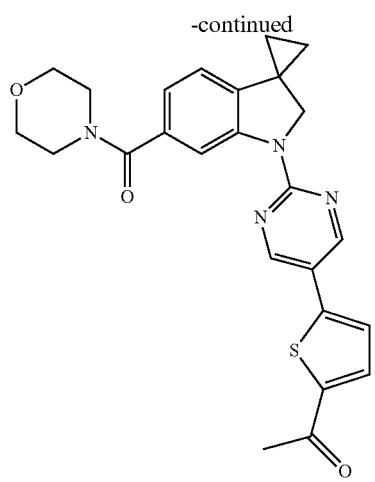

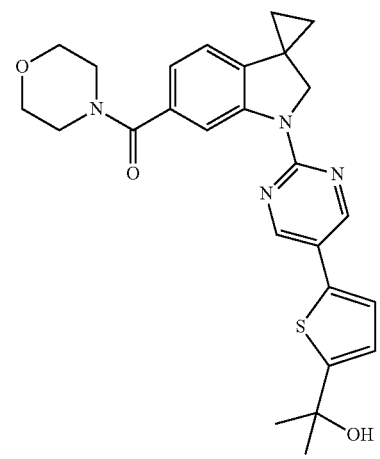

Step 6.2

To a mixture of 1-(5-bromo-pyrimidin-2-yl)-3,3-spirocyclopropyl-2,3-dihydro-1H-indole-6-carboxylic acid (1.5 g, 4.33 mmol) in DMF (15 mL) was added NMM (0.94 mL, 8.66 mmol), TBTU (1.66 g, 5.19 mmol) and morpholine (1.13 mL). The RM was stirred at RT for 16 h. Reaction mixture was diluted with ice water. Solid precipitate appeared was filtered and dissolved in DCM, washed with brine (50 mL) and dried over Na₂SO₄. Solvent was evaporated to get [1-(5-bromo-pyrimidin-2-yl)-3,3-spirocyclopropyl-2,3-dihydro-1H-indol-6-yl]-morpholin-4-yl-methanone as off white solid which was taken to next step without any further purification.

Step 3.2

To a stirred solution of (1'-(5-bromopyrimidin-2-yl)spiro[cyclopropane-1,3'-indolin]-6'-yl)-(morpholino)methanone (0.3 g, 0.72 mmol, 1 eq), in THF and water (20 mL, 4:1) at RT was added K₂CO₃ (218 mg, 1.16 mmol, 2.2 eq), degassed with Ar for 15 min and warmed to 45° C. (5-acetyl-thiophen-2-yl)-boronic acid (0.172 g, 1.12 mmol, 1.5 eq), $^t$Bu₃PHBF₄ (1.0 mg, 0.003 mmol, 0.005 eq), Pd₂dba₃ (28 mg, 0.031 mmol, 0.044 eq) were added at 45° C. and again degassed with Ar for 10 min. The RM was stirred at same temperature for 1 h. The RM cooled to RT, diluted with EtOAc (10 mL), filtered through a pad of celite, washed with water, dried (Na₂SO₄) and evaporated. The crude was washed with Et₂O (2×10 mL) to get 1-(5-(2-(6'-(morpholine-4-carbonyl)spiro[cyclopropane-1,3'-indolin]-1'-yl)pyrimidin-5-yl)thiophen-2-yl)-ethanone (300 mg, ~90%) as pale green solid To a stirred solution of 1-(5-(2-(6'-(morpholine-4-carbonyl)spiro[cyclopropane-1,3'-indolin]-1'-yl)pyrimidin-5-yl)thiophen-2-yl)ethanone (0.3 g, 0.652 mmol, 1 eq), in THF (20 mL) at −10° C. was added MeMgI (2M solution in Et₂O, (0.32 mL, 0.978 mmol, 1.5 eq) and stirred at RT for 3 h. The RM was quenched with sat. NH₄Cl solution at 0° C., and extracted with EtOAc (2×15 mL), dried (Na₂SO₄) and evaporated. The crude was purified by silica gel preparative TLC to get (1'-(5-(5-(2-hydroxypropan-2-yl)thiophen-2-yl)pyrimidin-2-yl)spiro[cyclopropane-1,3'-indolin]-6'-yl)(morpholino)methanone (0.050 g, ~16%) as a light green solid.

¹H NMR (300 MHz, DMSO-d₆): δ 8.87 (s, 2H), 8.36 (s, 1H), 7.30-7.34 (m, 1H), 6.99-6.92 (m, 2H), 6.87-6.58 (m, 1H), 5.52 (s, 1H), 4.25 (s, 2H), 3.71-3.49 (m, 8H), 1.53 (s, 6H), 1.26-1.07 (m, 4H).

A 29: Preparation of: (R)-(3-aminopyrrolidin-1-yl)(1'-(5-(4-cyclopropylpyridin-2-yl)pyrimidin-2-yl)spiro[cyclopropane-1,3'-indolin]-6'-yl)methanone (compound 335)

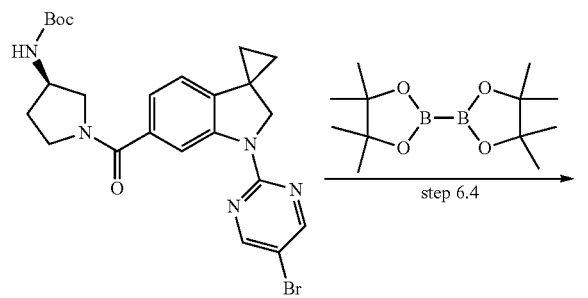

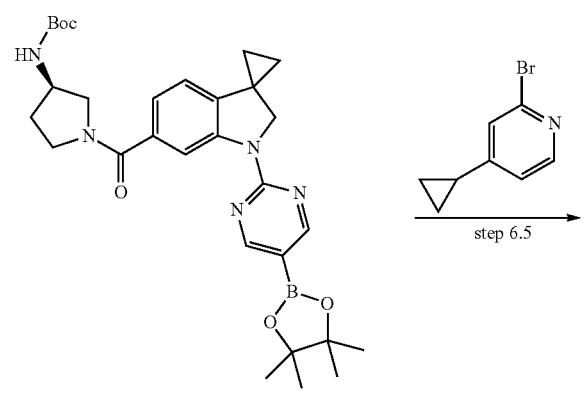

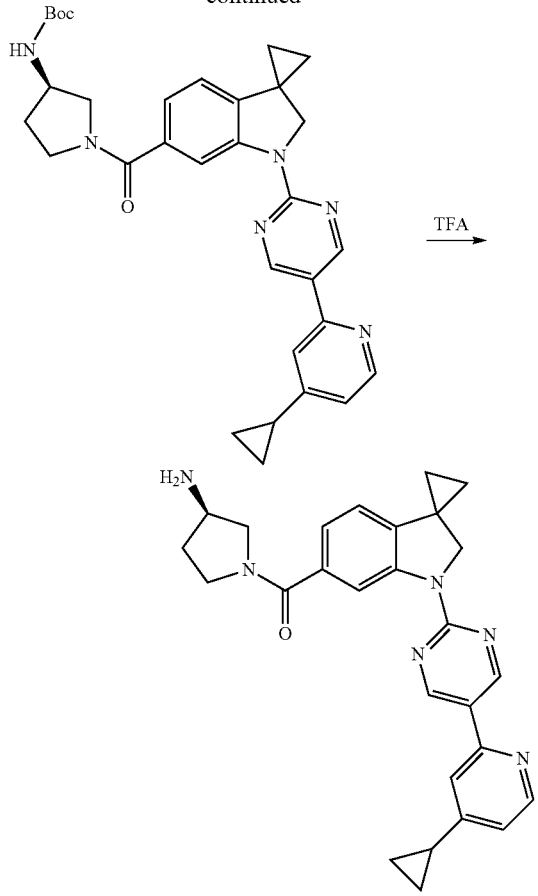

Step 6.4

To a stirred degassed solution of (R)-tert-butyl(1-(1'-(5-bromopyrimidin-2-yl)spiro[cyclopropane-1,3'-indolin]-6'-ylcarbonyl)pyrrolidin-3-yl)carbamate (1.0 g, 1.9 mmol, 1.0 eq), in 1,4-dioxane (10 mL) were added 4,4,4',4',5,5,5',5'-octamethyl-2,2'-bi(1,3,2-dioxaborolane) (711 mg, 2.8 mmol, 1.5 eq), KOAc (559 mg, 5.7 mmol, 3.0 eq), PdCl₂(dppf) (81 mg, 0.1 mmol, 0.1 eq). The RM was degassed with Ar for 10 min and stirred at 100° C. for 16 h. The RM was allowed to cool to RT, and filtered through a celite bed and washed with DCM (20 mL). The filtrate was evaporated to get crude (R)-tert-butyl(1-(1'-(5-(4,4,5,5-tetramethyl-1,3,2-dioxaborolan-2-yl)pyrimidin-2-yl)spiro[cyclopropane-1,3'-indolin]-6'-ylcarbonyl)pyrrolidin-3-yl)carbamate (1.1 g, crude) as dark brown oil. The crude was used for next step without further purification.

Step 6.5

To a stirred solution of (R)-tert-butyl(1-(1'-(5-(4,4,5,5-tetramethyl-1,3,2-dioxaborolan-2-yl)-pyrimidin-2-yl)spiro[cyclopropane-1,3'-indolin]-6'-ylcarbonyl)pyrrolidin-3-yl)carbamate (1.0 g, 1.7 mmol, 1.0 eq), in THF and H₂O (20 mL, 4:1) were added 2-bromo-4-cyclopropylpyridine (217 mg, 1.1 mmol, 0.7 eq), K₂CO₃ (331 mg, 2.4 mmol, 2.2 eq), and degassed with Ar for 15 min. Then Pd₂(dba)₃ (77 mg, 0.085 mmol, 0.05 eq), (ᵗBu)₃PHBF₄ (24 mg, 0.085 mmol, 0.05 eq) were added and again degassed with Ar for 10 min. The RM was stirred at the 50° C. for 2 h and allowed to cool to RT, diluted with EtOAc (100 mL), washed with water (50 mL), brine solution (50 mL), dried over anhydrous Na$_2$SO$_4$, and evaporated under vacuum. The crude was purified by CC to get (R)-tert-butyl(1-(1'-(5-(4-cyclopropylpyridin-2-yl)pyrimidin-2-yl)spiro[cyclopropane-1,3'-indolin]-6'-ylcarbonyl)pyrrolidin-3-yl)carbamate (260 mg, ~26%) as off white solid. To a stirred solution of (R)-tert-butyl(1-(1'-(5-(4-cyclopropylpyridin-2-yl)pyrimidin-2-yl)spiro-[cyclopropane-1,3'-indolin]-6'-ylcarbonyl)pyrrolidin-3-yl)carbamate (260 mg, 0.471 mmol, 1.0 eq), in DCM (10 mL), was added TFA (2 mL) at 0° C. The RM was stirred for 2 h at RT. The RM was evaporated and diluted with DCM (15 mL), washed with sat. NaHCO$_3$ solution (20 mL), water (20 mL), brine solution (20 mL), dried over anhydrous Na$_2$SO$_4$, and evaporated under vacuum. The crude was purified by preparative TLC, using 5% of MeOH in DCM as eluent to get (R)-(3-aminopyrrolidin-1-yl)(1'-(5-(4-cyclopropylpyridin-2-yl)pyrimidin-2-yl)spiro[cyclopropane-1,3'-indolin]-6'-yl)methanone (75 mg ~35%).

$^1$H NMR (400 MHz, DMSO-d$_6$): δ 9.28 (s, 2H), 8.52 (s, 1H), 8.46 (d, J=4.8 Hz, 1H), 7.69 (s, 1H), 7.07-7.06 (m, 2H), 6.87 (d, J=7.6 Hz, 1H), 4.29 (s, 2H), 3.70-3.40 (m, 4H), 3.20-3.05 (m, 1H), 2.10-1.80 (m, 4H), 1.65-1.62 (m, 1H), 1.30-1.20 (m, 3H), 1.19-1.05 (m, 4H), 0.95-0.91 (m, 2H).

A 30: Preparation of: 1'-(5-(4-cyclopropyl-6-methoxypyridin-2-yl)pyrimidin-2-yl)-N-(2-hydroxyethyl)-N-methylspiro[cyclopropane-1,3'-indoline]-6'-carboxamide (compound 361)

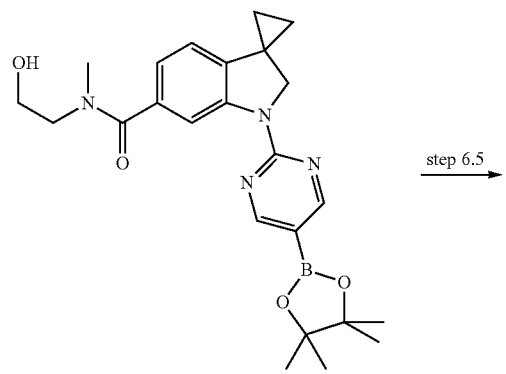

step 6.5

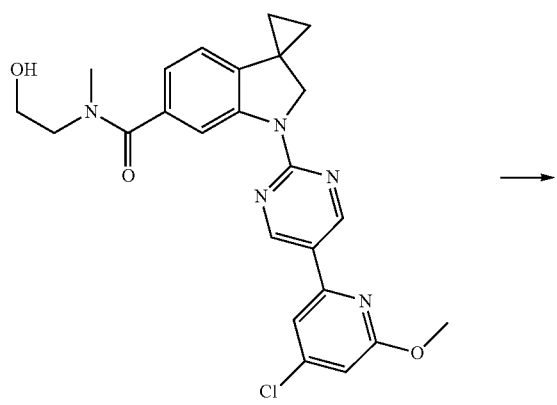

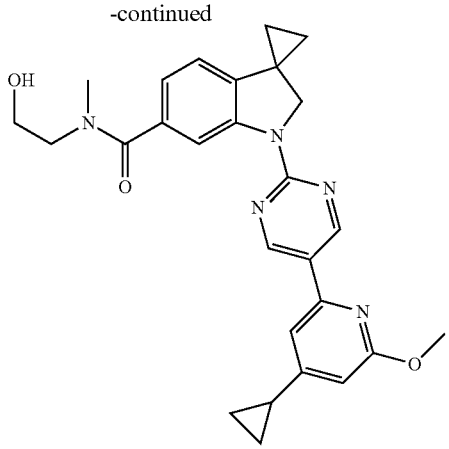

Step 6.5

To a solution of N-(2-hydroxyethyl)-N-methyl-1'-(5-(4,4,5,5-tetramethyl-1,3,2-dioxaborolan-2-yl)-pyrimidin-2-yl)spiro[cyclopropane-1,3'-indoline]-6'-carboxamide (0.4 g, 0.89 mmol, 1 eq) in 1,4-dioxane (15 mL), 2-bromo-4-chloro-6-methoxy-pyridine (0.217 g, 0.978 mmol, 1.1 eq) and K$_2$CO$_3$ (2M) (1.3 mL, 2.66 mmol, 3.0 eq) was added at RT. After degassing the RM, Pd(PPh$_3$)$_4$ (0.051 g, 0.044 mmol, 0.05 eq) was added at RT and heated the reaction mixture at 100° C. for another 16 h. After completion of reaction, RM was filtered through cintered and diluted with water (20 mL). Extract the aqueous layer with EtOAc (3×50 mL). Combined organic layer was washed with water (50 mL), brine (50 mL), dried over anhydrous Na$_2$SO$_4$ and evaporated to get the crude product which was purified by SFC purification to afford 1'-(5-(4-chloro-6-methoxypyridin-2-yl)pyrimidin-2-yl)-N-(2-hydroxyethyl)-N-methylspiro[cyclopropane-1,3'-indoline]-6'-carboxamide (0.35 g, 86%) as white solid.

To a solution of 1'-(5-(4-chloro-6-methoxypyridin-2-yl)pyrimidin-2-yl)-N-(2-hydroxyethyl)-N-methylspiro-[cyclopropane-1,3'-indoline]-6'-carboxamide (0.3 g, 0.645 mmol, 1 eq) in isoamylalcohol (10 mL) and water (2 mL), cyclopropylboronic acid (0.083 g, 0.967 mmol, 1.5 eq) and K$_2$CO$_3$ (0.267 g, 1.93 mmol, 3.0 eq) was added at RT. After degassing the reaction mixture Ataphos (0.045 g, 0.064 mmol, 0.01 eq) was added at RT and the RM was heated at 100° C. for another 16 h. After completion of reaction, RM was filtered through cintered and diluted with water (20 mL). Extract the aqueous layer with EtOAc (3×50 mL). Combined organic layer was washed with water (50 mL), brine (50 mL), dried over anhydrous Na$_2$SO$_4$ and evaporated to get the crude product which was purified by preperative HPLC purification to afford 1'-(5-(4-cyclopropyl-6-methoxypyridin-2-yl)pyrimidin-2-yl)-N-(2-hydroxyethyl)-N-methylspiro[cyclopropane-1,3'-indoline]-6'-carboxamide (0.113 g, 37%) as white solid.

$^1$H NMR (400 MHz, DMSO-d$_6$): δ 9.29 (s, 2H), 8.40 (s, 1H), 7.28 (s, 1H), 6.95 (d, J=8.0 Hz, 1H), 6.86 (s, 1H), 6.50 (s, 1H), 4.74 (bs, 1H), 4.28 (s, 2H), 3.92 (s, 3H), 3.63 (s, 1H), 3.50 (s, 2H), 2.98 (s, 3H), 1.95 (bs, 1H), 1.22 (s, 2H), 1.13 (s, 2H), 1.05 (d, J=6.0 Hz, 2H), 0.91 (s, 2H).

A 31: Preparation of: (1'-(5-(4-(methylsulfinyl)pyridin-2-yl)pyrimidin-2-yl)spiro[cyclopropane-1,3'-indolin]-6'-yl)(morpholino)methanone (compound 344)

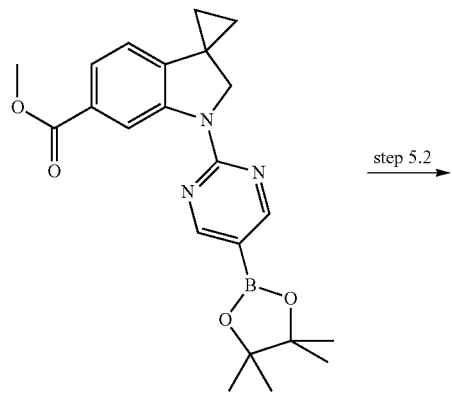

↓ step 5.2

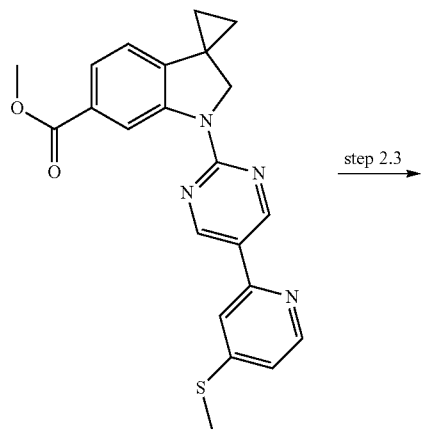

↓ step 2.3

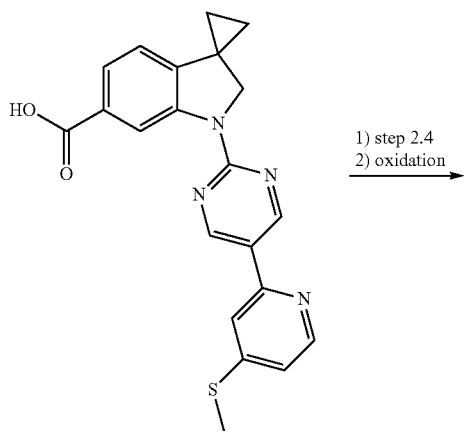

1) step 2.4
2) oxidation
→

-continued

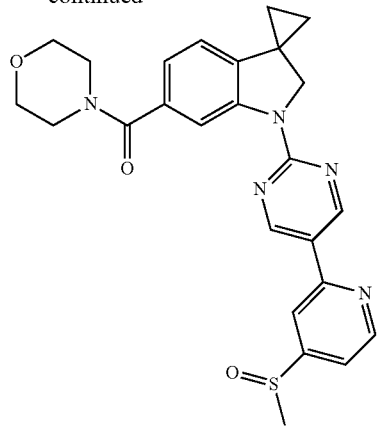

Step 5.2

To a solution of methyl 1'-(5-(4,4,5,5-tetramethyl-1,3,2-dioxaborolan-2-yl)pyrimidin-2-yl)spiro-[cyclopropane-1,3'-indoline]-6'-carboxylate (1.8 g, 4.42 mmol, 1 eq) in 1,4-dioxane (50 mL) were added $K_2CO_3$ (2M) (6.63 mL, 13.267 mmol, 3 eq) and 2-bromo-4-methylsulfanyl-pyridine (0.993 g, 4.867 mmol, 1.1 eq). The solution was degassed with Ar for 20 min followed by addition of $Pd(PPh_3)_4$ (0.255 g, 0.221 mmol, 0.05 eq). The reaction mixture was refluxed for 16 h. After completion of reaction, RM was diluted with water (75 mL), extracted with EtOAc (3×75 mL). Combined organic layer was washed with water (100 mL), brine (100 mL), dried over anhydrous $Na_2SO_4$ and evaporated to get the crude product, which was purified by CC to afford methyl 1'-(5-(4-(methylthio)pyridin-2-yl)pyrimidin-2-yl)spiro[cyclopropane-1,3'-indoline]-6'-carboxylate (0.76 g, 42.6%) as brown solid.

Step 2.3

To a solution of methyl 1'-(5-(4-(methylthio)pyridin-2-yl)pyrimidin-2-yl)spiro[cyclopropane-1,3'-indoline]-6'-carboxylate (0.76 g, 1.88 mmol, 1 eq) in THF (20 mL), MeOH (10 mL) and $H_2O$ (5 mL), LiOH (0.395 g, 9.4 mmol, 5 eq) was added at RT. RM was stirred at RT for 16 h. After completion of reaction, RM was evaporated under reduced pressure to get the crude product. Crude product was dissolved in $H_2O$ (50 mL) and washed with $Et_2O$ (2×50 mL). After acidification of aqueous layer with 2N HCl (aq.), a solid was precipitated out of the solvent. The solid was filtered through sintered funnel and dried under reduced pressure. The solid was triturated with $Et_2O$-Pentane to afford 1'-(5-(4-(methylthio)pyridin-2-yl)-pyrimidin-2-yl) spiro[cyclopropane-1,3'-indoline]-6'-carboxylic acid (0.71 g, 97%) as white solid.

Step 2.4

To a solution of 1'-(5-(4-(methylthio)pyridin-2-yl)pyrimidin-2-yl)spiro[cyclopropane-1,3'-indoline]-6'-carboxylic acid (0.71 g, 1.82 mmol, 1 eq) in DMF (10 mL), the TBTU (0.701 g, 2.184 mmol, 1.2 eq), NMM (0.395 mL, 3.64 mmol, 2 eq) and morpholine (0.472 mL, 5.46 mmol, 3 eq) were added at RT. Reaction mixture was then stirred at RT for 16 h. After completion of reaction, RM was quenched with ice water (30 mL) and a solid was precipitated out. The solid was filter off and re-dissolved in EtOAc (30 mL). The EtOAc solution of the desired compound was washed with water (2×30 mL), brine (30 mL), dried over Na$_2$SO$_4$, filtered and evaporated under reduced pressure to get the crude product. The crude product was triturated with Et$_2$O-hexane (3 times) to afford (1'-(5-(4-(methylthio)pyridin-2-yl)pyrimidin-2-yl)spiro[cyclopropane-1,3'-indolin]-6'-yl)(morpholino)methanone (0.69 g, 82.6%) as white solid. To a solutions of (1'-(5-(4-(methylthio)pyridin-2-yl)pyrimidin-2-yl)spiro[cyclopropane-1,3'-indolin]-6'-yl)(morpholino) methanone (0.29 g, 0.632 mmol, 1 eq) in THF (30 mL), m-CPBA (0.098 g, 0.569 mmol, 0.9 eq) were added slowly at 0° C. The reaction mixture was stirred RT for 1 h. After completion reaction mixture was quenched with saturated NaHCO$_3$ and extracted with EtOAc. Combined organic layer was washed with water (2×50 mL), brine (100 mL), dried over anhydrous Na$_2$SO$_4$ and evaporated under reduced pressure. Crude product was purified by preperative HPLC to afford (1'-(5-(4-(methylsulfinyl)pyridin-2-yl)pyrimidin-2-yl)spiro[cyclopropane-1,3'-indolin]-6'-yl)(morpholino) methanone (0.13 g, 43.3%) as white solid.

$^1$H NMR (400 MHz, DMSO-d$_6$): δ 9.33 (s, 2H), 8.86 (d, J=4.0 Hz, 1H), 8.44 (s, 1H), 8.23 (s, 1H), 7.67 (d, J=4.4 Hz, 1H), 6.99 (d, J=8.0 Hz, 1H), 6.89 (d, J=7.6 Hz, 1H), 4.31 (s, 2H), 3.46-3.62 (bs, 8H), 2.92 (s, 2H), 1.14-1.23 (m, 4H).

A 32: Preparation of: N-(2-amino-2-oxoethyl)-N-methyl-1'-(5-(pyridin-2-yl)pyrimidin-2-yl)spiro[cyclopropane-1,3'-indoline]-6'-carboxamide (compound 320)

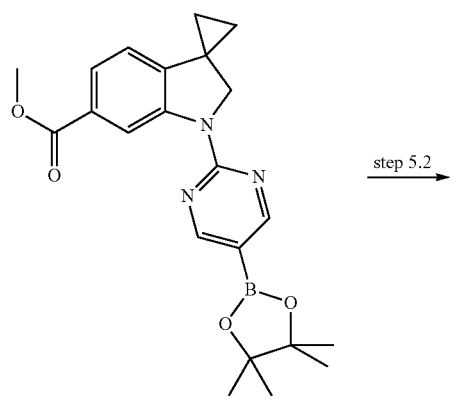

step 5.2

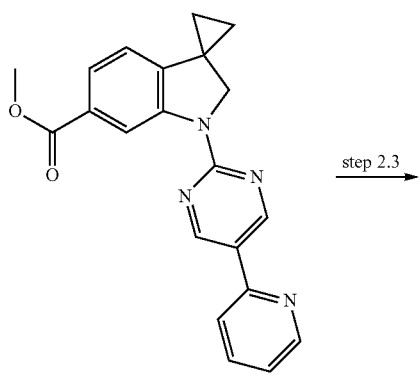

step 2.3

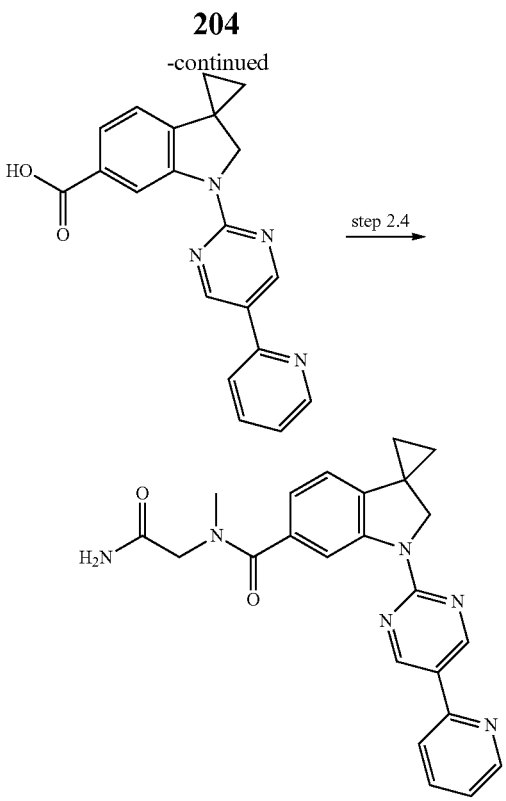

Step 5.2

To a solution of methyl 1'-(5-(4,4,5,5-tetramethyl-1,3,2-dioxaborolan-2-yl)pyrimidin-2-yl)spiro-[cyclopropane-1,3'-indoline]-6'-carboxylate (1 g, 2.457 mmol, 1 eq) in 1,4-dioxane (50 mL) were added K$_2$CO$_3$ (2M) (3.7 mL, 7.371 mmol, 3 eq) and 2-bromo-pyridine (0.24 mL, 2.457 mmol, 1 eq). The solution was degassed with Ar for 20 min followed by addition of Pd(PPh$_3$)$_4$ (0.14 g, 0.1237 mmol, 0.05 eq). The reaction mixture was refluxed for 16 h. After completion of reaction, reaction mixture was diluted with water (75 mL), extracted with EtOAc (3×75 mL). Combined organic layer was washed with water (100 mL), brine (100 mL), dried over anhydrous Na$_2$SO$_4$ and the solvent was evaporated to get the crude, which was purified by CC to afford methyl 1'-(5-(pyridin-2-yl)pyrimidin-2-yl)spiro[cyclopropane-1,3'-indoline]-6'-carboxylate (0.7 g, 80%) as brown solid.

Step 2.3

To a solution of methyl 1'-(5-(pyridin-2-yl)pyrimidin-2-yl)spiro[cyclopropane-1,3'-indoline]-6'-carboxylate (1 g, 2.793 mmol, 1 eq) in THF (8 ml), MeOH (4 mL) and H$_2$O (2 mL), LiOH (0.586 g, 13.96 mmol, 5 eq) was added at RT. RM was stirred at RT for 16 h. After completion of reaction, RM was evaporated under reduced pressure to get the crude product. Crude was dissolved in H$_2$O (50 mL) and washed with Et$_2$O (2×50 mL). After acidification of aqueous layer with 2N HCl (aq.), a solid was precipitated out of the solvent. The solid was filtered through sintered funnel and dried under reduced pressure. The solid was triturated with Et$_2$O-Pentane to afford 1'-(5-(pyridin-2-yl)pyrimidin-2-yl) spiro[cyclopropane-1,3'-indoline]-6'-carboxylic acid (0.7 g, 72.9%) as white solid.

Step 2.4

To a solution of 1'-(5-(pyridin-2-yl)pyrimidin-2-yl)spiro[cyclopropane-1,3'-indoline]-6'-carboxylic acid (0.17 g, 0.45 mmol, 1 eq) in DMF (5 mL), the TBTU (0.19 g, 0.593 mmol, 1.2 eq), NMM (0.21 ml, 1.97 mmol, 4 eq) and 2-methylamino-acetamide (0.07 g, 0.593 mmol, 1.2 eq) were added at RT. The RM was then stirred at RT for 16 h. After completion of reaction, RM was quenched with ice water (30 mL) and a solid was precipitated out. The solid was filtered-off and the solid was re-dissolved in EtOAc (30 mL). The EtOAc solution of the desired compound was washed with water (2×30 mL), brine (30 mL), dried over $Na_2SO_4$, filtered and evaporated under reduced pressure to get the crude product. The crude was triturated with $Et_2O$-hexane (3 times) to afford N-(2-amino-2-oxoethyl)-N-methyl-1'-(5-(pyridin-2-yl)-pyrimidin-2-yl)spiro[cyclopropane-1,3'-indoline]-6'-carboxamide (0.09 g, 50%) as white solid.

$^1$H NMR (400 MHz, DMSO-$d_6$): δ 9.28 (d, J=8.8 Hz, 2H), 8.67 (d, J=4.0 Hz, 1H), 8.43 (d, J=9.2 Hz, 1H), 8.02 (d, J=8.0 Hz, 1H), 7.90 (t, J=8.0 Hz, 1H), 7.35-7.45 (m, 2H), 7.09-7.14 (m, 1H), 6.89-7.09 (m, 1H), 6.84 (m, 1H), 4.29 (s, 2H), 3.84-4.03 (m, 2H), 2.96 (s, 1H), 1.14-1.22 (m, 4H).

B-1. Preparation of INT-1 Derivatives According to Step 1.1

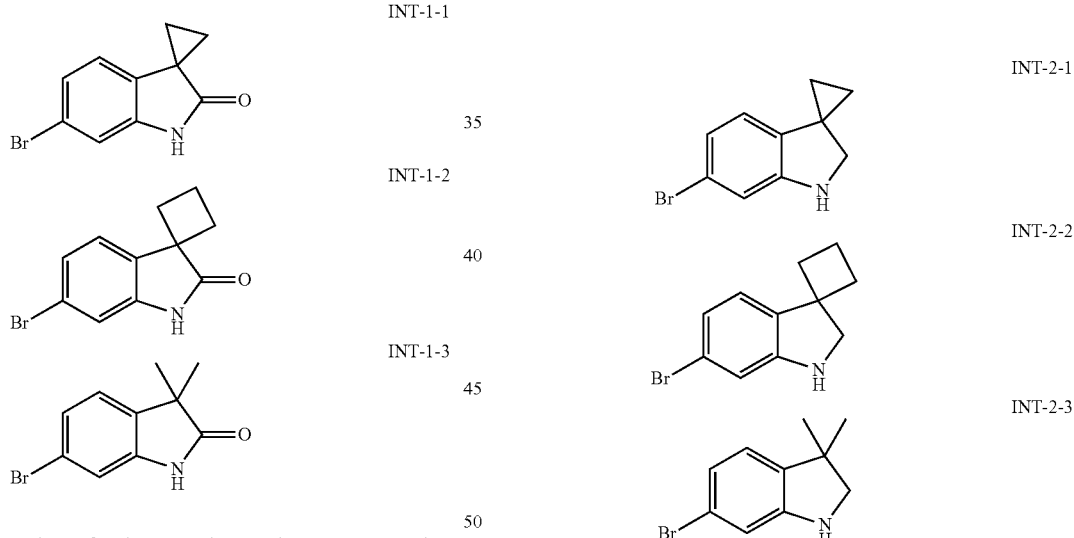

B-1a: Preparation of 6'-bromospiro[cyclopropane-1,3'-indolin]-2'-one (INT-1-1) n-BuLi (2.5M in hexane, 158 mL, 396 mmol) was added dropwise to a stirred and cooled (−40° C.) suspension of 6-bromoindolin-2-one (21.0 g, 99 mmol) and i-Pr$_2$NH (29.4 mL, 208 mmol) in dry THF (225 mL) under Ar. During addition the temperature is maintained below −20° C. After complete addition, the temperature was allowed to warm to 0° C., then a solution of 1,2-dibromoethane (25.6 mL, 297 mmol) in dry THF (25 mL) was added dropwise maintaining a temperature of below 10° C. After complete addition, the reaction mixture was stirred at room temperature for 18 h. The reaction mixture was concentrated to a smaller volume (~75 mL) under reduced pressure.

The residue was diluted with EtOAc (200 mL) and brine (100 mL). The biphasic mixture was then stirred vigorously. The pH of the solution was brought to a value of 5 by slowly adding 4M aqueous HCl (~50 mL). The biphasic system was filtered through a glass filter in order to remove the solids which appeared in the bisphasic system. The solids were rinsed with EtOAc (~10 mL), collected and dried on the air to give a first batch of INT-1 as a pale solid (13.99 g, 58.8 mmol, 59.3%).

The filtrate layers were separated. The aqueous phase was extracted with EtOAc (2×100 mL). The combined organic phases were washed with brine (100 mL), dried over $Na_2SO_4$ and the solvent was distilled off. The viscous dark-brown residue was stirred with EtOAc (25 mL) for 5 min at rt. The suspension was then slowly diluted with heptane (75 mL) while stirring which again resulted in solids which were filtered off, rinsed with heptane (10 mL), collected and air-dried to give a second batch of INT-1 (1) as a brown solid (6.04 g, 25.4 mmol, 25.6%).

LCMS: calculated for [M+H]$^+$: 238/240. found: 238/240, mono-Br isotope pattern observed.

B-1 b: Preparation of 6'-bromospiro[cyclobutane-1,3'-indolin]-2'-one (INT-1-2)

The compound INT-1-2 was prepared in analogous manner as described for compound INT-1-1, only 1,3-dibromopropane (14.4 mL, 141 mmol) is used instead of 1,2-dibromoethane. 6'-bromo-spiro[cyclobutane-1,3'-indolin]-2'-on was isolated as a pale orange solid. (5.54 g, 18.8 mmol, 40%) LCMS: calculated for [M+H]$^+$: 252/254. found: 252/254, mono-Br isotope pattern observed.

Preparation of INT-1-3 in an Analogous Manner to INT-1-1 and INT-1-2.

B-2. Preparation of INT-2 Derivatives According to Step 1.2

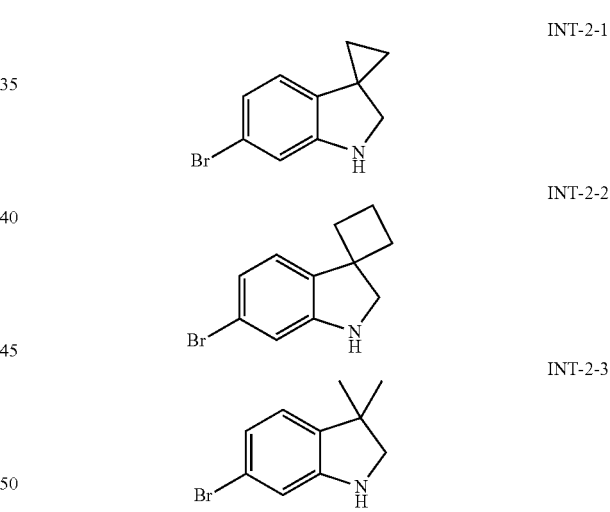

B-2a: Preparation of 6'-bromospiro[cyclopropane-1,3'-indoline (INT-2-1)

LiAlH$_4$ (2.4M in THF, 56 mL, 134 mmol) was added dropwise to a stirred and cooled (0° C.) suspension of indolinone INT-1 (1) (10.0 g, 42.0 mmol) in dry THF (175 mL) under Ar. After complete addition, the mixture was heated at 60° C. for 1 h. The reaction mixture was cooled to 0° C., diluted with Et$_2$O (100 mL) and then quenched by careful addition of water (5.1 mL), 1M aqueous NaOH (5.1 mL) and again water (15.3 mL). A heavy white precipitate was formed which was filtered off through Celite. The filtercake was rinsed well with EtOAc (2×100 mL). The combined filtrates were evaporated under reduced pressure. The residue was purified by flash column chromatography (silica, 0%->75% EtOAc in heptane) to give indoline INT-2 (1) (7.00 g, 31.2 mmol, 74%) as a pale solid. LCMS: calculated for [M+H]$^+$: 224/226. found: 224/226, mono-Br isotope pattern observed.

B-2b: Preparation of 6'-bromospiro[cyclobutane-1, 3'-indoline (INT-2-2)

The compound INT-2-2 was prepared in analogous manner as described for compound INT-2-1. 6'-Bromospiro[cyclobutane-1,3'-indoline has been isolated as a pale red oil (4.26 g, 17.9 mmol, 82%). The crude was used as such in the next reaction. LCMS: calculated for [M+H]$^+$: 238/240. found: 238/240, mono-Br isotope pattern observed.

Preparation of INT-2-3 in an Analogous Manner to INT-2-1.

B-3. Preparation of INT-3 Derivatives According to Step 1.3

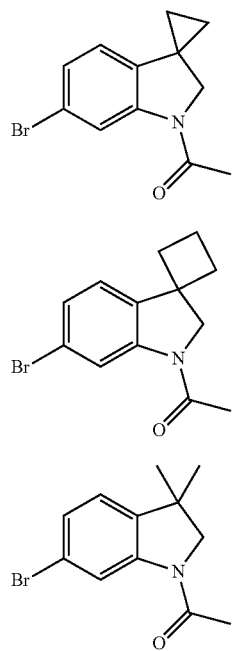

INT-3-1

INT-3-2

INT-3-3

B-3a: Preparation of (INT-3-1) 1-(6'-bromospiro [cyclopropane-1,3'-indoline]-1'-yl)ethanone A solution of AcCl (2.17 mL, 30.5 mmol) in CH$_2$Cl$_2$ (25 mL) was added dropwise to a stirred and cooled (0° C.) solution of indoline INT-2-1 (6.50 g, 29.0 mmol), Et$_3$N (4.43 mL, 31.9 mmol) and DMAP (0.089 g, 0.73 mmol) in CH$_2$Cl$_2$ (75 mL). The reaction mixture was stirred at rt for 18 h, after which the mixture was washed with water (2×100 mL). The organic layer was dried on Na$_2$SO$_4$ and evaporated to give 1-(6'-bromospiro[cyclopropane-1,3'-indoline]-1'-yl)ethanone as a pale brown solid (7.09 g, 26.6 mmol, 92%). LCMS: calculated for [M+H]$^+$: 266/268. found: 266/268, mono-Br isotope pattern observed.

B-3b. Preparation of INT-3-2: 1-(6'-bromospiro[cyclobutane-1,3'-indoline]-1'-yl)ethanone The compound INT-3-2 was prepared in analogous manner as described for compound INT-3-1, only INT-2-2 has been used instead of INT-2-1.

1-(6'-Bromospiro[cyclobutane-1,3'-indoline]-1'-yl)ethanone has been isolated as a colorless solid (3.30 g, 11.8 mmol, 66%). LCMS: calculated for [M+H]$^+$: 280/282. found: 280/282, mono-Br isotope pattern observed.

Preparation of INT-3-3 in an Analogous Manner to INT-3-1 and INT-3-2.

B-4. Preparation of INT-4 Derivatives According to Step 1.4

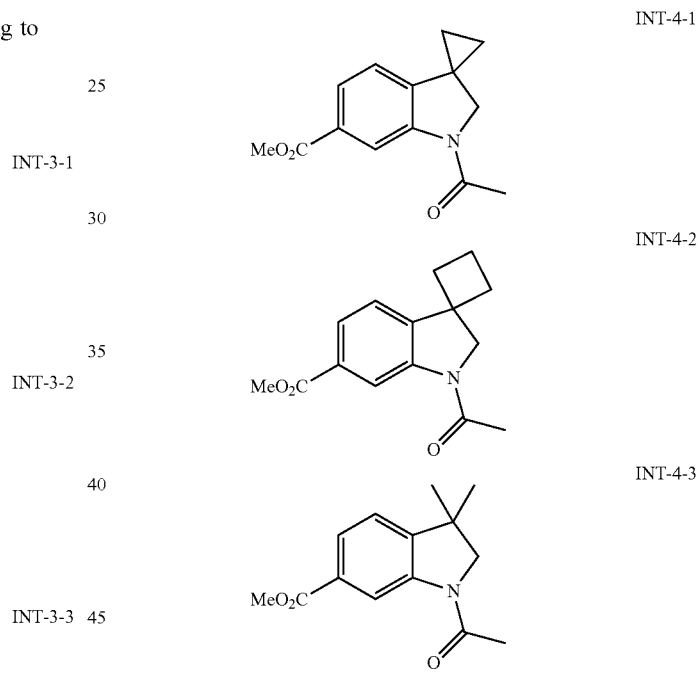

INT-4-1

INT-4-2

INT-4-3

B-4a. Preparation of INT-4-1: 1-(6'-bromospiro[cyclopropane-1,3'-indoline]-1'-yl)ethanone A solution of amide INT-3-1 (9.5 g, 35.7 mmol) and Et$_3$N (10.9 mL, 79 mmol) in a mixture of dry DMF (200 mL)/dry MeOH (100 mL) in an autoclave was flushed thoroughly with CO-gas for 10 min. Pd(dppf)Cl$_2$ (3.64 g, 4.46 mmol) was added neat and the reaction mixture flushed again with CO-gas for 5 min. The autoclave was closed and stirred under 40 bar of CO-pressure at 100° C. for 3 days. After cooling down and pressure release, the reaction mixture was concentrated to a smaller volume (~40 mL) under reduced pressure. The residue was diluted with EtOAc (100 mL) and air was bubbled through the stirred suspension for 5 minutes at room temperature. The suspension was filtered through Celite. The filtercake was rinsed well with EtOAc (2×50 mL). The combined filtrates were evaporated. Purification by flash column chromatography (silica, 10%->85% EtOAc in heptane) gave a first batch of 1-(6'-bromospiro-[cyclopropane-1,3'-indoline]-1'-yl)ethanone (6.22 g, 25.4 mmol, 71%) as a pale red solid. Mixed product fractions also containing residual starting material INT-3-1 were purified again by flash column chromatography (silica, 10%->85% EtOAc in heptane) to give a second batch of methyl ester 1-(6'-bromospiro-[cyclopropane-1,3'-indoline]-1'-yl)ethanone (1.01 g, 4.12 mmol, 12%) as a pale solid. LCMS: calculated for $[M+H]^+$: 246. found: 246.

B-4b. Preparation of INT-4-2: methyl 1'-acetylspiro[cyclobutane-1,3'-indoline]-6'-carboxylate The compound INT-4-2 was prepared in analogous manner as described for compound INT-4-1. Methyl 1'-acetylspiro[cyclobutane-1,3'-indoline]-6'-carboxylate has been isolated as a pale solid (3.11 g, 12.0 mmol, 82%). LCMS: calculated for $[M+H]^+$: 260. found: 260.

Preparation of INT-4-3 in an Analogous Manner to INT-4-1 and INT-4-2.

B-5. Preparation of INT-5 Derivatives According to Step 1.5

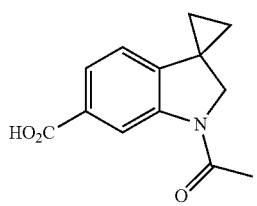

INT-5-1

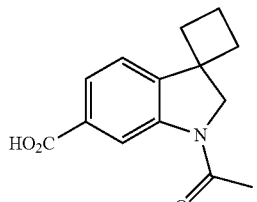

INT-5-2

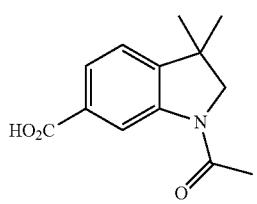

INT-5-3

Preparation of INT-5-1: 1'-acetylspiro[cyclopropane-1,3'-indoline]-6'-carboxylic acid A solution of LiOH.H$_2$O (1.67 g, 39.8 mmol) in water (7.5 mL) was added to a stirred solution of methyl ester INT-4-1 (6.50 g, 26.5 mmol) in THF (23 mL) at room temperature and mixture was stirred at 50° C. for 2 h. The mixture was concentrated to a smaller volume (~15 mL) under reduced pressure and diluted with water (25 mL). The aqueous solution was neutralised to pH~5 with 1M aqueous HCl. A heavy pale precipitate was formed. The solids were filtered off, rinsed with water (10 mL) and dried in a vacuum-oven at 40° C. to give 1'-acetylspiro[cyclopropane-1,3'-indoline]-6'-carboxylic acid (6.07 g, 26.2 mmol, 99%) as a pale solid. LCMS: calculated for $[M-H]^-$: 230. found: 230.

The compounds INT-5-2 and INT-5-3, respectively, can be prepared in analogous manner as described for compound INT-5-1.

B-6. Preparation of INT-6 Derivatives According to Step 1.6

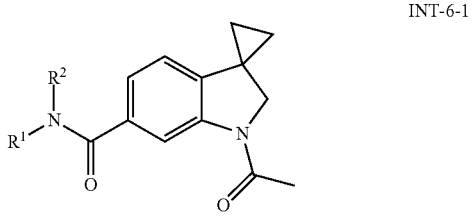

INT-6-1

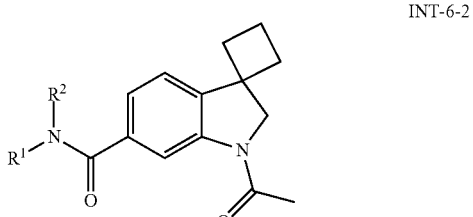

INT-6-2

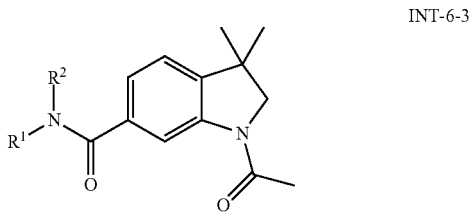

INT-6-3

Preparation of INT-6-1: 1-(6'-(morpholine-4-carbonyl)spiro[cyclopropane-1,3'-indoline]-1'-yl)ethanone EDCl (6.52 g, 34.0 mmol) and HOAt (0.24 g, 1.78 mmol) were added to a stirred solution of acid INT-5-1 (7.15 g, 30.9 mmol) and morpholine (3.25 mL, 37.1 mmol) in dry DMF (50 mL) at rt and the mixture was stirred for 5 h. The reaction mixture was concentrated to a smaller volume and partitioned between 0.5 M aqueous KHSO$_4$ (100 mL) and EtOAc (100 mL). The aqueous phase was extracted with EtOAc (100 mL). The combined organic layers were washed with water (3×50 mL) and brine (50 mL), dried on Na$_2$SO$_4$ and then concentrated to a smaller volume (~20 mL). A heavy precipitate was formed. The solids were filtered off, rinsed with heptane (2×10 mL) and air-dried to give a first batch of amide INT-6-1 (6.66 g, 22.2 mmol, 72%) as a pale solid. The combined filtrates were evaporated and purified by flash column chromatography (silica, 50%->100% EtOAc in heptane) to give a second batch of amide INT-6-1 (0.40 g, 1.33 mmol, 4%) as a pale solid. LCMS: calculated for $[M+H]^+$: 301. found: 301.

The compounds INT-6-2 and INT-6-3, respectively, can be prepared in analogous manner as described for compound INT-6-1.

B-7. Preparation of INT-7-Derivatives (1)

B-7a: 2-chloro-5-(2-fluorophenyl)pyrimidine (INT-7-1)

A mixture of 5-bromo-2-chloropyrimidine (10.0 g, 51.7 mmol), 2-fluorophenyl boronic acid (7.23 g, 51.7 mmol) and NaHCO$_3$ (6.51 g, 78 mmol) were dissolved in DME (160 mL)/water (40 mL). The solution was degassed with Ar for 15 min. Pd(dppf)Cl$_2$ (2.13 g, 2.58 mmol) was added and the mixture was heated at 90° C. for 18 h. The reaction mixture was filtered; the filtrate was bubbled trough with air and evaporated. Purification by flash chromatography (silica, 5%->25% EtOAc in heptane, compound coated on silica) gave product with some small impurities. Trituration with Et$_2$O gave final compound INT-7-1 (5.60 g, 26.8 mmol, 52%) as a white solid. LCMS: calculated for [M+H]$^+$: 209. found: 209.

B-7b: 2-chloro-5-(2-chlorophenyl)pyrimidine (INT-7-2)

To an Argon-flushed mixture of 5-bromo-2-chloropyrimidine (600 mg, 3.10 mmol), (2-chlorophenyl)-boronic acid (485 mg, 3.10 mmol) and Na$_2$CO$_3$ (493 mg, 4.65 mmol) in 1,4-dioxane (4 mL)/Water (1.5 mL) was added Pd(PPh$_3$)$_4$ (90 mg, 0.078 mmol) and the mixture was stirred at 90° C. for 18 h. A white precipitate was formed. Water was added, an off-white precipitate remained. The solid was filtered off, washed with water and air-dried. Purification by column chromatography (silica, 5%->25% EtOAc in heptane) gave pyrimidine INT-7 (2) (504 mg, 2.24 mmol, 72%) as an off-white solid. LCMS calculated for [M+H]$^+$: 225. found: 225.

B-7c: 2-chloro-5-phenylpyrimidine (INT-7-3)

Prepared according to the method described under B-7b, using the following reactants: 5-bromo-2-chloropyrimidine (600 mg, 3.10 mmol), phenylboronic acid (378 mg, 3.10 mmol) and Na$_2$CO$_3$ (493 mg, 4.65 mmol) in 1,4-dioxane (4 mL)/water (1.5 mL), Pd(PPh$_3$)$_4$ (90 mg, 0.078 mmol) yield INT-7-3 (412 mg, 2.16 mmol, 70%) as an off-white solid. LCMS calculated for [M+H]$^+$: 191. found: 191.

B-7d: 2-chloro-5-(2,4-difluorophenyl)pyrimidine (INT-7-4)

Prepared according to the method described under B-7b, using the following reactants: 5-bromo-2-chloropyrimidine (600 mg, 3.10 mmol), 2,4-difluorophenylboronic acid (490 mg, 3.10 mmol) and Na$_2$CO$_3$ (493 mg, 4.65 mmol) in 1,4-dioxane (4 mL)/Water (1.5 mL), Pd(PPh$_3$)$_4$ (90 mg, 0.078 mmol) yield INT-7-4 (453 mg, 2.00 mmol, 64%) as an off-white solid. LCMS calculated for [M+H]$^+$: 227. found: 227.

B-7e: 2-chloro-5-(2-fluorobenzyl)pyrimidine (INT-7-5)

(2-Chloropyrimidin-5-yl)boronic acid (586 mg, 3.70 mmol) and 1-(bromomethyl)-2-fluorobenzene (700 mg, 3.70 mmol) were dissolved in Tol (10 mL) and EtOH (2.5 mL). Pd(PPh$_3$)$_4$ (214 mg, 0.19 mmol) was added followed by Na$_2$CO$_3$ (392 mg, 3.70 mmol) in H$_2$O (5 mL). The reaction mixture was heated at 85° C. for 16 h. The resultant mixture was diluted with EtOAc (25 mL), washed with water and brine, dried over Na$_2$SO$_4$ and evaporated. Purification by column chromatography (silica, 0%->50% EtOAc in heptane) gave INT-7-5 (591 mg, 2.65 mmol, 72%) as white crystals. LCMS: calculated for [M+H]$^+$: 223. found: 223.

B-7f: 2-chloro-5-o-tolylpyrimidine (INT-7-6)

To a stirred solution of 5-bromo-2-chloropyrimidine (1.0 g, 5.78 mmol, 1 eq), o-tolylboronic acid (0.704 g, 5.78 mmol, 1.0 eq) in 1,4-dioxane and water (40 mL, 4:1) at RT was added Cs$_2$CO$_3$ (3.36 g, 10.36 mmol, 2.0 eq) and degassed with Ar for 15 min. Pd (PPh$_3$)$_4$ (0.299 g, 0.25 mmol, 0.05 eq) was added and again degassed with argon for 15 min. The RM was heated to 90° C. for 2 h. The RM was diluted with EtOAc (2×30 mL), washed with water (60 mL), dried (Na$_2$SO$_4$) and evaporated. The crude was purified by column chromatography (100-200 mesh) using 10% EtOAc in pet ether as eluent to get INT-7-6 (0.400 g, ~40%) TLC system: EtOAc/pet ether (2:3), R$_f$: 0.4.

B-7g: 2-chloro-5-(2-(trifluoromethoxy)phenyl)pyrimidine (INT-7-7)

Prepared according to the method described under B-7f, using the following reactants: 5-bromo-2-chloropyrimidine (1.0 g, 5.78 mmol, 1 eq), 2-(trifluoromethoxy)phenylboronic acid (1.0 g, 5.78 mmol, 1.0 eq) in 1,4-dioxane/water (20 mL, 4:1), Cs$_2$CO$_3$ (3.36 g, 10.36 mmol, 2.0 eq), Pd(Ph$_3$)$_4$ (0.299 g, 0.2 mmol, 0.05 eq) yield INT-7-7 (0.440 g, ~31%) TLC system: EtOAc/pet ether (1:4), R$_f$: 0.65.
$^1$H NMR (400 MHz, DMSO-d6): δ 8.97 (s, 2H), 7.73 (dd, J=7.8, 1.8 Hz, 1H), 7.66-7.64 (m, 1H), 7.61-7.53 (m, 2H).

B-7h: 2-chloro-5-(2-(trifluoromethyl)phenyl)pyrimidine (INT-7-8)

Prepared according to the method described under B-7f, using the following reactants: 5-bromo-2-chloropyrimidine (0.5 g, 2.59 mmol, 1 eq), 2-(trifluoromethyl)phenylboronic acid (0.491 g, 2.58 mmol, 1.0 eq), Cs$_2$CO$_3$ (2.5 g, 7.75 mmol, 3.0 eq), in 1,4-dioxane/water (20 mL, 4:1), Pd(PPh$_3$)$_4$ (0.149 g, 0.129 mmol, 0.05 eq). yield INT-7-8 (0.3 g, ~45%) TLC system: EtOAc/pet ether (2:3), R$_f$: 0.4.
$^1$H NMR (400 MHz, DMSO-d6): δ 8.83 (s, 2H), 7.94 (d, J=8.0 Hz, 1H), 7.84 (t, J=7.2 Hz, 1H), 7.76 (t, J=8.0 Hz, 1H), 7.60 (d, J=8.0 Hz, 1H).

B-7i: 2-chloro-5-(2,3-difluorophenyl)pyrimidine (INT-7-9)

Prepared according to the method described under B-7f, using the following reactants: 5-bromo-2-chloropyrimidine (0.635 g, 3.2 mmol, 1 eq), 2,3-difluorophenylboronic acid (0.499 g, 2.5 mmol, 1.0 eq) in 1,4-dioxane/water (20 mL, 4:1) at RT, Cs$_2$CO$_3$ (3.2 g, 9.87 mmol, 3.0 eq), Pd(PPh$_3$)$_4$ (0.379 g, 0.32 mmol, 0.1 eq) yield INT-7-9 (0.3 g, ~40%) TLC system: EtOAc/pet ether (1:9), R$_f$: 0.35.
$^1$H NMR (400 MHz, DMSO-d$_6$): δ 9.06 (d, J=1.4 Hz, 2H), 7.68-7.49 (m, 2H), 7.46-7.36 (m, 1H).

B-7j. 2-chloro-5-(2-fluoro-5-methoxyphenyl)pyrimidine (INT-7-10)

Prepared according to the method described under B-7f, using the following reactants: 5-bromo-2-chloropyrimidine (0.5 g, 2.58 mmol, 1 eq), 2-fluoro-5-methoxyphenylboronic acid (0.439 g, 2.58 mmol, 1.0 eq) in 1,4-dioxane/water (20 mL, 4:1), Cs$_2$CO$_3$ (2.5 g, 7.74 mmol, 3.0 eq), Pd(PPh$_3$)$_4$ (149 mg, 0.129 mmol, 0.05 eq) yield INT-7-10 (0.475 g, ~77%) TLC system: EtOAc/pet ether (3:7), R$_f$: 0.4.

$^1$H NMR (300 MHz, DMSO-d$_6$): δ 9.03 (d, J=1.5 Hz, 2H), 7.38-7.24 (m, 2H), 7.11-7.05 (m, 1H), 3.82 (s, 3H).

B-7k: 2-chloro-5-(2-fluoro-4-methoxyphenyl)pyrimidine (INT-7-11)

Prepared according to the method described under B-7f, using the following reactants: 5-bromo-2-chloropyrimidine (0.5 g, 2.59 mmol, 1 eq), 2-fluoro-4-methoxyphenylboronic acid (0.440 g, 2.58 mmol, 1.0 eq) in 1,4-dioxane/water (20 mL, 4:1), Cs$_2$CO$_3$ (2.5 g, 7.76 mmol, 3.0 eq), Pd(PPh$_3$)$_4$ (0.149 g, 0.961 mmol, 0.05 eq), yield INT-7-11 (0.475 g, ~77%) TLC system: EtOAc/pet ether (3:7), R$_f$: 0.4.

$^1$H NMR (300 MHz, DMSO-d$_6$): δ 8.96 (s, 2H), 7.65 (t, J=8.9 Hz, 1H), 7.12-6.92 (m, 2H), 3.84 (s, 3H).

B-7m: 2-(2-chloropyrimidin-5-yl)benzonitrile (INT-7-12)

Prepared according to the method described under B-7f, using the following reactants: 5-bromo-2-chloropyrimidine (0.2 g, 1.03 mmol, 1 eq), in THF and water (20 mL, 4:1), K$_2$CO$_3$ (0.312 g, 2.56 mmol, 2.2 eq), 2-cyanophenylboronic acid (0.182 g, 1.24 mmol, 1.2 eq), [(t-Bu)$_3$PH]BF$_4$ (1 mg, 0.005 mmol, 0.005 eq), Pd$_2$dba$_3$ (41 mg, 0.45 mmol, 0.044 eq) yield INT-7-12 (0.1 g, ~49%) TLC system: EtOAc/pet ether (1:4), R$_f$: 0.25.

$^1$H NMR (400 MHz, DMSO-d$_6$): δ 9.08 (s, 2H), 8.07 (dd, J=7.7, 1.3 Hz, 1H), 7.91-7.87 (m, 1H), 7.81 (dd, J=7.8, 1.4 Hz, 1H), 7.74-7.69 (m, 1H).

B-7n: 2-chloro-5-(2-fluoro-6-methoxyphenyl)pyrimidine (INT-7-13)

Prepared according to the method described under B-7f, using the following reactants: 5-bromo-2-chloropyrimidine (1.0 g, 5.18 mmol, 1 eq), 2-fluoro-6-methoxyphenylboronic acid (0.88 g, 5.18 mmol, 1.0 eq) in 1,4-dioxane and water (20 mL, 4:1), Cs$_2$CO$_3$ (3.36 g, 10.36 mmol, 2.0 eq), Pd(Ph$_3$)$_4$ yield INT-7-13 (0.4 g, ~33%) TLC system: EtOAc/pet ether (1:4), R$_f$: 0.65.

$^1$H NMR (400 MHz, DMSO-d$_6$): δ 8.87 (d, J=1.3 Hz, 2H), 7.51 (dd, J=8.5, 6.9 Hz, 1H), 7.11-6.97 (m, 2H), 3.81 (s, 3H).

B-7o: 2-(2-chloropyrimidin-5-yl)-3-fluorobenzonitrile (INT-7-14)

Prepared according to the method described under B-7f, using the following reactants: 5-bromo-2-chloropyrimidine (0.3 g, 1.55 mmol, 1 eq), in THF/water (10 mL, 4:1) at rt, K$_2$CO$_3$ (0.470 g, 3.41 mmol, 2.2 eq), 2-cyano-6-fluorophenylboronic acid (0.282 g, 1.70 mmol, 1.1 eq), [(t-Bu)$_3$PH]BF$_4$ (2 mg, 0.007 mmol, 0.005 eq), Pd$_2$dba$_3$ (57 mg, 0.062 mmol, 0.04 eq) yield INT-7-14 (0.135 g, ~37%) TLC system: EtOAc/pet ether (4:6), R$_f$: 0.3

$^1$H NMR (400 MHz, DMSO-d$_6$): δ 9.11 (d, J=1.0 Hz, 2H), 7.96 (dd, J=7.6, 1.3 Hz, 1H), 7.88-7.76 (m, 2H).

B-7p: 2-(2-chloropyrimidin-5-yl)-N,N-dimethylbenzamide (INT-7-15)

Step 1:

To a stirred solution of compound 5-bromo-2-chloropyrimidine (1.5 g, 7.72 mmol, 1 eq), 2-borono-benzoic acid (1.54 g, 9.3 mmol, 1.2 eq) and Cs$_2$CO$_3$ (5.0 g, 10.mmol, 2.0 eq), in 1,4-dioxanel water (30 mL, 4:1) was degassed with Ar for 15 min and added Pd(PPh$_3$)$_4$ (0.9 g, 0.7 mmol, 0.1 eq). The RM was stirred at 90° C. for 4 h, cooled to rt, diluted with water (25 mL), washed with EtOAc (25 mL). Aqueous layer was acified (pH ~6) with 1N HCl to get solid precipitate. Solid precipitated was filtered, washed with pet ether (20 mL) to get a carboxylic acid intermediate (0.600 g, ~33%) TLC system: EtOAc/pet ether (1:1), R$_f$: 0.10.

$^1$H NMR (400 MHz, DMSO-d6): δ 13.12 (s, 1H), 8.76 (s, 2H), 8.04 (dd, J=7.7, 1.4 Hz, 1H), 7.74-7.69 (m, 1H), 7.64-7.59 (m, 1H), 7.52-7.49 (m, 1H).

Step 2

To a stirred solution of intermediate 2-(2-chloropyrimidin-5-yl)benzoic acid (250 mg, 1.068 mmol, 1.0 eq) in DCM (5 mL) was added SOCl$_2$ (2.0 mL) and stirred at 40° C. for 2 h. The RM was evaporated under N$_2$ and diluted with dry THF (10 mL), cooled to 0° C., added N,N-dimethylamine. HCl (174 mg, 2.13 mmol, 2 eq), TEA (0.4 mL, 3.2 mmol, 3 eq) and stirred for 1 h at rt. The RM was basified (pH~8) with aq.NaHCO$_3$, extracted with DCM (2×20 mL), washed with brine (10 mL), dried over anhydrous Na$_2$SO$_4$ and evaporated under vacuum to get INT-7-15 (200 mg, ~72%). The crude was taken to next step without purification. TLC system: EtOAc/pet ether (5:5), R$_f$: 0.5.

$^1$H NMR (300 MHz, DMSO-d$_6$): δ 8.76 (s, 2H), 7.61-7.56 (m, 4H), 2.86 (s, 3H), 2.66 (s, 3H).

B-7q: 3-(2-chloropyrimidin-5-yl)-4-fluorobenzonitrile (INT-7-16)

Prepared according to the method described under B-7f, using the following reactants: 5-bromo-2-chloropyrimidine (0.3 g, 1.55 mmol, 1 eq), in THF/water (10 mL, 4:1), K$_2$CO$_3$ (0.470 g, 3.41 mmol, 2.2 eq), 5-Cyano-2-fluorophenylboronic acid (0.282 g, 1.70 mmol, 1.1 eq), [(t-Bu)$_3$PH]BF$_4$ (2 mg, 0.007 mmol, 0.005 eq), Pd$_2$(dba)$_3$ (57 mg, 0.062 mmol, 0.04 eq) yields INT-7-16 (0.135 g, ~37%) TLC system: EtOAc/pet ether (2:3), R$_f$: 0.3.

$^1$H NMR (300 MHz, DMSO-d$_6$) δ 9.09 (d, J=1.4 Hz, 2H), 8.35 (dd, J=7.1, 2.2 Hz, 1H), 8.12-8.07 (m, 1H), 7.72-7.66 (m, 1H).

B-7r: 2-chloro-5-(2-fluoro-5-(trifluoromethyl)phenyl)pyrimidine (INT-7-17)

Prepared according to the method described under B-7f, using the following reactants: 5-bromo-2-chloropyrimidine (467 mg, 2.415 mmol, 1 eq), 2-fluoro-5-(trifluoromethyl)phenylboronic acid (500 mg, 2.415 mmol, 1.0 eq) in 1,4-dioxane/water (10 mL, 4:1), Cs$_2$CO$_3$ (2.35 g, 7.246 mmol, 2.0 eq), Pd(PPh$_3$)$_4$ (278 mg, 0.241 mmol, 0.1 eq) yields INT-7-17 (300 mg; ~60%). TLC system: EtOAc/pet ether (1:9); R$_f$: 0.5.

$^1$H NMR (400 MHz, CDCl$_3$): δ 8.84 (s, 2H), 7.77-7.71 (m, 2H), 7.41-7.30 (m, 1H).

B-8. Preparation of INT-8 Derivatives According to Step 1.7

Preparation of INT-8-1; morpholino(spiro[cyclopropane-1,3'-indoline]-6'-yl)methanone

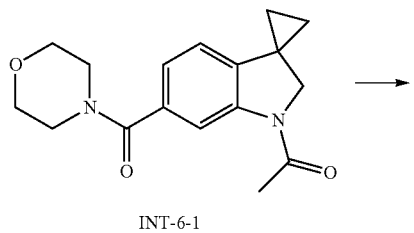

INT-6-1

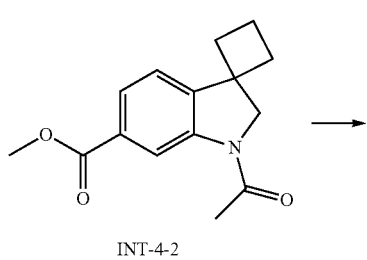

INT-8-1

Concentrated HCl (75 mL, 900 mmol) was added slowly to a stirred solution of amide INT-6-1 (6.85 g, 22.81 mmol) in MeOH (175 mL) at rt. The reaction mixture was then heated at 50° C. for 2.5 h. The reaction mixture was cooled to 0° C. and neutralised to pH~5 with 6M aqueous NaOH. The volatiles were removed under reduced pressure. The aqueous residue was extracted with EtOAc (1×250 mL+2× 100 mL). The combined organics were washed with brine (100 mL), dried on Na$_2$SO$_4$ and evaporated. Purification by flash column chromatography (silica, 0%->7.5% MeOH in EtOAc) gave INT-8-1 as a pale yellow solid (4.31 g, 16.7 mmol, 73%). LCMS: calculated for [M+H]$^+$: 259. found: 259.

Other compounds of general formula INT-8 can be prepared in analogous manner starting with the appropriate INT-6 derivative.

B-9. Preparation of INT-9 Derivatives According to Step 2.1

Preparation of B-9-2: methyl spiro[cyclobutane-1,3'-indoline]-6'-carboxylate

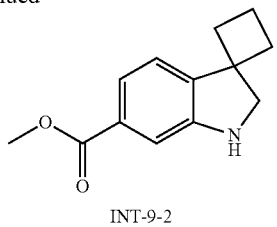

INT-4-2

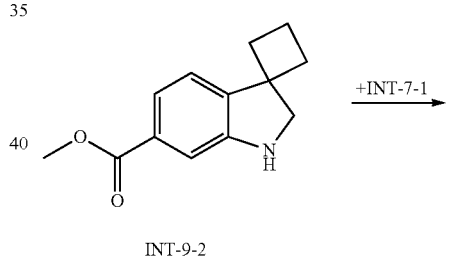

INT-9-2

A solution of concentrated HCl (5.0 mL, 60.0 mmol) in H$_2$O (7.5 mL) was added to a stirred solution of methyl ester INT-4-2 (0.50 g, 1.93 mmol) in MeOH (23 mL) at rt. The mixture was then heated under reflux for 1 h. After cooling to rt, the mixture was basified to pH~7 by careful addition of 2M aqueous NaOH. The mixture was extracted with EtOAc (2×25 mL). The combined organics were washed with brine (1×25 mL), dried on Na$_2$SO$_4$ and evaporated. Purification by flash column chromatography (silica, 0%->50% EtOAc in heptane) gave INT-9-2 (302 mg, 1.39 mmol, 72%) as a pale solid. LCMS: calculated for [M+H]$^+$: 218. found: 218.

Other compounds of general formula INT-8 can be prepared in analogous manner starting with the appropriate INT-6 derivative.

B-10. Preparation of INT-10 Derivatives According to Step 2.2

INT-10-2: methyl 1'-(5-(2-fluorophenyl)pyrimidin-2-yl)spiro[cyclobutane-1,3'-indoline]-6'-carboxylate

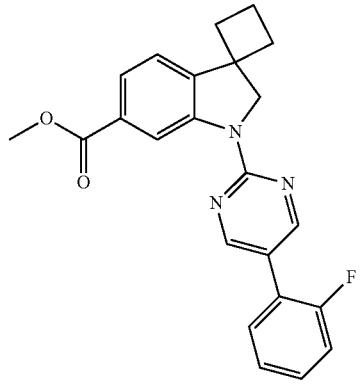

INT-10-2

A solution of INT-9-2 (300 mg, 1.38 mmol), pyrimidine INT-7-1 (317 mg, 1.52 mmol) and Cs$_2$CO$_3$ (810 mg, 2.48 mmol) in a mixture of dry dioxane (2.0 mL)/CF$_3$-Tol (0.5 mL) at rt was flushed thoroughly with Ar for 10 min. Pd(OAc)$_2$ (31.0 mg, 0.14 mmol) and Xantphos (160 mg, 0.28 mmol) were added and the reaction mixture was heated in the microwave at 110° C. for 1 h. The reaction mixture was partitioned between water (20 mL) and EtOAc (20 mL). The aqueous phase was extracted with EtOAc (20 mL). The combined organic layers were washed with brine (20 mL), dried on $Na_2SO_4$ and evaporated. Purification by flash column chromatography (silica, 0%->50% EtOAc in heptane) gave INT-10-2 (291 mg, 0.75 mmol, 54%) as a white solid. LCMS: calculated for $[M+H]^+$: 390. found: 390.

Other compounds of general formula INT-10 can be prepared in analogous manner starting with the appropriate INT-9 and INT-7 derivatives.

B-11. Preparation of INT-11 Derivatives According to Step 2.3

INT-11-2: 1'-(5-(2-fluorophenyl)pyrimidin-2-yl) spiro[cyclobutane-1,3'-indoline]-6'-carboxylic acid Other compounds of general formula INT-10 can be prepared in analogous manner starting with the appropriate INT-9 and INT-7 derivatives.

Synthesis of (1'-(5-(2-fluorophenyl)pyrimidin-2-yl)-1',2'-dihydrospiro[cyclopropane-1,3'-pyrrolo[2,3-b] pyridin]-6'-yl)(morpholino)methanone (107)

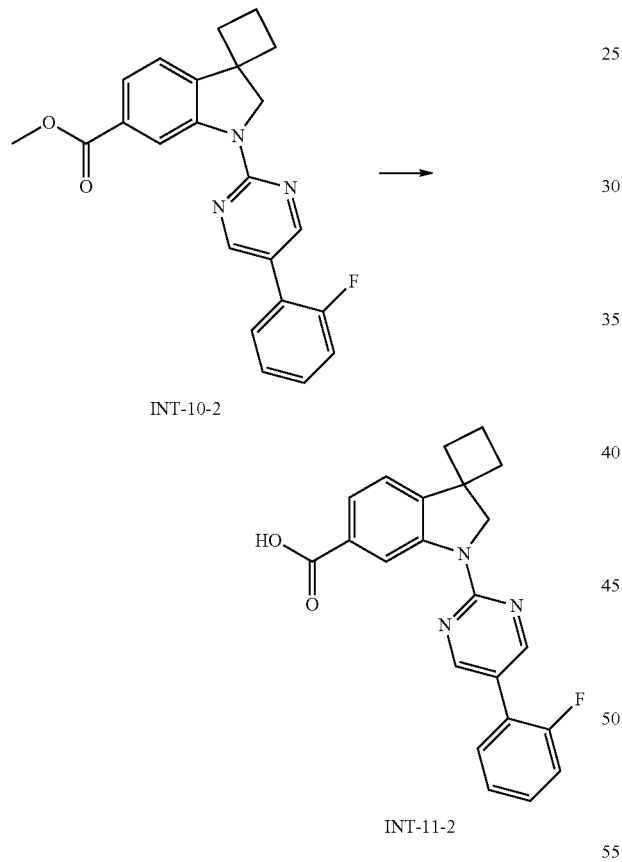

INT-10-2

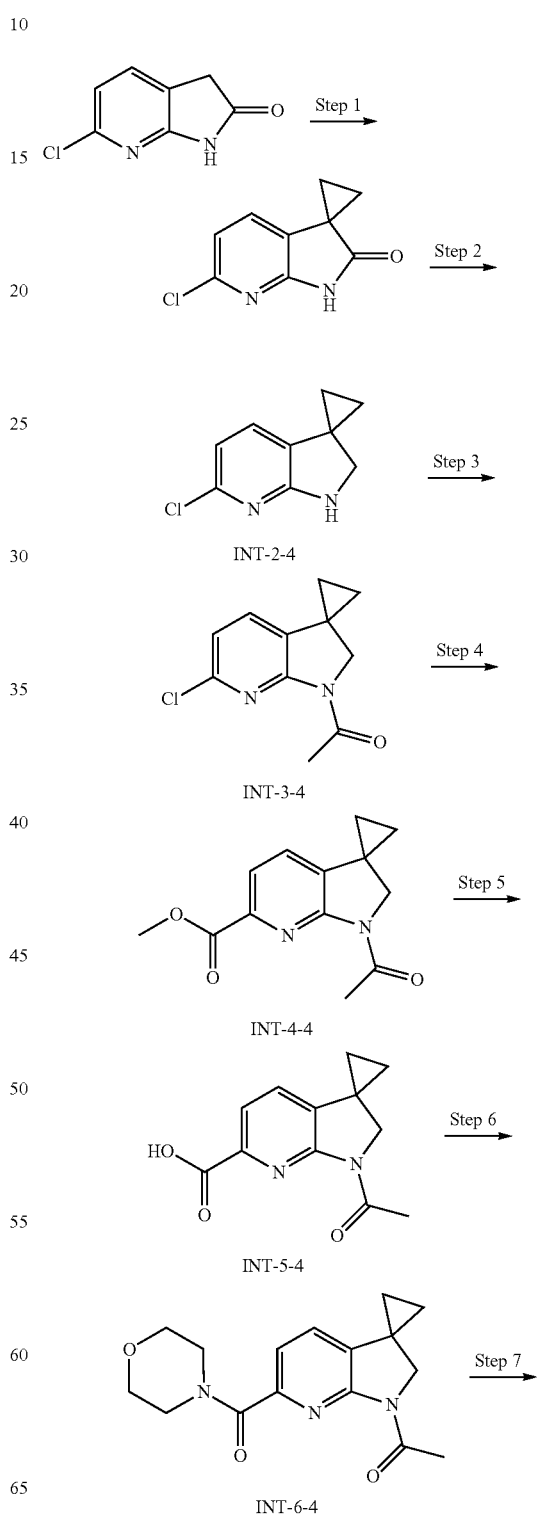

INT-11-2

A solution of $LiOH \cdot H_2O$ (156 mg, 3.72 mmol) in $H_2O$ (1.0 mL) was added to a stirred solution of methyl ester INT-10-2 (290 mg, 0.75 mmol) in THF (3 mL) at rt and the mixture was stirred at 50° C. for 6 h. The mixture was diluted with water (3.0 mL). The aqueous solution was neutralised to pH~5 with 1M aqueous HCl. A thick pale precipitate was formed. The solids were filtered off, rinsed with water (2×2.0 mL) and dried in a vacuum-oven at 40° C. to give carboxylic acid INT-11-2 (260 mg, 0.69 mmol, 93%) as a white solid. LCMS: calculated for $[M-H]^-$: 376. found: 376.

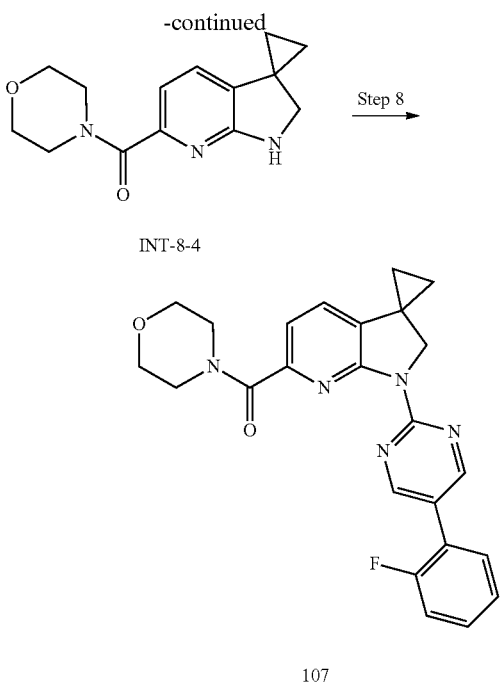

INT-8-4

107

Step 1:

A suspension of 6-chloro-1H-pyrrolo[2,3-b]pyridin-2(3H)-one (5.0 g, 29.7 mmol) in DMF (15 mL) was added dropwise to a stirred suspension of NaH (60% dispersion in oil, 7.12 g, 178 mmol) in DMF (50 mL) under Ar at 0° C., gas evolution was observed. After complete addition, the mixture was stirred for 15 minutes before dropwise addition of a solution of 1,2-dibromoethane (7.67 mL, 89 mmol) in DMF (15 mL). During addition, also gas evolution takes place. The reaction mixture was stirred at rt for 18 h. The solvent was evaporated under reduced pressure, subsequently the material was partitioned between EtOAc (100 mL) and water (100 mL). The aqueous layer was extracted with EtOAc (4×). The combined organic layer was washed with water (3×) and brine, dried over $Na_2SO_4$ and evaporated. The mixture was triturated in $Et_2O$ to afford 6'-chlorospiro[cyclopropane-1,3'-pyrrolo[2,3-b]pyridin]-2'(1'H)-one (2.81 g, 14.4 mmol, 49%) after filtration. LCMS: calculated for [M+H]$^+$: 195. found: 195.

Step 2: (6'-chloro-1',2'-dihydrospiro[cyclopropane-1,3'-pyrrolo[2,3-b]pyridine]; INT-2-4)

To a solution of indolinone 6'-chlorospiro[cyclopropane-1,3'-pyrrolo[2,3-b]pyridin]-2'(1'H)-one (3.78 g, 19.4 mmol) in THF (40 mL) was added dropwise a solution of LiAlH$_4$ (2.4 M in THF, 12.1 mL, 29.1 mmol) at 0° C. and the mixture was stirred at rt for 3 h. The mixture was cooled to 0° C. and was quenched with 9 mL of THF/H$_2$O (1:1). The reaction mixture was stirred at rt for 1 h. The mixture was filtered over Celite and the filtrate was dried (Na$_2$SO$_4$) and evaporated to dryness to afford indoline INT-2-4 (2.31 g, 12.8 mmol, 66%). LCMS: calculated for [M+H]$^+$: 181. found: 181.

Step 3: (1-(6'-chlorospiro[cyclopropane-1,3'-pyrrolo[2,3-b]pyridin]-1'(2'H)-yl)ethanone; INT-3-4)

A solution of AcCl (1.00 mL, 14.1 mmol) in CH$_2$Cl$_2$ (20 mL) was added dropwise to a stirred solution of indoline INT-2-4 (2.31 g, 12.8 mmol), Et$_3$N (2.05 mL, 14.7 mmol) and DMAP (156 mg, 1.28 mmol) in CH$_2$Cl$_2$ (20 mL). The reaction mixture was stirred at rt for 18 h. The mixture was washed with NH$_4$Cl (75 mL) and H$_2$O. The organic layer was dried on Na$_2$SO$_4$ and evaporated. Purification by column chromatography (silica, 5%->100% EtOAc in heptane) gave compound INT-3-4 (2.58 g, 11.6 mmol, 91%) as an off-white solid. LCMS: calculated for [M+H]$^+$: 223. found: 223.

Step 4: (methyl 1'-acetyl-1',2'-dihydrospiro[cyclopropane-1,3'-pyrrolo[2,3-b]pyridine]-6'-carboxylate; INT-4-4)

A solution of indoline INT-3-4 (2.58 g, 11.6 mmol) and Et$_3$N (3.92 mL, 28.2 mmol) in a mixture of DMF (60 mL)/MeOH (30 mL) in an autoclave was flushed thoroughly with N$_2$ for 10 min. PdCl$_2$(dppf) (843 mg, 1.15 mmol) was added. The autoclave was closed and pressurised to 35 bar with CO-gas. The reaction mixture was then stirred and heated at 110° C. for the weekend, the pressure of CO increased to 42 bar. The autoclave was cooled to rt and vented to release the CO-gas and flushed with N$_2$. The solvents were evaporated and the residue was partitioned between H$_2$O and EtOAc. The aqueous layer was extracted twice with EtOAc, the combined organic layers were washed with water and brine, dried over Na$_2$SO$_4$ and evaporated. Purification by column chromatography (silica, 0%->100% EtOAc in heptane followed by 0%->5% MeOH in CH$_2$Cl$_2$) afforded methylester INT-4-4 (1.14 g, 4.65 mmol, 40%) as a yellow solid. LCMS: calculated for [M+H]$^+$: 247. found: 247.

Step 5: (1'-acetyl-1',2'-dihydrospiro[cyclopropane-1,3'-pyrrolo[2,3-b]pyridine]-6'-carboxylic acid; INT-5-4)

A solution of LiOH.H$_2$O (320 mg, 7.61 mmol) in H$_2$O (2 mL) was added to a stirred suspension of methylester INT-4-4 (1.10 g, 4.45 mmol) in THF (6 mL)/MeOH (6 mL) and the mixture was stirred at rt for 18 h. The mixture was concentrated under reduced pressure and diluted with water (5 mL) and THF (2 mL). The aqueous solution was neutralised to pH~5 with 1 M aqueous HCl. A precipitate was formed. The solids were filtered off, rinsed with water (10 mL) and air-dried. The aqueous layer was concentrated partially and crystals were formed upon standing which were filtered off. Both solids were combined and dried in a vacuum stove to afford a mixture of carboxylic acid INT-5-4 and 1',2'-dihydrospiro[cyclopropane-1,3'-pyrrolo[2,3-b]pyridine]-6'-carboxylic acid (763 mg, 3.29 mmol, 74%). LCMS: calculated for [M+H]$^+$: 233. found: 233. This was used as such for the next step.

Step 6: (1'-acetyl-1',2'-dihydrospiro[cyclopropane-1,3'-pyrrolo[2,3-b]pyridine]-6'-carboxylic acid; INT-6-4)

EDCl (686 mg, 3.58 mmol) and HOAt (22.1 mg, 0.16 mmol) are added neat to a stirred solution of a mixture of carboxylic acids INT-5-4,1',2'-dihydrospiro[cyclopropane-1,3'-pyrrolo[2,3-b]pyridine]-6'-carboxylic acid (755 mg, 3.25 mmol) and morpholine (341 µL, 3.90 mmol) in DMF (6 mL) at rt. The reaction mixture was stirred at rt over the weekend. Subsequently, the mixture was concentrated to a smaller volume under reduced pressure. The residue was partitioned between 1 M aqueous KHSO$_4$ (250 mL) and EtOAc (250 mL). The aqueous layer was extracted again with EtOAc (250 mL). The combined organics were washed with water (3×100 mL) and brine (100 mL), sequentially, dried on Na₂SO₄ and then concentrated to afford INT-6-4 (175 mg, 0.58 mmol, 18%) as an orange oil/solid. LCMS: calculated for [M+H]⁺: 302. found: 302. The aqueous layer still contained the deacetylated material. The aqueous layer was evaporated to dryness and the residue was partitioned between H₂O and EtOAc. The aqueous layer was extracted with EtOAc, the combined organic layers were washed with brine, dried over Na₂SO₄ and evaporated. Purification by column chromatography (silica, 0%->10% MeOH in CH₂Cl₂) gave indoline (1',2'-dihydrospiro[cyclopropane-1, 3'-pyrrolo[2,3-b]pyridin]-6'-yl)(morpholino)methanone (61 mg, 0.23 mmol, 7%). LCMS: calculated for [M+H]⁺: 260. found: 260.

Step 7: (1',2'-dihydrospiro[cyclopropane-1,3'-pyrrolo[2,3-b]pyridin]-6'-yl)(morpholino)methanone; INT-8-4)

Concentrated HCl (0.97 mL, 11.6 mmol) was added slowly to a stirred solution of amide INT-6-4 (175 mg, 0.58 mmol) in MeOH (2.5 mL) at rt. The reaction mixture was then heated to 66° C. and stirred for 3 h. Subsequently, the reaction mixture was cooled to rt. The reaction mixture was added slowly to Na₂CO₃ (739 mg, 6.97 mmol) in 3 mL H₂O, gas evolution was observed. The aqueous layer was extracted with EtOAc twice. The combined organics were washed with brine, dried on Na₂SO₄ and the solvent was removed under reduced pressure to give indoline INT-8-4 (48 mg, 0.18 mmol, 32%). LCMS: calculated for [M+H]⁺: 260. found: 260.

Step 8: (1'-(5-(2-fluorophenyl)pyrimidin-2-yl)-1',2'-dihydrospiro[cyclopropane-1,3'-pyrrolo[2,3-b]pyridin]-6'-yl)(morpholino)methanone (107)

A suspension of amine INT-8-4 (95 mg, 0.37 mmol), pyrimidine INT-7-1 (76 mg, 0.37 mmol) and Cs₂CO₃ (179 mg, 0.55 mmol) in dioxane (2 mL)/CF₃-Tol (0.5 mL) was flushed thoroughly with Ar for 10 min. Xantphos (42.4 mg, 0.07 mmol) and Pd(OAc)₂ (8.23 mg, 0.04 mmol) were added and the mixture was irradiated in a Biotage Microwave at 120° C. for 1 h. The crude reaction mixture was added to EtOAc (25 mL) and brine (25 mL). The organic layer was dried over Na₂SO₄ and evaporated to dryness. Purification by preperative LCMS to afford final compound 107 (43 mg, 0.10 mmol, 26%) as a solid. LCMS: calculated for [M+H]⁺: 432. found: 432.

¹H NMR (400 MHz, DMSO-d₆) δ 8.86 (d, J=1.3 Hz, 2H), 7.70 (td, J=7.8, 1.6 Hz, 1H), 7.53-7.43 (m, 1H), 7.43-7.34 (m, 2H), 7.32 (d, J=7.6 Hz, 1H), 7.26 (d, J=7.6 Hz, 1H), 4.30 (s, 2H), 4.09-3.98 (m, 2H), 3.81-3.72 (m, 2H), 3.72-3.59 (m, 4H), 1.30-1.15 (m, 4H).

Synthesis of (1'-(5-(2-fluorophenyl)pyrimidin-2-yl)-1',2'-dihydrospiro[cyclopropane-1,3'-pyrrolo[3,2-c]pyridin]-6'-yl)(morpholino)methanone (108)

Preparation of INT-2-5 (6'-chloro-1',2'-dihydrospiro[cyclopropane-1,3'-pyrrolo[3,2-c]pyridine])

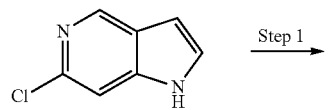

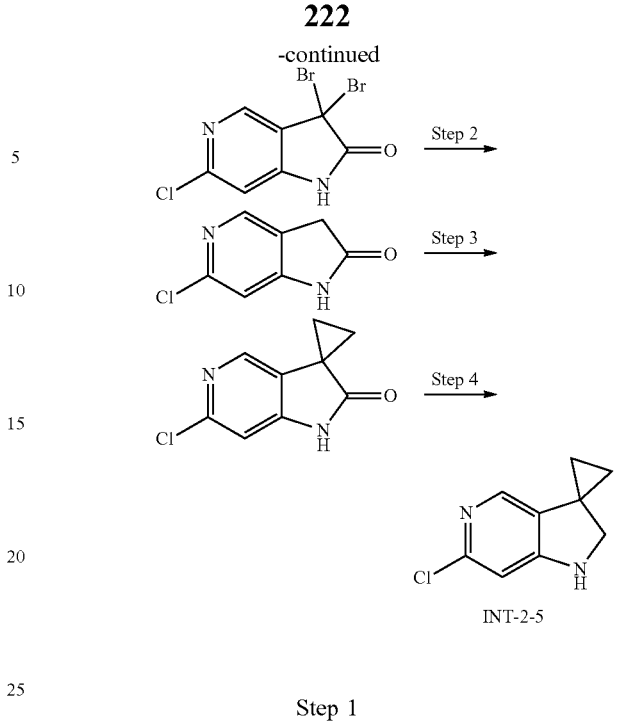

Step 1

To a stirred solution of 6-chloro-1H-pyrrolo[3,2-c]pyridine (4.2 g, 27.5 mmol) in ᵗBuOH (200 mL) was added slowly pyridinium bromide perbromide (29.3 g, 83 mmol) over 45 min (when finishing the addition, a yellow precipitate was formed) and the mixture was stirred at 35° C. for 18 h. The solvent was evaporated and the residue was partitioned between water and EtOAc. The aqueous layer was extracted with EtOAc; the combined organic layer was washed with water and brine, dried over Na₂SO₄ and evaporated to give (8.36 g, 25.6 mmol, 93%) as a light-brown solid.

Step 2

To a suspension 3,3-dibromo-6-chloro-1H-pyrrolo[3,2-c]pyridin-2(3H)-one (8.36 g, 25.6 mmol) in AcOH (150 mL) was added Zn (16.75 g, 256 mmol) and the mixture was stirred at rt for 1.5 h. MeOH was added, the insoluble particles were filtered off and the solvent was evaporated. The residue was partitioned between water and EtOAc. The aqueous layer was extracted twice with EtOAc, the combined organic layer was washed with water and brine, dried over Na₂SO₄ and evaporated to give 6-chloro-1H-pyrrolo[3,2-c]pyridin-2(3H)-one (3.7 g, 22.0 mmol, 86%) as a light-brown solid. LCMS: calculated for [M+H]⁺: 169. found: 169.

Step 3

A solution of 6-chloro-1H-pyrrolo[3,2-c]pyridin-2(3H)-one (3.0 g, 17.8 mmol) in dry DMF (5 mL) was added dropwise to a stirred suspension NaH (60% dispersion in oil, 4.27 g, 107 mmol) in dry DMF (50 mL) under argon atmosphere at 0° C. After complete addition, the mixture was stirred for 15 min before dropwise addition of a solution of 1,2-dibromoethane (4.60 mL, 53.4 mmol) in dry DMF (3 mL). The brown reaction mixture was stirred at rt for 18 h. The mixture was diluted with EtOAc (100 mL) and water (100 mL). The layers were separated and the aqueous layer was extracted with EtOAc (4×). The combined organic layer was washed with water (3×) and brine, dried over Na$_2$SO$_4$ and evaporated. Trituration from CH$_2$Cl$_2$ (10 mL) gave 6'-chlorospiro[cyclopropane-1,3'-pyrrolo[3,2-c]pyridin]-2'(1'H)-one (1.36 g, 7.01 mmol, 33%) as a brown solid. LCMS: calculated for [M+H]$^+$: 195. found: 195.

Step 4

To a brown suspension of 6'-chlorospiro[cyclopropane-1, 3'-pyrrolo[3,2-c]pyridin]-2'(1'H)-one (1.36 g, 7.01 mmol) in dry THF (60 mL) at 0° C. was added slowly LiAlH$_4$ (2.4M in THF, 9.63 mL, 23.12 mmol) (gas and heat formation and formation of a clear, yellow solution) and the mixture was stirred at 60° C. for 1 h. The reaction was cooled down to 0° C. and quenched by slow addition of Na$_2$SO$_4$.10H$_2$O until gas evolution had ceased. Na$_2$SO$_4$ was added and the suspension was filtered over Celite. The residue was washed with THF and the combined organics were evaporated to yield azaindoline INT-2-5 (1.09 g, 6.04 mmol, 86%) as an off-white solid. LCMS: calculated for [M+H]$^+$: 181. found: 181.

Preparation of (1'-(5-(2-fluorophenyl)pyrimidin-2-yl)-1',2'-dihydrospiro[cyclopropane-1,3'-pyrrolo-[3,2-c]pyridin]-6'-yl)(morpholino)methanone (108)

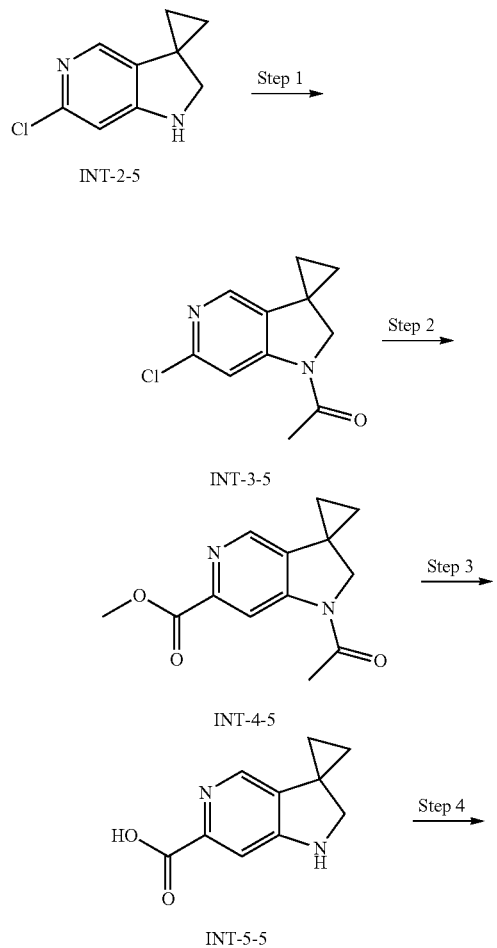

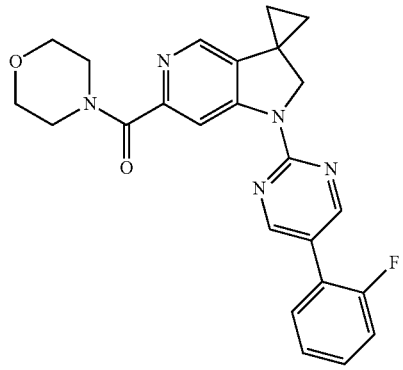

Step 1: (1-(6'-chlorospiro[cyclopropane-1,3'-pyrrolo[3,2-c]pyridin]-1'(2'H)-yl)ethanone; INT-3-5)

A solution of AcCl (0.60 mL, 8.45 mmol) in CH$_2$Cl$_2$ (1 mL) was added dropwise to a stirred and cooled (0° C.) solution of azaindoline INT-2-5 (1.09 g, 6.04 mmol), Et$_3$N (0.93 mL, 6.65 mmol) and DMAP (0.074 g, 0.604 mmol) in CH$_2$Cl$_2$ (20 mL). The reaction mixture was stirred at rt for 18 h. The mixture was washed with water (2×10 mL). The organic layer was dried on Na$_2$SO$_4$ and evaporated. Purification by column chromatography (silica, 5%->100% EtOAc in heptane) gave INT-3-5 (820 mg, 3.68 mmol, 61%) as an off-white solid. LCMS: calculated for [M+H]$^+$: 223. found: 223.

Step 2: (methyl 1'-acetyl-1',2'-dihydrospiro[cyclopropane-1,3'-pyrrolo[3,2-c]pyridine]-6'-carboxylate; INT-4-5)

A solution of azaindoline INT-3-5 (900 mg, 4.04 mmol) and Et$_3$N (1.24 mL, 8.89 mmol) in a mixture of dry DMF (20 mL)/dry MeOH (10 mL) in an autoclave was flushed thoroughly with N$_2$ for 10 min. PdCl$_2$(dppf) (266 mg, 0.36 mmol) was added and the mixture was flushed with N$_2$ for 1 min. The autoclave was closed, pressurised to 35 bar with CO-gas and stirred at 110° C. for 72 h (pressure CO=42 bar). The autoclave was cooled to rt and vented to release the CO-gas. The solvents were evaporated and the residue was partitioned between H$_2$O and EtOAc. The aqueous layer was extracted twice with EtOAc, the combined organic layers were washed with water and brine, dried over Na$_2$SO$_4$ and evaporated. Purification by column chromatography (silica, 0%->5% MeOH in CH$_2$Cl$_2$) gave methylester INT-4-5 (630 mg, 2.56 mmol, 63%) as a red-brown solid. LCMS: calculated for [M+H]$^+$: 247. found: 247.

Step 3: (1',2'-dihydrospiro[cyclopropane-1,3'-pyrrolo[3,2-c]pyridine]-6'-carboxylic acid; INT-5-5)

A solution of LiOH.H$_2$O (161 mg, 3.84 mmol) in H$_2$O (1 mL) was added to a stirred suspension of methylester INT-4-5 (630 mg, 2.56 mmol) in THF (3 mL)/MeOH (3 mL) and the mixture was stirred at rt for 18 h. The mixture was concentrated under reduced pressure and diluted with water (5 mL) and THF (2 mL). The aqueous solution was neutralised to pH~5 with 1M aqueous HCl. A precipitate was formed. The solids were filtered off, rinsed with water (10 mL) and air-dried.

The aqueous layer of the filtrate was thoroughly extracted with CH$_2$Cl$_2$; the combined organic layer was dried over Na$_2$SO$_4$ and evaporated.

Both batches were combined to give carboxylic acid INT-5-5 (438 mg, 2.30 mmol, 90%) as a brown solid. LCMS: calculated for [M+H]$^+$: 191. found: 191.

Step 4: (1',2'-dihydrospiro[cyclopropane-1,3'-pyrrolo[3,2-c]pyridin]-6'-yl)(morpholino)methanone; INT-6-5)

Morpholine (0.28 mL, 3.15 mmol) was added to a stirred solution of acid INT-5-5 (438 mg, 2.56 mmol), DIPEA (1.10 mL, 6.31 mmol) and HATU (973 mg, 2.56 mmol) in dry DMF (4 mL) and the reaction mixture was stirred at rt for 18 h. The mixture was partitioned between CH$_2$Cl$_2$ and water. The aqueous layer was extracted with CH$_2$Cl$_2$ (product can not be extracted with EtOAc). The combined organic layers were washed with water, dried on Na$_2$SO$_4$ and evaporated. Purification by column chromatography (silica, 0%->10% MeOH in CH$_2$Cl$_2$) gave amide INT-6-5 (300 mg, 1.16 mmol, 45%) as a yellow/brown glass. LCMS: calculated for [M+H]$^+$: 260. found: 260.

Step 5: ((1'-(5-(2-fluorophenyl)pyrimidin-2-yl)-1',2'-dihydrospiro[cyclopropane-1,3'-pyrrolo[3,2-c]pyridin]-6'-yl)(morpholino)methanone (108)

To a degassed (Ar) solution of indoline INT-6-5 (300 mg, 1.16 mmol), pyrimidine INT-7-1 (241 mg, 1.16 mmol) and Cs$_2$CO$_3$ (679 mg, 2.08 mmol) in 1,4-dioxane (10 mL)/CF$_3$-Tol (3 mL) were added Xantphos (66.9 mg, 0.12 mmol) and PdOAc$_2$ (13.0 mg, 0.058 mmol). The solution was degassed with Ar again and stirred at 120° C. for 75 min in the microwave. Brine and EtOAc were added, the layers were separated and the organic layer was dried over Na$_2$SO$_4$ and evaporated. Purification by column chromatography (silica, 5%->100% EtOAc in heptane), followed by trituration with CH$_3$CN gave final compound 108 (155 mg, mmol, 31%) as a white solid. LCMS: calculated for [M+H]$^+$: 432. found: 432.

$^1$H NMR (400 MHz, DMSO-d$_6$) δ 8.93 (s, 2H), 8.37 (s, 1H), 7.97 (s, 1H), 7.72-7.64 (m, 1H), 7.53-7.44 (m, 1H), 7.43-7.32 (m, 2H), 4.32 (s, 2H), 3.72-3.60 (m, 4H), 3.58-3.42 (m, 4H), 1.32-1.22 (m, 4H).

Synthesis of (1'-(5-(2-fluorophenyl)pyrimidin-2-yl)-1',2'-dihydrospiro[cyclopropane-1,3'-pyrrolo[3,2-b]pyridin]-6'-yl)(morpholino)methanone (109)

Preparation of intermediate INT-2-6: 6'-bromo-1',2'-dihydrospiro[cyclopropane-1,3'-pyrrolo[3,2-b]pyridine]

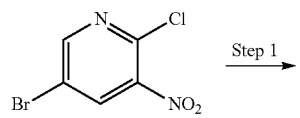

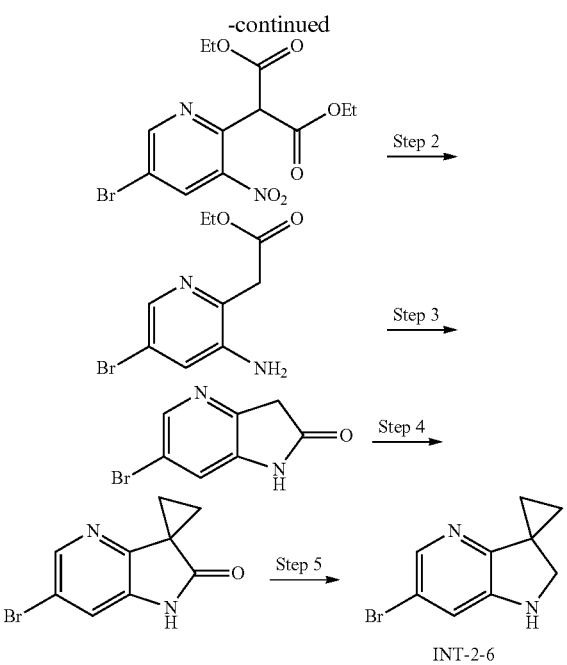

Step 1

To a stirred solution of K$_2$CO$_3$ (43.7 g, 316 mmol) in dry DMF (150 mL) was added slowly diethyl malonate (19.1 mL, 126 mmol) and 5-bromo-2-chloro-3-nitropyridine (25 g, 105 mmol). The resulting mixture was stirred at rt for 18 h. The reaction mixture was poured into a mixture of 5N HCl (100 mL) and crushed ice (150 ml). The aqueous layer was extracted with EtOAc (3×100 mL). The combined organic layer was washed with water and brine, dried over Na$_2$SO$_4$ and evaporated. The residue was purified by column chromatography (silica, 33% EtOAc in heptane) to give diethyl 2-(5-bromo-3-nitropyridin-2-yl)-malonate (38.1 g, 99 mmol, 94%) as a yellow oil.

Step 2

To a stirred solution of diethyl 2-(5-bromo-3-nitropyridin-2-yl)malonate (28 g, 72.9 mmol) in EtOH (300 mL) was added slowly Fe (12.2 g, 219 mmol) and HCl (conc, 9.11 mL, 109 mmol). Slowly the temperature was raised to 82° C. and the reaction mixture was stirred for 1 h. The mixture was taken over celite while hot and washed twice with warm EtOH (150 mL). An aqueous saturated solution of NaHCO$_3$ was added to the organic layer till pH~7 was reached. EtOH was removed in vacuo and EtOAc (1200 mL) was added. The suspension was stirred overnight. The layers were separated and the aqueous layer was extracted with EtOAc (50 mL). The combined organic layer was washed with water (100 mL) and brine (50 mL), dried over Na$_2$SO$_4$ and evaporated to give ethyl 2-(3-amino-5-bromopyridin-2-yl) acetate (20.1 g, 65.2 mmol, 89%, 84% purity) as a yellow solid.

Step 3

To ethyl 2-(3-amino-5-bromopyridin-2-yl)acetate (3.5 g, 13.5 mmol) was added 1N aqueous HCl-solution (97 mL, 97 mmol). The reaction mixture was stirred at 50° C. for 18 h.

The reaction mixture was cooled to room temperature and solid NaHCO$_3$ was added. The aqueous layer was extracted with EtOAc (3×100 mL). The combined organic layer was washed with water and brine, dried over Na$_2$SO$_4$ and evaporated to give azaindolinone 6-bromo-1H-pyrrolo[3,2-b]pyridin-2(3H)-one (1.9 g, 8.12 mmol, 60%) as a brown solid. LCMS: calculated for [M+H]$^+$: 215. found: 215, isotope pattern present.

Step 4

A solution of 6'-bromospiro[cyclopropane-1,3'-pyrrolo[3,2-b]pyridin]-2'(1'H)-one (5.7 g, 24.6 mmol) in dry DMF (10 mL) was added dropwise to a stirred suspension NaH (60% dispersion in oil, 5.91 g, 148 mmol) in dry DMF (50 mL) under Ar at 0° C. After complete addition, the mixture was stirred for 15 min before dropwise addition of a solution of 1,2-dibromoethane (6.36 mL, 73.8 mmol) in dry DMF (10 mL). The brown reaction mixture was stirred at rt for 18 h. The mixture was reduced in volume and diluted with EtOAc (100 mL) and water (100 mL). The layers were separated and the aqueous layer was extracted with EtOAc (2×100 mL). The combined organic layer was washed with brine, dried over Na$_2$SO$_4$ and evaporated. Purification by column chromatography (silica, 33#% EtOAc in heptane), followed by titruation from CH$_2$Cl$_2$ afforded 6'-bromospiro[cyclopropane-1,3'-pyrrolo[3,2-b]pyridin]-2'(1'H)-one (3.62 g, 14.4 mmol, 58%) as a yellow solid. LCMS: calculated for [M+H]$^+$: 241. found: 241, isotope pattern present.

Step 5

To a brown suspension of 6'-bromospiro[cyclopropane-1,3'-pyrrolo[3,2-b]pyridin]-2'(1'H)-on (3.58 g, 14.3 mmol) in dry THF (60 mL) at 0° C. was added slowly LiAlH$_4$ (2.4M in THF, 18.7 mL, 44.9 mmol) (gas and heat formation and formation of a clear, yellow solution) and the mixture was stirred at 60° C. for 1 h. The reaction was cooled down to 0° C. and quenched by slow addition of Na$_2$SO$_4$.10H$_2$O until gas evolution had ceased. Na$_2$SO$_4$ was added and the suspension was filtered over Celite. The residue was washed with THF (20 mL) and the combined organics were evaporated to yield azaindoline INT-2-6 (2.75 g, 12.3 mmol, 86%,) as an yellow solid. LCMS: calculated for [M+H]$^+$: 227. found: 227, isotope pattern present.

Preparation of (1'-(5-(2-fluorophenyl)pyrimidin-2-yl)-1',2'-dihydrospiro[cyclopropane-1,3'-pyrrolo[3,2-b]pyridin]-6'-yl)(morpholino)methanone (109)

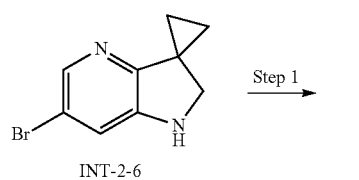

INT-2-6

Step 1

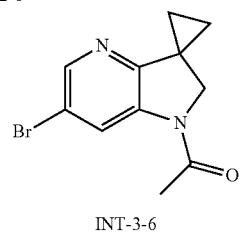

INT-3-6

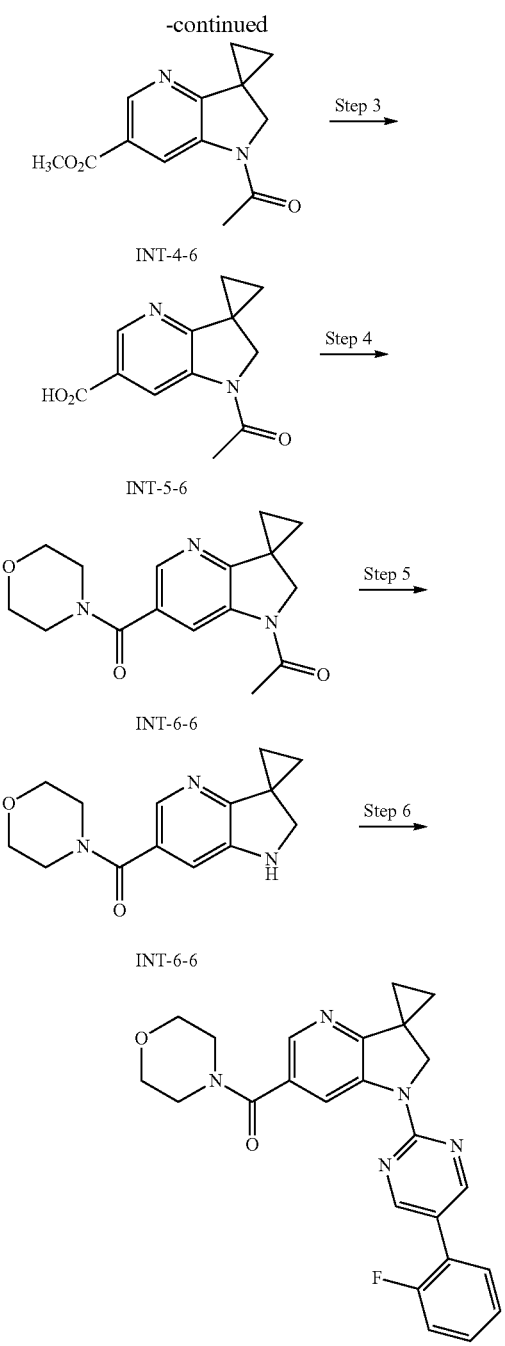

Step 1: (1-(6'-bromospiro[cyclopropane-1,3'-pyrrolo[3,2-b]pyridin]-1'(2'H)-yl)ethanone; INT-3-6)

A solution of AcCl (1 mL, 14.1 mmol) in CH$_2$Cl$_2$ (2 mL) was added dropwise to a stirred and cooled (0° C.) solution of azaindoline INT-2-6 (2.75 g, 12.3 mmol), TEA (2.05 mL, 14.7 mmol) and DMAP (150 mg, 1.22 mmol) in CH$_2$Cl$_2$ (20 mL). The reaction mixture was stirred at rt for 18 h. The mixture was washed with water (2×10 mL). The organic layer was dried on Na$_2$SO$_4$ and evaporated. Purification by column chromatography (silica, 33% EtOAc in heptane)

gave INT-3-6 (2.04 g, 7.39 mmol, 60%) as an off-white solid. LCMS: calculated for [M+H]$^+$: 267. found: 267, isotope pattern present.

Step 2: (Methyl 1'-acetyl-1',2'-dihydrospiro[cyclopropane-1,3'-pyrrolo[3,2-b]pyridine]-6'-carboxylate; INT-4-6)

A solution of azaindoline INT-3-6 (2.04 g, 7.39 mmol) and Et$_3$N (2.27 mL, 16.3 mmol) in a mixture of dry DMF (40 mL)/dry MeOH (20 mL) in an autoclave was flushed thoroughly with N$_2$ for 10 min. PdCl$_2$(dppf) (487 mg, 0.66 mmol) was added and the mixture was flushed with N$_2$ for 10 min. The autoclave was closed, pressurised to 35 bar with CO-gas and stirred at 110° C. for 48 h (pressure CO=39 bar). The autoclave was cooled to rt and vented. The solvents were evaporated and the residue was partitioned between H$_2$O (20 mL) and EtOAc (30 mL). The aqueous layer was extracted twice with EtOAc, the combined organic layers were washed with water and brine, dried over Na$_2$SO$_4$ and evaporated. Purification by column chromatography (silica, 0%->10% MeOH in CH$_2$Cl$_2$) gave methylester INT-4-6 (1.86 g, 7.18 mmol, 94%) as a red-brown solid. LCMS: calculated for [M+H]$^+$: 247. found: 247.

Step 3: (1'-acetyl-1',2'-dihydrospiro[cyclopropane-1, 3'-pyrrolo[3,2-b]pyridine]-6'-carboxylic acid; INT-5-6)

A solution of LiOH.H$_2$O (475 mg, 11.3 mmol) in H$_2$O (2 mL) was added to a stirred suspension of methylester INT-4-6 (1.86 g, 7.18 mmol) in THF (9 mL)/MeOH (9 mL) and the mixture was stirred at rt for 18 h. The mixture was concentrated under reduced pressure and diluted with water (5 mL) and THF (2 mL). The aqueous solution was neutralised to pH~3 with 1M aqueous HCl. A precipitate was formed. The solids were filtered off, rinsed with water (10 ml) and air-dried. The aqueous layer of the filtrate was thoroughly extracted with CH$_2$Cl$_2$; the combined organic layer was dried over Na$_2$SO$_4$ and evaporated. Both batches were combined and dried in a vacuum oven to give carboxylic acid INT-5-6 (1.29 g, 5.52 mmol, 77%) as a grey solid. LCMS: calculated for [M+H]$^+$: 233. found: 233.

Step 4: (1-(6'-(morpholine-4-carbonyl)spiro[cyclopropane-1,3'-pyrrolo[3,2-b]pyridin]-1'(2'H)-yl)ethanone; INT-6-6)

Morpholine (0.33 mL, 3.80 mmol) was added to a stirred solution of acid INT-5-6 (600 mg, 2.53 mmol), DIPEA (1.30 mL, 7.6 mmol) and HATU (963 mg, 2.53 mmol) in dry DMF (6 mL) and the reaction mixture was stirred at rt for 18 h. The mixture was partitioned between CH$_2$Cl$_2$ (50 mL) and brine (50 mL). The aqueous layer was extracted with CH$_2$Cl$_2$ (50 mL). The combined organic layers were washed with brine (50 mL), dried on Na$_2$SO$_4$ and evaporated. Purification by flash column chromatography (silica, 0%->10% MeOH in CH$_2$Cl$_2$, followed by trituration from heptane gave amide INT-6-6 (599 mg, 1.98 mmol, 79%) as a pink solid. LCMS: calculated for [M+H]$^+$: 302. found: 302.

Step 5: ((1',2'-dihydrospiro[cyclopropane-1,3'-pyrrolo[3,2-b]pyridin]-6'-yl)(morpholino)methanone; INT-8-6)

To a stirred suspension of amide INT-6-6 (599 mg, 1.99 mmol) in dry THF (40 mL) was added slowly concentrated HCl (2.94 mL, 35.8 mmol). The resulting mixture was stirred at 65° C. for 6 h. The reaction mixture was poured into a saturated aqueous solution of NaHCO$_3$. The organic solvent was removed in vacuo. The aqueous layer was extracted with EtOAc (3×20 mL). The combined organic layer was washed with water and brine (2×100 mL), dried over Na$_2$SO$_4$ and evaporated. Purification by flash column chromatography (silica, 0%->10% MeOH in CH$_2$Cl$_2$) gave indoline INT-8-6 (258 mg, 1.0 mmol, 50%) as a beige solid. LCMS: calculated for [M+H]$^+$: 260. found: 260.

Step 6: (1'-(5-(2-fluorophenyl)pyrimidin-2-yl)-1',2'-dihydrospiro[cyclopropane-1,3'-pyrrolo[3,2-b]pyridin]-6'-yl)(morpholino)methanone (109)

To a degassed (Argon) solution of indoline INT-8-6 (125 mg, 0.48 mmol), pyrimidine INT-7-1 (106 mg, 0.48 mmol) and Cs$_2$CO$_3$ (283 mg, 0.87 mmol) in 1,4-dioxane (8 mL)/CF$_3$-Tol (2 mL) were added Xantphos (27.9 mg, 0.05 mmol) and Pd(OAc)$_2$ (5.41 mg, 0.024 mmol). The solution was degassed with Ar again during 5 min and stirred at 120° C. for 75 min in the microwave. Water (20 mL) and CH$_2$Cl$_2$ (10 mL) were added, the layers were separated and the organic layer was dried over Na$_2$SO$_4$ and evaporated. Purification by preparative column chromatography gave final compound 109 (105 mg, 0.24 mmol, 50%) as an off white solid. LCMS: calculated for [M+H]$^+$: 432. found: 432.

$^1$H NMR (400 MHz, DMSO-d$_6$) δ 8.90 (d, J=1.2 Hz, 2H), 8.48 (d, J=1.7 Hz, 1H), 8.03 (d, J=1.7 Hz, 1H), 7.68 (td, J=7.0, 1.6 Hz, 1H), 7.52-7.43 (m, 1H), 7.43-7.32 (m, 2H), 4.37 (s, 2H), 3.74-3.39 (m, H), 1.33-1.22 (m, 4H).

TABLE 6

Table of the pyhsico chemical data (NMR, LCMS: [M + 1.0079]; mass found, M.p.)

| No. | LCMS | physico chemical data M.p./NMR |
|---|---|---|
| 1 | 431.2 | see experimental section (A-1, A-2) |
| 2 | 389.2 | see experimental section (A-3) |
| 3 | 415.2 | see experimental section (A-4) |
| 4 | 444.2 | see experimental section (A-5) |
| 5 | 430.2 | see experimental section (A-6) |
| 6 | 447.2 | see experimental section (A-7) |
| 7 | 413.2 | see experimental section (A-8) |
| 8 | 449.2 | see experimental section (A-9) |
| 9 | 433.2 | $^1$H NMR (400 MHz, DMSO-d$_6$) δ 8.85 (d, J = 1.2 Hz, 2H), 8.39 (d, J = 1.1 Hz, 1H), 7.67 (dd, J = 7.9, 1.6 Hz, 1H), 7.50-7.42 (m, 1H), 7.42-7.30 (m, 3H), 7.02 (dd, J = 7.6, 1.3 Hz, 1H), 4.05 (s, 2H), 3.73-3.37 (m, 8H), 1.38 (s, 6H). |
| 12 | 427.2 | see experimental section (A-12) |
| 13 | 497.2 | see experimental section (A-13) |
| 14 | | see experimental section (A-14) |
| 15 | 449.2 | see experimental section (A-15) |
| 16 | 461.2 | see experimental section (A-16) |
| 17 | 461.2 | see experimental section (A-17) |
| 18 | 438.2 | see experimental section (A-18) |
| 19 | 461.2 | see experimental section (A-19) |
| 20 | 456.2 | see experimental section (A-20) |
| 21 | 484.2 | see experimental section (A-21) |
| 22 | 456.2 | see experimental section (A-22) |
| 23 | 499.2 | see experimental section (A-23) |
| 24 | 499.2 | M.p. 175-178° C.; $^1$H NMR (300 MHz, DMSO-d$_6$): δ 8.64 (s, 2H), 8.38 (d, J = 1.4 Hz, 1H), 7.83-7.69 (m, 3H), 6.98 (dd, J = 7.7, 1.5 Hz, 1H), 6.89 (d, J = 7.6 Hz, 1H), 4.29 (s, 2H), 3.60 (brs, 8H), 1.22-1.15 (m, 4H). |
| 25 | 456.2 | M.p. 258-261° C.; $^1$H NMR (300 MHz, DMSO-d$_6$): δ 8.63 (s, 2H), 8.38 (s, 1H), 7.81 (s, 1H), 7.54-7.43 (m, 5H), 6.95 (dd, J = 7.6, 1.5 Hz, 1H), 6.87 (d, J = 7.6 Hz, 1H), 4.26 (s, 2H), 3.60 (brs, 8H), 1.23-1.12 (m, 4H). |

TABLE 6-continued

Table of the pyhsico chemical data
(NMR, LCMS: [M + 1.0079]; mass found, M.p.)

| No. | LCMS | physico chemical data M.p./NMR |
|---|---|---|
| 26 | 474.2 | M.p. 265-268° C.; $^1$H NMR (300 MHz, DMSO-d$_6$): δ 8.91 (s, 2H), 8.42 (s, 1H), 8.12 (brs, 1H), 7.85-7.75 (m, 3H), 7.57 (brs, 1H), 6.99-6.87 (m, 2H), 4.29 (s, 2H), 3.61 (brs, 8H), 1.22-1.15 (m, 4H). |
| 27 | 449.2 | M.p. 203-206° C.; $^1$H NMR (400 MHz, DMSO-d$_6$): δ 8.76 (s, 2H), 8.39 (d, J = 1.4 Hz, 1H), 7.57-7.47 (m, 1H), 7.29 (t, J = 7.8 Hz, 2H), 6.98 (dd, J = 7.6, 1.5 Hz, 1H), 6.89 (d, J = 7.6 Hz, 1H), 4.28 (s, 2H), 3.60 (brs, 8H), 1.23-1.07 (m, 4H). |
| 28 | 491.2 | M.p. 228-231° C.; $^1$H NMR (300 MHz, DMSO-d$_6$): δ 8.65 (s, 2H), 8.41 (d, J = 1.4 Hz, 1H), 8.13 (dd, J = 7.9, 1.4 Hz, 1H), 7.83 (td, J = 7.5, 1.5 Hz, 1H), 7.74 (td, J = 7.7, 1.4 Hz, 1H), 7.54 (dd, J = 7.6, 1.4 Hz, 1H), 6.96 (dd, J = 7.6, 1.5 Hz, 1H), 6.88 (d, J = 7.6 Hz, 1H), 4.29 (s, 2H), 3.60 (brs, 8H), 3.03 (s, 3H), 1.28-1.09 (m, 4H). |
| 29 | 509.2 | M.p. 246-249° C.; $^1$H NMR (300 MHz, DMSO-d$_6$): δ 8.93 (d, J = 1.6 Hz, 2H), 8.42 (d, J = 1.4 Hz, 1H), 8.03-7.84 (m, 3H), 6.99 (dd, J = 7.7, 1.5 Hz, 1H), 6.90 (d, J = 7.6 Hz, 1H), 4.30 (s, 2H), 3.61 (brs, 8H), 3.33 (s, 3H), 1.29-1.12 (m, 4H). |
| 30 | 456.2 | M.p. 239-242° C.; $^1$H NMR (400 MHz, DMSO-d$_6$) δ 8.92 (s, 2H), 8.41 (d, J = 1.4 Hz, 1H), 8.03 (dd, J = 10.8, 1.5 Hz, 1H), 7.92 (t, J = 7.9 Hz, 1H), 7.85 (dd, J = 8.1, 1.6 Hz, 1H), 6.99 (dd, J = 7.7, 1.5 Hz, 1H), 6.89 (d, J = 7.6 Hz, 1H), 4.29 (s, 2H), 3.61 (brs, 8H), 1.23-1.16 (m, 4H). |
| 31 | 443.2 | M.p. 166-169° C.; $^1$H NMR (400 MHz, CDCl$_3$): δ 8.79 (s, 2H), 7.46-7.41 (m, 1H), 7.31 (dd, J = 7.6, 1.7 Hz, 1H), 7.12-7.07 (m, 1H), 7.03 (d, J = 8.3 Hz, 1H), 3.85 (s, 3H). |
| 32 | 474.2 | M.p. 284-288° C.; $^1$H NMR (300 MHz, DMSO-d$_6$): δ 8.58 (d, J = 1.2 Hz, 2H), 8.38 (d, J = 1.2 Hz, 1H), 7.85 (s, 1H), 7.59-7.34 (m, 4H), 6.96 (dd, J = 7.2, 1.2 Hz, 1H), 6.88 (d, J = 7.2 Hz, 1H), 4.27 (s, 2H), 3.60 (brs, 8H), 1.27-1.09 (m, 4H). |
| 33 | 471.2 | 1H NMR (400 MHz, DMSO-d6) δ 8.84 (d, J = 1.1 Hz, 2H), 8.37 (d, J = 1.2 Hz, 1H), 7.71-7.63 (m, 1H), 7.50-7.43 (m, 1H), 7.42-7.31 (m, 2H), 6.95-6.84 (m, 2H), 4.34 (s, 4H), 4.28 (s, 2H), 3.54 (br s, 2H), 3.30 br (s, 2H), 1.81 (br s, 4H), 1.26-1.10 (m, 4H). |
| 34 | 474.2 | M.p. 142-146° C.; $^1$H NMR (400 MHz, DMSO-d$_6$): δ 8.85 (d, J = 1.6 Hz, 2H), 8.39 (s, 1H), 7.69-7.64 (m, 1H), 7.48-7.33 (m, 3H), 6.96-6.87 (m, 2H), 4.42 (t, J = 5.3 Hz, 1H), 4.28 (s, 2H), 3.72-3.40 (m, 6H), 2.53-2.42 (m, 6H), 1.23-1.13 (m, 4H). |
| 35 | 474.2 | M.p. 245-248° C.; $^1$H NMR (400 MHz, DMSO-d$_6$): δ 8.91 (s, 2H), 8.42 (s, 1H), 8.16 (dd, J = 8.0, 2.4 Hz, 1H), 8.07 (s, 1H), 7.96-7.92 (m, 1H), 7.49-7.43 (m, 2H), 6.98 (dd, J = 7.6, 1.2 Hz, 1H), 6.88 (d, J = 8.0 Hz, 1H), 4.29 (s, 2H), 3.61 (brs, 8H), 1.24-1.13 (m, 4H). |
| 36 | 417.2 | $^1$H NMR (400 MHz, DMSO-d$_6$) δ 8.86 (d, J = 0.9 Hz, 2H), 8.62 (s, 1H), 7.72-7.65 (m, 1H), 7.50-7.42 (m, 1H), 7.42-7.32 (m, 2H), 7.18 (dd, J = 7.7, 1.3 Hz, 1H), 6.88 (d, J = 7.7 Hz, 1H), 5.76 (d, J = 5.1 Hz, 1H), 4.54-4.43 (m, 2H), 4.28 (s, 2H), 4.28-4.20 (m, 1H), 4.04 (m, 1H), 3.79 (m, 1H), 1.27-1.13 (m, 4H). |
| 37 | 472.2 | $^1$H NMR (400 MHz, DMSO-d$_6$) δ 8.85 (s, 2H), 8.39 (s, 1H), 7.67 (t, J = 7.9 Hz, 1H), 7.51-7.42 (m, 1H), 7.42-7.30 (m, 2H), 6.93 (d, J = 7.6 Hz, 1H), 6.87 (d, J = 7.6 Hz, 1H), 4.28 (s, 2H), 3.75-3.39 (m, 8H), 2.75-2.62 (m, 1H), 1.27-1.09 (m, 4H), 0.97 (d, J = 6.5 Hz, 6H). |
| 38 | 458.2 | $^1$H NMR (400 MHz, DMSO-d$_6$) δ 8.85 (d, J = 0.8 Hz, 2H), 8.44 (s, 1H), 7.71-7.62 (m, 1H), 7.50-7.42 (m, 1H), 7.41-7.31 (m, 2H), 7.02 (d, J = 7.0 Hz, 1H), 6.91 (d, J = 7.6 Hz, 1H), 4.29 (s, 2H), 4.19-3.57 (m, 4H), 3.45-3.36 (m, 2H), 2.88 (s, 3H), 1.27-1.12 (m, 4H). |
| 39 | 463.2 | M.p. 157-160° C.; $^1$H NMR (300 MHz, DMSO-d$_6$): δ 8.63 (s, 2H), 8.41 (d, J = 1.4 Hz, 1H), 7.78 (d, J = 6.0 Hz, 1H), 7.67-7.58 (m, 2H), 7.50 (d, J = 5.7 Hz, 1H), 7.13-6.86 (m, 3H), 4.29 (s, 2H), 3.60 (brs, 8H), 1.24-1.21 (m, 2H), 1.16-1.13 (m, 2H). |
| 40 | 430.2 | M.p. 151-154° C.; $^1$H NMR (400 MHz, DMSO-d$_6$): δ 8.85 (s, 2H), 8.49 (d, J = 3.9 Hz, 1H), 7.68-7.65 (m, 1H), 7.64-7.32 (m, 3H), 7.06-7.04 (m, 1H), 6.86 (d, J = 7.7 Hz, 1H), 4.28 (s, 2H), 3.59-3.39 (m, 4H), 3.20-3.08 (m, 1H), 1.96-1.61 (m, 4H), 1.22-1.15 (m, 2H), 1.15-1.07 (m, 2H). |
| 41 | 418.2 | M.p. 150-154° C.; $^1$H NMR (300 MHz, DMSO-d$_6$): δ 8.84 (d, J = 1.5 Hz, 2H), 8.39 (s, 1H), 7.69-7.63 (m, 1H), 7.49-7.31 (m, 3H), 7.00 (br s, 1H), 6.88 (d, J = 7.6 Hz, 1H), 5.35 (br s, 2H), 4.29 (s, 2H), 3.58 (br s, 2H), 2.96-2.80 (m, 5H), 1.25-1.21 (m, 2H), 1.16-1.12 (m, 2H). |
| 42 | 509.2 | M.p. 225-229° C.; $^1$H NMR (300 MHz, DMSO-d$_6$) δ 8.94 (s, 2H), 8.42 (s, 1H), 8.22 (dd, J = 7.2, 2.3 Hz, 1H), 8.02-7.98 (m, 1H), 7.69-7.63 (m, 1H), 7.00-6.88 (m, 2H), 4.30 (s, 2H), 3.59 (m, 8H), 3.32 (s, 3H), 1.23-1.09 (m, 2H), 1.11-1.09 (m, 2H). |
| 43 | 431.2 | M.p. 182-185° C.; $^1$H NMR (300 MHz, DMSO-d$_6$): δ 8.97 (s, 2H), 8.41 (d, J = 1.4 Hz, 1H), 7.85-7.75 (m, 2H), 7.38-7.28 (m, 2H), 6.95 (dd, J = 7.6, 1.5 Hz, 1H), 6.87 (d, J = 7.6 Hz, 1H), 4.27 (s, 2H), 3.80-3.40 (m, 8H), 1.29-1.12 (m, 4H). |
| 44 | 431.2 | $^1$H NMR (400 MHz, DMSO-d$_6$) δ 8.85 (s, 2H), 8.50 (s, 1H), 7.67 (t, J = 7.8 Hz, 1H), 7.51-7.41 (m, 1H), 7.41-7.30 (m, 2H), 7.12-7.02 (m, 1H), 6.87 (d, J = 7.6 Hz, 1H), 4.99 (d, J = 42.0 Hz, 1H), 4.38-4.17 (m, 3H), 3.66-3.47 (m, 3H), 3.26-3.19 (m, 1H), 2.04-1.72 (m, 2H), 1.29-1.09 (m, 4H). |
| 45 | 431.2 | $^1$H NMR (400 MHz, DMSO-d$_6$) δ 8.85 (s, 2H), 8.50 (s, 1H), 7.67 (t, J = 7.9 Hz, 1H), 7.50-7.41 (m, 1H), 7.41-7.30 (m, 2H), 7.11-7.04 (m, 1H), 6.87 (d, J = 7.6 Hz, 1H), 4.99 (br d, J = 41.6 Hz, 1H), 4.27 (br. d, J = 41.6 Hz, 1H), 4.28 (s, 2H), 3.65-3.50 (m, 3H), 3.45-3.23 (m, 1H), 2.02-1.72 (m, 2H), 1.26-1.11 (m, 4H). |
| 46 | 415.2 | $^1$H NMR (400 MHz, DMSO-d$_6$) δ 8.84 (s, 2H), 8.48 (s, 1H), 7.72-7.62 (m, 1H), 7.51-7.41 (m, 1H), 7.41-7.28 (m, 2H), 7.08 (d, J = 7.2 Hz, 1H), 6.85 (d, J = 7.7 Hz, 1H), 4.28 (s, 2H), 2.97 (s, 3H), 2.94-2.87 (m, 1H), 1.27-1.09 (m, 4H), 0.51 (br d, J = 35.9 Hz, 4H). |
| 47 | 417.2 | $^1$H NMR (400 MHz, DMSO-d$_6$) δ 8.85 (d, J = 0.8 Hz, 2H), 8.36 (s, 1H), 7.72-7.63 (m, 1H), 7.51-7.41 (m, 1H), 7.41-7.30 (m, 2H), 6.95-6.84 (m, 2H), 4.28 (s, 2H), 3.42 (br s, 2H), 3.24 (br s, 2H), 1.26-1.19 (m, 2H), 1.19-1.06 (m, 8H). |
| 48 | 443.2 | M.p. 184-188° C.; $^1$H NMR (300 MHz, DMSO-d$_6$) δ 8.99 (s, 2H), 8.42 (d, J = 1.4 Hz, 1H), 7.43-7.30 (m, 3H), 6.97-6.93 (m, 2H), 6.87 (d, J = 7.6 Hz, 1H), 4.28 (s, 2H), 3.83 (s, 3H), 3.7-3.4 (m, 8H), 1.25-1.20 (m, 2H), 1.16-1.10 (m, 2H). |
| 49 | 412.2 | M.p. 188-192° C.; $^1$H NMR (300 MHz, DMSO-d$_6$): δ 8.98 (s, 2H), 8.39 (s, 1H), 7.76-7.72 (m, 2H), 7.53-7.40 (m, 3H), 7.43-7.35 (m, 1H), 6.95-6.85 (m, 2H), 4.28 (s, 2H), 3.65-3.38 (m, 4H), 2.74 (brs, 4H), 1.3-1.06 (m, 4H). |
| 50 | 449.2 | M.p. 214-218° C.; $^1$H NMR (300 MHz, DMSO-d$_6$) δ 9.07 (s, 2H), 8.42 (s, 1H), 7.59 (d, J = 7.5, 2H), 7.27-7.20 (m, 1H), 7.02-6.96 (m, 1H), 6.90-6.87 (m, 1H), 4.28 (s, 2H), 3.7-3.48 (m, 8H), 1.28-1.09 (m, 4H). |
| 51 | 447.2 | M.p. 179-183° C.; $^1$H NMR (300 MHz, DMSO-d$_6$) δ 9.02 (s, 2H), 8.41 (s, 1H), 7.86-7.84 (m, 1H), 7.74 (d, J = 7.6 Hz, 1H), 7.54-7.42 (m, 2H), 6.97-6.95 (m, 1H), 6.88 (d, J = 7.6 Hz, 1H), 4.28 (s, 2H), 3.78-3.48 (m, 8H), 1.25-1.12 (m, 4H). |
| 52 | 445.2 | M.p. 175-179° C.; $^1$H NMR (300 MHz, DMSO-d$_6$) δ 8.83 (d, J = 1.5 Hz, 2H), 8.40 (d, J = 1.2 Hz, 1H), 7.44 (d, J = 7.6 Hz, 1H), 7.22 (d, J = 8.4 Hz, 2H), 6.97 (dd, J = 7.7, 1.5 Hz, 1H), 6.88 (d, J = 7.6 Hz, 1H), 4.28 (s, 2H), 3.7-3.48 (m, 8H), 2.36 (s, 3H), 1.22-1.18 (m, 2H), 1.14-1.10 (m, 2H). |
| 53 | 449.2 | M.p. 205-208° C.; $^1$H NMR (300 MHz, DMSO-d$_6$): δ 9.00 (s, 2H), 8.41 (s, 1H), 7.98-7.86 (m, 1H), 7.68-7.50 (m, 2H), 6.96 (dd, J = 7.3, 1.5 Hz, 1H), 6.88 (d, J = 7.6 Hz, 1H), 4.27 (s, 2H), 3.7-3.48 (m, 8H), 1.28 1.11 (m, 4H). |

TABLE 6-continued

Table of the pyhsico chemical data
(NMR, LCMS: [M + 1.0079]; mass found, M.p.)

| No. | LCMS | physico chemical data M.p./NMR |
|---|---|---|
| 54 | 456.2 | M.p. 247-250° C.; $^1$H NMR (300 MHz, DMSO-d$_6$): δ 9.05 (s, 2H), 8.43 (s, 1H), 8.23 (s, 1H), 8.0-7.86 (m, 2H), 7.60-7.47 (m, 1H), 7.00-6.96 (m, 1H), 6.88 (d, J = 7.6 Hz, 1H), 4.29 (s, 2H), 3.8-3.4 (m, 8H), 1.24-1.13 (m, 4H). |
| 55 | 426.2 | M.p. 199-198° C.; $^1$H NMR (300 MHz, DMSO-d$_6$): δ 8.98 (s, 2H), 8.44 (d, J = 1.5 Hz, 1H), 8.11-8.10 (m, 1H), 7.79-7.70 (m, 1H), 7.54-7.45 (m, 2H), 7.44-7.35 (m, 1H), 7.00 (dd, J = 7.6, 1.6 Hz, 1H), 6.89 (d, J = 7.6 Hz, 1H), 4.29 (s, 2H), 4.06 (s, 2H), 3.61 (s, 2H), 3.26 (s, 2H), 1.29-1.11 (m, 4H). |
| 56 | 438.2 | M.p. 240-244° C.; $^1$H NMR (400 MHz, DMSO-d$_6$): δ 9.07 (s, 2H), 8.42 (s, 1H), 8.29 (s, 1H), 8.12 (d, J = 8.4 Hz, 1H), 7.84 (d, J = 7.6 Hz, 1H), 7.71-7.67 (m, 1H), 6.98-6.96 (m, 1H), 6.88 (d, J = 7.6 Hz, 1H), 4.29 (s, 2H), 3.78-3.48 (m, 8H), 1.24-1.13 (m, 4H). |
| 57 | 431.2 | M.p. 212-215° C.; $^1$H NMR (400 MHz, DMSO-d$_6$): δ 9.03 (s, 2H), 8.41 (s, 1H), 7.69-7.61 (m, 2H), 7.56-7.50 (m, 1H), 7.23-7.19 (m, 1H), 6.96 (d, J = 7.7 Hz, 1H), 6.88 (d, J = 7.6 Hz, 1H), 4.28 (s, 2H), 3.82-3.50 (s, 8H), 1.23-1.14 (m, 4H). |
| 58 | 465.1 | M.p. 187-190° C.; $^1$H NMR (400 MHz, DMSO-d$_6$) δ 8.87 (s, 2H), 8.41 (s, 1H), 7.80-7.78 (m, 1H), 7.53-7.48 (m, 1H), 7.46-7.40 (m, 1H), 6.98-6.96 (m, 1H), 6.89 (d, J = 7.6 Hz, 1H), 4.28 (s, 2H), 3.78-3.48 (m, 8H), 1.23-1.17 (m, 2H), 1.17-1.13 (m, 2H). |
| 59 | 397.2 | M.p. 168-172° C.; $^1$H NMR (300 MHz, DMSO-d$_6$): δ 8.98 (s, 2H), 8.51 (d, J = 1.6 Hz, 1H), 7.75 (d, J = 7.2 Hz, 2H), 7.52-7.47 (m, 2H), 7.41-7.36 (m, 1H), 7.08-7.04 (m, 1H), 6.85 (d, J = 7.6 Hz, 1H), 4.28 (s, 2H), 3.51-3.40 (m, 4H), 1.89-1.81 (m, 4H), 1.25-1.12 (m, 4H). |
| 60 | 444.2 | $^1$H NMR (400 MHz, DMSO-d$_6$) δ 8.84 (d, J = 1.3 Hz, 2H), 8.39 (d, J = 1.1 Hz, 1H), 7.71-7.62 (m, 1H), 7.50-7.42 (m, 1H), 7.41-7.31 (m, 2H), 6.96-6.84 (m, 2H), 4.28 (s, 2H), 3.75-3.35 (br d, 4H), 2.33 (br s, 4H), 2.20 (s, 3H), 1.26-1.11 (m, 4H). |
| 61 | 375.2 | $^1$H NMR (400 MHz, DMSO-d$_6$) δ 8.86 (d, J = 1.0 Hz, 3H), 8.78 (d, J = 1.1 Hz, 1H), 8.33 (br d, J = 4.5 Hz, 1H), 7.68 (t, J = 7.9 Hz, 1H), 7.51-7.32 (m, 4H), 6.88 (d, J = 7.8 Hz, 1H), 4.28 (s, 2H), 2.78 (d, J = 4.5 Hz, 3H), 1.26-1.12 (m, 4H). |
| 62 | 453.2 | M.p. 190-194° C.; $^1$H NMR (400 MHz, DMSO-d$_6$): δ 8.73 (s, 2H), 8.41 (s, 1H), 7.47-7.28 (m, 3H), 7.10 (d, J = 7.5 Hz, 1H), 6.95 (dd, J = 7.5, 1.5 Hz, 1H), 6.87 (d, J = 7.6 Hz, 1H), 4.28 (s, 2H), 3.70-3.40 (m, 8H), 1.91-1.92 (m, 1H), 1.24-1.13 (m, 4H), 0.88-0.84 (m, 2H), 0.69-0.64 (m, 2H). |
| 63 | 456.2 | M.p. 300° C.; $^1$H NMR (300 MHz, DMSO-d$_6$): δ 9.06 (s, 2H), 8.43 (s, 1H), 8.07-7.94 (m, 3H), 7.87-7.84 (m, 2H), 7.40 (s, 1H), 7.01-6.82 (m, 2H), 4.29 (s, 2H), 3.61-3.51 (m, 8H), 1.28-1.09 (m, 4H). |
| 64 | 443.2 | M.p. 210-213° C.; $^1$H NMR (300 MHz, DMSO-d$_6$): δ 8.87 (s, 2H), 8.62 (s, 1H), 7.72-7.63 (m, 1H), 7.51-7.31 (m, 3H), 7.19 (dd, J = 7.8, 1.5 Hz, 1H), 6.88 (d, J = 7.8 Hz, 1H), 4.69 (s, 4H), 4.49 (s, 2H), 4.28 (s, 2H), 4.22 (s, 2H), 1.28-1.12 (m, 4H). |
| 65 | 502.2 | M.p. 198-202° C.; 1H NMR (300 MHz, DMSO-d6): δ 8.89 (s, 2H), 8.41 (s, 1H), 7.74 (t, J = 7.9 Hz, 1H), 7.45-7.34 (m, 2H), 6.97 (dd, J = 7.6, 1.5 Hz, 1H), 6.89 (d, J = 7.6 Hz, 1H), 4.29 (s, 2H), 3.61 (s, 8H), 2.99 (d, J = 15.5 Hz, 6H), 1.27-1.11 (m, 4H). |
| 66 | 470.2 | M.p. 146-150° C.; 1H NMR (400 MHz, DMSO-d6): δ 8.84 (s, 2H), 8.39 (s, 1H), 7.69-7.63 (m, 1H), 7.56-7.26 (m, 3H), 7.04-6.85 (m, 2H), 4.28 (s, 2H), 3.70-3.30 (m, 4H), 2.64-2.39 (m, 4H), 1.68-1.67 (m, 1H), 1.24-0.91 (m, 4H), 0.53-0.19 (m, 4H). |
| 67 | 515.2 | M.p. 160-164° C.; $^1$H NMR (300 MHz, DMSO-d$_6$): δ 8.88 (s, 2H), 8.41 (s, 1H), 7.77 (dd, J = 6.4, 2.7 Hz, 1H), 7.60-7.42 (m, 2H), 6.98 (dd, J = 7.7, 1.5 Hz, 1H), 6.88 (d, J = 7.6 Hz, 1H), 4.28 (s, 2H), 3.61-3.50 (m, 8H), 1.23-1.12 (m, 4H). |
| 68 | 457.2 | M.p. 178-181° C.; $^1$H NMR (300 MHz, DMSO-d$_6$): δ 8.84 (s, 2H), 8.49 (bs, 1H), 7.69-7.63 (m, 1H), 7.47-7.31 (m, 3H), 7.12-7.03 (m, 1H), 6.90-6.86 (m, 1H), 4.69-4.39 (m, 4H), 4.28 (bs, 2H), 3.70 (d, J = 13.5 Hz, 2H), 3.50-3.37 (m, 2H), 2.19-2.13 (m, 2H), 1.23-1.10 (m, 4H). |
| 69 | 445.2 | M.p. 165-169° C.; $^1$H NMR (400 MHz, DMSO-d$_6$): δ (8.64 d, J = 1.0 Hz, 2H), 8.40 (d, J = 1.5 Hz, 1H), 7.38-7.35 (m, 1H), 7.23-7.14 (m, 2H), 6.96 (dd, J = 7.6, 1.5 Hz, 1H), 6.88 (d, J = 7.6 Hz, 1H), 4.28 (s, 2H), 3.80-3.40 (m, 8H), 2.25 (s, 3H), 1.24-1.12 (m, 4H). |
| 70 | 452.2 | M.p. 175-179° C.; $^1$H NMR (300 MHz, DMSO-d$_6$): δ 7.37 (s, 5H), 6.94 (d, J = 7.9 Hz, 1H), 6.81 (d, J = 7.7 Hz, 1H), 5.10 (s, 2H), 3.94 (s, 2H), 3.37 (s, 8H), 2.89 (s, 1H), 2.73 (s, 1H), 1.50 (s, 9H), 1.20-0.99 (m, 4H). |
| 71 | 448.2 | M.p. 175-179° C.; $^1$H NMR (300 MHz, DMSO-d$_6$): δ 8.82 (d, J = 1.5 Hz, 2H), 8.39 (s, 1H), 7.76-7.64 (m, 1H), 7.47-7.43 (m, 1H), 7.26-7.22 (m, 1H), 6.96-6.86 (m, 2H), 5.5-5.0 (bs, 1H), 4.27 (s, 1H), 3.56-3.46 (s, 4H), 2.82 (s, 4H), 1.21-1.12 (m, 4H). |
| 72 | 514.2 | M.p. 123-127° C.;$^1$H NMR (300 MHz, DMSO-d$_6$): δ 8.88 (d, J = 1.5 Hz, 2H), 8.39 (s, 1H), 7.77 (dd, J = 6.4, 2.8 Hz, 2H), 7.54-7.40 (m, 2H), 7.12-6.72 (m, 2H), 4.28 (s, 2H), 3.70-3.40 (m, 4H), 2.80-2.60 (m, 4H), 1.24-1.10 (m, 4H). |
| 73 | 460.2 | M.p. 170-173° C.; 1H NMR : (400 MHz, DMSO-d6) δ 8.86 (d, J = 1.5 Hz, 2H), 8.42 (s, 1H), 7.36 (d, J = 3.9 Hz, 6H), 7.20 (dd, J = 6.5, 3.1 Hz, 1H), 7.02-6.94 (m, 2H), 6.92-6.79 (m, 1H), 5.10 (s, 2H), 4.28 (s, 2H), 3.81 (s, 3H), 3.48 (s, 8H), 1.34-1.08 (m, 4H). |
| 74 | 456.2 | M.p. 189-193° C.; $^1$H NMR (300 MHz, DMSO-d$_6$) δ 8.84 (s, 2H), 8.49 (s, 1H), 7.68-7.64 (m, 1H), (7.48-7.44 (m, 1H), 7.40-7.31 (m, 2H), 7.09-7.06 (m, 1H), 6.88-6.85 (m, 1H), 4.28 (s, 2H), 3.90-3.88 (m, 1H), 3.79-3.53 (m, 5H), 3.51-3.33 (m, 2H), 2.17-1.97 (m, 2H), 1.35 (s, 9H), 1.23-1.21 (m, 2H), 1.19-1.09 (m, 2H). |
| 75 | 433.2 | |
| 76 | 483.2 | |
| 77 | 458.2 | |
| 78 | 472.2 | |
| 79 | 471.2 | |
| 80 | 471.2 | |
| 81 | 445.2 | |
| 82 | 459.2 | |
| 83 | 446.2 | |
| 84 | 429.2 | |
| 85 | 472.2 | |
| 86 | 458.2 | |
| 87 | 461.2 | |
| 88 | 452.2 | |
| 89 | 401.2 | |
| 90 | 403.2 | |
| 91 | 455.2 | |
| 92 | 459.2 | |
| 93 | 447.2 | |
| 94 | 474.2 | |
| 95 | 419.2 | $^1$H NMR (400 MHz, DMSO-d$_6$, T = 373K): δ 1.14-1.23 (4H), 2.98 (s, 3H), 3.46-3.66 (3H), 4.27 (s, 2H), 4.71-4.78 (1H), 6.84-6.87 (1H), 6.94-6.96 (1H), 7.32-7.39 (2H), 7.43-7.47 (1H), 7.64-7.69 (1H), 8.37 (s, 1H), 8.84 (s, 2H). |
| 96 | 445.2 | |
| 97 | 459.2 | |
| 98 | 459.2 | |
| 99 | 446.2 | |
| 100 | 459.2 | |
| 101 | 459.2 | |
| 102 | 459.2 | |
| 103 | 445.2 | |
| 104 | 459.2 | |
| 105 | 459.2 | |
| 106 | 479.2 | |
| 107 | 442.2 | $^1$H NMR (300 MHz, DMSO-d$_6$): δ 8.84 (s, 2H), 8.52 (s, 1H), 7.69-7.57 (m, 1H), 7.48-7.32 (m, 3H), 7.07 (d, J = 7.2 Hz, 1H), 6.85 (d, J = 7.5, Hz, 1H), 4.52 (bs, 1H), 4.29 (s, 2H), 3.92 (s, 1H), 3.57 (d, J = 10.7 Hz, 1H), 3.38 (d, J = 10.9 Hz, 1H), 3.25-2.90 (m, 3H), |

TABLE 6-continued

Table of the pyhsico chemical data
(NMR, LCMS: [M + 1.0079]; mass found, M.p.)

| No. | LCMS | physico chemical data M.p./NMR |
|---|---|---|
| | | 1.90-1.82 (m, 1H), 1.75-1.60 (m, 1H), 1.29-1.07 (m, 4H). |
| 108 | 412.2 | $^1$H NMR (300 MHz, DMSO-$d_6$): δ 8.98 (s, 2H), 8.51 (s, 1H), 7.78-7.71 (m, 2H), 7.53-7.47 (m, 2H), 7.43-7.36 (m, 1H), 7.08-7.04 (m, 1H), 6.86 (d, J = 7.7 Hz, 1H), 4.28 (s, 2H), 3.66-3.40 (m, 5H), 3.27-3.11 (m, 2H), 2.00-1.90 (m, 1H), 1.70-1.67 (m, 1H), 1.23-1.12 (m, 4H). |
| 109 | 455.2 | $^1$H NMR (400 MHz, DMSO-$d_6$): δ 8.90 (s, 2H), 8.39 (s, 1H), 8.27 (dd, J = 7.2, 2.1 Hz, 1H), 7.99-7.95 (m, 1H), 7.64-7.60 (m, 1H), 6.98-6.85 (m, 2H), 4.29 (s, 2H), 3.51 (br s, 1H), 3.39 (br s, 4H), 2.82 (s, 4H), 1.23-1.04 (m, 4H). |
| 110 | 458.2 | $^1$H NMR (300 MHz, DMSO-$d_6$): δ 8.84 (s, 2H), 8.49 (s, 1H), 7.69-7.64 (m, 1H), 7.50-7.30 (m, 3H), 7.08 (t, J = 6.8 Hz, 1H), 6.87 (d, J = 7.6 Hz, 1H), 4.28 (s, 2H), 3.83-3.47 (m, 4H), 3.32-3.29 (m, 1H), 2.73-2.64 (m, 1H), 2.20 (s, 3H), 2.07-1.97 (m, 3H), 1.76-1.69 (m, 1H), 1.26-1.15 (m, 4H). |
| 111 | 456.2 | $^1$H NMR (300 MHz, DMSO-$d_6$): δ 8.86 (s, 2H), 8.63 (s, 1H), 7.71-7.64 (m, 1H), 7.48-7.43 (m, 1H), 7.41-7.31 (m, 2H), 7.21 (dd, J = 7.7, 1.5 Hz, 1H), 6.87 (d, J = 7.8 Hz, 1H), 4.31-4.20 (m, 4H), 3.96 (s, 2H), 2.93 (d, J = 3.4 Hz, 2H), 2.80 (t, J = 7.1 Hz, 2H), 1.93 (t, J = 7.5 Hz, 2H), 1.26-1.13 (m, 4H). |
| 112 | 442.2 | $^1$H NMR (300 MHz, DMSO-$d_6$): δ 8.87 (s, 2H), 8.62 (s, 1H), 7.70-7.64 (m, 1H), 7.49-7.33 (m, 3H), 7.19 (d, J = 7.7 Hz, 1H), 6.89 (d, J = 7.7 Hz, 1H), 4.45 (s, 2H), 4.29 (s, 2H), 4.18 (s, 2H), 3.90 (s, 4H), 1.24-1.16 (m, 4H). |
| 113 | 486.2 | $^1$H NMR (300 MHz, DMSO-$d_6$): δ 8.61 (s, 2H), 8.39 (s, 1H), 7.67 (s, 1H), 7.51 (d, J = 8.4 Hz, 1H), 7.27 (s, 1H), 7.06-6.86 (m, 4H), 4.26 (s, 2H), 3.85 (s, 3H), 3.70-3.41 (m, 8H), 1.22-1.14 (m, 4H). |
| 114 | 448.2 | $^1$H NMR (300 MHz, DMSO-$d_6$): δ 8.88 (s, 2H), 8.49 (d, J = 3.6 Hz, 1H), 7.54-7.44 (m, 2H), 7.39-7.31 (m, 1H), 7.11-7.04 (m, 1H), 6.87 (d, J = 7.7 Hz, 1H), 4.28 (s, 2H), 3.66-3.38 (m, 4H), 3.12 (ddd, J = 25.0, 11.0, 4.4 Hz, 1H), 2.03-1.53 (m, 4H), 1.26-1.11 (m, 4H). |
| 115 | 430.2 | $^1$H NMR (300 MHz, DMSO-$d_6$): δ 8.85 (s, 2H), 8.50 (s, 1H), 7.69-7.63 (m, 1H), 7.47-7.32 (m, 3H), 7.07-7.04 (m, 1H), 6.86 (d, J = 7.7 Hz, 1H), 4.28 (s, 2H), 3.60-3.32 (m, 4H), 3.20-3.09 (m, 1H), 2.37-2.27 (m, 1H), 1.98-1.78 (m, 2H), 1.66-1.61 (m, 1H), 1.22-1.15 (m, 4H). |
| 116 | 473.2 | $^1$H NMR (300 MHz, DMSO-$d_6$): δ 8.90 (s, 2H), 8.39 (d, J = 5.2 Hz, 1H), 8.17-8.15 (m, 1H), 8.07 (s, 1H), 7.95-7.93 (m, 1H), 7.48-7.41 (m, 2H), 6.95-6.86 (m, 2H), 4.29 (s, 2H), 3.70-3.40 (m, 4H), 2.78-2.56 (m, 4H), (1.23-1.14 (m, 4H). |
| 117 | 470.2 | $^1$H NMR (300 MHz, DMSO-$d_6$): δ 8.86 (s, 2H), 8.62 (s, 1H), 7.72-7.63 (m, 1H), 7.48-7.32 (m, 3H), 7.23-7.18 (m, 1H), 6.87 (d, J = 7.7 Hz, 1H), 4.28-4.23 (m, 4H), 3.97 (s, 2H), 2.64 (s, 2H), 2.50-2.43 (m, 2H), 2.21 (s, 3H), 2.04 (t, J = 7.1 Hz, 2H), 1.26-1.17 (m, 4H). |
| 118 | 455.2 | $^1$H NMR (300 MHz, DMSO-$d_6$): δ 9.04 (s, 2H), 8.52 (s, 1H), 8.23 (s, 1H), 8.07 (s, 1H), 7.92-7.86 (m, 2H), 7.57 (t, J = 7.5 Hz, 1H), 7.47 (s, 1H), 7.09-7.01 (s, 1H), 6.86 (d, J = 7.7 Hz, 1H), 4.29 (s, 2H), 3.59-3.31 (m, 4H), 3.17-3.11 (m, 1H), 2.02-1.95 (m, 1H), 1.68-1.64 (m, 3H), 1.22-1.15 (m, 4H). |
| 119 | 473.2 | $^1$H NMR (300 MHz, DMSO-$d_6$): δ 8.90 (s, 2H), 8.38 (s, 1H), 8.12 (s, 1H), 7.91-7.65 (m, 3H), 7.57 (s, 1H), 6.97-6.85 (m, 2H), 4.29 (s, 2H), 3.32 (s, 4H), 2.90 (s, 1H), 2.50 (s, 4H), 1.32-0.93 (m, 4H). |
| 120 | 456.2 | $^1$H NMR (300 MHz, DMSO-$d_6$): δ 8.86 (s, 2H), 8.61 (s, 1H), 7.7-7.65 (m, 1H), 7.46-7.33 (m, 3H), 7.19 (dd, J = 7.7, 1.5 Hz, 1H), 6.88 (d, J = 7.7 Hz, 1H), 4.38 (s, 2H), 4.28 (s, 2H), 4.12 (s, 2H), 3.40 (s, 4H), 2.25 (s, 3H), 1.30-1.08 (m, 4H). |
| 121 | 444.2 | $^1$H NMR (300 MHz, DMSO-$d_6$): δ 8.85 (s, 2H), 8.49-8.48 (m, 1H), 7.68-7.63 (m, 1H), 7.46-7.43 (m, 1H), 7.39-7.32 (m, 2H), 7.06 (d, J = 7.5 Hz, 1H), 6.86 (dd, J = 7.6, 2.0 Hz, 1H), 4.28 (s, 2H), 3.60-3.50 (m, 3H), 3.28-3.09 (m, 2H), 2.30 (s, 2H), 2.18 (s, 2H), 2.05-1.96 (m, 1H), 1.80-1.70 (m, 1H), 1.22-1.15 (m, 4H). |
| 122 | 485.2 | $^1$H NMR (300 MHz, DMSO-$d_6$): δ 8.61 (s, 2H), 8.36 (s, 1H), 7.67 (s, 1H), 7.51 (d, J = 8.4 Hz, 1H), 7.28-7.26 (m, 1H), 7.07-6.81 (m, 4H), 4.26 (s, 2H), 3.84 (s, 3H), 3.50 (s, 4H), 2.70 (s, 4H), 2.32 (br s, 1H), 1.27 1.08 (m, 4H). |
| 123 | 455.2 | $^1$H NMR (300 MHz, DMSO-$d_6$): δ 8.90 (s, 2H), 8.50 (s, 1H), 8.27 (dd, J = 7.3, 2.2 Hz, 1H), 8.01-7.93 (m, 1H), 7.65-9.57 (m, 1H), 7.10-7.05 (m, 1H), 6.87 (d, J = 7.6 (Hz, 1H), 4.29 (s, 2H), 3.61-3.31 (m, 5H), 3.18-3.08 (m, 1H), 2.08-1.61 (m, 3H), 1.23-1.11 (m, 4H). |
| 124 | 371.2 | $^1$H NMR (400 MHz, DMSO-$d_6$) δ 8.98 (s, 2H), 8.39 (d, J = 1.2 Hz, 1H), 7.75 (d, J = 7.4 Hz, 2H), 7.55-7.44 (m, 2H), 7.44-7.35 (m, 1H), 6.93 (dd, J = 7.6, 1.3 Hz, 1H), 6.86 (d, J = 7.6 Hz, 1H), 4.28 (s, 2H), 3.04-2.90 (m, 6H), 1.25-1.11 (m, 4H). |
| 125 | 389.2 | $^1$H NMR (400 MHz, DMSO-$d_6$) δ 9.03 (s, 2H), 8.39 (d, J = 1.1 Hz, 1H), 7.74-7.59 (m, 2H), 7.59-7.44 (m, 1H), 7.22 (td, J = 8.4, 2.3 Hz, 1H), 6.94 (dd, J = 7.6, 1.3 Hz, 1H), 6.87 (d, J = 7.6 Hz, 1H), 4.28 (s, 2H), 2.99 (s, 3H), 2.94 (s, 3H), 1.27-1.06 (m, 4H). |
| 126 | 437.2 | $^1$H NMR (400 MHz, DMSO-$d_6$) δ 9.06 (s, 2H), 8.39 (s, 1H), 7.60 (d, J = 7.3 Hz, 2H), 7.25 (t, J = 9.3 Hz, 1H), 6.96 (d, J = 7.5 Hz, 1H), 6.86 (d, J = 7.0 Hz, 1H), 4.83-4.75 (m, 1H), 4.28 (s, 2H), 3.63-3.51 (m, 3H), 3.36-3.34 (m, 1H), 2.99 (s, 3H), 1.22-1.14 (m, 4H). |
| 127 | 361.1 | $^1$H NMR (400 MHz, DMSO-$d_6$) δ 8.86 (s, 2H), 8.82 (s, 1H), 7.88 (br s, 1H), 7.68 (t, J = 7.8 Hz, 1H), 7.51-7.42 (m, 2H), 7.42-7.32 (m, 2H), 7.29 (br s, 1H), 6.87 (d, J = 7.8 Hz, 1H), 4.28 (s, 2H), 1.27-1.12 (m, 4H). |
| 128 | 462.2 | $^1$H NMR (400 MHz, DMSO-$d_6$) δ 9.06 (s, 2H), 8.44 (s, 1H), 8.15 (s, 1H), 7.60 (d, J = 7.1 Hz, 2H), 7.25 (t, J = 9.3 Hz, 1H), 7.02 (d, J = 7.6 Hz, 1H), 6.91 (d, J = 7.6 Hz, 1H), 4.29 (s, 2H), 4.17-3.46 (m, 4H), 3.26 (s, 2H), 1.21 (m, 4H). |
| 129 | 419.2 | $^1$H NMR (400 MHz, DMSO-$d_6$) δ 9.03 (s, 2H), 8.39 (s, 1H), 7.71-7.58 (m, 2H), 7.58-7.48 (m, 1H), 7.26-7.17 (m, 1H), 6.95 (d, J = 7.6 Hz, 1H), 6.86 (d, J = 7.3 Hz, 1H), 4.88-4.73 (m, 1H), 4.28 (s, 2H), 3.63 (br s, 1H), 3.52 (br s, 2H), 3.31 (br s, 1H), 2.99 (s, 3H), 1.26-1.09 (m, 4H). |
| 130 | 415.2 | $^1$H NMR (400 MHz, DMSO-$d_6$) δ 9.02 (s, 2H), 8.51 (s, 1H), 7.71-7.57 (m, 2H), 7.52 (td, J = 7.7; 7.6 Hz, 1H), 7.21 (t, J = 7.6 Hz, 1H), 7.07 (d, J = 7.5 Hz, 1H), 6.85 (d, J = 7.6 Hz, 1H), 4.27 (s, 2H), 3.55-3.37 (m, 4H), 1.95-1.73 (m, 4H), 1.27-1.06 (m, 4H). |
| 131 | 453.1 | |
| 132 | 453.1 | |
| 133 | 453.1 | |
| 134 | 485.2 | |
| 135 | 432.2 | |
| 136 | 416.2 | |
| 137 | 417.2 | |
| 138 | 417.2 | |
| 139 | 449.2 | |
| 140 | 471.2 | |
| 141 | 416.2 | |
| 142 | 433.2 | |
| 143 | 444.1 | |
| 144 | 431.2 | |
| 145 | 432.2 | |
| 146 | 414.2 | |
| 147 | 432.2 | |
| 148 | 437.1 | $^1$H NMR (300 MHz, DMSO-$d_6$): δ 8.87 (s, 2H), 8.36 (s, 1H), 7.26-7.23 (m, 1H), 6.97-6.94 (m, 1H), 6.86 (m, 1H), 6.88-6.81 (m, 2H), 4.25 (s, 2H), 3.70-3.40 (m, 8H), 1.24-1.10 (m, 4H). |
| 149 | 449.2 | $^1$H NMR (400 MHz, DMSO-$d_6$): δ 8.89 (s, 2H), 8.37 (s, 1H), 7.38 (d, J = 3.6 Hz, 1H), 7.01-6.92 (m, 2H), 6.86 (d, J = 7.6 Hz, 1H), 5.54 (t, J = 5.7 Hz, 1H), |

TABLE 6-continued

Table of the pyhsico chemical data
(NMR, LCMS: [M + 1.0079]; mass found, M.p.)

| No. | LCMS | physico chemical data M.p./NMR |
|---|---|---|
| 150 | 414.2 | 4.65 (d, J = 5.7 Hz, 2H), 4.25 (s, 2H), 3.70-3.40 (s, 8H), 1.23-1.11 (m, 4H).<br>$^1$H NMR (400 MHz, DMSO-$d_6$) δ 9.30 (s, 2H), 8.67 (d, J = 4.3 Hz, 1H), 8.44 (d, J = 0.9 Hz, 1H), 8.03 (d, J = 8.0 Hz, 1H), 7.91 (td, J = 7.8, 1.7 Hz, 1H), 7.37 (dd, J = 7.1, 5.0 Hz, 1H), 6.98 (dd, J = 7.6, 1.2 Hz, 1H), 6.89 (d, J = 7.6 Hz, 1H), 4.30 (s, 2H), 3.71-3.38 (m, 8H), 1.27-1.11 (m, 4H). |
| 151 | 432.2 | $^1$H NMR (400 MHz, DMSO-$d_6$) δ 9.26 (s, 2H), 8.43 (s, 1H), 8.10 (dd, J = 8.0, 8.0 Hz, 1H), 7.99 (dd, J = 7.5, 2.3 Hz, 1H), 7.15 (dd, J = 8.0, 2.4 Hz, 1H), 6.99 (d, J = 7.6 Hz, 1H), 6.90 (d, J = 7.6 Hz, 1H), 4.30 (s, 2H), 3.76-3.38 (m, 8H), 1.29-1.11 (m, 4H). |
| 152 | 462.2 | $^1$H NMR (300 MHz, DMSO-$d_6$): δ 8.98 (s, 2H), 8.39 (s, 1H), 8.02-7.98 (m, 1H), 7.77 (d, J = 3.9 Hz, 1H), 7.56 (d, J = 3.9 Hz, 1H), 7.41-7.39 (m, 1H), 7.01-6.95 (m, 1H), 6.88 (d, J = 7.6 Hz, 1H), 4.27 (s, 2H), 3.7-3.41 (m, 8H), 1.19-1.01 (m, 4H). |
| 153 | 444.1 | $^1$H NMR (300 MHz, DMSO-$d_6$): δ 8.97 (s, 2H), 8.40 (s, 1H), 7.86 (d, J = 5.1 Hz, 1H), 7.60 (d, J = 5.1 Hz, 1H), 7.02-6.99 (m, 1H), 6.91 (d, J = 6.0 Hz, 1H), 4.30 (s, 2H), 3.80-3.41 (m, 8H), 1.23-1.15 (m, 4H). |
| 154 | 448.2 | $^1$H NMR (300 MHz, DMSO-$d_6$): δ 8.72 (s, 2H), 8.37 (s, 1H), 6.96 (dd, J = 7.5, 1.5 Hz, 1H), 6.88 (d, J = 7.6 Hz, 1H), 4.26 (s, 2H), 3.61-3.55 (m, 8H), 2.64 (s, 3H), 2.38 (s, 3H), 1.30-0.99 (m, 4H). |
| 155 | 434.2 | $^1$H NMR (300 MHz, DMSO-$d_6$): δ 8.98 (s, 2H), 8.39 (s, 1H), 7.63 (s, 1H), 7.01-6.97 (m, 1H), 6.91-6.87 (m, 1H), 4.27 (s, 2H), 3.61-3.55 (m, 8H), 2.49 (s, 3H), 1.25-0.97 (m, 4H). |
| 156 | 446.2 | $^1$H NMR (300 MHz, DMSO-$d_6$): δ 9.15 (s, 2H), 8.40 (s, 1H), 7.95 (br s, 1H), 7.48 (br s, 1H), 7.17 (d, J = 3.6 Hz, 1H), 7.09 (d, J = 3.6 Hz, 1H), 6.97 (d, J = 7.80 Hz, 1H), 6.88 (d, J = 7.6 Hz, 1H), 4.28 (s, 2H), 3.80-3.40 (m, 8H), 1.29-1.10 (m, 4H). |
| 157 | 432.2 | $^1$H NMR (400 MHz, DMSO-$d_6$) δ 9.11 (s, 2H), 8.95-8.88 (m, 1H), 8.60 (d, J = 2.6 Hz, 1H), 8.45-8.39 (m, 1H), 8.26-8.16 (m, 1H), 6.98 (d, J = 7.6 Hz, 1H), 6.89 (d, J = 7.6 Hz, 1H), 4.29 (s, 2H), 3.78-3.41 (m, 8H), 1.34-1.08 (m, 4H). |
| 158 | 476.2 | $^1$H NMR (300 MHz, DMSO-$d_6$): δ 11.33 (s, 1H), 8.84 (s, 2H), 8.36 (s, 1H), 7.27 (d, J = 3.9 Hz, 1H), 6.98-6.90 (m, 1H), 6.86 (d, J = 7.6 Hz, 1H), 6.65 (d, J = 3.9 Hz, 1H), 4.25 (s, 2H), 3.56-3.50 (m, 8H), 2.09 (s, 3H), 1.28-1.07 (m, 4H). |
| 159 | 428.2 | $^1$H NMR (400 MHz, DMSO-$d_6$) δ 9.10 (s, 2H), 8.50 (d, J = 5.2 Hz, 1H), 8.43 (s, 1H), 7.69 (s, 1H), 7.60 (dd, J = 5.2, 1.8 Hz, 1H), 6.98 (dd, J = 7.7, 1.5 Hz, 1H), 6.88 (d, J = 7.6 Hz, 1H), 4.29 (s, 2H), 3.80-3.62 (m, 8H), 2.53 (s, 3H), 1.25-0.97 (m, 4H). |
| 160 | 432.2 | $^1$H NMR (400 MHz, DMSO-$d_6$) δ 9.18 (s, 2H), 8.43 (s, 1H), 8.31 (d, J = 5.3 Hz, 1H), 7.82 (d, J = 5.3 Hz, 1H), 7.68 (s, 1H), 7.00 (dd, J = 1.2, 7.6 Hz, 1H), 6.89 (d, J = 7.6 Hz, 1H), 4.28 (s, 2H), 3.74-3.37 (m, 8H), 1.28-1.10 (m, 4H). |
| 161 | 444.1 | $^1$H NMR (300 MHz, DMSO-$d_6$): δ 8.98 (s, 2H), 8.58 (s, 1H), 8.38 (s, 1H), 7.95 (s, 1H), 6.99-6.92 (m, 1H), 6.89-6.85 (m, 1H), 4.26 (s, 2H), 3.60-3.43 (m, 8H), 1.23-1.15 (m, 4H). |
| 162 | 415.2 | $^1$H NMR (400 MHz, DMSO-$d_6$) δ 9.23 (s, 2H), 9.19 (s, 1H), 9.11 (s, 2H), 8.42 (d, J = 1.5 Hz, 1H), 6.98 (dd, J = 7.7, 1.5 Hz, 1H), 6.89 (d, J = 7.6 Hz, 1H), 4.28 (s, 2H), 3.68-3.56 (m, 8H), 1.23-1.13 (m, 4H). |
| 163 | 450.2 | $^1$H NMR (400 MHz, DMSO-$d_6$) δ 8.94 (s, 2H), 8.41 (s, 1H), 8.35-8.32 (m, 1H), 8.27-8.26 (m, 1H), 6.99 (d, J = 7.6 Hz, 1H), 6.89 (d, J = 7.6 Hz, 1H), 4.29 (s, 2H), 3.85-3.61 (m, 8H), 1.25-1.07 (m, 4H). |
| 164 | 457.2 | $^1$H NMR (400 MHz, DMSO-$d_6$) δ 9.32 (s, 2H), 8.79 (d, J = 5.2 Hz, 1H), 8.45 (s, 1H), 8.37 (s, 1H), 8.27 (bs, 1H), 7.79 (bs, 1H), 7.72 (d, J = 5.2, 1.5 Hz, 1H), 6.99 (dd, J = 7.7, 1.5 Hz, 1H), 6.89 (d, J = 7.6 Hz, 1H), 4.31 (s, 2H), 3.70-3.40 (m, 8H), 1.26-1.12 (m, 4H). |
| 165 | 432.2 | $^1$H NMR (400 MHz, DMSO-$d_6$) δ 9.26 (s, 2H), 8.67 (d, J = 2.9 Hz, 1H), 8.43 (s, 1H), 8.12-8.09 (m, 1H), 7.89-7.84 (m, 1H), 6.98 (dd, J = 7.6, 1.5 Hz, 1H), 6.88 (d, J = 7.6 Hz, 1H), 4.30 (s, 2H), 3.80-3.56 (m, 8H), 1.28-0.96 (m, 4H). |
| 166 | 450.2 | $^1$H NMR (400 MHz, DMSO-$d_6$): δ 8.88 (s, 2H), 8.69 (s, 1H), 8.40 (s, 1H), 7.00 (dd, J = 7.6, 1.5 Hz, 1H), 6.90 (d, J = 7.6 Hz, 1H), 4.29 (s, 2H), 3.61-3.37 (m, 8H), 1.28-1.03 (m, 4H). |
| 167 | 428.2 | $^1$H NMR (400 MHz, DMSO-$d_6$) δ 8.73 (s, 2H), 8.49 (dd, J = 4.8, 1.4 Hz, 1H), 8.40 (s, 1H), 7.73 (dd, J = 7.7, 1.4 Hz, 1H), 7.35 (dd, J = 7.6, 4.8 Hz, 1H), 6.95 (dd, J = 7.6, 0.9 Hz, 1H), 6.88 (d, J = 7.6 Hz, 1H), 4.28 (s, 2H), 3.70-3.35 (m, 8H), 2.51 (s, 3H), 1.25-1.10 (m, 4H). |
| 168 | 432.2 | |
| 169 | 432.2 | |
| 170 | 432.2 | |
| 171 | 445.2 | see experimental section (A-10) |
| 172 | 415.2 | $^1$H NMR (400 MHz, DMSO-$d_6$): δ 8.78 (s, 2H), 8.43-8.42 (m, 1H), 7.23 (s, 1H), 7.02-6.99 (m, 1H), 6.82-6.79 (m, 2H), 6.48-6.44 (m, 1H), 4.22 (s, 2H), 3.65 (s, 3H), 3.61-3.38 (m, 4H), 3.17-3.06 (m, 1H), 2.00-1.85 (m, 3H), 1.65-1.58 (m, 1H), 1.22-1.12 (m, 4H). |
| 173 | 416.2 | $^1$H NMR (400 MHz, DMSO-$d_6$) δ 8.86 (s, 2H), 8.44 (s, 1H), 8.17 (s, 1H), 7.92 (s, 1H), 7.02-7.00 (m, 1H), 6.84-6.81 (d, J = 7.6 Hz, 1H), 4.23 (s, 2H), 3.88 (s, 3H), 3.67-3.32 (m, 4H), 3.10-3.09 (m, 1H), 2.07-1.95 (m, 3H), 1.65-1.55 (m, 1H), 1.2- 1.08 (m, 4H). |
| 174 | 390.2 | $^1$H NMR (400 MHz, DMSO-$d_6$) δ 8.91 (s, 2H), 8 .39 (s, 1H), 8.31-8.22 (m, 2H), 7.54-7.50 (m, 1H), 6.96 (dd, J = 7.6, 1.1 Hz, 1H), 6.88 (d, J = 7.6 Hz, 1H), 4.28 (s, 2H), 2.99 (s, 3H), 2.94 (s, 3H), 1.26-1.11 (m, 4H). |
| 175 | 398.2 | $^1$H NMR (400 MHz, DMSO-$d_6$) δ 9.29 (s, 2H), 8.67-8.66 (m, 1H), 8.53 (s, 1H), 8.02-8.00 (m, 1H), 7.92-7.87 (m, 1H), 7.37-7.34 (m, 1H), 7.09 (d, J = 7.6 Hz, 1H), 6.86 (d, J = 7.6 Hz, 1H), 4.30 (s, 2H), 3.50-3.37 (m, 4H), 1.90-1.80 (m, 1H), 1.24-1.12 (m, 4H). |
| 176 | 445.2 | $^1$H NMR (400 MHz, DMSO-$d_6$) δ 8.91 (s, 2H), 8.43 (s, 1H), 8.26 (m, 2H), 8.13 (s, 1H), 7.51 (t, J = 5.3 Hz, 1H), 7.02 (d, J = 7.2 Hz, 1H), 6.90 (d, J = 7.6 Hz, 1H), 4.29 (s, 2H), 4.16-3.55 (m, 4H), 3.24 (s, 2H), 1.20 (m, 4H). |
| 177 | 462.2 | $^1$H NMR (400 MHz, DMSO-$d_6$) δ 8.85 (s, 2H), 8.38 (s, 1H), 8.15 (s, 1H), 7.54 (d, J = 5.5 Hz, 1H), 7.18 (d, J = 5.6 Hz, 1H), 6.98 (d, J = 7.6 Hz, 1H), 6.88 (d, J = 7.6 Hz, 1H), 4.25 (s, 2H), 4.09-3.93 (m, 2H), 3.92 (s, 3H), 3.88-3.56 (m, 2H), 3.24 (br s, 2H), 1.24-1.13 (m, 4H). |
| 178 | 445.2 | see experimental section (A-11) |
| 179 | 447.2 | $^1$H NMR (300 MHz, DMSO-$d_6$): δ 8.58 (s, 2H), 8.29 (s, 1H), 7.42-7.31 (m, 1H), 7.20-7.11 (m, 3H), 6.93-6.87 (m, 2H), 4.22 (s, 2H), 3.80-3.59 (m, 8H), 1.26-0.99 (m, 4H). |
| 180 | 427.2 | $^1$H NMR (300 MHz, DMSO-$d_6$): δ 9.28 (s, 2H), 8.67 (d, J = 3.1 Hz, 1H), 8.46 (s, 1H), 8.18-8.12 (m, 1H), 8.06-7.99 (m, 1H), 7.91-7.88 (m, 1H), 7.38-7.35 (m, 1H), 7.03-7.01 (m, 1H), 6.91 (d, J = 6.2 Hz, 1H), 4.31 (s, 2H), 4.07-4.01 (s, 2H), 3.80-3.62 (s, 2H), 3.31-3.26 (m, 2H), 1.30-1.14 (m, 4H). |
| 181 | 432.2 | $^1$H NMR (400 MHz, DMSO-$d_6$) δ 9.31 (s, 2H), 8.71-8.67 (m, 1H), 8.44 (s, 1H), 8.00 (dd, J = 11.0, 2.4 Hz, 1H), 7.31-7.27 (m, 1H), 6.99 (dd, J = 7.7, 1.5 Hz, 1H), 6.89 (d, J = 7.6 Hz, 1H), 4.30 (s, 2H), 3.80-3.60 (m, 8H), 1.27-1.08 (m, 4H). |
| 182 | 445.2 | $^1$H NMR (400 MHz, DMSO-$d_6$) δ 9.28 (s, 2H), 8.44 (s, 1H), 8.24 (d, J = 9.3 Hz, 1H), 7.37 (d, J = 9.2 Hz, 1H), 6.99 (dd, J = 7.6, 1.5 Hz, 1H), 6.89 (d, J = 7.6 Hz, 1H), 4.31 (s, 2H), 4.08 (s, 3H), 3.80-3.60 (m, 8H), 1.26-1.02 (m, 4H). |
| 183 | 482.2 | $^1$H NMR (300 MHz, DMSO-$d_6$): δ 9.40 (s, 2H), 8.94 (d, J = 5.1 Hz, 1H), 8.51-8.26 (m, 2H), 7.73 (dd, J = 5.0, 1.5 Hz, 1H), 7.00 (dd, J = 7.6, 1.5 Hz, 1H), 6.90 (d, J = 7.7 Hz, 1H), 4.32 (s, 2H), 3.80-3.60 (m, 8H), 1.31-1.05 (m, 4H). |

TABLE 6-continued

Table of the pyhsico chemical data
(NMR, LCMS: [M + 1.0079]; mass found, M.p.)

| No. | LCMS | physico chemical data M.p./NMR |
|---|---|---|
| 184 | 444.2 | 1H NMR (400 MHz, DMSO-d6) δ 9.03 (s, 2H), 8.46-8.41 (d, J = 0.8 Hz, 1H), 8.15 (s, 1H), 7.71-7.58 (m, 2H), 7.58-7.49 (m, 1H), 7.22 (td, J = 8.5, 2.3 Hz, 1H), 7.01 (d, J = 6.9 Hz, 1H), 6.90 (d, J = 7.6 Hz, 1H), 4.29 (s, 2H), 4.19-3.43 (m, 4H), 3.26 (m, 2H), 1.27-1.12 (m, 4H). |
| 185 | 456.2 | 1H NMR (400 MHz, DMSO-d6) δ 8.99 (s, 2H), 8.44 (s, 1H), 8.15 (s, 1H), 7.40 (t, J = 8.2 Hz, 1H), 7.35-7.26 (m, 2H), 7.04-6.92 (m, 2H), 6.89 (d, J = 7.6 Hz, 1H), 4.28 (s, 2H), 4.20-3.88 (m, 2H), 3.83 (s, 3H), 3.79-3.40 (m, 2H), 3.30-3.22 (br s, 2H), 1.28-1.10 (m, 4H). |
| 186 | 431.2 | 1H NMR (400 MHz, DMSO-d6) δ 8.99 (s, 2H), 8.39 (s, 1H), 7.40 (t, J = 8.1 Hz, 1H), 7.35-7.27 (m, 2H), 6.99-6.90 (m, 2H), 6.85 (d, J = 7.6 Hz, 1H), 4.86-4.72 (m, 1H), 4.27 (s, 2H), 3.83 (s, 3H), 3.71-3.57 (br s, 1H), 3.56-3.45 (m, 2H), 3.38-3.25 (m, 1H), 2.99 (s, 3H), 1.26-1.10 (m, 4H). |
| 187 | 428.2 | $^{1}$H NMR (400 MHz, DMSO-d$_{6}$): δ 9.26 (s, 2H), 8.43 (s, 1H), 7.82-7.76 (m, 1H), 7.23-7.22 (m, 1H), 6.98-6.96 (m, 1H), 6.88 (d, J = 7.6 Hz, 1H), 4.29 (s, 2H), 3.71-3.62 (m, 8H), 2.54 (s, 3H), 1.26-1.03 (m, 4H). |
| 188 | 446.2 | $^{1}$H NMR (400 MHz, DMSO-d$_{6}$): δ 8.74 (s, 2H), 8.39 (d, J = 1.5 Hz, 1H), 7.02-6.94 (m, 2H), 6.87 (d, J = 7.6 Hz, 1H), 6.72-6.69 (m, 1H), 6.60-6.56 (m, 1H), 5.07 (s, 2H), 4.26 (s, 2H), 3.71-3.41 (m, 8H), 1.22-1.12 (m, 4H). |
| 189 | 444.2 | $^{1}$H NMR (400 MHz, DMSO-d$_{6}$): δ 9.29 (s, 2H), 8.52-8.33 (m, 2H), 7.59 (d, J = 2.4 Hz, 1H), 7.01-6.94 (m, 2H), 6.88 (d, J = 7.6 Hz, 1H), 4.30 (s, 2H), 3.92 (s, 3H), 3.80-3.60 (m, 8H), 1.29-1.01 (m, 4H). |
| 190 | 429.2 | $^{1}$H NMR (400 MHz, DMSO-d$_{6}$): δ 9.09 (s, 2H), 8.42 (s, 1H), 8.10 (d, J = 5.7 Hz, 1H), 7.03-6.94 (m, 2H), 6.88 (d, J = 7.6 Hz, 1H), 6.52-6.51 (m, 1H), 6.39 (s, 2H), 4.28 (s, 2H), 3.80-3.60 (m, 8H), 1.27-0.88 (m, 4H). |
| 191 | 430.2 | $^{1}$H NMR (400 MHz, DMSO-d$_{6}$): δ 10.76 (s, 1H), 9.19 (s, 2H), 8.42-8.34 (m, 2H), 7.32-7.34 (m, 1H), 6.97 (d, J = 7.6 Hz, 1H), 6.86 (d, J = 7.6 Hz, 1H), 6.76-6.72 (m, 1H), 4.29 (s, 2H), 4.08-3.39 (m, 8H), 1.22-1.14 (m, 4H). |
| 192 | 428.2 | $^{1}$H NMR (400 MHz, DMSO-d$_{6}$): δ 9.27 (s, 2H), 8.43 (s, 1H), 7.90-7.64 (m, 2H), 7.23 (dd, J = 6.7, 1.8 Hz, 1H), 6.97 (dd, J = 7.6, 1.5 Hz, 1H), 6.88 (d, J = 7.6 Hz, 1H), 4.29 (s, 2H), 3.80-3.60 (m, 8H), 2.54 (s, 3H), 1.33-0.96 (m, 4H). |
| 193 | 415.2 | $^{1}$H NMR (400 MHz, DMSO-d$_{6}$): δ 9.37 (s, 2H), 9.22 (dd, J = 4.8, 1.5 Hz, 1H), 8.46 (d, J = 1.4 Hz, 1H), 8.30 (dd, J = 8.9, 1.5 Hz, 1H), 7.82-7.79 (m, 1H), 7.00 (dd, J = 7.5, 1.5 Hz, 1H), 6.90 (d, J = 7.6 Hz, 1H), 4.32 (s, 2H), 3.80-3.60 (m, 8H), 1.27-1.05 (m, 4H). |
| 194 | 429.2 | $^{1}$H NMR (400 MHz, DMSO-d$_{6}$): δ 9.33 (s, 2H), 8.44 (s, 1H), 8.18 (d, J = 8.8 Hz, 1H), 7.68 (d, J = 8.8 Hz, 1H), 6.99 (dd, J = 7.6, 1.5 Hz, 1H), 6.89 (d, J = 7.6 Hz, 1H), 4.31 (s, 2H), 3.80-3.60 (m, 8H), 2.66 (s, 3H), 1.19-1.11 (m, 4H). |
| 195 | 510.2 | $^{1}$H NMR (400 MHz, DMSO-d$_{6}$): δ 8.87 (s, 2H), 8.41 (s, 1H), 8.08-8.06 (m, 1H), 7.90-7.86 (m, 1H), 7.60-7.56 (m, 1H), 7.44 (s, 2H), 6.98 (dd, J = 7.7, 1.5 Hz, 1H), 6.89 (d, J = 7.6 Hz, 1H), 4.29 (s, 2H), 3.80-3.60 (m, 8H), 1.29-0.95 (m, 4H). |
| 196 | 405.2 | $^{1}$H NMR (400 MHz, DMSO-d$_{6}$): δ 8.86 (s, 2H), 8.32 (d, J = 1.2 Hz, 1H), 8.18 (s, 1H), 7.93 (s, 1H), 6.91 (dd, J = 7.6, 1.2 Hz, 1H), 6.83 (d, J = 7.5 Hz, 1H), 4.78 (m, 1H), 4.23 (s, 2H), 3.88 (s, 3H), 3.72-3.58 (m, 1H), 3.57-3.44 (m, 2H), 3.32-3.24 (m, 1H), 2.99 (s, 3H), 1.24-1.07 (m, 4H). |
| 197 | 440.2 | $^{1}$H NMR (400 MHz, DMSO-d$_{6}$): δ 11.47 (br s, 1H), 8.97 (s, 2H), 8.44 (s, 1H), 7.75 (d, J = 7.5 Hz, 1H), 7.50 (t, J = 7.6 Hz, 2H), 7.39 (t, J = 7.3 Hz, 1H), 7.01 (d, J = 7.6 Hz, 1H), 6.92 (d, J = 7.6 Hz, 1H), 4.37 (br s, 4H), 4.29 (s, 2H), 1.32-1.11 (m, 4H). |
| 198 | 415.2 | $^{1}$H NMR (400 MHz, DMSO-d$_{6}$): δ 9.40 (s, 2H), 9.23 (s, 1H), 8.86 (d, J = 5.4 Hz, 1H), 8.45 (s, 1H), 8.15 (d, J = 5.1 Hz, 1H), 7.02 (d, J = 7.6 Hz, 1H), 6.91 (d, J = 7.6 Hz, 1H), 4.32 (s, 2H), 3.77-3.42 (m, 8H), 1.29-1.11 (m, 4H). |
| 199 | 429.2 | $^{1}$H NMR (400 MHz, DMSO-d$_{6}$) δ 9.37 (s, 2H), 8.75 (d, J = 5.4 Hz, 1H), 8.45 (d, J = 1.0 Hz, 1H), 7.93 (d, J = 5.4 Hz, 1H), 7.01 (dd, J = 7.6, 1.3 Hz, 1H), 6.91 (d, J = 7.6 Hz, 1H), 4.31 (s, 2H), 3.76-3.38 (m, 8H), 2.67 (s, 3H), 1.31-1.08 (m, 4H). |
| 200 | 444.2 | $^{1}$H NMR (400 MHz, DMSO-d$_{6}$) δ 9.04 (s, 2H), 8.40 (d, J = 1.1 Hz, 1H), 8.23 (s, 1H), 8.09 (s, 1H), 7.89 (dd, J = 15.8, 7.8 Hz, 2H), 7.58 (t, J = 7.7 Hz, 1H), 7.50 (s, 1H), 6.99-6.91 (m, 1H), 6.86 (d, J = 7.5 Hz, 1H), 4.87-4.73 (m, 1H), 4.29 (s, 2H), 3.64 (br s, 1H), 3.52 (br s, 2H), 3.33 (br s, 1H), 3.00 (s, 3H), 1.27-1.09 (m, 4H). |
| 201 | 426.2 | $^{1}$H NMR (400 MHz, DMSO-d$_{6}$) δ 9.05 (s, 2H), 8.38 (s, 1H), 8.27 (s, 1H), 8.11 (d, J = 7.1 Hz, 1H), 7.83 (d, J = 7.0 Hz, 1H), 7.68 (t, J = 7.4 Hz, 1H), 6.95 (d, J = 6.7 Hz, 1H), 6.86 (d, J = 6.7 Hz, 1H), 4.89-4.71 (m, 1H), 4.27 (s, 2H), 3.63 (br s, 1H), 3.51 (br s, 2H), 3.33 (br s, 1H), 2.99 (s, 3H), 1.27-1.06 (m, 4H). |
| 202 | 415.2 | $^{1}$H NMR (400 MHz, DMSO-d$_{6}$) δ 9.76 (s, 1H), 9.33-9.19 (m, 3H), 8.44 (s, 1H), 8.12 (dd, J = 5.4, 2.4 Hz, 1H), 7.01 (d, J = 7.4 Hz, 1H), 6.91 (d, J = 7.6 Hz, 1H), 4.30 (s, 2H), 3.84-3.46 (m, 8H), 1.28-1.12 (m, 4H). |
| 203 | 433.2 | $^{1}$H NMR (400 MHz, DMSO-d$_{6}$): δ 9.41 (s, 2H), 9.01 (d, J = 2.0 Hz, 1H), 8.45 (d, J = 1.5 Hz, 1H), 8.03 (s, 1H), 7.03 (d, J = 7.5 Hz, 1H), 6.91 (d, J = 7.6 Hz, 1H), 4.32 (s, 2H), 3.60-3.50 (m, 8H), 1.26-1.23 (m, 2H), 1.18-1.13 (m, 2H). |
| 204 | 449.1 | $^{1}$H NMR (400 MHz, DMSO-d$_{6}$): δ 9.41 (s, 2H), 9.07 (s, 1H), 8.45 (s, 1H), 8.36 (s, 1H), 7.02 (dd, J = 6.8, 1.4 Hz, 1H), 6.91 (d, J = 7.6 Hz, 1H), 4.32 (s, 2H), 3.60-3.50 (m, 8H), 1.24-1.23 (m, 2H), 1.16-1.15 (m, 2H). |
| 205 | 477.2 | see experimental section (A-28) |
| 206 | 457.2 | $^{1}$H NMR (400 MHz, DMSO-d$_{6}$) δ 9.25 (s, 2H), 8.43 (s, 1H), 8.21 (d, J = 6.1 Hz, 1H), 7.17 (d, J = 2.6 Hz, 1H), 6.97 (d, J = 7.6 Hz, 1H), 6.88 (d, J = 7.5 Hz, 1H), 6.64 (d, J = 6.1 Hz, 1H), 4.29 (s, 2H), 3.60-3.50 (m, 8H), 3.07 (s, 6H), 1.27-1.10 (m, 4H). |
| 209 | 415.2 | $^{1}$H NMR (400 MHz, dmso-d6, T = 373K): δ 8.89 (s, 2H), 8.39 (s, 1H), 7.52-7.48 (m, 2H), 7.37 (t, 1H, J = 7.6 Hz), 7.19 (d, 1H, J = 7.4 Hz), 6.93 (dd, 1H, J = 1.4 & 7.7 Hz), 6.81 (d, 1H, J = 7.5 Hz), 4.38 (bs, 1H), 4.28 (s, 2H), 3.62 (t, 2H, J = 5.9 Hz), 3.45 (t, 2H, J = 5.9 Hz), 3.02 (s, 3H), 2.4 (s, 3H), 1.23-1.13 (m, 4H). |
| 210 | 416.2 | 1H NMR (400 MHz, dmso-d6, T = 373K): δ 9.22 (s, 2H), 8.5 (d, 1H, J = 5.1 Hz), 8.4 (s, 1H), 7.79 (s, 1H), 7.16 (d, 1H, J = 4.7 Hz), 6.95 (d, 1H, J = 7.6 Hz), 6.82 (d, 1H, J = 7.5 Hz), 4.38 (bs, 1H), 4.31 (s, 2H), 3.64-3.62 (m, 2H), 3.46 (bs, 2H), 3.03 (s, 3H), 2.32 (s, 3H), 1.22-1.15 (m, 4H). |
| 211 | 432.2 | $^{1}$H NMR (400 MHz, CDCl$_{3}$): δ 1.16-1.7 (4H), 3.12 (s, 3H), 3.54-3.92 (5H), 4.01 (s, 3H), 4.32 (s, 2H), 6.67-6.70 (2H), 7.02-7.04 (1H), 7.24 (s, 1H), 7.60-7.64 (1H), 8.59 (bs, 1H), 9.15 (2H). |
| 212 | 454.2 | $^{1}$H NMR (400 MHz, CDCl$_{3}$): δ 1.47-1.22 (4H), 1.53-1.68 (2H), 1.75-1.79 (6H), 2.88-2.95 (2H), 3.04-3.07 (1H), 4.26-4.27 (2H), 6.77-6.80 (1H), 6.83-6.89 (1H), 7.01-7.15 (3H), 7.25-7.30 (1H), 8.50 (1H), 8.87-8.90 (2H). |
| 213 | 432.2 | $^{1}$H NMR (400 MHz, DMSO-d$_{6}$): δ 1.16-1.24 (4H), 2.63-2.73 (2H), 2.89 (s, 3H), 3.19-3.22 (1H), 3.69-3.71 (1H), 4.28 (s, 2H), 6.88-6.91 (1H), 7.02-7.08 (1H), 7.34-7.40 (1H), 7.42-7.48 (1H), 8.34-8.45 (3H), 8.84 (s, 2H). |
| 214 | 416.2 | $^{1}$H NMR (400 MHz, DMSO-d$_{6}$): δ 1.14-1.23 (4H), 2.99 (s, 3H), 3.26-3.29 (1H), 3.48-3.65 (5H), 4.29 (s, 2H), 4.72-4.76 (1H), 6.86-6.88 (1H), 6.97-6.99 (1H), 7.66 (s, 1H), 7.80-7.82 (1H), 8.30-8.32 (1H), 8.40 (s, 1H), 9.18 (s, 2H). |
| 215 | 473.2 | $^{1}$H NMR (400 MHz, DMSO-d$_{6}$): δ 1.15-1.23 (4H), 1.50-1.56 (2H), 1.82-1.90 (2H), 2.90-3.03 (2H), |

TABLE 6-continued

Table of the pyhsico chemical data
(NMR, LCMS: [M + 1.0079]; mass found, M.p.)

| No. | LCMS | physico chemical data M.p./NMR |
|---|---|---|
| | | 3.56-3.70 (1H), 4.26-4.30 (3H), 6.86-6.88 (1H), 6.92-6.94 (1H), 7.32-7.35 (2H), 7.43-7.46 (1H), 7.64-7.68 (1H), 8.38 (s, 1H), 8.84 (s, 2H). |
| 216 | 472.2 | $^1$H NMR (400 MHz, DMSO-$d_6$): δ 1.15-1.22 (4H), 1.47-1.52 (2H), 1.53-1.80 (2H), 2.32-2.37 (1H), 2.75-3.10 (2H), 3.28-3.34 (1H), 4.28 (s, 2H), 4.34-4.44 (1H), 6.80 (bs, 1H), 7.32-7.39 (2H), 7.43-7.47 (1H), 6.64-6.68 (1H), 8.39 (s, 1H), 8.84 (s, 2H). |
| 217 | 473.2 | $^1$H NMR (400 MHz, DMSO-$d_6$): δ 1.15-1.23 (6H), 1.59-1.85 (3H), 2.66-2.80 (1H), 2.90-3.05 (1H), 3.20-3.24 (5H), 4.27 (2H), 4.43-4.47 (1H), 6.85-6.87 (1H), 6.90-6.93 (1H), 7.32-7.39 (2H), 7.43-7.48 (1H), 7.64-7.68 (1H), 8.37 (s, 1H), 8.83 (s, 2H). |
| 218 | 486.2 | $^1$H NMR (400 MHz, DMSO-$d_6$): δ 1.12-1.22 (4H), 1.58-1.88 (2H), 2.61-2.99 (3H), 3.37-3.63 (5H), 4.28 (s, 2H), 4.40-4.60 (2H), 6.82-6.89 (1H), 7.03-7.09 (1H), 7.32-7.40 (2H), 7.45-7.48 (1H), 7.65-7.70 (1H), 8.51 (s, 1H), 8.83-8.86 (2H). |
| 219 | 445.2 | 1H NMR (400 MHz, dmso-d6, T = 373K): δ 8.84 (s, 2H), 8.37 (s, 1H), 7.28 (s, 1H), 7.17 (d, 1H, J = 8.0 Hz), 6.98 (d, 1H, J = 8.1 Hz), 6.92 (d, 1H, J = 7.6 Hz), 6.8 (d, 1H, J = 7.5 Hz), 6.04 (s, 2H), 4.39 (bs, 1H), 4.28 (s, 2H), 3.64-3.6 (m, 2H), 3.46-3.43 (m, 2H), 3.01 (s, 3H), 1.2 (bs, 2H), 1.14 (bs, 2H). |
| 220 | 442.2 | $^1$H NMR (400 MHz, DMSO-$d_6$, T = 363K): δ 8.80 (s, 2H), 8.50 (s, 1H), 7.65-7.60 (m, 1H), 7.44-7.40 (m, 1H), 7.33-7.28 (m, 2H), 7.05 (dd, J = 7.6, 1.6 Hz, 1H), 6.83 (d, J = 7.6, 1H), 4.29 (s, 3H), 3.65 (s, 1H), 3.51 (dd, J = 10.4, 2.2 Hz, 1H), 3.27-3.19 (m, 1H), 3.00 (s, 2H), 2.91 (d, J = 2.1 Hz, 1H), 1.72 (d, J = 9.4 Hz, 1H), 1.59 (d, J = 9.4 Hz, 1H), 1.24-1.14 (m, 4H). |
| 221 | 442.2 | $^1$H NMR (400 MHz, DMSO-$d_6$, T = 363K): δ 8.80 (s, 2H), 8.50 (s, 1H), 7.65-7.60 (m, 1H), 7.44-7.40 (m, 1H), 7.33-7.28 (m, 2H), 7.05 (d, J = 7.6 Hz, 1H), 6.83 (d, J = 7.6, 1H), 4.29 (s, 3H), 3.65 (s, 1H), 3.51 (d, J = 10.4 Hz, 1H), 3.27-3.19 (m, 1H), 3.00 (s, 2H), 2.91 (d, J = 2.1 Hz, 1H), 1.72 (d, J = 9.4 Hz, 1H), 1.59 (d, J = 9.4 Hz, 1H), 1.20-1.21 (m, 2H), 1.15-1.12 (m, 2H). |
| 222 | 441.2 | 1H NMR (400 MHz, dmso-d6, T = 373K): δ 9.22 (s, 2H), 8.51-8.46 (m, 2H), 7.78-7.72 (m, 2H), 7.16 (bs, 1H), 7.02 (d, 1H, J = 7.2 Hz), 6.86 (d, 1H, J = 7.2 Hz), 4.32 (s, 2H), 4.07 (s, 2H), 3.69 (s, 2H), 3.31 (s, 2H), 2.4 (s, 3H), 1.23-1.17 (m, 4H). |
| 223 | 442.2 | 1H NMR (400 MHz, DMSO-$d_6$, T = 373K): δ 1.14-1.17 (4H), 1.60-1.63 (1H), 1.72-1.75 (1H), 3.03-3.06 (1H), 3.24-3.27 (1H), 3.51-3.54 (1H), 3.65 (bs, 1H), 4.30 (s, 1H), 4.43 (bs, 1H), 6.57-6.59 (1H), 6.84-6.86 (1H), 7.15-7.20 (1H), 7.49-7.58 (1H), 8.52 (s, 1H), 8.95 (s, 2H). |
| 224 | 432.2 | see experimental section (A-25) |
| 225 | 437.2 | $^1$H NMR (400 MHz, DMSO-d,): δ 1.14-1.22 (4H), 2.98 (s, 3H), 3.51-3.65 (3H), 4.72-4.77 (1H), 6.85-6.87 (1H), 6.95-6.98 (1H), 7.33-7.37 (1H), 7.44-7.51 (2H), 8.37 (s, 1H), 8.87 (s, 2H). |
| 226 | 470.2 | $^1$H NMR (400 MHz, DMSO-$d_6$): δ 1.15-1.22 (4H), 1.58-1.60 (2H), 1.61-1.80 (3H), 1.84-1.86 (1H), 2.78-2.87 (2H), 3.25-3.27 (1H), 3.37-3.40 (1H), 3.52-3.60 (3H), 4.27 (s, 1H), 6.84-6.87 (1H), 7.04-7.08 (1H), 7.32-7.39 (2H), 7.43-7.49 (1H), 7.64-7.69 (1H), 8.48 (s, 1H), 8.85 (2H). |
| 227 | 433.2 | $^1$H NMR (400 MHz, DMSO-$d_6$): δ 1.09-1.21 (4H), 2.35 (s, 1H), 2.99 (s, 3H), 3.50-3.68 (3H), 4.27 (s, 2H), 4.70-4.78 (1H), 6.85-6.87 (1H), 6.94-6.96 (1H), 7.22-7.25 (2H), 7.45-7.48 (1H), 8.37 (s, 1H), 8.82 (s, 2H). |
| 228 | 434.2 | $^1$H NMR (400 MHz, DMSO-$d_6$): δ 1.14-1.21 (4H), 2.99 (s, 3H), 3.50-3.65 (3H), 4.26 (s, 2H), 4.73-4.78 (1H), 50.07 (s, 2H), 6.57-6.59 (1H), 6.69-6.71 (1H), 6.83-6.86 (1H), 6.93-7.02 (2H), 8.35 (s, 1H), 8.72 (s, 2H). |
| 229 | 402.2 | $^1$H NMR (400 MHz, DMSO-$d_6$): δ 1.14-1.22 (4H), 3.00 (s, 3H), 3.51-3.64 (3H), 4.30 (s, 2H), 4.73-4.76 (1H), 6.85-6.87 (1H), 6.96-6.98 (1H), 7.34-7.38 (1H), 8.01-8.03 (1H), 8.40 (s, 1H), 8.65-8.68 (1H), 9.28 (s, 2H). |
| 230 | 420.2 | $^1$H NMR (600 MHz, DMSO-$d_6$): δ 1.15-1.23 (4H), 2.99 (s, 3H), 3.48-3.65 (3H), 4.30 (s, 2H), 4.72-4.80 (1H), 6.86-6.88 (1H), 6.97-6.99 (1H), 7.13-7.15 (1H), 7.97-7.99 (1H), 8.07-8.11 (1H), 8.41 (s, 1H), 9.25 (s, 2H). |
| 231 | 420.2 | $^1$H NMR (400 MHz, DMSO-$d_6$): δ 1.15-1.23 (4H), 3.01 (s, 3H), 3.51-3.65 (3H), 4.30 (s, 2H), 4.72-4.76 (1H), 6.86-6.88 (1H), 6.97-6.99 (1H), 7.66 (s, 1H), 7.80-7.82 (1H), 8.30-8.32 (1H), 8.40 (s, 1H), 9.18 (s, 2H). |
| 232 | 420.2 | $^1$H NMR (400 MHz, DMSO-$d_6$): δ 1.14-1.22 (4H), 2.99 (s, 3H), 3.51-3.65 (3H), 4.29 (s, 2H), 4.74-4.76 (1H), 6.85-6.87 (1H), 6.95-6.98 (1H), 7.85-7.89 (1H), 8.07-8.12 (1H), 8.39 (s, 1H), 8.66-8.68 (1H), 9.25 (s, 2H). |
| 233 | 420.2 | $^1$H NMR (400 MHz, DMSO-$d_6$): δ 1.15-1.22 (4H), 3.00 (3H), 3.52-3.-3.65 (3H), 4.30 (s, 2H), 4.73-4.77 (1H), 6.86-6.88 (1H), 6.97-6.99 (1H), 7.28-7.32 (1H), 7.98-8.01 (1H), 8.40 (s, 1H), 8.68-8.72 (1H), 9.30 (s, 2H). |
| 234 | 416.2 | $^1$H NMR (400 MHz, DMSO-$d_6$): δ 1.14-1.24 (4H), 3.00 (s, 3H), 3.50-3.82 (3H), 4.29 (s, 2H), 4.70-4.77 (1H), 6.85-6.87 (1H), 6.94-6.97 (1H), 7.22-7.24 (1H), 7.77-7.80 (2H), 8.40 (s, 1H), 9.26 (s, 2H). |
| 235 | 488.2 | $^1$H NMR (400 MHz, DMSO-$d_6$, T = 353K): δ 1.14-1.22 (4H), 2.40-2.48 (4H), 2.53-2.58 (2H), 3.24 (s, 2H), 3.45-3.56 (6H), 4.29 (s, 2H), 6.84-6.86 (1H), 6.92-6.94 (1H), 7.30-7.35 (2H), 7.42-7.44 (1H), 7.62-7.64 (1H), 8.39 (s, 1H), 8.81 (s, 2H). |
| 236 | 487.2 | $^1$H NMR (400 MHz, DMSO-$d_6$): δ 1.14-1.25 (6H), 2.56-2.64 (4H), 3.06 (s, 2H), 3.55-3.65 (2H), 3.78-3.90 (2H), 4.29 (s, 2H), 6.82-6.84 (1H), 6.97-6.99 (1H), 7.21-7.31 (2H), 7.38-7.41 (1H), 7.53-7.55 (1H), 8.51 (s, 1H), 8.75 (s, 2H). |
| 237 | 488.2 | 1H NMR (400 MHz, dmso-d6, T = 373K): δ 1.14-1.24 (4H), 2.97 (bs, 4H), 3.61 (bs, 1H), 3.69 (bs, 4H), 4.31 (s, 2H), 6.86-6.88 (1H), 6.97-6.99 (1H), 7.32-7.36 (2H), 7.44-7.46 (1H), 7.61-7.64 (1H), 8.42 (s, 1H), 8.81 (s, 2H). |
| 238 | 473.2 | $^1$H NMR (400 MHz, DMSO-$d_6$, T = 373K): δ 1.14-1.23 (4H), 1.42-1.53 (1H), 1.60-1.80 (2H), 2.01-2.08 (1H), 2.46-2.49 (1H), 3.00-3.20 (2H), 3.85-3.94 (1H), 4.10-4.20 (1H), 4.30 (s, 2H), 6.84-6.86 (1H), 6.94-6.97 (1H), 7.29-7.35 (2H), 7.42-7.44 (1H), 7.61-7.65 (1H), 8.40 (s, 1H), 8.81 (s, 2H), 11.80-12.02 (1H). |
| 239 | 488.2 | $^1$H NMR (400 MHz, DMSO-$d_6$): δ 1.02-1.04 (3H), 1.14-1.23 (4H), 2.17-2.22 (2H), 2.25-2.29 (4H), 3.31-3.68 (4H), 3.71.3.82 (1H), 4.27-4.33 (2H), 6.85-6.87 (1H), 6.92-6.95 (1H), 7.34-7.39 (2H), 7.43-7.45 (1H), 7.64-7.66 (1H), 8.38 (s, 1H), 8.84 (s, 2H). |
| 240 | 488.2 | $^1$H NMR (400 MHz, DMSO-$d_6$): δ 1.02-1.04 (3H), 1.14-1.23 (4H), 2.17-2.22 (2H), 2.25-2.29 (4H), 3.31-3.68 (4H), 3.71.3.82 (1H), 4.27-4.33 (2H), 6.85-6.87 (1H), 6.92-6.95 (1H), 7.34-7.39 (2H), 7.43-7.45 (1H), 7.64-7.66 (1H), 8.38 (s, 1H), 8.84 (s, 2H). |
| 241 | 430.2 | 1H NMR (400 MHz, dmso-d6, T = 373K): δ 9.24 (s, 2H), 8.53 (1H, d, J = 4.9 Hz), 8.42 (s, 1H), 7.81 (s, 1H), 7.19 (d, 1H, J = 4.9 Hz), 6.95 (d, 1H, J = 7.5 Hz), 6.82 (d, 1H, J = 7.56 Hz), 4.4 (bs, 1H), 4.31 (s, 2H), 3.64-3.62 (m, 2H), 3.48-3.45 (m, 2H), 3.02 (s, 3H), 2.71 (q, 2H, J = 7.5 Hz), 1.28 (t, 3H, J = 7, 5 Hz), 1.22 (bs, 2H), 1.15 (bs, 2H). |
| 242 | 444.2 | 1H NMR (400 MHz, dmso-d6, T = 373K): δ 9.25 (s, 2H), 8.54 (d, 1H, J = 5.2 Hz), 8.42 (s, 1H), 7.82 (s, 1H), 7.21 (d, 1H, J = 4.4 Hz), 6.95 (d, 1H, J = 7.6 Hz), 6.83 (d, 1H, J = 7.6 Hz), 4.39 (bs, 1H), 4.32 (s, 2H), 3.64-3.62 (m, 2H), |

TABLE 6-continued

Table of the pyhsico chemical data
(NMR, LCMS: [M + 1.0079]; mass found, M.p.)

| No. | LCMS | physico chemical data M.p./NMR |
|---|---|---|
| | | 3.48-3.46 (m, 2H), 3.03-2.98 (m, 4H), 1.3 (d, 6H, J = 6.4 Hz), 1.22 (bs, 2H), 1.15 (bs, 2H). |
| 243 | 455.2 | 1H NMR (400 MHz, dmso-d6, T = 373K): δ 9.24 (s, 2H), 8.58 (d, 1H, J = 3.5 Hz), 8.46 (s, 1H), 7.8 (s, 1H), 7.73 (bs, 1H), 7.19 (d, 1H, J = 4.4 Hz), 7.02-7 (m, 1H), 6.88-6.86 (m, 1H), 4.32 (s, 2H), 4.07 (s, 2H), 3.7-3.67 (m, 2H), 3.3 (bs, 2H), 2.75-2.66 (m, 2H), 1.44-117 (m, 7H). |
| 244 | 457.2 | 1H NMR (400 MHz, dmso-d6): δ 1.88 (s, 2H), 8.47-8.45 (m, 2H), 8.12 (bs, 1H), 7.57 (s, 1H), 7.02-6.88 (m, 3H), 4.29 (s, 2H), 4.07 (bs, 2H), 3.91 (s, 3H), 3.58 (bs, 2H), 3.26 (bs, 2H), 1.23 (bs, 2H), 1.15 (bs, 2H). |
| 245 | 433.2 | 1H NMR (400 MHz, dmso-d$_6$): δ 12.82 (bs, 1H), 8.85-8.83 (m, 2H), 8.41-8.36 (m, 1H), 7.66 (t, 1H, J = 7.4 Hz), 7.5-7.42 (m, 1H), 7.4-7.32 (m, 2H), 6.98-6.87 (m, 2H), 4.28-4.27 (m, 2H), 4.14 (s, 1H), 4.01 (s, 1H), 2.98 (s, 3H), 1.22 (bs, 2H), 1.15 (bs, 2H). |
| 246 | 447.2 | 1H NMR (400 MHz, dmso-d6, T = 373K): δ 8.81 (s, 2H), 8.39 (s, 1H), 7.64 (t, 1H, J = 7.5 Hz), 7.45-7.43 (m, 1H), 7.34-7.29 (m, 2H), 6.95-6.93 (m, 1H), 6.86-6.85 (m, 1H), 4.3 (s, 2H), 4.19 (s, 2H), 3.7 (s, 3H), 3.03 (s, 3H), 1.22 (bs, 2H), 1.16 (bs, 2H). |
| 248 | 424.2 | $^1$H NMR (400 MHz, DMSO-d$_6$, T = 363K): δ 8.92 (s, 2H), 8.51 (s, 1H), 7.72 (d, J = 7.8 Hz, 2H), 7.50-7.46 (m, 1H), 7.40-7.36 (m, 1H), 7.05 (d, J = 7.2 Hz, 1H), 6.84 (d, J = 7.6 Hz, 1H), 4.29 (s, 3H), 3.74 (s, 1H), 3.54 (d, J = 10.8 Hz, 1H), 3.29 (d, J = 10.8 Hz, 1H), 2.98 (s, 3H), 1.80-1.70 (m, 1H), 1.65-1.55 (m, 1H), 1.25-1.16 (m, 2H), 1.15-1.05 (m, 2H). |
| 249 | 424.2 | $^1$H NMR (400 MHz, DMSO-d$_6$, T = 363K): δ 8.90 (s, 2H), 8.51 (s, 1H), 7.70 (d, J = 7.8 Hz, 2H), 7.48-7.45 (m, 1H), 7.40-7.37 (m, 1H), 7.05 (d, J = 7.6 Hz, 1H), 6.83 (d, J = 7.8 Hz, 1H), 4.80-4.40 (m, 2H), 4.28 (s, 2H), 3.81 (s, 1H), 3.55 (d, J = 10.8 Hz, 1H), 3.32 (d, J = 10.1 Hz, 1H), 3.12 (d, J = 8.8 Hz, 1H), 3.05-2.95 (m, 1H), 1.85-1.75 (m, 1H), 1.70-1.60 (m, 1H), 1.25-1.16 (m, 2H), 1.15-1.05 (m, 2H). |
| 250 | 440.2 | $^1$H NMR (400 MHz, DMSO-d$_6$, T = 373K): δ 1.15-1.23 (4H), 1.60-1.63 (1H), 1.71-1.73 (1H), 2.93-2.96 (1H), 3.04-3.06 (1H), 3.24-3.27 (1H), 3.49-3.52 (1H), 3.54 (bs, 1H), 4.29 (s, 2H), 4.44-4.54 (1H), 6.80-6.83 (2H), 7.04-7.12/3H), 7.26-7.30 (1H), 8.51 (s, 1H), 8.83 (s, 2H). |
| 251 | 417.2 | $^1$H NMR (400 MHz, DMSO-d$_6$): δ 1.14-1.22 (4H), 2.52-2.58 (1H), 3.00 (s, 3H), 3.48-3.55 (3H), 4.28 (s, 2H), 4.73-4.76 (1H), 6.55-6.57 (1H), 6.61-6.71 (1H), 6.85-6.87 (1H), 6.96-7.00 (2H), 8.10-8.12 (1H), 8.38 (s, 2H). |
| 252 | 459.2 | $^1$H NMR (400 MHz, DMSO-d$_6$): δ 1.14-1.22 (4H), 2.18 (s, 3H), 3.00 (s, 3H), 3.51-3.55 (1H), 3.60-3.63 (1H), 4.29 (s, 2H), 4.75-7.78 (1H), 6.85-6.87 (1H), 6.95-6.98 (1H), 7.52-7.54 (1H), 8.02 (s, 1H), 8.40 (s, 1H), 8.50-8.52 (1H), 9.11 (s, 12H), 10.44 (s, 1H). |
| 253 | 449.2 | $^1$H NMR (400 MHz, MEOD): δ 1.17-1.20 (4H), 3.11-3.14 (3H), 3.45-3.47 (1H), 3.66-3.69 (2H), 3.83 (s, 3H), 4.29 (s, 2H), 6.82-6.84 (1H), 6.92-6.95 (1H), 6.99-7.07 (1H), 7.12-7.18 (1H), 8.52 (s, 1H), 8.75 (s, 2H). |
| 254 | 442.2 | 1H NMR (400 MHz, dmso-d6, T = 373K): δ 9.23 (s, 2H), 8.45 (d, 1H, J = 5.1 Hz), 8.4 (d, J = 7.4 Hz, 1H), 7.64 (s, 1H), 7.03 (d, 1H, J = 5.0 Hz), 6.94 (d, 1H, J = 7.5 Hz), 6.82 (d, 1H, J = 7.6 Hz), 4.3 (bs, 1H), 4.31 (s, 2H), 3.65-3.6 (m, 2H), 3.47-3.45 (m, 2H), 3.02 (s, 3H), 2.05-2.01 (m, 1H), 1.22-1.07 (m, 6H), 0.94-0.92 (m, 2H). |
| 255 | 470.2 | 1H NMR (400 MHz, dmso-d6, T = 373K): δ 9.21 (s, 2H), 8.46 (s, 1H), 8.2 (d, 1H, J = 5.9 Hz), 7.73 (bs, 1H), 7.1 (d, 1H, J = 2.0 Hz), 7.0-6.98 (m, 1H), 6.88-6.86 (m, 1H), 6.6-6.58 (m, 1H), 4.31 (s, 2H), 4.07 (s, 2H), 3.69-3.67 (m, 2H), 3.3 (bs, 2H), 3.05 (s, 6H), 1.27-1.17 (m, 4H). |
| 256 | 432.2 | 1H NMR (400 MHz, dmso-d6, T = 373K): δ 8.8 (s, 2H), 8.42 (s, 1H), 7.63 (t, 1H, J = 7.6 Hz), 7.47-7.42 (m, 1H), 7.34-7.29 (m, 2H), 6.9-6.82 (m, 4H), 4.3 (s, 2H), 3.96 (s, 2H), 2.99 (s, 3H), 1.27-1.15 (m, 4H). |
| 257 | 446.2 | 1H NMR (400 MHz, dmso-d6, T = 373K): δ 9.23 (s, 2H), 8.46-8.41 (m, 2H), 7.48 (s, 1H), 6.96-6.82 (m, 3H), 4.39 (bs, 1H), 4.31-4.25 (m, 4H), 3.62 (bs, 2H), 3.45 (bs, 2H), 3.02 (s, 3H), 1.39 (t, 3H, 6.6 Hz), 1.22 (bs, 2H), 1.15 (bs, 2H). |
| 258 | 442.2 | 1H NMR (400 MHz, dmso-d6, T = 373K): δ 9.09 (s, 2H), 8.43 (s, 1H), 8.11-8.08 (m, 2H), 7.01-6.97 (m, 2H), 6.9-6.88 (m, 1H), 6.46 (d, 1H, J = 4.0 Hz), 6.17 (s, 2H), 4.29 (s, 2H), 4.05 (bs, 2H), 3.6 (bs, 2H), 3.27 (bs, 2H), 1.22 (bs, 2H), 1.15 (bs, 2H). |
| 259 | 443.2 | 1H NMR (400 MHz, dmso-d6): δ 9.07 (s, 2H), 8.41 (s, 1H), 6.94 (d, 1H, J = 7.6 Hz), 6.88 (d, H, J = 7.6 Hz), 6.81 (bs, 1H), 6.33 (s, 1H), 6.01 (bs, 2H), 4.27 (s, 2H), 3.7-3.35 (m, 8H), 2.31 (s, 3H), 1.21 (bs, 2H), 1.13 (bs, 2H). |
| 260 | 430.2 | 1H NMR (400 MHz, dmso-d6, T = 373K): δ 9.2 (s, 2H), 8.41 (s, 1H), 7.58 (s, 1H), 7.04 (s, 1H), 6.94 (d, 1H, J = 7.5 Hz), 6.82 (d, 1H, J = 7.6 Hz), 4.4 (bs, 1H), 4.31 (s, 2H), 3.62 (bs, 2H), 3.46 (bs, 2H), 3.02 (s, 3H), 2.5 (s, 3H, masked with DMSO peak), 2.36 (s, 3H), 1.22 (bs, 2H), 1.15 (bs, 2H). |
| 261 | 431.2 | 1H NMR (400 MHz, dmso-d$_6$, T = 373K): δ 9.06 (s, 2H), 8.39 (s, 1H), 6.93 (d, 1H, J = 7.6 Hz), 6.85-6.81 (m, 2H), 6.39 (s, 1H), 5.74 (bs, 2H), 4.43 (bs, 1H), 4.29 (s, 2H), 3.63-3.62 (m, 2H), 3.47-3.44 (m, 2H), 3.02 (s, 3H), 2.34 (s, 3H), 1.21 (bs, 2H), 1.14 (bs, 2H). |
| 262 | 403.2 | $^1$H NMR (400 MHz, DMSO-d$_6$): δ 1.15-1.24 (4H), 3.00 (s, 3H), 3.51-3.55 (2H), 3.61-3.64 (1H), 4.75-4.78 (1H), 6.87-6.89 (1H), 6.98-7.00 (1H), 7.79-7.83 (1H), 8.28-8.30 (1H), 8.42 (s, 1H), 9.21-9.23 (1H), 9.36 (s, 2H). |
| 263 | 440.2 | $^1$H NMR (400 MHz, DMSO-d$_6$, T = 373K): δ 1.20-1.28 (4H), 1.91-1.94 (1H), 2.11-2.14 (1H), 3.33-3.35 (1H), 3.44-3.47 (1H), 3.53-3.57 (1H), 3.67.3.71 (2H), 4.34 (s, 2H), 4.43-4.45 (1H), 7.72-4.74 (1H), 6.81-6.83 (1H), 6.91-6.93 (1H), 7.10 (s, 1H), 7.17-7.19 (1H), 7.51-7.59 (1H), 8.11-8.13 (1H), 8.56 (s, 1H), 9.05 (s, 2H). |
| 264 | 417.2 | $^1$H NMR (400 MHz, DMSO-d$_6$, T = 373K): δ 1.15-1.21 (4H), 3.00-3.03 (3H), 3.45-3.52 (2H), 3.60-3.63 (2H), 4.29 (s, 2H), 4.39-4.41 (1H), 6.80-6.83 (2H), 6.93-6.95 (1H), 7.07-7.11 (2H), 7.27-7.30 (1H), 8.39 (s, 1H), 8.84 (s, 2H), 9.21 (s, 1H). |
| 265 | 443.2 | 1H NMR (400 MHz, dmso-d6, T = 373K): δ 9.12 (s, 2H), 8.45 (s, 1H), 8.26 (bs, 1H), 7.73 (bs, 1H), 7.18 (s, 1H), 7.02 (d, 1H, J = 7.4 Hz), 6.86 (d, 1H, J = 7.5 Hz), 6.69 (bs, 1H), 4.3 (s, 2H), 4.07 (s, 2H), 3.68 (t, 2H, J = 5.3 Hz), 3.3 (bs, 2H), 1.27-1.17 (m, 4H). |
| 266 | 429.2 | $^1$H NMR (400 MHz, DMSO-d$_6$): δ 8.95 (s, 2H), 8.35 (s, 1H), 7.59 (s, 1H), 7.54 (d, J = 8.12 Hz, 1H), 7.39 (t, J = 7.72 Hz, 1H), 7.23 (d, J = 7.4 Hz, 1H), 6.93 (d, J = 7.68 Hz, 1H), 6.84 (d, J = 7.52 Hz, 1H), 4.74 (bs, 1H), 4.27 (s, 2H), 3.64 (bs, 1H), 3.51 (bs, 2H), 2.99 (s, 3H), 2.67 (q, J = 7.84Hz, 7.52Hz, 2H), 1.24 (t, J = 7.76Hz, 5H), 1.14 (s, 2H). |

TABLE 6-continued

Table of the pyhsico chemical data
(NMR, LCMS: [M + 1.0079]; mass found, M.p.)

| No. | LCMS | physico chemical data M.p./NMR |
|---|---|---|
| 267 | 441.2 | $^1$H NMR (400 MHz, DMSO-$d_6$): δ 8.95 (s, 2H), 8.38 (s, 1H), 7.48 (d, J = 7.76 Hz, 1H), 7.41 (s, 1H), 7.34 (t, J = 7.68 Hz, 1H), 7.09 (d, J = 7.6 Hz, 1H), 6.93 (d, J = 7.6 Hz, 1H), 6.84 (d, J = 7.56 Hz, 1H), 4.74 (bs, 1H), 4.27 (s, 2H), 3.63 (bs, 1H), 3.51 (bs, 2H), 2.98 (s, 3H), 1.99-1.95 (m, 1H), 1.22-1.12 (m, 4H), 1.00-0.95 (m, 2H), 0.81-0.77 (m, 2H). |
| 268 | 430.2 | $^1$H NMR (400 MHz, DMSO-$d_6$): δ 9.28 (s, 2H), 8.40 (s, 1H), 7.80 (d, J = 6.48 Hz, 1H), 7.23 (d, J = 8.16 Hz, 1H), 6.95 (d, J = 6.92 Hz, 1H), 6.86 (d, J = 7.28 Hz, 1H), 4.74 (bs, 1H), 4.29 (s, 2H), 3.64 (bs, 1H), 3.52 (bs, 2H), 2.99 (s, 3H), 2.81 (q, J = 7.84 Hz, 7.64 Hz, 2H), 1.29 (t, J = 7.52 Hz, 3H), 1.22-1.14 (m, 4H). |
| 269 | 442.2 | $^1$H NMR (400 MHz, DMSO-$d_6$): δ 9.23 (s, 2H), 8.39 (s, 1H), 7.73 (d, J = 3.8 Hz, 2H), 7.26 (t, J = 4.52 Hz, 1H), 6.95 (d, J = 7.52 Hz, 1H), 6.85 (d, J = 7.6 Hz, 1H), 4.74 (bs, 1H), 4.28 (s, 2H), 3.64 (bs, 1H), 3.51 (bs, 2H), 2.99 (s, 3H), 2.16-2.12 (m, 1H), 1.21-1.14 (m, 4H), 1.06-0.97 (m, 4H). |
| 270 | 400.2 | 1H NMR (400 MHz, dmso-d6): δ 9.28 (s, 2H), 8.53 (d, 1H, J = 4.8 Hz), 8.41 (s, 1H), 7.89 (s, 1H), 7.2 (d, 1H, J = 4.6 Hz), 6.94 (d, 1H, J = 7.6 Hz), 6.85 (d, 1H, J = 7.6 Hz), 4.29 (s, 2H), 2.98 (bs, 6H), 2.67 (q, 2H, J = 7.5 Hz), 1.27-1.14 (m, 7H). |
| 271 | 415.2 | 1H NMR (400 MHz, dmso-d6): δ 9.25 (s, 2H), 8.41 (s, 1H), 8.19 (d, 1H, J = 5.9 Hz), 7.15 (s, 1H), 6.94 (d, 1H, J = 7.5 Hz), 6.86 (d, 1H, J = 7.5 Hz), 6.59 (d, 1H, J = 4.0 Hz), 4.28 (s, 2H), 3.04 (s, 6H), 2.96 (bs, 6H), 1.21-1.13 (m, 4H). |
| 272 | 445.2 | 1H NMR (400 MHz, dmso-d6): δ 9.26 (s, 2H), 8.4 (s, 1H), 8.19 (d, 1H, J = 5.9 Hz), 7.16 (d, 1H, J = 1.8 Hz), 6.93 (d, 1H, J = 7.6 Hz), 6.84 (d, 1H, J = 7.4 Hz), 6.6-6.58 (m, 1H), 4.76-4.71 (m, 1H), 4.28 (s, 2H), 3.65-3.51 (m, 4H), 3.04-2.99 (m, 9H), 1.21 (bs, 2H), 1.13 (bs, 2H). |
| 273 | 435.2 | $^1$H NMR (400 MHz, DMSO-$d_6$): δ 9.01 (s, 2H), 8.38 (s, 1H), 7.86 (s, 1H), 7.73 (d, J = 7.36 Hz, 1H), 7.51 (t, J = 7.84 Hz, 1H), 7.43 (d, J = 8.12 Hz, 1H), 6.95 (d, J = 7.52 Hz, 1H), 6.85 (d, J = 7.68 Hz, 1H), 4.75 (bs, 1H), 4.27 (s, 2H), 3.62 (bs, 1H), 3.51 (bs, 2H), 2.98 (s, 3H), 1.21-1.14 (m, 4H). |
| 274 | 426.2 | $^1$H NMR (400 MHz, DMSO-$d_6$, T = 373K): δ 1.19-1.27 (4H), 1.92-1.95 (1H), 2.11-2.15 (1H), 3.40-3.48 (2H), 3.68-3.76 (2H), 4.36 (s, 2H), 4.40 (s, 1H), 4.73-4.76 (1H), 6.90-6.92 (1H), 7.16-7.18 (1H), 7.75-7.78 (1H), 8.21-8.23 (1H), 8.59 (s, 1H), 9.06-9.09 (1H), 9.19-9.21 (1H), 9.34 (s, 2H), 9.82-9.86 (1H). |
| 275 | 426.2 | 1H NMR (400 MHz, dmso-d6): δ 9.28 (s, 2H), 8.53 (d, 2H, J = 4.6 Hz), 7.89 (s, 1H), 7.22 (d, 1H, J = 4.9 Hz), 7.07 (d, 1H, J = 7.7 Hz), 6.85 (d, 1H, J = 7.6 Hz), 4.29 (s, 2H), 3.49-3.42 (m, 4H), 2.68 (q, 2H, J = 7.5 Hz), 1.9-1.8 (m, 4H), 1.27-1.11 (m, 7H). |
| 276 | 441.2 | 1H NMR (400 MHz, dmso-d6): δ 9.26 (s, 2H), 8.53 (s, 1H), 8.19 (d, 1H, J = 5.9 Hz), 7.15 (d, 1H, J = 2.1 Hz), 7.06 (d, 1H, J = 7.76 Hz), 6.84 (d, 1H, J = 7.6 Hz), 6.6-6.58 (m, 1H), 4.28 (s, 2H), 3.49-3.41 (m, 4H), 3.04 (s, 6H), 1.9-1.79 (m, 4H), 1.22 (bs, 2H), 1.14 (bs, 2H). |
| 277 | 479.2 | $^1$H NMR (400 MHz, DMSO-$d_6$): δ 1.12-1.21 (4H), 2.96 (s, 3H), 3.47-3.60 (3H), 4.27 (s, 3H), 4.70-4.80 (1H), 6.82-6.84 (1H), 6.92-6.94 (1H), 7.72-7.76 (1H), 7.87-7.90 (1H), 8.08-8.10 (1H), 8.24 (bs, 1H), 8.38 (s, 1H), 9.05 (s, 2H). |
| 278 | 445.2 | $^1$H NMR (400 MHz, DMSO-$d_6$): δ 8.83 (s, 2H), 8.44 (s, 1H), 7.65 (t, J = 7.6 Hz, 1H), 7.43-7.46 (m, 1H), 7.34 (q, J = 7.2 Hz & 7.6 Hz, 2H), 7.05 (bs, 1H), 6.83 (d, J = 7.6 Hz, 1H), 4.77 (s, 1H), 4.28 (s, 2H), 3.60 (s, 2H), 3.48 (s, 2H), 2.86 (d, J = 11.6 Hz, 1H), 1.22 (s, 2H), 1.1.16 (d, J = 9.6 Hz, 2H), 0.57 (s, 2H), 0.47 (s, 2H). |
| 279 | 482.2 | see experimental section (A-26) |
| 280 | 418.2 | 1H NMR (400 MHz, dmso-d6, T = 373K): δ 9.04 (s, 2H), 8.95 (s, 1H), 7.7-7.56 (m, 2H), 6.96-6.88 (m, 2H), 6.47-6.45 (m, 1H), 4.54 (bs, 2H), 4.33 (s, 2H), 3.36 (bs, 2H), 2.7 (s, 3H), 1.29 (bs, 2H), 1.22 (bs, 2H). |
| 281 | 463.2 | $^1$H NMR (400 MHz, DMSO-$d_6$): δ 1.14-1.23 (4H), 2.83 (s, 3H), 2.99 (s, 3H), 3.48-3.66 (3H), 4.28 (s, 2H), 4.71-4.77 (1H), 6.84-6.86 (1H), 6.94-6.96 (1H), 7.70-7.72 (2H), 9.91-7.93 (1H), 7.99 (bs, 1H), 8.39 (bs, 1H), 9.04 (bs, 2H). |
| 282 | 446.2 | 1H NMR (400 MHz, dmso-d6, T = 373K): δ 9.22 (s, 2H), 8.41 (s, 1H), 7.32 (s, 1H), 6.94 (d, 1H, J = 7.5 Hz), 6.82 (d, 1H, J = 7.5 Hz), 6.78 (s, 1H), 4.39 (bs, 1H), 4.31 (s, 2H), 3.91 (s, 3H), 3.64-3.6 (m, 2H), 3.47-3.44 (m, 2H), 3.02 (s, 3H), 1.22 (bs, 2H), 1.15 (bs, 2H). |
| 283 | 433.2 | $^1$H NMR (400 MHz, DMSO-$d_6$): δ 8.83 (s, 2H), 8.37 (s, 1H), 7.66 (t, J = 7.6 Hz, 1H), 7.45 (d, J = 6.4 Hz, 1H), 7.35 (q, J = 6.8 Hz & 8.0 Hz, 2H), 6.95 (d, J = 7.6 Hz, 1H), 6.86 (s, 1H), 4.79 (d, J = 4.4 Hz, 1H), 4.27 (s, 2H), 3.86-3.98 (m, 1H), 3.17 (bs, 2H), 2.99 (s, 3H), 1.21 (s, 2H), 1.14 (s, 3H), 0.90 (bs, 2H). |
| 284 | 433.2 | $^1$H NMR (400 MHz, DMSO-$d_6$): δ 8.83 (s, 2H), 8.37 (s, 1H), 7.65 (t, J = 8.0 Hz, 1H), 7.43-7.48 (m, 1H), 7.32-7.38 (m, 2H), 6.95 (d, J = 7.6 Hz, 1H), 6.85 (d, J = 7.2 Hz, 1H), 4.79 (d, J = 4.8 Hz, 1H), 4.27 (s, 2H), 3.86-3.98 (m, 1H), 3.16 (bs, 2H), 2.99 (s, 3H), 1.16-1.21 (m, 2H), 1.12-1.14 (m, 3H), 0.90 (bs, 2H). |
| 285 | 433.2 | $^1$H NMR (400 MHz, DMSO-$d_6$): δ 8.82 (s, 2H), 8.38 (s, 1H), 7.65 (t, J = 8.0 Hz, 1H), 7.42-7.47 (m, 1H), 7.31-7.37 (m, 2H), 6.93 (d, J = 7.2 Hz, 1H), 6.84 (d, J = 7.6 Hz, 1H), 4.76 (bs, 1H), 4.26 (s, 2H), 3.85 (bs, 1H), 3.42 (bs, 2H), 3.27 (bs, 1H), 2.81 (s, 3H), 1.05-1.20 (m, 7H). |
| 286 | 441.2 | |
| 287 | 481.2 | $^1$H NMR (400 MHz, DMSO-$d_6$): δ 1.15-1.23 (4H), 2.83 (s, 3H), 2.98 (bs, 3H), 3.46-3.55 (2H), 3.60-3.68 (1H), 4.28 (s, 2H), 4.68-4.80 (1H), 6.85-6.88 (1H), 6.95-6.97 (1H), 7.59-7.64 (1H), 7.76-7.79 (1H), 7.93-7.95 (1H), 8.38 (s, 1H), 8.90 (s, 2H). |
| 288 | 464.2 | $^1$H NMR (400 MHz, DMSO-$d_6$): δ 1.15-1.23 (4H), 2.91 (s, 3H), 3.00 (s, 3H), 3.50-3.67 (3H), 4.31 (s, 2H), 4.74-4.78 (1H), 6.86-6.88 (1H), 6.97-6.99 (1H), 7.66-7.68 (1H), 8.22 (s, 1H), 8.42 (s, 1H), 8.45-8.47 (1H), 9.32 (s, 2H). |
| 289 | 480.2 | $^1$H NMR (400 MHz, DMSO-$d_6$): δ 1.15-1.24 (4H), 3.00 (s, 3H), 3.42 (s, 3H), 3.50-3.65 (3H), 4.32 (s, 2H), 4.70-4.80 (1H), 6.88-6.90 (1H), 6.98-7.00 (1H), 7.81-7.83 (1H), 8.43-8.48 (2H), 8.97-8.99 (1H), 9.37 (s, 2H). |
| 290 | 417.2 | see experimental section (A-27) |
| 291 | 483.2 | 1H NMR (400 MHz, dmso-d6 at T = 373K): 9.20 (s, 2H), 8.44 (s, 1H), 8.19 (d, 1H, J = 5.7 Hz), 6.97 (d, 2H, J = 7.5 Hz), 6.86 (d, 1H, J = 7.6 Hz), 6.45-6.44 (m, 1H), 4.30 (s, 2H), 3.65 (bs, 4H), 3.55 (bs, 4H), 3.40 (bs, 4H), 2.03-2.01 (m, 4H), 1.22-1.15 (m, 4H). |
| 292 | 457.2 | 1H NMR (400 MHz, dmso-d6, T = 373K): 9.13 (s, 2H), 8.43 (s, 1H), 8.13 (d, 1H, J = 5.6 Hz), 7.0-6.95 (m, 2H), 6.86 (d, 1H, J = 7.5 Hz), 6.48-6.47 (m, 1H), 6.22 (bs, 1H), 4.3 (s, 2H), |

TABLE 6-continued

Table of the pyhsico chemical data
(NMR, LCMS: [M + 1.0079]; mass found, M.p.)

| No. | LCMS | physico chemical data M.p./NMR |
|---|---|---|
| | | 3.64 (bs, 4H), 3.55 (bs, 4H), 3.26-3.19 (m, 2H), 1.27-1.09 (m, 7H). |
| 293 | 458.2 | 1H NMR (400 MHz, dmso-d6): 9.28 (s, 2H), 8.60 (d, 1H, J = 5.1 Hz), 8.43 (s, 1H), 7.94 (s, 1H), 7.35 (d, 1H, J = 4.2 Hz), 6.98 (d, 1H, J = 7.5 Hz), 6.89 (d, 1H, J = 7.5 Hz), 5.46 (d, 1H, J = 3.4 Hz), 4.79 (bs, 1H), 4.30 (s, 2H), 3.62 (bs, 8H), 1.40 (d, 3H, J = 6.2 Hz), 1.23 (bs, 2H), 1.14 (bs, 2H). |
| 294 | 472.2 | 1H NMR (400 MHz, dmso-d6): 9.29 (s, 2H), 8.59 (d, 1H, J = 5.1 Hz), 8.44 (s, 1H), 8.01 (s, 1H), 7.45 (d, 1H, J = 4.5 Hz), 6.98 (d, 1H, J = 7.5 Hz), 6.89 (d, 1H, J = 7.5 Hz), 5.30 (s, 1H), 4.30 (s, 2H), 3.61 (bs, 8H), 1.48 (s, 6H), 1.23 (bs, 2H), 1.14 (bs, 2H). |
| 295 | 483.2 | 1H NMR (400 MHz, dmso-d6): 9.17 (s, 2H), 8.42 (s, 1H,), 8.10 (d, 1H, J = 5.6 Hz), 7.04 (s, 1H), 6.96 (d, 1H, J = 7.7 Hz), 6.88 (d, 1H, J = 7.6 Hz), 6.72-6.70 (m, 1H), 6.51-6.5 (m, 1H), 4.28 (s, 2H), 3.61 (bs, 8H), 3.06-3.03 (m, 2H), 1.21-1.07 (m, 5H), 0.50-0.47 (m, 2H), 0.25-0.23 (m, 2H). |
| 296 | 497.2 | $^1$H NMR (400 MHz, DMSO-d$_6$): δ 1.14-1.23 (4H), 2.98 (s, 3H), 3.48-3.66 (3H), 4.29 (s, 2H), 4.70-4.78 (1H), 6.86-6.88 (1H), 6.96-6.98 (1H), 7.63-7.68 (1H), 7.97-8.01 (1H), 8.20-8.23 (1H), 8.39 (s, 1H), 8.93 (s, 2H). |
| 297 | 439.2 | $^1$H NMR (400 MHz, DMSO-d$_6$): δ 9.22 (s, 2H), 8.52 (t, J = 4.8 Hz, 2H), 7.80 (s, 1H), 7.17 (d, J = 4.4 Hz, 1H), 7.07 (d, J = 7.2 Hz, 1H), 6.85 (d, J = 7.6 Hz, 1H), 4.49 (bs, 1H), 4.32 (s, 2H), 3.71 (s, 1H), 3.55 (dd, J = 10.0 Hz & 10.0 Hz, 1H), 3.26 (d, J = 10.4 Hz, 1H), 3.06 (d, J = 9.6 Hz, 1H), 2.32 (s, 3H), 1.73 (d, J = 9.6 Hz, 1H), 1.61 (d, J = 9.2 Hz, 1H), 1.23 (s, 2H), 1.16 (s, 2H). |
| 298 | 453.2 | $^1$H NMR (400 MHz, DMSO-d$_6$): δ 9.23 (s, 2H), 8.54 (d, J = 5.6 Hz, 2H), 7.81 (s, 1H), 7.19 (d, J = 4.8 Hz, 1H), 7.07 (d, J = 7.6 Hz, 1H), 6.85 (d, J = 7.6 Hz, 1H), 4.49 (bs, 1H), 4.32 (s, 2H), 3.67 (s, 1H), 3.52-3.58 (m, 2H), 3.26 (d, J = 10.4 Hz, 1H), 3.06 (d, J = 9.6 Hz, 1H), 2.70 (q, J = 10.4 Hz & 7.2 Hz, 2H), 1.74 (d, J = 8.4 Hz, 1H), 1.62 (d, J = 9.2 Hz, 1H), 1.28 (t, J = 7.6 Hz, 3H), 1.23 (s, 2H), 1.16 (s, 2H). |
| 299 | 386.2 | 1H-NMR (400 MHz; DMSO-D$_6$,): δ 9.26 (s, 2H), 8.51 (d, J = 4.8 Hz, 1H), 8.40 (s, 1H), 7.86 (s, 1H), 7.19 (d, J = 4.8 Hz, 1H), 6.95 (d, J = 7.6 Hz, 1H), 6.86 (d, J = 7.6 Hz, 1H), 4.29 (s, 2H), 2.97 (bs, 6H), 1.22 (s, 2H), 1.14-1.15 (m, 2H). |
| 300 | 429.2 | $^1$H NMR (400 MHz, DMSO-d$_6$): δ 9.25 (s, 2H), 8.51 (s, 1H), 8.42 (s, 1H), 7.87 (s, 1H), 7.40 (s, 1H), 7.19 (s, 1H), 7.09-7.13 (m, 1H), 6.92-7.00 (m, 1H), 6.86 (s, 1H), 4.29 (s, 2H), 4.03 (s, 1H), 3.86 (s, 1H), 2.96 (s, 3H), 2.39 (s, 3H), 1.14-1.22 (m, 4H). |
| 301 | 440.2 | $^1$H NMR (400 MHz, DMSO-d$_6$): δ 9.07 (s, 2H), 8.53 (s, 1H), 8.10 (d, J = 5.2 Hz, 1H), 7.02-7.07 (m, 2H), 6.84 (d, J = 7.6 Hz, 1H), 6.5 (s, 1H), 5.5 (s, 2H), 4.5 (bs, 1H), 4.3 (s, 2H), 3.65 (s, 1H), 3.53 (d, J = 10.0 Hz, 1H), 3.21-3.27 (m, 2H), 3.05 (m, 1H), 1.73 (d, J = 8.4 Hz, 1H), 1.61 (d, J = 8.4 Hz, 1H), 1.22 (s, 2H), 1.15 (s, 2H). |
| 302 | 468.2 | $^1$H NMR (400 MHz, DMSO-d$_6$): δ 9.21 (s, 2H), 8.54 (s, 1H), 8.21 (d, J = 6.0 Hz, 1H), 7.11 (s, 1H), 7.05 (d, J = 7.6 Hz, 1H), 6.84 (d, J = 8.0 Hz, 1H), 6.57-6.59 (m, 1H), 4.5 (bs, 1H), 4.31 (s, 2H), 3.66 (s, 1H), 3.51-3.54 (m, 1H), 3.26 (d, J = 10.4 Hz, 1H), 3.05 (s, 6H), 1.74 (d, J = 9.2 Hz, 1H), 1.61 (d, J = 9.2 Hz, 1H), 1.22 (s, 2H), 1.16-1.18 (m, 2H). |
| 303 | 386.2 | 1H-NMR (400 MHz; DMSO-D$_6$,): δ 9.26 (s, 2H), 8.41 (s, 1H), 7.78 (d, J = 6.8 Hz, 2H), 7.22 (d, J = 6.8 Hz, 1H), 6.95 (d, J = 7.6 Hz, 1H), 6.95 (d, J = 7.6 Hz, 1H), 6.86 (d, J = 7.6 Hz, 1H), 4.29 (s, 2H), 2.95-2.98 (bs, 6H), 2.54 (s, 3H), 1.22 (s, 2H), 1.12-1.14 (m, 2H). |
| 304 | 425.2 | $^1$H NMR (400 MHz, DMSO-d$_6$): δ 9.24 (s, 2H), 8.66 (d, J = 4.0 Hz, 1H), 8.54 (s, 1H), 7.96 (d, J = 8.0 Hz, 1H), 7.87 (t, J = 8.0 Hz, 1H), 7.33 (q, J = 5.2 Hz & 2.4 Hz, 1H), 7.07 (d, J = 7.6 Hz, 1H), 6.85 (d, J = 7.6 Hz, 1H), 4.50 (bs, 1H), 4.32 (s, 2H), 3.65 (s, 1H), 3.53 (d, J = 10.0 Hz, 1H), 3.26 (d, J = 10.0 Hz, 1H), 3.05 (d, J = 9.6 Hz, 1H), 1.73 (d, J = 9.2 Hz, 1H), 1.61 (d, J = 9.2 Hz, 1H), 1.22 (d, J = 8.4 Hz, 2H), 1.16 (S, 2H). |
| 305 | 439.2 | $^1$H NMR (400 MHz, DMSO-d$_6$): δ 9.21 (s, 2H), 8.54 (s, 1H), 7.76 (t, J = 6.0 Hz, 2H), 7.21 (t, J = 3.6 Hz, 1H), 7.07 (d, J = 8.0 Hz, 1H), 6.85 (d, J = 7.6 Hz, 1H), 4.49 (bs, 1H), 4.32 (s, 2H), 3.65 (s, 1H), 3.53 (d, J = 10.4 Hz, 1H), 3.25 (d, J = 10.0 Hz, 1H), 3.05 (d, J = 9.6 Hz, 1H), 2.56 (s, 3H), 2.20 (bs, 1H), 1.73 (d, J = 9.6 Hz, 1H), 1.61 (d, J = 9.6 Hz, 1H), 1.23 (s, 2H), 1.16 (S, 2H). |
| 306 | 372.2 | 1H-NMR (400 MHz; DMSO-D$_6$,): δ 9.24 (s, 2H), 8.66 (d, J = 4.2 Hz, 1H), 8.42 (s, 1H), 7.95 (d, J = 8.04 Hz, 1H), 7.86 (dd, J = 7.6 Hz & 1.6 Hz, 1H), 7.32-7.35 (m, 1H), 6.96 (d, J = 7.2 Hz, 1H), 6.84 (d, J = 7.6 Hz, 1H), 4.30 (s, 2H), 2.95-2.98 (m, 6H), 1.20-1.27 (m, 2H), 1.14-1.18 (m, 2H). |
| 307 | 429.2 | $^1$H NMR (400 MHz, DMSO-d$_6$): δ 9.22 (s, 2H), 8.45 (s, 1H), 7.73-7.77 (m, 2H), 7.20 (q, J = 2.0 Hz & 4.0 Hz, 1H), 6.82-6.99 (m, 4H), 4.31 (s, 2H), 3.97 (s, 2H), 3.00 (s, 3H), 2.56 (s, 3H), 1.13-1.27 (m, 4H). |
| 308 | 443.2 | $^1$H NMR (400 MHz, DMSO-d$_6$): δ 9.28 (d, J = 9.6 Hz, 2H), 8.54 (d, J = 4.8 Hz, 1H), 8.43 (m, J = 10.4 Hz, 1H), 7.89 (s, 1H), 7.40-7.44 (m, 1H), 7.22 (d, J = 4.8 Hz, 1H), 6.84-7.13 (m, 3H), 4.29 (s, 2H), 4.03 (s, 1H), 3.85 (s, 1H), 2.96 (s, 3H), 2.69 (q, J = 7.2 Hz & 7.6 Hz, 2H), 1.23-1.27 (m, 5H), 1.14 (s, 1H). |
| 309 | 477.2 | 1H NMR (400 MHz, dmso-d6): 8.83 (s, 2H), 8.38 (s, 1H), 7.67-7.65 (m, 1H) 7.55-7.51 (m, 1H), 7.29-7.25 (m, 1H), 6.96 (d, 1H, J = 7.2 Hz), 6.87 (d, 1H, J = 7.5 Hz), 5.13 (s, 1H), 4.75 (bs, 1H), 4.28 (bs, 2H), 3.63 (bs, 1H), 3.51 (s, 2H), 3.33 (1H, merged with DMSO-H2O), 2.99 (s, 3H), 1.48 (s, 6H), 1.21 (bs, 2H), 1.14 (bs, 2H). |
| 310 | 445.2 | 1H NMR (400 MHz, dmso-d6, T = 353K): δ 8.82 (s, 2H), 8.49 (s, 1H), 7.64 (t, 1H, J = 7.3 Hz), 7.47-7.42 (m, 1H), 7.35-7.31 (m, 2H), 7.06 (d, 1H, J = 7.44 Hz), 6.85 (d, 1H, J = 7.6 Hz), 4.39 (bs, 1H), 4.29 (s, 1H), 3.56-3.39 (m, 5H), 3.30-3.26 (m, 1H), 2.35-2.32 (m, 1H), 1.97-1.92 (m, 1H), 1.69-1.64 (m, 1H), 1.22-1.16 (m, 4H). |
| 311 | 445.2 | 1H NMR (400 MHz): δ 8.85 (s, 2H), 8.48 (s, 1H), 7.67 (t, 1H, J = 7.68 Hz), 7.48-7.32 (m, 3H), 7.08 (d, 1H, J = 7.48 Hz), 6.87 (d, 1H, J = 7.48 Hz), 4.72-4.61 (m, 1H), 4.28 (s, 2H), 3.59-3.44 (m, 4H), 3.29-3.21 (m, 2H) 2.35-2.25 (m, 1H), 1.95-1.87 (m, 1H), 1.65-1.62 (m, 1H), 1.21-1.15 (m, 4H). |
| 312 | 463.2 | 1H NMR (400 MHz, dmso-d6): 8.82 (s, 2H), 8.37 (s, 1H), 7.57 (d, 1H, J = 7.1 Hz), 7.41 (bs, 1H), 7.29 (t, 1H, J = 9.8 Hz), 6.94 (d, 1H, J = 7.5 Hz), 6.86 (d, 1H, J = 7.1 Hz), 6.85 (d, 1H, J = 3.9 Hz), 4.79-4.76 (m, 2H), 4.27 (s, 2H), 3.62 (bs, 1H), 3.51 (bs, 2H), 3.3 (1H, merged with DMSO-H2O peak), 2.98 (s, 3H), 1.35 (d, 3H, J = 6.2 Hz), 1.21 (bs, 2H), 1.14 (bs, 2H). |

TABLE 6-continued

Table of the pyhsico chemical data
(NMR, LCMS: [M + 1.0079]; mass found, M.p.)

| No. | LCMS | physico chemical data M.p./NMR |
|---|---|---|
| 313 | 459.2 | 1H NMR (400 MHz, dmso-d6, T = 353K): δ 8.81 (s, 2H), 8.38 (s, 1H), 7.66-7.62 (m, 1H), 7.46-7.43 (m, 1H), 7.35-7.30 (m, 2H), 6.94-6.83 (m, 2H), 4.29 (s, 2H), 4.23-4.21 (m, 1H), 4.1-3.96 (m, 2H), 3.34-3.26 (m, 2H), 2.94-2.84 (m, 1H), 2.76-2.73 (m, 1H), 1.8-1.76 (m, 1H), 1.69-1.65 (m, 2H), 1.50-1.41 (m, 1H), 1.31-1.22 (m, 5H). |
| 314 | 460.2 | 1H NMR (400 MHz, dmso-d6): 9.29 (s, 2H), 8.59 (d, 1H, J = 5.1 Hz), 8.41 (s, 1H), 8.00 (s, 1H), 7.46 (d, 1H, J = 4.6 Hz), 6.97 (d, 1H, J = 7.5 Hz), 6.87 (d, H, J = 7.4 Hz), 5.31 (s, 1H), 4.76 (bs, 1H), 4.29 (s, 2H), 3.64 (bs, 1H), 3.56 (bs, 2H), 3.33 (1H, merged with DMSO-$H_2O$), 2.99 (s, 3H), 1.48 (s, 6H), 1.22 (bs, 2H), 1.06 (bs, 2H). |
| 315 | 471.2 | 1H NMR (400 MHz, dmso-d6): 9.24 (s, 2H), 8.40 (s, 1H), 8.18 (d, 1H, J = 5.9 5.9 Hz), 7.02 (s, 1H), 6.96 (d, 1H, J = 7.4 Hz), 6.86 (d, 1H, J = 7.4 Hz), 6.46 (d, 1H, J = 4.3 Hz), 4.76 (s, 1H), 4.28 (s, 2H), 3.63-3.51 (m, 4H), 3.37-3.32 (m, 4H), 2.99 (s, 3H), 1.98 (s, 4H), 1.21 (bs, 2H), 1.08 (bs, 2H). |
| 316 | 445.2 | 1H NMR (400 MHz, dmso-d6): 9.16 (s, 2H), 8.39 (s, 1H), 8.10 (d, 1H, J = 5.7 Hz), 7.01 (s, 1H), 6.96 (d, 1H, J = 7.6 Hz), 6.86 (d, 1H, J = 7.6 Hz), 6.76 (s, 1H), 6.50 (d, 1H, J = 4.4 Hz), 4.76 (bs, 1H), 4.28 (s, 2H), 3.64-3.52 (m, 3H), 3.32 (1H, merged with DMSO-H2O), 3.20 (t, 2H, J = 6.3 Hz), 2.99 (s, 3H), 1.21-1.13 (m, 7H). |
| 317 | 459.2 | 1H NMR (400 MHz, dmso-d6, T = 373K): δ 8.81 (s, 2H), 8.38 (s, 1H), 7.63-7.61 (m, 1H), 7.45-7.41 (m, 1H), 7.44-7.31 (m, 2H), 6.94-6.83 (m, 2H,), 4.31 (s, 2H), 4.12 (t, 2H, J = 5.22 Hz), 3.90 (s, 1H), 3.35-3.29 (m, 2H), 2.98-2.93 (m, 1H), 2.79-2.74 (m, 1H), 1.85-1.66 (m, 3H), 1.24-1.14 (m, 6H). |
| 318 | 446.2 | 1H NMR (400 MHz, dmso-d6): 9.24 (s, 2H), 8.56 (d, 1H, J = 5.1 Hz), 8.38 (s, 1H), 7.9 (s, 1H), 7.31 (d, 1H, J = 4.5 Hz), 6.92 (d, 1H, J = 8.0 Hz), 6.82 (d, 1H, J = 7.0 Hz), 5.43 (d, 1H, J = 4.3 Hz), 4.76 (bs, 2H), 4.27 (s, 2H), 3.62 (bs, 1H), 3.49 (bs, 2H), 3.33 (1H, merged with DMSO-H2O), 2.97 (s, 3H), 1.37 (d, 3H, J = 6.4 Hz), 1.19 (bs, 2H), 1.11 (bs, 2H). |
| 319 | 471.2 | 1H NMR (400 MHz, dmso-d6): 9.16 (s, 2H), 8.39 (s, 1H), 8.09 (d, 1H, J = 5.7 Hz), 7.04 (s, 1H), 6.96 (d, 1H, J = 7.6 Hz), 6.86-6.82 (m, 2H), 6.53 (d, 1H, J = 5.7 Hz), 4.80-4.76 (m, 1H), 4.28 (s, 2H), 3.64 (bs, 1H), 3.51 (bs, 2H), 3.33 (1H, merged with DMSO-H2O), 3.05 (t, 2H, J = 5.9 Hz), 2.99 (s, 3H), 1.21 (bs, 2H), 1.13 (bs, 2H), 1.07-1.04 (m, 1H), 0.51-0.48 (m, 2H) 0.25-0.24 (m, 2H). |
| 320 | 415.2 | see experimental section (A-32) |
| 321 | 445.2 | $^1$H NMR (400 MHz, DMSO-$d_6$): δ 9.29 (d, J = 9.6 Hz, 2H), 8.42-8.48 (m, 1H), 7.59 (s, 1H), 7.40-7.44 (m, 1H), 7.09-7.13 (m, 1H), 6.89-7.00 (m, 2H), 6.84 (d, J = 6.8 Hz, 1H), 4.28 (s, 2H), 4.03 (s, 1H), 3.91 (s, 3H), 3.84 (s, 1H), 2.96 (s, 3H), 1.14-1.22 (m, 4H). |
| 322 | 445.2 | $^1$H NMR (400 MHz, DMSO-$d_6$): δ 9.33 (s, 2H), 8.38 (s, 1H), 7.67 (s, 1H), 7.58 (d, J = 7.6 Hz, 1H), 7.43 (t, J = 7.2 Hz, 1H), 7.37 (d, J = 7.6 Hz, 1H), 6.93 (d, J = 7.6 Hz, 1H), 6.84 (d, J = 7.6 Hz, 1H), 5.20 (d, J = 4.4 Hz, 1H), 4.76-4.80 (m, 2H), 4.27 (s, 2H), 3.63 (s, 1H), 3.51 (s, 2H), 2.99 (s, 3H), 1.37 (d, J = 6.4 Hz, 3H), 1.20 (d, J = 10.8 Hz, 2H), 1.15 (d, J = 11.2 Hz, 2H). |
| 323 | 405.2 | $^1$H NMR (400 MHz, DMSO-$d_6$): δ 8.85 (s, 2H), 8.53 (s, 1H), 7.49 (s, 1H), 7.13 (s, 1H), 7.01 (d, J = 7.6 Hz, 1H), 6.66 (d, J = 7.6 Hz, 1H), 4.29 (s, 2H), 3.91 (s, 2H), 3.74 (s, 3H), 3.11 (s, 3H), 1.13 (s, 4H). |
| 324 | 422.2 | $^1$H NMR (400 MHz, DMSO-$d_6$): δ 9.11 (s, 2H), 8.36 (s, 1H), 7.96 (s, 1H), 6.94 (d, J = 7.6 Hz, 1H), 6.84 (d, J = 6.4 Hz, 1H), 4.76 (s, 1H), 4.26 (s, 2H), 3.63 (s, 1H), 3.52 (s, 2H), 2.99 (s, 3H), 2.73 (s, 3H), 1.2 (s, 2H), 1.12 (s, 2H). |
| 325 | 436.2 | $^1$H NMR (400 MHz, DMSO-$d_6$): δ 9.12 (s, 2H), 8.36 (s, 1H), 7.98 (s, 1H), 6.94 (d, J = 7.2 Hz, 1H), 6.84 (d, J = 6.4 Hz, 1H), 4.76 (bs, 1H), 4.26 (s, 2H), 3.63 (s, 1H), 3.51 (s, 2H), 3.05 (t, J = 7.2 Hz, 2H), 2.99 (s, 3H), 1.35 (t, J = 7.2 Hz, 3H), 1.20 (s, 2H), 1.12 (s, 2H). |
| 326 | 438.2 | $^1$H NMR (400 MHz, DMSO-$d_6$): δ 9.11 (s, 2H), 8.36 (s, 1H), 8.04 (s, 1H), 6.94 (d, J = 7.6 Hz, 1H), 6.84 (d, J = 7.2 Hz, 1H), 6.15 (t, J = 6.0 Hz, 1H), 4.74-4.81 (m, 3H), 4.26 (s, 2H), 3.63 (s, 1H), 3.51 (s, 2H), 2.99 (s, 3H), 1.19 (d, J = 11.6 Hz, 2H), 1.14 (d, J = 12.0 Hz, 2H). |
| 327 | 451.2 | $^1$H NMR (400 MHz, DMSO-$d_6$): δ 9.27 (s, 2H), 8.39 (d, J = 5.6 Hz, 2H), 8.28 (bs, 1H), 7.96 (bs, 1H), 6.95 (d, J = 7.6 Hz, 1H), 6.85 (d, J = 7.2 Hz, 1H), 4.74-4.78 (m, 1H), 4.28 (s, 2H), 3.63 (s, 1H), 3.51 (s, 2H), 2.99 (s, 3H), 1.20 (d, J = 14.0 Hz, 2H), 1.13 (s, 2H). |
| 328 | 462.2 | $^1$H NMR (400 MHz, DMSO-$d_6$): δ 9.28 (s, 2H), 8.39 (s, 1H), 7.24 (s, 1H), 6.95 (d, J = 7.6 Hz, 1H), 6.85 (d, J = 7.2 Hz, 1H), 6.31 (s, 1H), 4.74-4.79 (m, 1H), 4.28 (s, 2H), 3.94 (s, 3H), 3.86 (s, 3H), 3.63 (s, 1H), 3.50 (s, 3H), 1.21 (s, 2H), 1.13 (s, 2H). |
| 329 | 413.2 | $^1$H NMR (400 MHz, DMSO-$d_6$): δ 9.29 (s, 2H), 8.67 (d, J = 4.0 Hz, 1H), 8.52 (s, 1H), 8.03 (d, J = 8.0 Hz, 1H), 7.92-7.88 (m, 1H), 7.37-7.35 (m, 1H), 7.09-7.06 (m, 1H), 6.87 (d, J = 7.6, 1H), 4.30 (s, 2H), 3.65-3.52 (m, 2H), 3.50-3.37 (m, 2H), 3.18-3.09 (m, 1H), 1.96-1.88 (m, 3H), 1.66-1.59 (s, 1H), 1.24-1.18 (m, 2H), 1.15-1.13 (m, 2H). |
| 330 | 443.2 | $^1$H NMR (300 MHz, DMSO-$d_6$): δ 9.279 (s, 2H), 8.50 (s, 1H), 8.46 (d, J = 5.7 Hz, 1H), 7.57 (d, J = 1.8 Hz, 1H), 7.05-7.03 (m, 1H), 6.90 (dd, J = 6.0, 2.22 Hz, 1H), 6.85 (d, J = 7.8 Hz, 1H), 4.27 (s, 2H), 3.59 (s, 3H), 3.58-3.35 (m, 4H), 3.15-3.08 (m, 1H), 1.95-1.72 (m, 3H), 1.62-1.58 (m, 1H), 1.23-1.07 (m, 4H). |
| 331 | 455.3 | $^1$H NMR (400 MHz, DMSO-$d_6$): δ 9.30 (s, 2H), 8.56-8.53 (m, 2H), 7.91 (s, 1H), 7.26 (dd, J = 5.2, 1.2 Hz, 1H), 7.09-7.06 (m, 1H), 6.87 (d, J = 7.6 Hz, 1H), 4.30 (s, 2H), 3.61-3.53 (m, 4H), 3.21-3.10 (m, 1H), 2.98-2.94 (m, 1H), 1.94-1.85 (m, 1H), 1.78-1.61 (m, 3H), 1.27 (d, J = 6.8 Hz, 6H), 1.24-1.13 (m, 4H). |
| 332 | 482.3 | 1H NMR (400 MHz, dmso-d6, T = 353K): δ 9.23 (s, 2H), 8.47 (d, 1H, J = 5.16 Hz), 8.41 (s, 1H), 7.64 (s, 1H), 7.05 (d, 1H, 1.64 Hz), 7.03-6.82 (m, 2H), 4.31 (s, 2H), 4.12 (bs, 2H), 3.97-3.94 (m, 1H), 3.37-3.29 (m, 2H), 2.99-2.93 (m, 1H), 2.81-2.75 (m, 1H), 2.04-2.00 (m, 1H), 1.85-1.77 (m, 1H), 1.71-1.67 (m, 2H), 1.28-1.08 (m, 8H), 0.95-0.91 (m, 2H). |
| 333 | 488.2 | 1H NMR (400 MHz, dmso-d6): 8.77 (s, 2H), 8.36 (s, 1H), 7.05 (t, 1H, J = 9.6 Hz), 6.95 (d, 1H, J = 7.4 Hz), 6.86 (d, 1H, J = 7.3 Hz), 6.71-6.69 (m, 1H), 6.63-6.61 (m, 1H), 5.67 (bs, 1H), 4.74 (bs, 1H), 4.26 (s, 2H), 3.62 (bs, 1H), 3.51 (bs, 2H), 3.33 (1H, merged with DMSO-H2O), 2.98 (s, 3H), 2.92 (t, 2H, J = 5.6 Hz), 1.21 (s, 2H), 1.14 (s, 2H), 1.09-1.03 (m, 1H), 0.49-0.46 (m, 2H), 0.22-0.21 (m, 2H). |

TABLE 6-continued

Table of the pyhsico chemical data
(NMR, LCMS: [M + 1.0079]; mass found, M.p.)

| No. | LCMS | physico chemical data M.p./NMR |
|---|---|---|
| 334 | 427.2 | ¹H NMR (400 MHz, DMSO-d₆): δ 9.27 (s, 2H), 8.53-8.51 (m, 2H), 7.87 (s, 1H), 7.20 (d, J = 4.8 Hz, 1H), 7.10-7.06 (m, 1H), 6.87 (d, J = 7.6 Hz, 1H), 4.30 (s, 2H), 3.63-3.13 (m, 6H), 2.74-2.62 (m, 1H), 2.39 (s, 3H), 2.02-1.65 (m, 2H), 1.24-1.21 (m, 2H), 1.15-1.13 (m, 2H). |
| 335 | 453.2 | see experimental section (A-29) |
| 336 | 482.3 | 1H NMR (400 MHz, dmso-d6, T = 363K): δ 9.23 □ (s, 2H), 8.46 (d, J = 1H, J = 5.0 Hz), 8.41 (s, 1H), 7.64 (s, 1H), 7.05-7.04 (m, 1H), 6.94-6.82 (m, 2H), 4.32 (s, 2H), 4.13-4.10 (m, 2H), 3.98 (bs, 1H), 3.37-3.28 (m, 2H), 3.0-2.99 (m, 1H), 2.81-2.75 (m, 1H), 2.03-2.01 (m, 1H), 1.70-1.60 (m, 2H), 1.55-1.45 (m, 1H), 1.35-1.09 (m, 8H) 0.93-0.92 (m, 2H). |
| 337 | 455.2 | ¹H NMR (400 MHz, DMSO-d₆): δ 9.27 (d, J = 8.0 Hz, 2H), 8.45 (t, J = 10.0 Hz, 1H), 7.68 (s, 1H), 7.41 (m, 1H), 7.00-7.11 (m, 2H), 6.85-6.91 (m, 1H), 4.29 (s, 2H), 4.03 (s, 1H), 3.85 (s, 1H), 2.96 (s, 3H), 1.99 (s, 1H), 1.22 (s, 2H), 1.08-1.14 (m, 4H), 0.94 (s, 2H). |
| 338 | 482.2 | |
| 339 | 452.2 | ¹H NMR (400 MHz, DMSO-d₆): δ 9.08 (s, 2H), 8.38 (s, 1H), 7.37 (s, 1H), 6.98 (d, J = 7.6 Hz, 1H), 6.86 (d, J = 7.6 Hz, 1H), 4.75 (bs, 1H), 4.69 (t, J = 5.2 Hz, 2H), 4.28 (s, 2H), 3.75 (q, J = 6.4 Hz & 6.0 Hz, 2H), 3.51-3.56 (m, 4H), 2.99 (s, 3H), 2.91 (t, J = 6.8 Hz, 2H), 1.20 (d, J = 14.4 Hz, 2H), 1.16 (d, J = 13.6 Hz, 2H). |
| 340 | 433.2 | ¹H NMR (400 MHz, DMSO-d₆): δ 9.38 (s, 2H), 8.96 (d, J = 2.4 Hz, 1H), 8.43 (s, 1H), 7.84 (d, j = 2.0 Hz, 1H), 6.98 (d, J = 8.0 Hz, 1H), 6.87 (d, J = 7.2 Hz, 1H), 4.77 (bs, 1H), 4.31 (s, 2H), 4.00 (s, 3H), 3.63 (s, 1H), 3.51 (s, 2H), 2.99 (s, 3H), 1.20 (d, J = 14.8 Hz, 2H), 1.16 (d, J = 14.8 Hz, 2H). |
| 341 | 477.2 | ¹H NMR (400 MHz, DMSO-d₆): δ 9.04 (s, 2H), 8.39 (s, 1H), 7.91-7.95 (m, 2H), 7.64-7.72 (m, 2H), 6.95 (d, J = 7.6 Hz, 1H), 6.85 (d, J = 8.0 Hz, 1H), 4.74 (bs, 1H), 4.28 (s, 2H), 3.63 (s, 1H), 3.51 (s, 2H), 3.08-3.13 (m, 1H), 2.99 (s, 3H), 2.83-2.88 (m, 1H), 1.22 (s, 2H), 1.14 (s, 2H), 1.02-1.08 (m, 4H). |
| 342 | 477.2 | ¹H NMR (400 MHz, DMSO-d₆): δ 8.96 (s, 2H), 8.38 (s, 1H), 7.68-7.32 (m, 2H), 7.49 (t, J = 7.6 Hz, 1H), 7.33 (d, J = 7.6 Hz, 1H), 6.94 (d, J = 7.6 Hz, 1H), 6.85 (d, J = 7.6 Hz, 1H), 4.75-4.79 (m, 1H), 4.27 (s, 2H), 4.19 (d, J = 12.8 Hz, 1H), 4.00 (d, J = 12.8 Hz, 1H), 3.63 (s, 1H), 3.51 (s, 2H), 3.32 (s, 1H), 2.98 (s, 3H), 2.51 (s, 3H), 1.19 (d, J = 12.0 Hz, 2H), 1.15 (d, J = 12.4 Hz, 2H). |
| 343 | 462.2 | 1H NMR (400 MHz, dmso-d6): 8.77 (s, 2H), 8.36 (s, 1H), 7.08 (t, 1H, J = 9.7 Hz), 6.95 (d, 1H, J = 7.5 Hz), 6.86 (d, 1H, J = 7.3 Hz), 6.68-6.65 (m, 1H), 6.60-6.57 (m, 1H), 5.58 (t, 1H, J = 5.1 Hz), 4.75 (bs, 1H), 4.27 (s, 2H), 3.63 (bs, 1H), 3.51 (bs, 2H), 3.33 (1H, merged with DMSO-H2O), 3.09-3.02 (m, 2H), 2.98 (s, 3H), 1.21-1.14 (m, 7H). |
| 344 | 476.2 | see experimental section (A-31) |
| 345 | 492.2 | ¹H NMR (400 MHz, DMSO-d₆): δ 9.39 (s, 2H), 8.98 (d, J = 4.8 Hz, 1H), 8.46 (d, J = 10.0 Hz, 2H), 7.83 (d, J = 4.0 Hz, 1H), 6.99 (d, J = 8.0 Hz, 1H), 6.90 (d, J = 7.6 Hz, 1H), 4.32 (s, 2H), 3.62 (bs, 8H), 3.42 (s, 3H), 1.15-1.24 (m, 4H). |
| 346 | 471.2 | ¹H NMR (400 MHz, DMSO-d₆): δ 8.91 (s, 2H), 8.41 (s, 1H), 7.93-7.95 (m, 1H), 7.76-7.79 (m, 1H), 7.61 (t, J = 8.4 Hz, 1H), 6.97 (d, J = 7.2 Hz, 1H), 6.88 (d, J = 7.6 Hz, 1H), 4.28 (s, 2H), 3.38-3.60 (m, 8H), 2.83 (s, 3H), 1.14-1.22 (m, 2H), 1.08-1.10 (m, 2H). |
| 347 | 437.2 | ¹H NMR (400 MHz, DMSO-d₆): δ 8.89 (s, 2H), 8.34 (s, 1H), 7.45 (s, 1H), 7.32 (s, 1H), 6.94 (d, J = 7.2 Hz, 1H), 6.84 (d, J = 7.2 Hz, 1H), 5.20 (t, 5.6 Hz, 1H), 4.75 (s, 1H), 4.47 (d, J = 5.6 Hz, 2H), 4.25 (s, 2H), 3.63 (s, 1H), 3.50 (s, 2H), 2.98 (s, 3H), 1.20 (s, 2H), 1.13 (s, 2H). |
| 348 | 450.2 | ¹H NMR (400 MHz, DMSO-d₆): δ 8.91 (s, 2H), 8.34 (s, 1H), 8.13 (s, 1H), 7.81-7.85 (m, 2H), 7.32 (s, 1H), 6.95 (d, J = 7.6 Hz, 1H), 6.85 (d, J = 7.6 Hz, 1H), 4.76 (s, 1H), 4.26 (s, 2H), 3.62 (s, 1H), 3.51 (s, 2H), 2.98 (s, 3H), 1.13-1.21 (m, 4H). |
| 349 | 456.2 | ¹H NMR (400 MHz, DMSO-d₆): δ 9.08 (s, 2H), 8.38 (s, 1H), 7.34 (s, 1H), 6.98 (d, J = 8.0 Hz, 1H), 6.87 (d, J = 7.2 Hz, 1H), 4.76 (bs, 1H), 4.28 (s, 2H), 3.63 (s, 1H), 3.51 (s, 2H), 2.99 (s, 3H), 2.79 (q, J = 7.6 Hz & 7.2 Hz, 2H), 1.27 (t, J = 7.6 Hz, 3H), 1.20 (d, J = 13.6 Hz, 2H), 1.14 (s, 2H). |
| 350 | 447.2 | ¹H NMR (400 MHz, DMSO-d₆): δ 9.10 (s, 2H), 8.39 (s, 1H), 7.66 (s, 1H), 6.99 (d, J = 7.2 Hz, 1H), 6.87 (d, J = 7.6 Hz, 1H), 4.75 (bs, 1H), 4.29 (s, 2H), 4.23 (s, 2H), 3.52-3.63 (m, 4H), 2.99 (s, 3H), 1.23 (s, 2H), 1.14 (s, 2H). |
| 351 | 470.2 | 1H NMR (400 MHz, dmso-d6 at T = 373K): 9.23 (s, 2H), 8.53 (d, 1H, J = 5.1 Hz), 8.44 (s, 1H), 7.68 (s, 1H), 7.24 (d, 1H, J = 4.7 Hz), 6.98 (d, 1H, J = 7.5 Hz), 6.86 (d, 1H, J = 7.6 Hz), 5.83 (s, 1H), 4.31 (s, 2H), 3.64 (d, 4H, J = 4.2 Hz), 3.55 (d, 4H, J = 4.0 Hz), 1.26-1.15 (m, 8H). |
| 352 | 477.2 | ¹H NMR (400 MHz, DMSO-d₆): δ 8.83 (s, 2H), 8.36 (s, 1H), 7.48 (d, J = 4.0 Hz, 1H), 7.39-7.44 (m, 1H), 7.21 (d, J = 9.2 Hz, 1H), 6.96 (d, J = 7.6 Hz, 1H), 6.85 (d, J = 7.6 Hz, 1H), 4.75 (bs, 1H), 4.27 (s, 2H), 3.63 (s, 1H), 3.51 (s, 2H), 3.26 (s, 1H), 2.98 (s, 3H), 2.29 (s, 3H), 1.20 (d, J = 11.2 Hz, 2H), 1.16 (d, J = 6.4 Hz, 2H). |
| 354 | 461.2 | 1H NMR (400 MHz, dmso-d6, T = 373K): δ 8.81 (s, 2H), 8.41 (s, 1H), 7.66-7.61 (m, 1H), 7.45-7.43 (m, 1H), 7.35-6.29 (m, 2H), 6.98-6.86 (m, 1H), 6.86 (d, 1H, J = 7.3 Hz), 4.35-4.3 (m, 3H), 4.1-4.07 (m, 1H), 3.95-3.85 (m, 2H), 3.55-3.48 (m, 3H), 3.39 (bs, 1H), 3.13-3.07 (m, 1H), 2.91-2.85 (m, 1H), 1.24 (bs, 2H), 1.14 (bs, 2H). |
| 355 | 493.2 | ¹H NMR (400 MHz, DMSO-d₆): δ 9.13 (s, 2H), 8.51 (d, J = 5.2 Hz, 1H), 8.42 (s, 1H), 8.03 (s, 1H), 7.53 (d, J = 6.4 Hz, 1H), 6.98 (d, J = 7.6 Hz, 1H), 6.88 (d, J = 7.6 Hz, 1H), 4.29 (s, 2H), 3.62 (bs, 8H), 2.12 (s, 3H), 1.14-1.22 (m, 4H). |
| 356 | 440.2 | |
| 357 | 438.2 | ¹H NMR (400 MHz, DMSO-d₆): δ 9.08 (s, 2H), 8.38 (s, 1H), 7.47 (s, 1H), 6.98 (d, J = 7.6 Hz, 1H), 6.87 (d, J = 7.6 Hz, 1H), 5.41 (t, 5.6 Hz, 1H), 4.76 (bs, 1H), 4.62 (d, J = 5.2 Hz, 2H), 4.28 (s, 2H), 3.51-3.63 (m, 3H), 3.32 (s, 1H), 2.99 (s, 3H), 1.22 (s, 2H), 1.14 (s, 2H). |
| 358 | 459.2 | ¹H NMR (400 MHz, DMSO-d₆): δ 8.98 (s, 2H), 8.38 (s, 1H), 7.65 (d, J = 8.0 Hz, 1H), 7.50-7.54 (m, 2H), 7.14 (d, J = 7.6 Hz, 1H), 6.94 (d, J = 7.6 Hz, 1H), 6.85 (d, J = 7.6 Hz, 1H), 4.79 (bs, 1H), 4.27 (s, 2H), 3.62 (s, 1H), 3.50 (s, 2H), 2.98 (s, 3H), 2.30 (s, 3H), 1.13-1.21 (m, 4H). |
| 359 | 488.2 | 1H NMR (400 MHz, dmso-d6, T = 373K): 8.79 (s, 2H), 8.39 (s, 1H), 7.13-7.09 (m, 1H), 6.95 (d, 1H, J = 7.6 Hz), 6.84 (d, 1H, J = 7.6 Hz), 6.68-6.65 (m, 1H), 6.59-6.55 (m, 1H), 4.39 (bs, 1H), 4.29 (s, 2H), 3.62 (bs, 2H), 3.45 (t, 2H, J = 5.7 Hz), 3.29 (t, 4H, J = 6.30 Hz), 3.02 (s, 3H), 2.00-1.98 (m, 4H), 1.21 (bs, 2H), 1.16 (bs, 2H). |
| 360 | 443.2 | |
| 361 | 472.2 | see experimental section (A-30) |

TABLE 6-continued

Table of the pyhsico chemical data
(NMR, LCMS: [M + 1.0079]; mass found, M.p.)

| No. | LCMS | physico chemical data M.p./NMR |
|---|---|---|
| 362 | 461.2 | 1H NMR (400 MHz, dmso-d6, T = 373K): δ 8.81 (s, 2H), 8.41 (s, 1H), 7.65-7.62 (m, 1H), 7.45-7.44 (m, 1H), 7.35-7.29 (m, 2H), 6.98 (d, 1H, J = 7.4 Hz), 6.85 (d, 1H, J = 7.3 Hz), 4.35-4.3 (m, 3H), 4.1-4.07 (m, 1H), 3.95-3.85 (m, 2H), 3.55-3.48 (m, 3H), 3.39 (bs, 1H), 3.13-3.07 (m, 1H), 2.91-2.85 (m, 1H), 1.27 (bs, 2H), 1.16 (bs, 2H). |
| 363 | 1.0 | 1H NMR (400 MHz, dmso-$d_6$): 8.82 (s, 2H), 8.37 (s, 1H), 7.37-7.25 (m, 3H), 6.96-6.84 (m, 2H), 6.01 (s, 1H), 4.75 (bs, 1H), 4.27 (s, 2H), 3.63 (bs, 1H), 3.51 (bs, 2H), 3.33 (1H, merged with DMSO-H2O), 2.99 (s, 3H), 1.22-1.05 (m, 9H). |
| 364 | 437.2 | |
| 365 | 487.2 | |
| 366 | 454.2 | |
| 367 | 449.2 | |
| 368 | 463.2 | |
| 369 | 456.2 | |

Biological Testing cAMP HTRF® Assay to Determine the Activity of hPDE4B1

The inhibiting effect of the compounds on the enzyme activity of human PDE4B1 was measured by the quantification of 5'-adenosine monophosphate (5'-AMP), which is formed from 3',5'-cyclic adenosine monophosphate (cAMP). Human recombinant enzyme, expressed in Sf9 cells, and the HTRF (homogeneous time-resolved fluorescence) detection method were used in the assay.

The test compound or water (control) was mixed with the human recombinant PDE4B1 enzyme (4.8 U) in a buffer consisting of 44.4 mM tris-HCl, 5.28 mM $MgCl_2$, 2.64 mM DTT and 0.044% Tween 20 (pH 7.8). After adding the cAMP enzyme substrate (final concentration 40 nM), the mixture was incubated for 30 minutes at room temperature. Then a fluorescence acceptor (Dye2 marked with cAMP), a fluorescence donor (anti-cAMP antibody marked with a europium cryptate) and the non-specific phosphodiesterase inhibitor IBMX (3-isobutyl-1-methylxanthine; final concentration 1 mM) were added. After 60 min the fluorescence transfer, which correlates with the amount of remaining cAMP, was measured with a microplate reader (Rubystar, BMG) at λex=337 nm, λem=620 nm and λem=665 nm. The enzyme activity was calculated from the quotient formed from the measured signal at 665 nm and that at 620 nm. The result was expressed as the percentage inhibition of enzyme activity of the control (without PDE4 inhibitor). The enzyme was omitted for measurement of the basal control. [N. Saldou et al., Comparison of recombinant human PDE4 isoforms: interaction with substrate and inhibitors, Cell. Signal. Vol. 10, No. 6, 427-440, 1998]. Several compounds according to the invention are tested in the above-described assay. The results are given below.

TABLE 7

$IC_{50}$ inhibition of PDE4B (a <0.1 μM, b = 0.1-1 μM, c = 1-10 μM):

| No. | PDE4B $IC_{50}$ [μM] (mean) |
|---|---|
| 1 | a |
| 2 | a |
| 3 | a |
| 4 | a |
| 5 | a |
| 6 | b |
| 7 | a |
| 8 | a |
| 9 | b |
| 12 | a |
| 15 | a |
| 16 | a |
| 17 | a |
| 18 | b |
| 19 | b |
| 20 | b |
| 21 | b |
| 22 | a |
| 23 | a |
| 24 | c |
| 25 | b |
| 26 | a |
| 27 | a |
| 28 | b |
| 29 | a |
| 30 | b |
| 31 | a |
| 32 | b |
| 34 | a |
| 35 | a |
| 36 | b |
| 38 | a |
| 39 | b |
| 40 | a |
| 41 | a |
| 42 | a |
| 43 | a |
| 44 | a |
| 45 | b |
| 46 | b |
| 47 | b |
| 48 | a |
| 49 | a |
| 50 | a |
| 51 | b |
| 52 | a |
| 53 | b |
| 54 | a |
| 55 | a |
| 56 | a |
| 57 | a |
| 58 | a |
| 59 | a |
| 60 | a |
| 61 | b |
| 62 | c |
| 63 | a |
| 64 | c |
| 65 | a |
| 66 | c |
| 67 | b |
| 68 | b |
| 69 | b |
| 70 | b |
| 71 | b |
| 72 | a |
| 73 | a |
| 74 | c |
| 75 | b |
| 76 | b |
| 77 | b |
| 78 | b |
| 79 | c |
| 80 | b |
| 81 | |
| 82 | c |
| 84 | a |

TABLE 7-continued

IC$_{50}$ inhibition of PDE4B (a <0.1 μM, b = 0.1-1 μM, c = 1-10 μM):

| No. | PDE4B IC$_{50}$ [μM] (mean) |
|---|---|
| 85 | a |
| 86 | b |
| 87 | b |
| 88 | b |
| 89 | b |
| 90 | b |
| 91 | b |
| 92 | b |
| 93 | a |
| 94 | a |
| 95 | a |
| 96 | a |
| 97 | c |
| 98 | b |
| 99 | a |
| 100 | b |
| 101 | b |
| 102 | b |
| 103 | a |
| 104 | a |
| 105 | b |
| 106 | b |
| 107 | a |
| 108 | a |
| 109 | a |
| 110 | b |
| 111 | c |
| 113 | b |
| 114 | a |
| 115 | a |
| 116 | a |
| 118 | a |
| 119 | a |
| 121 | a |
| 122 | c |
| 123 | a |
| 124 | a |
| 125 | a |
| 126 | a |
| 127 | b |
| 128 | a |
| 129 | a |
| 130 | a |
| 131 | b |
| 132 | a |
| 133 | b |
| 134 | b |
| 135 | b |
| 136 | a |
| 137 | a |
| 138 | a |
| 139 | a |
| 140 | a |
| 141 | a |
| 142 | a |
| 143 | a |
| 144 | a |
| 145 | a |
| 146 | a |
| 147 | a |
| 148 | a |
| 149 | a |
| 150 | a |
| 151 | a |
| 152 | b |
| 153 | a |
| 154 | a |
| 155 | a |
| 156 | a |
| 157 | a |
| 158 | a |
| 159 | a |
| 160 | a |
| 161 | a |
| 162 | a |
| 163 | a |
| 164 | a |
| 165 | a |
| 166 | a |
| 167 | a |
| 168 | b |
| 169 | b |
| 170 | a |
| 171 | b |
| 172 | a |
| 173 | a |
| 174 | a |
| 175 | a |
| 176 | a |
| 177 | a |
| 178 | b |
| 179 | b |
| 180 | a |
| 181 | a |
| 182 | a |
| 183 | a |
| 184 | a |
| 185 | a |
| 186 | a |
| 187 | a |
| 188 | a |
| 189 | a |
| 190 | a |
| 191 | a |
| 192 | a |
| 193 | a |
| 194 | a |
| 195 | a |
| 196 | a |
| 197 | a |
| 198 | a |
| 199 | a |
| 200 | a |
| 201 | a |
| 202 | b |
| 203 | c |
| 205 | a |
| 206 | a |
| 207 | a |
| 208 | a |
| 210 | a |
| 211 | a |
| 212 | a |
| 213 | a |
| 214 | a |
| 215 | c |
| 216 | c |
| 217 | c |
| 218 | b |

TR-FRET Assay Using the LANCE® Ultra cAMP Kit to Determine the Activity of hPDE4B1

The effects of the compounds on the activity of the human PDE4B1 was quantified by measuring the production of 5'AMP from cAMP using a human recombinant enzyme expressed in Sf9 cells and the LANCE® Ultra cAMP kit, a TR-FRET detection method from PerkinElmer. The human PDE4B1 enzyme was purchased from SignalChem Lifesciences (Catalog #P92-31BG, Lot #H296-2).

The test compound, reference compound or water (control) was mixed with the enzyme (0.96 U) in a reaction buffer containing 50 mM Tris-HCl, 50 mM MgCl2 and 5 mM DTT (pH 8.5). Thereafter, the reaction was initiated by addition of 500 nM cAMP (substrate) and the mixture was incubated for 30 minutes at room temperature. For control basal measurements, the enzyme was omitted from the reaction mixture. After 30 minutes, the reaction was stopped and diluted by a factor of 100 with the reaction buffer supplemented with 500 μM IBMX. The fluorescence donor (europium chelate-labeled cAMP) and the fluorescence acceptor (anti-cAMP antibody labeled with the ULight™ dye) were then added together with 500 μM IBMX to a 10 μl aliquot. After 60 minutes, the fluorescence transfer corresponding to the amount of residual cAMP was measured at λex=337 nm, λem=620 nm and λem=665 nm using a microplate reader (PHERAstar, BMG). The enzyme activity was determined by dividing the signal measured at 665 nm by that measured at 620 nm (ratio) multiplied by 10000. The results were expressed as percent inhibition of the control enzyme activity. IC50 values (IC50=concentration causing a half-maximal inhibition of control specific activity) were derived from dose response measurements with ten different concentrations (n=3; N=1-3).

Several compounds according to the invention are tested with above mentioned assay. The results are given below.

TABLE 8

IC$_{50}$ inhibition of PDE4B
(a < 0.1 μM, b = 0.1-1 μM, c = 1-10 μM):

| No. | PDE4B IC$_{50}$ [μM] (mean) |
|---|---|
| 219 | a |
| 220 | b |
| 221 | a |
| 222 | a |
| 223 | a |
| 224 | a |
| 225 | a |
| 226 | b |
| 227 | a |
| 228 | a |
| 229 | a |
| 230 | a |
| 231 | a |
| 232 | a |
| 233 | a |
| 234 | a |
| 235 | b |
| 236 | b |
| 237 | b |
| 238 | a |
| 239 | a |
| 240 | b |
| 241 | a |
| 242 | a |
| 243 | a |
| 244 | a |
| 245 | a |
| 246 | b |
| 248 | b |
| 249 | a |
| 250 | a |
| 251 | a |
| 252 | a |
| 253 | a |
| 254 | a |
| 255 | a |
| 256 | a |
| 257 | a |
| 258 | a |
| 259 | a |
| 260 | a |
| 261 | a |
| 262 | a |
| 263 | a |
| 264 | a |
| 265 | a |
| 266 | a |
| 267 | a |
| 268 | a |
| 269 | a |
| 270 | a |
| 271 | a |
| 272 | a |
| 273 | a |
| 274 | a |
| 275 | a |
| 276 | a |
| 277 | a |
| 278 | a |
| 279 | a |
| 280 | a |
| 281 | a |
| 282 | a |
| 283 | a |
| 284 | a |
| 285 | a |
| 286 | a |
| 287 | a |
| 288 | a |
| 289 | a |
| 290 | a |
| 291 | a |
| 292 | a |
| 293 | a |
| 294 | a |
| 295 | a |
| 296 | a |
| 297 | a |
| 298 | a |
| 299 | a |
| 300 | a |
| 301 | a |
| 302 | a |
| 303 | a |
| 304 | a |
| 305 | a |
| 306 | a |
| 307 | a |
| 308 | a |
| 309 | a |
| 310 | a |
| 311 | a |
| 312 | a |
| 313 | a |
| 314 | a |
| 315 | a |
| 316 | a |
| 317 | a |
| 318 | a |
| 319 | a |
| 320 | a |
| 321 | a |
| 322 | a |
| 323 | a |
| 324 | a |
| 325 | a |
| 326 | a |
| 327 | a |
| 328 | a |
| 329 | a |
| 330 | a |
| 331 | a |
| 332 | a |
| 333 | a |
| 334 | a |
| 335 | a |
| 336 | a |
| 337 | a |
| 338 | a |
| 339 | a |
| 340 | a |
| 341 | a |
| 342 | a |

TABLE 8-continued

IC$_{50}$ inhibition of PDE4B
(a < 0.1 µM, b = 0.1-1 µM, c = 1-10 µM):

| No. | PDE4B IC$_{50}$ [µM] (mean) |
|---|---|
| 343 | a |
| 344 | a |
| 345 | a |
| 346 | a |
| 347 | a |
| 348 | a |
| 349 | a |
| 350 | a |
| 351 | a |
| 352 | |
| 354 | a |
| 355 | a |
| 356 | a |
| 357 | a |
| 358 | a |
| 359 | a |
| 360 | a |
| 361 | b |
| 362 | a |
| 363 | a |
| 364 | a |
| 365 | a |
| 366 | |
| 367 | |
| 368 | |
| 369 | |

The invention claimed is:

1. A compound of formula (I)

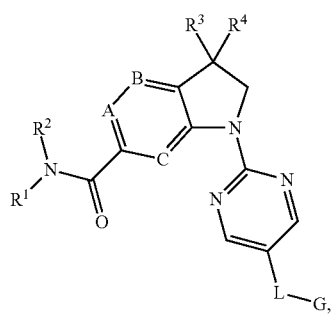

wherein

A, B and C independently represent CH or N;

$R^1$ and $R^2$ independently represent hydrogen or $(C_1$-$C_6)$-alkyl, whereby said $(C_1$-$C_6)$-alkyl is unsubstituted or substituted with at least one substituent $X^1$, or a group U, which is a 3- to 12-membered mono- or bi-cycloaliphatic ring, which is unsubstituted or substituted with at least one substituent $X^2$, whereby said group U may be connected to the nitrogen atom via a $C_{1-6}$-alkylene group, which in turn is unsubstituted or substituted with at least one substituent independently selected from the group consisting of F, Cl, CF$_3$, =O, OCF$_3$ and OH, or a group V, which is a 3- to 12-membered mono-or bi-cyclic heterocycloaliphatic ring comprising at least one heteroatom selected from the group consisting of O, S and N as a ring member, and which mono- or bicyclic heterocycloaliphatic ring is unsubstituted or substituted with at least one substituent $X^3$, whereby said group V may be connected to the nitrogen atom via a $C_{1-6}$-alkylene group, which in turn may be unsubstituted or substituted with at least one substituent independently selected from the group consisting of F, Cl, CF$_3$, =O, OCF$_3$ and OH, or a group W which is phenyl or 5- or 6-membered heteroaryl, wherein said phenyl or said heteroaryl is unsubstituted or substituted with at least one substituent $X^4$ and may be condensed with a 4-, 5-, 6- or 7-membered ring, being carbocyclic or heterocyclic, wherein said condensed ring may be saturated, partially unsaturated or aromatic and may be substituted with at least on substituent $X^5$, and whereby group W may be connected to the nitrogen atom via a $C_{1-6}$-alkylene group, which in turn may be unsubstituted or substituted with at least one substituent independently selected from the group consisting of F, Cl, CF$_3$, =O, OCF$_3$ and OH, or $R^1$ and $R^2$ together with the nitrogen atom to which they are attached form a 3- to 12-membered monocyclic or bicyclic non-aromatic or aromatic ring wherein said ring may contain at least one additional heteroatom selected from the group consisting of O, S and N and wherein said ring is unsubstituted or substituted with at least one substituent $X^6$;

$R^3$ and $R^4$, independently represent hydrogen, $(C_1$-$C_6)$-alkyl or $(C_3$-$C_6)$-cycloalkyl, wherein said $(C_1$-$C_6)$-alkyl and $(C_3$-$C_6)$-cycloalkyl are each unsubstituted or substituted with at least one substituent $Y^1$, or together with the carbon atom to which they are attached form a 3- to 6-membered cycloalkyl ring, which is unsubstituted or substituted with at least one substituent $Y^2$;

L represents a bond, O, S, $(C_1$-$C_6)$-alkylene or $(C_2$-$C_6)$-alkenylene, whereby the aforementioned alkylenes or alkenylenes are in each case unsubstituted or substituted with at least one substituent selected from the group consisting of F, Cl, CF$_3$, =O, OCF$_3$ and OH;

G represents a phenyl or 5- or 6-membered heteroaryl, wherein said phenyl or said heteroaryl may be substituted with at least one substituent Z;

$X^1$, $X^2$, $X^3$, $X^5$ and $X^6$, at each occurrence are independently from one another selected from the group consisting of OH, =O, CN, nitro, halogen, $(C_1$-$C_6)$-alkyl, $(C_1$-$C_6)$-hydroxyalkyl, $(C_1$-$C_6)$-alkoxy, S$(C_1$-$C_6)$-alkyl, S(O)—$(C_1$-$C_6)$-alkyl, S(O)$_2$—$(C_1$-$C_6)$-alkyl, $(C_1$-$C_6)$-haloalkyl, S$(C_1$-$C_6)$-haloalkyl, $(C_1$-$C_6)$-haloalkoxy, $(C_1$-$C_6)$-cyanoalkyl, $(C_3$-$C_8)$-cycloalkyl, NH$_2$, NH$(C_1$-$C_6)$-alkyl, N$((C_1$-$C_6)$-alkyl)$_2$, NH—CO—$(C_1$-$C_6)$-alkyl, NH—SO—$(C_1$-$C_6)$-alkyl, NH—S(O)$_2$—$(C_1$-$C_6)$-alkyl, NH$((C_1$-$C_6)$-alkylen)-SO—$(C_1$-$C_6)$-alkyl, NH$((C_1$-$C_6)$-alkylen)-SO—$(C_1$-$C_6)$-alkyl, NHCONH$_2$, NH—CO—NH—$(C_1$-$C_6)$-alkyl, NH$((C_1$-$C_6)$-alkylen)-CO—N$((C_1$-$C_6)$-alkyl)$_2$, CO—$(C_1$-$C_6)$-alkyl, CO$_2$H, CO—O—$(C_1$-$C_6)$-alkyl, CONH$_2$, CO—NH$(C_1$-$C_6)$alkyl and CO—N$((C_1$-$C_6)$-alkyl)$_2$;

$X^4$ at each occurrence are independently from one another selected from the group consisting of OH, CN, nitro, halogen, $(C_1$-$C_6)$-alkyl, $(C_1$-$C_6)$-hydroxyalkyl, $(C_1$-$C_6)$-alkoxy, S$(C_1$-$C_6)$-alkyl, S(O)—$(C_1$-$C_6)$-alkyl, S(O)$_2$—$(C_1$-$C_6)$-alkyl, $(C_1$-$C_6)$-haloalkyl, S$(C_1$-$C_6)$-haloalkyl, $(C_1$-$C_6)$-haloalkoxy, $(C_1$-$C_6)$-cyanoalkyl, $(C_3$-$C_8)$-cycloalkyl, NH$_2$, NH$(C_1$-$C_6)$-alkyl, N$((C_1$-$C_6)$-alkyl)$_2$, NH—CO—$(C_1$-$C_6)$-alkyl, NH—SO—

($C_1$-$C_6$)-alkyl, NH—S(O)$_2$—($C_1$-$C_6$)-alkyl, NH(($C_1$-$C_6$)-alkylen)-CO—($C_1$-$C_6$)-alkyl, NH(($C_1$-$C_6$)-alkylen)-SO—($C_1$-$C_6$)-alkyl, NH(($C_1$-$C_6$)-alkylen)-SO$_2$—($C_1$-$C_6$)-alkyl, NHCONH$_2$, NH—CO—NH—($C_1$-$C_6$)-alkyl, NH(($C_1$-$C_6$)-alkylen)-CO—N(($C_1$-$C_6$)-alkyl)$_2$, CO$_2$H, CO—O—($C_1$-$C_6$)-alkyl, CONH$_2$, CO—NH($C_1$-$C_6$)alkyl and CO—N(($C_1$-$C_6$)-alkyl)$_2$;

$Y^1$ and $Y^2$, at each occurrence are independently from one another selected from the group consisting of OH, =O CN, nitro, halogen, ($C_1$-$C_6$)-alkyl, ($C_1$-$C_6$)-hydroxyalkyl, ($C_1$-$C_6$)-alkoxy, S($C_1$-$C_6$)-alkyl, S(O)—($C_1$-$C_6$)-alkyl, S(O)$_2$—($C_1$-$C_6$)-alkyl, ($C_1$-$C_6$)-haloalkyl, S($C_1$-$C_6$)-haloalkyl, ($C_1$-$C_6$)-haloalkoxy, ($C_1$-$C_6$)-cyanoalkyl, ($C_3$-$C_8$)-cycloalkyl, NH$_2$, NH($C_1$-$C_6$)-alkyl, N(($C_1$-$C_6$)-alkyl)$_2$, NH—CO—($C_1$-$C_6$)-alkyl, NH—SO—($C_1$-$C_6$)-alkyl, NH—S(O)$_2$—($C_1$-$C_6$)-alkyl, NH(($C_1$-$C_6$)-alkylen)-CO—($C_1$-$C_6$)-alkyl, NH(($C_1$-$C_6$)-alkylen)-SO—($C_1$-$C_6$)-alkyl, NH(($C_1$-$C_6$)-alkylen)-SO$_2$—($C_1$-$C_6$)-alkyl, NHCONH$_2$, NH—CO—NH—($C_1$-$C_6$)-alkyl, NH(($C_1$-$C_6$)-alkylen)-CO—N(($C_1$-$C_6$)-alkyl)$_2$, CO$_2$H, CO—O—($C_1$-$C_6$)-alkyl, CONH$_2$, CO—NH($C_1$-$C_6$)alkyl and CO—N(($C_1$-$C_6$)-alkyl)$_2$;

Z at each occurrence is independently selected from the group consisting of halogen, OH, CN, SH, nitro, ($C_1$-$C_6$)-alkyl, ($C_2$-$C_6$)-alkenyl, ($C_2$-$C_6$)-alkinyl, ($C_1$-$C_6$)-hydroxyalkyl, ($C_1$-$C_6$)-cyanoalkyl, ($C_1$-$C_6$)-alkoxy, ($C_1$-$C_6$)-thioalkyl, ($C_1$-$C_6$)-haloalkyl, ($C_1$-$C_6$)-thiohaloalkyl, ($C_1$-$C_6$)-haloalkoxy, ($C_1$-$C_6$)-alkylen-S—($C_1$-$C_6$)-alkyl, ($C_3$-$C_8$)-cycloalkyl, ($C_3$-$C_6$)-cycloalkyl-($C_1$-$C_3$)-alkylenyl, ($C_3$-$C_8$)-heterocycloalkyl, NH$_2$, NH($C_1$-$C_6$)-alkyl, N(($C_1$-$C_6$)-alkyl)$_2$, NH—CO—($C_1$-$C_6$)-alkyl, NH—CO—O—($C_1$-$C_6$)-alkyl, NH—C(O)NH$_2$, NH—CO—NH—($C_1$-$C_6$)-alkyl, NH—CO—N(($C_1$-$C_6$)-alkyl)$_2$, NH(($C_1$-$C_6$)-alkylen)-CO—O—($C_1$-$C_6$)-alkyl, NH(($C_1$-$C_6$)-alkylen)-CONH$_2$, NH(($C_1$-$C_6$)-alkylen)-CO—NH—($C_1$-$C_6$)-alkyl, NH(($C_1$-$C_6$)-alkylen)-CO—N(($C_1$-$C_6$)-alkyl)$_2$, NH—S(O)$_2$OH, NH—S(O)$_2$($C_1$-$C_6$)-alkyl, NH—S(O)$_2$O($C_1$-$C_6$)-alkyl, NH—S(O)$_2$NH$_2$, NH—S(O)$_2$NH($C_1$-$C_6$)-alkyl, NH—S(O)$_2$N(($C_1$-$C_6$)-alkyl)$_2$, NH(($C_1$-$C_6$)-alkylen)-S(O)$_2$OH, NH(($C_1$-$C_6$)-alkylen)-S(O)$_2$($C_1$-$C_6$)-alkyl, NH(($C_1$-$C_6$)-alkylen)-S(O)$_2$O($C_1$-$C_6$)-alkyl, NH(($C_1$-$C_6$)-alkylen)-S(O)$_2$NH$_2$, NH(($C_1$-$C_6$)-alkylen)-S(O)$_2$NH($C_1$-$C_6$)-alkyl, CO($C_1$-$C_6$)-alkyl, CO—O($C_1$-$C_6$)-alkyl, O—CO($C_1$-$C_6$)-alkyl, O—CO—O($C_1$-$C_6$)-alkyl, CONH$_2$, CO—NH($C_1$-$C_6$)-alkyl, CO—N(($C_1$-$C_6$)-alkyl)$_2$, O—CO—NH($C_1$-$C_6$)-alkyl, O—CO—N(($C_1$-$C_6$)-alkyl)$_2$, O—S(O)$_2$—($C_1$-$C_6$)-alkyl, O—S(O)$_2$OH, O—S(O)$_2$—($C_1$-$C_6$)-alkoxy, O—S(O)$_2$NH$_2$, O—S(O)$_2$—NH($C_1$-$C_6$)-alkyl, O—S(O)$_2$—N(($C_1$-$C_6$)-alkyl)$_2$, S(O)($C_1$-$C_6$)-alkyl, S(O)$_2$($C_1$-$C_6$)-alkyl, S(O)$_2$OH, S(O)$_2$O($C_1$-$C_6$)-alkyl, S(O)$_2$NH$_2$, S(O)$_2$NH($C_1$-$C_6$)-alkyl, and S(O)$_2$N(($C_1$-$C_6$)-alkyl)$_2$;

optionally in the form of a single stereoisomer or a mixture of stereoisomers, in the form of the free compound and/or a physiologically acceptable salt and/or a physiologically acceptable solvate thereof.

2. The compound of claim 1, wherein
A, B and C independently represent CH or N;
$R^1$ and $R^2$ independently represent
hydrogen or ($C_1$-$C_6$)-alkyl, whereby said ($C_1$-$C_6$)-alkyl is unsubstituted or substituted with 1, 2, 3, 4 or 5 substituents $X^1$, or
a group U, which is a 3- to 12-membered mono- or bi-cycloaliphatic ring, which is unsubstituted or substituted with 1, 2, 3, 4 or 5 substituents $X^2$, whereby said group U may be connected to the nitrogen atom via a $C_{1-3}$-alkylene group, which in turn is unsubstituted or substituted with 1, 2 or 3 substituents independently selected from the group consisting of F, Cl, CF$_3$, =O, OCF$_3$ and OH, or a group V, which is a 3- to 12-membered mono-or bi-cyclic heterocycloaliphatic ring comprising at 1, 2 or 3 heteroatoms selected from the group consisting of O, S and N as ring members, and which mono- or bicyclic heterocycloaliphatic ring is unsubstituted or substituted with 1, 2, 3, 4 or 5 substituents $X^3$; whereby said group V may be connected to the nitrogen atom via a $C_{1-3}$-alkylene group, which in turn is unsubstituted or substituted with 1, 2 or 3 substituents independently selected from the group consisting of F, Cl, CF$_3$, =O, OCF$_3$ and OH, or a group W which is phenyl or 5- or 6-membered heteroaryl, wherein said phenyl or said heteroaryl is unsubstituted or substituted with 1, 2, 3, 4, or 5 substituents $X^4$, and wherein said phenyl or said heteroaryl may be condensed with a 4-, 5-, 6- or 7-membered ring, being carbocyclic or heterocyclic, wherein said condensed ring may be saturated, partially unsaturated or aromatic and is unsubstituted or substituted with 1, 2, 3, 4 or 5 substituents $X^5$; and wherein said group W may be connected to the nitrogen atom via a $C_{1-3}$-alkylene group, which in turn may be unsubstituted or substituted with at least one substituent independently selected from the group consisting of F, Cl, CF$_3$, =O, OCF$_3$ and OH, or $R^1$ and $R^2$ together with the nitrogen atom to which they are attached form a 3- to 12-membered monocyclic or bicyclic non-aromatic or aromatic ring wherein said ring may contain 1, 2 or 3 additional heteroatoms selected from the group consisting of O, S and N and wherein said ring is unsubstituted or substituted with 1, 2, 3, 4 or 5 substituents $X^6$;

$R^3$ and $R^4$,
independently of one another, each represent hydrogen, ($C_1$-$C_6$)-alkyl or ($C_3$-$C_6$)-cycloalkyl, wherein said ($C_1$-$C_6$)-alkyl and ($C_3$-$C_6$)-cycloalkyl are each unsubstituted or substituted with 1, 2, 3, 4 or 5 substituents $Y^1$, or
together with the carbon atom to which they are attached form a 3- to 6-membered cycloalkyl ring, which is unsubstituted or substituted with 1, 2, 3, 4 or 5 substituents $Y^2$;

L represents a bond, O, S, ($C_1$-$C_6$)-alkylene or ($C_2$-$C_6$)-alkenylene, whereby the aforementioned alkylenes or alkenylenes are in each case unsubstituted or substituted with 1, 2 or 3 substituents independently selected from the group consisting of F, Cl, CF$_3$, =O, OCF$_3$ and OH;

G represents a phenyl or 5- or 6-membered heteroaryl, wherein said phenyl or said heteroaryl is unsubstituted or substituted with 1, 2, 3, 4 or 5 substituents Z;

$X^1$, $X^2$, $X^3$, $X^5$ and $X^6$, at each occurrence are independently from one another selected from the group consisting of OH, =O, CN, F, Cl, Br, CHF$_2$, CH$_2$F, CF$_3$, OCF$_3$, SCF$_3$, ($C_1$-$C_6$)-alkyl, ($C_1$-$C_6$)-hydroxyalkyl, ($C_1$-$C_6$)-alkoxy, S($C_1$-$C_6$)-alkyl, S(O)—($C_1$-$C_6$)-alkyl, S(O)$_2$—($C_1$-$C_6$)-alkyl, ($C_1$-$C_6$)-cyanoalkyl, ($C_3$-$C_6$)-cycloalkyl, NH$_2$, NH($C_1$-$C_6$)-alkyl, N(($C_1$-$C_6$)-alkyl)$_2$, NH—CO—($C_1$-$C_6$)-alkyl, NH—SO—($C_1$-$C_6$)-alkyl, NH—S(O)$_2$—($C_1$-$C_6$)-alkyl, CO$_2$H, CO—($C_1$-$C_6$)- alkyl, CO—O—($C_1$-$C_6$)-alkyl, $CONH_2$, CO—NH($C_1$-$C_6$)alkyl and CO—N(($C_1$-$C_6$)-alkyl)$_2$;

$X^4$ at each occurrence is independently selected from the group consisting of OH, CN, F, Cl, Br, $CHF_2$, $CH_2F$, $CF_3$, $OCF_3$, $SCF_3$, ($C_1$-$C_6$)-alkyl, ($C_1$-$C_6$)-hydroxyalkyl, ($C_1$-$C_6$)-alkoxy, S($C_1$-$C_6$)-alkyl, S(O)—($C_1$-$C_6$)-alkyl, S(O)$_2$—($C_1$-$C_6$)-alkyl, ($C_1$-$C_6$)-cyanoalkyl, ($C_3$-$C_6$)-cycloalkyl, $NH_2$, NH($C_1$-$C_6$)-alkyl, N(($C_1$-$C_6$)-alkyl)$_2$, NH—CO—($C_1$-$C_6$)-alkyl, NH—SO—($C_1$-$C_6$)-alkyl, NH—S(O)$_2$—($C_1$-$C_6$)-alkyl, $CO_2H$, CO—O—($C_1$-$C_6$)-alkyl, $NHCONH_2$, NH—CO—NH—($C_1$-$C_6$)-alkyl, N(($C_1$-$C_6$)-alkyl)-CO—N(($C_1$-$C_6$)-alkyl)$_2$, $CO_2H$, CO—O—($C_1$-$C_6$)-alkyl, $CONH_2$, $CONH_2$, CO—NH($C_1$-$C_6$)alkyl and CO—N(($C_1$-$C_6$)-alkyl)$_2$;

$Y^1$ and $Y^2$, at each occurrence, are independently from one another selected from the group consisting of OH, =O, CN, F, Cl, Br, $CHF_2$, $CH_2F$, $CF_3$, $OCF_3$, $SCF_3$, ($C_1$-$C_6$)-alkyl, ($C_1$-$C_6$)-hydroxyalkyl, ($C_1$-$C_6$)-alkoxy, S($C_1$-$C_6$)-alkyl, S(O)—($C_1$-$C_6$)-alkyl, S(O)$_2$-($C_1$-$C_6$)-alkyl, ($C_1$-$C_6$)-cyanoalkyl, ($C_3$-$C_6$)-cycloalkyl, $NH_2$, NH($C_1$-$C_6$)-alkyl, N(($C_1$-$C_6$)-alkyl)$_2$, NH—CO—($C_1$-$C_6$)-alkyl, NH—SO—($C_1$-$C_6$)-alkyl, NH—S(O)$_2$—($C_1$-$C_6$)-alkyl, $CO_2H$, CO—O—($C_1$-$C_6$)-alkyl, $CONH_2$, CO—NH($C_1$-$C_6$)alkyl and CO—N(($C_1$-$C_6$)-alkyl)$_2$;

Z at each occurrence is independently selected from the group consisting F, Cl, Br, $CHF_2$, $CH_2F$, $CF_3$, $OCF_3$, $SCF_3$, OH, CN, SH, nitro, ($C_1$-$C_6$)-alkyl, ($C_2$-$C_6$)-alkenyl, ($C_2$-$C_6$)-alkinyl, ($C_1$-$C_6$)-hydroxyalkyl, ($C_1$-$C_6$)-cyanoalkyl, ($C_1$-$C_6$)-alkoxy, ($C_1$-$C_6$)-thioalkyl, ($C_1$-$C_6$)-alkylen-S—($C_1$-$C_6$)-alkyl, ($C_3$-$C_6$)-cycloalkyl, hydroxyl-($C_3$-$C_6$)-cycloalkyl, ($C_3$-$C_8$)-heterocycloalkyl, $NH_2$, NH($C_1$-$C_6$)-alkyl, N(($C_1$-$C_6$)-alkyl)$_2$, NH—CO—($C_1$-$C_6$)-alkyl, NH—CO—O—($C_1$-$C_6$)-alkyl, NH—S(O)$_2$OH, NH—S(O)$_2$($C_1$-$C_6$)-alkyl, NH—S(O)$_2$O($C_1$-$C_6$)-alkyl, NH—S(O)$_2$$NH_2$, NH—S(O)$_2$NH($C_1$-$C_6$)-alkyl, NH—S(O)$_2$N(($C_1$-$C_6$)-alkyl)$_2$, NH(($C_1$-$C_6$)-alkylen)-S(O)$_2$OH, NH(($C_1$-$C_6$)-alkylen)-S(O)$_2$($C_1$-$C_6$)-alkyl, NH(($C_1$-$C_6$)-alkylen)-S(O)$_2$O($C_1$-$C_6$)-alkyl, NH(($C_1$-$C_6$)-alkylen)-S(O)$_2$$NH_2$, NH(($C_1$-$C_6$)-alkylen)-S(O)$_2$NH($C_1$-$C_6$)-alkyl, $CO_2H$, CO($C_1$-$C_6$)-alkyl, CO—O($C_1$-$C_6$)-alkyl, O—CO($C_1$-$C_6$)-alkyl, $CONH_2$, CO—NH($C_1$-$C_6$)-alkyl, CO—N(($C_1$-$C_6$)-alkyl)$_2$, O—CO—NH($C_1$-$C_6$)-alkyl, O—CO—N(($C_1$-$C_6$)-alkyl)$_2$, O—S(O)$_2$—($C_1$-$C_6$)-alkyl, O—S(O)$_2$OH, O—S(O)$_2$—($C_1$-$C_6$)-alkoxy, O—S(O)$_2$$NH_2$, O—S(O)$_2$—NH($C_1$-$C_6$)-alkyl, O—S(O)$_2$—N(($C_1$-$C_6$)-alkyl)$_2$, S(O)($C_1$-$C_6$)-alkyl, S(O)$_2$($C_1$-$C_6$)-alkyl, $CH_2$S(O)($C_1$-$C_6$)-alkyl, $CH_2$S(O)$_2$($C_1$-$C_6$)-alkyl, S(O)$_2$OH, S(O)$_2$O($C_1$-$C_6$)-alkyl, S(O)$_2$$NH_2$, S(O)$_2$NH($C_1$-$C_6$)-alkyl, and S(O)$_2$N(($C_1$-$C_6$)-alkyl)$_2$;

optionally in the form of a single stereoisomer or a mixture of stereoisomers, in the form of the free compound and/or a physiologically acceptable salt and/or a physiologically acceptable solvate thereof.

3. The compound of claim 1, wherein

A, B and C independently represent CH or N;

$R^1$ and $R^2$ independently represent hydrogen or ($C_1$-$C_6$)-alkyl, whereby said ($C_1$-$C_6$)-alkyl is unsubstituted or substituted with 1, 2, 3, 4 or 5 substituents $X^1$; whereby at each occurrence $X^1$ is independently selected from the group consisting of F, Cl, Br, CN, ($C_1$-$C_6$)-alkoxy, OH, $CONH_2$, CONH($C_1$-$C_6$)-alkyl, CON(($C_1$-$C_6$)-alkyl)$_2$, $NH_2$, NH($C_1$-$C_6$)-alkyl and N(($C_1$-$C_6$)-alkyl)$_2$, or a group U, which is a 3- to 12-membered mono- or bi-cycloaliphatic ring, which is unsubstituted or substituted with 1, 2, 3, 4 or 5 substituents $X^2$, whereby at each occurrence $X^2$ is independently selected from the group consisting of OH, =O, CN, F, Cl, Br, $CF_3$, $CHF_2$, $CH_2F$, $OCF_3$, ($C_1$-$C_6$)-alkyl, ($C_1$-$C_6$)-alkoxy, $NH_2$, NH($C_1$-$C_6$)-alkyl, N(($C_1$-$C_6$)-alkyl)$_2$, NH—CO—($C_1$-$C_6$)-alkyl, $CO_2H$, CO—O—($C_1$-$C_6$)-alkyl, $CONH_2$, CO—NH($C_1$-$C_6$)alkyl and CO—N(($C_1$-$C_6$)-alkyl)$_2$; and whereby said group U may be connected to the nitrogen atom via a $C_{1-3}$-alkylene group, which in turn is unsubstituted or substituted with 1, 2 or 3 substituents independently selected from the group consisting of F, Cl, $CF_3$, =O, $OCF_3$ and OH, or a group V, which is a 3- to 12-membered mono-or bi-cyclic heterocycloaliphatic ring comprising at 1, 2 or 3 heteroatoms selected from the group consisting of O, S and N as ring members, and which mono- or bicyclic heterocycloaliphatic ring is unsubstituted or substituted with 1, 2, 3, 4 or 5 substituents $X^3$, whereby at each occurrence $X^3$ is independently selected from the group consisting of OH, =O, CN, F, Cl, Br, $CF_3$, $CHF_2$, $CH_2F$, $OCF_3$, ($C_1$-$C_6$)-alkyl, ($C_1$-$C_6$)-alkoxy, $NH_2$, NH($C_1$-$C_6$)-alkyl, N(($C_1$-$C_6$)-alkyl)$_2$, NH—CO—($C_1$-$C_6$)-alkyl, $CO_2H$, CO—O—($C_1$-$C_6$)-alkyl, $CONH_2$, CO—NH($C_1$-$C_6$)alkyl and CO—N(($C_1$-$C_6$)-alkyl)$_2$; and whereby said group V may be connected to the nitrogen atom via a $C_{1-3}$-alkylene group, which in turn is unsubstituted or substituted with 1, 2 or 3 substituents independently selected from the group consisting of F, Cl, $CF_3$, =O, $OCF_3$ and OH, or a group W which is phenyl or 5- or 6-membered heteroaryl, wherein said phenyl or said heteroaryl is unsubstituted or substituted with 1, 2, 3, 4, or 5 substituents $X^4$, whereby at each occurrence $X^4$ is independently selected from the group consisting of OH, CN, F, Cl, Br, $CF_3$, $CHF_2$, $CH_2F$, $OCF_3$, ($C_1$-$C_6$)-alkyl, ($C_1$-$C_6$)-hydroxyalkyl, ($C_1$-$C_6$)-alkoxy, S(O)—($C_1$-$C_6$)-alkyl, S(O)$_2$—($C_1$-$C_6$)-alkyl, ($C_3$-$C_6$)-cycloalkyl, $NH_2$, NH($C_1$-$C_6$)-alkyl, N(($C_1$-$C_6$)-alkyl)$_2$, NH—CO—($C_1$-$C_6$)-alkyl, NH—SO—($C_1$-$C_6$)-alkyl, NH—S(O)$_2$—($C_1$-$C_6$)-alkyl, N(($C_1$-$C_6$)-alkyl)-CO—($C_1$-$C_6$)-alkyl, N(($C_1$-$C_6$)-alkyl)-SO—($C_1$-$C_6$)-alkyl, N(($C_1$-$C_6$)-alkyl)-SO$_2$—($C_1$-$C_6$)-alkyl, $NHCONH_2$, NH—CO—NH—($C_1$-$C_6$)-alkyl, N(($C_1$-$C_6$)-alkyl)-CO—N(($C_1$-$C_6$)-alkyl)$_2$, $CO_2H$, CO—O—($C_1$-$C_6$)-alkyl, $CONH_2$, CO—NH($C_1$-$C_6$) alkyl and CO—N(($C_1$-$C_6$)-alkyl)$_2$; and wherein said phenyl or said heteroaryl may be condensed with a 4-, 5-, 6- or 7-membered ring, being carbocyclic or heterocyclic, wherein said condensed ring may be saturated, partially unsaturated or aromatic and is unsubstituted or substituted with 1, 2, 3, 4 or 5 substituents $X^5$, whereby at each occurrence $X^5$ is independently selected from the group consisting of OH, =O, CN, F, Cl, Br, $CF_3$, $CHF_2$, $CH_2F$, $OCF_3$, ($C_1$-$C_6$)-alkyl, ($C_1$-$C_6$)-alkoxy, $NH_2$, NH($C_1$-$C_6$)-alkyl, N(($C_1$-$C_6$)-alkyl)$_2$, NH—CO—($C_1$-$C_6$)-alkyl, $CO_2H$, CO—O—($C_1$-$C_6$)-alkyl, $CONH_2$, CO—NH($C_1$-$C_6$)alkyl and CO—N(($C_1$-$C_6$)-alkyl)$_2$; and wherein said group W may be connected to the nitrogen atom via a $C_{1-3}$-alkylene group, which in turn may be unsubstituted or substituted with at least one substituent independently selected from the group consisting of F, Cl, CF$_3$, =O, OCF$_3$ and OH, or R$^1$ and R$^2$ together with the nitrogen atom to which they are attached form a 3- to 12-membered monocyclic or bicyclic non-aromatic ring wherein said ring may contain at least one additional heteroatom selected from the group consisting of O, S and N and wherein said ring is unsubstituted or substituted with at least one substituent X$^6$; whereby at each occurrence X$^6$ is independently selected from the group consisting of OH, =O, CN, F, Cl, Br, CF$_3$, CHF$_2$, CH$_2$F, OCF$_3$, (C$_1$-C$_6$)-alkyl, (C$_1$-C$_6$)-hydroxyalkyl, (C$_1$-C$_6$)-cyanoalkyl, (C$_1$-C$_6$)-alkoxy, (C$_3$-C$_6$)-cycloalkyl, NH$_2$, NH(C$_1$-C$_6$)-alkyl, N((C$_1$-C$_6$)-alkyl)$_2$, NH—CO—(C$_1$-C$_6$)-alkyl, CO$_2$H, CO—(C$_1$-C$_6$)-alkyl, CO—O—(C$_1$-C$_6$)-alkyl, CONH$_2$, CO—NH(C$_1$-C$_6$)alkyl and CO—N((C$_1$-C$_6$)-alkyl)$_2$;

R$^3$ and R$^4$, independently of one another, each represent hydrogen, (C$_1$-C$_6$)-alkyl or (C$_3$-C$_6$)-cycloalkyl, wherein said (C$_1$-C$_6$)-alkyl and (C$_3$-C$_6$)-cycloalkyl are each unsubstituted or substituted with 1, 2, 3, 4 or 5 substituents Y$^1$, wherein at each occurrence Y$^1$ is independently selected from the group consisting of OH, =O, CN, F, Cl, Br, CF$_3$, CHF$_2$, CH$_2$F, OCF$_3$, (C$_1$-C$_6$)-alkyl, (C$_1$-C$_6$)-alkoxy, NH$_2$, NH(C$_1$-C$_6$)-alkyl, N((C$_1$-C$_6$)-alkyl)$_2$, NH—CO—(C$_1$-C$_6$)-alkyl, CO$_2$H, CO—O—(C$_1$-C$_6$)-alkyl, CONH$_2$, CO—NH(C$_1$-C$_6$)alkyl and CO—N((C$_1$-C$_6$)-alkyl)$_2$, or together with the carbon atom to which they are attached form a 3- to 6-membered cycloalkyl ring, which is unsubstituted or substituted with 1, 2, 3, 4 or 5 substituents Y$^2$, wherein at each occurrence Y$^2$ is independently selected from the group consisting of OH, =O, CN, F, Cl, Br, CF$_3$, CHF$_2$, CH$_2$F, OCF$_3$, (C$_1$-C$_6$)-alkyl, (C$_1$-C$_6$)-alkoxy, NH$_2$, NH(C$_1$-C$_6$)-alkyl, N((C$_1$-C$_6$)-alkyl)$_2$, NH—CO—(C$_1$-C$_6$)-alkyl, CO$_2$H, CO—O—(C$_1$-C$_6$)-alkyl, CONH$_2$, CO—NH(C$_1$-C$_6$)alkyl and CO—N((C$_1$-C$_6$)-alkyl)$_2$;

L represents a bond, O, S, or (C$_1$-C$_6$)-alkylene, whereby the aforementioned alkylenes are in each case unsubstituted or substituted with 1, 2 or 3 substituents independently selected from the group consisting of F, Cl, CF$_3$, =O, OCF$_3$ and OH;

G represents a phenyl or 5- or 6-membered heteroaryl, wherein said phenyl or said heteroaryl is unsubstituted or substituted with 1, 2, 3, 4 or 5 substituents Z;

whereby at each occurrence Z is independently selected from the group consisting of F, Cl, Br, CHF$_2$, CH$_2$F, CF$_3$, OCF$_3$, SCF$_3$, OH, CN, SH, nitro, (C$_1$-C$_6$)-alkyl, (C$_2$-C$_6$)-alkenyl, (C$_2$-C$_6$)-alkinyl, (C$_1$-C$_6$)-hydroxyalkyl, (C$_1$-C$_6$)-cyanoalkyl, (C$_1$-C$_6$)-alkoxy, (C$_1$-C$_6$)-thioalkyl, (C$_1$-C$_6$)-alkylen-S—(C$_1$-C$_6$)-alkyl, (C$_3$-C$_6$)-cycloalkyl, hydroxyl-(C$_3$-C$_6$)-cycloalkyl, (C$_3$-C$_8$)-heterocycloalkyl, NH$_2$, NH(C$_1$-C$_6$)-alkyl, N((C$_1$-C$_6$)-alkyl)$_2$, NH—CO—(C$_1$-C$_6$)-alkyl, NH—CO—O—(C$_1$-C$_6$)-alkyl, NH—S(O)$_2$OH, NH—S(O)$_2$(C$_1$-C$_6$)-alkyl, NH—S(O)$_2$O(C$_1$-C$_6$)-alkyl, NH—S(O)$_2$NH$_2$, NH—S(O)$_2$NH(C$_1$-C$_6$)-alkyl, NH—S(O)$_2$N((C$_1$-C$_6$)-alkyl)$_2$, NH((C$_1$-C$_6$)-alkylen)-S(O)$_2$OH, NH((C$_1$-C$_6$)-alkylen)-S(O)$_2$(C$_1$-C$_6$)-alkyl, NH((C$_1$-C$_6$)-alkylen)-S(O)$_2$O(C$_1$-C$_6$)-alkyl, NH((C$_1$-C$_6$)-alkylen)-S(O)$_2$NH$_2$, NH((C$_1$-C$_6$)-alkylen)-S(O)$_2$NH(C$_1$-C$_6$)-alkyl, CO$_2$H, CO(C$_1$-C$_6$)-alkyl, CO—O(C$_1$-C$_6$)-alkyl, O—CO(C$_1$-C$_6$)-alkyl, CONH$_2$, CO—NH(C$_1$-C$_6$)-alkyl, CO—N((C$_1$-C$_6$)-alkyl)$_2$, O—CO—NH(C$_1$-C$_6$)-alkyl, O—CO—N((C$_1$-C$_6$)-alkyl)$_2$, O—S(O)$_2$—(C$_1$-C$_6$)-alkyl, O—S(O)$_2$OH, O—S(O)$_2$—(C$_1$-C$_6$)-alkoxy, O—S(O)$_2$NH$_2$, O—S(O)$_2$—NH(C$_1$-C$_6$)-alkyl, O—S(O)$_2$—N((C$_1$-C$_6$)-alkyl)$_2$, S(O)(C$_1$-C$_6$)-alkyl, S(O)$_2$(C$_1$-C$_6$)-alkyl, CH$_2$S(O)(C$_1$-C$_6$)-alkyl, CH$_2$S(O)$_2$(C$_1$-C$_6$)-alkyl, S(O)$_2$OH, S(O)$_2$O(C$_1$-C$_6$)-alkyl, S(O)$_2$NH$_2$, S(O)$_2$NH(C$_1$-C$_6$)-alkyl, and S(O)$_2$N((C$_1$-C$_6$)-alkyl)$_2$;

optionally in the form of a single stereoisomer or a mixture of stereoisomers, in the form of the free compound and/or a physiologically acceptable salt and/or a physiologically acceptable solvate thereof.

4. The compound of claim 1, wherein each of A, B and C represents CH.

5. The compound of claim 1, wherein

R$^1$ and R$^2$ independently represent

Hydrogen or an alkyl selected from the group consisting of methyl, ethyl, n-propyl, i-propyl, n-butyl, i-butyl, s-butyl and t-butyl, whereby said alkyl is unsubstituted or substituted with 1, 2 or 3 substituents independently from one another selected from the group consisting of methoxy, ethoxy, OH, F, Cl, CN, CONH$_2$, CONH(CH$_3$), CON(CH$_3$)$_2$, NH$_2$, NH(CH$_3$) and N(CH$_3$)$_2$, or represent one of the following groups U1 to U11:

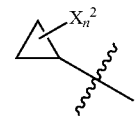

U1

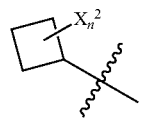

U2

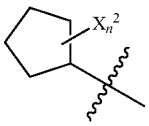

U3

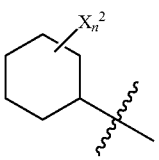

U4

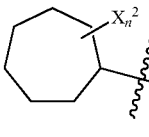

U5

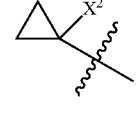

U6

U7

-continued

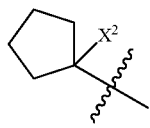 U8

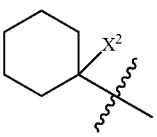 U9

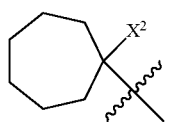 U10

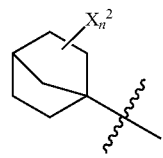 U11 whereby at each occurrence n is 0, 1, 2, 3, 4 or 5, and whereby at each occurrence $X^2$ is independently selected from the group consisting of OH, =O, CN, F, Cl, Br, $CF_3$, $CHF_2$, $CH_2F$, $OCF_3$, $(C_1$-$C_6)$-alkyl, $(C_1$-$C_6)$-alkoxy, $NH_2$, $NH(C_1$-$C_6)$-alkyl, $N((C_1$-$C_6)$-alkyl$)_2$, NH—CO—$(C_1$-$C_6)$-alkyl, $CO_2H$, CO—O—$(C_1$-$C_6)$-alkyl, $CONH_2$, CO—NH$(C_1$-$C_6)$alkyl and CO—N$((C_1$-$C_6)$-alkyl$)_2$, and whereby said group U may be connected to the nitrogen atom via a $C_{1-3}$-alkylene group, which in turn is unsubstituted or substituted with 1, 2 or 3 substituents independently selected from the group consisting of F, Cl, $CF_3$, =O, $OCF_3$ and OH, or represent one of the following groups V1 to V35:

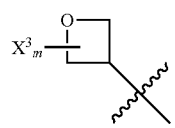 V1

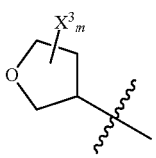 V2

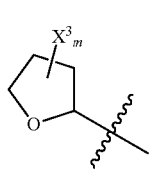 V3

-continued

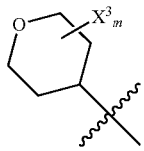 V4

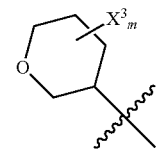 V5

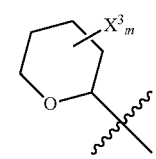 V6

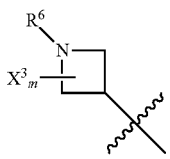 V7

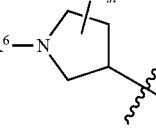 V8

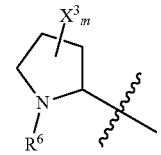 V9

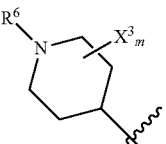 V10

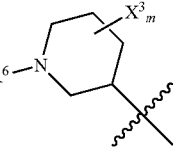 V11

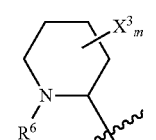 V12

-continued
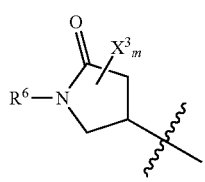 V13
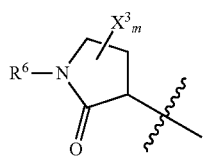 V14
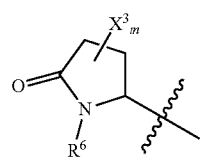 V15
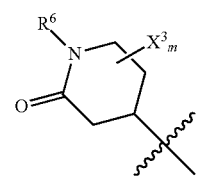 V16
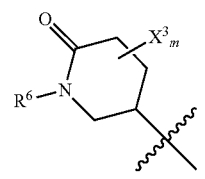 V17
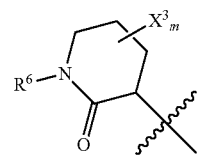 V18
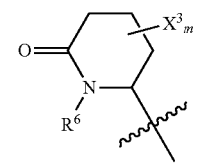 V19
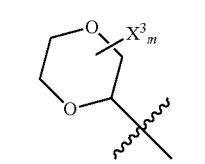 V20
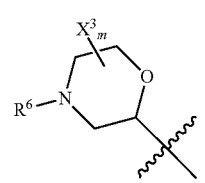 V21
-continued
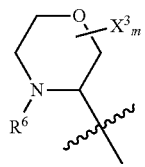 V22
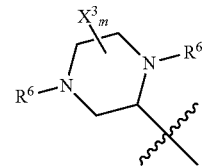 V23
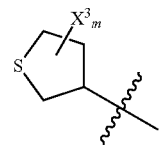 V24
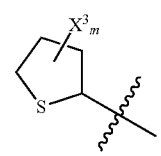 V25
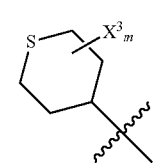 V26
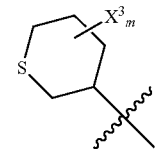 V27
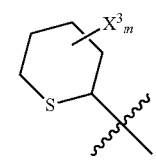 V28
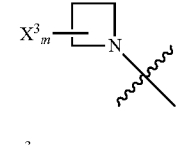 V29
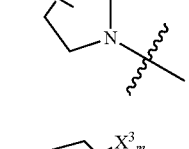 V30
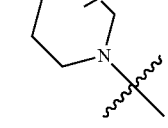 V31

-continued

V32
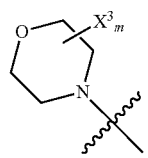

V33
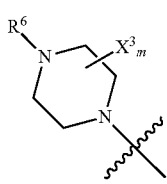

V34
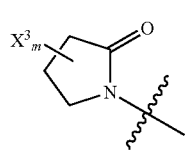

V35
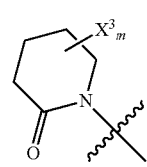

whereby at each occurrence m is 0, 1, 2, 3, 4 or 5, and $X^3$ at each occurrence is independently selected from the group consisting of OH, =O, CN, F, Cl, Br, $CF_3$, $CHF_2$, $CH_2F$, $OCF_3$, $(C_1-C_6)$-alkyl, $(C_1-C_6)$-alkoxy, $NH_2$, $NH(C_1-C_6)$-alkyl, $N((C_1-C_6)$-alkyl$)_2$, NH—CO—$(C_1-C_6)$-alkyl, $CO_2H$, CO—O—$(C_1-C_6)$-alkyl, $CONH_2$, CO—NH$(C_1-C_6)$alkyl and CO—N$((C_1-C_6)$-alkyl$)_2$; and wherein said group V may be connected to the nitrogen atom via a $C_{1-3}$-alkylene group, which in turn is unsubstituted or substituted with 1, 2 or 3 substituents independently selected from the group consisting of F, Cl, $CF_3$, =O, $OCF_3$ and OH, or represent one of the following groups W1 to W47:

W1
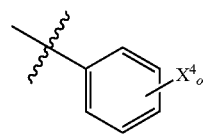

W2
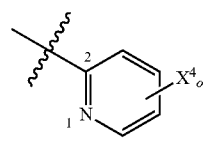

W3
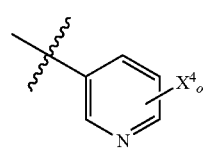

W4
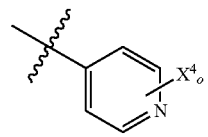

W5
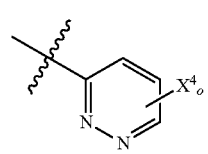

W6
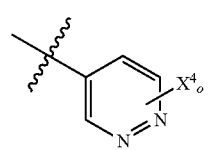

W7
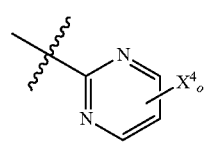

W8
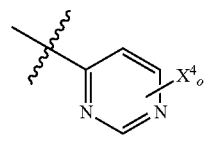

W9
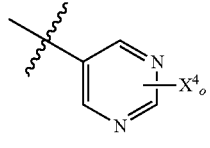

W10
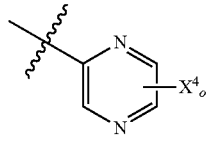

W11
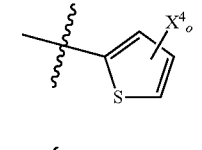

W12
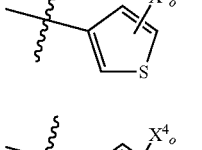

W13
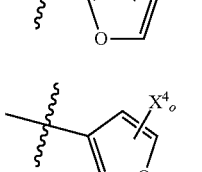

W14

-continued
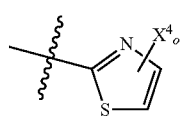 W15
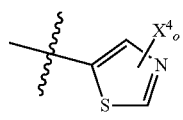 W16
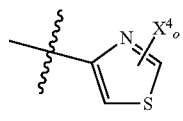 W17
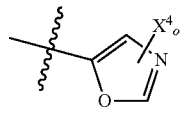 W18
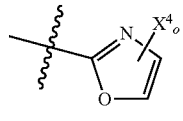 W19
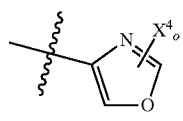 W20
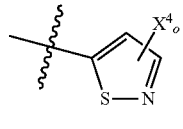 W21
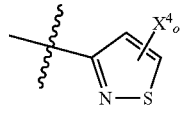 W22
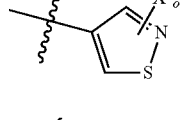 W23
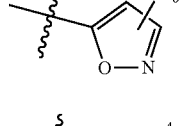 W24
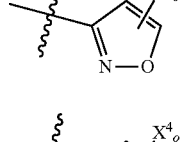 W25
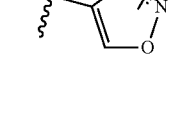 W26
-continued
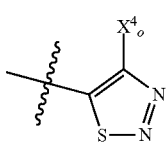 W27
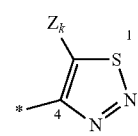 W28
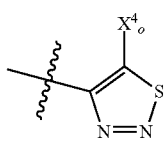 W29
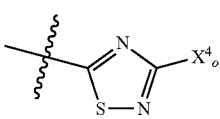 W30
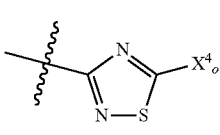 W31
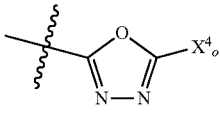 W32
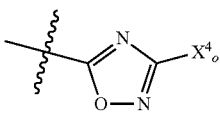 W33
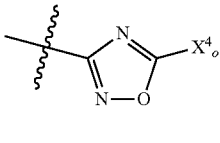 W34
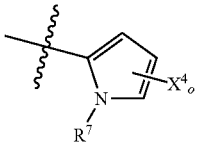 W35
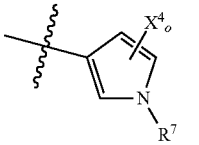 W36
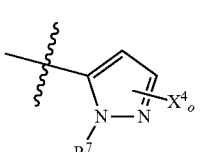 W37

-continued

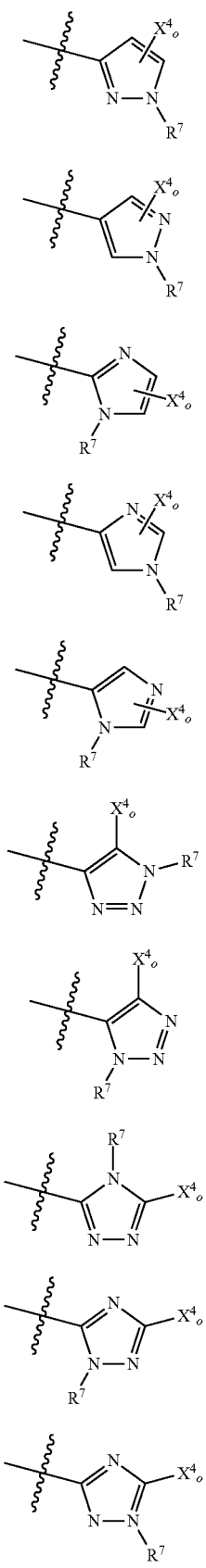

W38
W39
W40
W41
W42
W43
W44
W45
W46
W47 wherein at each occurrence o represents 0, 1, 2, 3, 4 or 5, and $X^4$ at each occurrence is independently selected from the group consisting of OH, CN, F, Cl, Br, ($C_1$-$C_6$)-alkyl, ($C_1$-$C_6$)-hydroxyalkyl, ($C_1$-$C_6$)-alkoxy, S(O)—($C_1$-$C_6$)-alkyl, S(O)$_2$—($C_1$-$C_6$)-alkyl, $CF_3$, $CHF_2$, $CH_2F$, $OCF_3$, ($C_3$-$C_6$)-cycloalkyl, $NH_2$, NH($C_1$-$C_6$)-alkyl, N(($C_1$-$C_6$)-alkyl)$_2$, NH—CO—($C_1$-$C_6$)-alkyl, NH—SO—($C_1$-$C_6$)-alkyl, NH—S(O)$_2$—($C_1$-$C_6$)-alkyl, N(($C_1$-$C_6$)-alkyl)-CO—($C_1$-$C_6$)-alkyl, N(($C_1$-$C_6$)-alkyl)-SO—($C_1$-$C_6$)-alkyl, N(($C_1$-$C_6$)-alkyl)-SO—($C_1$-$C_6$)-alkyl, $NHCONH_2$, NH—CO—NH—($C_1$-$C_6$)-alkyl, N(($C_1$-$C_6$)-alkyl)-CO—N(($C_1$-$C_6$)-alkyl)$_2$, $CO_2H$, CO—O—($C_1$-$C_6$)-alkyl, $CONH_2$, CO—NH($C_1$-$C_6$)alkyl and CO—N(($C_1$-$C_6$)-alkyl)$_2$; and wherein said group W may be connected to the nitrogen atom via a $C_{1-3}$-alkylene group, which in turn may be unsubstituted or substituted with at least one substituent independently selected from the group consisting of F, Cl, $CF_3$, =O, $OCF_3$ and OH.

6. The compound of claim 1, wherein $R^1$ and $R^2$ together with the nitrogen atom to which they are attached form a ring selected from the following groups Q1 to Q34:

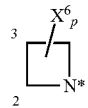 Q1

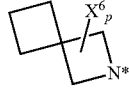 Q2

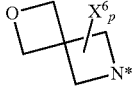 Q3

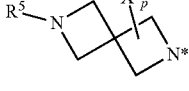 Q4

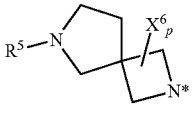 Q5

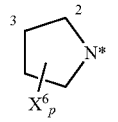 Q6

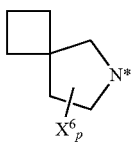 Q7

-continued
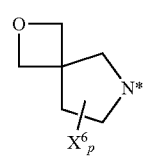
Q8
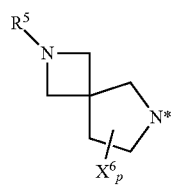
Q9
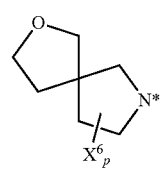
Q10
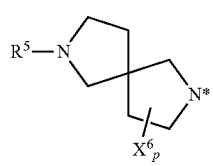
Q11
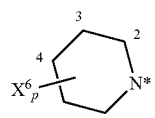
Q12
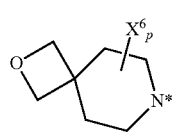
Q13
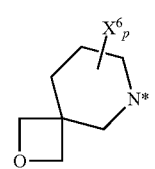
Q14
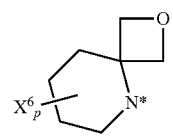
Q15
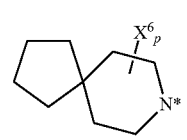
Q16
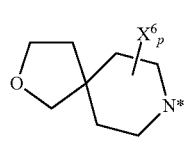
Q17
-continued
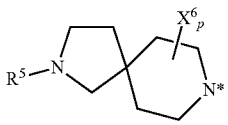
Q18
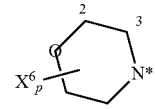
Q19
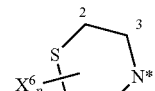
Q20
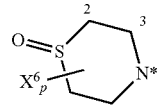
Q21
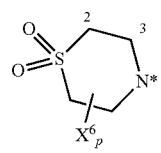
Q22
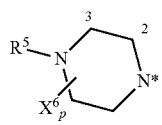
Q23
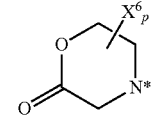
Q24
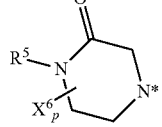
Q25
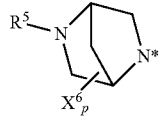
Q26
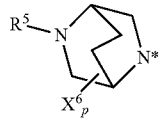
Q27
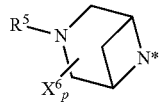
Q28

-continued

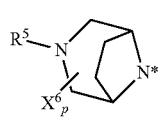
Q29

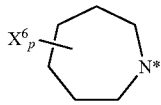
Q30

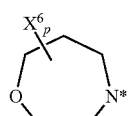
Q31

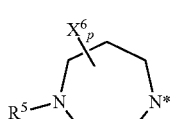
Q32

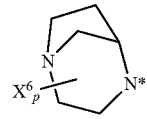
Q33

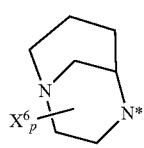
Q34 in which the site marked with an asterisk (*) indicates the binding site, which is bonded to the carbonyl group;

$R^5$ is H, $(C_1$-$C_6)$-alkyl, $(C_1$-$C_6)$-hydroxyalkyl, $(C_1$-$C_6)$-cyanoalkyl, $(C_3$-$C_6)$-cycloalkyl, CO—$(C_1$-$C_6)$-alkyl or $SO_2$—$(C_1$-$C_6)$-alkyl;

at each occurrence p is 0, 1, 2, 3, 4 or 5; and $X^6$ at each occurrence is independently selected from the group consisting of OH, =O, CN, F, Cl, Br, $CF_3$, $CHF_2$, $CH_2F$, $OCF_3$, $(C_1$-$C_6)$-alkyl, $(C_1$-$C_6)$-hydroxyalkyl, $(C_1$-$C_6)$-cyanoalkyl, $(C_1$-$C_6)$-alkoxy, $(C_3$-$C_6)$-cycloalkyl, $NH_2$, $NH(C_1$-$C_6)$-alkyl, $N((C_1$-$C_6)$-alkyl$)_2$, NH—CO—$(C_1$-$C_6)$-alkyl, $CO_2H$, CO—$(C_1$-$C_6)$-alkyl, CO—O—$(C_1$-$C_6)$-alkyl, $CONH_2$, CO—$NH(C_1$-$C_6)$alkyl and CO—$N((C_1$-$C_6)$-alkyl$)_2$.

7. The compound of claim 1, wherein the substructure M

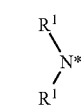
M represents one of the following substructures M1 to M60:

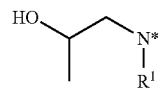
M1

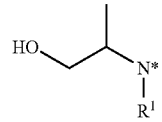
M2

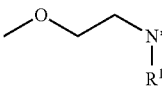
M3

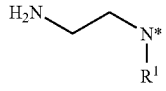
M4

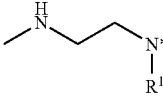
M5

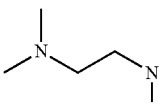
M6

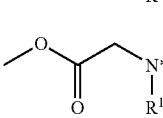
M7

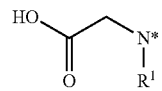
M8

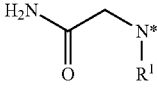
M9

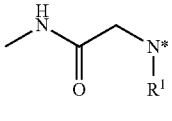
M10

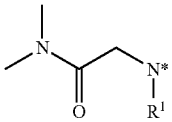
M11

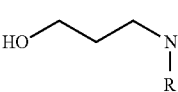
M12

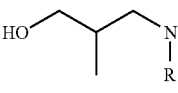
M13

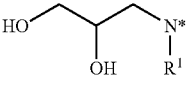
M14

M15

| | | | |
|---|---|---|---|
| 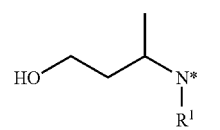 | M16 | 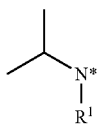 | M30 |
| 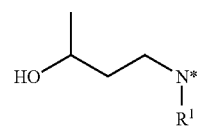 | M17 | 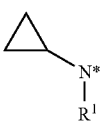 | M31 |
| 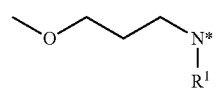 | M18 | 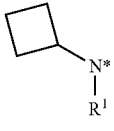 | M32 |
| 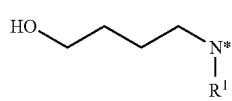 | M19 | 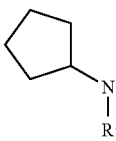 | M33 |
| 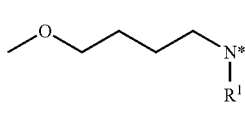 | M20 | 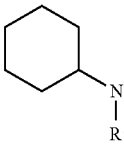 | M34 |
| 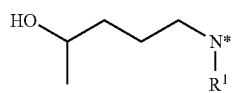 | M21 | 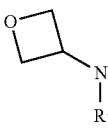 | M35 |
| 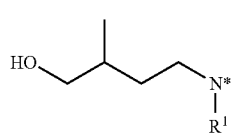 | M22 | 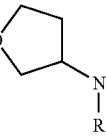 | M36 |
| 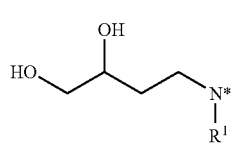 | M23 | 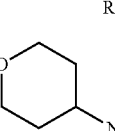 | M37 |
| 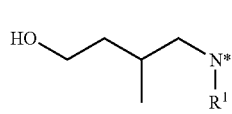 | M24 | 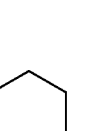 | M38 |
| 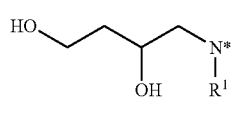 | M25 | 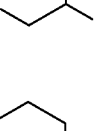 | M39 |
| 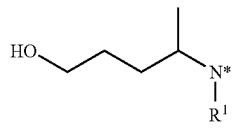 | M26 | 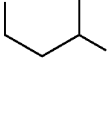 | M40 |
|  | M27 | 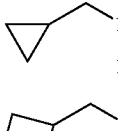 | M41 |
|  | M28 |  | |
| 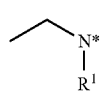 | M29 | | |

-continued

M42 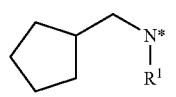

M43 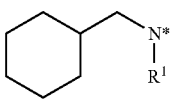

M44 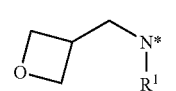

M45 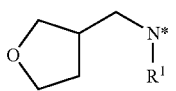

M46 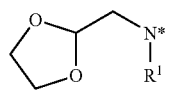

M47 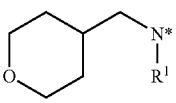

M48 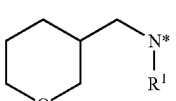

M49 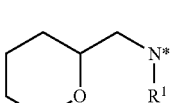

M50 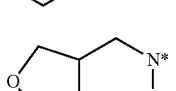

M51 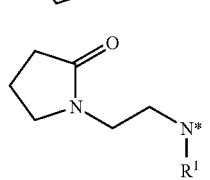

M52 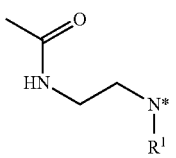

M53 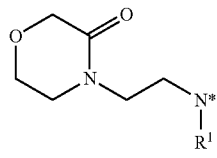

M54 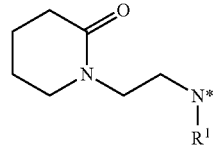

-continued

M55 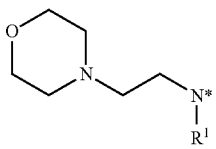

M56 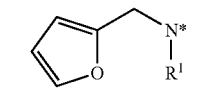

M57 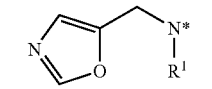

M58 

M59 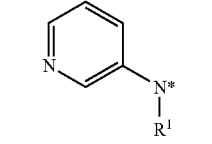

M60 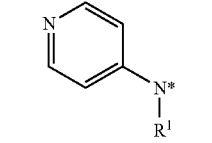

wherein $R^1$ is H, $CH_3$, $CH_2CH_3$, $CH(CH_3)_2$, $CH_2CH_2OH$, $CH_2CH_2OCH_3$ or cyclopropyl.

8. The compound of claim 1, wherein
$R^3$ and $R^4$ each represent $CH_3$, or
$R^3$ and $R^4$ together with the carbon atom to which they are attached form a cyclopropyl or cyclobutyl.

9. The compound of claim 1, wherein L represents a bond.

10. The compound of claim 1, wherein G is one of the following groups G1 to G44:

G1 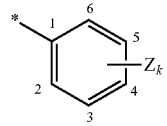

G2 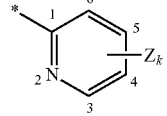

G3 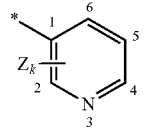

G4
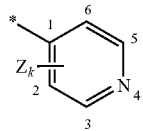
G5
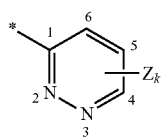
G6
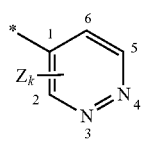
G7
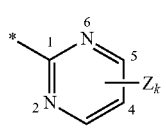
G8
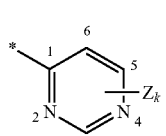
G9
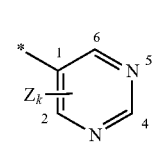
G10
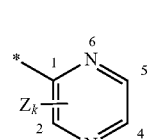
G11
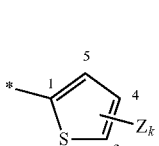
G12
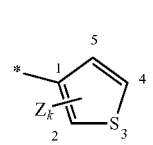
G13
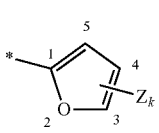
G14
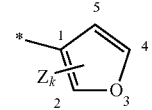
G15
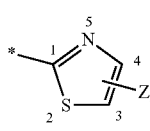
G16
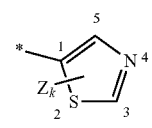
G17
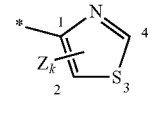
G18
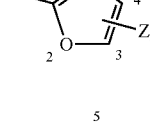
G19
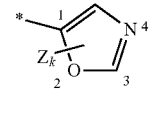
G20
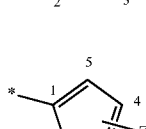
G21
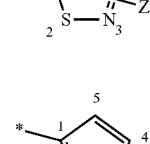
G22
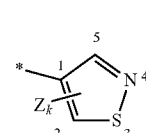
G23
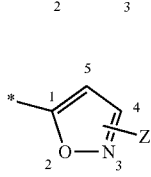
G24

-continued
G25 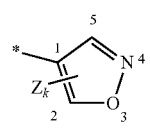
G26 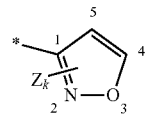
G27 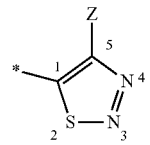
G28 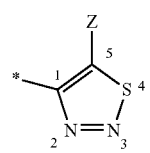
G29 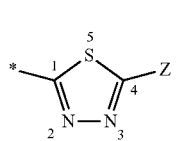
G30 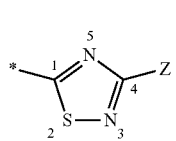
G31 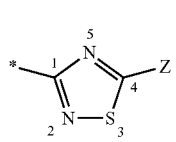
G32 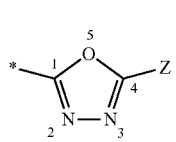
G33 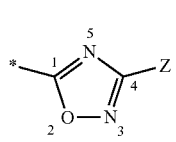
G34 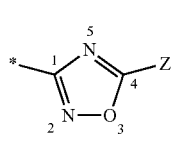
G35 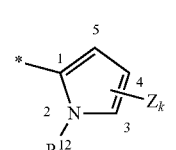
-continued
G36 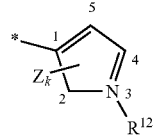
G37 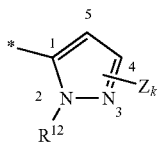
G38 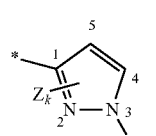
G39 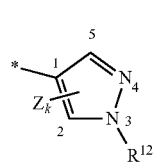
G40 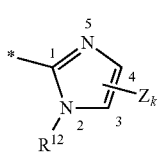
G41 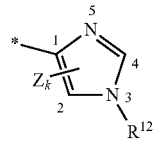
G42 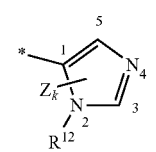
G43 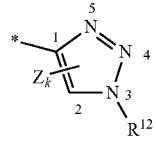
G44 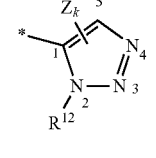
in which the site marked with an asterisk (*) indicates the binding site, which is bonded to the pyrimidine ring;
$R^{12}$ is selected H, $CH_3$ or $CH_2CH_3$;
k at each occurrence 0, 1, 2, 3, 4 or 5; and
Z at each occurrence is independently selected from the group consisting of F, Cl, CN, $CF_3$, $CHF_2$, $CH_2F$, OCF₃, OH, OCH₃, OC₂H₅, OCOCH₃, CH₃, CH₂CH₃, CH₂CH₂CH₃, CH(CH₃)₂, CH₂CH₂CH₂CH₃, CH(CH₃)CH₂CH₃, CH₂CH(CH₃)₂, C(CH₃)₃, CONH₂, CONHCH₃, CON(CH₃)₂, NH₂, NH(CH₃), NH(CH₂CH₃), NH(CH₂-c-propyl), N(CH₃)₂, NHCOCH₃, CH₂OH, CH₂CH₂OH, C(CH₃)₂OH, CH(CH₃)OH, CH₂CN, SOCH₃, SO₂CH₃, SOCH₂CH₃, SO₂CH₂CH₃, SO₂NH₂, CH₂SOCH₃, CH₂SO₂CH₃, N-pyrrolidinyl, cyclopropyl, 1-hydroxy-cycloprop-1-yl, cyclobutyl, cyclopentyl and cyclohexyl.

11. The compound of claim 10 having formula I'

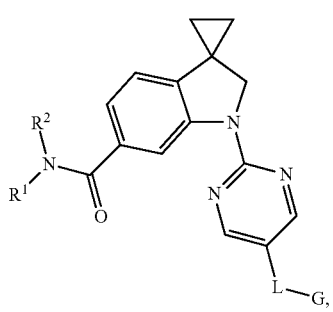

(I')

wherein R¹ and R² together with the nitrogen atom to which they are attached form one of the following heterocycles Q19, Q23, Q25 or Q26:

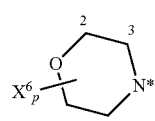

Q19

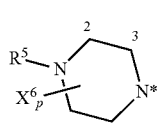

Q23

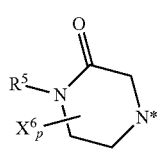

Q25

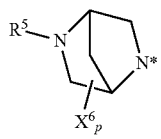

Q26 in which the site marked with an asterisk (*) indicates the binding site, which is bonded to the carbonyl group;

R⁵ is H, CH₃, CH₂CH₃, CH₂CH₂CH₃, CH(CH₃)₂, cyclopropyl, C(O)CH₃, C(O)CH₂CH₃, C(O)CH₂CH₂CH₃, C(O)CH(CH₃)₂, C(O)-cyclopropyl, CH₂CH₂CN, CH₂CH₂OH or CH₂CH₂OCH₃;

at each occurrence p is 0, 1, 2 or 3; and

X⁶ represents H, C(O)CH₃, C(O)CH₂CH₃, CH₃, CH₂CH₃, CH₂CH₂CH₃, CH(CH₃)₂, CH₂CH₂CH₂CH₃, CH₂CH(CH₃)₂, CH(CH₃) (CH₂CH₃), CH(CH₃)₃, cyclopropyl, cyclobutyl, cyclopentyl and cyclohexyl, OH, OCH₃, OCH₂CH₃, OCH(CH₃)₂, NH₂, N(H)CH₃, N(CH₃)₂, N(H)C(O)CH₃, CH₂OH, CH₂CH₂OH, CH₂OCH₃ or CH₂CH₂OCH₃;

or in which R¹ stands for CH₃ or cyclopropyl and R² stands for CH₂CH₂OH, CH₂CH₂CH₂OH, (R)—CH₂CH(OH)CH₂CH₂OH, (S)—CH₂CH(OH)CH₂CH₂OH, (R)-2-CH₂CH(CH₃)OH, (S)—CH₂CH(CH₃)OH, (R)—CH(CH₃)CH₂OH, (S)—CH(CH₃)CH₂OH.

12. A pharmaceutical composition comprising the compound of claim 1.

13. The compound of claim 7 having formula I-h

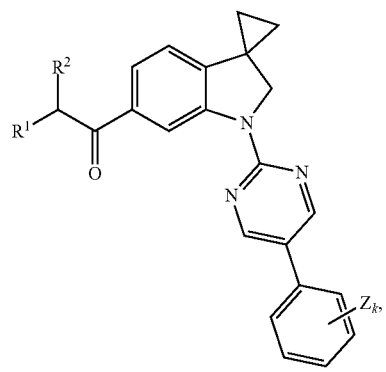

I-h wherein the substructure M is selected from the group consisting of M1 to M12, M25 and M27 to M30, R¹ is H or CH₃ or cyclopropyl, Z is selected from the group consisting of F, Cl, CN, CF₃, CHF2, CH2F, OCF₃, OH, OCH₃, OC₂H₅, CH₃, CH₂CH₃, CH₂CH₂CH₃, CH(CH₃)₂, CH₂CH₂CH₂CH₃, CH(CH₃)CH₂CH₃, CH₂CH(CH₃)₂, C(CH₃)₃, CONH₂, CONHCH₃, CON(CH₃)₂, NH₂, NH(CH₃), N(CH₃)₂, NHCOCH₃, CH₂OH, cyclopropyl, cyclobutyl, cyclopentyl and cyclohexyl, and k is 0, 1, or 2.

14. The compound of claim 1 having formula I-i,

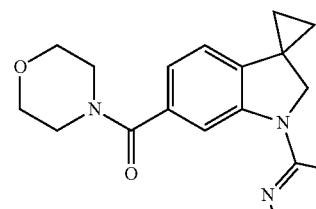

I-i wherein Z is selected from the group consisting of F, Cl, CN, CF₃, CHF₂, CH₂F, OCF₃, OH, OCH₃, OC₂H₅, OCOCH₃, CH₃, CH₂CH₃, CH₂CH₂CH₃, CH(CH₃)₂, CH₂CH₂CH₂CH₃, CH(CH₃)CH₂CH₃, CH₂CH(CH₃)₂, C(CH₃)₃, CONH₂, CONHCH₃, CON(CH₃)₂, NH₂, NH(CH₃), NH(CH₂CH₃), NH(CH₂-c-propyl), N(CH₃)₂, NHCOCH₃, CH₂OH, CH₂CH₂OH, C(CH₃)₂OH, CH(CH₃)OH, CH₂CN, SOCH₃, SO₂CH₃, SOCH₂CH₃, SO₂CH₂CH₃, SO₂NH₂, CH₂SOCH₃, CH₂SO₂CH₃, N-pyrrolidinyl, cyclopropyl, 1-hydroxy-cycloprop-1-yl, cyclobutyl, cyclopentyl and cyclohexyl, and k is 0, 1, or 2.

15. The compound of claim 1 having formula I-j,

I-j

[Structure]

wherein Z is selected from the group consisting of F, Cl, CN, CF₃, CHF₂, CH₂F, OCF₃, OH, OCH₃, OC₂H₅, OCOCH₃, CH₃, CH₂CH₃, CH₂CH₂CH₃, CH(CH₃)₂, CH₂CH₂CH₂CH₃, CH(CH₃)CH₂CH₃, CH₂CH(CH₃)₂, C(CH₃)₃, CONH₂, CONHCH₃, CON(CH₃)₂, NH₂, NH(CH₃), NH(CH₂CH₃), NH(CH₂-c-propyl), N(CH₃)₂, NHCOCH₃, CH₂OH, CH₂CH₂OH, C(CH₃)₂OH, CH(CH₃)OH, CH₂CN, SOCH₃, SO₂CH₃, SOCH₂CH₃, SO₂CH₂CH₃, SO₂NH₂, CH₂SOCH₃, CH₂SO₂CH₃, N-pyrrolidinyl, cyclopropyl, 1-hydroxy-cycloprop-1-yl, cyclobutyl, cyclopentyl and cyclohexyl, k is 0, 1, or 2, $R^5$ is H, CH₃, CH2CH₃, CH₂CH₂CH₃, CH(CH₃)₂, cyclopropyl, C(O)CH₃, C(O)CH₂CH₃, C(O)CH₂CH₂CH₃, C(O)CH(CH₃)₂, C(O)-cyclopropyl, CH₂CH₂CN, CH₂CH₂OH or CH₂CH₂OCH₃;

p is 0, 1, 2 or 3, and each $X^6$ represents CH₃, CH₂CH₃, CH₂CH₂CH₃, CH(CH₃)₂, CH(CH₃)₃, cyclopropyl, cyclobutyl, cyclopentyl cyclohexyl, OH, OCH₃, OCH2CH₃, OCH(CH₃)₂, NH₂, N(H)CH₃, N(CH₃)₂, N(H)C(O)CH₃, CH₂OH, CH₂CH₂OH, CH₂OCH₃ or CH₂CH₂OCH₃.

16. The compound of claim 1 haying formula I-k,

I-k

[Structure]

wherein Z is selected from the group consisting of F, Cl, CN, CF₃, CHF₂, CH₂F, OCF₃, OH, OCH₃, OC₂H₅, OCOCH₃, CH₃, CH₂CH₃, CH₂CH₂CH₃, CH(CH₃)₂, CH₂CH₂CH₂CH₃, CH(CH₃)CH₂CH₃, CH₂CH(CH₃)₂, C(CH₃)₃, CONH₂, CONHCH₃, CON(CH₃)₂, NH₂, NH(CH₃), NH(CH₂CH₃), NH(CH₂-c-propyl), N(CH₃)₂, NHCOCH₃, CH₂OH, CH₂CH₂OH, C(CH₃)₂OH, CH(CH₃)OH, CH₂CN, SOCH₃, SO₂CH₃, SOCH₂CH₃, SO₂CH₂CH₃, SO₂NH₂, CH₂SOCH₃, CH₂SO₂CH₃, N-pyrrolidinyl, cyclopropyl, 1-hydroxy-cycloprop-1-yl, cyclobutyl, cyclopentyl and cyclohexyl, k is 0, 1, or 2, $R^5$ is H, CH₃, CH₂CH₃, CH₂CH₂CH₃, CH(CH₃)₂, cyclopropyl, C(O)CH₃, C(O)CH₂CH₃, C(O)CH₂CH₂CH₃, C(O)CH(CH₃)₂, C(O)-cyclopropyl, CH₂CH₂CN, CH₂CH₂OH or CH₂CH₂OCH₃, p is 0, 1, 2 or 3, and each $X^6$ represents CH₃, CH₂CH₃, CH₂CH₂CH₃, CH(CH₃)₂, CH(CH₃)₃, cyclopropyl, cyclobutyl, cyclopentyl cyclohexyl, OH, OCH₃, OCH₂CH₃, OCH(CH₃)₂, NH₂, N(H)CH₃, N(CH₃)₂, N(H)C(O)CH₃, CH₂OH, CH₂CH₂OH, CH₂OCH₃ or CH₂CH₂OCH₃.

17. The compound of claim 1 haying formula I-l,

I-l

[Structure]

wherein Z is selected from the group consisting of F, Cl, CN, CF₃, CHF₂, CH₂F, OCF₃, OH, OCH₃, OC₂H₅, OCOCH₃, CH₃, CH₂CH₃, CH₂CH₂CH₃, CH(CH₃)₂, CH₂CH₂CH₂CH₃, CH(CH₃)CH₂CH₃, CH₂CH(CH₃)₂, C(CH₃)₃, CONH₂, CONHCH₃, CON(CH₃)₂, NH₂, NH(CH₃), NH(CH₂CH₃), NH(CH₂-c-propyl), N(CH₃)₂, NHCOCH₃, CH₂OH, CH₂CH₂OH, C(CH₃)₂OH, CH(CH₃)OH, CH₂CN, SOCH₃, SO₂CH₃, SOCH₂CH₃, SO₂CH₂CH₃, SO₂NH₂, CH₂SOCH₃, CH₂SO₂CH₃, N-pyrrolidinyl, cyclopropyl, 1-hydroxy-cycloprop-1-yl, cyclobutyl, cyclopentyl and cyclohexyl, k is 0, 1, or 2, $R^5$ is H, CH₃, CH₂CH₃, CH₂CH₂CH₃, CH(CH₃)₂, cyclopropyl, C(O)CH₃, C(O)CH₂CH₃, C(O)CH₂CH₂CH₃, C(O)CH(CH₃)₂, C(O)-cyclopropyl, CH₂CH₂CN, CH₂CH₂OH or CH₂CH₂OCH₃;

p is 0, 1, 2 or 3, and each $X^6$ represents CH₃, CH₂CH₃, CH₂CH₂CH₃, CH(CH₃)₂, CH(CH₃)₃, cyclopropyl, cyclobutyl, cyclopentyl cyclohexyl, OH, OCH₃, OCH₂CH₃, OCH(CH₃)₂, NH₂, N(H)CH₃, N(CH₃)₂, N(H)C(O)CH₃, CH₂OH, CH₂CH2OH, CH₂OCH₃ or CH₂CH₂OCH₃.

18. The compound of claim 1 having formula I-m,

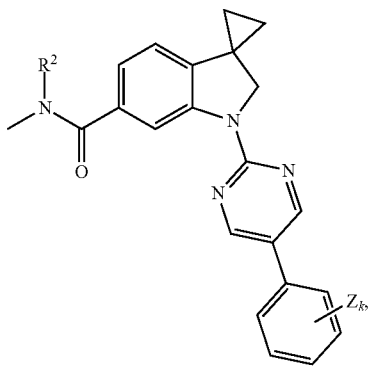

I-m wherein Z is selected from the group consisting of F, Cl, CN, CF₃, CHF₂, CH₂F, OCF₃, OH, OCH₃, OC₂H₅, OCOCH₃, CH₃, CH₂CH₃, CH₂CH₂CH₃, CH(CH₃)₂, CH₂CH₂CH₂CH₃, CH(CH₃)CH₂CH₃, CH₂CH(CH₃)₂, C(CH₃)₃, CONH₂, CONHCH₃, CON(CH₃)₂, NH₂, NH(CH₃), NH(CH₂CH₃), NH(CH₂-c-propyl), N(CH₃)₂, NHCOCH₃, CH₂OH, CH₂CH₂OH, C(CH₃)₂OH, CH(CH₃)OH, CH₂CN, SOCH₃, SO₂CH₃, SOCH₂CH₃, SO₂CH₂CH₃, SO₂NH₂, CH₂SOCH₃, CH₂SO₂CH₃, N-pyrrolidinyl, cyclopropyl, 1-hydroxy-cycloprop-1-yl, cyclobutyl, cyclopentyl and cyclohexyl, k is 0, 1, or 2, and R² represents CH₂CH₂OH, CH₂CH₂CH₂OH, (R)-2-CH₂CH(CH₃)OH, (S)-CH₂CH(CH₃)OH, (R)-CH(CH₃)CH₂OH (S)-CH(CH₃)CH₂OH, (R)-CH₂CH(OH)CH₂CH₂OH or (S)-CH₂CH(OH)CH₂CH₂OH.

19. The compound of claim 1 having formula I-n,

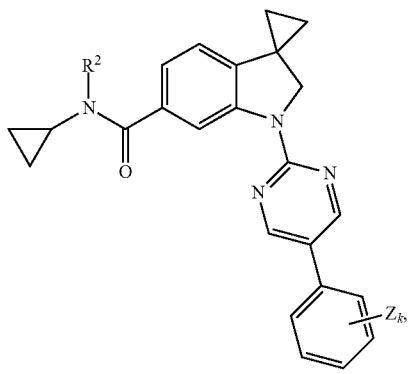

I-n wherein Z is selected from the group consisting of F, Cl, CN, CF₃, CHF₂, CH₂F, OCF₃, OH, OCH₃, OC₂H₅, OCOCH₃, CH₃, CH₂CH₃, CH₂CH₂CH₃, CH(CH₃)₂, CH₂CH₂CH₂CH₃, CH(CH₃)CH₂CH₃, CH₂CH(CH₃)₂, C(CH₃)₃, CONH₂, CONHCH₃, CON(CH₃)₂, NH₂, NH(CH₃), NH(CH₂CH₃), NH(CH₂-c-propyl), N(CH₃)₂, NHCOCH₃, CH₂OH, CH₂CH₂OH, C(CH₃)₂OH, CH(CH₃)OH, CH₂CN, SOCH₃, SO₂CH₃, SOCH₂CH₃, SO₂CH₂CH₃, SO₂NH₂, CH₂SOCH₃, CH₂SO₂CH₃, N-pyrrolidinyl, cyclopropyl, 1-hydroxy-cycloprop-1-yl, cyclobutyl, cyclopentyl and cyclohexyl, k is 0, 1, or 2, and R² represents CH₂CH₂OH, CH₂CH₂CH₂OH, (R)-2-CH₂CH(CH₃)OH, (S)-CH₂CH(CH₃)OH, (R)-CH(CH₃)CH₂OH (S)-CH(CH₃)CH₂OH, (R)-CH₂CH(OH)CH₂CH₂OH or (S)-CH₂CH(OH)CH₂CH₂OH.

20. The compound of claim 7 having formula I-o,

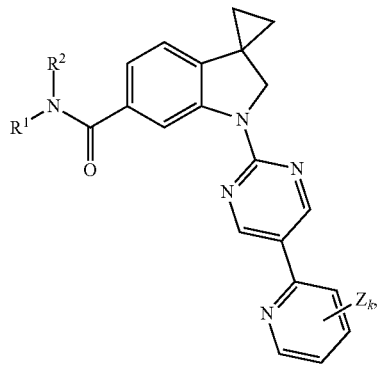

I-o wherein the substructure M is selected from the group consisting of M1 to M12, M25 and M27 to M30, R¹ is H or CH₃ or cyclopropyl, Z is selected from the group consisting of F, Cl, CN, CF₃, CHF₂, CH₂F, OCF₃, OH, OCH₃, OC₂H₅, OCOCH₃, CH₃, CH₂CH₃, CH₂CH₂CH₃, CH(CH₃)₂, CH₂CH₂CH₂CH₃, CH(CH₃)CH₂CH₃, CH₂CH(CH₃)₂, C(CH₃)₃, CONH₂, CONHCH₃, CON(CH₃)₂, NH₂, NH(CH₃), NH(CH₂CH₃), NH(CH₂-c-propyl), N(CH₃)₂, NHCOCH₃, CH₂OH, CH₂CH₂OH, C(CH₃)₂OH, CH(CH₃)OH, CH₂CN, SOCH₃, SO₂CH₃, SOCH₂CH₃, SO₂CH₂CH₃, SO₂NH₂, CH₂SOCH₃, CH₂SO₂CH₃, N-pyrrolidinyl, cyclopropyl, 1-hydroxy-cycloprop-1-yl, cyclobutyl, cyclopentyl and k is 0, 1, or 2.

21. The compound of claim 1 having formula I-p,

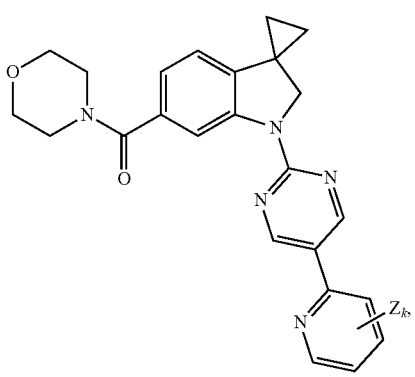

I-p wherein Z is selected from the group consisting of F, Cl, CN, CF₃, CHF₂, CH₂F, OCF₃, OH, OCH₃, OC₂H₅, OCOCH₃, CH₃, CH₂CH₃, CH₂CH₂CH₃, CH(CH₃)₂, CH₂CH₂CH₂CH₃, CH(CH₃)CH₂CH₃, CH₂CH(CH₃)₂, C(CH₃)₃, CONH₂, CONHCH₃, CON(CH₃)₂, NH₂, NH(CH₃), NH(CH₂CH₃), NH(CH₂-c-propyl), N(CH₃)₂, NHCOCH₃, CH₂OH, CH₂CH₂OH, C(CH₃)₂OH, CH(CH₃)OH, CH₂CN, SOCH₃, SO₂CH₃, SOCH₂CH₃, SO₂CH₂CH₃, SO₂NH₂, CH₂SOCH₃, CH$_2$SO$_2$CH$_3$, N-pyrrolidinyl, cyclopropyl, 1-hydroxy-cycloprop-1-yl, cyclobutyl, cyclopentyl and cyclohexyl, and k is 0, 1, or 2.

22. The compound of claim 1 having formula I-q,

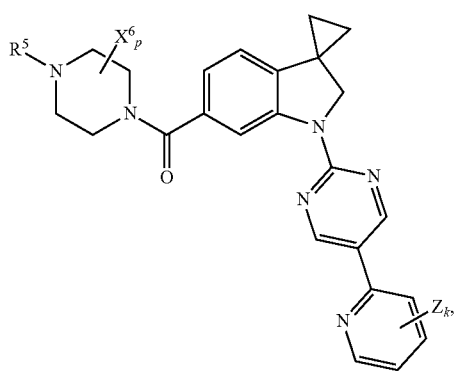

wherein Z is selected from the group consisting of F, Cl, CN, CF$_3$, CHF$_2$, CH$_2$F, OCF$_3$, OH, OCH$_3$, OC$_2$H$_5$, OCOCH$_3$, CH$_3$, CH$_2$CH$_3$, CH$_2$CH$_2$CH$_3$, CH(CH$_3$)$_2$, CH$_2$CH$_2$CH$_2$CH$_3$, CH(CH$_3$)CH$_2$CH$_3$, CH$_2$CH(CH$_3$)$_2$, C(CH$_3$)$_3$, CONH$_2$, CONHCH$_3$, CON(CH$_3$)$_2$, NH$_2$, NH(CH$_3$), NH(CH$_2$CH$_3$), NH(CH$_2$-c-propyl), N(CH$_3$)$_2$, NHCOCH$_3$, CH$_2$OH, CH$_2$CH$_2$OH, C(CH$_3$)$_2$OH, CH(CH$_3$)OH, CH$_2$CN, SOCH$_3$, SO$_2$CH$_3$, SOCH$_2$CH$_3$, SO$_2$CH$_2$CH$_3$, SO$_2$NH$_2$, CH$_2$SOCH$_3$, CH$_2$SO$_2$CH$_3$, N-pyrrolidinyl, cyclopropyl, 1-hydroxy-cycloprop-1-yl, cyclobutyl, cyclopentyl and cyclohexyl, k is 0, 1, or 2, R$^5$ is H, CH$_3$, CH$_2$CH$_3$, CH$_2$CH$_2$CH$_3$, CH(CH$_3$)$_2$, cyclopropyl, C(O)CH$_3$, C(O)CH$_2$CH$_3$, C(O)CH$_2$CH$_2$CH$_3$, C(O)CH(CH$_3$)$_2$, C(O)-cyclopropyl, CH$_2$CH$_2$CN, CH$_2$CH$_2$OH or CH$_2$CH$_2$OCH$_3$, p is 0, 1, 2 or 3, and each X$^6$ represents CH$_3$, CH$_2$CH$_3$, CH$_2$CH$_2$CH$_3$, CH(CH$_3$)$_2$, CH(CH$_3$)$_3$, cyclopropyl, cyclobutyl, cyclopentyl cyclohexyl, OH, OCH$_3$, OCH$_2$CH$_3$, OCH(CH$_3$)$_2$, NH$_2$, N(H)CH$_3$, N(CH$_3$)$_2$, N(H)C(O)CH$_3$, CH$_2$OH, CH$_2$CH$_2$OH, CH$_2$OCH$_3$ or CH$_2$CH$_2$OCH$_3$.

23. The compound of claim 1 having formula I-r,

I-r

[structure]

wherein Z is selected from the group consisting of F, Cl, CN, CF$_3$, CHF$_2$, CH$_2$F, OCF$_3$, OH, OCH$_3$, OC$_2$H$_5$, OCOCH$_3$, CH$_3$, CH$_2$CH$_3$, CH$_2$CH$_2$CH$_3$, CH(CH$_3$)$_2$, CH$_2$CH$_2$CH$_2$CH$_3$, CH(CH$_3$)CH$_2$CH$_3$, CH$_2$CH(CH$_3$)$_2$, C(CH$_3$)$_3$, CONH$_2$, CONHCH$_3$, CON(CH$_3$)$_2$, NH$_2$, NH(CH$_3$), NH(CH$_2$CH$_3$), NH(CH$_2$-c-propyl), N(CH$_3$)$_2$, NHCOCH$_3$, CH$_2$OH, CH$_2$CH$_2$OH, C(CH$_3$)$_2$OH, CH(CH$_3$)OH, CH$_2$CN, SOCH$_3$, SO$_2$CH$_3$, SOCH$_2$CH$_3$, SO$_2$CH$_2$CH$_3$, SO$_2$NH$_2$, CH$_2$SOCH$_3$, CH$_2$SO$_2$CH$_3$, N-pyrrolidinyl, cyclopropyl, 1-hydroxy-cycloprop-1-yl, cyclobutyl, cyclopentyl and cyclohexyl, k is 0, 1, or 2, R$^5$ is H, CH$_3$, CH$_2$CH$_3$, CH$_2$CH$_2$CH$_3$, CH(CH$_3$)$_2$, cyclopropyl, C(O)CH$_3$, C(O)CH$_2$CH$_3$, C(O)CH$_2$CH$_2$CH$_3$, C(O)CH(CH$_3$)$_2$, C(O)-cyclopropyl, CH$_2$CH$_2$CN, CH$_2$CH$_2$OH or CH$_2$CH$_2$OCH$_3$, p is 0, 1, 2 or 3, and each X$^6$ represents CH$_3$, CH$_2$CH$_3$, CH$_2$CH$_2$CH$_3$, CH(CH$_3$)$_2$, CH(CH$_3$)$_3$, cyclopropyl, cyclobutyl, cyclopentyl cyclohexyl, OH, OCH$_3$, OCH$_2$CH$_3$, OCH(CH$_3$)$_2$, NH$_2$, N(H)CH$_3$, N(CH$_3$)$_2$, N(H)C(O)CH$_3$, CH$_2$OH, CH$_2$CH$_2$OH, CH$_2$OCH$_3$ or CH$_2$CH$_2$OCH$_3$.

24. The compound of claim 1 having formula I-s,

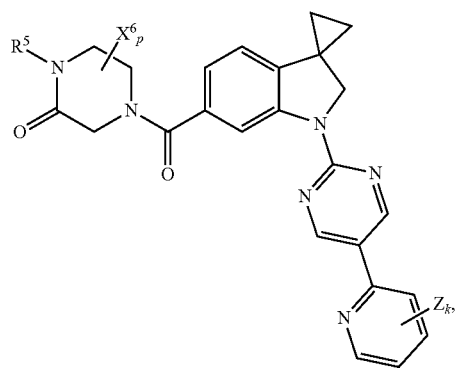

wherein Z is selected from the group consisting of F, Cl, CN, CF$_3$, CHF$_2$, CH$_2$F, OCF$_3$, OH, OCH$_3$, OC$_2$H$_5$, OCOCH$_3$, CH$_3$, CH$_2$CH$_3$, CH$_2$CH$_2$CH$_3$, CH(CH$_3$)$_2$, CH$_2$CH$_2$CH$_2$CH$_3$, CH(CH$_3$)CH$_2$CH$_3$, CH$_2$CH(CH$_3$)$_2$, C(CH$_3$)$_3$, CONH$_2$, CONHCH$_3$, CON(CH$_3$)$_2$, NH$_2$, NH(CH$_3$), NH(CH$_2$CH$_3$), NH(CH$_2$-c-propyl), N(CH$_3$)$_2$, NHCOCH$_3$, CH$_2$OH, CH$_2$CH$_2$OH, C(CH$_3$)$_2$OH, CH(CH$_3$)OH, CH$_2$CN, SOCH$_3$, SO$_2$CH$_3$, SOCH$_2$CH$_3$, SO$_2$CH$_2$CH$_3$, SO$_2$NH$_2$, CH$_2$SOCH$_3$, CH$_2$SO$_2$CH$_3$, N-pyrrolidinyl, cyclopropyl, 1-hydroxy-cycloprop-1-yl, cyclobutyl, cyclopentyl and cyclohexyl, k is 0, 1, or 2, R$^5$ is H, CH$_3$, CH$_2$CH$_3$, CH$_2$CH$_2$CH$_3$, CH(CH$_3$)$_2$, cyclopropyl, C(O)CH$_3$, C(O)CH$_2$CH$_3$, C(O)CH$_2$CH$_2$CH$_3$, C(O)CH(CH$_3$)$_2$, C(O)-cyclopropyl, CH$_2$CH$_2$CN, CH$_2$CH$_2$OH or CH$_2$CH$_2$OCH$_3$, p is 0, 1, 2 or 3, and each X$^6$ represents CH$_3$, CH$_2$CH$_3$, CH$_2$CH$_2$CH$_3$, CH(CH$_3$)$_2$, CH(CH$_3$)$_3$, cyclopropyl, cyclobutyl, cyclopentyl cyclohexyl, OH, OCH$_3$, OCH$_2$CH$_3$, OCH(CH$_3$)$_2$, NH$_2$, N(H)CH$_3$, N(CH$_3$)$_2$, N(H)C(O)CH$_3$, CH$_2$OH, CH$_2$CH$_2$OH, CH$_2$OCH$_3$ or CH$_2$CH$_2$OCH$_3$.

25. The compound of claim 1 having formula I-t,

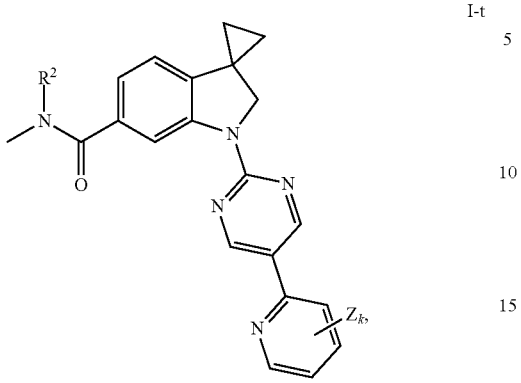

I-t wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2$-c-propyl), $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, and $R^2$ represents $CH_2CH_2OH$, $CH_2CH_2CH_2OH$, (R)-2-$CH_2CH(CH_3)OH$, (S)-$CH_2CH(CH_3)OH$, (R)-$CH(CH_3)CH_2OH$ (S)-$CH(CH_3)CH_2OH$, (R)-$CH_2CH(OH)CH_2CH_2OH$ or (S)-$CH_2CH(OH)CH_2CH_2OH$.

26. The compound of claim 1 having formula I-u,

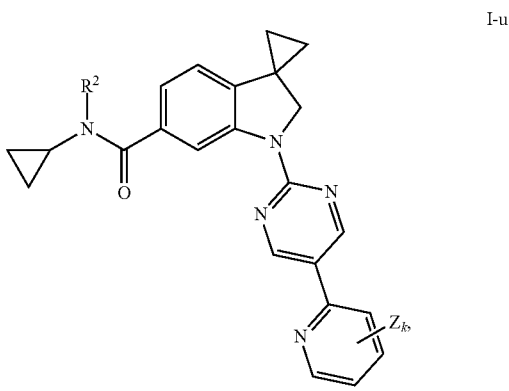

I-u wherein Z is selected from the group consisting of F, Cl, CN, $CF_3$, $CHF_2$, $CH_2F$, $OCF_3$, OH, $OCH_3$, $OC_2H_5$, $OCOCH_3$, $CH_3$, $CH_2CH_3$, $CH_2CH_2CH_3$, $CH(CH_3)_2$, $CH_2CH_2CH_2CH_3$, $CH(CH_3)CH_2CH_3$, $CH_2CH(CH_3)_2$, $C(CH_3)_3$, $CONH_2$, $CONHCH_3$, $CON(CH_3)_2$, $NH_2$, $NH(CH_3)$, $NH(CH_2CH_3)$, $NH(CH_2$-c-propyl), $N(CH_3)_2$, $NHCOCH_3$, $CH_2OH$, $CH_2CH_2OH$, $C(CH_3)_2OH$, $CH(CH_3)OH$, $CH_2CN$, $SOCH_3$, $SO_2CH_3$, $SOCH_2CH_3$, $SO_2CH_2CH_3$, $SO_2NH_2$, $CH_2SOCH_3$, $CH_2SO_2CH_3$, N-pyrrolidinyl, cyclopropyl, 1-hydroxy-cycloprop-1-yl, cyclobutyl, cyclopentyl and cyclohexyl, k is 0, 1, or 2, and $R^2$ represents $CH_2CH_2OH$, $CH_2CH_2CH_2OH$, (R)-2-$CH_2CH(CH_3)OH$, (S)-$CH_2CH(CH_3)OH$, (R)-$CH(CH_3)CH_2OH$ (S)-$CH(CH_3)CH_2OH$, (R)-$CH_2CH(OH)CH_2CH_2OH$ or (S)-$CH_2CH(OH)CH_2CH_2OH$.

* * * * *